US012473295B2

(12) United States Patent
Cai et al.

(10) Patent No.: US 12,473,295 B2
(45) Date of Patent: Nov. 18, 2025

(54) SUBSTITUTED STRAIGHT CHAIN SPIRO DERIVATIVES

(71) Applicant: Janssen Pharmaceutica NV, Beerse (BE)

(72) Inventors: Wei Cai, Shanghai (CN); Xuedong Dai, Shanghai (CN); Olivier Alexis Georges Querolle, Issy-les Moulineaux (FR); Johannes Wilhelmus John F. Thuring, Antwerp (BE); Yingtao Liu, Shanghai (CN); Lianzhu Liu, Shanghai (CN); Yanping Xu, Noblesville, IN (US); Liqiang Fu, Shanghai (CN); Ming Li, Shanghai (CN); Lichao Fang, Shanghai (CN); Xiangjun Deng, Shanghai (CN); Qiwu Zhao, Shanghai (CN); Kangying Li, Tianjin (CN); Alicia Tee Fuay Ng, Shanghai (CN); Nicolas Freddy J. Darville, Linkhout (BE); Edward Cleator, Cambridgeshire (GB); Gregor Thomas Urbanietz, Boom (BE); William Marc Maton, Mol (BE); Vineet Pande, Vosselaar (BE)

(73) Assignee: Janssen Pharmaceutica NV, Beerse (BE)

( * ) Notice: Subject to any disclaimer, the term of this patent is extended or adjusted under 35 U.S.C. 154(b) by 604 days.

(21) Appl. No.: 17/604,818

(22) PCT Filed: Dec. 17, 2020

(86) PCT No.: PCT/CN2020/137266
§ 371 (c)(1),
(2) Date: Oct. 19, 2021

(87) PCT Pub. No.: WO2021/121327
PCT Pub. Date: Jun. 24, 2021

(65) Prior Publication Data

US 2023/0142285 A1 May 11, 2023

Related U.S. Application Data

(60) Provisional application No. 62/961,775, filed on Jan. 16, 2020.

(30) Foreign Application Priority Data

Dec. 19, 2019 (WO) ................ PCT/CN2019/126760
Nov. 4, 2020 (WO) ................ PCT/CN2020/126595

(51) Int. Cl.

| | |
|---|---|
| ***C07D 487/10*** | (2006.01) |
| ***A61P 35/00*** | (2006.01) |
| ***A61P 35/02*** | (2006.01) |
| ***C07D 207/08*** | (2006.01) |
| ***C07D 403/04*** | (2006.01) |

(52) U.S. Cl.
CPC ............ *C07D 487/10* (2013.01); *A61P 35/00* (2018.01); *A61P 35/02* (2018.01); *C07D 207/08* (2013.01); *C07D 403/04* (2013.01)

(58) Field of Classification Search
CPC .. A61P 35/00; A61P 35/02; A61P 3/10; A61K 31/53; C07D 487/10; C07D 207/08; C07D 403/04; C07B 2200/07
See application file for complete search history.

(56) References Cited

U.S. PATENT DOCUMENTS

| | | | |
|---|---|---|---|
| 7,612,078 | B2 | 11/2009 | Dhanoa et al. |
| 8,722,717 | B2 | 5/2014 | Alig et al. |
| 9,586,961 | B2 | 3/2017 | Nielsen et al. |
| 9,730,940 | B2 | 8/2017 | Achab et al. |
| 10,611,778 | B2 | 4/2020 | Angibaud et al. |
| 10,745,409 | B2 | 8/2020 | Angibaud et al. |
| 10,975,100 | B2 | 4/2021 | Angibaud et al. |
| 11,220,517 | B2 | 1/2022 | Angibaud et al. |
| 11,396,517 | B1 | 7/2022 | Dai et al. |
| 11,530,226 | B2 | 12/2022 | Angibaud et al. |
| 2004/0043959 | A1 | 3/2004 | Bloom et al. |
| 2006/0074102 | A1 | 4/2006 | Cusack et al. |
| 2010/0331348 | A1 | 12/2010 | Selles et al. |

(Continued)

FOREIGN PATENT DOCUMENTS

| | | | |
|---|---|---|---|
| CL | 2022001583 | A1 | 2/2023 |
| CL | 2023001530 | A1 | 11/2023 |

(Continued)

OTHER PUBLICATIONS

Uy et al. "Hypomethylating Agents (HMA) Treatment for Myelodysplastic Syndromes: Alternatives in the Frontline and Relapse Settings" Expert Opin Pharmacother. Aug. 2017 ; 18(12): 1213-1224. doi: 10.1080/14656566.2017.1349100. (Year: 2017).*

(Continued)

*Primary Examiner* — Kortney L. Klinkel
*Assistant Examiner* — Sophia Reilly
(74) *Attorney, Agent, or Firm* — BakerHostetler

(57) ABSTRACT

The present invention relates to pharmaceutical agents useful for therapy and/or prophylaxis in a mammal, pharmaceutical composition comprising such compounds, and their use as menin/MLL protein/protein interaction inhibitors, useful for treating diseases such as cancer, including but not limited to leukemia, myelodysplastic syndrome (MDS), and myeloproliferative neoplasms (MPN); and diabetes.

20 Claims, 2 Drawing Sheets

Specification includes a Sequence Listing.

(56) References Cited

U.S. PATENT DOCUMENTS

| | | | | |
|---|---|---|---|---|
| 2013/0040934 | A1* | 2/2013 | Cmiljanovic | A61P 17/06 544/70 |
| 2013/0310333 | A1 | 11/2013 | Chesworth et al. | |
| 2013/0310334 | A1 | 11/2013 | Chesworth et al. | |
| 2014/0221345 | A1 | 8/2014 | Duncan et al. | |
| 2014/0228343 | A1 | 8/2014 | Duncan et al. | |
| 2014/0275070 | A1 | 9/2014 | Grembecka et al. | |
| 2014/0329794 | A1 | 11/2014 | Duncan et al. | |
| 2015/0322376 | A1 | 11/2015 | Holland et al. | |
| 2016/0176869 | A1 | 6/2016 | Chen et al. | |
| 2016/0244475 | A1 | 8/2016 | Tatlock et al. | |
| 2016/0264548 | A1 | 9/2016 | Qiu et al. | |
| 2017/0198006 | A1 | 7/2017 | Duncan et al. | |
| 2017/0275302 | A1 | 9/2017 | Pasternak et al. | |
| 2017/0355711 | A1 | 12/2017 | Tabar et al. | |
| 2018/0105531 | A1 | 4/2018 | Grembecka et al. | |
| 2018/0243328 | A1 | 8/2018 | Wu et al. | |
| 2019/0010167 | A1 | 1/2019 | Claremon et al. | |
| 2019/0092784 | A1 | 3/2019 | Wu et al. | |
| 2019/0211036 | A1 | 7/2019 | Angibaud et al. | |
| 2019/0218230 | A1 | 7/2019 | Angibaud et al. | |
| 2019/0322685 | A1 | 10/2019 | Angibaud et al. | |
| 2020/0172556 | A1 | 6/2020 | Angibaud et al. | |
| 2020/0339594 | A1 | 10/2020 | Angibaud et al. | |
| 2022/0227786 | A1 | 7/2022 | Angibaud et al. | |
| 2023/0039917 | A1 | 2/2023 | Dai et al. | |
| 2023/0174541 | A1 | 6/2023 | Cacatian et al. | |
| 2023/0250096 | A1 | 8/2023 | Cai et al. | |
| 2024/0101532 | A1 | 3/2024 | Watanabe et al. | |
| 2024/0261292 | A1* | 8/2024 | Daskalakis | A61P 35/00 |
| 2024/0417405 | A1 | 12/2024 | Querolle et al. | |

FOREIGN PATENT DOCUMENTS

| | | | | |
|---|---|---|---|---|
| CL | 2023001534 | A1 | 11/2023 | |
| CN | 101048412 | A | 10/2007 | |
| CN | 101107253 | A | 1/2008 | |
| CN | 102149718 | A | 8/2011 | |
| CN | 103664991 | A | 3/2014 | |
| CN | 105188705 | A | 12/2015 | |
| CN | 105330698 | A | 2/2016 | |
| CN | 105732636 | A | 7/2016 | |
| CN | 105939998 | A | 9/2016 | |
| CN | 109152784 | A | 1/2019 | |
| CN | 109689663 | A | 4/2019 | |
| CN | 109743875 | A | 5/2019 | |
| CN | 111297863 | A | 6/2020 | |
| CN | 114867721 | A | 8/2022 | |
| CN | 117337180 | A | 1/2024 | |
| CN | 117460513 | A | 1/2024 | |
| CN | 117597348 | A | 2/2024 | |
| EP | 3394064 | A1 | 10/2018 | |
| EP | 3468966 | A1 | 4/2019 | |
| JP | 05-279305 | A | 10/1993 | |
| JP | 2007-537296 | A | 12/2007 | |
| JP | 2010-532777 | A | 10/2010 | |
| JP | 2011-026305 | A | 2/2011 | |
| JP | 2013-503906 | A | 2/2013 | |
| JP | 2016-512514 | A | 4/2016 | |
| JP | 2018-538330 | A | 12/2018 | |
| JP | 2019-532100 | A | 11/2019 | |
| KR | 10-2021-0078631 | A | 6/2021 | |
| WO | 96/40686 | A1 | 12/1996 | |
| WO | 03/70739 | | 8/2003 | |
| WO | 03/74083 | | 9/2003 | |
| WO | 2004/014850 | A2 | 2/2004 | |
| WO | 2004/056800 | A1 | 7/2004 | |
| WO | 2005/110410 | A2 | 11/2005 | |
| WO | 2006/034511 | A1 | 3/2006 | |
| WO | 2006/078574 | A2 | 7/2006 | |
| WO | 2010/027236 | A2 | 3/2010 | |
| WO | 2010/041366 | A1 | 4/2010 | |
| WO | 2010/066629 | A2 | 6/2010 | |
| WO | 2011/029054 | A1 | 3/2011 | |
| WO | 2012/075500 | A2 | 6/2012 | |
| WO | 2012/082436 | A2 | 6/2012 | |
| WO | 2012/085574 | A2 | 6/2012 | |
| WO | 2013/014162 | A1 | 1/2013 | |
| WO | 2013/018404 | A1 | 2/2013 | |
| WO | 2013/037411 | A1 | 3/2013 | |
| WO | 2014/035140 | A2 | 3/2014 | |
| WO | 2014/100695 | A1 | 6/2014 | |
| WO | 2014/164543 | A1 | 10/2014 | |
| WO | 2015/191701 | A1 | 12/2015 | |
| WO | 2016/000581 | A1 | 1/2016 | |
| WO | 2016/040330 | A1 | 3/2016 | |
| WO | 2016/042452 | A1 | 3/2016 | |
| WO | 2016/060941 | A1 | 4/2016 | |
| WO | 2016/081732 | A1 | 5/2016 | |
| WO | 2016/195776 | A1 | 12/2016 | |
| WO | 2016/197027 | A1 | 12/2016 | |
| WO | 2017/112768 | A1 | 6/2017 | |
| WO | 2017/132398 | A1 | 8/2017 | |
| WO | 2017/161002 | A1 | 9/2017 | |
| WO | 2017/161028 | A1 | 9/2017 | |
| WO | 2017/192543 | A1 | 11/2017 | |
| WO | 2017/207387 | A1 | 12/2017 | |
| WO | 2017/214367 | A1 | 12/2017 | |
| WO | 2018/024602 | A1 | 2/2018 | |
| WO | 2018/047598 | A1 | 3/2018 | |
| WO | 2018/050684 | A1 | 3/2018 | |
| WO | 2018/050686 | A1 | 3/2018 | |
| WO | 2018/053267 | A1 | 3/2018 | |
| WO | 2018/106818 | A1 | 6/2018 | |
| WO | 2018/106820 | A1 | 6/2018 | |
| WO | 2018/109088 | A1 | 6/2018 | |
| WO | 2018/153312 | A1 | 8/2018 | |
| WO | 2018/175746 | A1 | 9/2018 | |
| WO | 2018/226976 | A1 | 12/2018 | |
| WO | 2018/232235 | A1 | 12/2018 | |
| WO | 2019/012328 | A1 | 1/2019 | |
| WO | 2019/060365 | A1 | 3/2019 | |
| WO | 2019/106388 | A1 | 6/2019 | |
| WO | 2019/120209 | A1 | 6/2019 | |
| WO | 2020/045334 | A1 | 3/2020 | |
| WO | 2020/069027 | A1 | 4/2020 | |
| WO | 2020/118194 | A1 | 6/2020 | |
| WO | 2020/212897 | A1 | 10/2020 | |
| WO | 2020/252229 | A2 | 12/2020 | |
| WO | 2021/121327 | A1 | 6/2021 | |
| WO | 2021/207335 | A1 | 10/2021 | |
| WO | 2022/237626 | A1 | 11/2022 | |
| WO | 2022/237627 | A1 | 11/2022 | |
| WO | 2022/237719 | A1 | 11/2022 | |
| WO | 2022/237720 | A1 | 11/2022 | |
| WO | 2022/241122 | A1 | 11/2022 | |
| WO | 2022/253167 | A1 | 12/2022 | |
| WO | 2022/253289 | A1 | 12/2022 | |
| WO | 2022/262796 | A1 | 12/2022 | |
| WO | 2023/114867 | A2 | 6/2023 | |
| WO | WO-2023098876 | A1 * | 6/2023 | A61K 31/506 |
| WO | WO-2023150635 | A1 * | 8/2023 | |
| WO | 2023/220098 | A1 | 11/2023 | |
| WO | 2024/114658 | A1 | 6/2024 | |
| WO | 2024/114662 | A1 | 6/2024 | |
| WO | 2024/114664 | A1 | 6/2024 | |
| WO | 2024/114666 | A1 | 6/2024 | |
| WO | 2024/218072 | A1 | 10/2024 | |

OTHER PUBLICATIONS

Acute Leukemia, Merck Manual, Online Edition, 2013, 1-6.

European Search Report EP17150502 completed Mar. 7, 2017.

European Search Report EP18201390 completed Nov. 14, 2018.

Gura, "Systems for identifying new drugs are often faulty.", Science, 278(5340): 1997, 1041-2.

International Application No. PCT/EP2017/073004, Written Opinion of the International Searching Authority, dated Mar. 8, 2019, 4 pages.

International Search Report PCT/CN2017/117536 mailed Jul. 31, 2018.

(56) References Cited

OTHER PUBLICATIONS

International Search Report PCT/EP2017/073001 mailed Nov. 6, 2017.
International Search Report PCT/EP2017/082826 mailed Feb. 14, 2018.
Liu, "MLL fusions: pathways to leukemia." Cancer biology & therapy 8.13, 2009, 1204-1211.
Pearce et al., "Failure modes in anticancer drug discovery and development.", Cancer Drug Design and Discovery Edited by Stephen Neidle, Chapter 18, pp. 424-435 (2008).
Shah et al., "Synthesis and evaluation of CCR5 antagonists containing modified 4-piperidinyl-2-phenyl-1-(phenylsulfonylamino)-butane", Bioorganic & Medicinal Chemistry Letters, 2005, pp. 977-982, vol. 15.
Simone, Introduction, Omenn, Cancer Prevention, Part XIV, Oncology, Cecil Textbook of Medecine, 201h Edition, vol. 1, pp. 1004-1010.
Written Opinion PCT/EP2017/073001 mailed Nov. 6, 2017.
Written Opinion PCT/EP2017/073004 mailed Nov. 28, 2017.
Written Opinion PCT/EP2017/082826, mailed Feb. 14, 2018.
Zheng et al., Journal of Chemical Information and Modeling , 2016, 56(9), 1-34.
Borkin D et al., "Property Focused Structure-Based Optimization of Small Molecule Inhibitors of the Protein-Protein Interaction between Menin and Mixed Lineage Leukemia (MLL)," J Med Chem, vol. 59, 2016, pp. 892-913.
Borkin et al., "Pharmacologic Inhibition of the Menin-MLL Interaction Blocks Progression of MLL Leukemia In Vivo", Cancer Cell, vol. 27, 2015, pp. 589-602.
Cermakova et al., "Validation and Structural Characterization of the LEDGF/p75-MLL Interface as a New Target for theTreatment of MLL-Dependent Leukemia," Cancer Res., vol. 74(18), Sep. 15, 2014, pp. 5139-5151.
Charron et al., "Recent developments in radiolabelled peptides for PET imaging of cancer," Tetrahedron Letters, vol. 57, 2016, pp. 4119-4127.
Chen et al., "The tumor suppressor menin regulates hematopoiesis and myeloid transformation by influencing Hox gene expression," PNAS, vol. 103(4), Jan. 24, 2006, pp. 1018-1023.
Cierpicki et al., "Challenges and opportunities in targeting the menin-MLL interaction," Future Med. Chem, vol. 6(4), (Mar. 2014), pp. 447-462.
Gennaro, A.R., Remington's 18th ed., Mack Publishing Company, (1990) see especially Part 8: Pharmaceutical preparations and their Manufacture, pp. 1435-1712.
Greene, T.W., et al., "Greene's Protective Groups in Organic Synthesis", 4th ed., Wilev-Interscience, Hoboken, New JerseY, (2007), pp. 1112.
Grembecka, J., et al., "Menin-MLL inhibitors reverse oncogenic activity of MLL fusion proteins in leukemia," Nature Chemical Biology, vol. 8, 2012, pp. 277-284.
Hamza, Daniel et al., "Synthesis of novel 2, 6-diazaspiro [3.3] heptanes," SY NLETT, Sep. 12, 2007, pp. 2584-2586.
Johnson et al., "Relationships between drug activity in NCI preclinical in vitro and in vivo models and early clinical trials," British Journal of Cancer, vol. 84(10), 2001, pp. 1424-1431.
Kopljar et al., "Development of a Human iPSC Cardiomyocyte-Based Scoring System for Cardiac Hazard Identification in Early Drug Safety De-risking," Stem Cell Reports, vol. 11, Issue 6, Dec. 2018, pp. 1365-1377.
Kopljar I. et al., "Impact of calcium-sensitive dyes on the beating properties and pharmacological responses of human iPS-derived cardiomyocytes using the calcium transient assay," Journal of Pharmacological and toxicological methods, vol. 91, 2018, pp. 80-86.
Krivtsov, et al., "A Menin-MLL Inhibitor Induces Specific Chromatin Changes and Eradicates Disease in Models of MLL Rearranged Leukemia" 2019, Cancer Cell, 36, 660-673.
Kurmasheva et al., "Evaluation of VTP-50469, a menin-MLL1 inhibitor, against Ewing sarcoma xenograft models by the pediatric preclinical testing consortium", Pediatr Blood Cancer, 2020, e28284, 1-4.
Li et al., "Distinct pathways regulated by menin and by MLL1 in hematopoietic stem cells and developing B cells," Blood, vol. 122(12), Sep. 19, 2013, pp. 2039-2046.
Lu et al., "Assessing Drug-Induced Long QT and Proarrhythmic Risk Using Human Stem-Cell-Derived Cardiomyocytes in a Ca2+ Imaging Assay: Evaluation of 28 CiPA Compounds at Three Test Sites," Toxicological Sciences, vol. 170, Issue 2, Aug. 2019, pp. 345-356.
Malik et al., "Targeting the MLL complex in castration resistant prostate cancer," Nat. Med., vol. 21(4), Apr. 2015, pp. 344-352.
Marschalek, R., "Mechanisms of leukemogenesis by MLL fusion proteins," British Journal of Haematology, vol. 152, vol. 2, 2010, pp. 141-154.
McDonald T.V. et al., "A minK-HERG complex regulates the cardiac potassium current IKr," Nature, vol. 388, 1997, pp. 289-292.
Meyer et al., "The MLL recombinome of acute leukemias in 2013," Leukemia, 2013, vol. 27, pp. 2165-2176.
Mishra et al., "The Histone Methyltransferase Activity of MLL 1 Is Dispensable for Hematopoiesis and Leukemogenesis," Cell Rep, vol. 7(4), May 22, 2014, pp. 1239-1247.
Obergrussberger et al., "Automated Patch Clamp Meets High-Throughput Screening: 384 Cells Recorded in Parallel on a Planar Patch Clamp Module," Journal of Laboratory Automation, vol. 21, Dec. 2016, pp. 779-793.
Orr, S.T.M. et al., "One-pot synthesis of chiral azetidines from chloroaldehyde and chiral amines," Tetrahedron Letters, vol. 52, May 14, 2011, pp. 3618-3620.
Pantel et al., "Molecular imaging to guide systemic cancer therapy: Illustrative examples of PET imaging cancer biomarkers," Cancer Lett., vol. 387, (2017), pp. 25-31.
Ren J. et al., "Design and synthesis of benzylpiperidine inhibitors targeting the menin-MLL1 interface," Bioorg Med Chem Letters, vol. 26, Issue 18, 2016, pp. 4472-4476.
Shihan He et al., "High-Affinity Small-Molecule Inhibitors of the Menin-Mixed Lineage Leukemia (MLL) Interaction Closely Mimic a Natural Protein-Protein Interaction," J Med Chem, vol. 57, 2014, pp. 1543-1556.
Stocks, Michael J. et al., "Concise synthesis of novel 2, 6-diazaspiro [3. 3] hept an-1-ones and their conversion into 2, 6-diazaspiro [3.3] heptanes," SYNLETT, Sep. 12, 2007, pp. 2587-2589.
Thiel et al., "Menin as a Hub Controlling Mixed Lineage Leukemia.", Bioessays, vol. 34(9), Sep. 2012, pp. 771-780.
Tomizawa et al., "Repetitive Cycles of High-Dose Cytarabine Are Effective for Childhood Acute Myeloid Leukemia: Long-Term Outcome of the Children With AML Treated on Two Consecutive Trials of Tokyo Children's Cancer Study Group," Pediatr. Blood Cancer, vol. 49, 2007, pp. 127-132.
Uckelmann, Hannah J. et al., "Therapeutic targeting of preleukelnia cells in a mouse model of NPMI mutant acute myeloid leukemia," Science, Jan. 31, 2020, vol. 367, Issue 6477, pp. 586-590.
Yokoyama et al., "The Menin Tumor Suppressor Protein Is an Essential Oncogenic Cofactor for MLL-Associated Leukemogenesis," Cell, vol. 123, Oct. 21, 2005, pp. 207-218.
Yokoyama, A. and Cleary, M., "Menin Critically Links MLL Proteins with LEDGF on Cancer-Associated Target Genes," Cancer Cell, vol. 1, Jul. 2008, pp. 36-46.
Zhou Z et al., "Properties of HERG Channels Stably Expressed in HEK 293 Cells Studied at Physiological Temperature," Biophysical Journal, vol. 74, Issue 1, Jan. 1998, pp. 230-241.
"Chemical Medicine," Second edition, eds. Lu et., Southeast University Press, Jun. 30, 2013, 440-441.
"STN search report" Benzamide, N-ethyl-5-fluoro-2-hydroxy-N-(1-methylethyl), CB85512331, CAS No. 1549490-65-4, available online at https://m.chemicalbook.com/Search_EN.aspx?keyword=1549490-65-4&start=0, retrieved on Feb. 7, 2025, 1 page.
Zukauskaite, et al., "Synthesis of 1,5-diazaspiro[2.3]hexanes, a novel diazaspirocyclic system", Tetrahedron, vol. 69, (2013) pp. 3437-3443.

(56) References Cited

OTHER PUBLICATIONS

Bloomfield et al., “Time to repeal and replace response criteria for acute myeloid leukemia?”, Blood Reviews, vol. 32, 2018, pp. 416-425.
Borght et al., “BIGL: Biochemically Intuitive Generalized Loewe null model for prediction of the expected combined effect compatible with partial agonism and antagonism”, Scientific Reports, vol. 7, Article No. 17935, Dec. 20, 2017, pp. 1-9.
Bundgaard, “Design of Prodrugs”, Elsevier, 1985, p. 96.
Carter et al., “AML-027: Menin Inhibition Decreases Bcl-2 and Bcl-xL and Enhances Venetoclax Activity in NPM1/ FLT3-Mutated AML”, Clinical Lymphoma Myeloma and Leukemia, vol. 21, Supplement 1, Sep. 2021, pp. S277- S278.
Carter et al., “Inhibition of menin, BCL-2, and FLT3 combined with a hypomethylating agent cures NPM1/FLT3-ITD/-TKD mutant acute myeloid leukemia in a patient-derived xenograft model”, Haematologica, vol. 108, Sep. 2023, pp. 2513-2519.
Chi et al., “Emerging Targeted Therapy for Specific Genomic Abnormalities in Acute Myeloid Leukemia”, Int. J. Mol. Sci., Feb. 21, 2022, vol. 23, 2362, pp. 1-16.
Dempke et al., “Targeting the undruggable: menin inhibitors ante portas”, J Cancer Res Clin Oncology, Apr. 27, 2023, vol. 149, No. 11, pp. 9451-9459.
Dohner et al., “Diagnosis and management of AML in adults: 2017 ELN recommendations from an international expert panel”, Blood, vol. 129, No. 4, Jan. 26, 2017, pp. 424-447.
Dohner et al., “Diagnosis and management of AML in adults: 2022 recommendations from an international expert panel on behalf of the ELN”, Blood, Sep. 22, 2022, vol. 140, No. 12, pp. 1345-1377.
Eagle et al., “Transcriptional Plasticity Drives Leukemia Immune Escape”, Blood Cancer Discovery, vol. 3, Sep. 2022, pp. 394-409.
Falini et al., “Diagnostic and therapeutic pitfalls in NPM1-mutated AML: notes from the field”, Leukemia, Apr. 20, 2021, vol. 35, pp. 3113-3126.
Goardon et al., “Coexistence of LMPP-like and GMP-like leukemia stem cells in acute myeloid leukemia”, Cancer Cell, Jan. 18, 2011, vol. 19, No. 1, pp. 138-152.
Greene et al., Protective Groups in Organic Synthesis, Third Edition, New York, Wiley, 1999.
Hoelzer et al., “Acute lymphoblastic leukaemia in adult patients: ESMO Clinical Practice Guidelines for diagnosis, treatment and follow-up”, Annals of Oncology, vol. 27, Supplement 5, Sep. 2016, pp. v69-v82.
Hortan et al., “MLL-AF9-mediated immortalization of human hematopoietic cells along different lineages changes during ontogeny”, Leukemia, vol. 27, 2013, pp. 1116-1126.
Issa et al., “Therapeutic implications of menin inhibition in acute leukemias”, Leukemia, vol. 35, No. 9, Jun. 15, 2021, p. 14.
Jabbour et al., “A First-in-Human Phase 1 Study of the Menin-KMT2A (MLL1) Inhibitor JNJ-75276617 in Adult Patients with Relapsed/Refractory Acute Leukemia Harboring KMT2A or NPM1 Alterations”, Blood, vol. 142, Supplement 1, Nov. 28, 2023, pp. 57-60.
Krivtsov et al., “Transformation from committed progenitor to leukaemia stem cell initiated by MLL-AF9”, Nature, vol. 442, Aug. 17, 2006, pp. 818-822.
Kwon et al., “Pharmacological Characterization of JNJ-75276617, a Menin-KMT2A Inhibitor, As Targeted Treatment for KMT2A-Altered and NPM1-Mutant Acute Leukemia”, Blood, vol. 140, Supplement 1, Nov. 15, 2022, pp. 5928-5929.
Kwon et al., “Preclinical Efficacy of the Menin-KMT2A Inhibitor JNJ-75276617 in Combination with Venetoclax and Azacitidine in AML”, Blood, vol. 142, Supplement 1, Nov. 28, 2023, p. 4167.
Marchal et al., “Cycloisomerization of ?- and d-acetylenic acids catalyzed by gold(I) chloride”, Tetrahedron, vol. 63, No. 40, 2007, pp. 9979-9990.
Mizuta et al., “Investigation of screening method for DNMT3A mutations by high-resolution melting analysis in acute myeloid leukemia”, Int J Lab Hematol., vol. 41, No. 5, May 13, 2019; pp. 593-600.
NCCN. National Comprehensive Cancer Network (NCCN). Clinical practice guidelines in oncology: Acute lymphoblastic leukemia (ALL). Version 2.2020, https://www.nccn.org/professionals/physician_gls/pdf/all.pdf. ,Accessed Nov. 16, 2020.
Novershtern et al., “Densely Interconnected Transcriptional Circuits Control Cell States in Human Hematopoiesis”, Cell, Jan. 2, 20111, vol. 144, No. 2, pp. 296-309.
Orlando et al., “Quantitative ChIP-Seq Normalization Reveals Global Modulation of the Epigenome”, Cell Reports, vol. 9, Nov. 6, 2014, pp. 1163-1170.
Rowe et al., “Handbook of Pharmaceutical Excipients”, Pharmaceutical Press, 6th edition, 1986, p. 917.
Skopek et al., “Choosing the Right Cell Line for Acute Myeloid Leukemia (AML) Research”, Int. J. Mol. Sci., Mar. 11, 2023, vol. 24, No. 6, 5377, pp. 1-34.
Suchand et al., “Palladium-Catalyzed Environmentally Benign Acylation”, The Journal of Organic Chemistry, Jul. 5, 2016, vol. 81, No. 15, pp. 6409-6423.
Thas et al., “Statistical detection of synergy: New methods and a comparative study”, vol. 21, No. 2, March/Apr. 2022, pp. 345-360.
Uckelmann, “MLL-Menin Inhibition Reverses Pre-Leukemic Progenitor Self-Renewal Induced By NPM1 Mutations and Prevents AML Development”, Blood, Nov. 2018, vol. 132, (Suppl_1), 546.
Van Den Boom et al., “Non-canonical PRC1.1 Targets Active Genes Independent of H3K27me3 and Is Essential for Leukemogenesis”, Cell Reports, vol. 14, Jan. 12, 2016, pp. 332-346.
Weng et al., “The m6A reader IGF2BP2 regulates glutamine metabolism and represents a therapeutic target in acute myeloid leukemia”, , Cancer Cell, vol. 40, Dec. 12, 2022, pp. 1566-1582.
Yang et al., “DNMT3A in haematological malignancies”, Nat Rev Cancer, Mar. 2015, vol. 15, No. 3, pp. 152-165.
Yi et al., “Chromatin-Based Classification of Genetically Heterogeneous AMLs into Two Distinct Subtypes with Diverse Stemness Phenotypes”, Cell Rep., Jan. 2, 20192, vol. 26, No. 4, pp. 1059-1069.
Zarka et al., “Nucleophosmin 1 Mutations in Acute Myeloid Leukemia”, Genes, 2020, vol. 11, 649, pp. 1-16.
“Menin-MLL Inhibitor 24”, CAS No. 2654081-35-1, 3 pages, Jan. 13, 2024.
Brazilian Search Report received for Brazilian Application No. BR112019004691-7, mailed on May 4, 2024, 5 pages.
Brehmer et al., “Abstract DDT02-04: A Novel PRMT5 Inhibitor with Potent in Vitro and in Vivo Activity in Preclinical Lung Cancer Models”, Cancer Research, vol. 77, Supplement 13, 1 page (Abstract only), Jul. 1, 2017.
Carter et al., “Menin Inhibition Decreases Bcl-2 and Synergizes with Venetoclax in NPM1/FL T3-Mutated AML”, Blood, vol. 138, No. 05, pp. 1637-1641, Oct. 28, 2021.
Chilean Search Report received for Chilean Application No. 202301531, mailed on Aug. 22, 2024, 25 pages.
Chilean Search Report, received for Chilean Application No. 202301530, mailed on Aug. 22, 2024, 25 pages.
Dyson et al., “Chemistry of Synthetic Drugs Substances”, Moscow: Mir, 9 p. 1964.
Extended European Search Report, received for European Application No. 16192424.6, mailed on Nov. 22, 2016, 8 pages.
Fiskus et al., “Effective Menin Inhibitor-Based Combinations Against AML with MLL Rearrangement or NPM1 Mutation (NPM1 c)”, Blood Cancer Journal, vol. 12, No. 01, pp. 1-11, Jan. 11, 2022.
Green Antibody Engineering via Genetic Engineering of the Mouse: Xenomouse Strains Are a Vehicle for the facile generation of therapeutic human monoclonal antibodies, Journal of Immunological Methods, vol. 231, No. 1-2, pp. 11-23, Dec. 10, 1999.
International Search Report and Written Opinion received for PCT Application No. PCT/CN2019/085517, mailed on Feb. 12, 2020, 14 pages.
International Search Report and Written Opinion received for PCT Application No. PCT/CN2019/126760, mailed on Sep. 23, 2020, 15 pages.
International Search Report and Written Opinion received for PCT Application No. PCT/CN2020/126595, mailed on Jul. 26, 2021, 18 pages.

(56) References Cited

OTHER PUBLICATIONS

International Search Report and Written Opinion received for PCT Application No. PCT/CN2020/137266, mailed on Mar. 16, 2021, 18 pages.
International Search Report and Written Opinion received for PCT Application No. PCT/CN2021/092256, mailed on Oct. 5, 2021, 17 pages.
International Search Report and Written Opinion received for PCT Application No. PCT/CN2021/092257, mailed on Oct. 7, 2021, 19 pages.
International Search Report and Written Opinion received for PCT Application No. PCT/CN2021/097679, mailed on Oct. 26, 2021, 17 pages.
International Search Report and Written Opinion received for PCT Application No. PCT/CN2021/100466, mailed on Oct. 27, 2021, 14 pages.
International Search Report and Written Opinion received for PCT Application No. PCT/CN2021/100523, mailed on Nov. 24, 2021, 16 pages.
International Search Report and Written Opinion received for PCT Application No. PCT/CN2022/085680, mailed on Aug. 18, 2022, 19 pages.
International Search Report and Written Opinion received for PCT Application No. PCT/CN2022/135433, mailed on Mar. 17, 2023, 13 pages.
International Search Report and Written Opinion received for PCT Application No. PCT/CN2022/135436, mailed on Mar. 16, 2023, 12 pages.
International Search Report and Written Opinion received for PCT Application No. PCT/CN2022/135444, mailed on May 16, 2023, 19 pages.
Johnston et al., "Metallaphotoredox-Catalysed sp3-sp3 Cross-Coupling of Carboxylic Acids with Alkyl Halides", Nature, vol. 536, No. 7616, pp. 322-325, Aug. 18, 2016.
Nguyen et al., "Anti-prion Activities and Drug-Like Potential of Functionalized Quinacrine Analogs with Basic Phenyl Residues at the 9-Amino Position", European Journal of Medicinal Chemistry, vol. 46, No. 07, pp. 2917-2929, Jul. 2011.
Office Action received for Japanese Patent Application No. 2019-531979 dated Nov. 9, 2021, 10 pages pages (5 pages of English Translation and 5 pages of Original Document).
Office Action received for Japanese Patent Application No. 2019-535974 dated Jul. 6, 2021, 6 pages pages (3 pages of English Translation and 3 pages of Original Document).
Stabile et al., "Mild, Convenient and Versatile Cu-Mediated Synthesis of N-aryl-2-imidazolidinones", Tetrahedron Letters, vol. 51, No. 24, pp. 3232-3235, Jun. 16, 2010.
Uniprot, RecName: Full=Histone-lysine N-methyltransferase 2A; Short=Lysine N-methyltransferase 2A; AltName: Full=ALL-1; AltName: Full=CXXC-type zinc finger protein 7; AltName: Full=Cysteine methyltransferase KMT2A; AltName: Full=Myeloid/lymphoid or mixed-lineage leukemia; AltName: Full=Myeloid/lymphoid or mixed-lineage leukemia protein 1; AltName: Full=Trithorax-like protein; AltName: Full=Zinc finger protein HRX; Contains: RecName: Full=MLL cleavage product N320; AltName: Full=N-terminal cleavage product of 320 kDa; Short=p320; May 1, 2007.
Zhang et al., "Palladium-Catalyzed Regioselective Allylation of Five-Membered Heteroarenes with Allyltributylstannane", Chemical Communications, vol. 51, No. 18, pp. 3842-3845, Feb. 17, 2015.
Zidar et al., "New N-phenyl-4,5-dibromopyrrolamides and N-Phenylindolamides as ATPase Inhibitors of DNA Gyrase", European Journal of Medicinal Chemistry, vol. 117, pp. 197-211, Jul. 19, 2016.

* cited by examiner

SEQUENCE LISTING

<160> NUMBER OF SEQ ID NOS: 2

<210> SEQ ID NO 1
<211> LENGTH: 616
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Gly Leu Lys Ala Ala Gln Lys Thr Leu Phe Pro Leu Arg Ser Ile
1 5 10 15

Asp Asp Val Val Arg Leu Phe Ala Ala Glu Leu Gly Arg Glu Glu Pro
20 25 30

Asp Leu Val Leu Leu Ser Leu Val Leu Gly Phe Val Glu His Phe Leu
35 40 45

Ala Val Asn Arg Val Ile Pro Thr Asn Val Pro Glu Leu Thr Phe Gln
50 55 60

Pro Ser Pro Ala Pro Asp Pro Pro Gly Gly Leu Thr Tyr Phe Pro Val
65 70 75 80

Ala Asp Leu Ser Ile Ile Ala Ala Leu Tyr Ala Arg Phe Thr Ala Gln
85 90 95

Ile Arg Gly Ala Val Asp Leu Ser Leu Tyr Pro Arg Glu Gly Gly Val
100 105 110

Ser Ser Arg Glu Leu Val Lys Lys Val Ser Asp Val Ile Trp Asn Ser
115 120 125

Leu Ser Arg Ser Tyr Phe Lys Asp Arg Ala His Ile Gln Ser Leu Phe
130 135 140

Ser Phe Ile Thr Gly Thr Lys Leu Asp Ser Ser Gly Val Ala Phe Ala
145 150 155 160

Val Val Gly Ala Cys Gln Ala Leu Gly Leu Arg Asp Val His Leu Ala
165 170 175

Leu Ser Glu Asp His Ala Trp Val Val Phe Gly Pro Asn Gly Glu Gln
180 185 190

Thr Ala Glu Val Thr Trp His Gly Lys Gly Asn Glu Asp Arg Arg Gly
195 200 205

Gln Thr Val Asn Ala Gly Val Ala Glu Arg Ser Trp Leu Tyr Leu Lys
210 215 220

Gly Ser Tyr Met Arg Cys Asp Arg Lys Met Glu Val Ala Phe Met Val
225 230 235 240

Cys Ala Ile Asn Pro Ser Ile Asp Leu His Thr Asp Ser Leu Glu Leu
245 250 255

Leu Gln Leu Gln Gln Lys Leu Leu Trp Leu Leu Tyr Asp Leu Gly His
260 265 270

Leu Glu Arg Tyr Pro Met Ala Leu Gly Asn Leu Ala Asp Leu Glu Glu
275 280 285

Leu Glu Pro Thr Pro Gly Arg Pro Asp Pro Leu Thr Leu Tyr His Lys
290 295 300

Gly Ile Ala Ser Ala Lys Thr Tyr Tyr Arg Asp Glu His Ile Tyr Pro
305 310 315 320

Tyr Met Tyr Leu Ala Gly Tyr His Cys Arg Asn Arg Asn Val Arg Glu
325 330 335

Ala Leu Gln Ala Trp Ala Asp Thr Ala Thr Val Ile Gln Asp Tyr Asn
340 345 350

Tyr Cys Arg Glu Asp Glu Glu Ile Tyr Lys Glu Phe Phe Glu Val Ala
355 360 365

Asn Asp Val Ile Pro Asn Leu Leu Lys Glu Ala Ala Ser Leu Leu Glu
370 375 380

Ala Gly Glu Glu Arg Pro Gly Glu Gln Ser Gln Gly Thr Gln Ser Gln
385 390 395 400

Gly Ser Ala Leu Gln Asp Pro Glu Cys Phe Ala His Leu Leu Arg Phe
405 410 415

Tyr Asp Gly Ile Cys Lys Trp Glu Glu Gly Ser Pro Thr Pro Val Leu
420 425 430

His Val Gly Trp Ala Thr Phe Leu Val Gln Ser Leu Gly Arg Phe Glu
435 440 445

Gly Gln Val Arg Gln Lys Val Arg Ile Val Ser Arg Glu Ala Glu Ala
450 455 460

Ala Glu Ala Glu Glu Pro Trp Gly Glu Glu Ala Arg Glu Gly Arg Arg
465 470 475 480

Arg Gly Pro Arg Arg Glu Ser Lys Pro Glu Glu Pro Pro Pro Pro Lys
485 490 495

Lys Pro Ala Leu Asp Lys Gly Leu Gly Thr Gly Gln Gly Ala Val Ser
500 505 510

Gly Pro Pro Arg Lys Pro Pro Gly Thr Val Ala Gly Thr Ala Arg Gly
515 520 525

Pro Glu Gly Gly Ser Thr Ala Gln Val Pro Ala Pro Ala Ala Ser Pro
530 535 540

Pro Pro Glu Gly Pro Val Leu Thr Phe Gln Ser Glu Lys Met Lys Gly
545 550 555 560

Met Lys Glu Leu Leu Val Ala Thr Lys Ile Asn Ser Ser Ala Ile Lys
565 570 575

Leu Gln Leu Thr Ala Gln Ser Gln Val Gln Met Lys Lys Gln Lys Val
580 585 590

Ser Thr Pro Ser Asp Tyr Thr Leu Ser Phe Leu Lys Arg Gln Arg Lys
595 600 605

Gly Leu His His His His His His
610 615

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Beta-alanine

<400> SEQUENCE: 2

Ala Ser Ala Arg Trp Arg Phe Pro Ala Arg Pro Gly Thr
1 5 10

SUBSTITUTED STRAIGHT CHAIN SPIRO DERIVATIVES

CROSS-REFERENCE TO RELATED APPLICATIONS

This application is the National Stage of International Patent Application No. PCT/CN2020/137266, filed Dec. 17, 2020, which claims priority to International Patent Application No. PCT/CN2019/126760, filed Dec. 19, 2019; U.S. Provisional Patent Application No. 62/961,775, filed Jan. 16, 2020 and International Patent Application No. PCT/CN2020/126595, filed Nov. 4, 2020. The foregoing applications are incorporated herein by reference in their entireties for any and all purposes.

SEQUENCE LISTING

The instant application contains a Sequence Listing which has been submitted electronically in ASCII format and is hereby incorporated by reference in its entirety. Said ASCII copy, created on Aug. 5, 2025, is named 103693_003364_SL.txt and is 6,127 bytes in size.

FIELD OF THE INVENTION

The present invention relates to pharmaceutical agents useful for therapy and/or prophylaxis in a mammal, pharmaceutical composition comprising such compounds, and their use as menin/MLL protein/protein interaction inhibitors, useful for treating diseases such as cancer, including but not limited to leukemia, myelodysplastic syndrome (MDS), and myeloproliferative neoplasms (MPN); and diabetes.

BACKGROUND OF THE INVENTION

Chromosomal rearrangements affecting the mixed lineage leukemia gene (MLL; MLL1; KMT2A) result in aggressive acute leukemias across all age groups and still represent mostly incurable diseases emphasizing the urgent need for novel therapeutic approaches. Acute leukemias harboring these chromosomal translocations of MLL represent as lymphoid, myeloid or biphenotypic disease and constitute 5 to 10% of acute leukemias in adults and approximately 70% in infants (Marschalek, Br J Haematol 2011. 152(2), 141-54; Tomizawa et al., Pediatr Blood Cancer 2007. 49(2), 127-32).

MLL is a histone methyltransferase that methylates histone H3 on lysine 4 (H3K4) and functions in multiprotein complexes. Use of inducible loss-of-function alleles of Mll1 demonstrated that Mll1 plays an essential role in sustaining hematopoietic stem cells (HSCs) and developing B cells although its histone methyltransferase activity is dispensable for hematopoiesis (Mishra et al., Cell Rep 2014. 7(4), 1239-47).

Fusion of MLL with more than 60 different partners has been reported to date and has been associated with leukemia formation/progression (Meyer et al., Leukemia 2013. 27, 2165-2176). Interestingly, the SET (Su(var)3-9, enhancer of zeste, and trithorax) domain of MLL is not retained in chimeric proteins but is replaced by the fusion partner (Thiel et al., Bioessays 2012. 34, 771-80). Recruitment of chromatin modifying enzymes like Dot1L and/or the pTEFb complex by the fusion partner leads to enhanced transcription and transcriptional elongation of MLL target genes including HOXA genes (e.g. HOXA9) and the HOX cofactor MEIS1 as the most prominent ones. Aberrant expression of these genes in turn blocks hematopoietic differentiation and enhances proliferation.

Menin which is encoded by the Multiple Endocrine Neoplasia type 1 (MEN1) gene is expressed ubiquitously and is predominantly localized in the nucleus. It has been shown to interact with numerous proteins and is, therefore, involved in a variety of cellular processes. The best understood function of menin is its role as an oncogenic cofactor of MLL fusion proteins. Menin interacts with two motifs within the N-terminal fragment of MLL that is retained in all fusion proteins, MBM1 (menin-binding motif 1) and MBM2 (Thiel et al., Bioessays 2012. 34, 771-80). Menin/MLL interaction leads to the formation of a new interaction surface for lens epithelium-derived growth factor (LEDGF). Although MLL directly binds to LEDGF, menin is obligatory for the stable interaction between MLL and LEDGF and the gene specific chromatin recruitment of the MLL complex via the PWWP domain of LEDGF (Cermakova et al., Cancer Res 2014. 15, 5139-51; Yokoyama & Cleary, Cancer Cell 2008. 8, 36-46). Furthermore, numerous genetic studies have shown that menin is strictly required for oncogenic transformation by MLL fusion proteins suggesting the menin/MLL interaction as an attractive therapeutic target. For example, conditional deletion of Men1 prevents leukomogenesis in bone marrow progenitor cells ectopically expressing MLL fusions (Chen et al., Proc Natl Acad Sci 2006. 103, 1018-23). Similarly, genetic disruption of menin/MLL fusion interaction by loss-of-function mutations abrogates the oncogenic properties of the MLL fusion proteins, blocks the development of leukemia in vivo and releases the differentiation block of MLL-transformed leukemic blasts. These studies also showed that menin is required for the maintenance of HOX gene expression by MLL fusion proteins (Yokoyama et al., Cell 2005. 123, 207-18). In addition, small molecule inhibitors of menin/MLL interaction have been developed suggesting druggability of this protein/protein interaction and have also demonstrated efficacy in preclinical models of AML (Borkin et al., Cancer Cell 2015. 27, 589-602; Cierpicki and Grembecka, Future Med Chem 2014. 6, 447-462). Together with the observation that menin is not a requisite cofactor of MLL1 during normal hematopoiesis (Li et al., Blood 2013. 122, 2039-2046), these data validate the disruption of menin/MLL interaction as a promising new therapeutic approach for the treatment of MLL rearranged leukemia and other cancers with an active HOX/MEIS1 gene signature. For example, an internal partial tandem duplication (PTD) within the 5'region of the MLL gene represents another major aberration that is found predominantly in de novo and secondary AML as well as myeloid dysplasia syndromes. Although the molecular mechanism and the biological function of MLL-PTD is not well understood, new therapeutic targeting strategies affecting the menin/MLL interaction might also prove effective in the treatment of MLL-PTD-related leukemias. Furthermore, castration-resistant prostate cancer has been shown to be dependent on the menin/MLL interaction (Malik et al., Nat Med 2015. 21, 344-52).

MLL protein is also known as Histone-lysine N-methyltransferase 2A (KMT2A) protein in the scientific field (UniProt Accession #Q03164).

Several references describe inhibitors targeting the menin-MLL interaction: WO2011029054, J Med Chem 2016, 59, 892-913 describe the preparation of thienopyrimidine and benzodiazepine derivatives: WO2014164543 describes thienopyrimidine and thienopyridine derivatives; *Nature Chemical Biology March* 2012, 8, 277-284 and Ren, J.; et al. *Bioorg Med Chem Lett* (2016), 26(18), 4472-4476 describe thienopyrimidine derivatives; *J Med Chem* 2014, 57, 1543-1556 describes hydroxy- and aminomethylpiperidine derivatives; *Future Med Chem* 2014, 6, 447-462 reviews small molecule and peptidomimetic compounds; WO2016195776 describes furo[2,3-d]pyrimidine, 9H-purine, [1,3]oxazolo[5,4-d]pyrimidine, [1,3]oxazolo[4,5-d]pyrimidine, [1,3]thiazolo[5,4-d]pyrimidine, thieno[2,3-b]pyridine and thieno[2,3-d]pyrimidine derivatives; WO2016197027 describes 5,6,7,8-tetrahydropyrido[3,4-d] pyrimidine, 5,6,7,8-tetrahydropyrido[4,3-d]pyrimidine, pyrido[2,3-d]pyrimidine and quinoline derivatives; and WO2016040330 describes thienopyrimidine and thienopyridine compounds. WO2017192543 describes piperidines as Menin inhibitors. WO2017112768, WO2017207387, WO2017214367, WO2018053267 and WO2018024602 describe inhibitors of the menin-MLL interaction. WO2017161002 and WO2017161028 describe inhibitors of menin-MLL. WO2018050686, WO2018050684 and WO2018109088 describe inhibitors of the menin-MLL interaction. WO2018226976 describes methods and compositions for inhibiting the interaction of menin with MLL proteins. WO2018175746 provides methods of treatment for hematological malignancies and Ewing's sarcoma. WO2018106818 and WO2018106820 provide methods of promoting proliferation of a pancreatic cell. WO2018153312 discloses azaspiro compounds relating to the field of medicinal chemistry. WO2017132398 discloses methods comprising contacting a leukemia cell exhibiting an NPM1 mutation with a pharmacologic inhibitor of interaction between MLL and Menin. WO2019060365 describes substituted inhibitors of menin-MLL. WO2020069027 describes the treatment of hematological malignancies with inhibitors of menin. Krivtsov et al., Cancer Cell 2019. No. 6 Vol. 36, 660-673 describes a menin-MLL inhibitor.

DESCRIPTION OF THE INVENTION

Figure 1:
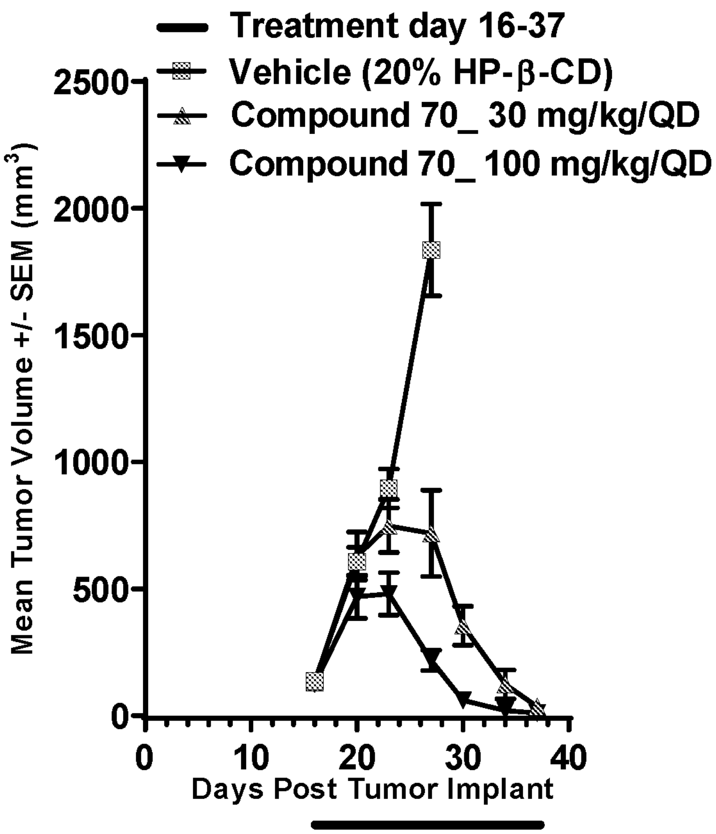
FIG. 1: Efficacy study in Molm-14 subcutaneous (sc) model.

The present invention concerns novel compounds of Formula (I), (I)

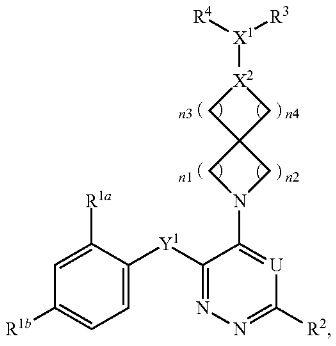

and the tautomers and the stereoisomeric forms thereof, wherein $R^{1a}$ represents —C(═O)—$NR^{xa}R^{xb}$; Het; or

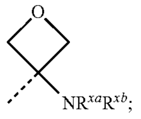

Het represents a 5- or 6-membered monocyclic aromatic ring containing one, two or three nitrogen atoms and optionally a carbonyl moiety;

wherein said 5- or 6-membered monocyclic aromatic ring is optionally substituted with one or two substituents selected from the group consisting of $C_{3-6}$cycloalkyl and $C_{1-4}$alkyl;

$R^{xa}$ and $R^{xb}$ are each independently selected from the group consisting of hydrogen, $C_{1-4}$alkyl and $C_{3-6}$cycloalkyl;

$R^{1b}$ represents F or Cl;

$Y^1$ represents —$CR^{5a}R^{5b}$—, —O— or —NR—;

$R^2$ is selected from the group consisting of hydrogen, halo, $C_{1-4}$alkyl, —O—$C_{1-4}$alkyl, and —$NR^{7a}R^{7b}$;

U represents N or CH;

n1, n2, n3 and n4 are each independently selected from 1 and 2;

$X^1$ represents CH, and $X^2$ represents N;

$R^4$ represents isopropyl;

$R^{5a}$, $R^{5b}$, $R^{5c}$, $R^{7a}$, and $R^{7b}$, are each independently selected from the group consisting of hydrogen, $C_{1-4}$alkyl and $C_{3-6}$cycloalkyl;

$R^3$ represents —$C_{1-6}$alkyl-$NR^{8a}R^{8b}$, —$C_{1-6}$alkyl-C(═O)—$NR^{9a}R^{9b}$, —$C_{1-6}$alkyl-OH, or —$C_{1-6}$alkyl-$NR^{11}$—C(═O)—O—$C_{1-4}$alkyl-O—C(═O)—$C_{1-4}$alkyl;

wherein each of the $C_{1-4}$alkyl or $C_{1-4}$alkyl moieties in the $R^3$ definitions independently of each other may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; —C(═O)—$C_{1-4}$alkyl; —C(═O)—O—$C_{1-4}$alkyl; —C(═O)—$NR^{12a}R^{12b}$; and $C_{1-4}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—$NR^{10a}R^{10b}$, and —$NR^{10c}$—C(═O)—$C_{1-4}$alkyl;

$R^{9a}$, $R^{9b}$, $R^{10a}$, $R^{10b}$, $R^{10c}$, $R^{11}$, $R^{12a}$, and $R^{12b}$ are each independently selected from the group consisting of hydrogen and $C_{1-6}$alkyl;

and the pharmaceutically acceptable salts and the solvates thereof.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, including but not limited to leukemia, myelodysplastic syndrome (MDS), and myeloproliferative neoplasms (MPN); and diabetes.

In a particular embodiment, the invention relates to a compound of Formula (I), a pharmaceutically acceptable salt, or a solvate thereof, for use in the treatment or in the prevention of cancer.

In a specific embodiment said cancer is selected from leukemias, lymphomas, myelomas or solid tumor cancers (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

In particular, compounds according to the present invention and the pharmaceutical compositions thereof may be useful in the treatment or prevention of leukemias, in particular nucleophosmin (NPM1)-mutated leukemias, e.g. NPM1c.

In an embodiment, compounds of Formula (I) and the pharmaceutically acceptable salts, and the solvates thereof, may have improved metabolic stability properties.

In an embodiment, compounds of Formula (I) and the pharmaceutically acceptable salts, and the solvates thereof, may have extended in vivo half-life (T1/2).

In an embodiment, compounds of Formula (I) and the pharmaceutically acceptable salts, and the solvates thereof, may have improved oral bioavailability.

In an embodiment, compounds of Formula (I) and the pharmaceutically acceptable salts, and the solvates thereof, may reduce tumor growth e.g., tumours harbouring MLL (KMT2A) gene rearrangements/alterations and/or NPM1 mutations.

In an embodiment, compounds of Formula (I) and the pharmaceutically acceptable salts, and the solvates thereof, may have improved PD properties in vivo during a prolonged period of time, e.g. inhibition of target gene expression such as MEIS1 and upregulation of differentiation marker over a period of at least 16 hours.

In an embodiment, compounds of Formula (I) and the pharmaceutically acceptable salts, and the solvates thereof, may have an improved safety profile (e.g. reduced hERG inhibition; improved cardiovascular safety).

In an embodiment, compounds of Formula (I) and the pharmaceutically acceptable salts, and the solvates thereof, may be suitable for Q.D. dosing (once daily).

The invention also relates to the use of a compound of Formula (I), a pharmaceutically acceptable salt, or a solvate thereof, in combination with an additional pharmaceutical agent for use in the treatment or prevention of cancer, including but not limited to leukemia, myelodysplastic syndrome (MDS), and myeloproliferative neoplasms (MPN); and diabetes.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof.

The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, including but not limited to leukemia, myelodysplastic syndrome (MDS), and myeloproliferative neoplasms (MPN); and diabetes.

Additionally, the invention relates to a method of treating or preventing a cell proliferative disease in a warm-blooded animal which comprises administering to the said animal an effective amount of a compound of Formula (I), a pharmaceutically acceptable salt, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-4}$alkyl group contains from 1 to 6 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

Similar, the term '$C_{1-6}$alkyl' as used herein as a group or part of a group represents a straight or branched chain saturated hydrocarbon radical having from 1 to 6 carbon atoms, such as methyl, ethyl, n-propyl, isopropyl, n-butyl, s-butyl, t-butyl, n-pentyl, n-hexyl and the like.

The term '$C_{3-6}$cycloalkyl' as used herein as a group or part of a group defines a saturated, cyclic hydrocarbon radical having from 3 to 6 carbon atoms, such as cyclopropyl, cyclobutyl, cyclopentyl and cyclohexyl.

It will be clear for the skilled person that $S(=O)_2$ or $SO_2$ represents a sulfonyl moiety.

It will be clear for the skilled person that CO or C(=O) represents a carbonyl moiety.

It will be clear for the skilled person that a group such as —CRR— represents

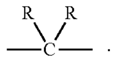

An example of such a group is $—CR^{5a}R^{5b}—$.

It will be clear for the skilled person that a group such as —NR— represents

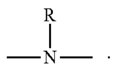

An example of such a group is $—NR^{5c}—$.

Non-limiting examples of 'monocyclic 5- or 6-membered aromatic rings containing one, two or three nitrogen atoms and optionally a carbonyl moiety', include, but are not limited to pyrazolyl, imidazolyl, pyridinyl, pyridazinyl, pyrimidinyl, pyrazinyl, triazinyl or 1,2-dihydro-2-oxo-4-pyridinyl.

The skilled person will understand that a 5- or 6-membered monocyclic aromatic ring containing one, two or three nitrogen atoms and a carbonyl moiety includes, but is not limited to

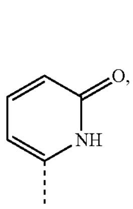 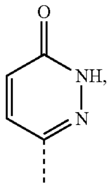 and 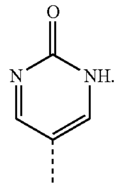

When any variable occurs more than one time in any constituent, each definition is independent.

When any variable occurs more than one time in any formula (e.g. Formula (I)), each definition is independent.

In general, whenever the term 'substituted' is used in the present invention, it is meant, unless otherwise indicated or clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using 'substituted' are replaced with a selection from the indicated group, provided that the normal valency is not exceeded, and that the substitution results in a chemically stable compound, i.e. a compound that is sufficiently robust to survive isolation to a useful degree of purity from a reaction mixture (isolation after a reaction e.g. purification by silica gel chromatography). In a particular embodiment, when the number of substituents is not explicitly specified, the number of substituents is one.

Combinations of substituents and/or variables are permissible only if such combinations result in chemically stable compounds. 'Stable compound' is in this context meant to indicate a compound that is sufficiently robust to survive isolation to a useful degree of purity from a reaction mixture (isolation after a reaction e.g. purification by silica gel chromatography).

The skilled person will understand that the term 'optionally substituted' means that the atom or radical indicated in the expression using 'optionally substituted' may or may not be substituted (this means substituted or unsubstituted respectively).

When two or more substituents are present on a moiety they may, where possible and unless otherwise indicated or clear from the context, replace hydrogens on the same atom or they may replace hydrogen atoms on different atoms in the moiety.

Within the context of this invention 'saturated' means 'fully saturated', if not otherwise specified.

Unless otherwise specified or clear from the context, aromatic rings groups, can be attached to the remainder of the molecule of Formula (I) through any available ring carbon atom (C-linked) or nitrogen atom (N-linked).

Unless otherwise specified or clear from the context, aromatic rings groups, may optionally be substituted, where possible, on carbon and/or nitrogen atoms according to the embodiments.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically acceptable salts include acid addition salts and base addition salts. Such salts may be formed by conventional means, for example by reaction of a free acid or a free base form with one or more equivalents of an appropriate base or acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable salts as mentioned hereinabove or hereinafter are meant to comprise the therapeutically active non-toxic acid and base salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine salt forms by treatment with appropriate organic and inorganic bases.

Appropriate base salt forms comprise, for example, the ammonium salts, the alkali and earth alkaline metal salts, e.g. the lithium, sodium, potassium, cesium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term "prodrug" includes any compound that, following oral or parenteral administration, in particular oral administration, is metabolised in vivo to a (more) active form in an experimentally-detectable amount, and within a predetermined time (e.g. within a dosing interval of between 0.5 and 24 hours, or e.g. within a dosing interval of between 6 and 24 hours (i.e. once to four times daily)). For the avoidance of doubt, the term "parenteral" administration includes all forms of administration other than oral administration, in particular intravenous (IV), intramuscular (IM), and subcutaneous (SC) injection.

Prodrugs may be prepared by modifying functional groups present on a compound in such a way that the modifications are cleaved in vivo when such prodrug is administered to a mammalian subject. The modifications typically are achieved by synthesising the parent compound with a prodrug substituent. In general, prodrugs include compounds wherein a hydroxyl, amino, sulfhydryl, carboxy or carbonyl group is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The term "enantiomerically pure" as used herein means that the product contains at least 80% by weight of one enantiomer and 20% by weight or less of the other enantiomer. Preferably the product contains at least 90% by weight of one enantiomer and 10% by weight or less of the other enantiomer. In the most preferred embodiment the term "enantiomerically pure" means that the composition contains at least 99% by weight of one enantiomer and 1% or less of the other enantiomer.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the isotope is selected from the group of $^{2}H$, $^{3}H$, $^{11}C$, $^{13}C$ and $^{18}F$. Preferably, the isotope is selected from the group of $^{2}H$, $^{3}H$, $^{11}C$ and $^{18}F$. More preferably, the isotope is $^{2}H$, $^{3}H$ or $^{13}C$. More preferably, the isotope is $^{2}H$ or $^{13}C$. More preferably, the isotope is $^{2}H$. In particular, deuterated compounds and $^{13}C$-enriched compounds are intended to be included within the scope of the present invention. In particular, deuterated compounds are intended to be included within the scope of the present invention.

Certain isotopically-labeled compounds of the present invention (e.g., those labeled with $^{3}H$ and $^{14}C$) may be useful for example in substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies. PET imaging in cancer finds utility in helping locate and identify tumours, stage the disease and determine suitable treatment. Human cancer cells overexpress many receptors or proteins that are potential disease-specific molecular targets. Radiolabelled tracers that bind with high affinity and specificity to such receptors or proteins on tumour cells have great potential for diagnostic imaging and targeted radionuclide therapy (Charron, Carlie L. et al. Tetrahedron Lett. 2016, 57(37), 4119-4127). Additionally, target-specific PET radiotracers may be used as biomarkers to examine and evaluate pathology, by for example, measuring target expression and treatment response (Austin R. et al. Cancer Letters (2016), doi: 10.1016/j.canlet.2016.05.008).

The present invention relates in particular to compounds of Formula (I) as defined herein, and the tautomers and the stereoisomeric forms thereof, wherein $R^{1a}$ represents —C(=O)—$NR^{xa}R^{xb}$; Het; or

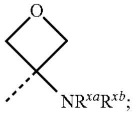

Het represents a 5- or 6-membered monocyclic aromatic ring containing one, two or three nitrogen atoms and optionally a carbonyl moiety;

wherein said 5- or 6-membered monocyclic aromatic ring is optionally substituted with one or two substituents selected from the group consisting of $C_{3-6}$cycloalkyl and $C_{1-4}$alkyl;

$R^{xa}$ and $R^{xb}$ are each independently selected from the group consisting of hydrogen, $C_{1-4}$alkyl and $C_{3-6}$cycloalkyl;

$R^{1b}$ represents F or Cl;

$Y^1$ represents —$CR^{5a}R^{5b}$—, —O— or —$NR^{5c}$—;

$R^2$ is selected from the group consisting of hydrogen, halo, $C_{1-4}$alkyl, —O—$C_{1-4}$alkyl, and —$NR^{7a}R^{7b}$;

U represents N or CH;

n1, n2, n3 and n4 are each independently selected from 1 and 2;

$X^1$ represents CH, and $X^2$ represents N;

$R^4$ represents isopropyl;

$R^{5a}$, $R^{5b}$, $R^{5c}$, $R^{7a}$, and $R^{7b}$, are each independently selected from the group consisting of hydrogen, $C_{1-4}$alkyl and $C_{3-6}$cycloalkyl;

$R^3$ represents —$C_{1-6}$alkyl-$NR^{8a}R^{8b}$, —$C_{1-6}$alkyl-C(=O)—$NR^{9a}R^{9b}$, —$C_{1-6}$alkyl-OH, or —$C_{1-6}$alkyl-$NR^{11}$—C(=O)—O—$C_{1-4}$alkyl-O—C(=O)—$C_{1-4}$alkyl;

wherein each of the $C_{1-4}$alkyl or $C_{1-4}$alkyl moieties in the $R^3$ definitions independently of each other may be substituted with one, two or three substituents each independently selected from the group consisting of cyano, halo or —O—$C_{1-4}$alkyl;

$R^{8a}$ and $R^{8b}$ are each independently selected from the group consisting of hydrogen; $C_{1-6}$alkyl; —C(=O)—$C_{1-4}$alkyl; —C(=O)—O—$C_{1-4}$alkyl; —C(=O)—$NR^{12a}R^{12b}$; and $C_{1-6}$alkyl substituted with one, two or three substituents each independently selected from the group consisting of cyano, halo, —$S(=O)_2$—$C_{1-4}$alkyl, —O—$C_{1-4}$alkyl, and —C=O)—$NR^{10a}R^{10b}$;

$R^{9a}$, $R^{9b}$, $R^{10a}$, $R^{10b}$, $R^{11}$, $R^{12a}$, and $R^{12b}$ are each independently selected from the group consisting of hydrogen and $C_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(=O)—$NR^{xa}R^{xb}$; Het; or

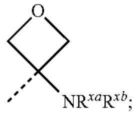

Het represents a 5- or 6-membered monocyclic aromatic ring containing one, two or three nitrogen atoms and optionally a carbonyl moiety;

wherein said 5- or 6-membered monocyclic aromatic ring is optionally substituted with one or two substituents selected from the group consisting of $C_{3-6}$cycloalkyl and $C_{1-4}$alkyl;

$R^{xa}$ and $R^{xb}$ are each independently selected from the group consisting of hydrogen, $C_{1-4}$alkyl and $C_{3-6}$cycloalkyl;

$R^{1b}$ represents F or Cl;

$Y^1$ represents —$CR^{5a}R^{5b}$—, —O— or —$NR^{5c}$—;

$R^2$ is selected from the group consisting of hydrogen, halo, $C_{1-4}$alkyl, —O—$C_{1-4}$alkyl, and —$NR^{7a}R^{7b}$;

U represents N or CH;

n1, n2, n3 and n4 are each independently selected from 1 and 2;

$X^1$ represents CH, and $X^2$ represents N;

$R^4$ represents isopropyl;

$R^{5a}$, $R^{5b}$, $R^{5c}$, $R^{7a}$, and $R^{7b}$, are each independently selected from the group consisting of hydrogen, $C_{1-4}$alkyl and $C_{3-6}$cycloalkyl;

$R^3$ represents —$C_{1-6}$alkyl-$NR^{8a}R^{8b}$;

wherein the $C_{1-4}$alkyl moiety in the $R^3$ definition may be substituted with one, two or three substituents each independently selected from the group consisting of cyano, halo, OH, and —O—$C_{1-4}$alkyl;

$R^{8a}$ and $R^{8b}$ are each independently selected from the group consisting of hydrogen; $C_{1-4}$alkyl; and $C_{1-4}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—NR$^{10a}$R$^{10b}$, and —NR$^{10c}$—C(═O)—$C_{1-4}$alkyl;

R$^{10a}$, R$^{10b}$, R$^{10c}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein R$^{1a}$ represents —C(═O)—NR$^{xa}$R$^{xb}$; Het; or

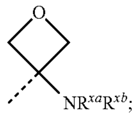

Het represents a 5- or 6-membered monocyclic aromatic ring containing one, two or three nitrogen atoms and optionally a carbonyl moiety;

wherein said 5- or 6-membered monocyclic aromatic ring is optionally substituted with one or two substituents selected from the group consisting of $C_{3-6}$cycloalkyl and $C_{1-4}$alkyl;

R$^{xa}$ and R$^{xb}$ are each independently selected from the group consisting of hydrogen, $C_{1-4}$alkyl and $C_{3-6}$cycloalkyl;

R$^{1b}$ represents F or Cl;

Y$^1$ represents —CR$^{5a}$R$^{5b}$—, —O— or —NR$^{5c}$—;

R$^2$ is selected from the group consisting of hydrogen, halo, $C_{1-4}$alkyl, —O—$C_{1-4}$alkyl, and —NR$^{7a}$R$^{7b}$;

U represents N or CH;

n1, n2, n3 and n4 are each independently selected from 1 and 2;

X$^1$ represents CH, and X$^2$ represents N;

R$^4$ represents isopropyl;

R$^{5a}$, R$^{5b}$, R$^{5c}$, R$^{7a}$, and R$^{7b}$, are each independently selected from the group consisting of hydrogen, $C_{1-4}$alkyl and $C_{3-6}$cycloalkyl;

R$^3$ represents —$C_{1-6}$alkyl-NR$^{8a}$R$^{8b}$;

wherein the $C_{1-4}$alkyl moiety in the R$^3$ definition may be substituted with one, two or three substituents each independently selected from the group consisting of cyano, halo and —O—$C_{1-4}$alkyl;

R$^{8a}$ and R$^{8b}$ are each independently selected from the group consisting of hydrogen; $C_{1-4}$alkyl; and $C_{1-4}$alkyl substituted with one, two or three substituents each independently selected from the group consisting of cyano, halo, —S(═O)$_2$—$C_{1-4}$alkyl, —O—$C_{1-4}$alkyl, and —C(═O)—NR$^{10a}$R$^{10b}$;

R$^{10a}$ and R$^{10b}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein R$^{1a}$ represents —C(═O)—NR$^{xa}$R$^{xb}$ or Het;

Het represents a 6-membered monocyclic aromatic ring containing two nitrogen atoms;

wherein said 6-membered monocyclic aromatic ring is substituted with one $C_{3-6}$cycloalkyl;

R$^{xa}$ and R$^{xb}$ represent $C_{1-4}$alkyl;

R$^{1b}$ represents F;

Y$^1$ represents —O—;

R$^2$ represents hydrogen;

U represents N or CH;

n1, n2, n3 and n4 are each independently selected from 1 and 2;

X$^1$ represents CH, and X$^2$ represents N;

R$^4$ represents isopropyl;

R$^3$ represents —$C_{1-6}$alkyl-NR$^{8a}$R$^{8b}$, —$C_{1-6}$alkyl-C(═O)—NR$^{9a}$R$^{9b}$, —$C_{1-6}$alkyl-OH, or —$C_{1-6}$alkyl-NR$^{11}$—C(═O)—O—$C_{1-4}$alkyl-O—C(═O)—$C_{1-4}$alkyl; wherein each of the $C_{1-4}$alkyl or $C_{1-4}$alkyl moieties in the R$^3$ definitions independently of each other may be substituted with one, two or three substituents each independently selected from the group consisting of —OH and —O—$C_{1-4}$alkyl;

R$^{8a}$ and R$^{8b}$ are each independently selected from the group consisting of hydrogen; $C_{1-4}$alkyl; —C(═O)—$C_{1-4}$alkyl; —C(═O)—O—$C_{1-4}$alkyl; —C(═O)—NR$^{12a}$R$^{12b}$; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—NR$^{10a}$R$^{10b}$, and —NR$^{10c}$—C(═O)—$C_{1-4}$alkyl;

R$^{9a}$, R$^{9b}$, R$^{10a}$, R$^{10b}$, R$^{10c}$, R$^{11}$, R$^{12a}$, and R$^{12b}$ are each independently selected from the group consisting of hydrogen and $C_{1-4}$alkyl;

and the pharmaceutically acceptable salts and the solvates thereof.

The present invention relates in particular to compounds of Formula (I) as defined herein, and the tautomers and the stereoisomeric forms thereof, wherein R$^{1a}$ represents —C(═O)—NR$^{xa}$R$^{xb}$ or Het;

Het represents a 6-membered monocyclic aromatic ring containing two nitrogen atoms;

wherein said 6-membered monocyclic aromatic ring is substituted with one $C_{3-6}$cycloalkyl;

R$^{xa}$ and R$^{xb}$ represent $C_{1-4}$alkyl;

R$^{1b}$ represents F;

Y$^1$ represents —O—;

R$^2$ represents hydrogen;

U represents N or CH;

n1, n2, n3 and n4 are each independently selected from 1 and 2;

X$^1$ represents CH, and X$^2$ represents N;

R$^4$ represents isopropyl;

R$^3$ represents —$C_{1-6}$alkyl-NR$^{8a}$R$^{8b}$;

wherein the $C_{1-6}$alkyl moiety in the R$^3$ definition may be substituted with one, two or three substituents each independently selected from the group consisting of —OH and —O—$C_{1-4}$alkyl;

R$^{8a}$ and R$^{8b}$ are each independently selected from the group consisting of hydrogen; $C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—NR$^{10a}$R$^{10b}$, and —NR$^{10c}$—C(═O)—$C_{1-4}$alkyl;

R$^{10a}$, R$^{10b}$, and R$^{10c}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;
$R^{xa}$ and $R^{xb}$ represent $C_{1-4}$alkyl;
$R^{1b}$ represents F;
$Y^1$ represents —O—;
$R^2$ represents hydrogen;
U represents N or CH;
n1, n2, n3 and n4 are each independently selected from 1 and 2;
$X^1$ represents CH, and $X^2$ represents N;
$R^4$ represents isopropyl;
$R^3$ represents —$C_{1-4}$alkyl-$NR^{8a}R^{8b}$;
wherein the $C_{1-6}$alkyl moiety in the $R^3$ definition may be substituted with one, two or three substituents each independently selected from the group consisting of —OH and —O—$C_{1-4}$alkyl;
$R^{8a}$ and $R^{8b}$ are each independently selected from the group consisting of hydrogen; $C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—$NR^{10a}R^{10b}$, and —$NR^{10c}$—C(═O)—$C_{1-4}$alkyl;
$R^{10a}$, $R^{10b}$, and $R^{10c}$ are each independently selected from the group consisting of hydrogen and $C_{1-4}$alkyl;
and the pharmaceutically acceptable salts and the solvates thereof.

The present invention relates in particular to compounds of Formula (I) as defined herein, and the tautomers and the stereoisomeric forms thereof, wherein
$R^{1a}$ represents —C(═O)—$NR^{xa}R^{xb}$ or Het;
Het represents pyrimidinyl substituted with one $C_{3-6}$cycloalkyl;
$R^{xa}$ and $R^{xb}$ represent $C_{1-4}$alkyl;
$R^{1b}$ represents F;
$Y^1$ represents —O—;
$R^2$ represents hydrogen;
U represents N;
n1, n2, n3 and n4 are each independently selected from 1 and 2;
$X^1$ represents CH, and $X^2$ represents N;
$R^4$ represents isopropyl;
$R^3$ represents —$C_{1-6}$alkyl-$NR^{8a}R^{8b}$;
wherein the $C_{1-6}$alkyl moiety in the $R^3$ definition may be substituted with one —OH;
$R^{8a}$ and $R^{8b}$ are each independently selected from the group consisting of hydrogen; $C_{1-4}$alkyl; and $C_{1-4}$alkyl substituted with one or two substituents each independently selected from the group consisting of halo, —O—$C_{1-4}$alkyl, and —$NR^{10c}$—C(═O)—$C_{1-4}$alkyl;
$R^{10a}$, $R^{10b}$, and $R^{10c}$ are each independently selected from the group consisting of hydrogen and $C_{1-4}$alkyl;
and the pharmaceutically acceptable salts and the solvates thereof.

The present invention relates in particular to compounds of Formula (I) as defined herein, and the tautomers and the stereoisomeric forms thereof, wherein
$R^{1a}$ represents —C(═O)—$NR^{xa}R^{xb}$ or Het;
Het represents pyrimidinyl substituted with one $C_{3-6}$cycloalkyl;
$R^{xa}$ and $R^{xb}$ represent $C_{1-4}$alkyl;
$R^{1b}$ represents F;
$Y^1$ represents —O—;
$R^2$ represents hydrogen;
U represents N;
n2 is 2;
n1, n3 and n4 are 1;
$X^1$ represents CH, and $X^2$ represents N;
$R^4$ represents isopropyl;
$R^3$ represents —$C_{1-6}$alkyl-$NR^{8a}R^{8b}$;
wherein the $C_{1-4}$alkyl moiety in the $R^3$ definition may be substituted with one —OH;
$R^{8a}$ and $R^{8b}$ are each independently selected from the group consisting of hydrogen; $C_{1-6}$alkyl; and $C_{1-6}$alkyl substituted with one or two substituents each independently selected from the group consisting of halo, —O—$C_{1-4}$alkyl, and —$NR^{10c}$—C(═O)—$C_{1-4}$alkyl;
$R^{10a}$, $R^{10b}$, and $R^{10c}$ are each independently selected from the group consisting of hydrogen and $C_{1-6}$alkyl;
and the pharmaceutically acceptable salts and the solvates thereof.

The present invention relates in particular to compounds of Formula (I) as defined herein, and the tautomers and the stereoisomeric forms thereof, wherein
$R^{1a}$ represents —C(═O)—$NR^{xa}R^{xb}$;
$R^{xa}$ and $R^{xb}$ represent $C_{1-4}$alkyl;
$R^{1b}$ represents F;
$Y^1$ represents —O—;
$R^2$ represents hydrogen;
U represents N;
n2 is 2;
n1, n3 and n4 are 1;
$X^1$ represents CH, and $X^2$ represents N;
$R^4$ represents isopropyl;
$R^3$ represents —$C_{1-6}$alkyl-$NR^{8a}R^{8b}$;
$R^{8a}$ and $R^{8b}$ are each independently selected from the group consisting of hydrogen; $C_{1-6}$alkyl; and $C_{1-6}$alkyl substituted with one or two substituents each independently selected from the group consisting of halo, —O—$C_{1-4}$alkyl, and —$NR^{10c}$—C(═O)—$C_{1-4}$alkyl;
$R^{10a}$, $R^{10b}$, and $R^{10c}$ are each independently selected from the group consisting of hydrogen and $C_{1-6}$alkyl;
and the pharmaceutically acceptable salts and the solvates thereof.

The present invention relates in particular to compounds of Formula (I) as defined herein, and the tautomers and the stereoisomeric forms thereof, wherein
$R^{1a}$ represents —C(═O)—$NR^{xa}R^{xb}$;
$R^{xa}$ and $R^{xb}$ represent $C_{1-4}$alkyl;
$R^{1b}$ represents F;
$Y^1$ represents —O—;
$R^2$ represents hydrogen;
U represents N;
n2 is 2;
n1, n3 and n4 are 1;
$X^1$ represents CH, and $X^2$ represents N;
$R^4$ represents isopropyl;
$R^3$ represents —$CH_2$—$CH_2$—$CH_2$—$NR^{8a}R^{8b}$;
$R^{8a}$ and $R^{8b}$ are each independently selected from the group consisting of hydrogen; $C_{1-6}$alkyl; and $C_{1-6}$alkyl substituted with one or two substituents each independently selected from the group consisting of halo, —O—$C_{1-4}$alkyl, and —$NR^{10c}$—C(═O)—$C_{1-4}$alkyl;
$R^{10a}$, $R^{10b}$, and $R^{10c}$ are each independently selected from the group consisting of hydrogen and $C_{1-6}$alkyl;
and the pharmaceutically acceptable salts and the solvates thereof.

The present invention relates in particular to compounds of Formula (I) as defined herein, and the tautomers and the stereoisomeric forms thereof, wherein
$R^{1a}$ represents —C(═O)—$NR^{xa}R^{xb}$;
$R^{xa}$ and $R^{xb}$ represent $C_{1-4}$alkyl;
$R^{1b}$ represents F;
$Y^1$ represents —O—;
$R^2$ represents hydrogen;
U represents N;

n1, n2, n3 and n4 are each independently selected from 1 and 2;

$X^1$ represents CH, and $X^2$ represents N;

$R^4$ represents isopropyl;

$R^3$ represents —$C_{1-4}$alkyl-$NR^{8a}R^{8b}$;

$R^{8a}$ and $R^{8b}$ are each independently selected from the group consisting of hydrogen; $C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, and —C(═O)—$NR^{10a}R^{10b}$;

$R^{10a}$ and $R^{10b}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;

$R^{xa}$ and $R^{xb}$ represent $C_{1-4}$alkyl;

$R^{1b}$ represents F;

$Y^1$ represents —O—;

$R^2$ represents hydrogen;

U represents N;

n1, n2, n3 and n4 are each independently selected from 1 and 2;

$X^1$ represents CH, and $X^2$ represents N;

$R^4$ represents isopropyl;

$R^3$ represents —$CH_2$—$CH_2$—$CH_2$—$NR^{8a}R^{8b}$;

$R^{8a}$ and $R^{8b}$ are each independently selected from the group consisting of hydrogen; $C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, and —C(═O)—$NR^{10a}R^{10b}$;

$R^{10a}$ and $R^{10b}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;

$R^{xa}$ and $R^{xb}$ represent hydrogen or $C_{1-4}$alkyl;

$R^{1b}$ represents F;

$Y^1$ represents —O—;

$R^2$ represents hydrogen;

U represents N;

n1, n2, n3 and n4 are each independently selected from 1 and 2;

$X^1$ represents CH, and $X^2$ represents N;

$R^4$ represents isopropyl;

$R^3$ represents —$CH_2$—$CH_2$—$CH_2$—$NR^{8a}R^{8b}$;

$R^{8a}$ and $R^{8b}$ are each independently selected from the group consisting of hydrogen; $C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, and —C(═O)—$NR^{10a}R^{10b}$;

$R^{10a}$ and $R^{10b}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;

$R^{xa}$ and $R^{xb}$ represent hydrogen or $C_{1-4}$alkyl;

$R^{1b}$ represents F;

$Y^1$ represents —O—;

$R^2$ represents hydrogen;

U represents N;

n1, n2, n3 and n4 are each independently selected from 1 and 2;

$X^1$ represents CH, and $X^2$ represents N;

$R^4$ represents isopropyl;

$R^3$ represents —$CH_2$—$CH_2$—$CH_2$—$NR^{8a}R^{8b}$;

$R^{8a}$ and $R^{8b}$ are each independently selected from the group consisting of hydrogen; $C_{1-6}$alkyl; and $C_{1-6}$alkyl substituted with one, two or three substituents each independently selected from the group consisting of —OH and —O—$C_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;

$R^{xa}$ and $R^{xb}$ represent $C_{1-4}$alkyl;

$R^{1b}$ represents F;

$Y^1$ represents —O—;

$R^2$ represents hydrogen;

U represents N;

n1, n2, n3 and n4 are each independently selected from 1 and 2;

$X^1$ represents CH, and $X^2$ represents N;

$R^4$ represents isopropyl;

$R^3$ represents —$C_{1-4}$alkyl-$NR^{8a}R^{8b}$;

$R^{8a}$ and $R^{8b}$ are each independently selected from the group consisting of $C_{1-6}$alkyl; and $C_{1-6}$alkyl substituted with one —O—$C_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;

$R^{xa}$ and $R^{xb}$ represent $C_{1-4}$alkyl;

$R^{1b}$ represents F;

$Y^1$ represents —O—;

$R^2$ represents hydrogen;

U represents N;

n1, n2, n3 and n4 are each independently selected from 1 and 2;

$X^1$ represents CH, and $X^2$ represents N;

$R^4$ represents isopropyl;

$R^3$ represents —$CH_2$—$CH_2$—$CH_2$—$NR^{8a}R^{8b}$;

$R^{8a}$ and $R^{8b}$ are each independently selected from the group consisting of $C_{1-6}$alkyl; and $C_{1-6}$alkyl substituted with one —O—$C_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$; or Het;

Het represents a 6-membered monocyclic aromatic ring containing two nitrogen atoms;

wherein said 6-membered monocyclic aromatic ring is optionally substituted with one $C_{3-6}$cycloalkyl;

$R^{xa}$ and $R^{xb}$ represent $C_{1-4}$alkyl;

$R^{1b}$ represents F;

$Y^1$ represents —O—;

$R^2$ is hydrogen;

U represents N;

n1, n2, n3 and n4 are each independently selected from 1 and 2;

$X^1$ represents CH, and $X^2$ represents N;

$R^4$ represents isopropyl;

$R^3$ represents —$C_{1-6}$alkyl-$NR^{8a}R^{8b}$, —$C_{1-6}$alkyl-C(═O)—$NR^{9a}R^{9b}$, —$C_{1-6}$alkyl-OH, or —$C_{1-6}$alkyl-$NR^{11}$—C(═O)—O—$C_{1-4}$alkyl-O—C(═O)—$C_{1-4}$alkyl;

$R^{8a}$ and $R^{8b}$ are each independently selected from the group consisting of hydrogen; $C_{1-4}$alkyl; —C(═O)—$C_{1-4}$alkyl; —C(═O)—O—$C_{1-4}$alkyl; —C(═O)—$NR^{12a}R^{12b}$; and $C_{1-6}$alkyl substituted with one, two or three substituents each independently selected from the group consisting of cyano, halo, —$S(═O)_2$—$C_{1-4}$alkyl, and —O—$C_{1-4}$alkyl;

$R^{9a}$, $R^{9b}$, $R^{12a}$, and $R^{12b}$ are each independently selected from the group consisting of hydrogen and $C_{1-6}$alkyl;

and the pharmaceutically acceptable salts and the solvates thereof.

The present invention relates in particular to compounds of Formula (I) as defined herein, and the tautomers and the stereoisomeric forms thereof, wherein $R^{1a}$ represents —C(═O)—$NR^{xa}R^{xb}$;

$R^{xa}$ and $R^{xb}$ represent $C_{1-4}$alkyl;

$R^{1b}$ represents F;

$Y^1$ represents —O—;

$R^2$ is hydrogen;

U represents N;

n1, n2, n3 and n4 are each independently selected from 1 and 2;

$X^1$ represents CH, and $X^2$ represents N;

$R^4$ represents isopropyl;

$R^3$ represents —$C_{1-6}$alkyl-$NR^{8a}R^{8b}$, —$C_{1-6}$alkyl-C(═O)—$NR^{9a}R^{9b}$, or —$C_{1-6}$alkyl-OH;

$R^{8a}$ and $R^{8b}$ are each independently selected from the group consisting of hydrogen; $C_{1-6}$alkyl; —C(═O)—$C_{1-4}$alkyl; —C(═O)—O—$C_{1-4}$alkyl; —C(═O)—$NR^{12a}R^{12b}$; and $C_{1-6}$alkyl substituted with one, two or three substituents each independently selected from the group consisting of cyano, halo, —$S(═O)_2$—$C_{1-4}$alkyl, and —O—$C_{1-4}$alkyl;

$R^{9a}$, $R^{9b}$, $R^{12a}$, and $R^{12b}$ are each independently selected from the group consisting of hydrogen and $C_{1-6}$alkyl;

and the pharmaceutically acceptable salts and the solvates thereof.

In an embodiment, the present invention relates to those compounds of Formula (I) and the pharmaceutically acceptable salts, and the solvates thereof, or any subgroup thereof as mentioned in any of the other embodiments, wherein $R^{1b}$ represents F.

In an embodiment, the present invention relates to those compounds of Formula (I) and the pharmaceutically acceptable salts, and the solvates thereof, or any subgroup thereof as mentioned in any of the other embodiments, wherein $R^2$ represents hydrogen.

In an embodiment, the present invention relates to those compounds of Formula (I) and the pharmaceutically acceptable salts, and the solvates thereof, or any subgroup thereof as mentioned in any of the other embodiments, wherein n1 is 1, n2 is 2, n3 is 1, and n4 is 1.

In an embodiment, the present invention relates to those compounds of Formula (I) and the pharmaceutically acceptable salts, and the solvates thereof, or any subgroup thereof as mentioned in any of the other embodiments, wherein $Y^1$ represents —O—.

In an embodiment, the present invention relates to those compounds of Formula (I) and the pharmaceutically acceptable salts, and the solvates thereof, or any subgroup thereof as mentioned in any of the other embodiments, wherein $Y^1$ represents —O—; and U represents N.

In an embodiment, the present invention relates to those compounds of Formula (I) and the pharmaceutically acceptable salts, and the solvates thereof, or any subgroup thereof as mentioned in any of the other embodiments, wherein $Y^1$ represents —O—;

U represents N;

$R^{1b}$ represents F; and $R^2$ represents hydrogen.

In an embodiment, the present invention relates to those compounds of Formula (I) and the pharmaceutically acceptable salts, and the solvates thereof, or any subgroup thereof as mentioned in any of the other embodiments, wherein Het represents

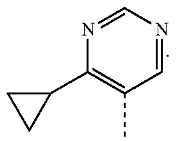

In an embodiment, the present invention relates to those compounds of Formula (I) and the pharmaceutically acceptable salts, and the solvates thereof, or any subgroup thereof as mentioned in any of the other embodiments, wherein Het represents a monocyclic 5- or 6-membered aromatic ring containing one or two nitrogen atoms; wherein said monocyclic 5- or 6-membered aromatic ring is substituted with one $C_{3-6}$cycloalkyl.

In an embodiment, the present invention relates to those compounds of Formula (I) and the pharmaceutically acceptable salts, and the solvates thereof, or any subgroup thereof as mentioned in any of the other embodiments, wherein Het represents a monocyclic 5- or 6-membered aromatic ring containing one or two nitrogen atoms; wherein said monocyclic 5- or 6-membered aromatic ring is substituted with one $C_{3-6}$cycloalkyl; and $R^{1b}$ represents F.

In an embodiment, the present invention relates to those compounds of Formula (I) and the pharmaceutically acceptable salts, and the solvates thereof, or any subgroup thereof as mentioned in any of the other embodiments, wherein Het represents a monocyclic 6-membered aromatic ring containing one or two nitrogen atoms; wherein said monocyclic 6-membered aromatic ring is substituted with one $C_{3-6}$cycloalkyl.

In an embodiment, the present invention relates to those compounds of Formula (I) and the pharmaceutically acceptable salts, and the solvates thereof, or any subgroup thereof as mentioned in any of the other embodiments, wherein Het represents a monocyclic 6-membered aromatic ring containing one or two nitrogen atoms; wherein said monocyclic 6-membered aromatic ring is substituted with one $C_{3-6}$cycloalkyl; and $R^{1b}$ represents F.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-4}$alkyl moiety in the $R^3$ definition may be substituted with one, two or three substituents each independently selected from the group consisting of cyano, halo and —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo, —OH, and —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—$NR^{10a}R^{10b}$, and —$NR^{10c}$—C(═O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of —OH, cyano, halo, —S(═O)$_2$—$C_{1-4}$alkyl, —O—$C_{1-4}$alkyl, —C(═O)—$NR^{10a}R^{10b}$, and —$NR^{10c}$—C(═O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(═O)$_2$—$C_{1-4}$alkyl, —O—$C_{1-4}$alkyl, and —C(═O)—$NR^{10a}R^{10b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(═O)$_2$—$C_{1-4}$alkyl, —O—$C_{1-4}$alkyl, —C(═O)—$NR^{10a}R^{10b}$, and —$NR^{10c}$—C(═O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(═O)$_2$—$C_{1-4}$alkyl, —O—$C_{1-4}$alkyl, and —C(═O)—$NR^{10a}R^{10b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

wherein the $C_{1-6}$alkyl moiety in the $R^3$ definition may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(═O)$_2$—$C_{1-4}$alkyl, —O—$C_{1-4}$alkyl, —C(═O)—$NR^{10a}R^{10b}$, and —$NR^{10c}$—C(═O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo and —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo, —OH, and —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of —OH, cyano, halo, —S(=O)$_2$—$C_{1-4}$alkyl, —O—$C_{1-4}$alkyl, —C(=O)—$NR^{10a}R^{10b}$, and —$NR^{10c}$—C(=O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of —OH, cyano, halo, —S(=O)$_2$—$C_{1-4}$alkyl, —O—$C_{1-4}$alkyl, —C(=O)—$NR^{10a}R^{10b}$, and —$NR^{10c}$—C(=O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(=O)$_2$—$C_{1-4}$alkyl, —O—$C_{1-4}$alkyl, and —C(=O)—$NR^{10a}R^{10b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(=O)$_2$—$C_{1-4}$alkyl, —O—$C_{1-4}$alkyl, and —C(=O)—$NR^{10a}R^{10b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

$R^{8a}$ and $R^{8b}$ are each independently selected from the group consisting of $C_{1-6}$alkyl; and $C_{1-6}$alkyl substituted with one, two or three substituents each independently selected from the group consisting of —OH, cyano, halo, —S(=O)$_2$—$C_{1-4}$alkyl, —O—$C_{1-4}$alkyl, and —C(=O)—$NR^{10a}R^{10b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo, —OH, and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(=O)$_2$—$C_{1-4}$alkyl, —O—$C_{1-4}$alkyl, —C(=O)—$NR^{10a}R^{10b}$, and —$NR^{10c}$—C(=O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{2-6}$alkyl-$NR^{8a}R^{8b}$;

wherein the $C_{2-6}$alkyl moiety in the $R^3$ definition may be substituted with one, two or three substituents each independently selected from the group consisting of cyano, halo and —O—$C_{1-4}$alkyl;

$R^{8a}$ and $R^{8b}$ are each independently selected from the group consisting of hydrogen;

$C_{1-6}$alkyl; and $C_{1-6}$alkyl substituted with one, two or three substituents each independently selected from the group consisting of cyano, halo, —S(=O)$_2$—$C_{1-4}$alkyl, —O—$C_{1-4}$alkyl, —C(=O)—$NR^{10a}R^{10b}$, and —$NR^{10c}$—C(=O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

$R^{8a}$ and $R^{8b}$ are each independently selected from the group consisting of $C_{1-6}$alkyl; and $C_{1-6}$alkyl substituted with one, two or three substituents each independently selected from the group consisting of —OH, cyano, halo, —S(=O)$_2$—$C_{1-4}$alkyl, —O—$C_{1-4}$alkyl, —C(=O)—$NR^{10a}R^{10b}$, and —$NR^{10c}$—C(=O)—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$;

$R^{8a}$ represents $C_{1-6}$alkyl; and $R^{8b}$ represents $C_{1-6}$alkyl substituted with one —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$, —$C_{1-6}$alkyl-C(=O)—$NR^{9a}R^{9b}$, —$C_{1-6}$alkyl-OH, or —$C_{1-6}$alkyl-$NR^{11}$—C(=O)—O—$C_{1-4}$alkyl-O—C(=O)—$C_{1-4}$alkyl;

wherein each of the $C_{1-4}$alkyl or $C_{1-6}$alkyl moieties in the $R^3$ definitions independently of each other may be substituted with one, two or three substituents each independently selected from the group consisting of cyano, halo or —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$C_{1-6}$alkyl-$NR^{8a}R^{8b}$, —$C_{1-6}$alkyl-C(═O)—$NR^{9a}R^{9b}$, or —$C_{1-6}$alkyl-$NR^{11}$—C(═O)—O—$C_{1-4}$alkyl-O—C(═O)—$C_{1-4}$alkyl;

wherein each of the $C_{1-4}$alkyl or $C_{1-6}$alkyl moieties in the $R^3$ definitions independently of each other may be substituted with one, two or three substituents each independently selected from the group consisting of cyano, halo, —OH, and —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein $R^3$ represents —$CH_2$—$CH_2$—$CH_2$—$NR^{8a}R^{8b}$.

In an embodiment, the present invention relates to those compounds of Formula (I) and the pharmaceutically acceptable salts, and the solvates thereof, or any subgroup thereof as mentioned in any of the other embodiments, wherein $R^3$ represents —$CH_2$—$CH_2$—$CH_2$—$NR^{8a}R^{8b}$;

$R^{8a}$ represents methyl; and $R^{8b}$ represents —$CH_2$—$CH_2$—$OCH_3$.

In an embodiment, the present invention relates to those compounds of Formula (I) and the pharmaceutically acceptable salts, and the solvates thereof, or any subgroup thereof as mentioned in any of the other embodiments, wherein $C_{1-6}$alkyl in the $R^3$ definition —$C_{1-6}$alkyl-$NR^{8a}R^{8b}$ is limited to —$CH_2$—$CH_2$—$CH_2$—.

In an embodiment, the present invention relates to those compounds of Formula (I) and the pharmaceutically acceptable salts, and the solvates thereof, or any subgroup thereof as mentioned in any of the other embodiments, wherein the compounds of Formula (I) are restricted to compounds of Formula (I-y):

(I-y)

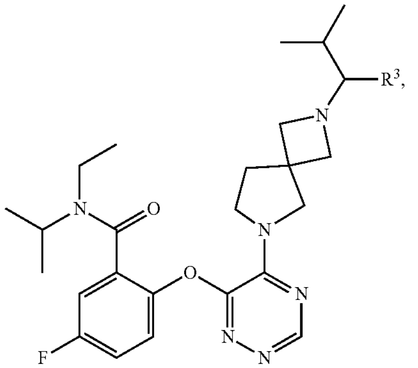

wherein $R^3$ is as defined for the compounds of Formula (I) or any subgroup thereof as mentioned in any of the other embodiments.

In Formula (I-y) n1 is 1, n2 is 2, n3 is 1, and n4 is 1.

In an embodiment the compound of Formula (I) is

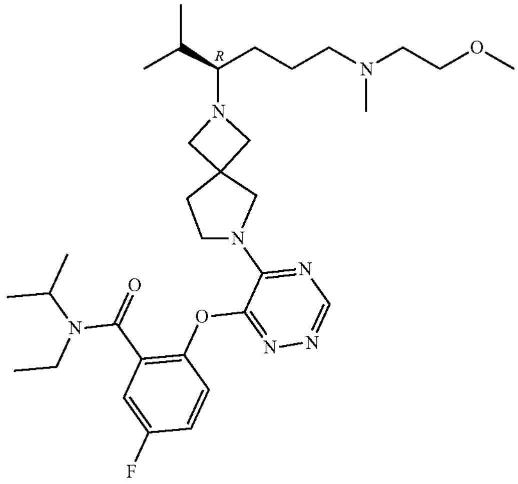

and pharmaceutically acceptable addition salts, and solvates thereof.

In an embodiment the compound of Formula (I) is

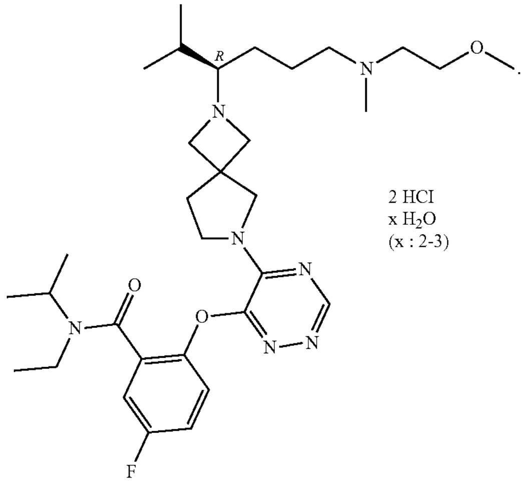

2 HCl
x $H_2O$
(x : 2-3)

In an embodiment the compound of Formula (I) is

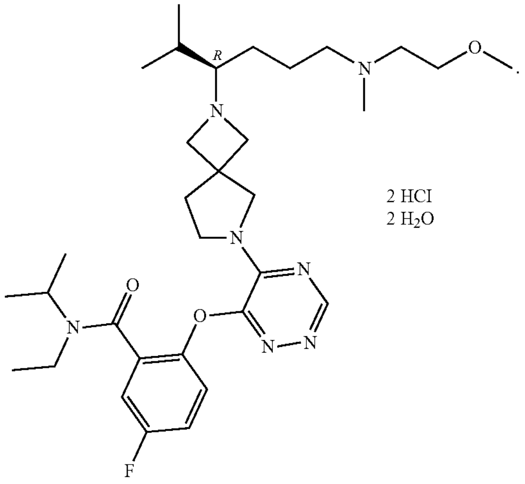

In an embodiment the compound of Formula (I) is

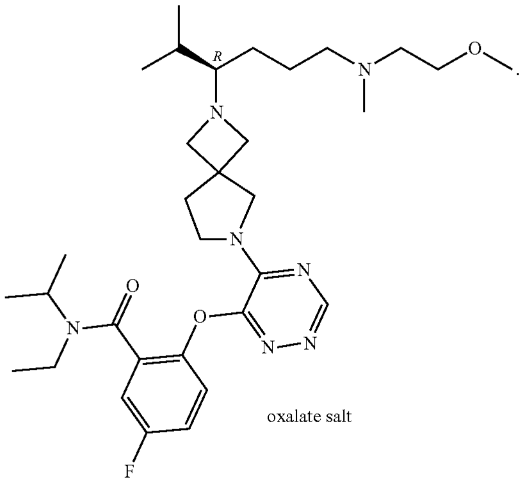

In an embodiment, the present invention relates to a subgroup of Formula (I) as defined in the general reaction schemes.

In an embodiment the compound of Formula (I) is selected from the group consisting of any of the exemplified compounds, tautomers and stereoisomeric forms thereof, and the free bases, any pharmaceutically acceptable salts, and the solvates thereof.

All possible combinations of the above indicated embodiments are considered to be embraced within the scope of the invention.

In another embodiment, the present invention relates to the intermediate

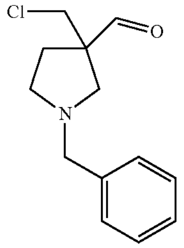 [SMILES: O=CC1(CCl)CCN(Cc2ccccc2)C1]

tautomers and stereoisomeric forms thereof, and any pharmaceutically acceptable salts, and the solvates thereof.

In another embodiment, the present invention relates to a process for the preparation of an intermediate comprising the following steps:

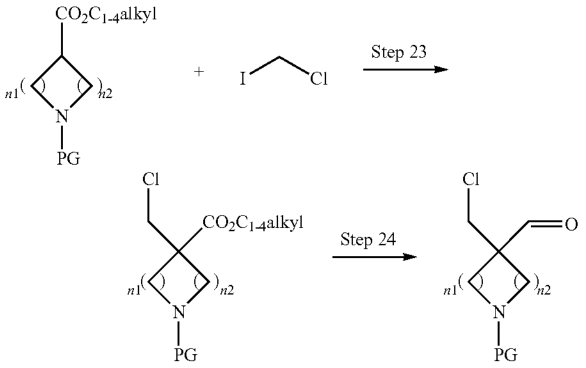

wherein PG is a suitable protecting group such as benzyl;

wherein n1 and n2 are as defined for formula (I);

Step 23: at a suitable temperature such as for example from −78° C. to −25° C., in the presence of suitable bases such as for example DIEA and n-BuLi, in a suitable solvent such as for example THF;

Step 24: at a suitable temperature such as for example between −55° C. and −65° C., in the presence of suitable reducing agent such as for example DIBAL-H, in a suitable solvent such as for example toluene, conducted in a suitable flow chemistry system.

In another embodiment, the present invention relates to a process for the preparation of an intermediate comprising the following steps:

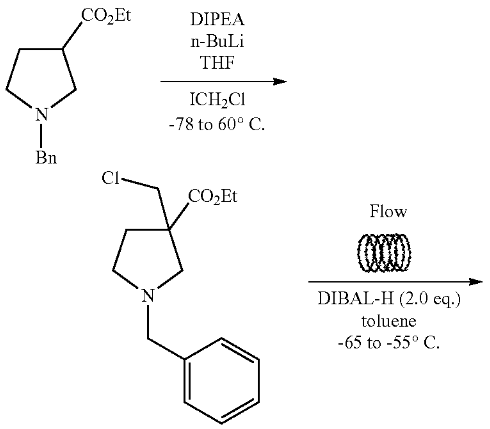

-continued

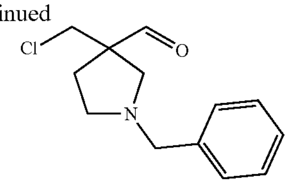

first reaction at a suitable temperature such as for example from −78° C. to −25° C., in the presence of suitable bases such as for example DIEA and n-BuLi, in a suitable solvent such as for example THF;

then, reaction at a suitable temperature such as for example between −55° C. and −65° C., in the presence of suitable reducing agent such as for example DIBAL-H, in a suitable solvent such as for example toluene, conducted in a suitable flow chemistry system.

In another embodiment, the present invention relates to a process for the preparation of an intermediate comprising the following steps:

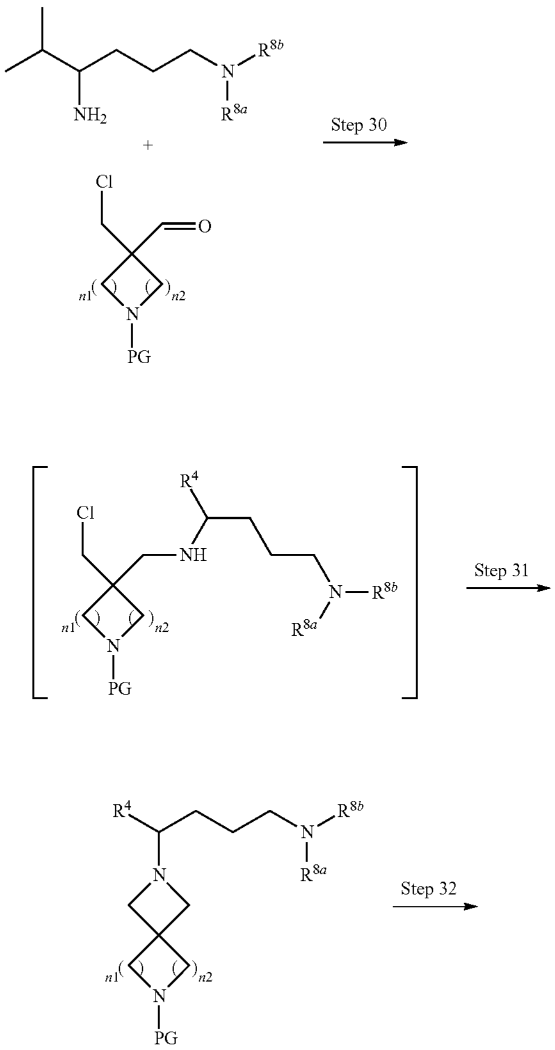

-continued

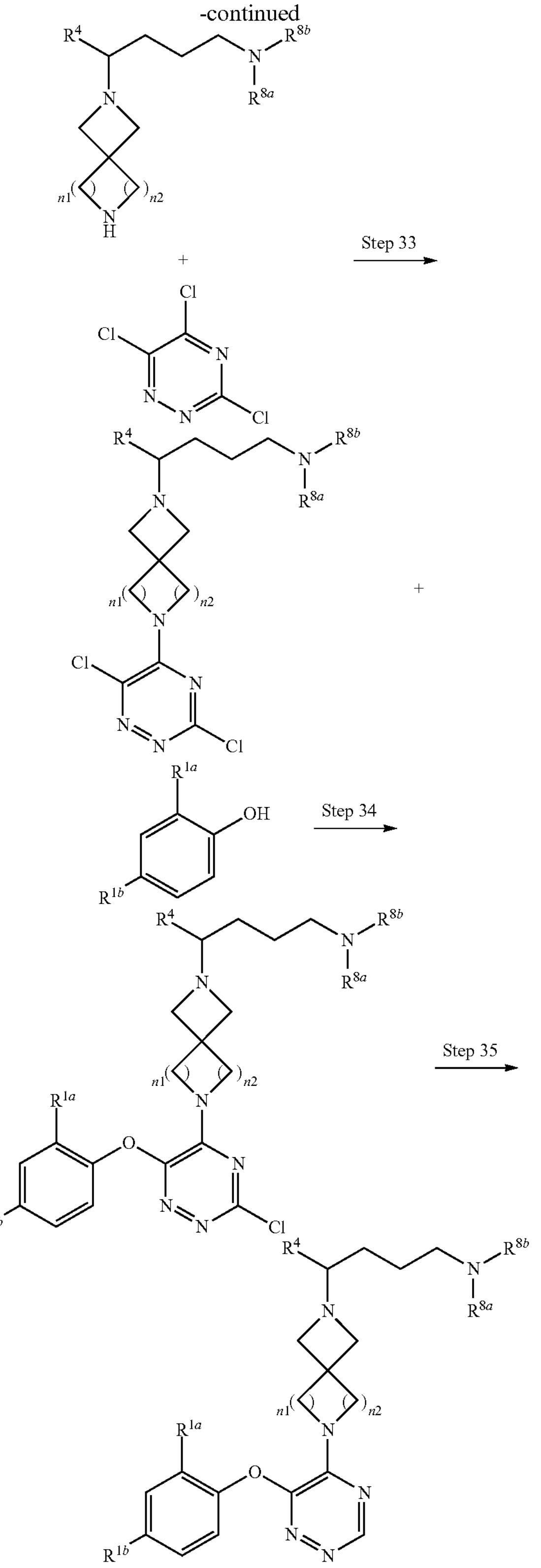

PG is a suitable protecting group such as benzyl;

other variables are as defined for formula (I).

In another embodiment, the present invention relates to a process for the preparation of an intermediate comprising the following steps:

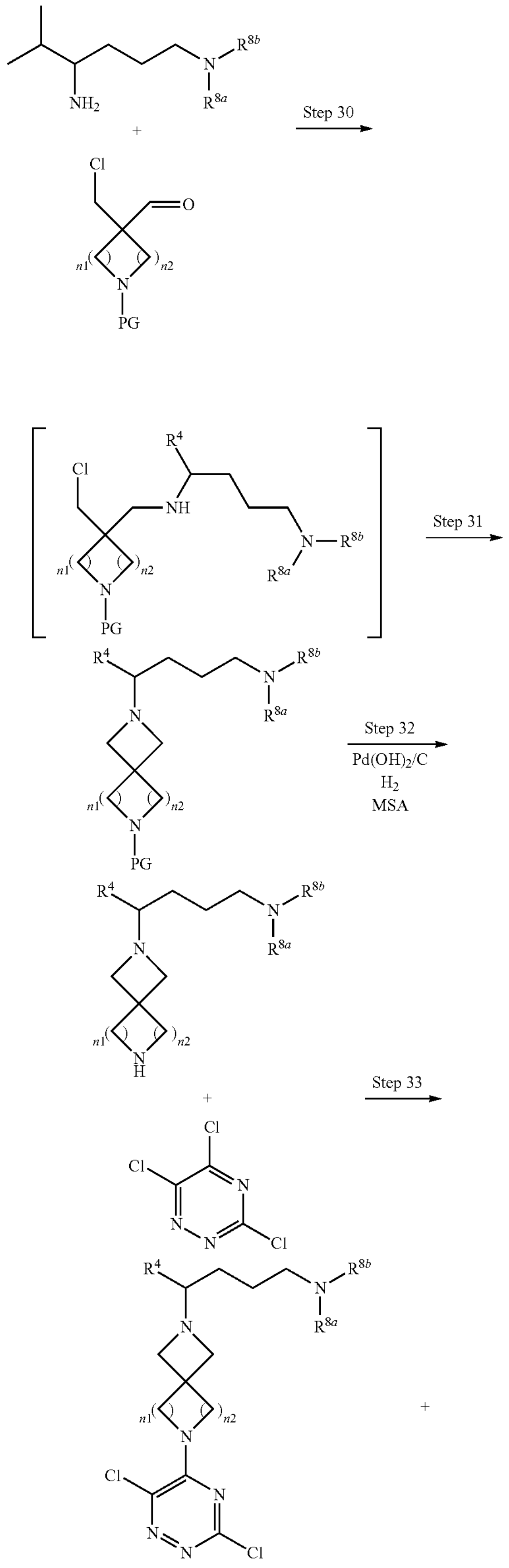

-continued

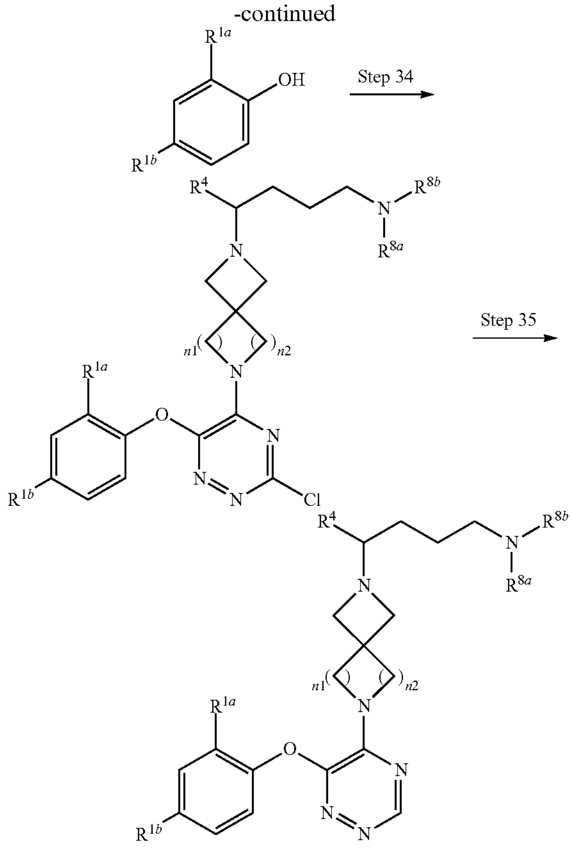

PG is a suitable protecting group such as benzyl;

other variables are as defined for formula (I);

Step 30: at a suitable temperature such as for example from 5° C. to 30° C., in the presence of a suitable base such as for example TEA, in the presence of suitable reducing agent such as for example $NaBH(OAc)_3$, in a suitable solvent such as for example toluene;

Step 31: at a suitable temperature such as for example from 50° C. to 55° C., in the presence of a suitable base such as for example $K_2HPO_4$, in a suitable solvent such as for example $H_2O$;

Step 32: at a suitable temperature such as for example from −5° C. to 45° C., under a hydrogen atmosphere within a suitable pressure range such as for example from 0.27 to 0.40 MPa, in the presence of palladium hydroxide on carbon, in the presence of MSA in a suitable solvent such as EtOH;

Step 33: at a suitable temperature such as for example from −50° C. to −40° C., in the presence of suitable base such as for example TEA, in a suitable solvent such as 2-methyltetrahydrofuran;

Step 34: at a suitable temperature such as for example from 20° C. to 30° C., in the presence of suitable base such as for example TMG, in a suitable solvent such as 2-methyltetrahydrofuran;

Step 35: at a suitable temperature such as for example from 20° C. to 30° C., under a hydrogen atmosphere within a suitable pressure range such as for example from 0.20 to 0.30 Mpa, in the presence of a suitable catalyst such as for example palladium on carbon, in a suitable solvent such as MeOH.

In another embodiment, the present invention relates to a process for the preparation of a compound comprising the following steps:

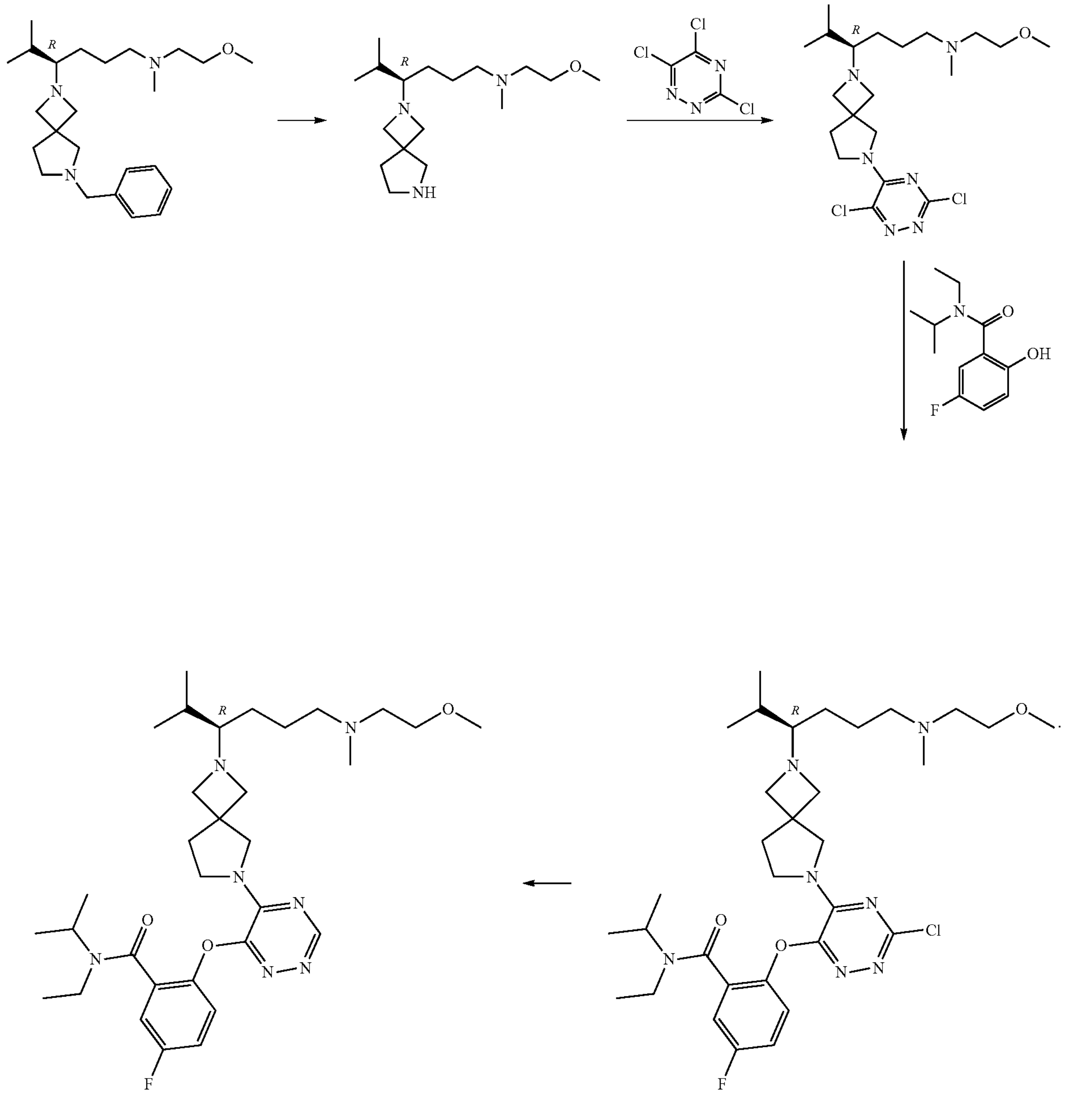
In another embodiment, the present invention relates to a process for the preparation of a compound comprising the following steps:
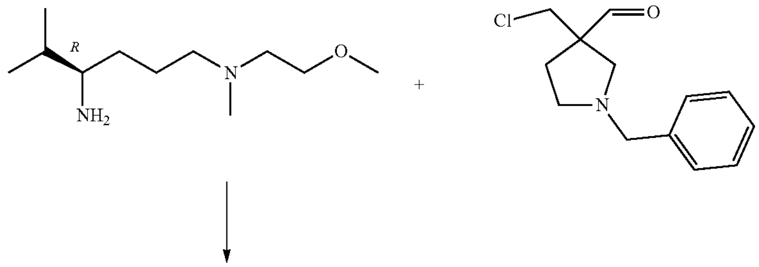

-continued
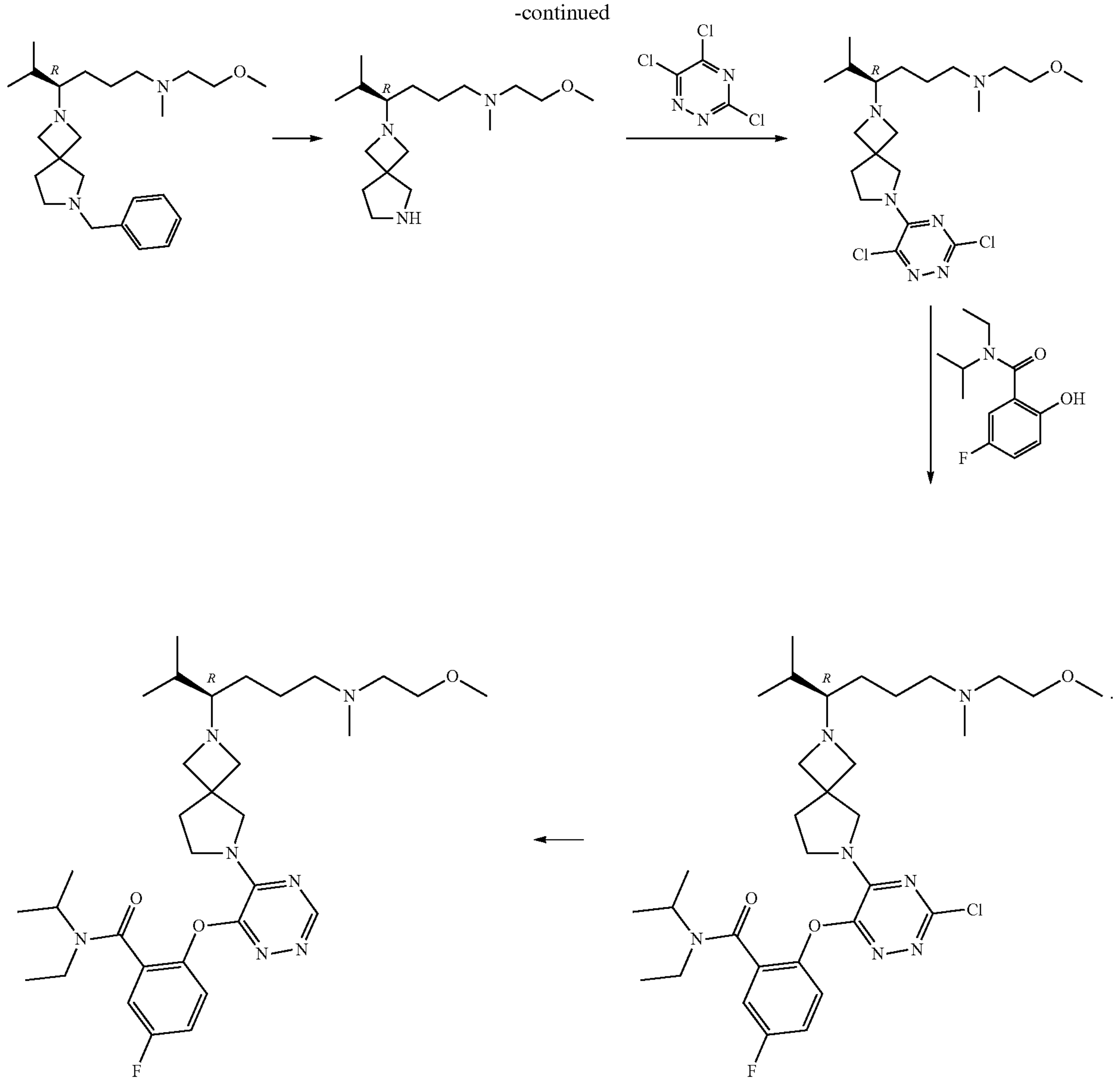
In another embodiment, the present invention relates to a process for the preparation of a compound comprising the following steps:
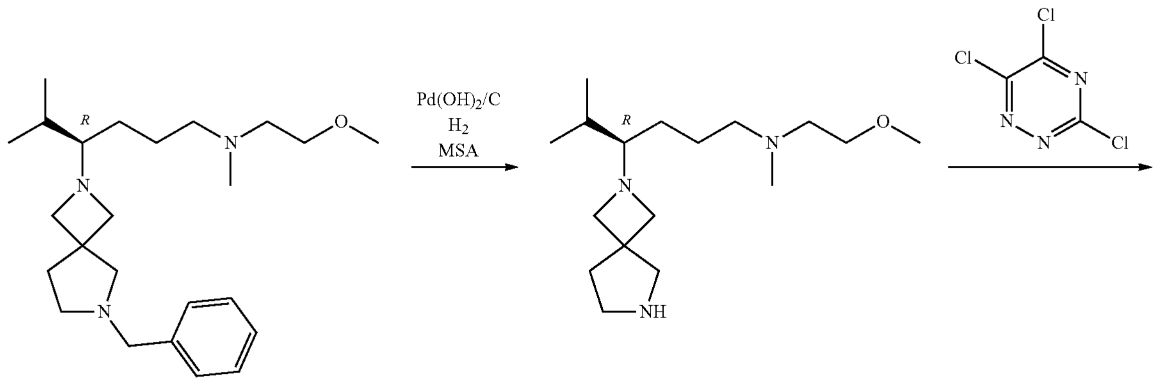

-continued
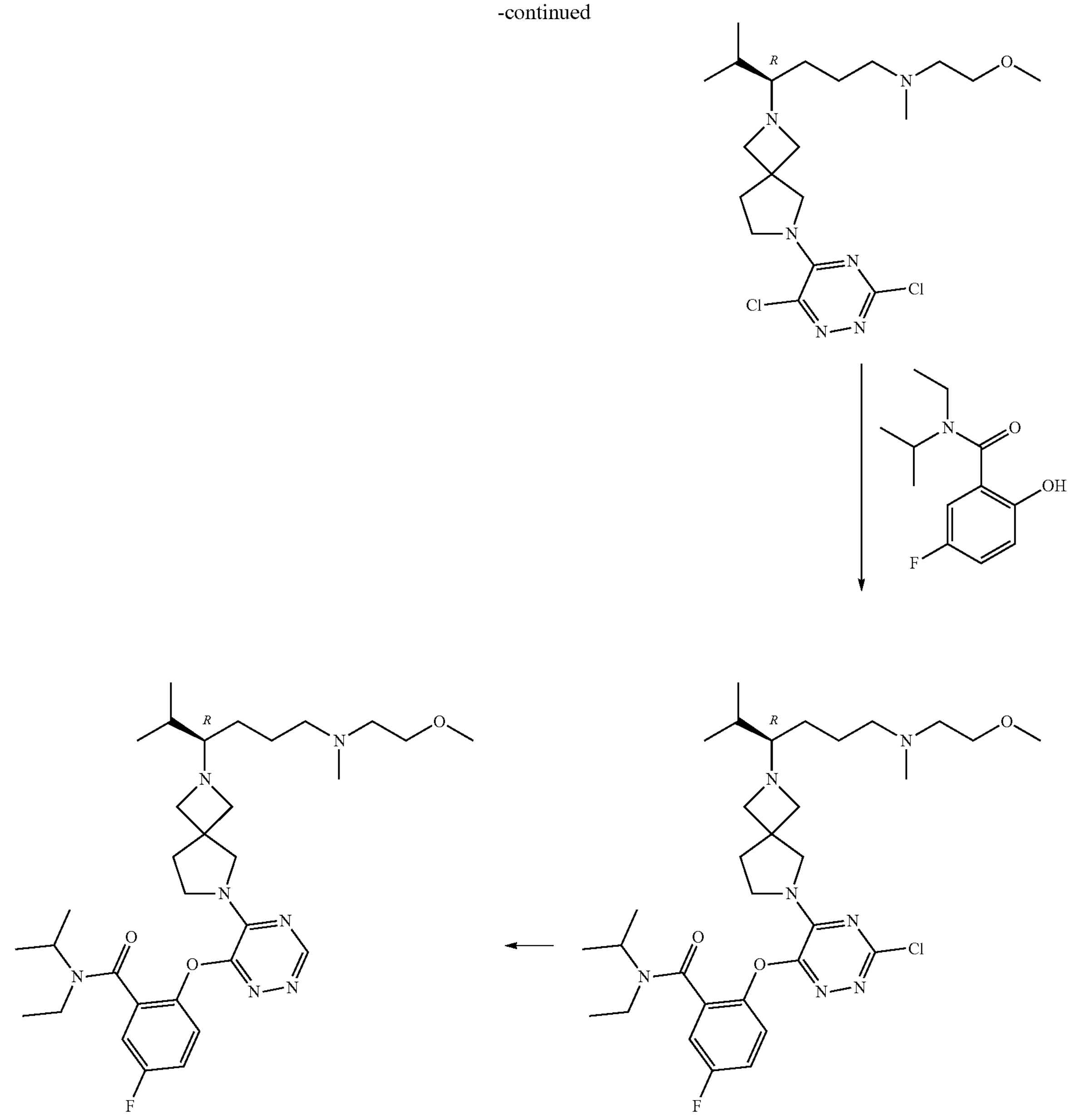
In another embodiment, the present invention relates to a process for the preparation of a compound comprising the following steps:
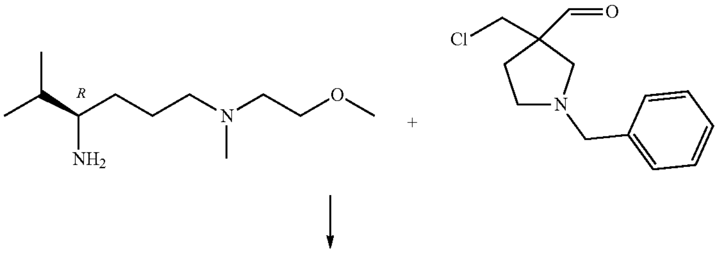

-continued
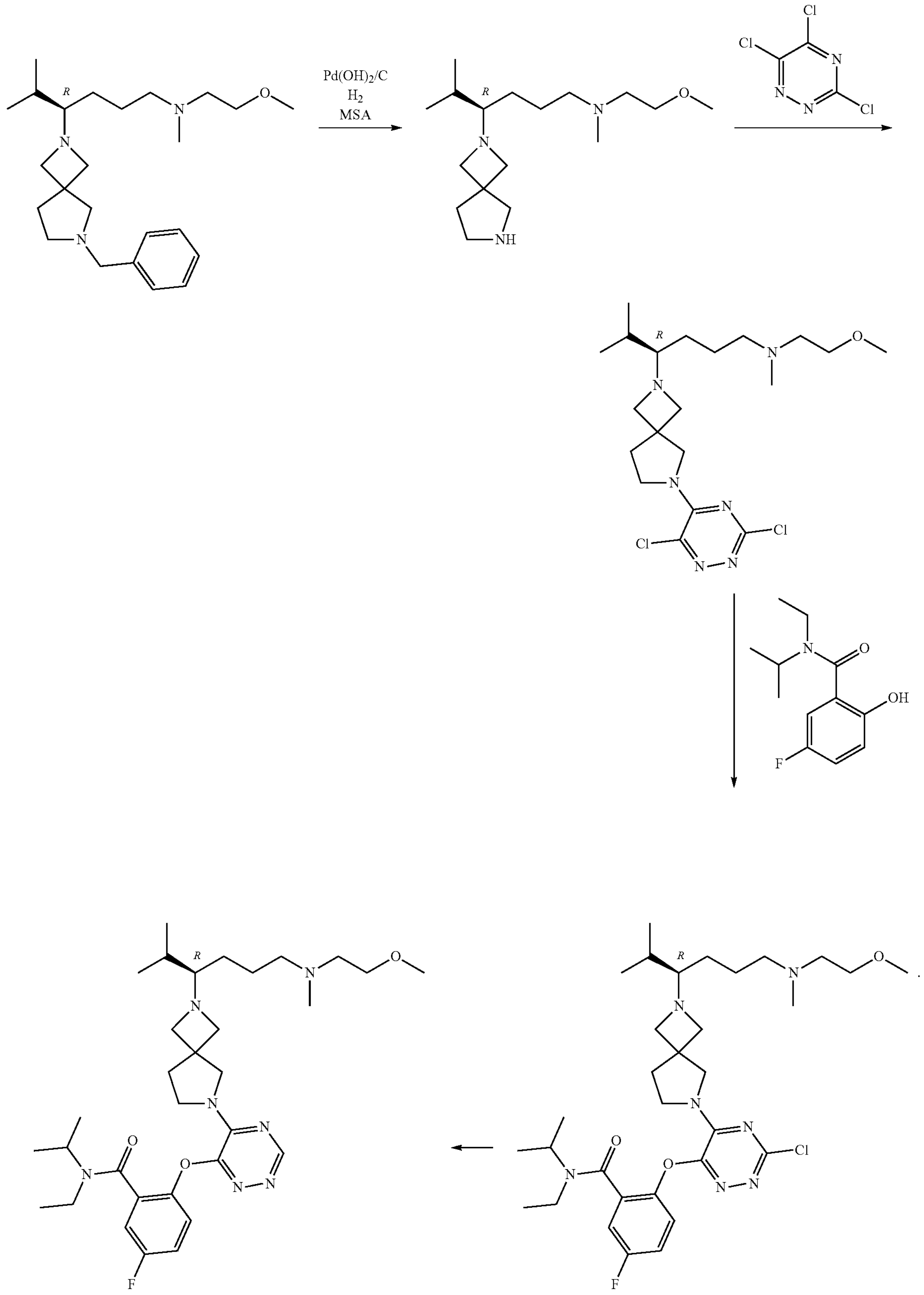

In another embodiment, the present invention relates to a process for the preparation of a compound comprising the following steps:

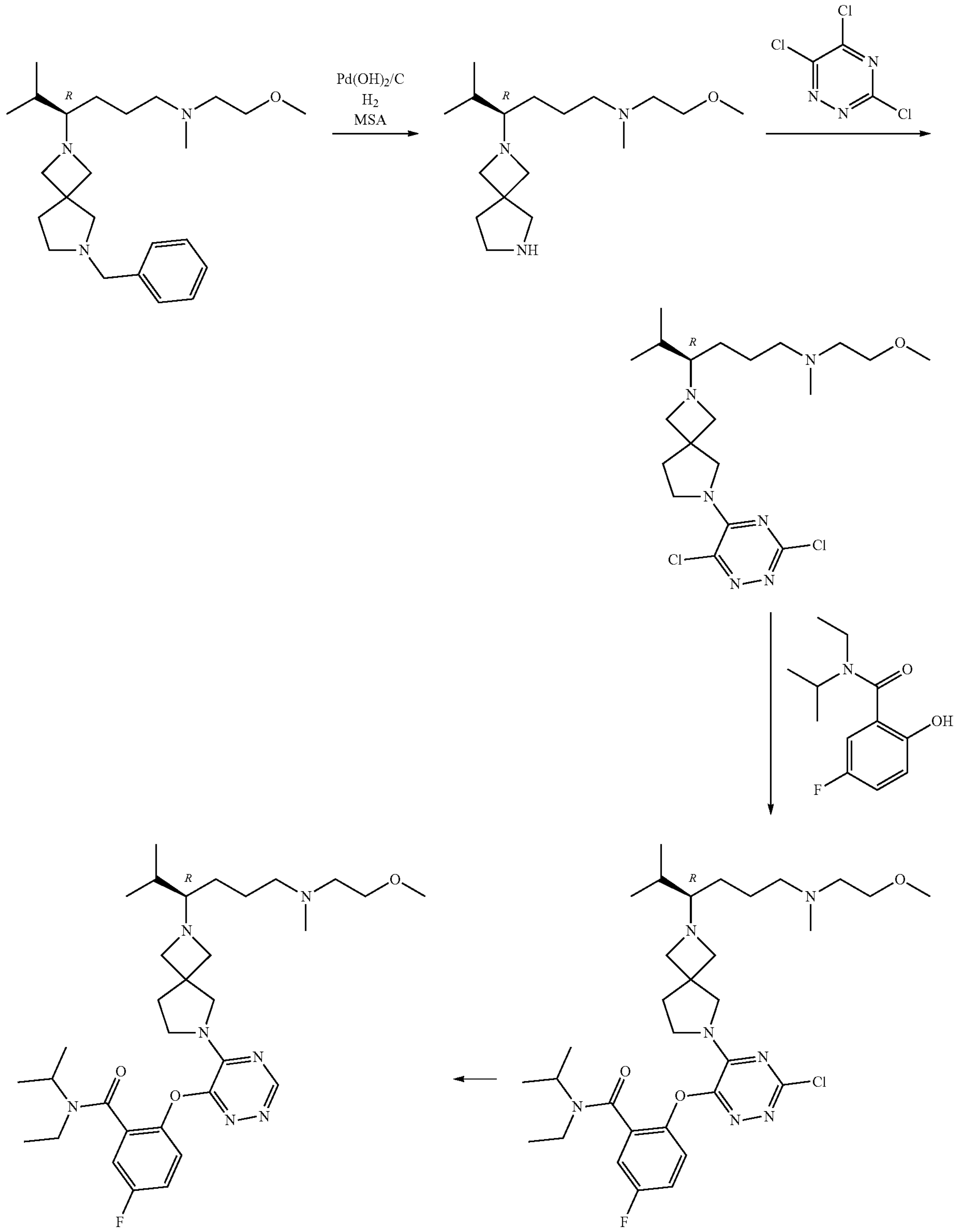

in a first step, at a suitable temperature such as for example from −5° C. to 45° C., under a hydrogen atmosphere within a suitable pressure range such as for example from 0.27 to 0.40 MPa, in the presence of palladium hydroxide on carbon, in the presence of MSA in a suitable solvent such as EtOH;

in a next step at a suitable temperature such as for example from −50° C. to −40° C., in the presence of suitable base such as for example TEA, in a suitable solvent such as 2-methyltetrahydrofuran;

in a next step at a suitable temperature such as for example from 20° C. to 30° C., in the presence of suitable base such as for example TMG, in a suitable solvent such as 2-methyltetrahydrofuran; in a next step at a suitable temperature such as for example from 20° C. to 30° C., under a hydrogen atmosphere within a suitable pressure range such as for example from 0.20 to 0.30 Mpa, in the presence of a suitable catalyst such as for example palladium on carbon, in a suitable solvent such as MeOH.

In another embodiment, the present invention relates to a process for the preparation of a compound comprising the following steps:

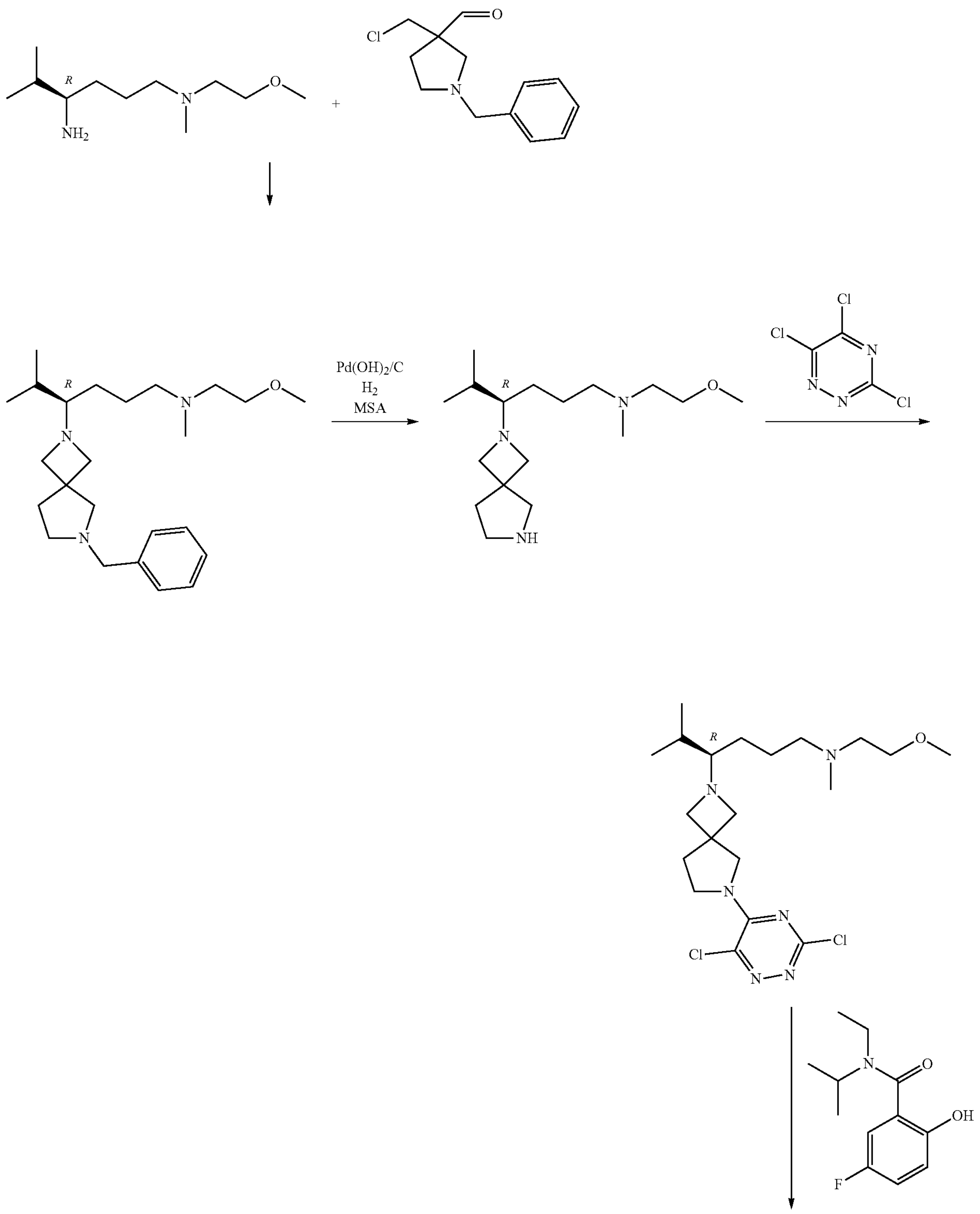

-continued

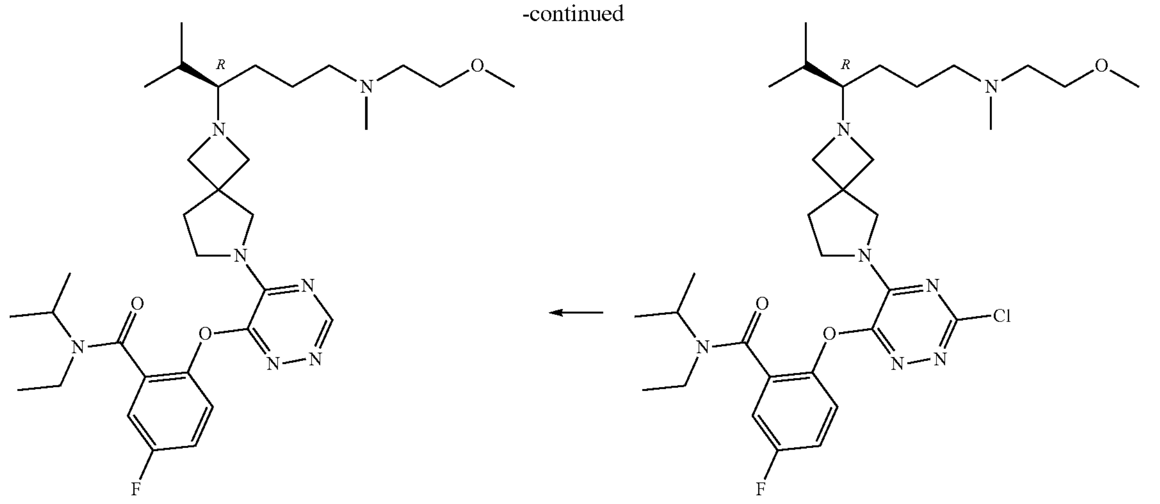

In a first step first at a suitable temperature such as for example from 5° C. to 30° C., in the presence of a suitable base such as for example TEA, in the presence of suitable reducing agent such as for example $NaBH(OAc)_3$, in a suitable solvent such as for example toluene; and then at a suitable temperature such as for example from 50° C. to 55° C., in the presence of a suitable base such as for example $K_2HPO_4$, in a suitable solvent such as for example $H_2O$;

- in a next step, at a suitable temperature such as for example from −5° C. to 45° C., under a hydrogen atmosphere within a suitable pressure range such as for example from 0.27 to 0.40 MPa, in the presence of palladium hydroxide on carbon, in the presence of MSA in a suitable solvent such as EtOH;
- in a next step at a suitable temperature such as for example from −50° C. to −40° C., in the presence of suitable base such as for example TEA, in a suitable solvent such as 2-methyltetrahydrofuran;
- in a next step at a suitable temperature such as for example from 20° C. to 30° C., in the presence of suitable base such as for example TMG, in a suitable solvent such as 2-methyltetrahydrofuran; in a next step at a suitable temperature such as for example from 20° C. to 30° C., under a hydrogen atmosphere within a suitable pressure range such as for example from 0.20 to 0.30 Mpa, in the presence of a suitable catalyst such as for example palladium on carbon, in a suitable solvent such as MeOH.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art of organic chemistry. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. In general, conventional protecting groups (PG) can be used in accordance with standard practice. The protecting groups may be removed at a convenient subsequent stage using methods known from the art.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt, or a solvate thereof. The intermediates and compounds described herein may be synthesized in the form of mixtures of tautomers and stereoisomeric forms that can be separated from one another following art-known resolution procedures.

General Synthetic Schemes

All abbreviations used in the general schemes are as defined in the Table in the part Examples. Variables are as defined in the scope or as specifically defined in the general Schemes.

Part A) Schemes 1a, 1b, 1c, 2a, 2b and 3

Scheme 1a

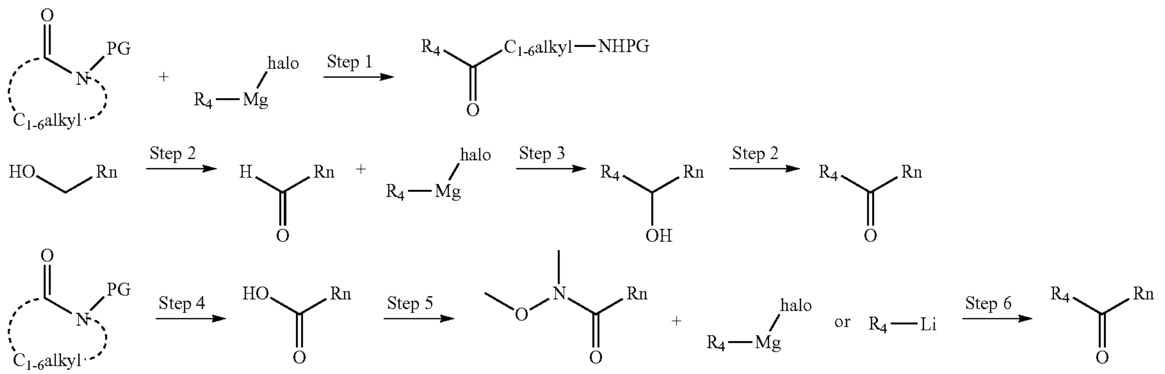

Scheme 1b

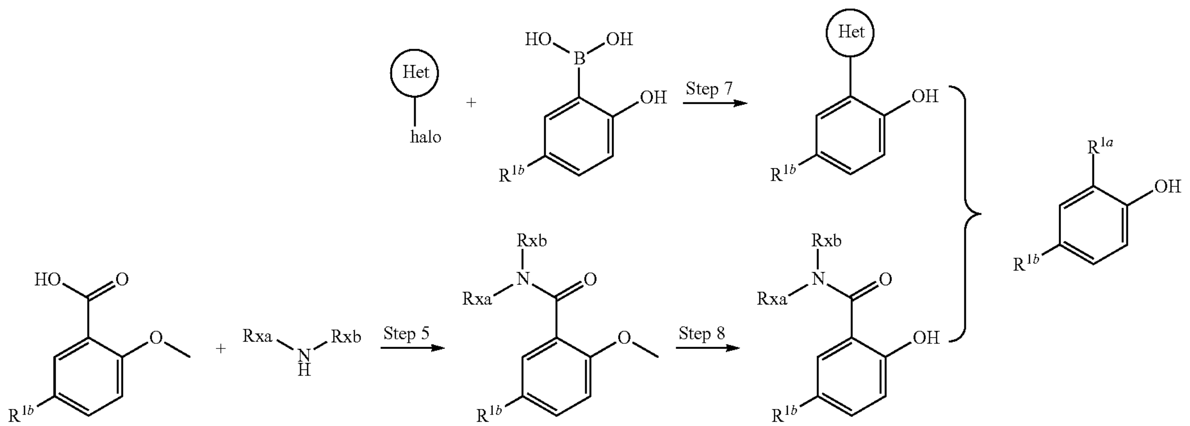

Scheme 1c

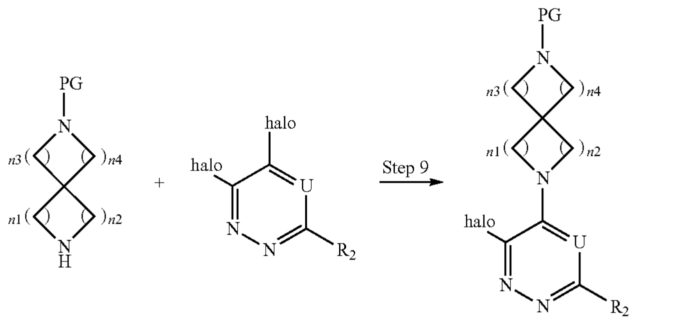

Rn = $C_{1-6}$alkyl—$NR^{8a}$PG or $C_{1-6}$alkyl—OPG or $C_{1-6}$alkyl—C(=O)$OR^{9a}$, PG = protecting group In Scheme 1a, 1b and 1c the following reaction conditions apply:

Step 1: at a suitable temperature such as for example −70° C., in the presence of a suitable base such as for example TMEDA and a suitable organometallic reagent such as for example isopropylmagnesium bromide, in a suitable solvent such as for example THF;

Step 2: at a suitable temperature such as for example from 0° C. to RT, in the presence of a suitable oxidative reagent such as for example DMP, in a suitable solvent such as for example DCM;

Step 3: at a suitable temperature such as for example from −20° C. to RT, in the presence of a suitable organometallic reagent such as for example isopropylmagnesium bromide, in a suitable solvent such as for example THF;

Step 4: at a suitable temperature such as for example 80° C., in the presence of a suitable base such as for example NaOH, in suitable solvents such as for example THF and $H_2O$;

Step 5: at a suitable temperature such as for example RT, in the presence of suitable amide condensation reagents such as for example EDCI and HOBt, in the presence of a suitable base such as for example NMM, in a suitable solvent such as for example DCM;

Step 6: at a suitable temperature such as for example −70° C., in the presence of a suitable organometallic reagent such as for example isopropyllithium, in a suitable solvent such as for example THF;

Step 7: at a suitable temperature such as for example 90° C., in the presence of a suitable organometallic catalyst such as for example Pd(dppf)$Cl_2$, in the presence of a suitable base such as for example $Na_2CO_3$, in suitable solvents such as for example 1,4-dioxane and $H_2O$;

Step 8: at a suitable temperature such as for example from 0° C. to RT, in the presence of a suitable Lewis acid such as for example $BBr_3$, in a suitable solvent such as for example DCM;

Step 9: at a suitable temperature such as for example from −78° C. to 40° C., in particular from 0° C. to RT, in the presence of a suitable base such as for example TEA, DBU or $K_2CO_3$, in a suitable solvent such as for example DCM, THF or DMF;

Scheme 2a

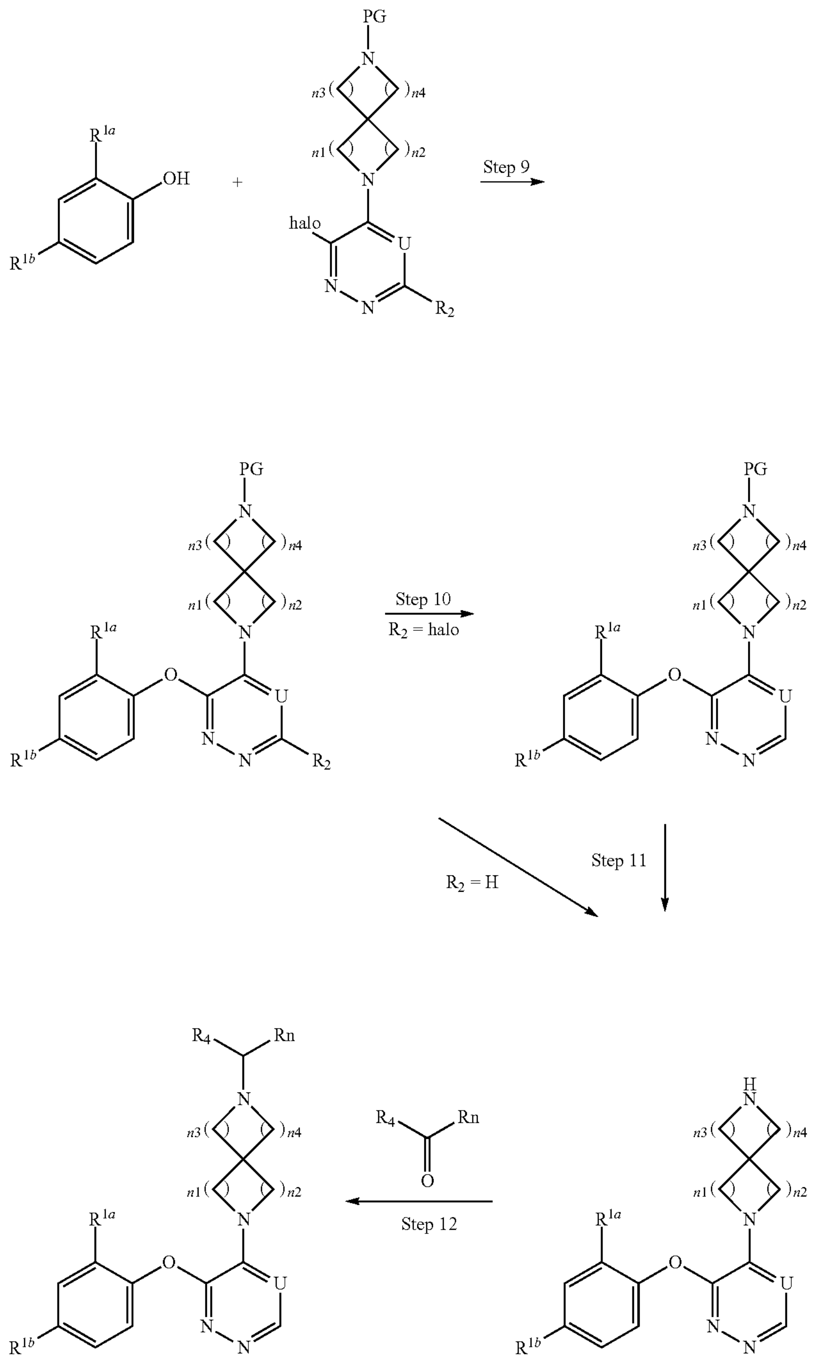

Scheme 2b

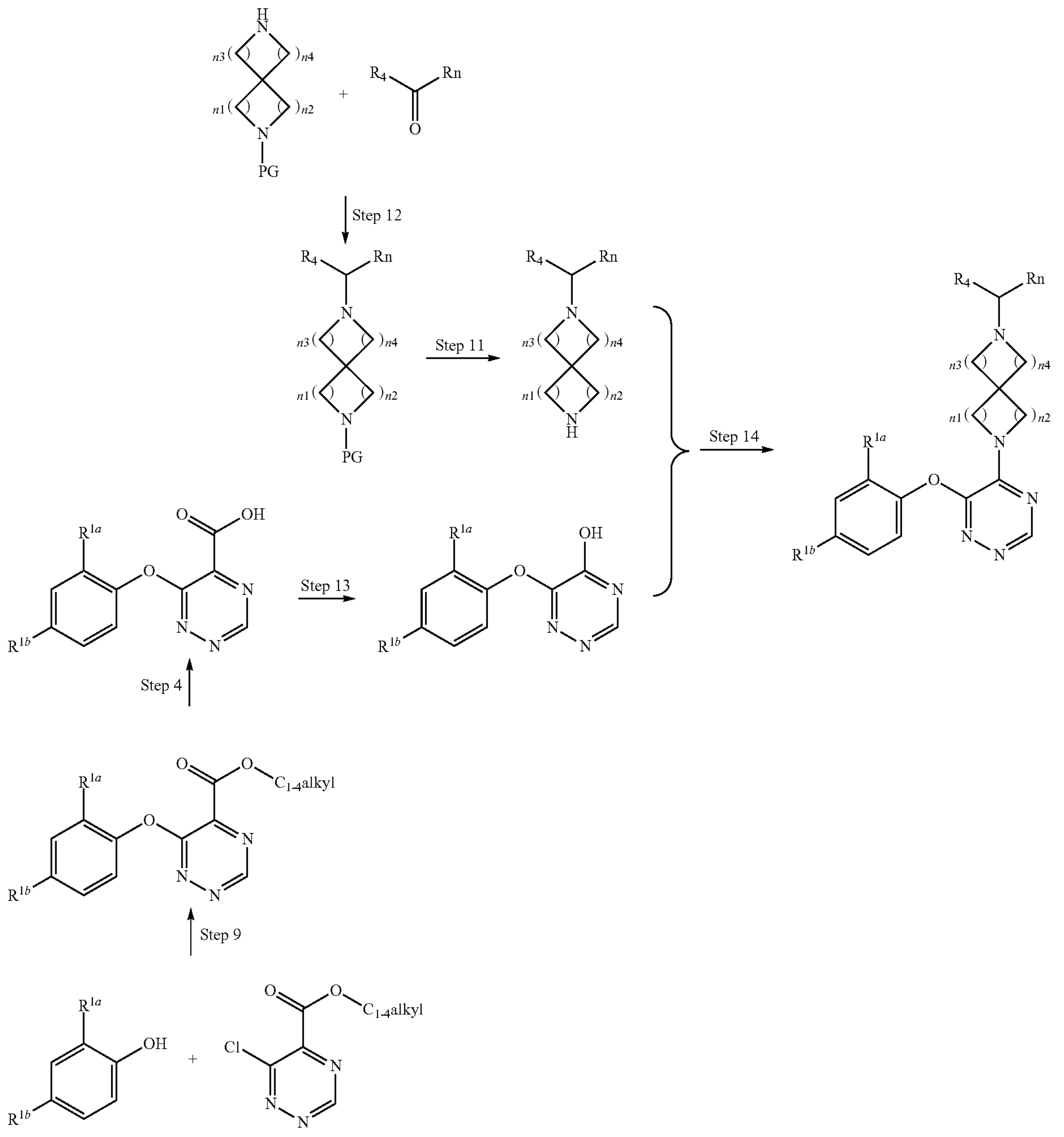

In Scheme 2a and 2b, the following reaction conditions apply:

Step 9: See Step 9 in Scheme 1;

Step 10: at a suitable temperature such as for example RT, in the presence of a suitable catalyst such as for example Pd/C, in the presence of a suitable reductive reagent such as for example $H_2$, optionally in the presence of a suitable base such as for example TEA, in a suitable solvent such as for example THF;

Alternatively, at a suitable temperature such as RT, in the presence of a suitable catalyst such as for example Pd(dppf) $Cl_2$.DCM complex, a suitable reducing agent such $NaBH_4$, a suitable base such as for example TMEDA, in a suitable solvent such as for example THF.

Step 11: for N deprotection, at a suitable temperature such as for example RT, in the presence of a suitable acid as for example TFA, in a suitable solvent such as for example DCM; for 0 deprotection, at a suitable temperature such as for example RT, in the presence of a suitable acid as for example 4-methylbenzenesulfonic acid, in a suitable solvent such as for example MeOH;

Step 12: at a suitable temperature such as for example 80° C., optionally in the presence of a suitable Lewis acid such as for example $ZnCl_2$, in the presence of a suitable reductive reagent such as for example $NaBH_3CN$, in a suitable solvent such as for example MeOH;

Step 13: at a suitable temperature such as for example RT, in the presence of a suitable organometallic catalyst such as for example $Ag(Phen)_2OTf$, in the presence of a suitable brominating reagent such as for example 1,3-dibromo-1,3,5-triazinane-2,4,6-trione, in a suitable solvent such as for example DCE;

Step 14: at a suitable temperature such as for example RT, in the presence of a suitable chlorinating reagent such as for example oxalyl chloride, in the presence of DMF, in a suitable solvent such as for example DCM.

Scheme 3

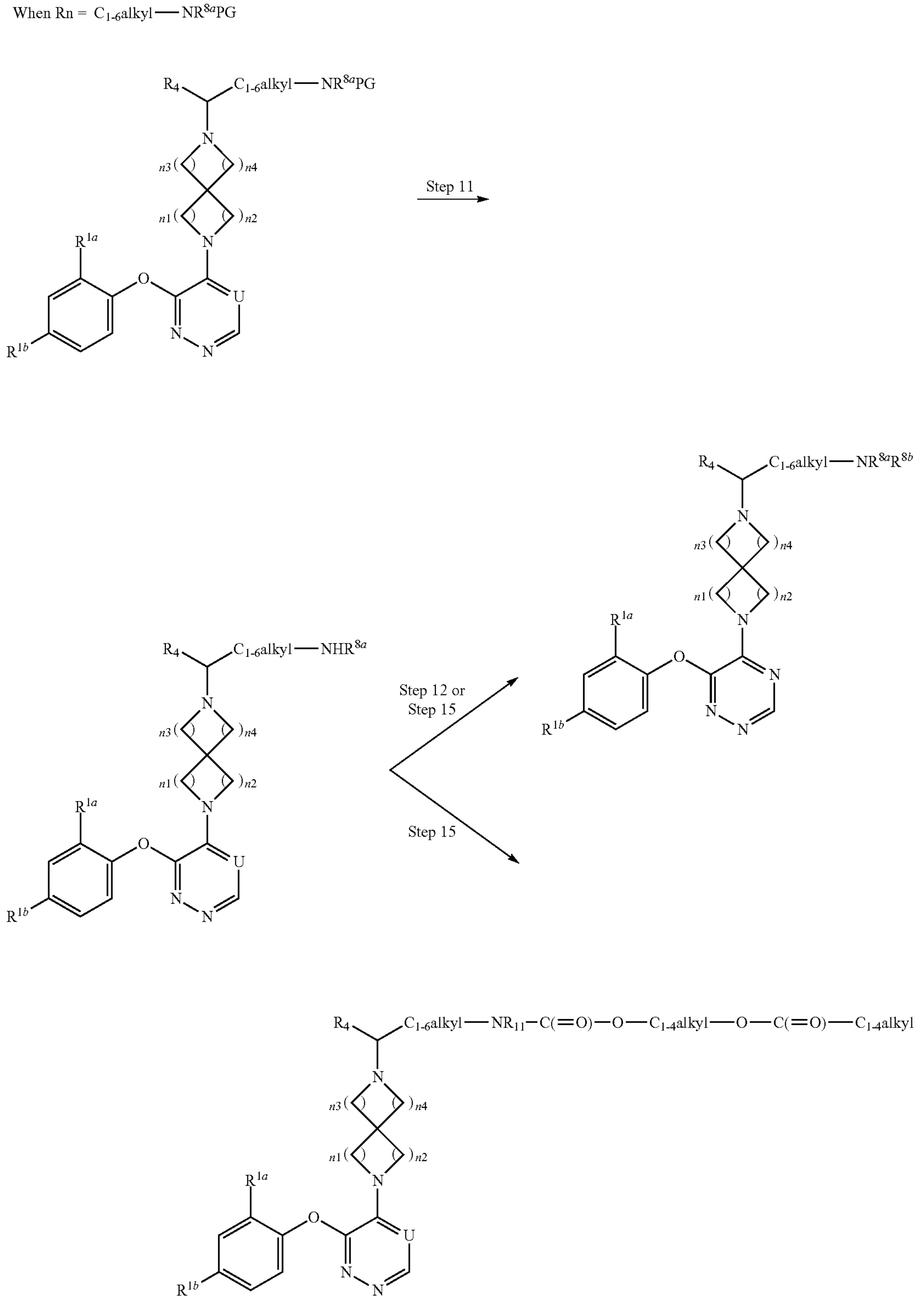

-continued

When Rn = $C_{1-6}$alkyl—OPG

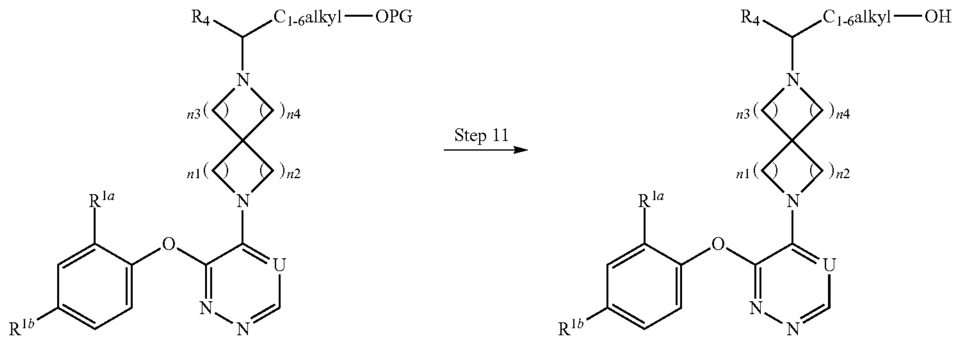

When Rn = $C_{1-6}$alkyl—C(=O)OR$^{9a}$

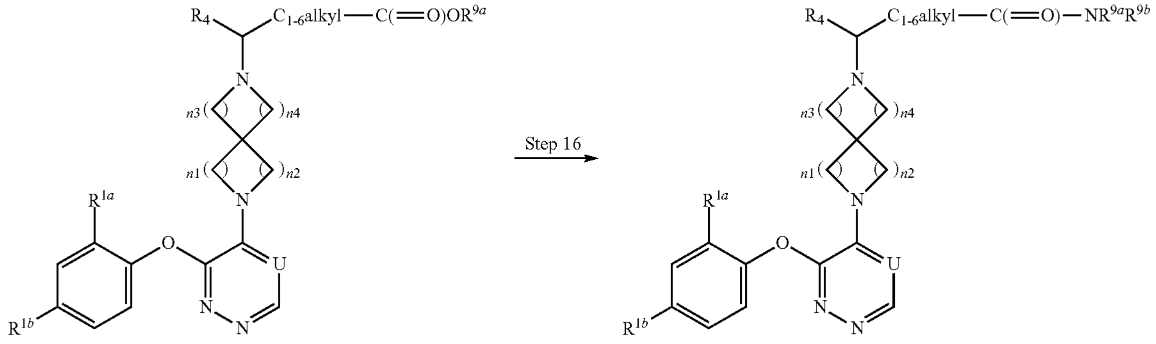

In Scheme 3, the following reaction conditions apply:

Step 11-12: See Step 11-12 in Scheme 2;

Step 15: at a suitable temperature such as for example 80° C., in the presence of a suitable base such as for example $Cs_2CO_3$, in suitable solvent such as for example DMF.

Step 16: at a suitable temperature such as for example 40° C., in the presence of a suitable base such as for example ammonia, in suitable solvent such as for example 1,4-dioxane.

Part B) Schemes 4, 5, 6, 7, 8, 9, 10, 11 and 12

Scheme 4

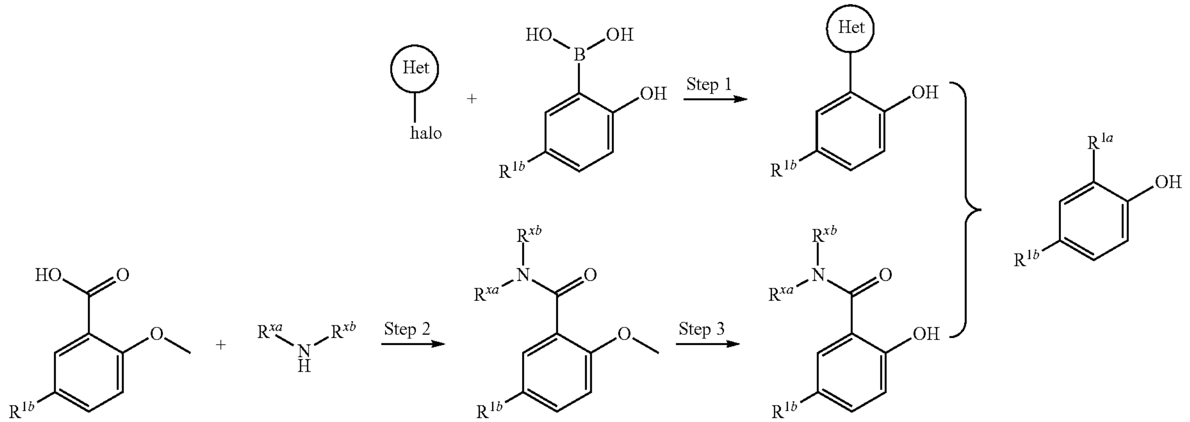

-continued

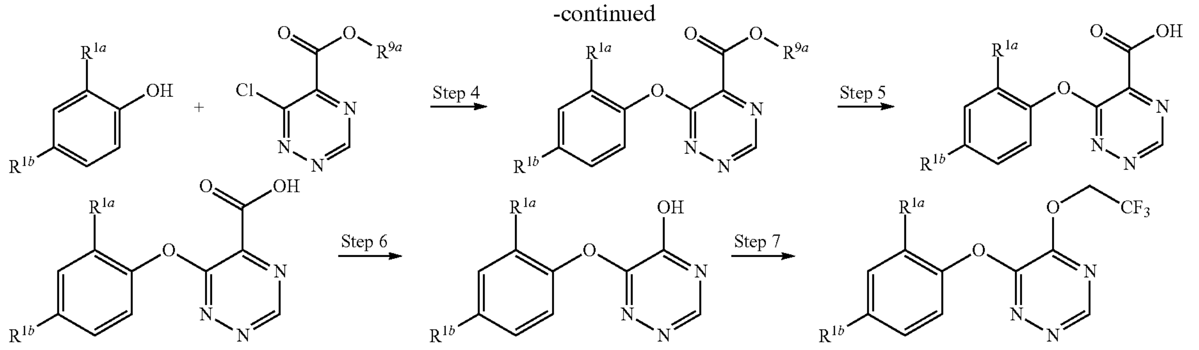

In Scheme 4, the following reaction conditions apply:

Step 1: at a suitable temperature such as for example 90° C., in the presence of a suitable organometallic catalyst such as for example Pd(dppf)$Cl_2$, in the presence of a suitable base such as for example $Na_2CO_3$, in suitable solvents such as for example 1,4-dioxane and $H_2O$;

Step 2: at a suitable temperature such as for example RT, in the presence of suitable amide condensation reagent such as for example HATU, in the presence of a suitable base such as for example DIEA, in a suitable solvent such as for example DCM;

Step 3: at a suitable temperature such as for example from −78° C. to RT, in the presence of a suitable Lewis acid such as for example $BBr_3$, in a suitable solvent such as for example DCM;

Step 4: at a suitable temperature such as for example from −78° C. to 40° C., in particular from 0° C. to RT, in the presence of a suitable base such as for example TEA, DBU or $K_2CO_3$, in a suitable solvent such as for example DCM, THF or DMF;

Step 5: at a suitable temperature such as for example RT, in the presence of a suitable base such as for example LiOH·$H_2O$, in suitable solvents such as for example THF and $H_2O$;

Step 6: at a suitable temperature such as for example RT, in the presence of a suitable organometallic catalyst such as for example Ag(Phen)$_2$OTf, in the presence of a suitable brominating reagent such as for example 1,3-dibromo-1,3,5-triazinane-2,4,6-trione, in a suitable solvent such as for example DCE;

Step 7: at a suitable temperature such as for example RT, in the presence of a suitable brominating reagent such as 1,3-dibromo-1,3,5-triazinane-2,4,6-trione, in the presence of 2,2,2-trifluoroethan-1-ol as solvent.

Scheme 5

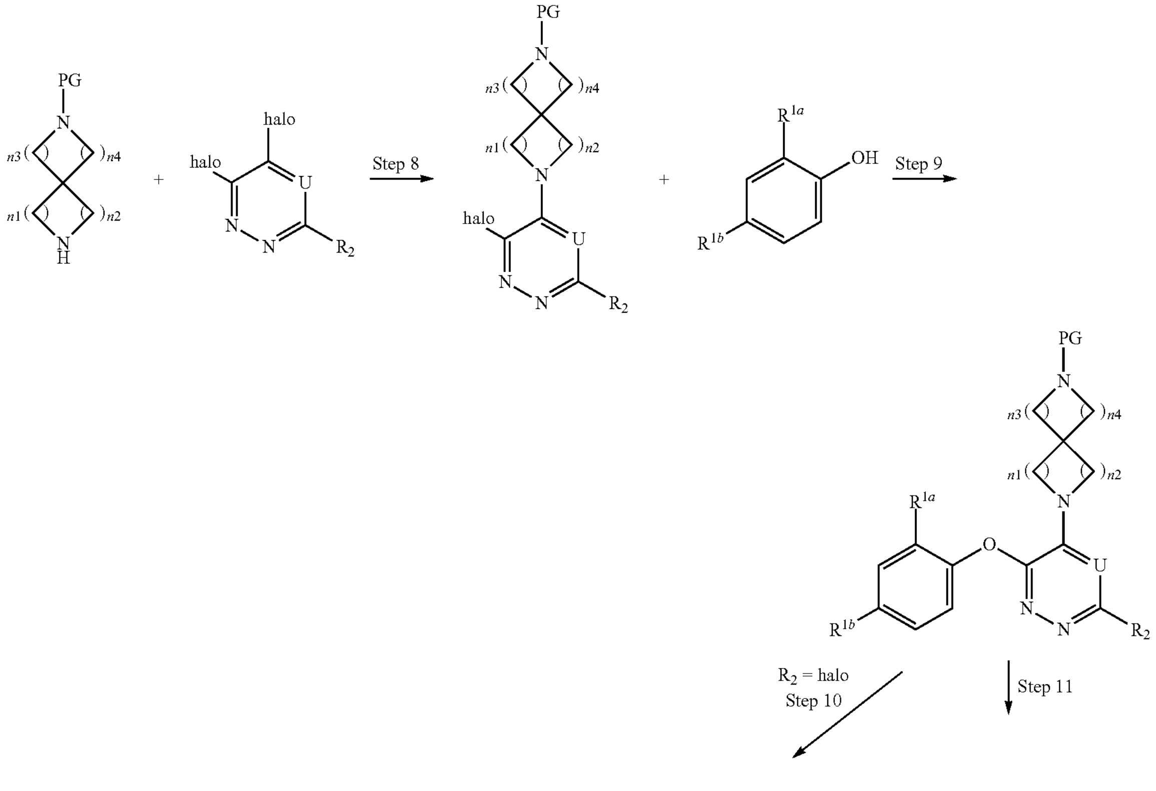

-continued

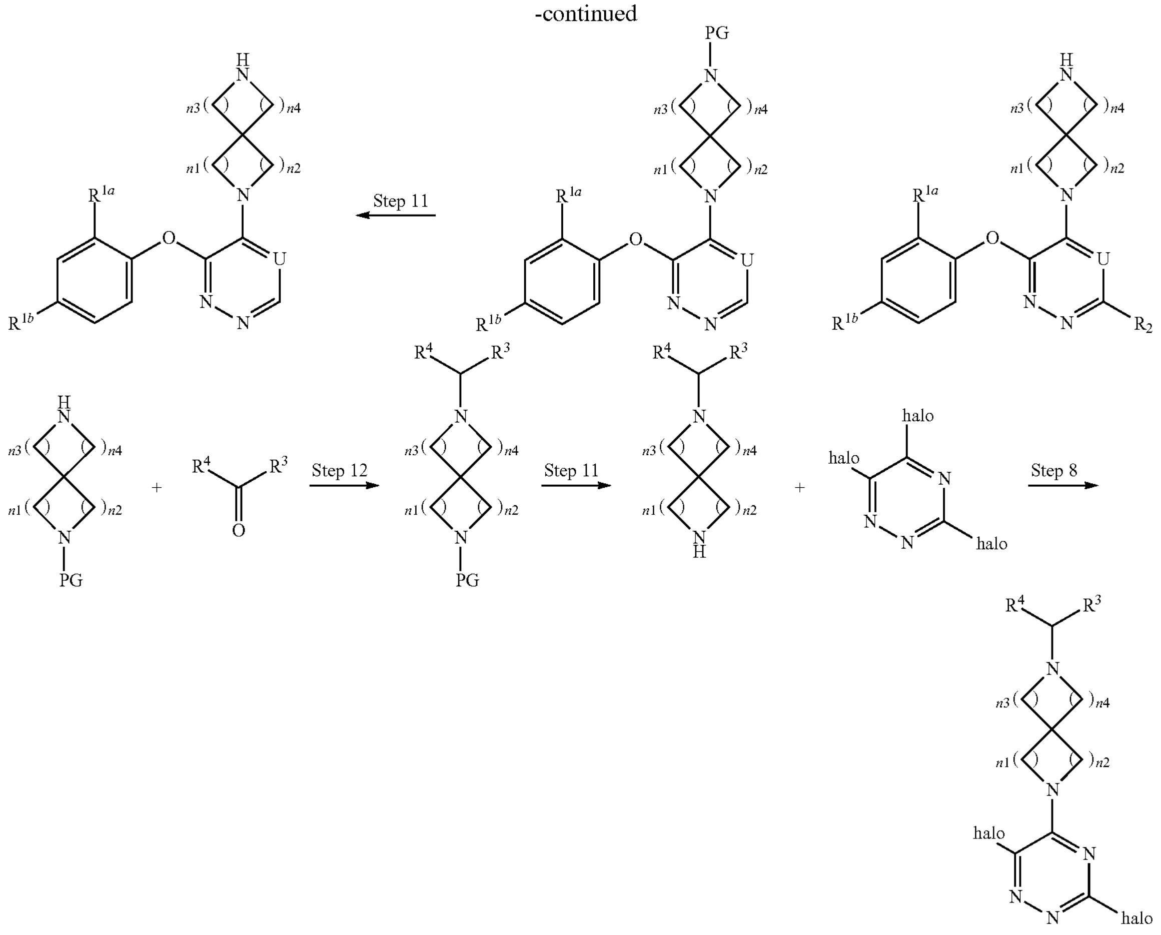

In Scheme 5, the following reaction conditions apply:

Step 8: at a suitable temperature such as for example from −78° C. to 40° C., in particular from 0° C. to RT, in the presence of a suitable base such as for example TEA, DBU or $K_2CO_3$, in a suitable solvent such as for example DCM, THF or DMF;

Step 9: at a suitable temperature such as for example from −78° C. to 40° C., in particular from 0° C. to RT, in the presence of a suitable base such as for example TEA, DBU or $K_2CO_3$, in a suitable solvent such as for example DCM, THF or DMF;

Step 10: at a suitable temperature such as for example RT, in the presence of a suitable organometallic catalyst as for example Pd/C and a suitable base as for example TEA, in a suitable solvent such as for example MeOH under $H_2$ atmosphere;

Step 11: When PG is Boc, at a suitable temperature such as for example RT, in the presence of a suitable acid as for example TFA, in a suitable solvent such as for example DCM.

Scheme 6

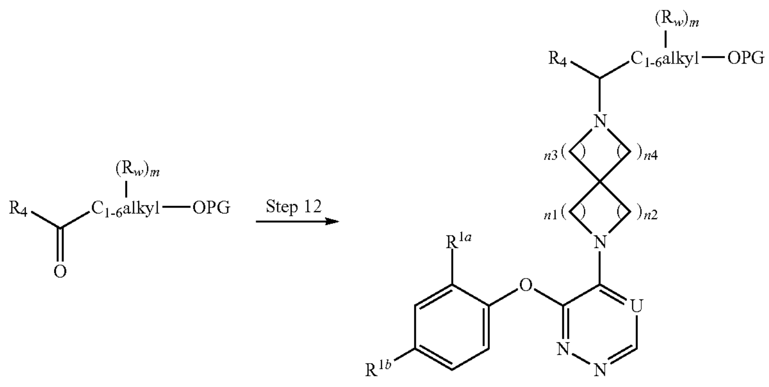

-continued

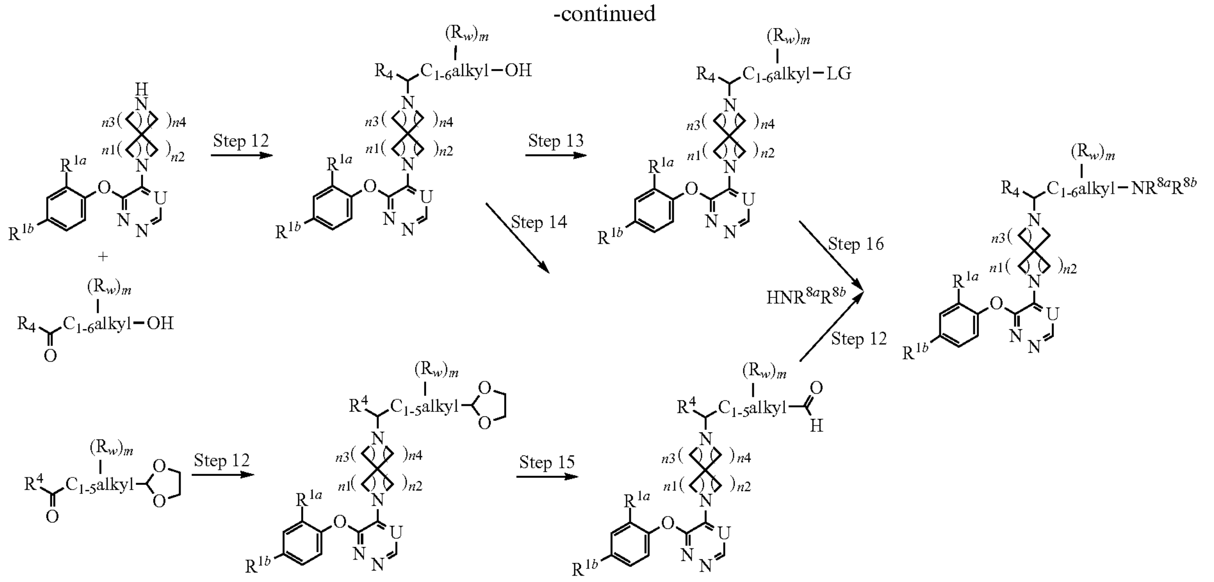

m = 1, 2, 3
Rw = H, CN, halo, OH, O—$C_{1-4}$alkyl

In Scheme 6, the following reaction conditions apply:

Step 12: reductive amination condition, at a suitable temperature such as for example from RT to 80° C., in the presence or absence of a suitable Lewis acid such as for example $ZnCl_2$ or an acid for example AcOH, in the presence of a suitable reducing agent such as for example $NaBH_3CN$, in a suitable solvent such as for example MeOH;

Step 13: at a suitable temperature such as for example 0° C., in the presence of a suitable electrophile as for example MsCl, in the presence of a suitable base such as for example TEA, in a suitable solvent such as for example DCM;

Step 14: at a suitable temperature such as for example from 0° C. to RT, in the presence of a suitable oxidizing agent as for example DMP, in a suitable solvent such as for example DCM;

Step 15: at a suitable temperature such as for example 50° C., in the presence of a suitable acid as for example HCl, in a suitable solvent such as for example ACN;

Step 16: at a suitable temperature such as for example RT, in the presence or absence of a suitable base as for example TEA, in a suitable solvent such as for example THF.

Scheme 7

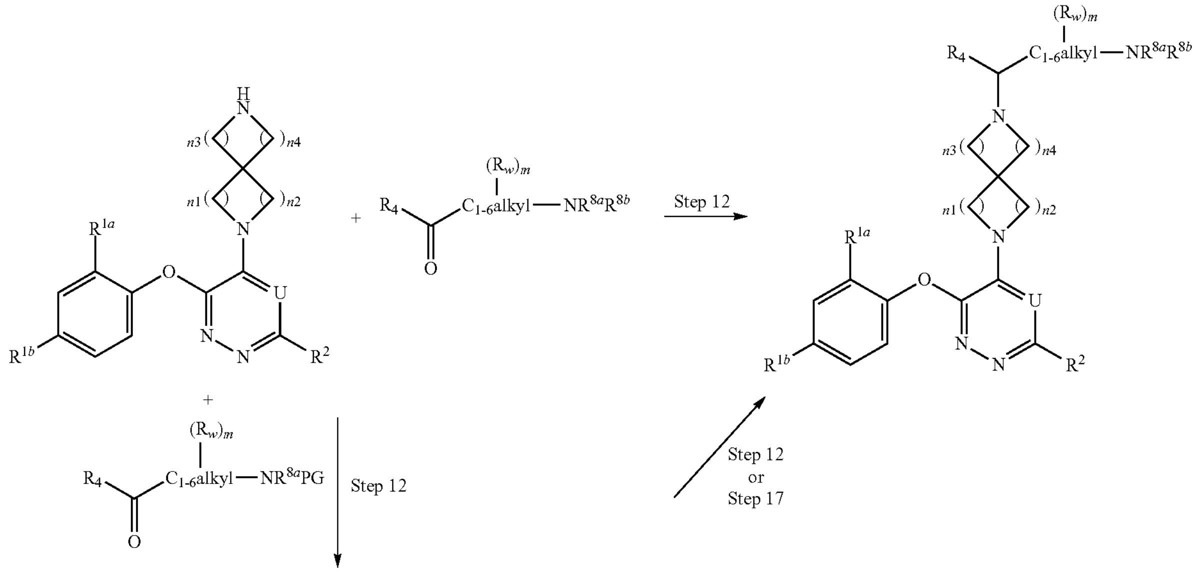

-continued

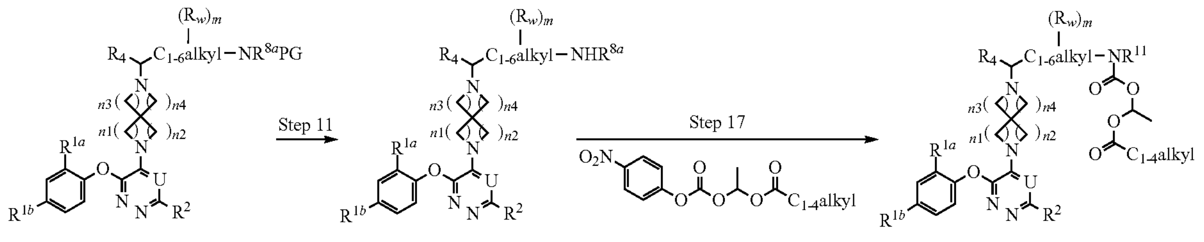

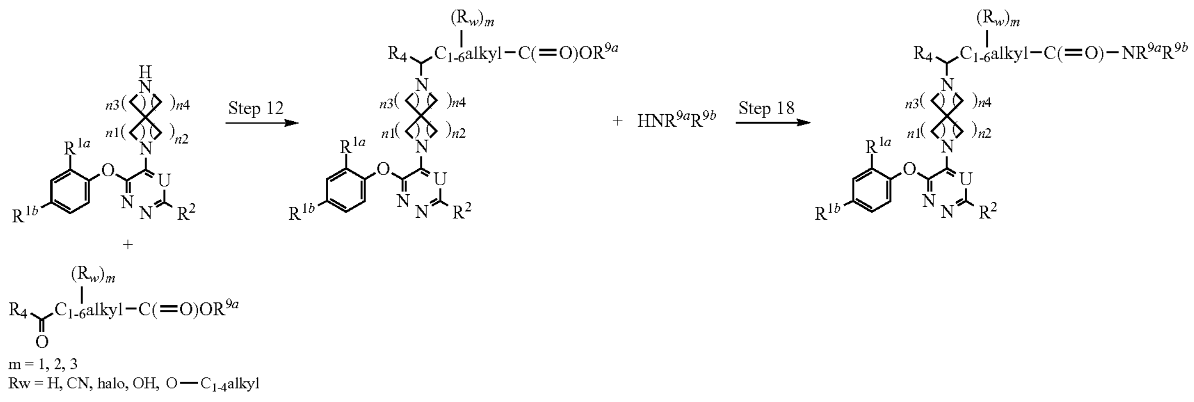

In Scheme 7, the following reaction conditions apply:

Step 11: When PG is Boc, at a suitable temperature such as for example RT, in the presence of a suitable acid as for example TFA, in a suitable solvent such as for example DCM;

Step 12: reductive amination condition, at a suitable temperature such as for example from RT to 80° C., in the presence or absence of a suitable Lewis acid such as for example $ZnCl_2$ or an acid for example AcOH, in the presence of a suitable reducing agent such as for example $NaBH_3CN$, in a suitable solvent such as for example MeOH;

Step 17: at a suitable temperature such as for example from RT to 80° C., in the presence of a suitable base such as for example DIEA or $Cs_2CO_3$, in suitable solvent such as for example DCM or DMF;

Step 18: at a suitable temperature such as for example 40° C., in the presence of a suitable base such as for example ammonia, in suitable solvent such as for 1,4-dioxane.

Scheme 8

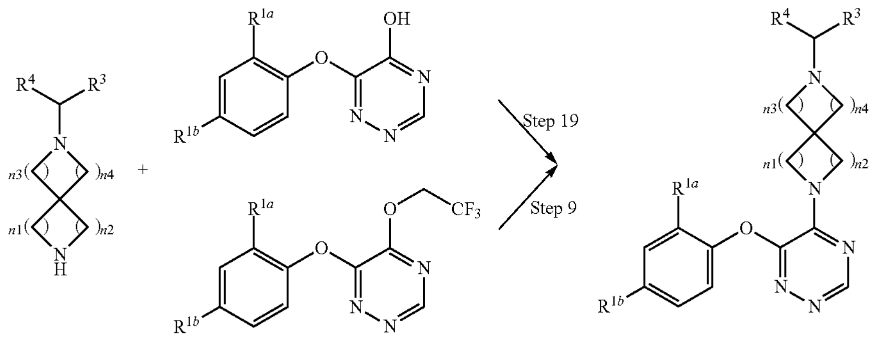

-continued

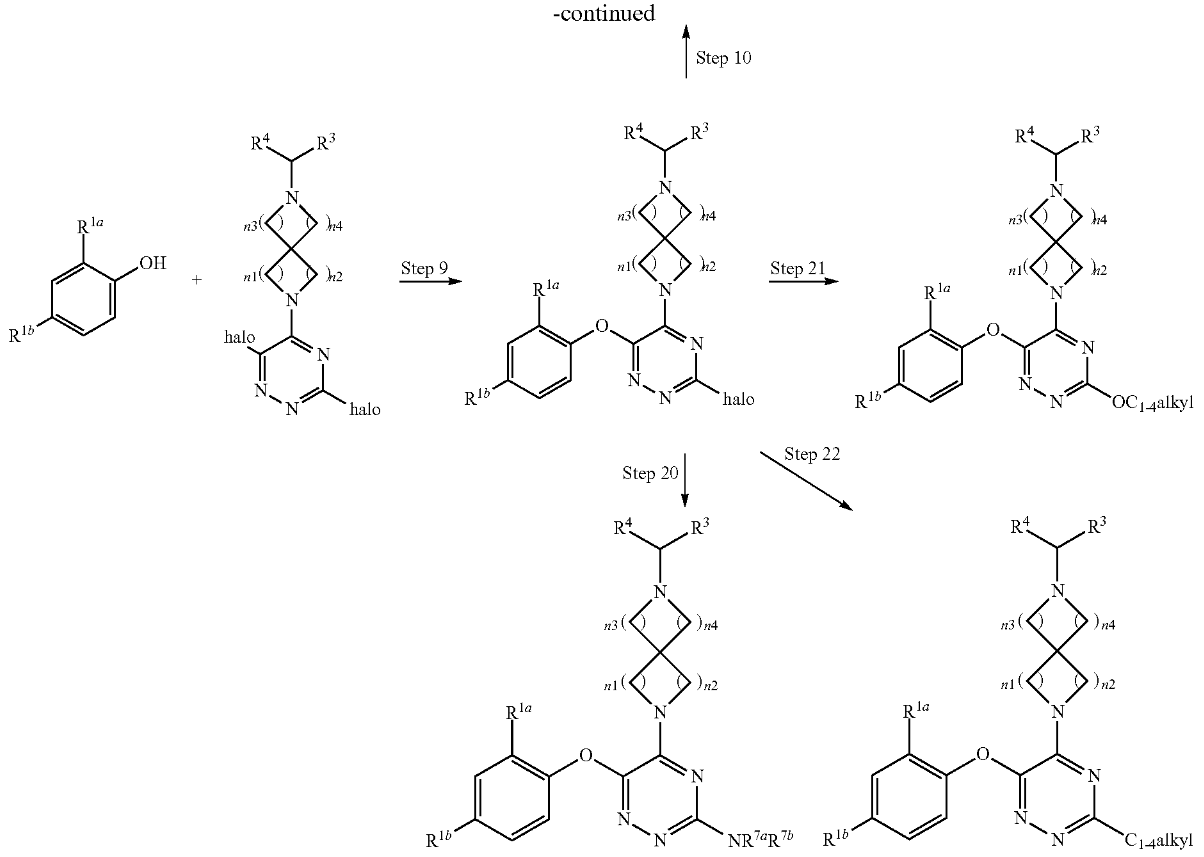

In Scheme 8, the following reaction conditions apply:

Step 9: at a suitable temperature such as for example from −78° C. to 40° C., in particular from 0° C. to RT, in the presence of a suitable base such as for example TEA, DBU or $K_2CO_3$, in a suitable solvent such as for example DCM, THF or DMF;

Step 10: at a suitable temperature such as for example RT, in the presence of a suitable organometallic catalyst as for example Pd/C, optionally in the presence of a suitable base as for example TEA, in a suitable solvent such as for example MeOH under $H_2$ atmosphere;

Step 19: at a suitable temperature such as for example RT, in the presence of a suitable chlorinating reagent such as for example oxalyl chloride, in the presence of DMF, in a suitable solvent such as for example DCM;

Step 20: at a suitable temperature such as for example 90° C., in the presence of a suitable nucleophilic amine, in a suitable solvent such as for example EtOH;

Step 21: at a suitable temperature such as for example RT, in the presence of a suitable acid such as for example HCl in dioxane, in a suitable solvent such as for example MeOH;

Step 22: at a suitable temperature such as for example 110° C., in the presence of a suitable boron reagent such as for example trimethylboroxine, in the presence of a suitable organometallic catalyst such as for example tetrakis(triphenylphosphine)palladium(0), in the presence of a suitable base such as for example $K_2CO_3$, in a suitable solvent such as for example 1,4-dioxane;

Scheme 9

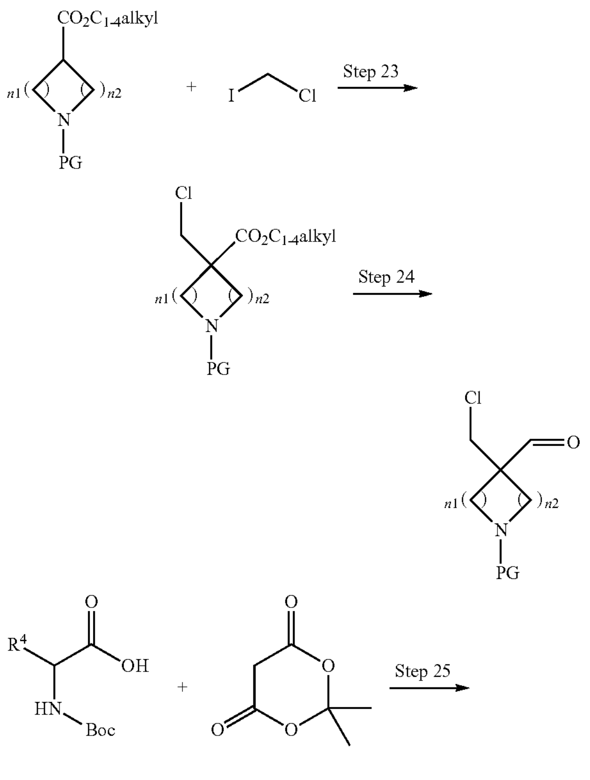

-continued
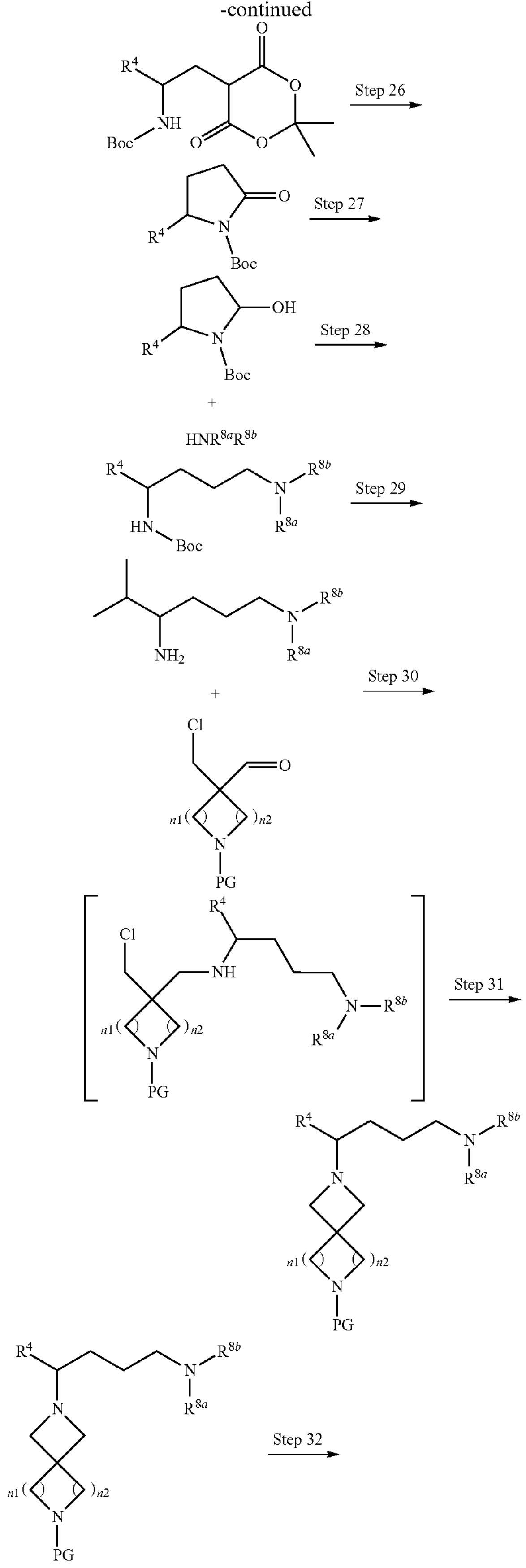
-continued
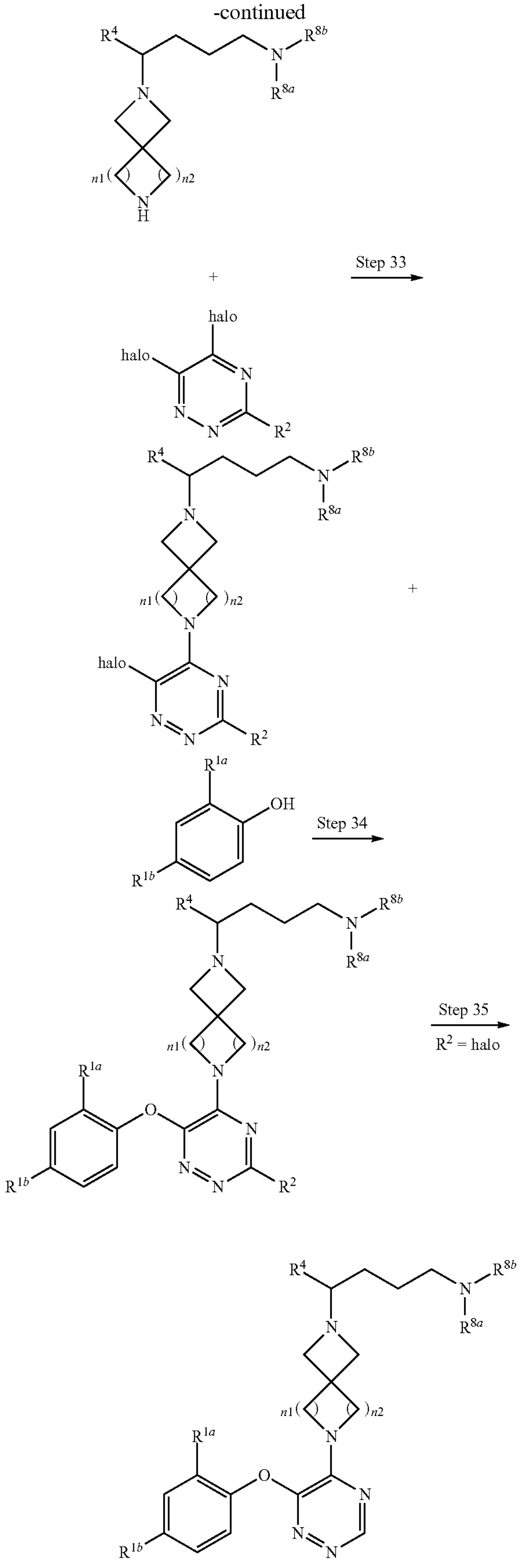

In Scheme 9, the following reaction conditions apply:

Step 23: at a suitable temperature such as for example from −78° C. to −25° C., in the presence of suitable bases such as for example DIEA and n-BuLi, in a suitable solvent such as for example THFs;

Step 24: at a suitable temperature such as for example between −65° C. and −55° C., in the presence of suitable reducing agent such as for example DIBAL-H, in a suitable solvent such as for example toluene, preferably conducted in a suitable flow chemistry system;

Step 25: first at a suitable temperature such as for example from −10° C. to 10° C., in the presence of a suitable base such as for example DMAP, in the presence of a suitable condensation agent such as for example DCC, in a suitable solvent such as for example DCM; then at a suitable temperature such as for example from −10° C. to 0° C., in the presence of a suitable acid such as for example AcOH, in the presence of a suitable reducing agent such as for example $NaBH_4$, in a suitable solvent such as for example DCM;

Step 26: in a suitable solvent such as for example toluene and heated to reflux;

Step 27: at a suitable temperature such as for example from −5° C. to 5° C., in the presence of suitable reducing agent such as for example $LiBH_4$, in a suitable solvent such as for example 2-methyltetrahydrofuran;

Step 28: at a suitable temperature such as for example from 15° C. to 25° C., in the presence of a suitable reducing agent such as for example $NaBH(OAc)_3$, in a suitable solvent such as for example DCM;

Step 29: at a suitable temperature such as for example from 15° C. to 25° C., in the presence of a suitable acid such as for HCl, in a suitable solvent such as for example IPA;

Step 30: at a suitable temperature such as for example from 5° C. to 30° C., in the presence of a suitable base such as for example TEA, in the presence of suitable reducing agent such as for example $NaBH(OAc)_3$, in a suitable solvent such as for example toluene;

Step 31: at a suitable temperature such as for example from 50° C. to 55° C., in the presence of a suitable base such as for example $K_2HPO_4$, in a suitable solvent such as for example $H_2O$;

Step 32: When PG is Bn at a suitable temperature such as for example from −5° C. to 45° C., under a hydrogen atmosphere within a suitable pressure range such as for example from 0.27 to 0.40 MPa, in the presence of a suitable catalyst such as for example palladium hydroxide on carbon, in the presence of a suitable acid as for example MSA in a suitable solvent such as EtOH;

Step 33: at a suitable temperature such as for example from −50° C. to −40° C., in the presence of suitable base such as for example TEA, in a suitable solvent such as 2-methyltetrahydrofuran;

Step 34: at a suitable temperature such as for example from 20° C. to 30° C., in the presence of suitable base such as for example TMG, in a suitable solvent such as 2-methyltetrahydrofuran;

Step 35: at a suitable temperature such as for example from 20° C. to 30° C., under a hydrogen atmosphere within a suitable pressure range such as for example from 0.20 to 0.30 Mpa, in the presence of a suitable catalyst such as for example palladium on carbon, in a suitable solvent such as MeOH;

alternatively, at a suitable temperature such as room temperature, in the presence of a suitable catalyst such as for example 1,1'-Bis(diphenylphosphino)ferrocene-palladium (II)dichloride dichloromethane complex, a suitable reducing agent such sodium borohydride, a suitable base such as for example N,N,N',N'-tetramethylethylenediamine, in a suitable solvent such as for example tetrahydrofuran.

Scheme 10

In general, compounds of Formula (I) wherein $Y^1$ is limited to —$CH_2$—, and $R^2$ is limited to $W^1$, hereby named compounds of Formula (Ia), can be prepared according to the following reaction Scheme 10. In Scheme 10, W represents chloro, bromo or iodo; all other variables are defined according to the scope of the present invention.

Scheme 10

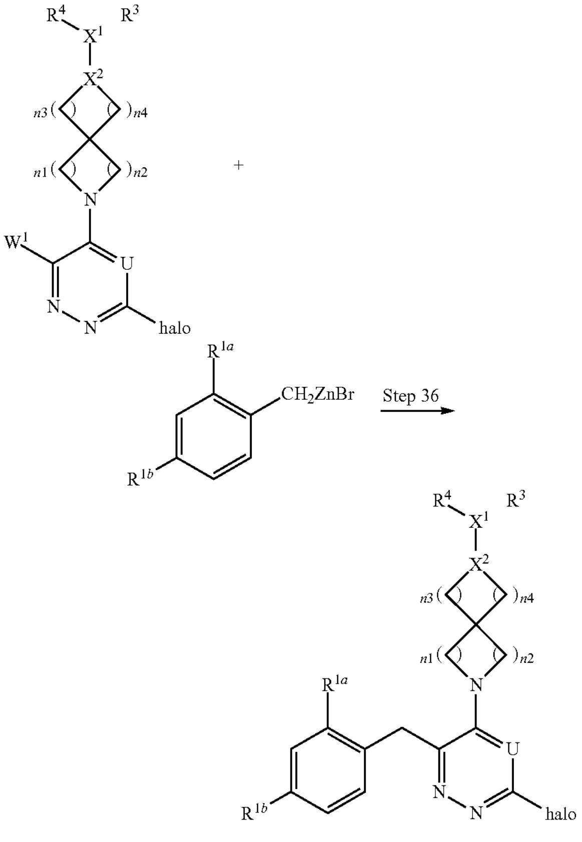

(Ia)

In Scheme 10, the following reaction conditions apply:

Step 36: at a suitable temperature ranged from 60° C. to 100° C., in presence of a suitable catalyst such as palladium acetate ($Pd(OAc)_2$) or tris(dibenzylideneacetone)dipalladium(0) ($Pd_2(dba)_3$) or tetrakis(triphenylphosphine)palladium(0), in a suitable solvent such as for example tetrahydrofuran or dioxane.

The skilled person will realize that starting from compound (Ia), analogous chemistry as reported in step 10 in scheme 5 and in steps 20, 21 and 22 in scheme 8 could be performed.

Scheme 11

In general, compounds of Formula (I) wherein $Y^1$ is limited to —$CR^{5a}R^{5b}$— and $R^2$ is limited to $W^1$, hereby named compounds of Formula (Ib), can be prepared according to the following reaction Scheme 11. In Scheme 11 at least one of $R^{5a}$ and $R^{5b}$ is other than hydrogen. All other variables are defined according to the scope of the present invention.

Scheme 11

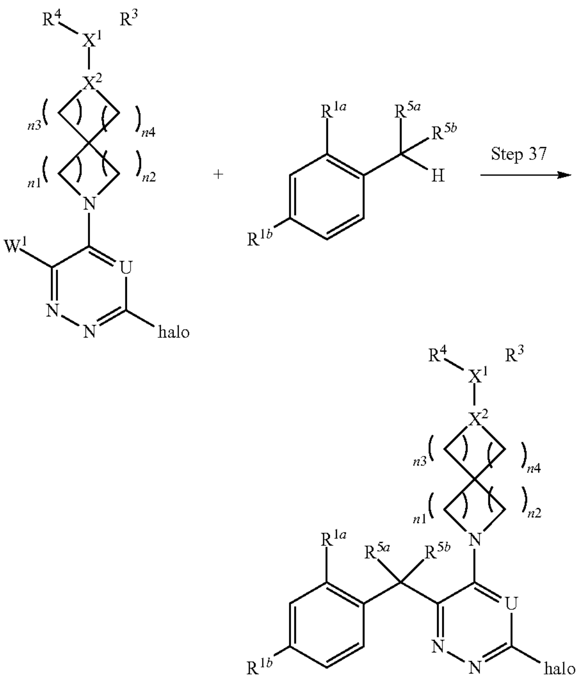

(Ib)

In Scheme 11, the following reaction condition apply:

Step 37: at a suitable temperature ranged from 80° C. to 200° C., in presence of a suitable catalyst such as palladium acetate ($Pd(OAc)_2$), in the presence of a suitable ligand such as for example triphenylphosphine or tricyclohexylphosphine, in a suitable solvent such as for example dioxane, preferably in sealed conditions, optionally under microwave irradiation.

The skilled person will realize that starting from compound (Ib), analogous chemistry as reported in step 10 in scheme 5 and in steps 20, 21 and 22 in scheme 8 could be performed.

Scheme 12

Scheme 12

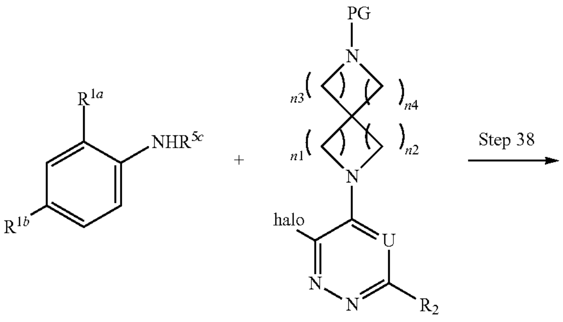

-continued

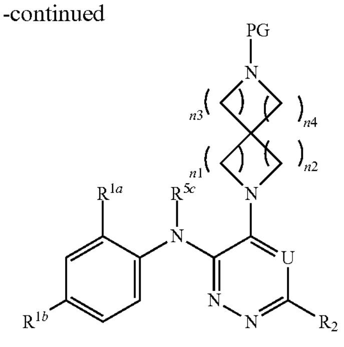

A

In Scheme 12, the following reaction condition apply:

Step 38: at a suitable temperature such as for example from RT to 80° C., in the presence of a suitable base such as for example DIEA, $Cs_2CO_3$ or DBU, in suitable solvent such as for example DCM, THF or DMF;

Alternatively, at a suitable temperature such as for example RT to 100° C., in the presence of a suitable catalyst such as for example $Pd_2dba_3$, in the presence of a suitable ligand such as for example Xantphos, in the presence of a suitable base such as $Cs_2CO_3$ or $Na_2CO_3$, in a suitable solvent such dioxane or a mixture of dioxane and water The skilled person will realize that starting from intermediate A, analogous chemistry as reported in case $Y^1$ represents O can be performed.

It will be appreciated that where appropriate functional groups exist, compounds of various formulae or any intermediates used in their preparation may be further derivatized by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formvlation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G.

M. Wuts, Protective Groups in Organic Synthesis, 4th ed., Wiley, Hoboken, New Jersey, 2007.

Pharmacology

It has been found that the compounds of the present invention block the interaction of menin with MLL proteins and oncogenic MLL fusion proteins per se, or can undergo metabolism to a (more) active form in vivo (prodrugs). Therefore the compounds according to the present invention and the pharmaceutical compositions comprising such compounds may be useful for the treatment or prevention, in particular treatment, of diseases such as cancer, including but not limited to leukemia, myelodysplastic syndrome (MDS), and myeloproliferative neoplasms (MPN); and diabetes.

In particular, the compounds according to the present invention and the pharmaceutical compositions thereof may be useful in the treatment or prevention of cancer. According to one embodiment, cancers that may benefit from a treatment with menin/MLL inhibitors of the invention comprise leukemias, lymphomas, myelomas or solid tumor cancers (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

In particular, the compounds according to the present invention and the pharmaceutical compositions thereof may be useful in the treatment or prevention of myelodysplastic syndrome (MDS) or myeloproliferative neoplasms (MPN).

In particular, compounds according to the present invention and the pharmaceutical compositions thereof may be useful in the treatment or prevention of leukemias, in particular nucleophosmin (NPM1)-mutated leukemias, e.g. NPM1c.

In particular, compounds according to the present invention and the pharmaceutical compositions thereof may be useful in the treatment or prevention of AML, in particular nucleophosmin (NPM1)-mutated AML (i.e., $NPM1^{mut}$ AML), more in particular abstract NPM1-mutated AML.

In particular, compounds according to the present invention and the pharmaceutical compositions thereof may be useful in the treatment or prevention of MLL-rearranged leukemias, in particular MLL-rearranged AML or ALL.

In particular, compounds according to the present invention and the pharmaceutical compositions thereof may be useful in the treatment or prevention of leukemias with MLL gene alterations, in particular AML or ALL with MLL gene alterations.

In particular, compounds according to the present invention and the pharmaceutical compositions thereof may be suitable for Q.D. dosing (once daily).

In particular, compounds according to the present invention and the pharmaceutical compositions thereof may be useful in the treatment or prevention of hematological cancer in a subject exhibiting NPM1 gene mutations and/or mixed lineage leukemia gene (MLL; MLL1; KMT2A) alterations, mixed lineage leukemia (MLL), MLL-related leukemia, MLL-associated leukemia, MLL-positive leukemia, MLL-induced leukemia, rearranged mixed lineage leukemia, leukemia associated with a MLL, rearrangement/alteration or a rearrangement/alteration of the MLL gene, acute leukemia, chronic leukemia, myelodysplastic syndrome (MDS), myeloproliferative neoplasms (MPN), insulin resistance, pre-diabetes, diabetes, or risk of diabetes, hyperglycemia, chromosomal rearrangement on chromosome 11q23, type-1 diabetes, type-2 diabetes; promoting proliferation of a pancreatic cell, where pancreatic cell is an islet cell, beta cell, the beta cell proliferation is evidenced by an increase in beta cell production or insulin production; and for inhibiting a menin-MLL interaction, where the MLL fusion protein target gene is HOX or MEIS1 in human.

Hence, the invention relates to compounds of Formula (I), the tautomers and the stereoisomeric forms thereof, and the pharmaceutically acceptable salts, and the solvates thereof, for use as a medicament.

The invention also relates to the use of a compound of Formula (I), a tautomer or a stereoisomeric form thereof, or a pharmaceutically acceptable salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable salt, or a solvate thereof, or a pharmaceutical composition according to the invention, for use in the treatment, prevention, amelioration, control or reduction of the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

Also, the present invention relates to the use of a compound of Formula (I), a tautomer or a stereoisomeric form thereof, or a pharmaceutically acceptable salt, or a solvate thereof, or a pharmaceutical composition according to the invention, for the manufacture of a medicament for treating, preventing, ameliorating, controlling or reducing the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

The invention also relates to a compound of Formula (I), a tautomer or a stereoisomeric form thereof, or a pharmaceutically acceptable salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), the tautomers and the stereoisomeric forms thereof, and the pharmaceutically acceptable salts, and the solvates thereof, there is provided a method of treating warm-blooded animals, including humans, suffering from any one of the diseases mentioned hereinbefore.

Said method comprises the administration, i.e. the systemic or topical administration, of a therapeutically effective amount of a compound of Formula (I), a tautomer or a stereoisomeric form thereof, or a pharmaceutically acceptable salt, or a solvate thereof, to warm-blooded animals, including humans.

Therefore, the invention also relates to a method for the treatment or prevention of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. An effective therapeutic daily amount would be from about 0.005 mg/kg to 100 mg/kg. The amount of a compound according to the present invention, also referred to herein as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture).

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition, in particular tumour, being treated and the particular host being treated.

The following examples further illustrate the present invention.

EXAMPLES

Several methods for preparing the compounds of this invention are illustrated in the following examples. Unless otherwise noted, all starting materials were obtained from commercial suppliers and used without further purification, or alternatively can be synthesized by a skilled person by using well-known methods.

| Abbreviation | Meaning |
|---|---|
| $Ag(Phen)_2OTf$ | silver triflate-bis(1,10-phenanthroline) complex |
| 2-MeTHF | 2-methyltetrahydrofuran |
| ACN | acetonitrile |
| AcCl | acetyl chloride |
| AcOH | acetic acid |
| $Ac_2O$ | acetic anhydride |
| aq. | aqueous |
| Ar | argon |
| $BBr_3$ | tribromoborane |
| bn | benzyl |
| Boc | tert-butyloxy carbonyl |
| $Boc_2O$ | di-tert-butyl dicarbonate |
| n-BuLi | n-butyllithium |
| Cbz | benzyloxy carbonyl |
| $CD_3OD$ | Methanol-$d_4$ |
| $CHCl_3$ | chloroform |
| $Cs_2CO_3$ | cesium carbonate |
| conc. | concentrated |
| DBU | 1,8-diazabicyclo[5.4.0]undec-7-ene |
| DCC | dicyclohexylcarbodiimide |
| DCE | dichloroethane |
| DCM | dichloromethane |
| DDQ | 4,5-dichloro-3,6-dioxocyclohexa-1,4-diene-1,2-dicarbonitrile |
| DEA | diethylamine |
| DIBAL-H | diisobutylaluminum hydride |
| DIEA or DIPEA | N,N-diisopropylethylamine |
| DMAP | N,N-dimethylpyridin-4-amine |
| DMF | N,N-dimethylformamide |
| DMP | Dess-Martin periodinane |
| DMSO | dimethyl sulfoxide |
| dppf | 1,1'-ferrocenediyl-bis(diphenylphosphine) |
| EDCI | N-(3-Dimethylaminopropyl)-N'-ethylcarbodiimide hydrochloride |
| EA or EtOAc | ethyl acetate |
| EtOH | ethanol |
| eq. | equivalent(s) |
| FA | formic acid |
| FCC | flash column chromatography |
| h | hour(s) |
| $H_2$ | hydrogen |
| HATU | 1-[bis(dimethylamino)methylene]-1H-1,2,3-triazolo [4,5-b]pyridinium 3-oxid hexafluorophosphate |
| $H_2O$ | water |

-continued

| Abbreviation | Meaning |
|---|---|
| HCl | hydrochloric acid |
| HOBt | 1-Hydroxy benzotriazole |
| HPLC | high performance liquid chromatography |
| $ICH_2Cl$ | chloroiodomethane |
| IPA | isopropyl alcohol |
| IPAc | isopropyl acetate |
| $K_2CO_3$ | potassium carbonate |
| KI | potassium iodide |
| $K_2HPO_4$ | dipotassium phosphate |
| $K_3PO_4$ | tripotassium phosphate |
| $LiAlD_4$ | lithium aluminum deuteride |
| LAH | lithium aluminum hydride |
| $LiBH_4$ | lithium borohydride |
| LDA | lithium diisopropylamide |
| LiCl | lithium chloride |
| LG | leaving group |
| Me | methyl |
| MeOH | methanol |
| 2-MeTHF | 2-methyltetrahydrofuran |
| min | minute(s) |
| mL | milliliters |
| mmol | millimoles |
| mg | milligram |
| $MgSO_4$ | magnesium sulfate |
| MSA | methanesulfonic acid |
| MsCl | methanesulfonyl chloride |
| MS | molecular sieve |
| MTBE | methyl tert-butyl ether |
| $N_2$ | nitrogen |
| NA | not available |
| $NaBH_3CN$ | sodium cyanoborohydride |
| $NaBH(OAc)_3$ | sodium triacetoxyborohydride |
| $NaBD_3CN$ | sodium cyanoborodeuteride |
| $Na_2CO_3$ | sodium carbonate |
| NaH | sodium hydride |
| $NaHCO_3$ | sodium bicarbonate |
| NaI | sodium iodide |
| NaOAc | sodium acetate |
| NaOH | sodium hydroxide |
| $Na_2SO_3$ | sodium sulfite |
| $Na_2SO_4$ | sodium sulfate |
| $NH_4Cl$ | ammonium chloride |
| NMM | 1-4-Methylmorpholine |
| $Pd_2dba_3$ | tris(dibenzylideneacetone)dipalladium(0) |
| $Pd(dppf)Cl_2$•DCM | [1,1'-bis(diphenylphosphino)ferrocene] dichloropalladium(II), complex with dichloromethane |
| $Pd(PPh_3)_4$ | tetrakis(triphenylphosphine)palladium(0) |
| PE | petroleum ether |
| PG | protecting group |
| Phen | phenanthroline |
| psi | pound per square inch |
| p-TsOH | p-toluenesulfonic acid |
| p-TsOH•$H_2O$ | p-toluenesulfonic acid monohydrate |
| $R_t$ | retention time |
| Rochelle's salt | potassium sodium tartrate tetrahydrate |
| RT | room temperature |
| sat. | saturated |
| SFC | supercritical fluid chromatography |
| TBAF | tetrabutyl ammonium fluoride |
| TBDMS | tert-butyldimethylsilyl |
| TBDPS | tert-butyldiphenylsilyl |
| t-BuOK | potassium tert-butoxide |
| TEA | triethylamine |
| Tf | trifluoromethanesulfonyl |
| TFA | trifluoroacetic acid |
| THF | tetrahydrofuran |
| $Ti(OiPr)_4$ | titanium(IV) isopropoxide |
| TLC | thin layer chromatography |
| TMEDA | N,N,N',N'-tetramethylethylenediamine |
| TMG | 1,1,3,3-tetramethylguanidine |
| TMSI | iodotrimethylsilane |
| Ts | p-toluenesulfonyl |
| TsCl | p-toluenesulfonyl chloride |
| v/v | volume per volume |
| Abbreviation | Meaning |
| vol. | volume(s) |

-continued

| Abbreviation | Meaning |
|---|---|
| wt | weight |
| Xantphos | 4,5-bis(diphenylphosphino)-9,9-dimethylxanthene |

As understood by a person skilled in the art, compounds synthesized using the protocols as indicated may exist as a solvate e.g. hydrate, and/or contain residual solvent or minor impurities. Compounds or intermediates isolated as a salt form, may be integer stoichiometric i.e. mono- or di-salts, or of intermediate stoichiometry. When an intermediate or compound in the experimental part below is indicated as 'HCl salt' without indication of the number of equivalents of HCl, this means that the number of equivalents of HCl was not determined. The same principle will also apply to all other salt forms referred to in the experimental part, such as e.g. 'oxalate salt', 'formate salt' or

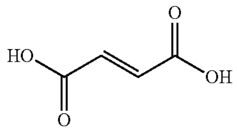
salt'.

The stereochemical configuration for centers in some compounds may be designated "R" or "S" when the mixture(s) was separated and absolute stereochemistry was known, or when only one enantiomer was obtained and absolute stereochemistry was known; for some compounds, the stereochemical configuration at indicated centers has been designated as "*R" (first eluted from the column in case the column conditions of the separation are described in the synthesis protocol and when only one stereocenter present or indicated) or "*S" (second eluted from the column in case the column conditions of the separation are described in the synthesis protocol and when only one stereocenter present or indicated) when the absolute stereochemistry is undetermined (even if the bonds are drawn stereo specifically) although the compound itself has been isolated as a single stereoisomer and is enantiomerically pure. In case a compound designated as "*R" is converted into another compound, the "*R" indication of the resulting compound is derived from its starting material.

For example, it will be clear that Compound 25

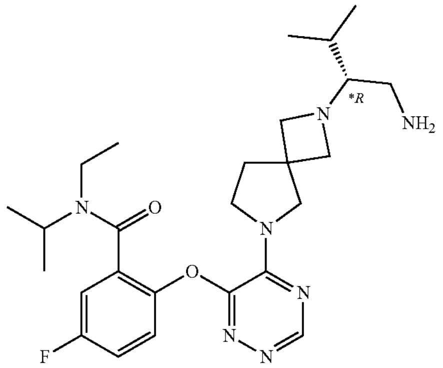
is

-continued

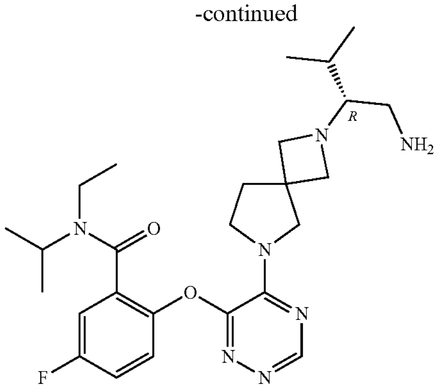

or

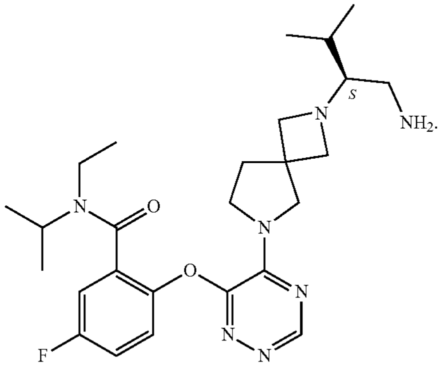

When "*R" or "*S" occurs together with a 2nd stereocentre which is designated "R" or "S" (known absolute stereochemistry for 2nd stereocentre) in the same molecule, the absolute stereochemistry of the stereocentre designated "*R" or "*S" is undetermined (even if the bonds are drawn stereo specifically) although the compound itself has been isolated as a single stereoisomer and is enantiomerically pure. "*R" or "*S" is assigned randomly for such molecules. For example, it will be clear that Compound 340

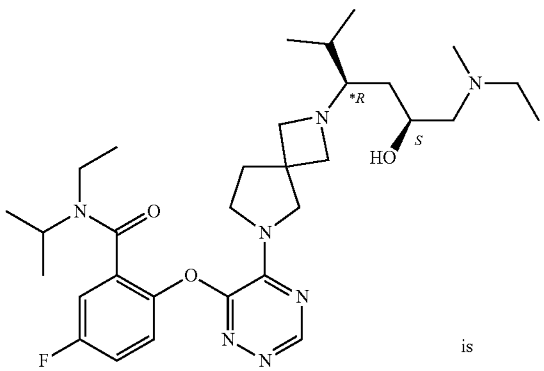

is

-continued

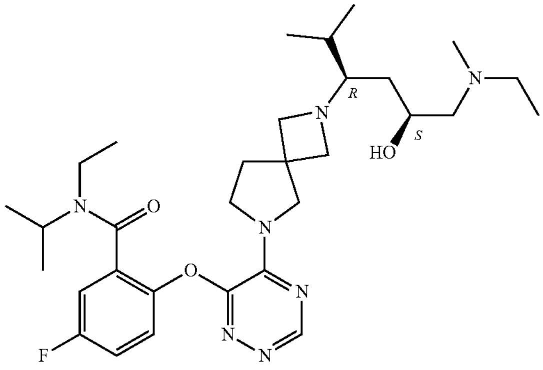

or

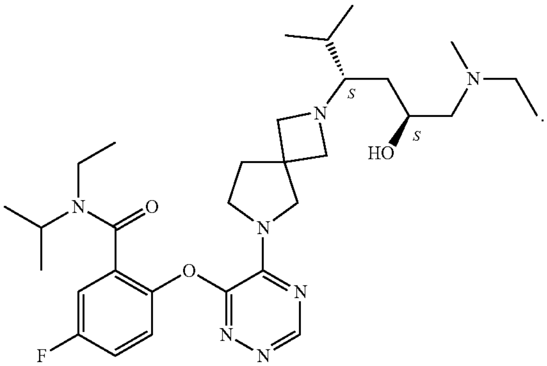

For compounds wherein the stereochemical configuration of two stereocentres is indicated by * (e.g. *R or *S), the absolute stereochemistry of the stereocentres is undetermined (even if the bonds are drawn stereospecifically), although the compound itself has been isolated as a single stereoisomer and is enantiomerically pure. In this case, the configuration of the first stereocentre is independent of the configuration of the second stereocentre in the same compound. "*R" or "*S" is assigned randomly for such molecules.

For example, for Compound 306

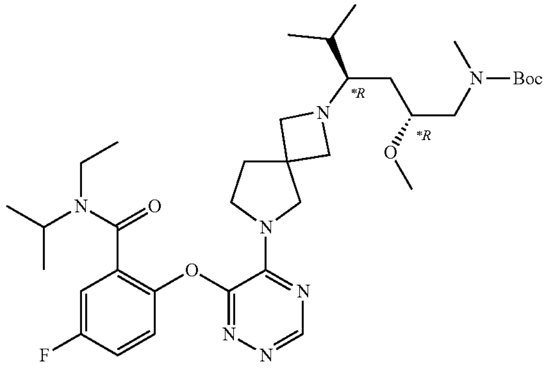

this means that the compound is

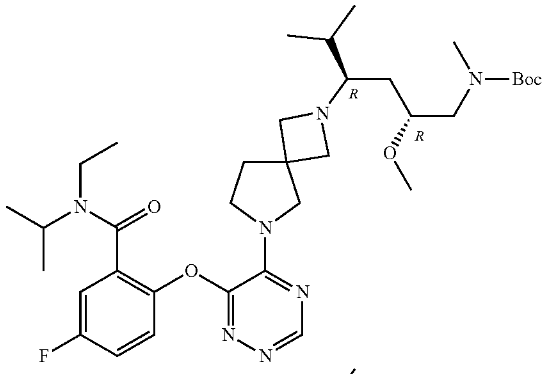

or

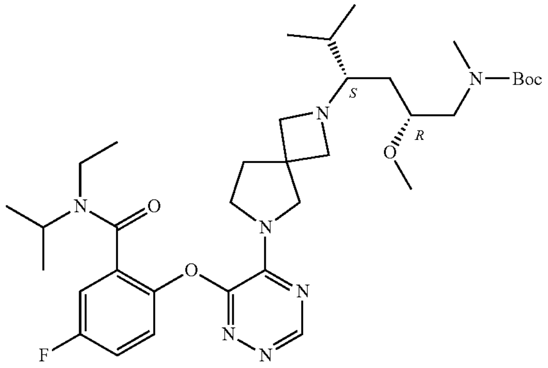

or

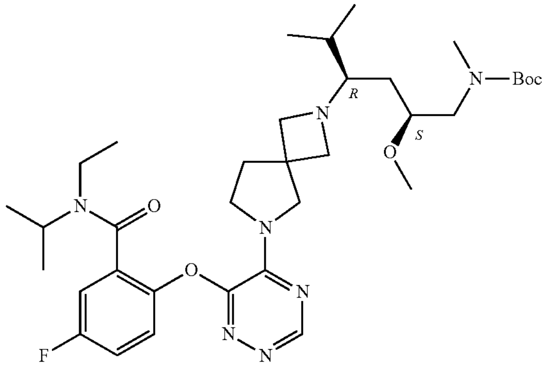

or

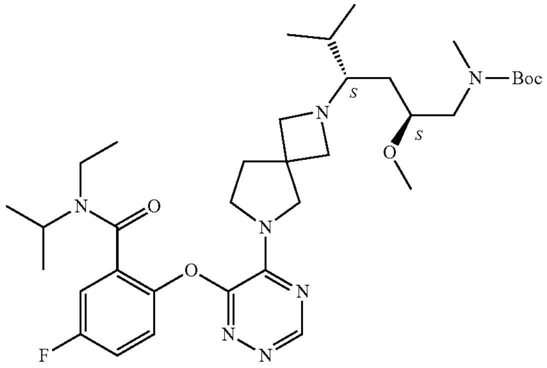

A skilled person will realize that the paragraphs above about stereochemical configurations, also apply to intermediates.

A skilled person will realize that, even where not mentioned explicitly in the experimental protocols below, typically after a column chromatography purification, the desired fractions were collected and the solvent was evaporated.

In case no stereochemistry is indicated, this means it is a mixture of stereoisomers, unless otherwise is indicated or is clear from the context.

When a stereocenter is indicated with 'RS' this means that a racemic mixture was obtained at the indicated centre, unless otherwise indicated.

Preparation of Intermediates

For intermediates that were used in a next reaction step as a crude or as a partially purified intermediate, in some cases no mol amounts are mentioned for such intermediate in the next reaction step or alternatively estimated mol amounts or theoretical mol amounts for such intermediate in the next reaction step are indicated in the reaction protocols described below.

Preparation of Intermediate 27

N-ethyl-5-fluoro-N-isopropyl-2-methoxybenzamide

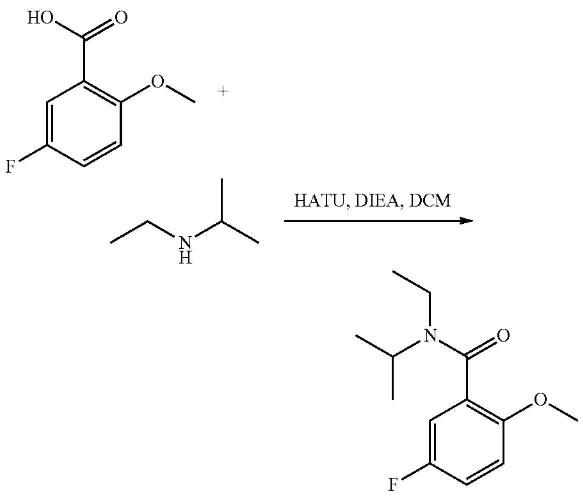

To the mixture of 5-fluoro-2-methoxybenzoic acid (8.00 g, 47.0 mmol) and N-ethylpropan-2-amine (8.19 g, 94.0 mmol) in dry DCM (150 mL) cooled at 0° C., were slowly added HATU (21.5 g, 56.5 mmol) and DIEA (9.10 g, 70.4 mmol) in portions. The resulting mixture was slowly warmed to RT and stirred for 8 h. The organic layer was washed with water (20 mL×3) and dried over anhydrous $Na_2SO_4$. After filtration, the solvent was removed under reduced pressure and the crude product was purified by FCC (EtOAc/PE=0% to 20%) to afford the title intermediate (12.0 g, 96% yield) as a white solid.

Preparation of Intermediate 67, 235, 246

5-fluoro-N,N-diisopropyl-2-methoxybenzamide 5-fluoro-2-methoxy-N-(propan-2-yl-$^{13}C_3$)benzamide 5-fluoro-N-isopropyl-2-methoxy-N-methylbenzamide The following intermediate was synthesized by an analogous method as described above for intermediate 27

| Int. No. | Structure | Starting Materials |
|---|---|---|
| 67 | 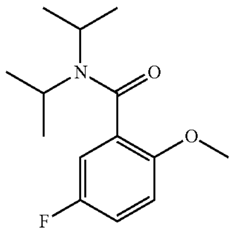 [SMILES: COc1ccc(F)cc1C(=O)N(C(C)C)C(C)C] | 5-fluoro-2-methoxybenzoic acid, diisopropylamine |
| 235 | 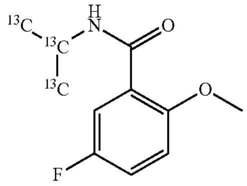 | 5-fluoro-2-methoxybenzoic acid, propan-2-amine-1,2,3 -$^{13}C_3$ |
| 246 | 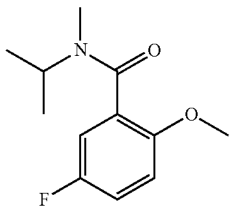 [SMILES: COc1ccc(F)cc1C(=O)N(C)C(C)C] | 5-fluoro-2-methoxybenzoic acid, N-methylpropan-2-amine |

Preparation of Intermediate 28

N-ethyl-5-fluoro-2-hydroxy-N-isopropylbenzamide

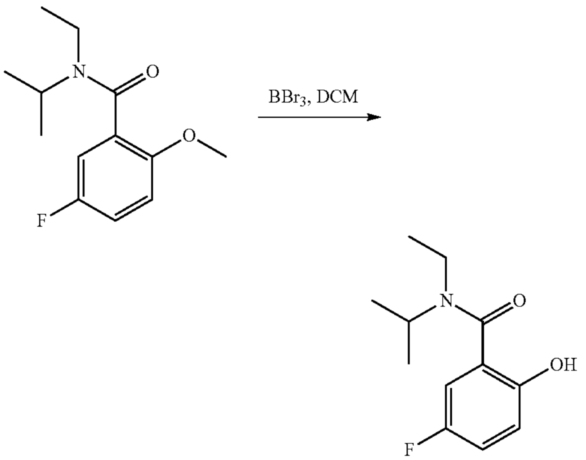

To the solution of N-ethyl-5-fluoro-N-isopropyl-2-methoxybenzamide (intermediate 27) (12.0 g, 50.1 mmol) in dry DCM (100 mL) cooled at −78° C. was slowly added $BBr_3$ (14.4 mL, 152 mmol), the resulting mixture was slowly warmed to RT and stirred for 8 h. The mixture was cooled to −78° C. again and MeOH (5 mL) was added dropwise to quench the reaction. The resulting mixture was slowly warmed to RT and the pH value was adjusted to about 8 by adding sat. aq. $NaHCO_3$ solution. The aqueous layer was extracted by DCM (50 mL×3) and the combined organic layers were dried over anhydrous $Na_2SO_4$, filtered and concentrated under reduced pressure to give the crude product which was purified by FCC (EtOAc/PE=0% to 20%) to afford the title intermediate (9.0 g, 78% yield) as a white solid.

Preparation of Intermediate 68, 237, 247

5-fluoro-2-hydroxy-N,N-diisopropylbenzamide

N-(ethyl-$^{13}C_2$)-5-fluoro-2-hydroxy-N-(propan-2-yl-$^{13}C_3$)benzamide 5-fluoro-2-hydroxy-N-isopropyl-N-methylbenzamide The following intermediate was synthesized by an analogous method as described above for intermediate 28

| Int. No. | Structure | Starting Materials |
|---|---|---|
| 68 | 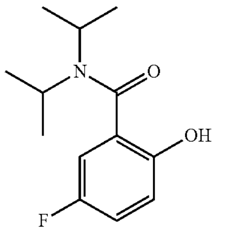 [SMILES: CC(C)N(C(=O)c1cc(F)ccc1O)C(C)C] | intermediate 67 |
| 237 | 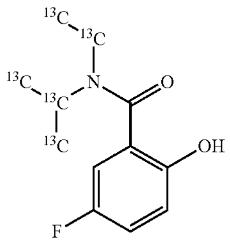 [SMILES: [13CH3][13CH2]N(C(=O)c1cc(F)ccc1O)[13CH]([13CH3])[13CH3]] | intermediate 236 |
| 247 | 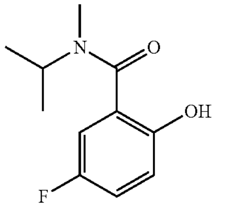 | intermediate 246 |

Preparation of Intermediate 60

5-bromo-4-cyclopropylpyrmidine

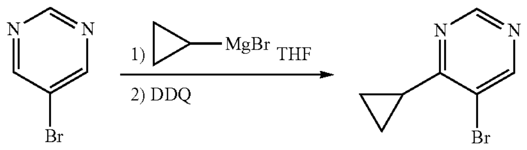

To a solution of 5-bromopyrimidine (30 g, 189 mmol) in THF (1000 mL) was added cyclopropylmagnesium bromide (396 mL, 198 mmol, 0.5 M in THF) at 0° C. under $N_2$ atmosphere. After addition, the reaction mixture was stirred at RT for 4 h, then a solution of DDQ (42.8 g, 189 mmol) in THF (500 mL) was added dropwise into the reaction mixture at 0° C. After addition, the reaction mixture was stirred at RT for 16 h. The reaction mixture was concentrated in vacuo and the residue was partitioned between EtOAc (200 mL) and water (200 mL), and the aqueous layer was extracted by EtOAc (200 mL×3). The combined organic layers were washed with 1N NaOH (200 mL×2), brine (200 mL), dried over $Na_2SO_4$, filtered. The filtrate was concentrated in vacuo and the residue was purified by FCC (EtOAc/PE=0% to 15%) to afford the title intermediate (21.4 g, 55% yield) as white solid.

Preparation of Intermediate 61

2-(4-cyclopropylpyrimidin-5-yl)-4-fluorophenol

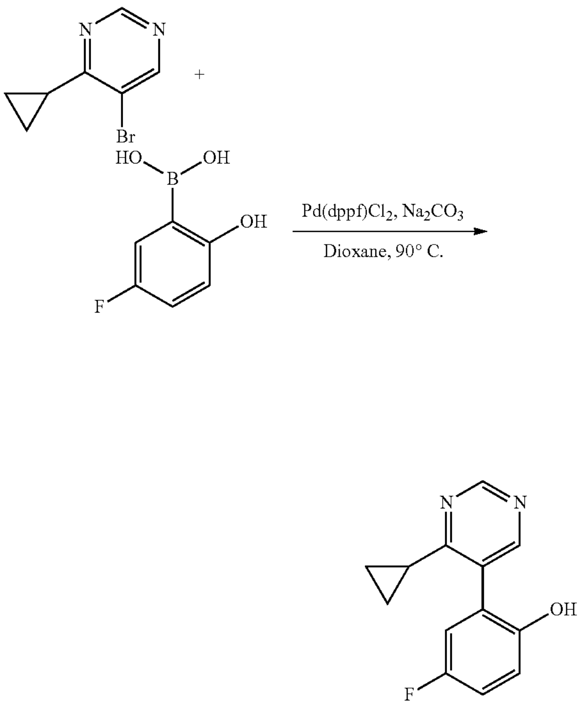

The mixture of 5-bromo-4-cyclopropylpyrimidine (intermediate 60) (20.0 g, 100 mmol), (5-fluoro-2-hydroxyphenyl)boronic acid (18.7 g, 120 mmol), $Pd(dppf)Cl_2$ (3.68 g, 5.03 mmol) and $Na_2CO_3$ (2 M in $H_2O$, 101 mL, 202 mmol) in 1,4-dioxane (350 mL) was heated at 90° C. for 12 h under $N_2$ atmosphere. After cooled to RT, the reaction mixture was filtered through a celite pad, the filtrate was suspended into water (400 mL) and further extracted with EtOAc (200 mL×3). The combined organic layers were dried over anhydrous $Na_2SO_4$, filtered and concentrated under reduced pressure to give the crude product, which was purified by FCC on silica gel (PE/EtOAc=1:0 to 3:1) to afford the title intermediate (24.0 g, 95% purity, 98.6% yield) as a brown solid.

Preparation of Intermediate 13 tert-butyl 6-(3,6-dichloro-1,2,4-triazin-5-yl)-2,6-diazaspiro[3.4]octane-2-carboxylate

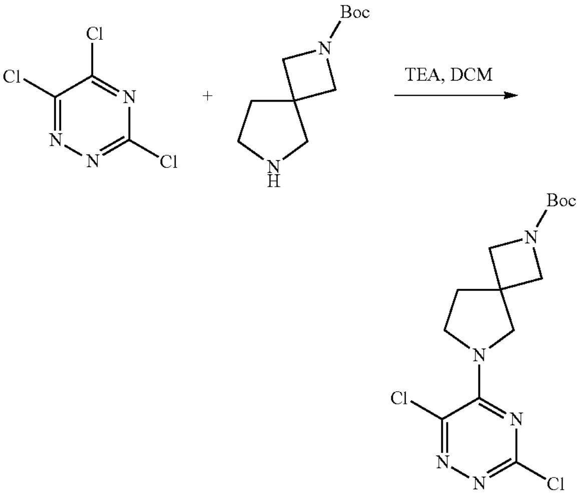

To the solution of 3,5,6-trichloro-1,2,4-triazine (10.0 g, 54.2 mmol) and TEA (15.2 mL, 109 mmol) in DCM (100 mL) cooled at 0° C. was added tert-butyl 2,6-diazaspiro[3.4]octane-2-carboxylate (9.21 g, 43.4 mmol), the mixture was warmed to RT and stirred for 1 h. The mixture was diluted with water (20 mL) and extracted with DCM (30 mL×3). The combined organic layers were washed with brine, dried over $Na_2SO_4$, filtered and concentrated under reduced pressure to give the crude product which was purified by FCC on silica gel (PE/EtOAc=1:0 to 3:1) to afford the title intermediate (12.0 g, 58% yield) as a yellow solid.

Preparation of Intermediate 69 tert-butyl 6-(3-chloropyridazin-4-yl)-2,6-diazaspiro[3.4]octane-2-carboxylate

The following intermediate was synthesized by an analogous method as described above for intermediate 13

| Int. No. | Structure | Starting Materials |
|---|---|---|
| 69 | 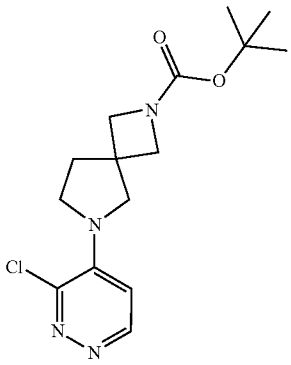 [SMILES: CC(C)(C)OC(=O)N1CC2(CCN(c3ccnnc3Cl)C2)C1] | 3,4-dichloropyridazine, tert-butyl 2,6-diazaspiro[3.4] octane-2-carboxylate |

Preparation of Intermediate 14 tert-butyl 6-(3-chloro-6(2-(ethyl(isopropyl)carbamoyl)-4-fluorophenoxy)-1,2,4-triazin-5-yl)-2,6-diazaspiro[3.4]octane-2-carboxylate

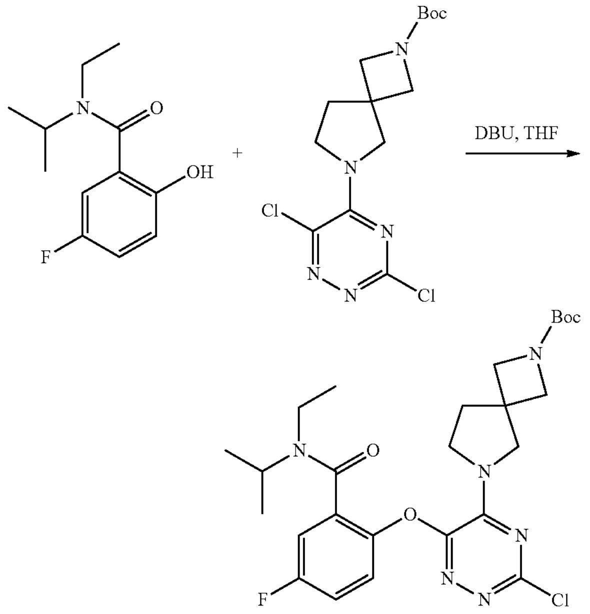

The mixture of tert-butyl 6-(3,6-dichloro-1,2,4-triazin-5-yl)-2,6-diazaspiro[3.4]octane-2-carboxylate (intermediate 13) (12.0 g, 33.3 mmol), N-ethyl-5-fluoro-2-hydroxy-N-isopropylbenzamide (intermediate 28) (7.5 g, 33.3 mmol) and DBU (6.1 g, 40.1 mmol) in THF (120 mL) was stirred at 25° C. for 8 h. The mixture was diluted with water (30 mL) and extracted with DCM (30 mL×3). The combined organic layers were washed with brine, dried over $Na_2SO_4$, filtered and concentrated under reduced pressure to give the crude product which was purified by FCC (PE/EtOAc=1:0 to 3:1) to afford the title intermediate (14.0 g, 73% yield) as green solid.

Preparation of Intermediates 57, 74, 70, and 83 tert-butyl 6-(3-chloro-(2-(4-cyclopropylpyrimidin-5-yl)-4-fluorophenoxy)-1,2,4-triazin-5-yl)-2,6-diazaspiro[3.4]octane-2-carboxylate tert-butyl 6-(3-(2-(ethyl(isopropyl)carbamoyl)-4-fluorophenoxy)pyridazin-4-yl)-2,6-diazaspiro[3.4]octane-2-carboxylate tert-butyl 6-(3-(2-(diisopropylcarbamoyl)-4-fluorophenoxy)pyridazin-4-yl)-2,6-diazaspiro[3.4]octane-2-carboxylate tert-butyl 6-(3-chloro-6-(2-(diisopropylcarbamoyl)-4-fluorophenoxy)-1,2,4-triazin-5-yl)-2,6-diazaspiro[3.4]octane-2-carboxylate The following intermediates were synthesized by an analogous method as described above for intermediate 14

| Int. No. | Structure | Starting Materials |
|---|---|---|
| 57 | 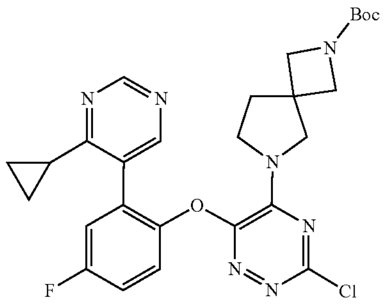 [SMILES: CC(C)(C)OC(=O)N1CC2(CCN(c3nc(Cl)nnc3Oc3ccc(F)cc3-c3cncnc3C3CC3)C2)C1] | intermediate 61, intermediate 13 |
| 74 | 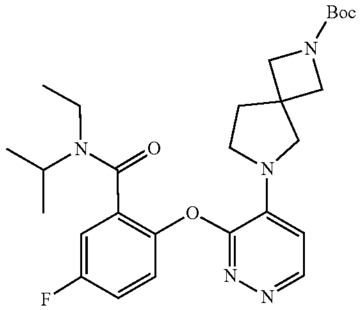 [SMILES: CCN(C(=O)c1cc(F)ccc1Oc1nnccc1N1CCC2(CN(C(=O)OC(C)(C)C)C2)C1)C(C)C] | intermediate 28, intermediate 69 |
| 70 | 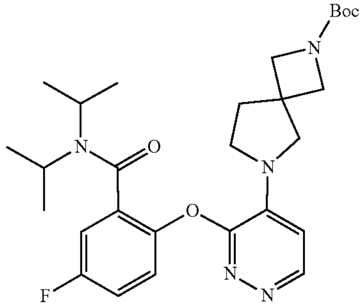 [SMILES: CC(C)N(C(=O)c1cc(F)ccc1Oc1nnccc1N1CCC2(CN(C(=O)OC(C)(C)C)C2)C1)C(C)C] | intermediate 68, intermediate 69 |
| 83 | 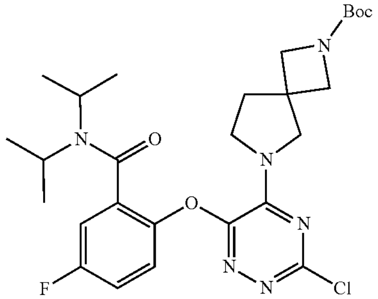 [SMILES: CC(C)N(C(=O)c1cc(F)ccc1Oc1nnc(Cl)nc1N1CCC2(CN(C(=O)OC(C)(C)C)C2)C1)C(C)C] | intermediate 68, intermediate 13 |

Preparation of Intermediate 2 tert-butyl 6-(6-(2-(ethyl(isopropyl)carbamoyl)-4-fluorophenoxy)-1,2,4-triazin-5-yl)-2,6-diazaspiro[3.4]octane-2-carboxylate Method A

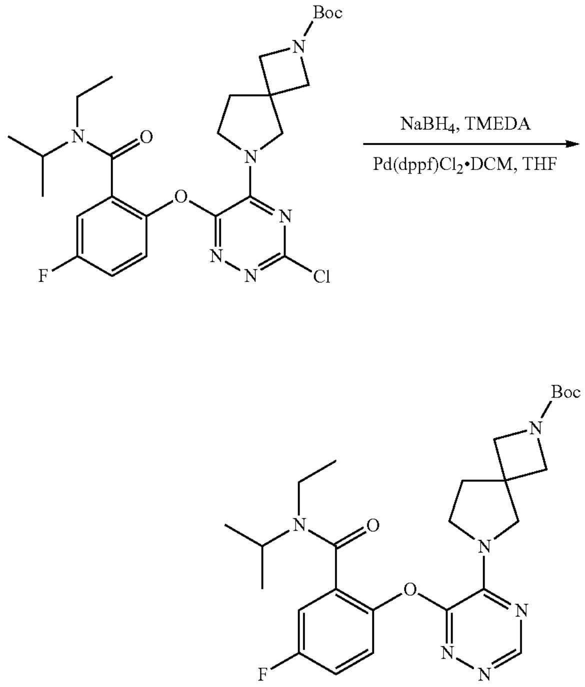

To the mixture of tert-butyl 6-(3-chloro-6-(2-(ethyl(isopropyl)carbamoyl)-4-fluorophenoxy)-1,2,4-triazin-5-yl)-2,6-diazaspiro[3.4]octane-2-carboxylate (intermediate 14) (20 g, 36.4 mmol), $NaBH_4$ (2.48 g, 65.7 mmol) and TMEDA (8.54 g, 73.5 mmol) in THF (500 mL) was added Pd(dppf)$Cl_2$.DCM (1.70 g, 2.08 mmol) under $N_2$ atmosphere. After addition, the reaction mixture was stirred at 25° C. for 14 h. The reaction mixture was filtered and the filtrate was concentrated, the residue was purified by FCC on silica gel (EtOAc) to afford the title intermediate (15 g, 93% purity, 74% yield) as brown solid.

Method B

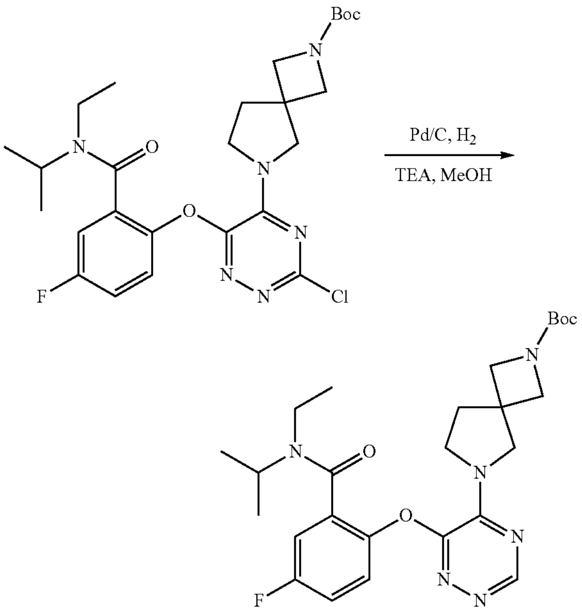

To the solution of tert-butyl 6-(3-chloro-6-(2-(ethyl(isopropyl)carbamoyl)-4-fluorophenoxy)-1,2,4-triazin-5-yl)-2,6-diazaspiro[3.4]octane-2-carboxylate (intermediate 14) (22.0 g, 40.1 mmol), TEA (15 mL) in MeOH (100 mL) was added Pd/C (wet, 5.0 g, 10%) The resulting mixture was stirred under $H_2$ atmosphere (30 psi) at 25° C. for 8 h. The reaction mixture was filtered through a celite pad and the filtrate was concentrated in vacuo to afford the title intermediate (25.0 g, crude), which was used directly in next step without further purification.

Preparation of Intermediate 58, 84 tert-butyl 6-(6-(2-(4-cyclopropylpyrimidin-5-yl)-4-fluorophenoxy)-1,2,4-triazin-5-yl)-2,6-diazaspiro[3.4]octane-2-carboxylate tert-butyl 6-(6-(2-(diisopropylcarbamoyl)-4-fluorophenoxy)-1,2,4-triazin-5-yl)-2,6-diazaspiro[3.4]octane-2-carboxylate The following intermediates were synthesized by an analogous method described above for intermediate 2

| Int. No. | Structure | Starting Material | Conditions |
|---|---|---|---|
| 58 | 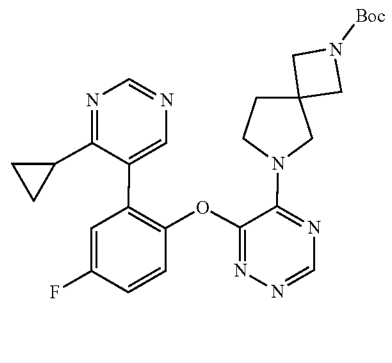 [SMILES: CC(C)(C)OC(=O)N1CC2(CCN(c3ncnnc3Oc3ccc(F)cc3-c3cncnc3C3CC3)C2)C1] | intermediate 57 | $NaBH_4$, TMEDA, Pd(dppf)$Cl_2$•DCM, THF |

-continued

| Int. No. | Structure | Starting Material | Conditions |
|---|---|---|---|
| 84 | 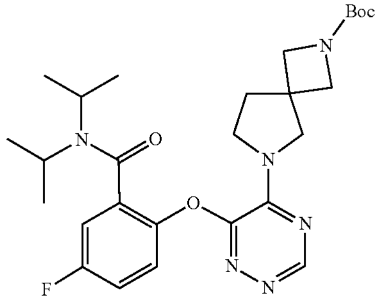 [SMILES: CC(C)N(C(=O)c1cc(F)ccc1Oc1nncnc1N1CCC2(CN(C(=O)OC(C)(C)C)C2)C1)C(C)C] | intermediate 83 | Pd/C, $H_2$, TEA, MeOH |

Preparation of Intermediate 3

2-((5-(2,6-diazaspiro[3.4]octan-6-yl)-1,2,4-triazin-6-yl)oxy)-N-ethyl-5-fluoro-N-isopropylbenzamide

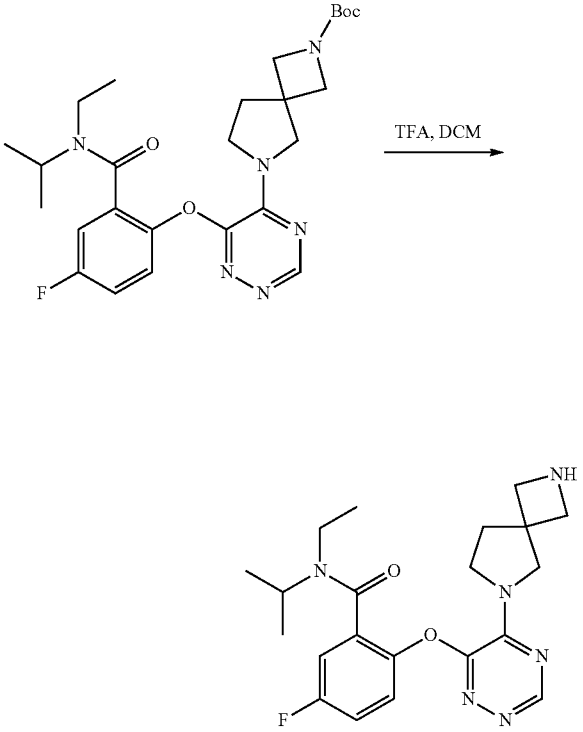 [SMILES: CCN(C(=O)c1cc(F)ccc1Oc1nncnc1N1CCC2(CN(C(=O)OC(C)(C)C)C2)C1)C(C)C ; CCN(C(=O)c1cc(F)ccc1Oc1nncnc1N1CCC2(CNC2)C1)C(C)C]

To the solution of tert-butyl 6-(6-(2-(ethyl(isopropyl)carbamoyl)-4-fluorophenoxy)-1,2,4-triazin-5-yl)-2,6-diazaspiro[3.4]octane-2-carboxylate (intermediate 2) (300 mg, 0.583 mmol) in DCM (5 mL) was added TFA (0.5 mL, 6.4 mmol), the resulting mixture was stirred at RT for 3 h. Then 10% NaOH (5 mL) solution was slowly added into the mixture to adjust the pH value to about 12, the resulting mixture was extracted with DCM (10 mL×3). The combined organic layers were dried over anhydrous $Na_2SO_4$, filtered, and concentrated in vacuo to afford the title intermediate (220 mg, 90% yield) as a white solid.

Preparation of Intermediate 59, 75, 85

6-(6-(2-(4-cyclopropylpyrimidin-5-yl)-4-fluorophenoxy)-1,2,4-triazin-5-yl)-2,6-diazaspiro[3.4]octane 2-((4-(2,6-diazaspiro[3.4]octan-6-yl)pyridazin-3-yl)oxy)-N-ethyl-5-fluoro-N-isopropylbenzamide 2-((5-(2,6-diazaspiro[3.4]octan-6-yl)-1,2,4-triazin-1-yl)oxy)-5-fluoro-N,N-diisopropylbenzamide The following intermediates were synthesized by an analogous method described above for intermediate 3

| Int. No. | Structure | Starting Material |
|---|---|---|
| 59 | 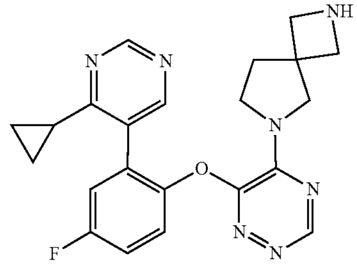 [SMILES: Fc1ccc(Oc2nncnc2N2CCC3(CNC3)C2)c(-c2cncnc2C2CC2)c1] | intermediate 58 |
| 75 | 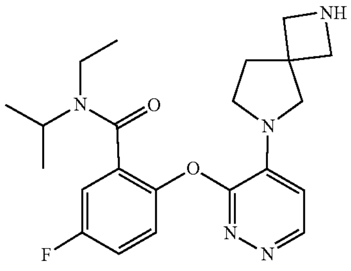 [SMILES: CCN(C(=O)c1cc(F)ccc1Oc1nnccc1N1CCC2(CNC2)C1)C(C)C] | intermediate 74 |
| 85 | 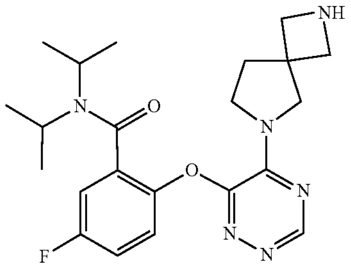 [SMILES: CC(C)N(C(=O)c1cc(F)ccc1Oc1nncnc1N1CCC2(CNC2)C1)C(C)C] | intermediate 84 |

Preparation of Intermediate 160

N-methoxy-N-methyl-4-(methylamino)butanamide hydrochloride

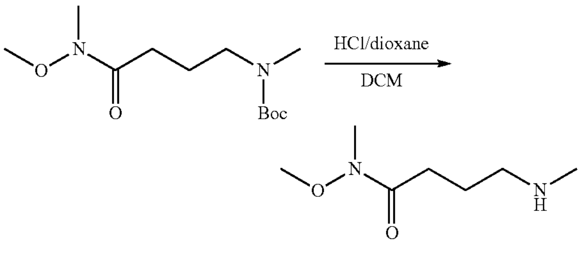

HCl salt

To a solution of tert-butyl (4-(methoxy(methyl)amino)-4-oxobutyl)(methyl)carbamate (intermediate 8) (220 g, crude) in DCM (200 mL) was slowly added HCl/1,4-dioxane (750 mL, 3 mol) at 0° C. The resulting mixture was slowly warmed to RT and stirred at this temperature for 2 h. The mixture was concentrated in vacuo to afford the title intermediate (197 g, crude) which was used directly in next step without further purification.

Intermediate 164, 238, 243, 244

N-(2-methoxyethyl)-N,5-dimethyl-4-(2,6-diazaspiro[3.4]octan-6-yl)hexan-1-amine hydrochloride

2-((3-chloro-5-(2,6-diazaspiro[3.4]octan-6-yl)-1,2,4-triazin-1-yl)oxy)-N-ethyl-5-fluoro-N-isopropylbenzamide hydrochloride

2-((5-(2,6-diazaspiro[3.4]octan-6-yl)-1,2,4-triazin-6-yl)oxy)-5-fluoro-N,N-diisopropylbenzamide hydrochloride

2-((5-(2,6-diazaspiro[3.4]octan-6-yl)-1,2,4-triazin-6-yl)oxy)-N-ethyl-5-fluoro-N-isopropylbenzamide hydrochloride The following intermediates were synthesized by an analogous method described above for intermediate 160

| Int. No. | Structure | Starting Material |
|---|---|---|
| 164 | 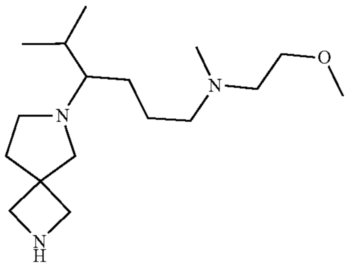 HCl salt | intermediate 163 |

-continued

| Int. No. | Structure | Starting Material |
|---|---|---|
| 238 | HCl salt 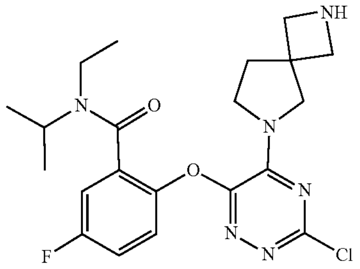 | intermediate 14 |
| 243 | HCl salt 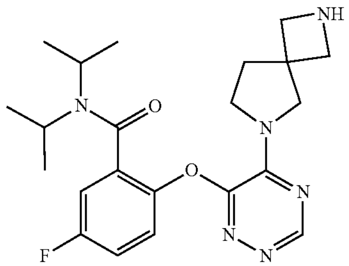 | intermediate 84 |
| 244 | HCl salt 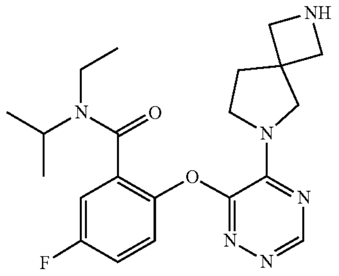 | intermediate 2 |

Preparation of Intermediate 71

2-((4-(2,6-diazaspiro[3.4]octan-6-yl)pyridazin-3-yl)oxy)-5-fluoro-N,N-diisopropylbenzamide

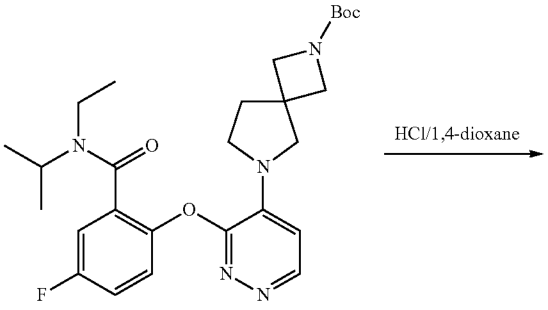

-continued

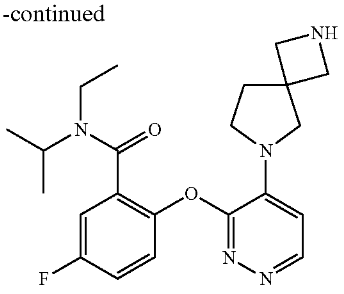

To the solution of tert-butyl 6-(3-(2-(diisopropylcarbamoyl)-4-fluorophenoxy)pyridazin-4-yl)-2,6-diazaspiro[3.4] octane-2-carboxylate (intermediate 70) (5.0 g, 9.4 mmol) in 1,4-dioxane (30 mL) cooled at 0° C. was slowly added HCl in 1.4-dioxane (20 mL, 4 M, 80 mmol) The resulting mixture was stirred at RT for 2 h. Then, the mixture was concentrated and the residue was re-dissolved in DCM (50 mL), to which 1 M NaOH (20 mL) was slowly added and the pH value was adjusted to 12, the resulting mixture was extracted by DCM (30 mL×3). The combined organic layers were dried over anhydrous $Na_2SO_4$, filtered, and concentrated in vacuo to afford the title intermediate (4 g, crude) as a yellow solid, which was used in the next step without further purification.

Preparation of Intermediate 29 tert-butyl 2,2-dimethyl-5-oxopyrrolidine-1-carboxylate

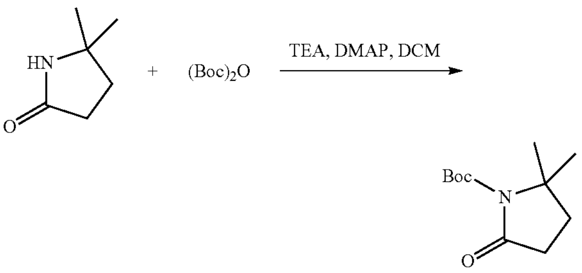

To a solution of 5,5-dimethylpyrrolidin-2-one (3.00 g, 26.5 mmol) in DCM (30 mL) were added TEA (8.10 g, 80.0 mmol) and DMAP (325 mg, 2.66 mmol), and followed by addition of di-tert-butyl dicarbonate (8.70 g, 39.8 mmol). The reaction was stirred at 40° C. overnight. After cooled to RT, the reaction mixture was washed with brine (30 mL×2), dried over $Na_2SO_4$, filtered and concentrated under reduced pressure to give a crude product. The crude product was further purified by FCC on silica gel (PE/EtOAc=100:0 to 3:1) to afford the title intermediate (2.8 g, 50% yield) as a yellow powder.

Preparation of Intermediate 1 tert-butyl (5-methyl-4-oxohexyl)carbamate

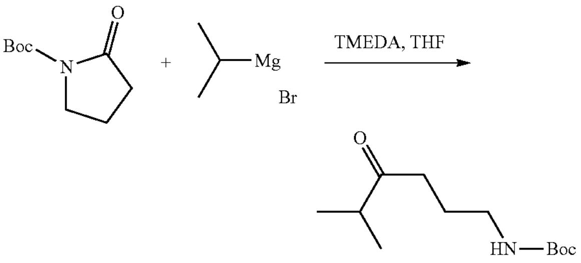

To a solution of tert-butyl 2-oxopyrrolidine-1-carboxylate (5.0 g, 27 mmol) and TMEDA (5.0 mL, 33 mmol) in THF (60 mL) cooled at −70° C. was slowly added isopropylmagnesium bromide solution (19 mL, 55 mmol, 2.9 M in 2-methyltetrahydrofuran), the resulting mixture was slowly warmed to RT and stirred for 12 h. The mixture was poured into sat. aq. $NH_4Cl$ (50 mL) solution and extracted with EtOAc (50 mL×3). The combined organic layers were dried over anhydrous $Na_2SO_4$, filtered, and concentrated under reduced pressure to give the crude product, which was further purified by FCC (PE/EtOAc=1:0 to 100:1) to afford the title intermediate (3.7 g, 60% yield) as a yellow oil.

Preparation of Intermediate 30, 110, 141 tert-butyl (2,6-dimethyl-5-oxoheptan-2-yl)carbamate tert-butyl (6-methyl-5-oxoheptyl)carbamate 6-hydroxy-2,4-dimethylhexan-3-one The following intermediates were synthesized by an analogous method described above for intermediate 1

| Int. No. | Structure | Starting Materials |
|---|---|---|
| 30 | 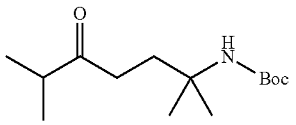 [SMILES: CC(C)C(=O)CCC(C)(C)NC(=O)OC(C)(C)C] | isopropylmagnesium bromide, intermediate 29 |
| 110 | 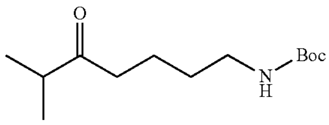 [SMILES: CC(C)C(=O)CCCCNC(=O)OC(C)(C)C] | isopropylmagnesium bromide, tert-butyl 2-oxopiperidine-1-carboxylate |

-continued

| Int. No. | Structure | Starting Materials |
|---|---|---|
| 141 | 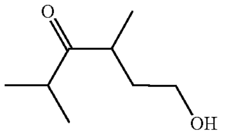 | isopropylmagnesium chloride, 3-methyldihydrofuran-2(3H)-one |

Preparation of Intermediate 34 benzyl 2,2-dimethyl-5-oxopyrrolidine-1-carboxylate

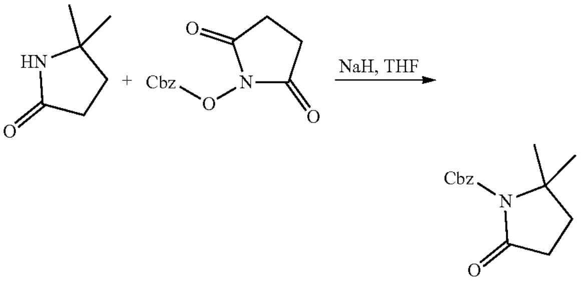

To a solution of 5,5-dimethylpyrrolidin-2-one (5.00 g, 44.2 mmol) in THF (150 mL) cooled at 0° C. was added NaH (1.94 g, 48.5 mmol, 60%), the resulting mixture was stirred at this temperature for 30 min. Subsequently N-(benzyloxycarbonyloxy)succinimide (12.1 g, 48.6 mmol) was added and the reaction mixture was slowly warmed to RT and stirred for additional 16 h. The solvent was evaporated under reduced pressure, sat. aq. $NH_4Cl$ solution (30 mL) was added and extracted with EtOAc (2×30 mL). The combined organic layers were washed with brine (40 mL), dried over $Na_2SO_4$, filtered, and concentrated under reduced pressure to afford the crude product, which was further purified by FCC (PE/EtOAc=1:0 to 3:1) to afford the title intermediate (5.16 g, 39% yield) as colorless oil.

Preparation of Intermediate 35

4-(((benzyloxy)carbonyl)amino)-4-methylpentanoic acid

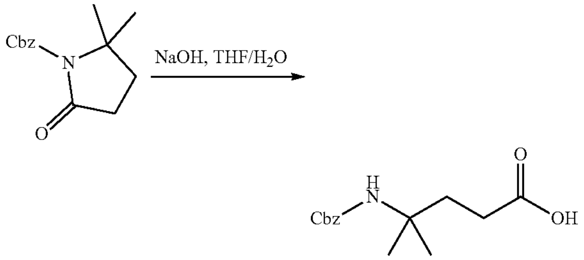

NaOH (4.18 g, 16.9 mmol) was added to a solution of benzyl 2,2-dimethyl-5-oxopyrrolidine-1-carboxylate (intermediate 34) (5.16 g, 20.9 mmol) in THF (60 mL) and $H_2O$ (15 mL). The mixture was stirred at 80° C. for 16 h. The reaction mixture was cooled to 25° C. and acidified by 1 M HCl to adjust the pH value to about 3, then the mixture was extracted by EtOAc (20×2 mL). The combined organic layers were washed with brine (20 mL), dried over $Na_2SO_4$, filtered, and concentrated in vacuo to afford the title intermediate (4.48 g, crude) as colorless oil, which was used directly in next step without further purification.

Preparation of Intermediate 7

4-((tert-butoxycarbonyl)(methyl)amino)butanoic acid

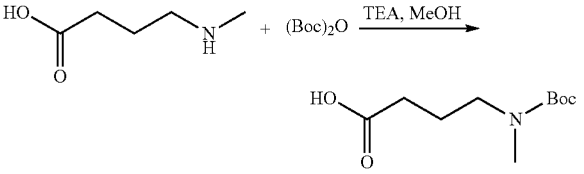

To a solution of 4-(methylamino)butanoic acid hydrochloride (3.0 g, 19.5 mmol) and TEA (7.78 mL, 58.6 mmol) in MeOH (30 mL) was added $Boc_2O$ (4.69 g, 21.5 mmol) dropwise. The mixture was stirred at RT for 2 h. The mixture was concentrated under reduced pressure and the residue was diluted with EtOAc (100 mL), washed with cooled 0.1 N HCl (70 mL×2), $H_2O$ (50 mL×2) and brine (50 mL), dried over $Na_2SO_4$, filtered and concentrated to afford the title intermediate (1.80 g, crude) as colorless oil.

Preparation of Intermediate 8 tert-butyl (4-(methoxy(methyl)amino)-4-oxobutyl)(methyl)carbamate

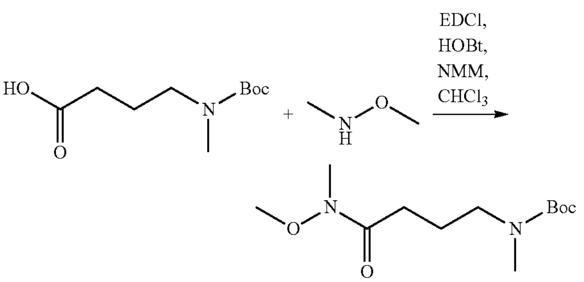

To a solution of 4-((tert-butoxycarbonyl)(methyl)amino) butanoic acid (intermediate 7) (1.80 g, crude) in $CHCl_3$ (30 mL) was added N,O-dimethylhydroxylamine hydrochloride (960 mg, 9.84 mmol), HOBt (1.24 g, 9.18 mmol) and NMM (2.80 mL, 25.1 mmol). And, then EDCI (2.23 g, 11.6 mmol) was added and the reaction mixture was stirred at RT for 4 h. The reaction mixture was diluted with DCM (100 mL), washed with 1N HCl (30 mL×3), sat. aq. $NaHCO_3$ (30 mL×3) and brine (30 mL), dried over $Na_2SO_4$, filtered and concentrated under in vacuo to afford the title intermediate (1.70 g, crude) as colorless oil.

Preparation of Intermediates 19, 36, 189, 190, 203, 204 tert-butyl (3-(methoxy(methyl)amino)-3-oxopropyl)carbamate benzyl (5-(methoxy(methyl)amino)-2-methyl-5-oxopentan-2-yl)carbamate

(S)-3-((tert-butyldiphenylsilyl)oxy)-4-(ethyl(methyl)amino)-N-methoxy-N-methylbutanamide

(R)-3-((tert-butyldiphenylsilyl)oxy)-4-(ethyl(methyl)amino)-N-methoxy-N-methylbutanamide

(S)-3-((tert-butyldiphenylsilyl)oxy)-N-methoxy-4-((2-methoxyethyl)(methyl)amino)-N-methylbutanamide

(R)-3-((tert-butyldiphenylsilyl)oxy)-N-methoxy-4-((2-methoxyethyl)(methyl)amino)-N-methylbutanamide The following intermediates were synthesized by an analogous method described above for intermediate 8

| Int. No. | Structure | Starting Materials |
|---|---|---|
| 19 | 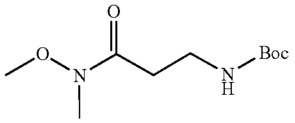 [SMILES: CON(C)C(=O)CCNC(=O)OC(C)(C)C] | 3-((tert-butoxycarbonyl)amino)propanoic acid<br>N,O-dimethylhydroxylamine hydrochloride |
| 36 | 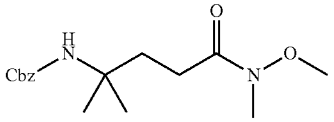 [SMILES: CON(C)C(=O)CCC(C)(C)NC(=O)OCc1ccccc1] | intermediate 35<br>N,O-dimethylhydroxylamine hydrochloride |
| 189 | 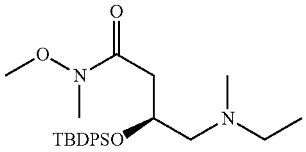 | intermediate 187,<br>N,O-dimethylhydroxylamine hydrochloride |
| 190 | 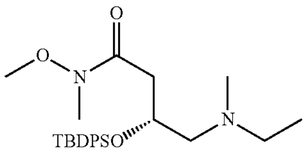 | intermediate 188,<br>N,O-dimethylhydroxylamine hydrochloride |

-continued

| Int. No. | Structure | Starting Materials |
|---|---|---|
| 203 | 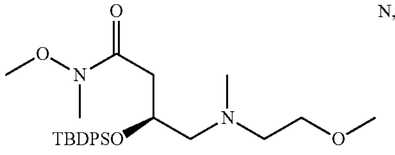 | N,O-dimethylhydroxylamine hydrochloride |
| 204 | 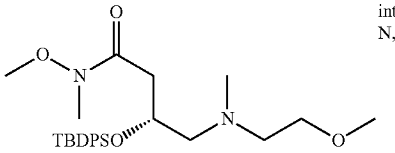 | intermediate 202, N,O-dimethylhydroxylamine hydrochloride |

Preparation of Intermediate 37 benzyl (5-(methoxy(methyl)amino)-2-methyl-5-oxopentan-2-yl)(methyl)carbamate

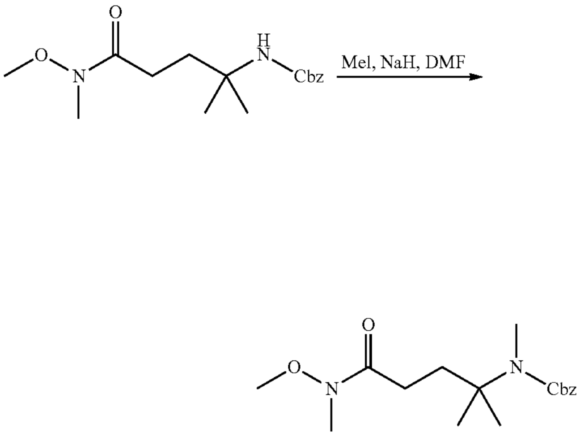

To a solution of benzyl (5-(methoxy(methyl)amino)-2-methyl-5-oxopentan-2-yl)(methyl)carbamate (intermediate 36) (2.30 g, 7.46 mmol) in DMF (30 mL) cooled at 0 DC under $N_2$ atmosphere was added NaH (358 mg, 8.95 mmol, 60%). Then, MeI (8.87 g, 62.5 mmol) was added and the mixture was stirred at 25° C. for 12 h. The mixture was quenched with sat. aq. $NH_4Cl$ (30 mL) and extracted with EtOAc (30 mL×2). The combined organic layers washed with brine (40 mL), dried over $Na_2SO_4$, filtered and concentrated in vacuo to give the crude product, which was further purified by FCC on silica gel (PE/EtOAc=1:0 to 3:1) to afford the title intermediate (2.15 g, 76% yield) as yellow oil.

Preparation of Intermediate 236

N-(ethyl-$^{13}C_2$)-5-fluoro-2-methoxy-N-(propan-2-yl-$^{13}C_2$)benzamide

The following intermediate was synthesized by an analogous method as described above for intermediate 37

| Int. No. | Structure | Starting Materials | Conditions |
|---|---|---|---|
| 236 | 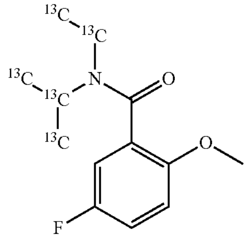 [SMILES: COc1ccc(F)cc1C(=O)N([13CH2][13CH3])[13CH]([13CH3])[13CH3]] | intermediate 235, iodoethane-1,2-$^{13}C_2$ | NaH, DMF, from 0° C. to 90° C. |

Preparation of Intermediate 9 tert-butyl methyl(5-methyl-4-oxohexyl)carbamate

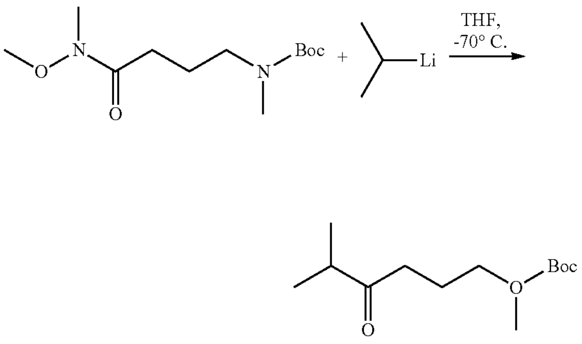

To a solution of tert-butyl (4-(methoxy(methyl)amino)-4-oxobutyl)(methyl)carbamate (intermediate 8) (200 mg, crude) in THF (5 mL) cooled at −70° C. under $N_2$ atmosphere was added dropwise isopropyllithium (3.2 mL, 2.24 mmol, 0.7M in pentane). The resulting mixture was stirred at −70° C. for 2 h. The mixture was quenched with sat. aq. $NH_4Cl$ (15 mL), extracted with EtOAc (30 mL×2). The combined organic layers were washed with brine (30 mL), dried over $Na_2SO_4$, filtered and concentrated under reduced pressure to give a crude product. The crude product was further purified by FCC (PE/EtOAc=10:1) to afford the title intermediate (60 mg) as colorless oil.

Preparation of Intermediates 20, 38, 162, 191, 192, 205, 206 tert-butyl (4-methyl-3-oxopentyl)carbamate benzyl (2,6-dimethyl-5-oxoheptan-2-yl)(methyl)carbamate 6-((2-methoxyethyl)(methyl)amino)-2-methylhexan-3-one (S)-5-((tert-butyldiphenylsilyl)oxy)-6-(ethyl(methyl)amino)-2-methylhex-1-en-3-one (R)-5-((tert-butyldiphenylsilyl)oxy)-6-(ethyl(methyl)amino)-2-methylhex-1-en-3-one (S)-5-((tert-butyldiphenylsilyl)oxy)-6-((2-methoxyethyl)(methyl)amino)-2-methylhex-1-en-3-one (R)-5-((tert-butyldiphenylsilyl)oxy)-6-((2-methoxyethyl)(methyl)amino)-2-methylhex-1-en-3-one The following intermediates were synthesized by an analogous method described above for intermediate 9

| Int. No. | Structure | Starting Materials |
|---|---|---|
| 20 | 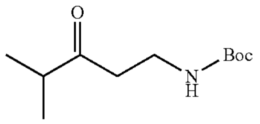 | intermediate 19, isopropylmagnesium chloride |
| 38 | 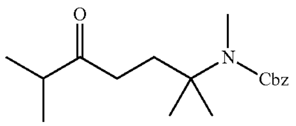 [SMILES: CC(C)C(=O)CCC(C)(C)N(C)C(=O)OCc1ccccc1] | intermediate 37 isopropylmagnesium chloride |
| 162 | 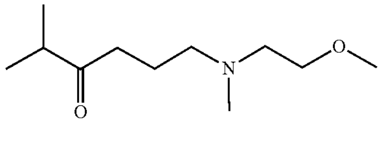 | intermediate 161, isopropyllithium |
| 191 | 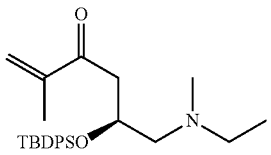 | intermediate 189, isopropenylmagnesium bromide |
| 192 | 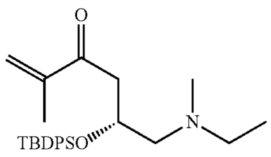 | intermediate 190, isopropenylmagnesium bromide |
| 205 | 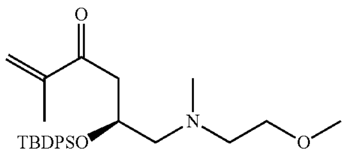 | intermediate 203, isopropenylmagnesium bromide |

-continued

| Int. No. | Structure | Starting Materials |
|---|---|---|
| 206 | 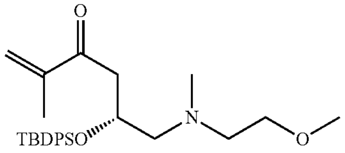 | intermediate 204, isopropenylmagnesium bromide |

Preparation of Intermediate 15

2-(3-methyl-2-oxobutyl)isoindoline-1,3-dione

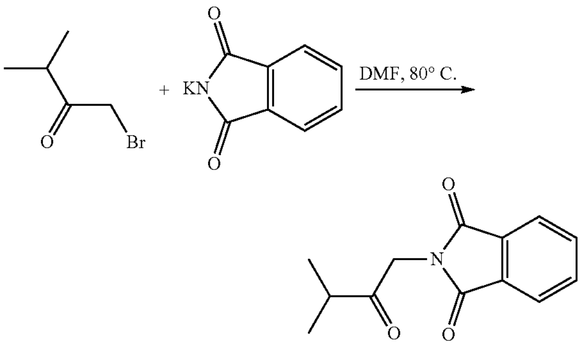

To the solution of 1-bromo-3-methylbutan-2-one (200 mg, 1.21 mmol) in DMF (4 mL) was added potassium phthalimide (1.12 g, 6.05 mmol) and the mixture was stirred at 80° C. for 12 h. After cooled to RT, water (15 mL) was added and the mixture was extracted with EtOAc (40 mL×3). The combined organic layers were dried over anhydrous $Na_2SO_4$, filtered and concentrated under reduced pressure to afford the crude product, which was further purified by preparative TLC (PE/EtOAc=3:1) to afford the title intermediate (200 mg, 69% yield) as a white solid.

Preparation of Intermediate 46 methyl 5-methyl-4-oxohexanoate

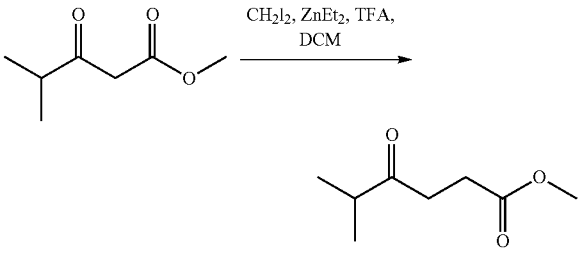

To a solution of $ZnEt_2$ (104 mL, 104 mmol) in DCM (150 mL) at 0° C. under $N_2$ was added dropwise TFA (11.9 g, 104 mmol) slowly via syringe and the mixture was stirred at 0° C. for 30 min. Then, methylene iodide (27.9 g, 104 mmol) was added dropwise with stirring and the suspension was stirred for another 30 min. And, then methyl 4-methyl-3-oxopentanoate (5.00 g, 34.7 mmol) was added rapidly by syringe and the resulting mixture was stirred at RT for 16 h and refluxed at 50° C. for 20 h. After cooled to RT, the reaction mixture was quenched with sat. aq. $NH_4Cl$ (50 mL) and extracted with EtOAc (30 mL×3). The combined organic layers were washed with brine, dried over $MgSO_4$, and concentrated under reduced pressure to an oil residue which was purified by FCC (PE/EtOAc=1:0 to 20:1) to afford the title intermediate (300 mg, 5% yield) as a yellow oil.

Preparation of Intermediate 22 tert-butyl (4-methyl-3-(2,6-diazaspiro[3.4]octan-2-yl)pentyl)carbamate hydrochloride

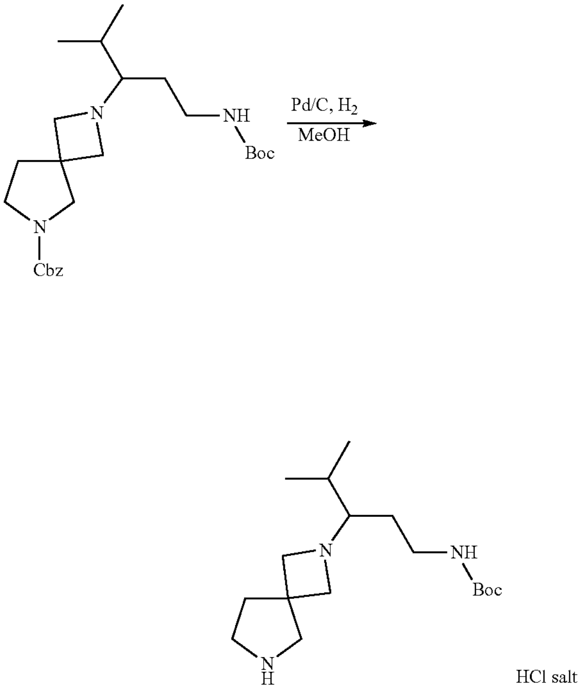

To a solution of benzyl 2-(1-((tert-butoxycarbonyl)amino)-4-methylpentan-3-yl)-2,6-diazaspiro[3.4]octane-6-carboxylate (intermediate 21) (0.580 g, 1.30 mmol) in MeOH (50 mL) were added 1,1,2-trichloroethane (0.260 g, 1.95 mmol) and Pd/C (0.05 g, 10%) under Ar and the reaction was stirred at 35° C. for 8 h under $H_2$ (15 psi) atmosphere. The reaction mixture was filtered. The filtrate was concentrated in vacuo to afford the title intermediate (280 mg, crude) as colorless oil.

Preparation of Intermediate 23 ethyl 6-(2-(ethyl(isopropyl)carbamoyl)-4-fluorophenoxy)-1,2,4-triazine-8-carboxylate

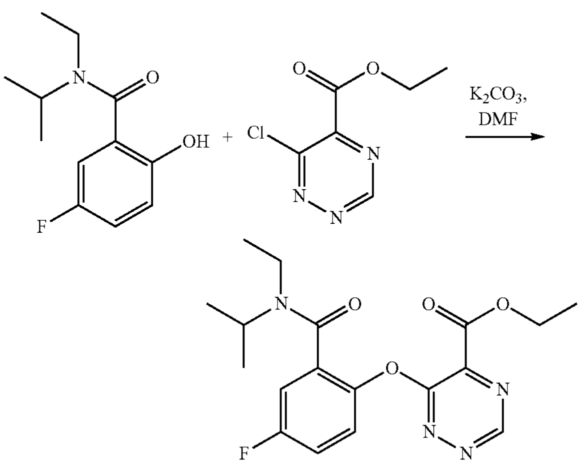

To the mixture of ethyl 6-chloro-1,2,4-triazine-5-carboxylate (13 g, 69 mmol) and N-ethyl-5-fluoro-2-hydroxy-N-isopropylbenzamide (intermediate 28) (15.6 g, 69.3 mmol) in DMF (150 mL) was added $K_2CO_3$ (28.6 g, 204 mmol). The resulting mixture was stirred at RT for 2 h. The reaction mixture was filtered and the filtrate was concentrated under reduced pressure to give the crude residue, which was diluted with water (100 mL) and extracted with EtOAc (100 mL×2). The combined organic layers were dried over anhydrous $Na_2SO_4$, filtered, and concentrated under reduced pressure to give the crude product, which was further purified by FCC (PE/EtOAc=1:0 to 1:1) to afford the title intermediate (30 g, 81% purity, 92% yield) as a yellow solid.

Preparation of Intermediate 24

6-(2-(ethyl(isopropyl)carbamoyl)-4-fluorophenoxy)-1,2,4-triazine-5-carboxylic acid

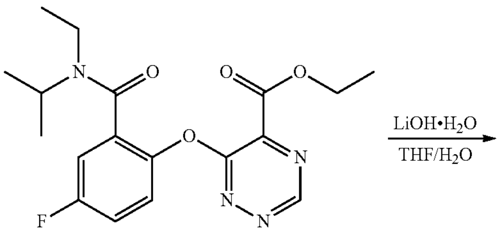

-continued

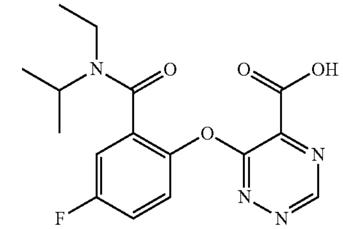

To the mixture of ethyl 6-(2-(ethyl(isopropyl)carbamoyl)-4-fluorophenoxy)-1,2,4-triazine-5-carboxylate (intermediate 23) (8.6 g, 23 mmol) in THF (100 mL) and $H_2O$ (25 mL) was added LiOH·$H_2O$ (2.0 g, 48 mmol) and the reaction mixture was stirred at RT for 1 h. The mixture was acidified with 0.5M HCl to adjust the pH value to 5~6, and further extracted with EtOAc (150 mL). The aqueous phase was purified by preparative HPLC over Boston Prime (column: C18 150×30 mm 5 um; eluent: ACN/$H_2O$ (0.225% FA) from 19% to 49%, v/v) to afford the title intermediate (5.0 g, 62% yield).

Preparation of Intermediates 187, 188, 201, 202

(S)-3-((tert-butyldiphenylsilyl)oxy)-4-(ethyl(methyl)amino)butanoic acid (R)-3-((tert-butyldiphenylsilyl)oxy)-4-(ethyl(methyl)amino)butanoic acid (S)-3-((tert-butyldiphenylsilyl)oxy)-4-((2-methoxyethyl)(methyl)amino)butanoic acid (R)-3-((tert-butyldiphenylsilyl)oxy)-4-((2-methoxyethyl)(methyl)amino)butanoic acid The following intermediates were synthesized by an analogous method as described above for intermediate 24

| Int. No. | Structure | Starting Material | Conditions |
|---|---|---|---|
| 187 | 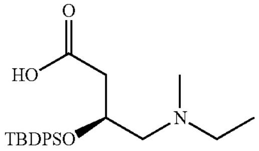 | intermediate 185 | NaOH, THF/MeOH/$H_2O$, RT |

-continued

| Int. No. | Structure | Starting Material | Conditions |
|---|---|---|---|
| 188 | 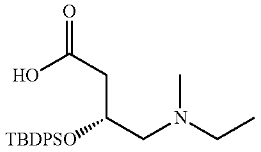 | intermediate 186 | NaOH, THF/MeOH/$H_2O$, RT |
| 201 | 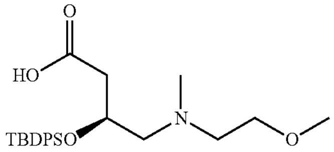 | intermediate 199 | NaOH, THF/EtOH/$H_2O$, RT |
| 202 | 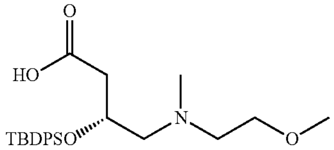 | intermediate 200 | NaOH, THF/MeOH/$H_2O$, RT |

Preparation of Intermediate 25

N-ethyl-5-fluoro-2-((5-hydroxy-1,2,4-triazin-6-yl)oxy)-N-isopropylbenzamide

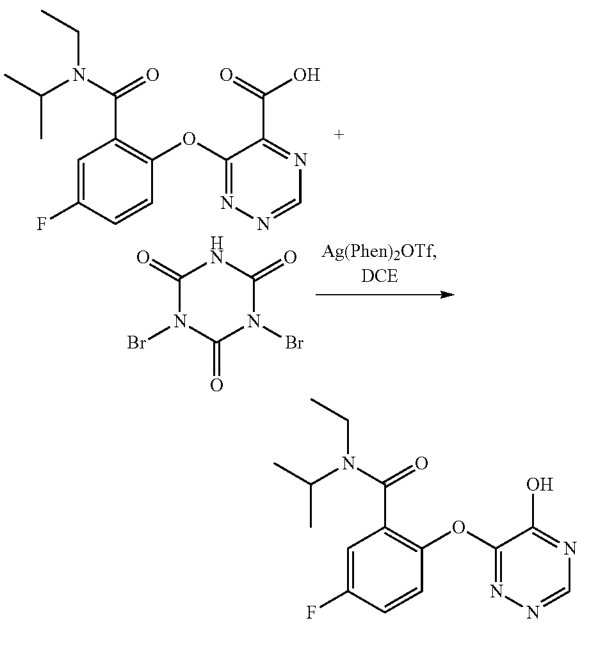

To the solution of 6-(2-(ethyl(isopropyl)carbamoyl)-4-fluorophenoxy)-1,2,4-triazine-5-carboxylic acid (intermediate 24) (50 mg, 0.14 mmol) and 1,3-dibromo-1,3,5-triazinane-2,4,6-trione (50 mg, 0.17 mmol) in DCE (1 mL) was added Ag(Phen)$_2$OTf (30 mg, 0.049 mmol) and the resulting mixture was stirred at RT for 2 h. The reaction mixture was filtered through a celite pad and washed with ACN (10 mL). The filtrate was concentrated under reduced pressure to afford the crude product, which was further purified by preparative HPLC using a Xtimate (column: C18 150×40 mm 10 μm; eluent: ACN/$H_2O$ (0.2% FA) from 20% to 50% v/v) to afford the title intermediate (20 mg, 41%) as a white solid.

Preparation of Intermediate 159

N-ethyl-5-fluoro-N-isopropyl-2-((5-(2,2,2-trifluoroethoxy)-1,2,4-triazin-6-yl)oxy)benzamide

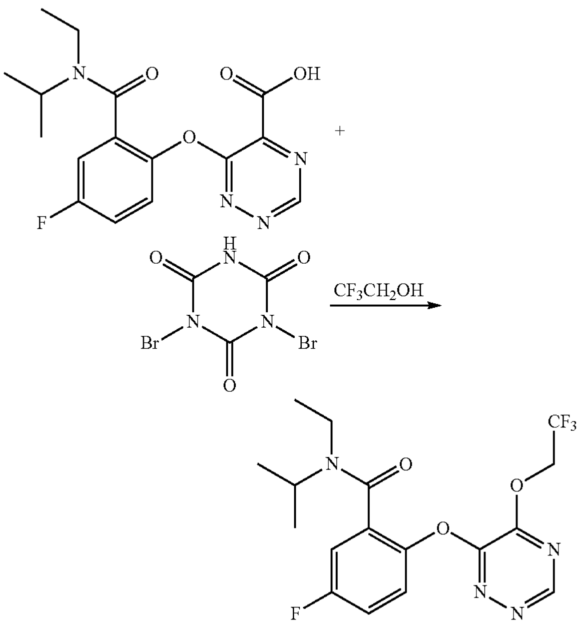

4 Å molecular sieve (8 g) was added to the mixture of 6-(2-(ethyl(isopropyl)carbamoyl)-4-fluorophenoxy)-1,2,4-triazine-5-carboxylic acid (intermediate 24) (8.0 g, 23.0 mmol) in 2,2,2-trifluoroethan-1-ol (100 mL). The resulting mixture was stirred under $N_2$ atmosphere at 70° C. for 1 h. Then cooled to RT and 1,3-dibromo-1,3,5-triazinane-2,4,6-trione (13.1 g, 45.7 mmol) was added to above mixture. The resulting mixture was further stirred under $N_2$ atmosphere at RT overnight. The reaction mixture was filtered over a celite pad. The filtrate was concentrated under reduced pressure and the crude residue was purified by FCC (PE:EtOAc from 1:0 to 2:1) to afford the title intermediate (3.1 g, purity 84%, yield 28%) as a yellow solid.

Preparation of Intermediate 51

4-((tert-butyldimethylsilyl)oxy)butan-1-ol

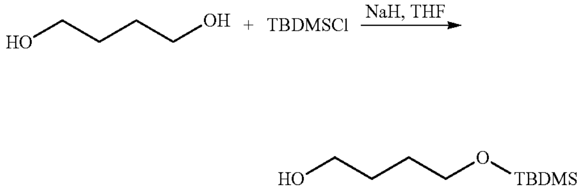

To the solution of butane-1,4-diol (5.00 g, 55.5 mmol) in THF (100 mL) cooled at 0° C. was added NaH (1.55 g, 38.8 mmol, 60%), the resulting mixture was stirred at 0° C. for 20 min. Then TBDMSCl (5.85 g, 38.8 mmol) was added to the reaction mixture and the reaction was further stirred at 0° C. for additional 1 h. The mixture was quenched with water (80 mL) and extracted with EtOAc (80 mL×3). The combined organic layers were dried over anhydrous $Na_2SO_4$, filtered and concentrated under reduced pressure to afford the crude product which was further purified by FCC (PE/EtOAc=1:0 to 10:1) to afford the title intermediate (7.2 g, 63%) as a colorless liquid.

Preparation of Intermediates 183, 184 ethyl (S)-3-((tert-butyldiphenylsilyl)oxy)-4-iodobutanoate ethyl (R)-3-((tert-butyldiphenylsilyl)oxy)-4-iodobutanoate The following intermediates were synthesized by an analogous method as described above for intermediate 51

| Int. No. | Structure | Starting Materials | Conditions |
|---|---|---|---|
| 183 | 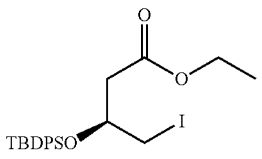 | TBDPSCl, intermediate 181 | imidazole, DCM, RT |
| 184 | 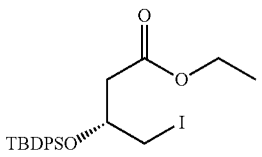 | TBDPSCl, intermediate 182 | imidazole, DCM, RT |

Preparation of Intermediate 52

4-((tert-butyldimethylsilyl)oxy)butanal

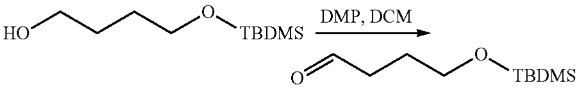

To the solution of 4-((tert-butyldimethylsilyl)oxy)butan-1-ol (intermediate 51) (7.20 g, 35.2 mmol) in DCM (200 mL) cooled at 0° C. was added DMP (22.4 g, 52.8 mmol) and the reaction mixture was slowly warmed to RT and stirred for 2 h. The reaction mixture was diluted with DCM (100 mL) and stirred with of sat. aq. ($NaHCO_3$/$Na_2SO_3$=1/1, 100 mL) for 2 min, the separated organic layer was washed with brine (100 mL×3), dried over anhydrous $Na_2SO_4$, filtered, and concentrated under reduced pressure to give the crude product which was further purified by FCC (PE/EtOAc=1:0 to 12:1) to afford the title intermediate (2.95 g, 41%) as a colorless liquid.

Preparation of Intermediate 54, 145, 146, 158

6-((term-butyldimethylsilyl)oxy)-2-methylhexan-3-one 2-((5-(2-(2,4-dimethyl-6-oxohexan-3-yl)-2,6-diazaspiro[3.4]octan-6-yl)-1,2,4-triazin-6-yl)oxy)-N-ethyl-5-fluoro-N-isopropylbenzamide (mixture of R,S and S,R; or mixture of R,R and S,S)

2-((5-(2-(2,4-dimethyl-6-oxohexan-3-yl)-2,6-diazaspiro[3.4]octan-6-yl)-1,2,4-triazin-6-yl)oxy)-N-ethyl-5-fluoro-N-isopropylbenzamide (mixture of R,R and S,S; or mixture of R,S and S,R)

(R)-N-ethyl-5-fluoro-N-isopropyl-2-((5-(2-(2-methyl-6-oxoheptan-3-yl)-2,6-diazaspiro[3.4]octan-6-yl)-1,2,4-triazin-6-yl)oxy)benzamide The following intermediates were synthesized by an analogous method described above for intermediate 52

| Int. No. | Structure | Starting Material |
|---|---|---|
| 54 | 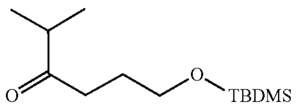 | intermediate 53 |
| 145 | 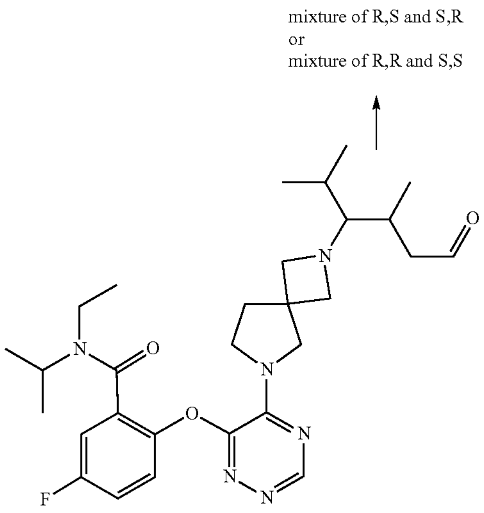 [SMILES: CCN(C(=O)c1cc(F)ccc1Oc1nncnc1N1CCC2(C1)CN(C(C(C)C)C(C)CC=O)C2)C(C)C] | Compound 261 |
| 146 | 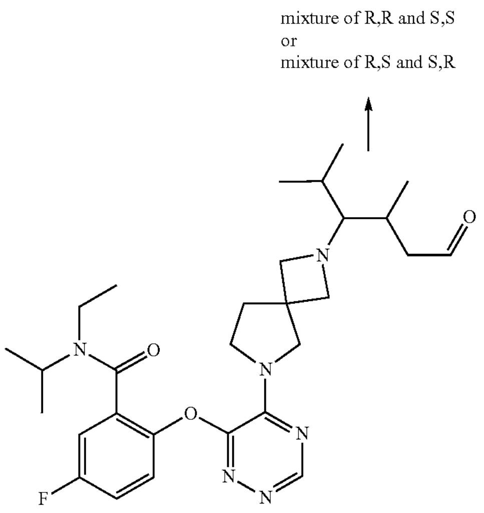 [SMILES: CCN(C(=O)c1cc(F)ccc1Oc1nncnc1N1CCC2(C1)CN(C(C(C)C)C(C)CC=O)C2)C(C)C] | Compound 262 |
| 158 | 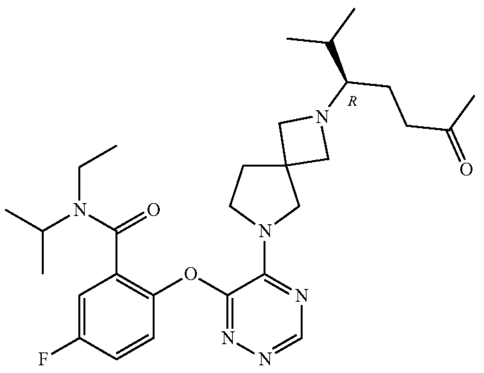 | Compound 298 |

Preparation of Intermediate 6-((tert-butyldimethylsilyl)oxy)-2-methylhexan-3-ol

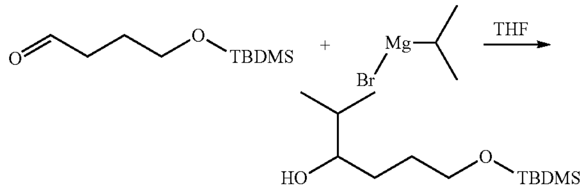

To the solution of 4-((tert-butyldimethylsilyl)oxy)butanal (intermediate 52) (1.00 g, 4.94 mmol) in THF (4.9 mL) cooled at −20° C. under $N_2$ atmosphere was added dropwise isopropylmagnesium bromide (4.94 mL, 14.8 mmol, 3 M in THF) and the reaction mixture was slowly warmed to RT and stirred for 2 h. The mixture was quenched with sat. aq. $NH_4Cl$ (20 mL), and extracted with EtOAc (50 mL×3). The combined organic layers were dried over anhydrous $Na_2SO_4$, filtered, and concentrated in vacuo to give the crude product which was further purified by FCC (PE/EtOAc=1:0 to 20:1) to afford the title intermediate (580 mg, 48%) as a white oil.

Preparation of Intermediates 16, 21, 39, 47, 55, 94, 98, 161, 163

2-((5-(2-(1-(1,3-dioxoisoindolin-2-yl)-3-methylbutan-2-yl)-2,6-diazaspiro[3.4]octan-6-yl)-1,2,4-triazin-6-yl)oxy)-N-ethyl-5-fluoro-N-isopropylbenzamide benzyl 2-(1-((ter-butoxycarbonyl)amino)-4-methylpentan-3-yl)-2,6-diazaspiro[3.4]octane-6-carboxylate benzyl (5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)(methyl)carbamate methyl 4-(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanoate 2-((5-(2-(6-((tert-butyldimethylsilyl)oxy)-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-(1-(1,3-dioxolan-2-yl)-4-methylpentan-3-yl)-2,6-diazaspiro[3.4]octan-6-yl)-1,2,4-triazin-6-yl)oxy)-N-ethyl-5-fluoro-N-isopropylbenzamide 2-((5-(2-(1-(1,3-dioxolan-2-yl)-4-methylpentan-3-yl)-2,6-diazaspiro[3.4]octan-6-yl)-1,2,4-triazin-6-yl)oxy)-5-fluoro-N,N-diisopropylbenzamide N-methoxy 4-((2-methoxyethyl)(methyl)amino)-N-methylbutanamide tert-butyl 6-(6-n2-methoxyethyl)(methyl)amino-2-methylhexan-3-yl)-2,6-diazaspiro[3.4]octane-2-carboxylate The following intermediates were synthesized by an analogous method as described for Compound 60 and Compound 61

| Int. No. | Structure | Starting Materials | Conditions |
|---|---|---|---|
| 16 | 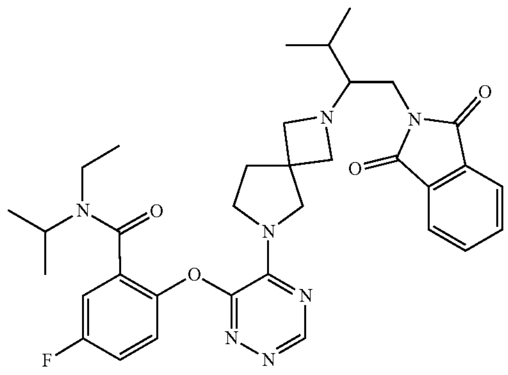 [SMILES: CCN(C(=O)c1cc(F)ccc1Oc1nncnc1N1CCC2(C1)CN(C(CN1C(=O)c3ccccc3C1=O)C(C)C)C2)C(C)C] | intermediate 3, intermediate 15 | $ZnCl_2$, $NaBH_3CN$, MeOH, 65° C. |
| 21 | 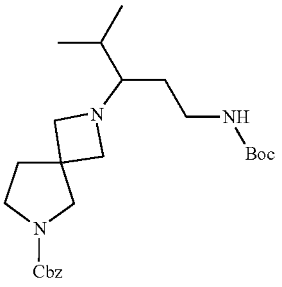 [SMILES: CC(C)C(CCNC(=O)OC(C)(C)C)N1CC2(CCN(C(=O)OCc3ccccc3)C2)C1] | intermediate 20, benzyl 2,6-diazaspiro[3.4]octane-6-carboxylate | AcOH, $NaBH_3CN$, MeOH, 45° C. |

-continued
| Int. No. | Structure | Starting Materials | Conditions |
|---|---|---|---|
| 39 | 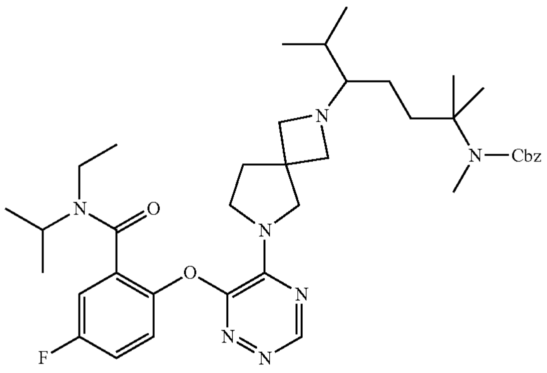 [SMILES: CCN(C(=O)c1cc(F)ccc1Oc1nncnc1N1CCC2(C1)CN(C(CCC(C)(C)N(C)C(=O)OCc1ccccc1)C(C)C)C2)C(C)C] | intermediate 3, intermediate 38 | $ZnCl_2$, $NaBH_3CN$, MeOH, 65° C. |
| 47 | 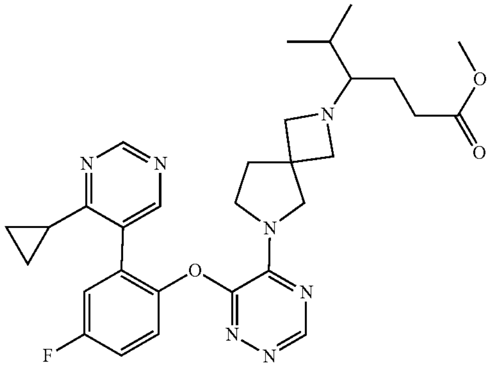 [SMILES: COC(=O)CCC(C(C)C)N1CC2(CCN(c3ncnnc3Oc3ccc(F)cc3-c3cncnc3C3CC3)C2)C1] | intermediate 59 intermediate 46 | $ZnCl_2$, $NaBH_3CN$, MeOH, 80° C. |
| 55 | 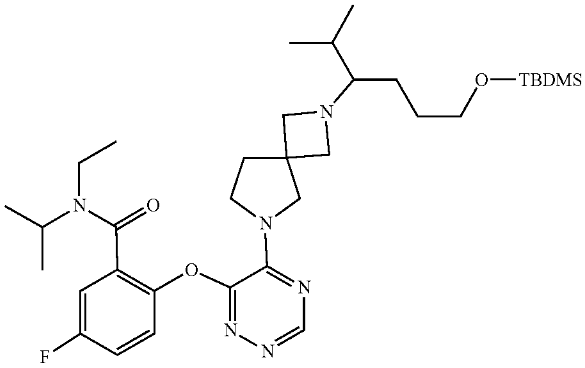 | intermediate 3, intermediate 54 | $ZnCl_2$, $NaBH_3CN$, MeOH, 80° C. |
| 94 | 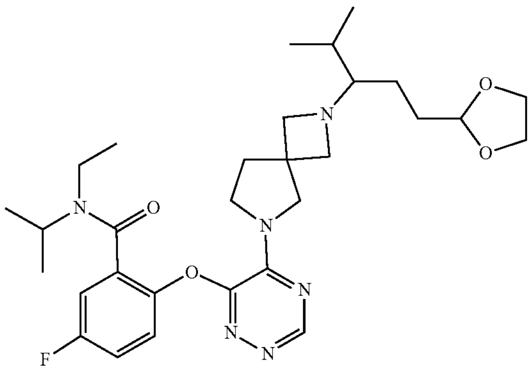 [SMILES: CCN(C(=O)c1cc(F)ccc1Oc1nncnc1N1CCC2(C1)CN(C(CCC1OCCO1)C(C)C)C2)C(C)C] | intermediate 3, intermediate 93 | AcOH, $NaBH_3CN$, MeOH, 45° C. |

-continued

| Int. No. | Structure | Starting Materials | Conditions |
|---|---|---|---|
| 98 | 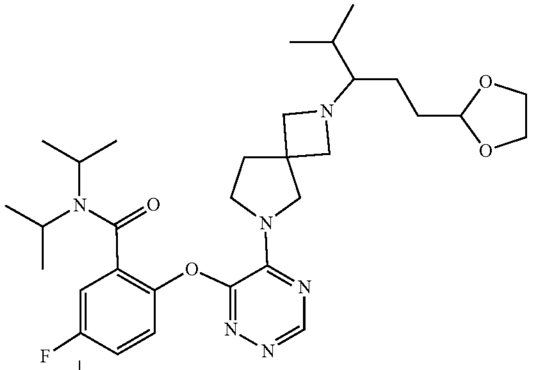 | intermediate 85, intermediate 93 | AcOH, $NaBH_3CN$, MeOH, 60° C. |
| 161 | 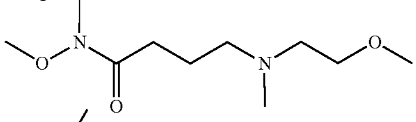 | intermediate 160, 1,1,2-trimethoxy ethane, HCl | AcOH, $NaBH_3CN$, EtOH, RT |
| 163 | 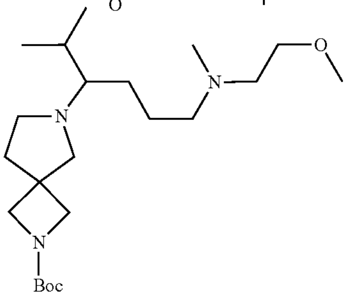 | intermediate 162, tert-butyl 2,6-diazaspiro[3.4]octane-2-carboxylate | NaOAc, $NaBH_3CN$, MeOH, 55° C. |

Preparation of Intermediate 17 and 18

(*R)-2-((5-(2-(1-(1,3-dioxoisoindolin-2-yl)-3-methylbutan-2-yl)-2,6-diazaspiro[3.4]octan-6-yl)-1,2,4-triazin-6-yl)oxy)-N-ethyl-5-fluoro-N-isopropylbenzamide (*S)-2-((5-(2-(1-(1,3-dioxoisoindolin-2-yl)-3-methylbutan-2-yl)-2,6-diazaspiro[3.4]octan-6-yl)-1,2,4-triazin-6-yl)oxy)-N-ethyl-5-fluoro-N-isopropylbenzamide

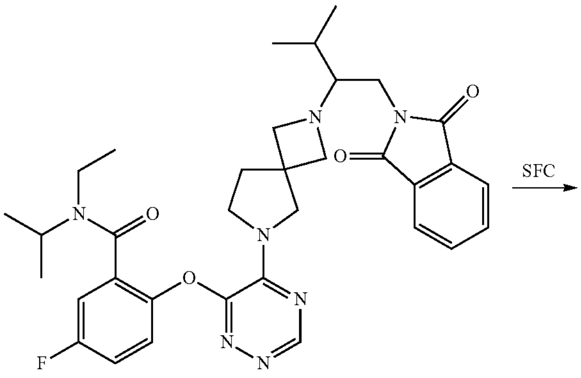

intermediate 16

-continued

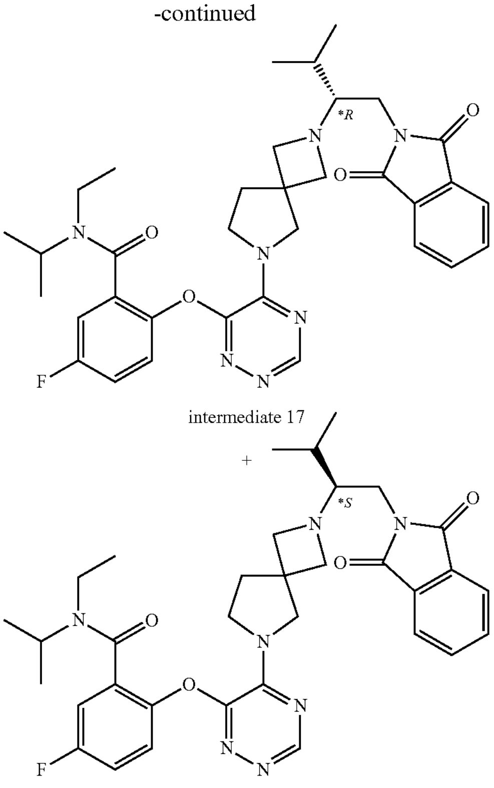

intermediate 17

+ intermediate 18

2-((5-(2-(1-(1,3-dioxoisoindolin-2-yl)-3-methylbutan-2-yl)-2,6-diazaspiro[3.4]octan-6-yl)-1,2,4-triazin-6-yl)oxy)-N-ethyl-5-fluoro-N-isopropylbenzamide (intermediate 16) (200 mg, 0.254 mmol) was purified by SFC over DAICEL CHIRALCEL OD (column: 250×50 mm 10 μm; Mobile phase: A: Supercritical $CO_2$, B: IPA (0.1% ammonia), A:B=65:35 at 70 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title intermediates intermediate 17 (100 mg, 95% purity, 42% yield) and intermediate 18 (100 mg, 99% purity, 44% yield) both as colorless oil.

Preparation of Intermediate 40 and 41 benzyl (*R)-(5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)(methyl)carbamate benzyl (*S)-(5-(6-(6-(2-(ethyl(isopropyl)carbamoyl)-4-fluorophenoxy)-1,2,4-triazin-5-yl) 2,6-diazaspiro[3.4]octan-2-yl)-2,6-dimethylheptan-2-yl)(methyl)carbamate

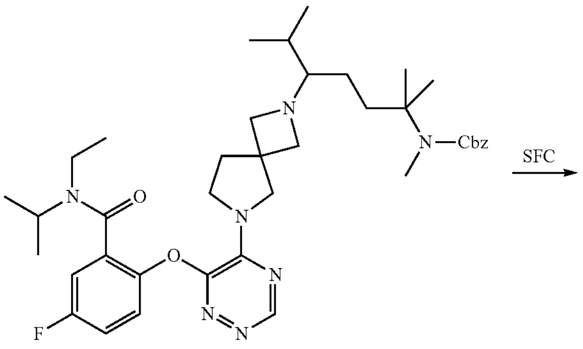

intermediate 39

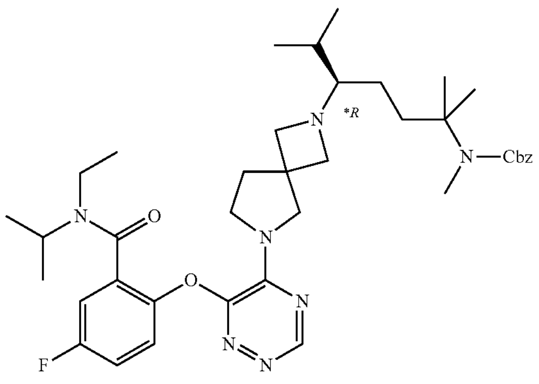

intermediate 40

+

-continued

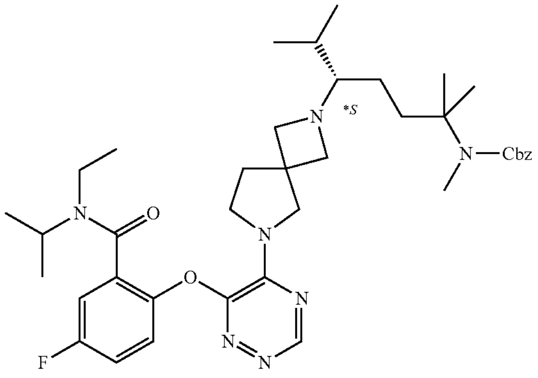

intermediate 41 benzyl (5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)(methyl)carbamate (intermediate 39) (650 mg, 0.923 mmol) was separated by SFC over DAICEL CHIRALPAK AD-H (column: 250×30 mm 5 μm; eluent: 30% (v/v) super critical $CO_2$ in EtOH (0.1% ammonia), flow rate: 60 mL/min) to afford the title intermediates intermediate 40 (250 mg, 96% purity, 37% yield) and intermediate 41 (220 mg, 99.9% purity, 34% yield) both as a colorless oil.

Preparation of Intermediate 48 and 49 methyl (*R)-4(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanoate methyl (*S)-4-(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanoate

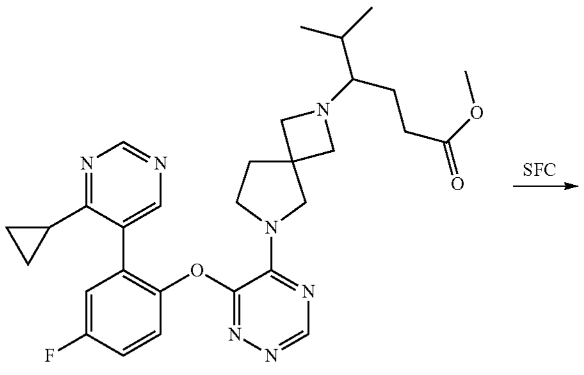

intermediate 47

-continued

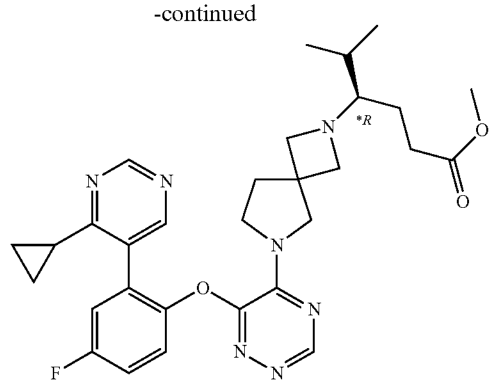

intermediate 48

+

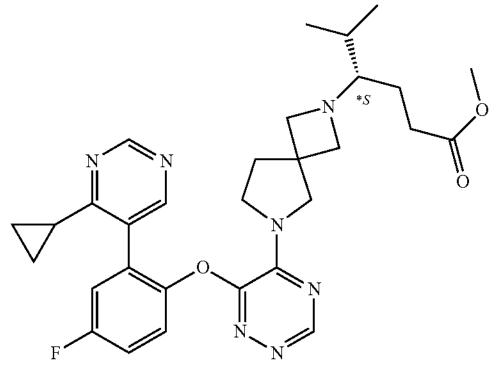

intermediate 49 methyl 4-(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanoate (intermediate 47) (360 mg, 0.513 mmol) was purified by SFC over Phenomenex-Cellulose-2 (column: 250×30 mm, 10 μm; eluent: 35% (v/v) supercritical $CO_2$ in MeOH with 0.1% ammonia) to afford the title intermediates intermediate 48 (110 mg, 35% yield) and intermediate 49 (90 mg, 31% yield) both as white solid.

Preparation of Intermediate 93

1-(1,3-dioxolan-2-yl)-4-methylpentan-3-one

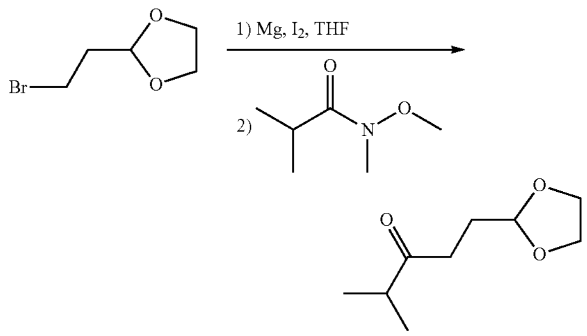

To the mixture of magnesium (6.0 g, 247 mmol) and iodine (100 mg, 0.394 mmol) in THF (70 mL) at 25° C. was slowly added a solution of 2-(2-bromoethyl)-1,3-dioxolane (20.0 g, 110 mmol) in THF (30 mL), the resulting mixture was stirred at 25° C. for 1 h. Then, the mixture was slowly added to the solution of N-methoxy-N-methylisobutyramide (10 g, 76.2 mmol) in THF (100 mL) cooled at 0° C. The reaction mixture was slowly warmed to 25° C. and stirred at this temperature for 8 h. The mixture was quenched by sat. aq. $NH_4Cl$ (300 mL), extracted with MTBE (200 mL×3). The combined organic layers were dried over $Na_2SO_4$, filtered and concentrated under reduced pressure to give the crude product, which was purified by FCC (PE:EtOAc=1:0 to 20:1) to afford the title intermediate (13 g, crude) as colorless oil which was used directly in next step without further purification.

Preparation of Intermediate 95 and %

(R)-2-((5-(2-(1-(1,3-dioxolan-2-yl)-4-methylpentan-3-yl)-2,6-diazaspiro[3.4]octan-6-yl)-1,2,4-triazin-6-yl)oxy)-N-ethyl-5-fluoro-N-isopropylbenzamide (S)-2-((5-(2-(1-(1,3-dioxolan-2-yl)-4-methylpentan-3-yl)-2,6-diazaspiro[3.4]octan-6-yl)-1,2,4-triazin-6-yl)oxy)-N-ethyl-5-fluoro-N-isopropylbenzamide

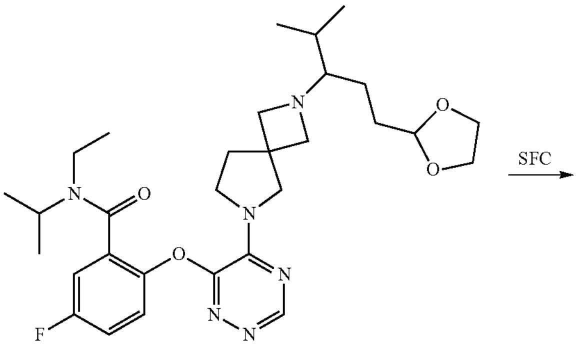

intermediate 94

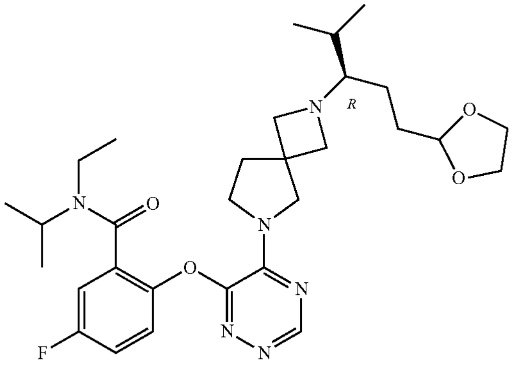

intermediate 95

+

-continued

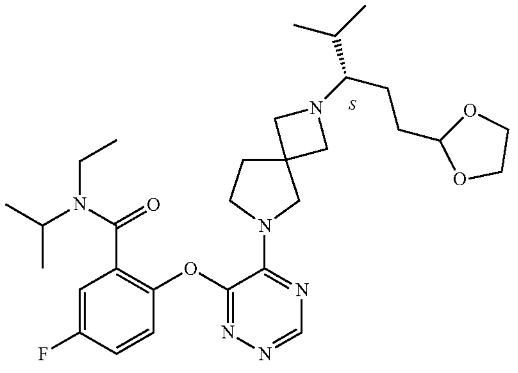

intermediate 96

2-((5-(2-(1-(1,3-dioxolan-2-yl)-4-methylpentan-3-yl)-2,6-diazaspiro[3.4]octan-6-yl)-1,2,4-triazin-6-yl)oxy)-N-ethyl-5-fluoro-N-isopropylbenzamide (intermediate 94) (4.00 g, 7.01 mmol) separated by SFC over DAICEL CHIRALCEL OD (column: 250×50 mm 10 um; Mobile phase: A: Supercritical $CO_2$, B: MeOH (0.1% ammonia), A:B=75:25 at 200 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title intermediates intermediate 95 (1.72 g, 98.76% purity, 42.5% yield) and intermediate 96 (1.57 g, 98.09% purity, 38.5% yield) as white solid.

Preparation of Intermediate 99 and 100

(*R)-2-((5-(2-(1-(1,3-dioxolan-2-yl)-4-methylpentan-3-yl)-2,6-diazaspiro[3.4]octan-6-yl)-1,2,4-triazin-6-yl)oxy)-5-fluoro-N,N-diisopropylbenzamide (*S)-2-((5-(2-(1-(1,3-dioxolan-2-yl)-4-methylpentan-3-yl)-2,6-diazaspiro[3.4]octan-6-yl)-1,2,4-triazin-6-yl)oxy)-5-fluoro-N,N-diisopropylbenzamide

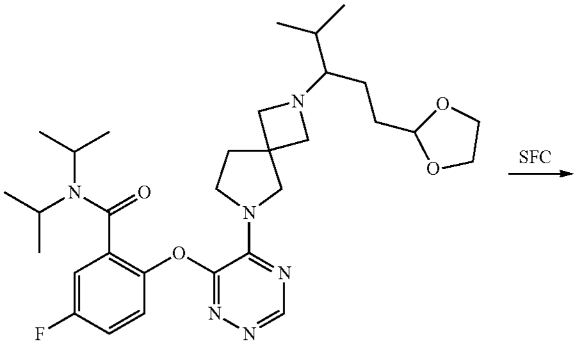

intermediate 98

-continued

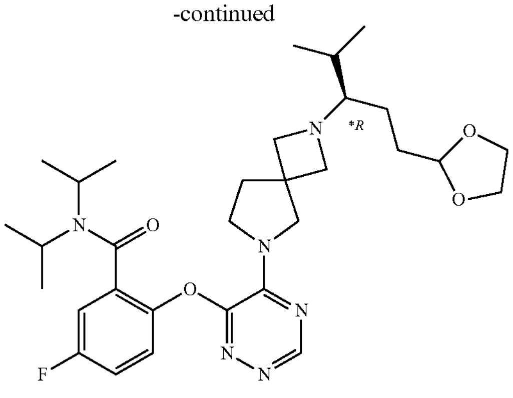

intermediate 99

+

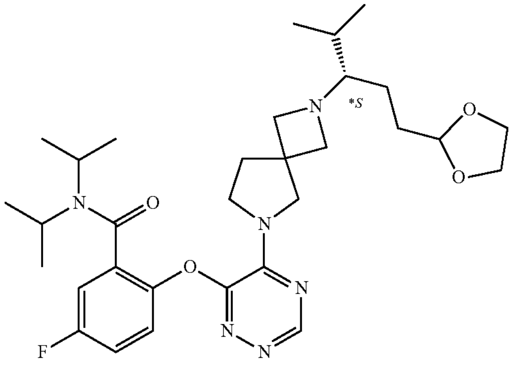

intermediate 100

2-((5-(2-(1-(1,3-dioxolan-2-yl)-4-methylpentan-3-yl)-2,6-diazaspiro[3.4]octan-6-yl)-1,2,4-triazin-6-yl)oxy)-5-fluoro-N,N-diisopropylbenzamide (intermediate 98) (6.5 g) was separated by SFC over DAICEL CHIRALPAK IG (column: 250×50 mm 10 um; Mobile phase: A: Supercritical $CO_2$, B: MeOH (0.1% ammonia), A:B=65:35 at 200 mL/min; Column Temp: 38; Nozzle Pressure: 100 Bar; Nozzle Temp: 60° C.; Evaporator Temp: 20° C.; Trimmer Temp: 25° C.; Wavelength: 220 nm) to afford the title intermediates intermediate 99 (2.7 g) and intermediate 100 (2.8 g).

Preparation of Intermediate 97

(R)-N-ethyl-S-fluoro-N-isopropyl-2-((5-(2-(2-methyl-6-oxohexan-3-yl)-2,6-diazaspiro[3.4]octan-6-yl)-1,2,4-triazin-6-yl)oxy)benzamide

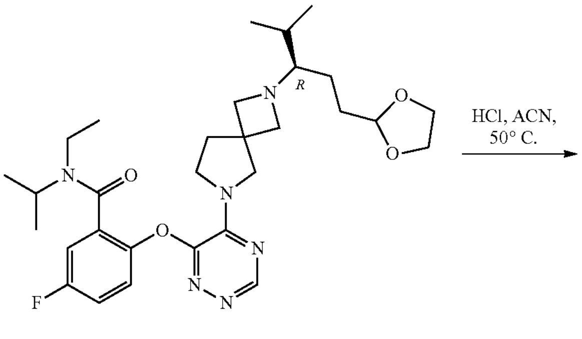

-continued

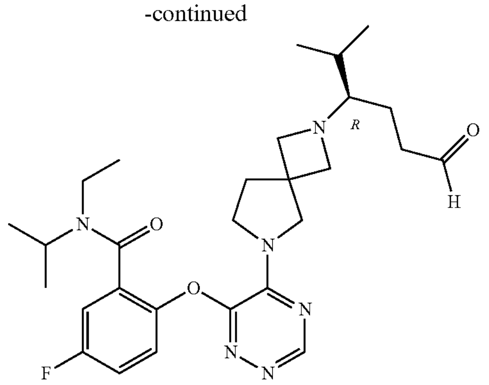

To a solution of (R)-2-((5-(2-(1-(1,3-dioxolan-2-yl)-4-methylpentan-3-yl)-2,6-diazaspiro[3.4]octan-6-yl)-1,2,4-triazin-6-yl)oxy)-N-ethyl-5-fluoro-N-isopropylbenzamide (intermediate 95) (1.00 g, 1.75 mmol) in ACN (10 mL) was added 1M HCl (10.0 mL, 10.0 mmol) and the resulting mixture was stirred at 50° C. for 1 h. After cooling to RT, the reaction mixture was concentrated under reduced pressure. The resulting residue was diluted with DCM (50 mL) and basified to pH=14 by 10% aq. NaOH. The mixture was further extracted by DCM (30 mL×3) and the combined organic layers were dried over anhydrous $Na_2SO_4$, filtered and concentrated in vacuo to afford the title intermediate (900 mg, 87% purity, 85% yield) as a white solid, which was used directly in next step without further purification.

Preparation of Intermediates 101, 102, 103

(*R)-5-fluoro-N,N-propyl-2-((5-(2-(2-methyl-6-oxohexan-3-yl)-2,6-diazaspiro[3.4]octan-6-yl)-1,2,4-triazin-6-yl)oxy)benzamide (*S)-5-fluoro-N,N-diisopropyl-2-((5-(2-(2-methyl-6-oxohexan-3-yl)-2,6-diazaspiro[3.4]octan-6-yl)-1,2,4-triazin-6-yl)oxy)benzamide N-ethyl-5-fluoro-N-isopropyl-2-((5-(2-(2-methyl-6-Oxohexan-3-yl)-2,6-diazaspiro[3.4]octan-6-yl)-1,2,4-triazin-6-yl)oxy)benzamide The following intermediates were synthesized by an analogous method as described for intermediate 97

| Int. No. | Structure | Starting Material |
|---|---|---|
| 101 | 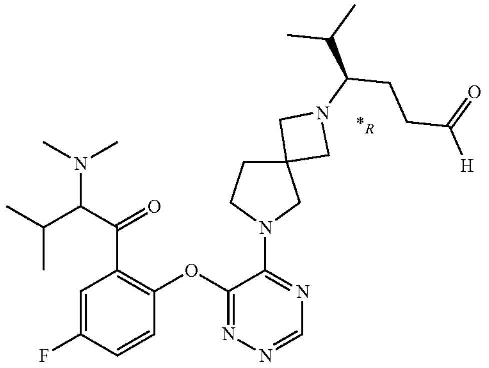 [SMILES: CC(C)C(C(=O)c1cc(F)ccc1Oc1nncnc1N1CCC2(C1)CN([C@H](CCC=O)C(C)C)C2)N(C)C] | intermediate 99 |
| 102 | 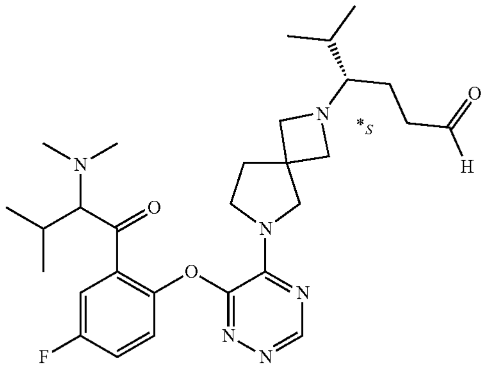 [SMILES: CC(C)C(C(=O)c1cc(F)ccc1Oc1nncnc1N1CCC2(C1)CN([C@@H](CCC=O)C(C)C)C2)N(C)C] | intermediate 100 |

-continued

| Int. No. | Structure | Starting Material |
|---|---|---|
| 103 | 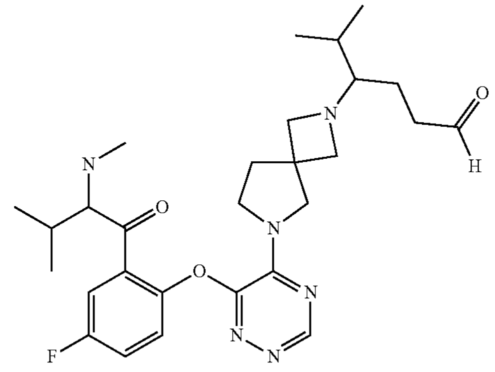 [SMILES: CNC(C(=O)c1cc(F)ccc1Oc1nncnc1N1CCC2(C1)CN(C(CCC=O)C(C)C)C2)C(C)C] | intermediate 94 |

Preparation of Intermediate 114 methyl 2-(2-isopropyl-1,3-dioxolan-2-yl)acetate

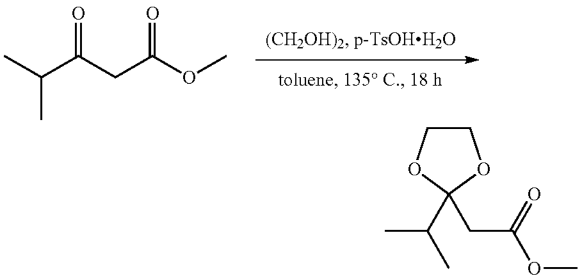

In a 1000 mL flask equipped with a Dean-Stark apparatus, methyl 4-methyl-3-oxopentanoate (50 g, 347 mmol) was added to a solution consisting of ethane-1,2-diol (43 g, 693 mmol), p-toluenesulfonic acid monohydrate (597 mg, 3.47 mmol) and toluene (500 mL). The mixture was stirred at 135° C. for 18 h. After cooling to RT, 1M $Na_2CO_3$ (300 mL) aqueous solution was added to the reaction mixture. The organic layer was separated and washed with $H_2O$ (100 mL), dried over anhydrous $Na_2SO_4$, filtered, and concentrated in vacuo to afford the title intermediate (41 g, crude) as a yellow oil which was used directly in next step without further purification.

Preparation of Intermediate 115

2-(2-isopropyl-1,3-dioxolan-2-yl)ethan-1-ol

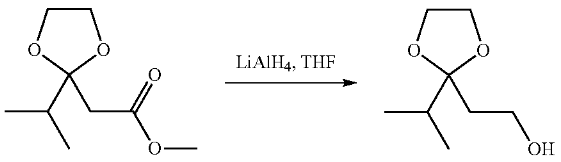

$LiAlH_4$ (2.5 g, 66 mmol) was added in portions to THF (250 mL) cooled at 0° C. under $N_2$ atmosphere. A solution of methyl 2-(2-isopropyl-1,3-dioxolan-2-yl)acetate (intermediate 114) (10 g, crude) in THF (20 mL) was added drop-wise to above mixture at 0° C. under $N_2$ atmosphere. The resulting mixture was slowly warmed to RT and stirred at this temperature for 18 h under $N_2$ atmosphere. Then 2.5 mL $H_2O$ was slowly added to above mixture, followed with addition of aq. NaOH solution (15%, 7.5 mL). The resulting mixture was stirred at RT for 0.5 h. Then anhydrous $MgSO_4$ was added to above mixture. The suspension was filtered through a celite pad and washed with THF (200 mL). The filtrate was concentrated in vacuo to afford the title intermediate (6.8 g, crude) as a yellow oil which was used directly in next step without further purification.

Preparation of Intermediate 116

1-hydroxy-4-methylpentan-3-one

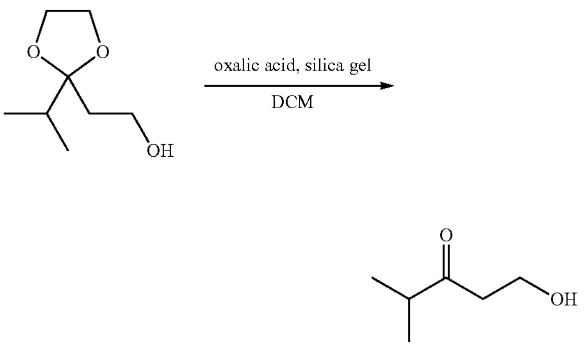

Oxalic acid (4.2 mL, 10% in water, 4.7 mmol) was added to a mixture of silica gel (27 g, 449 mmol) in DCM (230 mL). Once the aqueous layer vanished, a solution of 2-(2-isopropyl-1,3-dioxolan-2-yl)ethan-1-ol (intermediate 115) (3.7 g, crude) in DCM (7 mL) was added and the reaction mixture was stirred at RT for 5 h. Then $NaHCO_3$ (800 mg) was added. The resulting mixture was filtered and washed with DCM (50 mL×3). The filtrate was concentrated in vacuo to afford the title intermediate (2.4 g, crude) as a colorless oil which was used directly in next step without further purification.

Preparation of Intermediate 124

(*R)-3-(6-(6-(2-(ethyl(isopropyl)carbamoyl)-4-fluorophenoxy)-1,2,4-triazin-5-yl)-2,6-diazaspiro[3.4]octan-2-yl)-4-methylpentyl methanesulfonate

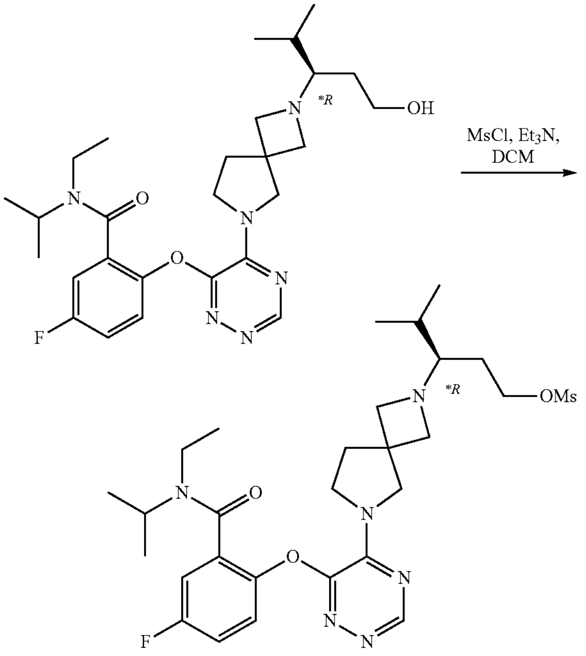

MsCl (250 mg, 2.18 mmol) was added dropwise to a solution of N-ethyl-5-fluoro-2-((5-(2-(1-hydroxy-4-methylpentan-3-yl)-2,6-diazaspiro[3.4]octan-6-yl)-1,2,4-triazin-6-yl)oxy)-N-isopropylbenzamide (Compound 213) (500 mg, 0.972 mmol) and TEA (0.27 mL, 1.9 mmol) in DCM (10 mL) cooled at 0° C. under $N_2$ atmosphere. The resulting mixture was stirred at 0° C. under $N_2$ for 45 min. Then the reaction mixture was quenched with $H_2O$ (5 mL) and extracted with DCM (10 mL×3). The combined organic layers were washed with brine (5 mL), dried over anhydrous $Na_2SO_4$ and filtered. The filtrate was concentrated in vacuo to afford the title intermediate (400 mg, crude) as a yellow oil which was used directly in next step without further purification.

Preparation of Intermediate 130, 139 methyl 3-methyl-4-(tosyloxy)butanoate 2-methoxypropyl 4-methylbenzenesulfonate

The following intermediates were synthesized by an analogous method as described above for intermediate 124

| Int. No. | Structure | Starting Materials | Conditions |
|---|---|---|---|
| 130 | 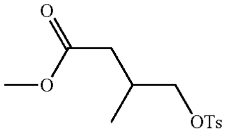 [SMILES: COC(=O)CC(C)COS(=O)(=O)c1ccc(C)cc1] | intermediate 129, TsCl | DMAP, TEA, DCM, RT |
| 139 | 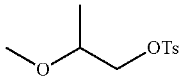 | 2-methoxypropan-1-ol, TsCl | DMAP, TEA, DCM, RT |

Preparation of Intermediate 125

N-benzyl-2-methoxy-N-methylacetamide

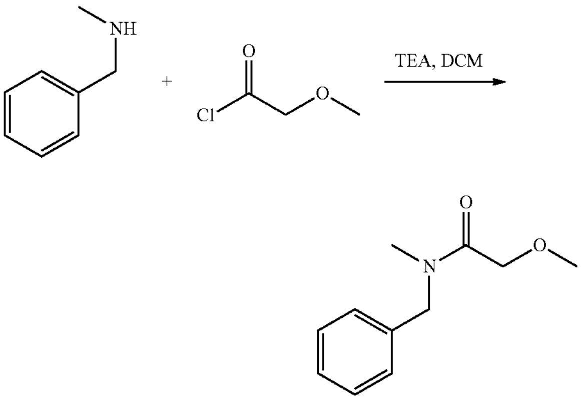

To a solution of N-methyl-1-phenylmethanamine (5.5 g, 45.4 mmol) and TEA (14 g, 138.4 mmol) in DCM (60 mL) cooled at 0° C. was dropwise added 2-methoxyacetyl chloride (5 g, 46.073 mmol). The resulting mixture was slowly warmed to 25° C. and stirred at this temperature for 1 h. Then, aq. sat. $NaHCO_3$ solution (50 mL) was added to above mixture and extracted with DCM (50 mL×3). The combined organic layers were washed with brine (100 mL), dried over $Na_2SO_4$, filtered and concentrated in vacuo give a crude residue which was purified by FCC (EA:PE=from 0 to 80%) to afford the title intermediate (3.4 g, 34% yield) as a colorless oil.

Preparation of Intermediate 126

N-benzyl-2-methoxy-N-methylethan-1-amine-1,1-$d_2$

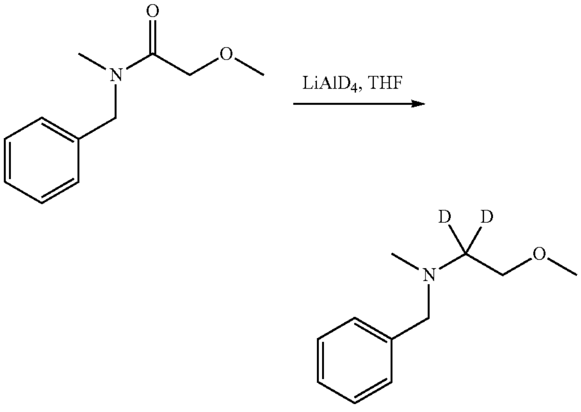

To the mixture of $LiAlD_4$ (1.5 g, 35.732 mmol) in THF (25 mL) cooled at 0° C. under $N_2$ atmosphere was added dropwise a solution of N-benzyl-2-methoxy-N-methylacetamide (intermediate 125) (3.4 g, 17.6 mmol) in THF (25 mL). The reaction mixture was first stirred at 25° C. for 1 h and at 50° C. for additional 2 h. Then the reaction mixture was cooled to 0° C. and quenched with aq. NaOH (1 M, 10 mL) dropwise. The resulting mixture was filtered and the filter cake was washed with EtOAc (100 mL). The filtrate was washed with $H_2O$ (50 mL) and brine (50 mL), dried over $Na_2SO_4$, and filtered. The solvent was concentrated under reduced pressure to afford a residue which was purified by FCC (EtOAc:PE=from 0 to 100%) to afford the title intermediate (2.0 g, 60% yield) as a colorless oil.

Preparation of Intermediate 127

2-methoxy-N-methylethan-1,1-$d_{2-1}$-amine, hydrochloride

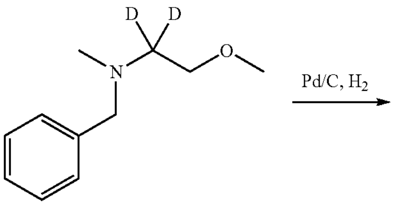

-continued

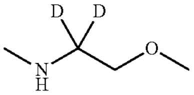

HCl salt

To the solution of N-benzyl-2-methoxy-N-methylethan-1-amine-1,1-$d_2$ (800 mg, 4.413 mmol) in MeOH (20 mL) and THF (60 mL) was added 1,1,2-trichloroethane (1.2 g, 9.0 mmol) and Pd/C (wet, 10%, 0.5 g). The resulting mixture was stirred under $H_2$ atmosphere (50 psi) at 50° C. for 18 h. After cooling to RT, the reaction mixture was filtered by celite and the filtrate was concentrated in vacuo to afford the title intermediate (600 mg, crude) as yellow oil which was used directly in next step without further purification.

Preparation of Intermediate 128 methyl 4-hydroxy-3-methylbut-2-enoate

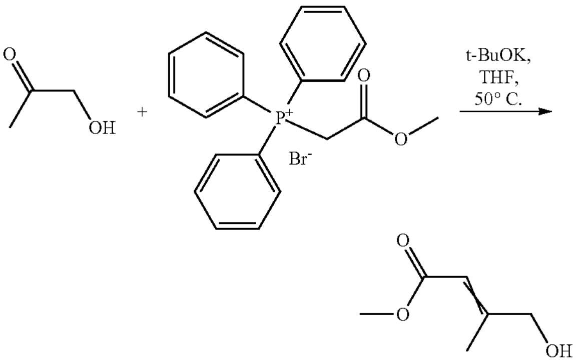

undetermined mixture of E/Z t-BuOK (16.0 g, 143 mmol) was added to a solution of (2-methoxy-2-oxoethyl)triphenylphosphonium bromide (59.0 g, 142 mmol) in THF (220 mL). The resulting mixture was stirred at 50° C. for 1 h. Then 1-hydroxypropan-2-one (7.2 g, 97 mmol) in THF (30 mL) was added to above mixture and the reaction mixture was stirred at 50° C. for another 16 h. After cooling to RT, $H_2O$ (200 mL) was added and the mixture was extracted with EtOAc (200 mL×3). The combined organic layers were washed with $H_2O$ (300 mL), dried over anhydrous $Na_2SO_4$ and filtered. The filtrate was concentrated to in vacuo to afford a crude compound which was purified by FCC (PE:EtOAc=1:0 to 1:1) to afford the title intermediate (3.4 g, 27% yield) as a light yellow oil.

Preparation of Intermediate 129 methyl 4-hydroxy-3-methylbutanoate

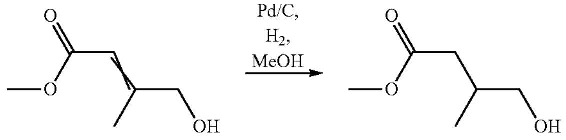

To the solution of methyl 4-hydroxy-3-methylbut-2-enoate (intermediate 128) (3.4 g, 26 mmol) in MeOH (100 mL) was added dry Pd/C (500 mg, 10%) and the suspension was stirred at RT under $H_2$ (15 psi) atmosphere for 4 h. Then the reaction mixture was filtered through a celite pad and washed with MeOH (200 mL). The filtrate was concentrated in vacuo afford the title intermediate (2.3 g, 67% yield) as a yellow oil which was used directly in the next step without further purification.

Preparation of Intermediates 193, 194, 207, 208

(S)-5-((tert-butyldiphenylsilyl)oxy)-6-(ethyl(methyl)amino)-2-methylhexan-3-one (R)-5-((tert-butyldiphenylsilyl)oxy)-6-(ethyl(methyl)amino)-2-methylhexan-3-one (S)-5-((tert-butyldiphenylsilyl)oxy)-6-((2-methoxyethyl)(methyl)amino)-2-methylhexan-3-one (R)-5-((tert-butyldiphenylsilyl)oxy)-6-((2-methoxyethyl)(methyl)amino)-2-methylhexan-3-one The following intermediates were synthesized by an analogous method as described for intermediate 129

| Int. No. | Structure | Starting Material |
|---|---|---|
| 193 | 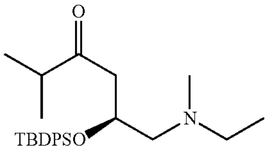 | intermediate 191 |
| 194 | 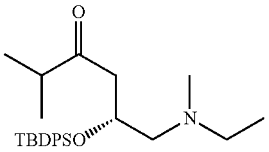 | intermediate 192 |
| 207 | 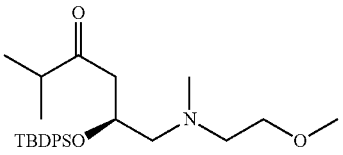 | intermediate 205 |
| 208 | 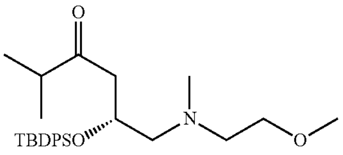 | intermediate 206 |

Preparation of Intermediate 131 and 132 methyl (*R)-3-methyl-4-(tosyloxy)butanoate methyl (*S)-3-methyl-4-(tosyloxy)butanoate

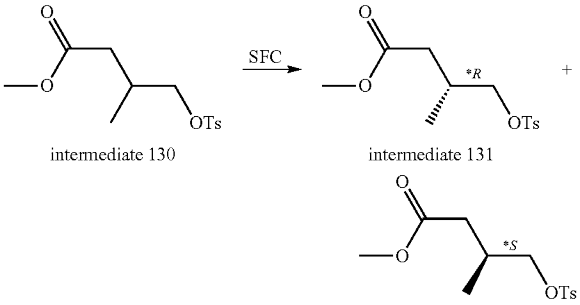

intermediate 130 intermediate 131 intermediate 132

Methyl 3-methyl-4-(tosyloxy)butanoate (intermediate 130) (3.3 g) was purified by SFC over DAICEL CHIRALPAK AY-H (column: 250×30 mm Sum; Mobile phase: A: Supercritical $CO_2$, B: EtOH (0.1% ammonia), A:B=90:10 at 60 mL/min) to afford the title intermediates (intermediate 131) (1.28 g, 97% purity, 36% yield) and (intermediate 132) (1.27 g, 85% purity, 33% yield) both as white solid.

Preparation of Intermediate 134 methyl (*S)-4-((2-methoxyethyl)(methyl)amino)-3-methylbutanoate

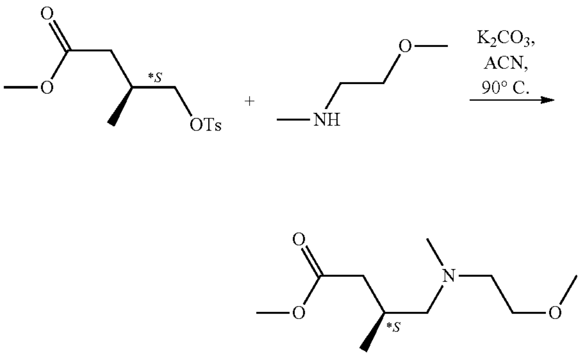

A mixture of methyl (*S)-3-methyl-4-(tosyloxy)butanoate (intermediate 132) (1.27 g, 4.44 mmol), 2-methoxy-N-methylethan-1-amine (593 mg, 6.65 mmol), and $K_2CO_3$ (1.23 mg, 8.87 mmol) in ACN (5 mL) was stirred at 90° C. overnight. After cooling to RT, the reaction mixture was filtered and the filtrate was concentrated in vacuo to afford the title intermediate (670 mg, crude) as a brown oil which was used directly in next step without further purification.

Preparation of Intermediates 133, 185, 186, 199, 200, 219 methyl (*R)-4-((2-methoxyethyl)(methyl)amino)-3-methylbutanoate ethyl (S)-3-((tert-butyldiphenylsilyl)oxy)-4-(ethyl(methyl)amino)butanoate ethyl (R)-3-((tert-butyldiphenylsilyl)oxy)-4-(ethyl(methyl)amino)butanoate ethyl (S)-3-((tert-butyldiphenylsilyl)oxy)-4-((2-methoxyethyl)(methyl)amino)butanoate ethyl (R)-3-((tert-butyldiphenylsilyl)oxy)-4-((2-methoxyethyl)(methyl)amino)butanoate N-(2-methoxyethyl)-N,2-dimethylprop-2-en-1-amine The following intermediates were synthesized by an analogous method as described for intermediate 134

| Int. No. | Structure | Starting Materials | Conditions |
|---|---|---|---|
| 133 | 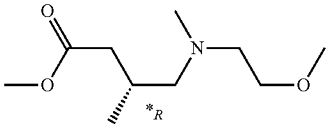 | intermediate 131, 2-methoxy-N-methylethan-1-amine | $K_2CO_3$, ACN, 90° C. |
| 185 | 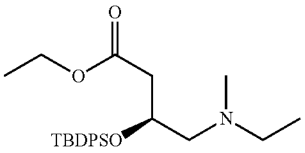 | intermediate 183, N-methylethanamine | $K_2CO_3$, ACN, 80° C. |
| 186 | 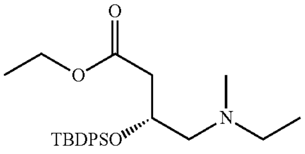 | intermediate 184, N-methylethanamine | $K_2CO_3$, ACN, 80° C. |
| 199 | 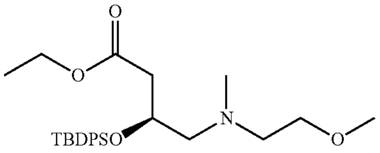 | intermediate 183, 2-methoxy-N-methylethan-1-amine | $K_2CO_3$, ACN, 85° C. |
| 200 | 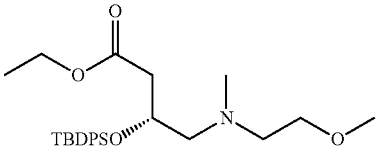 | intermediate 184, 2-methoxy-N-methylethan-1-amine | $K_2CO_3$, ACN, 85° C. |
| 219 | 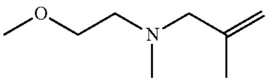 | 3-bromo-2-methylprop-1-ene, 2-methoxy-N-methylethan-1-amine | $K_2CO_3$, $H_2O$, RT |

Preparation of Intermediate 136

(*S)-6-((2-methoxyethyl)(methyl)amino)-2,5-dimethylhexan-3-one

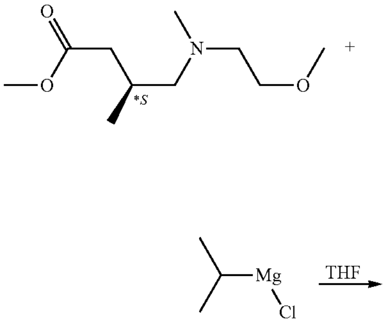

-continued

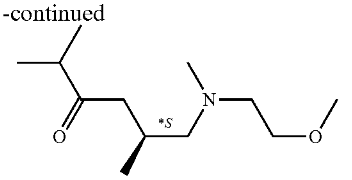

To the solution of methyl (*S)-4-((2-methoxyethyl)(methyl)amino)-3-methylbutanoate (intermediate 134) (670 mg, crude) in THF (5 mL) cooled at 0° C. under $N_2$ was added dropwise isopropylmagnesium chloride (4.94 mL, 9.88 mmol, 2 M, in THF). The resulting mixture was stirred at 50° C. for 5 h under $N_2$. After cooling to RT, the reaction mixture was quenched with sat. aq. $NH_4Cl$ solution (1.5 mL) and filtered. The filtrate was concentrated in vacuo to afford the title intermediate (507.1 mg, crude) as a yellow oil which was used directly in next step without further purification.

Preparation of Intermediate 135

(*R)-6-((2-methoxyethyl)(methyl)amino)-2,5-dimethylhexan-3-one

The following intermediate was synthesized by an analogous method as described for intermediate 136

| Int. No. | Structure | Starting Materials | Conditions |
|---|---|---|---|
| 135 | 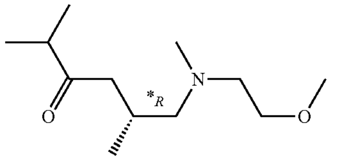 | intermediate 133, isopropylmagnesium chloride | THF, 50° C. |

Preparation of Intermediate 165 tert-butyl (2-hydroxy-5-methyl-4-oxohexyl)(methyl)carbamate

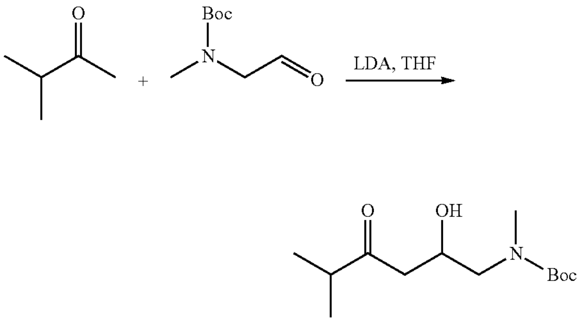

To the solution of 3-methylbutan-2-one (6.0 g, 70.0 mmol) in THF (150 mL) cooled at −40° C. under $N_2$ atmosphere was added dropwise LDA (40 mL, 2 M in THF, 80.0 mmol). The resulting mixture was stirred at −40° C. for 1 h. Then a solution of tert-butyl methyl(2-oxoethyl)carbamate (8.0 g, 46.2 mmol) in THF (50 mL) was added dropwise to above mixture and the reaction was further stirred at −40° C. for 2 h. The reaction was quenched by the dropwise addition of $H_2O$ (20 mL) at −40° C. Then the mixture was warmed to RT and concentrated under reduced pressure. The crude residue was diluted with $H_2O$ (200 mL) and extracted with EtOAc (200 mL×2). The combined organic layers were washed with brine (200 mL), dried over anhydrous $Na_2SO_4$, filtered and concentrated. The crude product was purified by FCC (PE/EtOAc=20/1 to 3/1) to afford the title intermediate (8.8 g, 85% purity, 62% yield) as colorless oil.

The following intermediate was synthesized by an analogous method as described for intermediate 165

| Int. No. | Structure | Starting Materials |
|---|---|---|
| 174 | 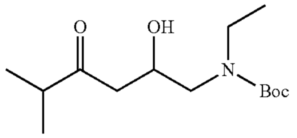 [SMILES: CCN(CC(O)CC(=O)C(C)C)C(=O)OC(C)(C)C] | 3-methylbutan-2-one, tert-butyl ethyl(2-oxoethyl)carbamate |

Preparation of Intermediate 166 tert-butyl (2-methoxy-5-methyl-4-oxohexyl)(methyl)carbamate

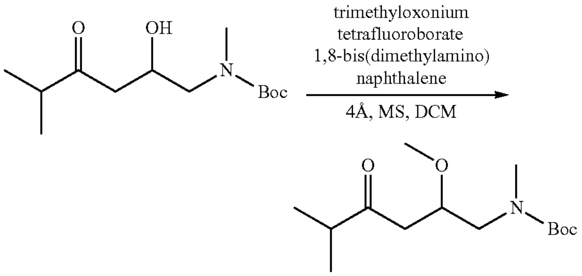

To a solution of tert-butyl (2-hydroxy-5-methyl-4-oxohexyl)(methyl)carbamate (intermediate 165) (4.00 g, 15.4 mmol) in DCM (200 mL) was added 4 Å molecular sieve (4 g) under $N_2$ atmosphere and the mixture was stirred at 25° C. for 10 min. Then 1,8-bis(dimethylamino)naphthalene (8.26 g, 38.6 mmol) was added and the mixture was cooled to 0° C., followed with addition of trimethyloxonium tetrafluoroborate (5.93 g, 40.1 mmol). The reaction mixture was first stirred at 0° C. for 2 h, then warmed up to 25° C. and stirred at this temperature for additional 16 h. The suspension was filtered and washed with DCM (40 mL×2). The filtrate was concentrated in vacuo and the residue was purified by FCC (PE/EtOAc=5/1 to 4/1) to afford the title intermediate (2.00 g, 44% yield) as colorless oil.

Preparation of Intermediate 181 ethyl (S)-3-hydroxy-4-iodobutanoate

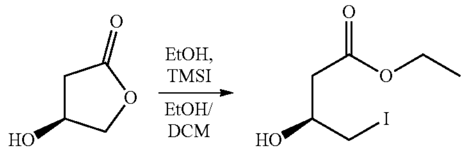

To a solution of (S)-4-hydroxydihydrofuran-2(3H)-one (5 g, 50.0 mmol) in EtOH (8.6 mL) in DCM (20 mL) under $N_2$ atmosphere was slowly added TMSI (14.8 g, 74.0 mmol). The resulting mixture was stirred at RT for 16 h. A solution of sat. $Na_2SO_3$ (40 mL) was added. The organic layer was separated and concentrated in vacuo to afford the title intermediate (8.8 g, crude) as yellow oil which was used directly in next step without further purification.

Preparation of Intermediate 182 ethyl (R)-3-hydroxy-4-iodobutanoate

The following intermediate was synthesized by an analogous method as described above for intermediate 181

| Int. No. | Structure | Starting Material |
|---|---|---|
| 182 | 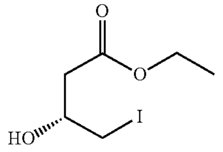 | (R)-4-hydroxydihydrofuran-2(3H)-one |

Preparation of Intermediate 195

(S)-6-(ethyl(methyl)amino)-5-hydroxy-2-methylhexan-3-one

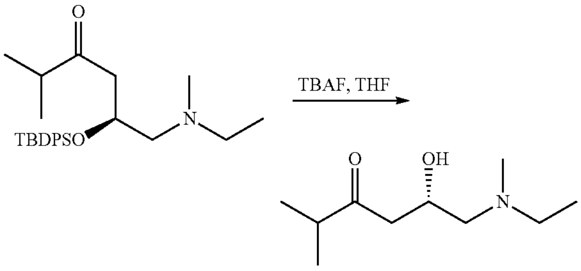

To a solution of (S)-5-((tert-butyldiphenylsilyl)oxy)-6-(ethyl(methyl)amino)-2-methylhexan-3-one (intermediate 193) (2.33 g, 5.04 mmol) in THF (3 mL) was added TBAF (0.65 mL, 1.0 M in THF, 0.65 mmol) under $N_2$ atmosphere. The resulting mixture was stirred at RT for 16 h. The reaction mixture was concentrated under reduced pressure and the crude residue was diluted with $H_2O$ (25 mL) and extracted with DCM (60 mL×3). The combined organic layers were washed with brine (40 mL×2), dried over $Na_2SO_4$ and filtered. The filtrate was concentrated in vacuo to afford the title intermediate (2.2 g, crude) as yellow oil which was used directly in next step without further purification.

Preparation of Intermediate 196, 209, 210

(R)-6-(ethyl(methyl)amino)-5-hydroxy-2-methylhexan-3-one (S)-5-hydroxy-6-((2-methoxyethyl)(methyl)amino)-2-methylhexan-3-one (R)-5-hydroxy-6-((2-methoxyethyl)(methyl)amino)-2-methylhexan-3-one The following intermediates were synthesized by an analogous method as described above for intermediate 195

| Int. No. | Structure | Starting Material |
|---|---|---|
| 196 | 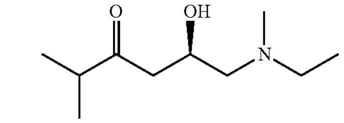 | intermediate 194 |
| 209 | 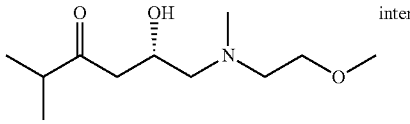 | intermediate 207 |
| 210 | 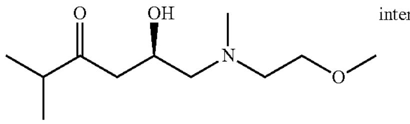 | intermediate 208 |

Preparation of Intermediate 220

N-((3-isopropyl-5-methyl-4,5-dihydroisoxazol-5-yl)methyl)-2-methoxy-N-methylethan-1-amine

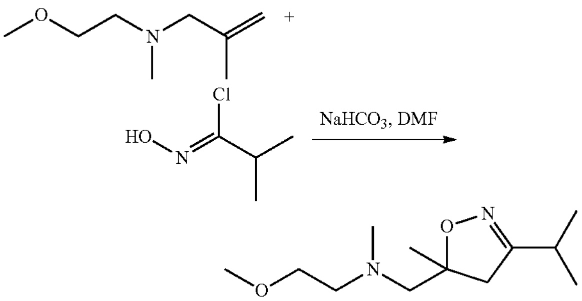

To a solution of N-(2-methoxyethyl)-N,2-dimethylprop-2-en-1-amine (intermediate 219) (2.90 g, 20.2 mmol) in DMF (50 mL) cooled at 0° C. were added $NaHCO_3$ (6.82 g, 81.2 mmol) and (Z)—N-hydroxyisobutyrimidoyl chloride (2.47 g, 20.3 mmol). The reaction mixture was stirred at 0° C. for 30 min and then at RT for 16 h. The reaction mixture was quenched by $H_2O$ (50 mL) and extracted with EtOAc (30 mL×2). The combined organic layers were washed with sat. aq. LiCl solution (50 mL), dried over anhydrous $Na_2SO_4$ and filtered. The filtrate was concentrated in vacuo to give the crude product, which was purified by FCC (MeOH: DCM=1:10) to afford the title intermediate (1.20 g, 89.9% purity, 25.9% yield) as brown oil.

Preparation of Intermediate 221

5-hydroxy-6-((2-methoxyethyl)(methyl)amino)-2,5-dimethylhexan-3-one

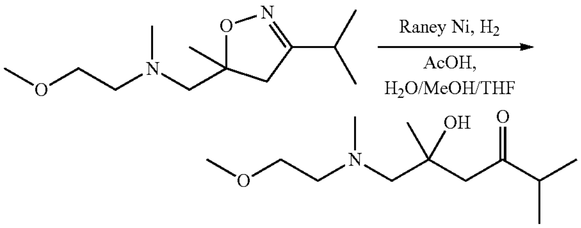

To a solution of N-((3-isopropyl-5-methyl-4,5-dihydroisoxazol-5-yl)methyl)-2-methoxy-N-methylethan-1-amine (intermediate 220) (1.20 g, 5.26 mmol) in MeOH and THF (40 mL, MeOH/THF=1/2) were added AcOH (3.15 g, 52.5 mmol) and $H_2O$ (9.50 mL, 572.3 mmol). Raney-Ni (750 mg) was added to the solution under $N_2$ atmosphere at 0° C. The suspension was degassed and purged with $H_2$ for 3 times and the mixture was stirred under $H_2$ atmosphere (30 Psi) at 25° C. overnight.

The reaction mixture was filtered through a celite pad and the filtrate was extracted with DCM. The combined organic layers were washed with $NaHCO_3$ (20 mL×2) and brine (20 mL×2), dried over $Na_2SO_4$ and filtered. The filtrate was concentrated in vacuo to afford the title intermediate (1.10 g, crude) as brown oil, which was used directly in next step without further purification.

Preparation of Intermediate 227 tert-butyl (R)-(1-(2,2-dimethyl-4,6-dioxo-1,3-dioxan-5-yl)-3-methylbutan-2-yl)carbamate

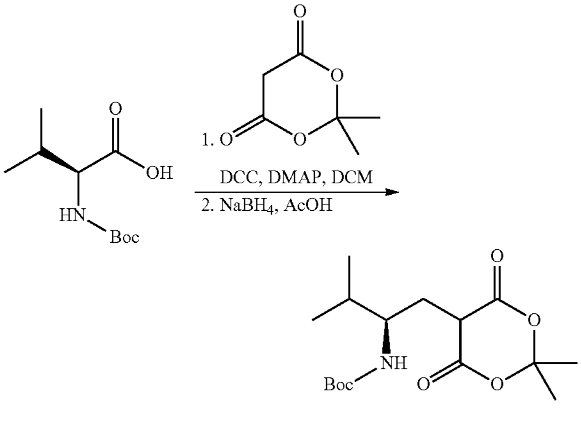

Boc-L-valine (44.9 kg), 2,2-dimethyl-1,3-dioxane-4,6-dione (32.9 kg) and DMAP (35.5 kg) in DCM (607 kg) pre-cooled at −10 to 0° C. were added to a solution of DCC (55.5 kg) in DCM (613 kg) over 3 h and aged for 16 h at −10 to 0° C. 10% citric acid aqueous solution (449 kg) was added whilst maintaining a temperature below 10° C. The resulting slurry was aged for 2 h at 0 to 10° C. then filtered. The filter cake was washed with DCM (91 kg). The filtrate was separated and the organic layer was washed with 10% citric acid aqueous solution (two times 450 kg) and 10% NaCl aqueous solution (449 kg). To organic phase (1200 kg), was added acetic acid (75.0 kg) whilst maintaining a temperature between −10 to 0° C. Sodium Borohydride (18.0 kg) was added in portions over 5 h whilst maintaining a temperature in the range −10 to 0° C. and then resulting mixture was aged at −10 to 0° C. for an additional 16 h. The mixture was warmed to 15 to 25° C., and aged for 2 h. The mixture was then washed with 14% NaCl aqueous solution (450 kg) followed by a second wash with 14% NaCl aqueous solution (432 kg) and a final water wash (444 kg). The organic phase was concentrated under reduced pressure to 2-4 vol. Iso-propanol (143 kg) was added to the residue and concentrated to 4-5 vol. under reduced pressure. After cooling to −10 to 0° C. and aging for 8 h, the resulting slurry was filtered, washed with IPA (38 kg) and dried to afford the title intermediate (46.7 kg, 69% yield) as a white solid.

Preparation of Intermediate 228 tert-butyl (R)-2-isopropyl-5-oxopyrrolidine-1-carboxylate

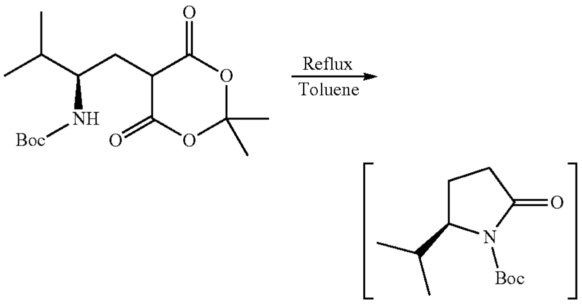

tert-butyl (R)-(1-(2,2-dimethyl-4,6-dioxo-1,3-dioxan-5-yl)-3-methylbutan-2-yl)carbamate (intermediate 227) (46.7 kg) in toluene (333 kg) was heated to reflux and aged for 4 h. The mixture was cooled to ambient temperature, filtered and washed with toluene (20 kg). The combined filtrates were concentrated to dryness at reduced pressure to afford the desired compound (31.05 kg, 96% yield) as an oil which was used directly without further purification.

Preparation of Intermediate 229 tert-butyl (5R)-2-hydroxy-5-isopropylpyrrolidine-1-carboxylate

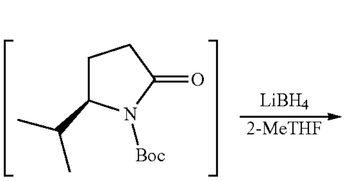

-continued

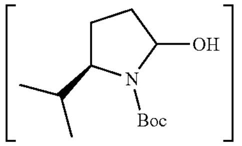

tert-butyl (R)-2-isopropyl-5-oxopyrrolidine-1-carboxylate (intermediate 228) (30.9 kg) in 2-MeTHF (26.7 kg) was cooled to −5 to 5° C. A solution of $LiBH_4$ in 2-MeTHF (1M, 45.2 kg, 54.4 mol) was added over 3 h and the mixture was aged for 4 h. A cold aqueous solution of 5% $NaHCO_3$ (163 kg) was added at −5 to 5° C. over 3 h and aged for an additional 2 h. The mixture was warmed to ambient temperature and aged for a further 2 h. The aqueous layer was separated and the organic layer was washed with 10% NaCl aqueous solution (170 kg) and water (155 kg). During the water wash, an emulsion formed and solid NaCl (3.1 kg) was added to affect the separation. After removal of the aqueous layer, the organic layer was concentrated under reduced pressure to dryness to afford the desired compound (28.5 kg, 91% yield) as an oil, which was used directly without further purification.

Preparation of Intermediate 230 tert-butyl (R)-(6-((2-methoxyethyl)(methyl)amino)-2-methylhexan-3-yl)carbamate

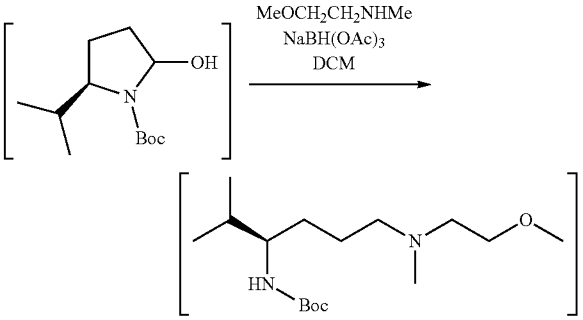

tert-butyl (5R)-2-hydroxy-5-isopropylpyrrolidine-1-carboxylate (intermediate 229) (28.55 kg) in DCM (344 kg), at 15 to 25° C. was treated with 2-methoxy-N-methylethan-1-amine (12.3 kg, 138.0 mol) and the resulting mixture was aged for 1 h. Sodium triacetoxyborohydride (40.12 kg) was added in portions over 5 h whilst maintaining a temperature between 15 to 25° C. and the resulting mixture was aged for 48 h. The reaction mixture was quenched by the addition of 8% NaOH aqueous solution (184 kg) over 2 h whilst maintaining a temperature between 15 to 25° C. and the mixture was aged for a further 2 h. The water layer was separated, and the organic layer was washed with water (169 kg). The organic layer was then concentrated under reduced pressure to dryness to afford the title intermediate (33.26 kg, 88% yield) as an oil which was used directly without further purification.

Preparation of Intermediate 231

(R)-$N^1$-(2-methoxyethyl)-$N^1$,5-dimethylhexane-1,4-diamine, dihydrochloride

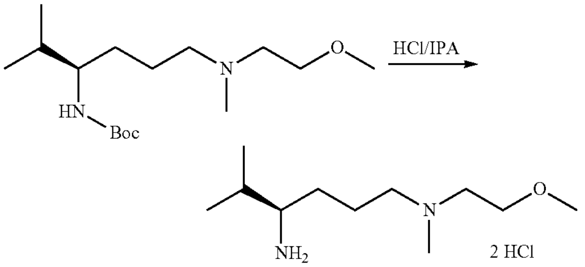

To 4 molar solution of HCl in iso-propanol (84.80 kg) at ambient temperature was added a solution of tert-butyl (R)-(6-((2-methoxyethyl)(methyl)amino)-2-methylhexan-3-yl)carbamate (intermediate 230) (32.38 kg) in iso-propanol (25.6 kg) over 3 h and the mixture was aged at ambient temperature for an additional 19 h. Methyl tert-butyl ether (95.25 kg) was then added over 1 h and the mixture was aged for 2.5 h. The resulting slurry was filtered and washed with MTBE (53 kg). The filter cake was dried to afford the title compound (23.92 kg, 81% yield) as a white solid.

Preparation of Intermediate 232 ethyl 1-benzyl-3-(chloromethyl)pyrrolidine-3-carboxylate

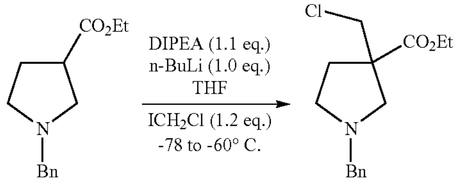 [SMILES: CCOC(=O)C1CCN(Cc2ccccc2)C1 ; CCOC(=O)C1(CCl)CCN(Cc2ccccc2)C1]

To a solution of DIPEA (952 g, 1.1 eq.) in THF (6 L) which was cooled to −35 to −25° C. was added n-BuLi (2.33 kg, 2.5 M in hexane, 1.0 eq.) whilst maintaining a temperature below −25° C. The resulting mixture was aged at −35 to −25° C. for an additional 30 min then cooled to between −78 to −60° C. A solution of ethyl 1-benzylpyrrolidine-3-carboxylate (2 kg, 1.0 eq.) in THF (2 L) at −78 to −60° C. was added and stirred for an addition 30 min. Chloroiodomethane (1.81 kg, 1.2 eq.) was then charged at −78 to −60° C. The reaction mixture was aged at −60 to −40° C. for 2 h. To the reaction mixture was added to citric acid aqueous solution (660 g in 6 L $H_2O$) at a temperature between 0 to 10° C. and the resulting mixture was aged at 20 to 30° C. for an additional 20 min. After separating the layers, the aqueous layer was extracted with EtOAc (6 L) and the combined organic layers washed with brine (6 L) then warmed to 50 to 60° C. Oxalic acid (2.22 kg) was charged at 50 to 60° C. The resulting mixture was stirred at 50 to 60° C. for 3 h then cooled to 20 to 30° C. and aged overnight. The resulting solid was filtered and the cake was washed with ethyl acetate (2 L). The wet cake was added to toluene (4 L), $H_2O$ (8 L) and $K_3PO_4$ (1.5 eq.) and the resulting mixture was aged at 20 to 30° C. for 20 min. After separating the layers, the aqueous layer was extracted with toluene (2 L). The organic layers were combined and washed twice with water (2 L). The organic phase was concentrated under reduced pressure to afford 4.2 kg of the desired compound as a toluene solution (46 wt % by assay, giving an assay yield of 80%).

Preparation of Intermediate 233

1-benzyl-3-(chloromethyl)pyrrolidine-3-carbaldehyde

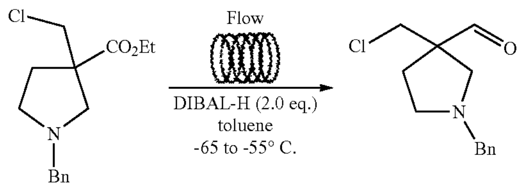 [SMILES: CCOC(=O)C1(CCl)CCN(Cc2ccccc2)C1 ; O=CC1(CCl)CCN(Cc2ccccc2)C1]

Reaction conducted in a flow chemistry system: A solution of ethyl 1-benzyl-3-(chloromethyl)pyrrolidine-3-carboxylate (intermediate 232) (4.4 kg) in toluene (26 L) was pumped at 26.7 mL/min and cooled to −60° C. After cooling, it was then mixed with a cooled solution of DIBAL-H (28.1 mol) in toluene at −60° C. (28 L) with a pumping rate of 32.1 mL/min. The mixture was passed through a Perfluoroalkoxy (PFA) coil tube reactor at −60° C. (total flow rate of 58.8 mL/min with a residence time of 5 seconds). The resulting mixture was mixed with cooled MeOH (−60° C.) which was pumped at the rate of 15.2 mL/min. This mixed solution was pumped to another PFA coil tube reactor at −60° C. (total flow rate of 74 mL/min with a residence time of 5 seconds). The resulting mixture was collected into a receiver which contained 20 wt % aq. solution Rochelle's salt (20 V). The layers were separated, and the organic phase was twice washed with water (2×44 L). The organic phase was combined with another 3.0 kg batch prepared in an analogous manner and concentrated under reduced pressure to afford 20.8 kg of a toluene solution of the desired compound (25.5 wt % assay by HPLC, giving an assay yield of 85%) which was used directly without further purification.

$^1$H NMR (300 MHz, Chloroform-d): δ 9.62 (s, 1H), 7.39-7.20 (m, 5H), 3.83-3.57 (m, 4H), 2.96 (d, J=10.2 Hz, 1H), 2.80-2.55 (m, 3H), 2.17 (ddd, J=13.9, 7.9, 6.1 Hz, 1H), 1.83 (ddd, J=13.4, 7.8, 5.5 Hz, 1H).

Preparation of Intermediate 234

(R)-4-(6-benzyl-2,6-diazaspiro[3.4]octan-2-yl)-N-(2-methoxyethyl)-N,5-dimethylhexan-1-amine

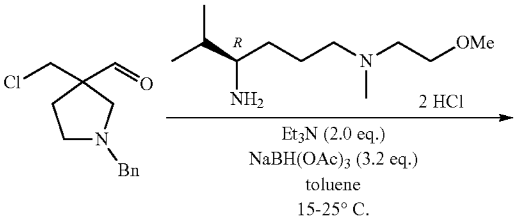

-continued

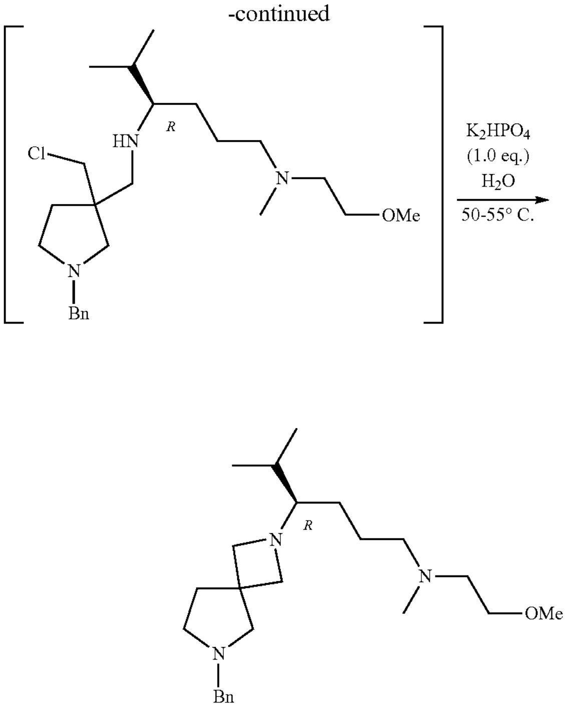

To a solution of 1-benzyl-3-(chloromethyl)pyrrolidine-3-carbaldehyde (intermediate 233) in toluene (3.0 kg, 10 wt %) diluted with toluene (30 L) and (R)-N$^1$-(2-methoxyethyl)-N$^1$,5-dimethylhexane-1,4-diamine, dihydrochloride (intermediate 231) (3.47 kg) was added triethylamine (2.55 kg, 25.2 mol) at 20 to 30° C. The resulting mixture was aged for 2 h at 20 to 30° C. Then sodium triacetoxyborohydride (9.0 kg) was charged at 20 to 30° C. and the mixture was aged for 12 h. The reaction mixture was cooled to 5 to 15° C. and 25 wt % NaOH aqueous solution (25 L, ~16.75 eq.) was added maintaining a temperature below 35° C. The resulting mixture was aged at 20 to 30° C. for 25 mins and the layers were separated. The organic layer was washed with 15 wt % aq. NaCl (10 L) and the layers were again separated and water (18 L) was charged to the organic phase. The pH of the aqueous phase was adjusted to 6~7 with 4M aq. HCl whilst maintaining an internal temperature below 35° C. The organic phase was then discarded and the aqueous phase was separated and basified to pH 8~9 with $K_2HPO_4$.

The resulting mixture was warmed to 50 to 55° C. and aged for 3 h. The reaction mixture was then cooled to ambient temperature and combined with other two batches (2.4 kg+3.0 kg). The combined streams were washed with methyl tert-butyl ether three times (3×40 L). To the resulting aqueous layer was added additional methyl tert-butyl ether (83 L) and the aqueous phase was basified to pH 9~10 using 8 wt % aq. NaOH whilst maintaining a temperature between 15 to 35° C. The aqueous layer was separated, and the organic layer was washed with three times water (3×30 L). The organic layer was then concentrated under reduced pressure to approximately 3 volumes and then flushed with methanol three times (3×30 L) and concentrated to dryness to afford the desired compound (12.4 kg, 90% isolated yield) as light-yellow oil, which was used directly without further purification.

Preparation of Intermediate 224

(R)-N-(2-methoxyethyl)-N,5-dimethyl-4-(2,6-diazaspiro[3.4]octan-2-yl)hexan-1-amine

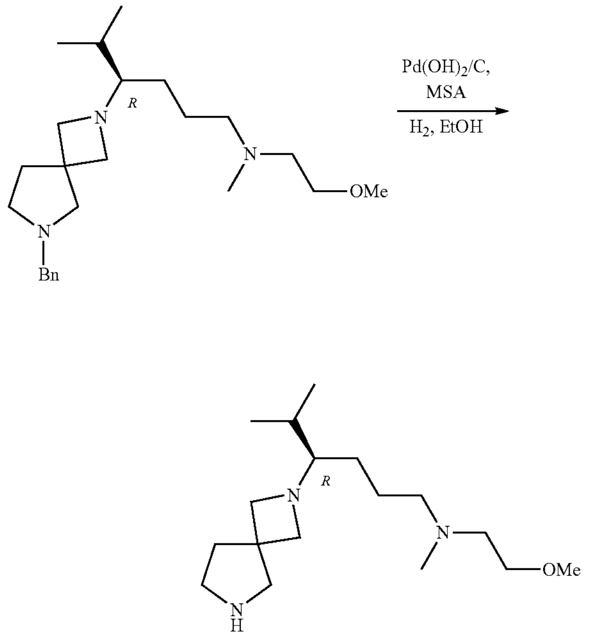

To palladium hydroxide on carbon (1.2 kg) in EtOH (1.47 kg) cooled to −5 to 5° C. were added methanesulfonic acid (MSA) (11 kg), (R)-4-(6-benzyl-2,6-diazaspiro[3.4]octan-2-yl-N-(2-methoxyethyl)-N,5-dimethylhexan-1-amine (intermediate 234) (10 kg) and EtOH (250 L). The mixture was warmed to 35-45° C. and stirred under a hydrogen atmosphere (0.27 to 0.40 MPa) for 16-20 h. The mixture was filtered over diatomite (20 kg) and the pad was washed with EtOH (24 L). The filtrate was concentrated under reduced pressure (<40° C.) to 2~3 vol. and then flushed twice with 2-MeTHF (73 kg and 47 kg) to give a 2~3 vol. solution. After dilution with 2-MeTHF (65 kg), 10% aq. sodium sulfate (30 kg) was added and the mixture was cooled to 0 to 10° C., followed by the addition of 16% aq. NaOH (50 kg) to adjust the pH to 13~14. The temperature was adjusted to 15 to 25° C. and stirred for 30 to 60 min. The aqueous layer was separated and extracted twice with 2-MeTHF (47 kg×2). The combined organic layers were concentrated under reduced pressure (<40° C.) to 3~4 vol. and 2-MeTHF (950 g) was added. After concentration under reduced pressure (<40° C.) to 3~4 vol., the resulting solution was diluted with 2-MeTHF (30 kg), dried by passing through 4A molecular sieves (25 kg) and washed with 2-MeTHF (30 kg). The final solution was concentrated to afford the desired compound (6.7 kg) as an oil with 90.1% assay purity in a 79% corrected yield.

Preparation of Intermediate 225

(R)-4-(6-(3,6-dichloro-1,2,4-triazin-5-yl)-2,6-diazaspiro[3.4]octan-2-yl)-N-(2-methoxyethyl)-N,5-dimethylhexan-1-amine

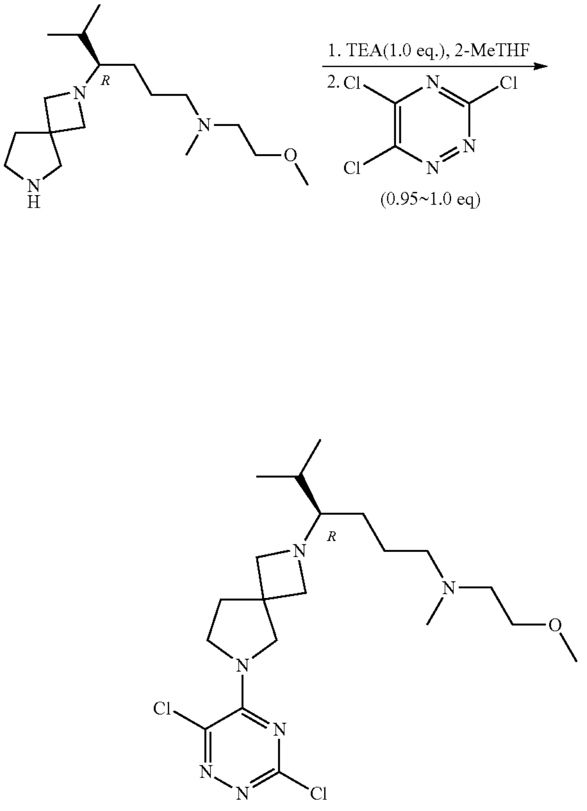

To (R)-N-(2-methoxyethyl)-N,5-dimethyl-4-(2,6-diazaspiro[3.4]octan-2-yl)hexan-1-amine (intermediate 224) (100 g) was added 2-MeTHF (430 g) and TEA (68 g) and the mixture was cooled to −50 to −40° C. 3,5,6-trichloro-1,2,4-triazine (62 g) in 2-MeTHF (172 g) was added and the mixture was stirred for 1 to 3 h. The resulting mixture was warmed to −20 to −10° C. and a 7% $NaHCO_3$ aqueous solution was added, the mixture was warmed to 20 to 30° C. and stirred for 30 to 60 min. The aqueous layer was removed and the organic layer was washed with 10% $Na_2SO_4$ (500 g). The organic layer was dried by passing through 4 Å molecular sieves (220 g) and washed with 2-MeTHF (180 g). The title intermediate was afforded in 90% assay yield as a solution 14.8 wt % in 2-MeTHF.

Preparation of Intermediate 245

(R)-2-((5(2-(6-((2-((tert-butyldimethylsilyl)oxy) ethyl)methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

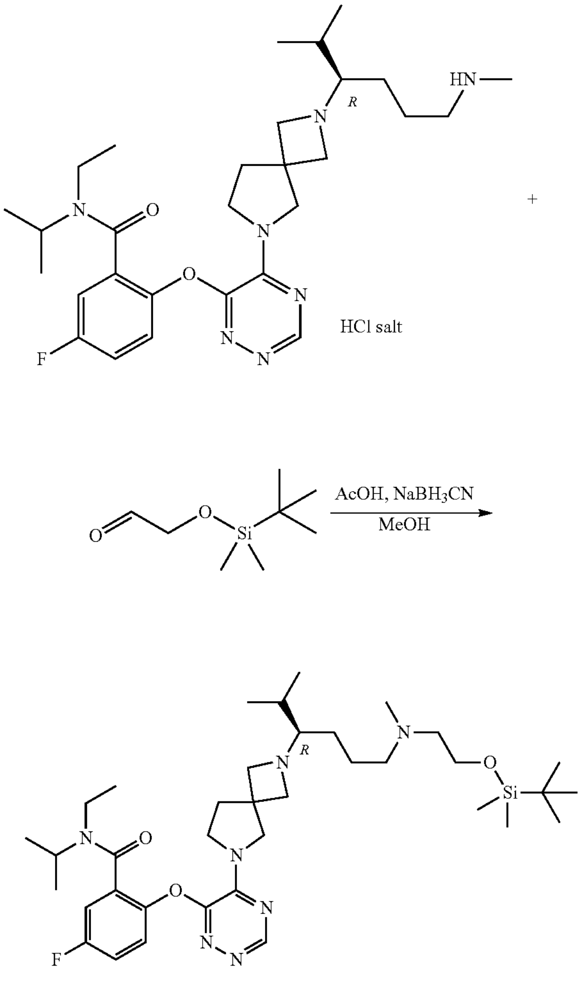

$NaBH_3CN$ (23.2 mg, 0.37 mmol) was added to a solution of (R)-N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide hydrochloride (Compound 19) (100 mg, 0.18 mmol), 2-((tert-butyldimethylsilyl) oxy)acetaldehyde (71 μL, 0.37 mmol) and AcOH (11 μL, 0.18 mmol) in MeOH (2 mL). Then, the reaction mixture was stirred at RT for 24 h. The reaction mixture was poured into water, basified with an aqueous solution of $K_2CO_3$ and DCM was added. The organic layer was separated, dried over $MgSO_4$, filtered and evaporated till dryness to give a crude (152 mg) which was purified by silica gel chromatography (Stationary phase: irregular bare silica 4 g, Mobile phase: 0.5% NH4OH, 95% DCM, 5% MeOH). The fractions containing the product were mixed and concentrated to afford the title intermediate (46 mg, 36% yield).

Preparation of Compounds

Preparation of Compound 61 tert-butyl (4-(6-(6-(2-(ethyl(isopropyl)carbamoyl)-4-fluorophenoxy)-1,2,4-triazin-5-yl)-2,6-diazaspiro [3.4]octan-2-yl)-5-methylhexyl)carbamate

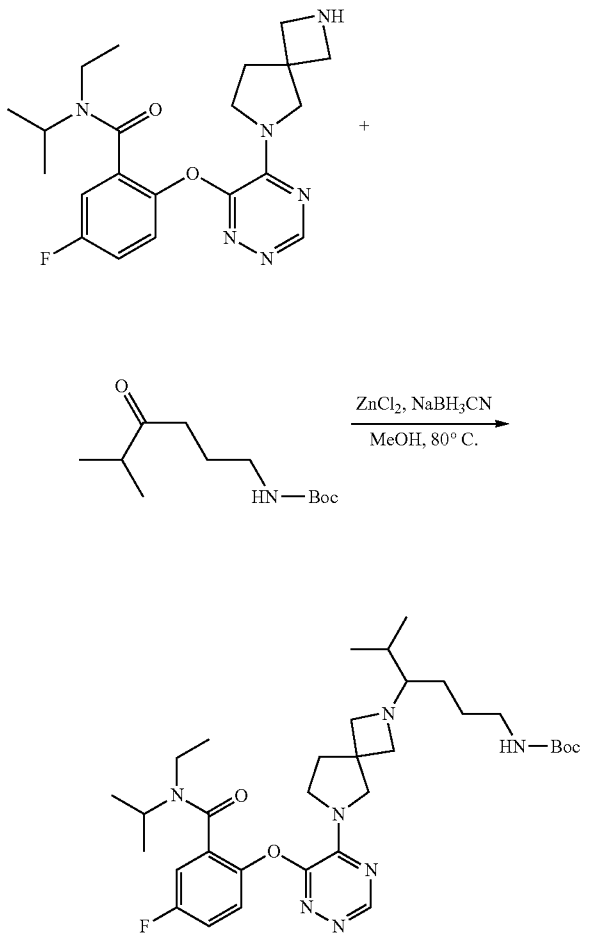 [SMILES: CCN(C(=O)c1cc(F)ccc1Oc1nncnc1N1CCC2(CNC2)C1)C(C)C ; "+" ; CC(C)C(=O)CCCNC(=O)OC(C)(C)C ; CCN(C(=O)c1cc(F)ccc1Oc1nncnc1N1CCC2(C1)CN(C(CCCNC(=O)OC(C)(C)C)C(C)C)C2)C(C)C]

The mixture 2-((5-(2,6-diazaspiro[3.4]octan-6-yl)-1,2,4-triazin-6-yl)oxy)-N-ethyl-5-fluoro-N-isopropylbenzamide (intermediate 3) (1.0 g, 2.4 mmol), tert-butyl (5-methyl-4-oxohexyl)carbamate (intermediate 1) (830 mg, 3.62 mmol) and $ZnCl_2$ (660 mg, 4.84 mmol) in MeOH (15 mL) was stirred at 80° C. for 0.5 h. Then $NaBH_3CN$ (310 mg, 4.93 mmol) was added and the resulting mixture was stirred at 80° C. for 6 h. After cooled to RT, the mixture was concentrated under reduced pressure to give the crude product, which was further purified by preparative HPLC using a Waters Xbridge Prep OBD (column: C18 150×40 mm 10 um; eluent: $ACN/H_2O$ (0.05% ammonia) from 45% to 75% v/v) to afford the title compound (700 mg, 46% yield) as colorless oil.

Preparation of Compounds 62 and 63 tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate tert-butyl (S)-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate

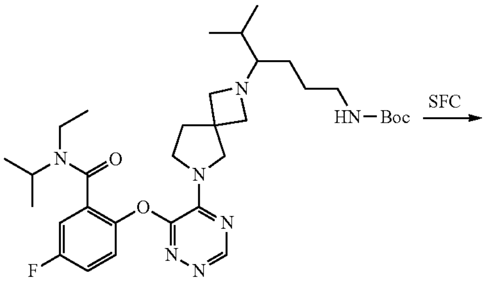

Compound 61

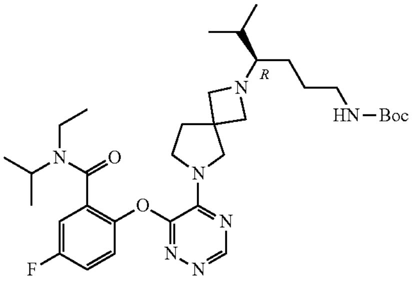

Compound 62

+

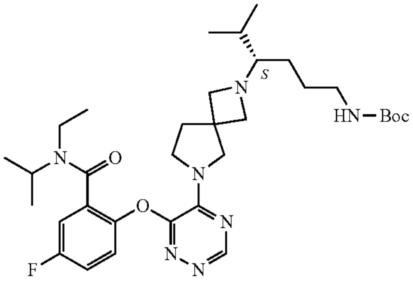

Compound 63 tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate (Compound 61) (200 mg, 0.319 mmol) was purified by SFC over DAICEL CHIRALPAK IG (column: 250×30 mm 10 um; isocratic elution: EtOH (containing 0.1% of 25% ammonia): supercritical $CO_2$, 40%: 60% (v/v)) to afford the title compounds (Compound 62) (85 mg, 42% yield) and (Compound 63) (80 mg, 40% yield) both as light yellow oil.

Compound 207 and 208 tert-butyl (*R)-(5-(6-(6-(2-(ethyl(isopropyl)carbamoyl)-4-fluorophenoxy)-1,2,4-triazin-5-yl)-2,6-diazaspiro[3.4]octan-2-yl)-6-methylheptyl)carbamate tert-butyl (*S)-(5-(6-(6-(2-(ethyl(isopropyl)carbamoyl)-4-fluorophenoxy)-1,2,4-triazin-5-yl)-2,6-diazaspiro[3.4]octan-2-yl)-6-methylheptyl)carbamate

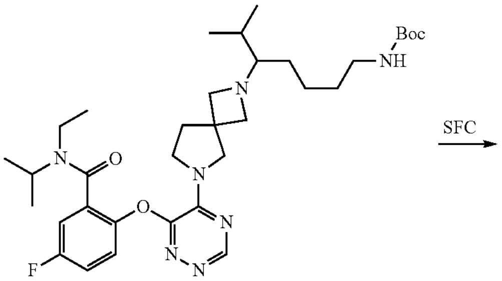

Compound 206

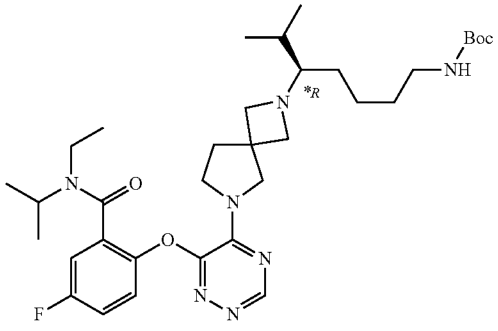

Compound 207

+

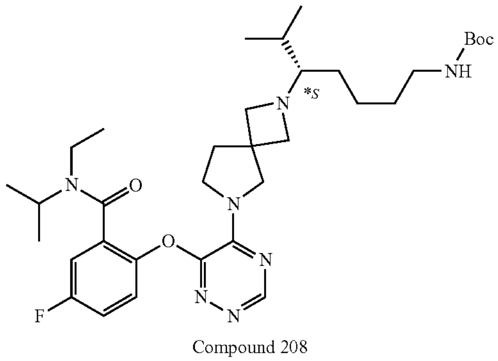

Compound 208

Tert-butyl (5-(6-(6-(2-(ethyl(isopropyl)carbamoyl)-4-fluorophenoxy)-1,2,4-triazin-5-yl)-2,6-diazaspiro[3.4]octan-2-yl)-6-methylheptyl)carbamate (Compound 206) (1.4 g) was purified by SFC over DAICEL CHIRALPAK IG (column: 250×30 mm, 10 μm; Mobile phase: A: Supercritical $CO_2$, B: MeOH (0.1% ammonia), A:B=55:45 at 200 mL/min) to afford the title compounds (Compound 207) (700 mg) and (Compound 208) (700 mg) both as white solid.

Compound 304 and 305 tert-butyl ((4*R)-4(6-(6-(2-(ethyl(isopropyl)carbamoyl)-4-fluorophenoxy)-1,2,4-triazin-5-yl)-2,6-diazaspiro[3.4]octan-2-yl)-2-methoxy-5-methylhexyl)(methyl)carbamate tert-butyl ((4*S)-4-(6(6-(2-(ethyl(isopropyl)carbamoyl)-4-fluorophenoxy)-1,2,4-triazin-5-yl)-2,6-diazaspiro[3.4]octan-2-yl)-2-methoxy-5-methylhexyl)(methyl)carbamate

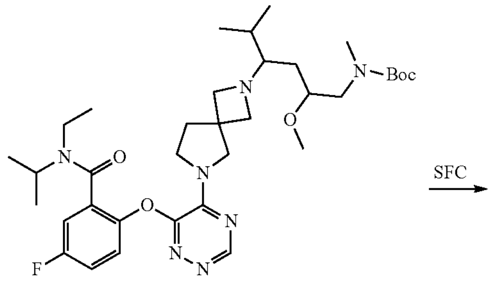

Compound 303

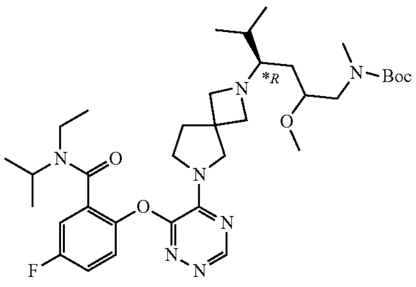

Compound 304

+

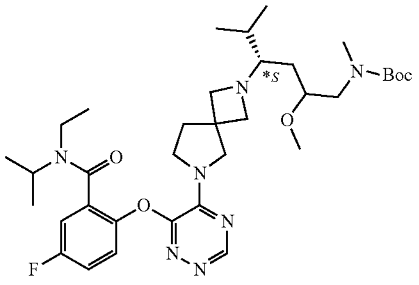

Compound 305 tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-2-methoxy-5-methylhexyl)(methyl)carbamate (Compound 303) (250 mg) was separated by SFC over DAICEL CHIRALPAK IG (column: 250×30 mm, 10 μm; Mobile phase: A: Supercritical $CO_2$, B: MeOH (0.1% ammonia), A:B=60:40; Flow rate: 80 mL/min) to afford the title compounds (Compound 304) (124 mg) and (Compound 305) (124 mg) both as colorless sticky oil.

Compound 306 and 307 tert-butyl ((2*R,4*R)-4(6-(6-(2-(ethyl(isopropyl) carbamoyl)-4-fluorophenoxy)-1,2,4-triazin-5-yl)-2,6-diazaspiro[3.4]octan-2-yl)-2-methoxy-5-methylhexyl)(methyl)carbamate tert-butyl ((2*S,4*R)-4(6-(6-(2-(ethyl(isopropyl) carbamoyl)-4-fluorophenoxy)-1,2,4-triazin-5-yl)-2,6-diazaspiro[3.4]octan-2-yl)-2-methoxy-5-methylhexyl)(methyl)carbamate

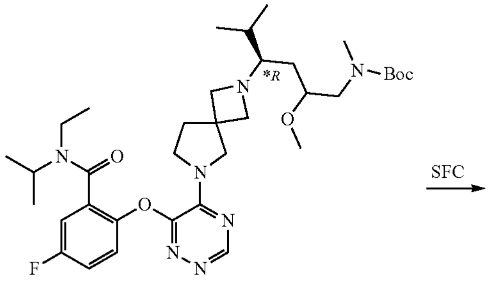

Compound 304

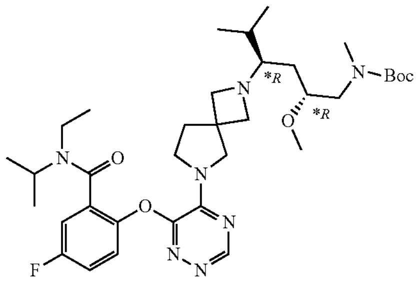

Compound 306

+

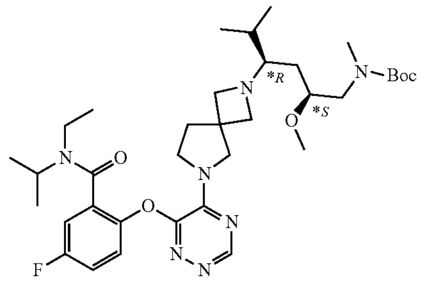

Compound 307

Tert-butyl ((4*R)-4-(6-(6-(2-(ethyl(isopropyl)carbamoyl)-4-fluorophenoxy)-1,2,4-triazin-5-yl)-2,6-diazaspiro[3.4]octan-2-yl)-2-methoxy-5-methylhexyl)(methyl)carbamate (Compound 304) (120 mg) was separated by SFC over DAICEL CHIRALPAK IG (column: 250×30 mm, 10 um; Mobile phase: A: Supercritical $CO_2$, B: MeOH (0.1% ammonia), A:B=70:30 at 80 mL/min) to afford the title compounds (Compound 306) (45 mg) and (Compound 307) (46 mg) both as colorless sticky oil.

Compound 371 and 372 tert-butyl ((2*S,4*S)-4-(6-(6-(2-(ethyl(isopropyl) carbamoyl)-4-fluorophenoxy)-1,2,4-triazin-5-yl)-2, 6-diazaspiro[3.4]octan-2-yl)-2-methoxy-5-methylhexyl)(methyl)carbamate tert-butyl ((2*R,4*S)-4(6-(6-(2-(ethyl(isopropyl) carbamoyl)-4-fluorophenoxy)-1,2,4-triazin-5-yl)-2, 6-diazaspiro[3.4]octan-2-yl)-2-methoxy-5-methylhexyl)(methyl)carbamate

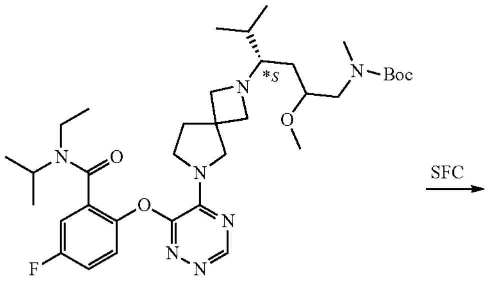

Compound 305

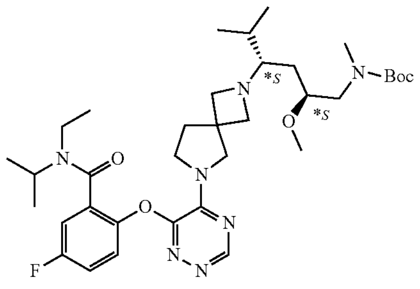

Compound 371

+

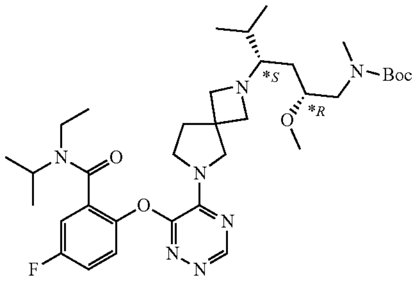

Compound 372

Tert-butyl ((4*S)-4-(6-(6-(2-(ethyl(isopropyl)carbamoyl)-4-fluorophenoxy)-1,2,4-triazin-5-yl)-2,6-diazaspiro [3.4]octan-2-yl)-2-methoxy-5-methylhexyl)(methyl)carbamate (Compound 305) (120 mg) was separated by SFC over DAICEL CHIRALPAK IG (column: 250×30 mm, 10 μm; Mobile phase: A: Supercritical $CO_2$, B: IPA (0.1% ammonia), A:B=60:40; Flow rate: 80 mL/min) to afford the title compounds (Compound 371) (45 mg) and (Compound 372) (46 mg) both as colorless sticky oil.

Compound 404 and 405 tert-butyl (R)-(4-(6-(3-chloro-6-(2-(ethyl(isopropyl) carbamoyl)-4-fluorophenoxy)-1,2,4-triazin-5-yl)-2, 6-diazaspiro[3.4]octan-2-yl)-5-methylhexyl)carbamate tert-butyl (S)-(4-(6-(3-chloro-6-(2-(ethyl(isopropyl) carbamoyl)-4-fluorophenoxy)-1,2,4-triazin-5-yl)-2, 6-diazaspiro[3.4]octan-2-yl)-5-methylhexyl)carbamate

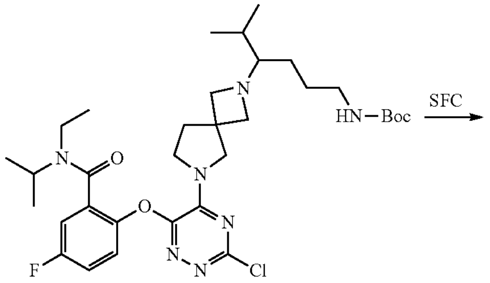

Compound 403

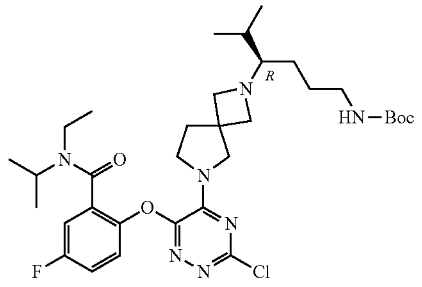

Compound 404

+

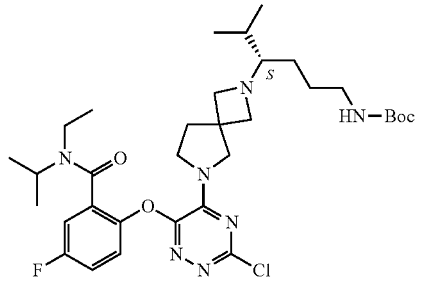

Compound 405

Tert-butyl (4-(6-(3-chloro-6-(2-(ethyl(isopropyl)carbamoyl)-4-fluorophenoxy)-1,2,4-triazin-5-yl)-2,6-diazaspiro [3.4]octan-2-yl)-5-methylhexyl)carbamate (Compound 403) (19.5 g) was separated by SFC over DAICEL CHIRALPAK IG (column: 250×30 mm, 10 um; Mobile phase: A: Supercritical $CO_2$, B: MeOH (0.1% ammonia), A:B=55:45 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compounds (Compound 404) (8.00 g) and (Compound 405) (7.00 g) both as sticky oil.

Compound 1

(R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide formate

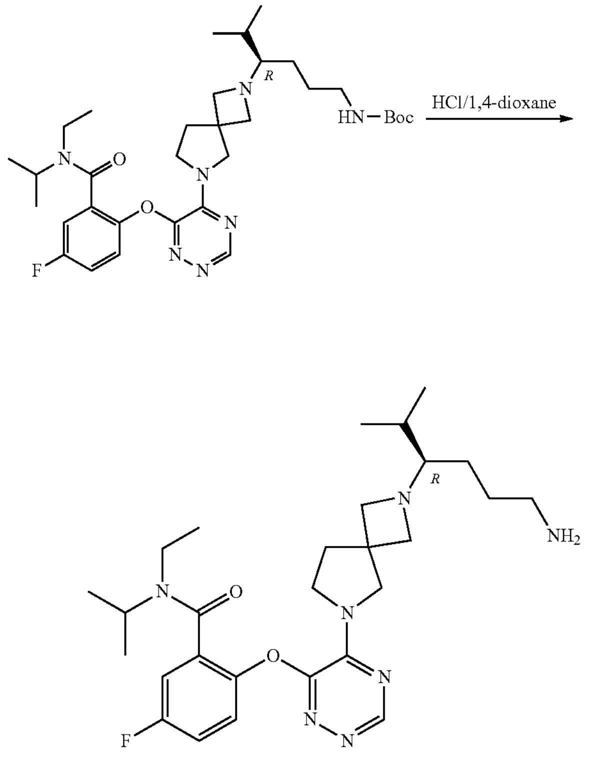

formate salt

HCl/1,4-dioxane (0.5 mL, 2.0 mmol) was added to a solution of tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate (Compound 62) (85 mg, 0.14 mmol) in 1,4-dioxane (2 mL). The reaction mixture was stirred at RT for 4 h. The mixture was concentrated under reduced pressure and the residue was first neutralized by ammonia (5 mL) and further purified by preparative HPLC using a Welch Xtimate C18 (column: 150×25 mm 5 μm; eluent: ACN/$H_2O$ (0.225% FA) from 1% to 31% (v/v)) to afford the title compound (32 mg, 41% yield) as a colorless oil.

$^1H$ NMR (400 MHz, Methanol-$d_4$): δ=8.45-8.41 (m, 3H), 7.48-7.13 (m, 3H), 4.50-4.01 (m, 6H), 3.98-3.66 (m, 3H), 3.56-3.38 (m, 1H), 3.25-3.12 (m, 1H), 3.10-3.01 (m, 1H), 2.99-2.87 (m, 2H), 2.43-2.18 (m, 2H), 2.13-1.96 (m, 1H), 1.84-1.44 (m, 4H), 1.25-0.92 (m, 13H), 0.87-0.69 (m, 2H).

LC-MS (ESI) (Method 1): $R_t$=2.957 min, m/z found 528.3 $[M+H]^+$.

SFC (Method 12): $R_t$=1.151 min.

Preparation of Compound 60 tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate

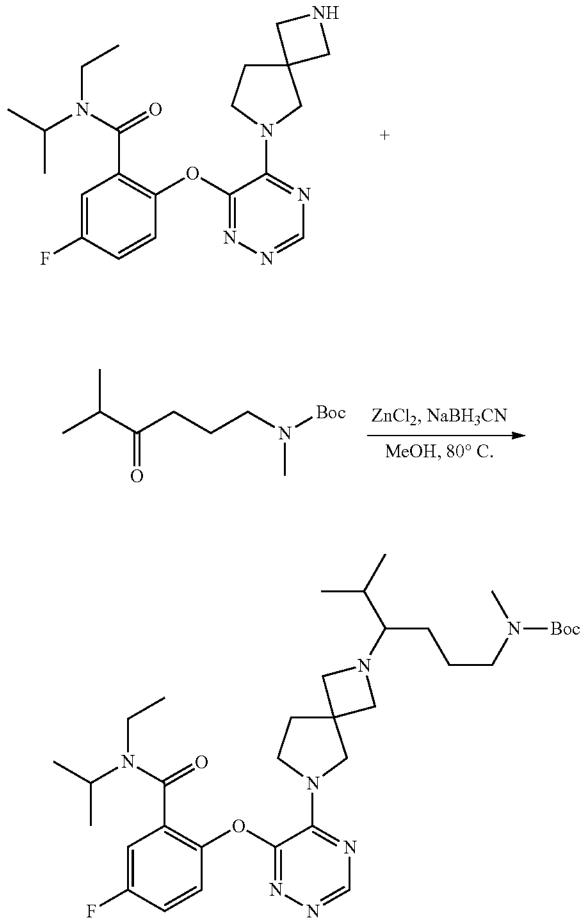 [SMILES: CCN(C(=O)c1cc(F)ccc1Oc1nncnc1N1CCC2(CNC2)C1)C(C)C ; CC(C)C(=O)CCCN(C)C(=O)OC(C)(C)C ; CCN(C(=O)c1cc(F)ccc1Oc1nncnc1N1CCC2(C1)CN(C(CCCN(C)C(=O)OC(C)(C)C)C(C)C)C2)C(C)C]

To a solution of 2-((5-(2,6-diazaspiro[3.4]octan-6-yl)-1,2,4-triazin-6-yl)oxy)-N-ethyl-5-fluoro-N-isopropylbenzamide (intermediate 3) (600 mg, 1.45 mmol) and tert-butyl methyl(5-methyl-4-oxohexyl)carbamate (intermediate 9) (330 mg, 1.37 mmol) in MeOH (50 mL) was added $ZnCl_2$ (789 mg, 5.79 mmol). The resulting mixture was stirred at 80° C. for 2 h. Then $NaBH_3CN$ (729 mg, 11.6 mmol) was added and the reaction mixture was stirred at 80° C. overnight. After cooling to RT, the mixture was concentrated under reduced pressure to give a crude residue, which was diluted with DCM (50 mL), quenched with sat. aq. $NH_4Cl$ (50 mL) and extracted with DCM (50 mL×3). The combined organic layers were washed with brine (50 mL), dried over $Na_2SO_4$, filtered and the filtrate was concentrated under reduced pressure to give a crude product which was further purified by FCC (DCM/MeOH=10:1) to afford the title compound (400 mg, 42% yield) as white solid.

Compound 56 and 57 tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate tert-butyl (S)-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate

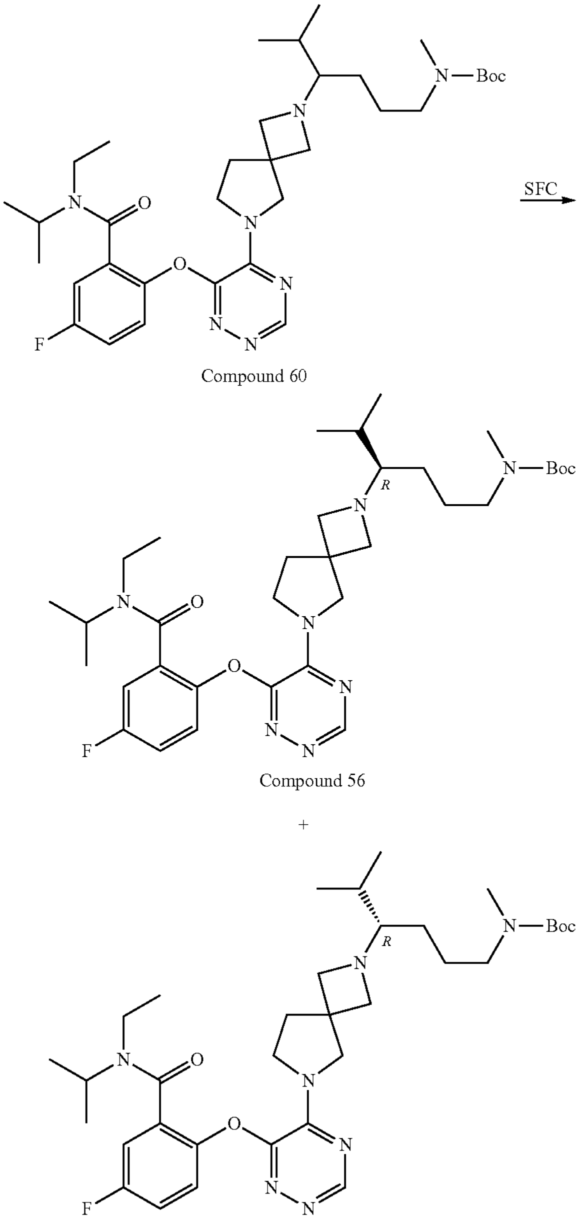

Compound 60

Compound 56

+

Compound 57

Tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate (Compound 60) (419 mg, 0.653 mmol) was purified by SFC over DAICEL CHIRALPAK AD (column: 250×30 mm 10 μm; Mobile phase: A: Supercritical $CO_2$, B: IPA (0.1% ammonia), A:B=80:20 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compounds (Compound 56) (146 mg, 34% yield) and (Compound 57) (149 mg, 36% yield) both as white solid.

Compound 19

(R)-N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide hydrochloride

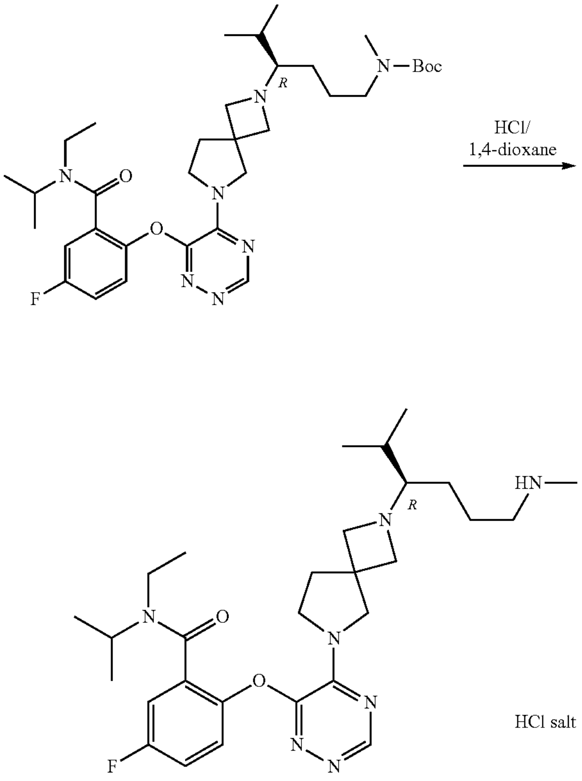

To a solution of tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate (Compound 56) (130 mg, 0.203 mmol) in 1,4-dioxane (3 mL) was added HCl/1,4-dioxane (5 mL, 20.0 mmol), and the reaction mixture was stirred at RT for 1 h. The reaction mixture was concentrated in vacuo and the residue was purified by preparative HPLC over Phenomenex Gemini-NX (column: 150×30 mm 5 um, Mobile Phase A: water (0.05% HCl), Mobile Phase B: ACN, Flow rate: 25 mL/min, gradient condition B/A from 0% B to 26% (0% B to 26% B)) to afford the title compound (105 mg, 84% yield) as colorless oil.

LC-MS (ESI) (Method 1): $R_t$=2.939 min, m/z found 542.4 $[M+H]^+$.

SFC (Method 1): $R_t$=1.201 min.

Compound 398

(R)-N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide

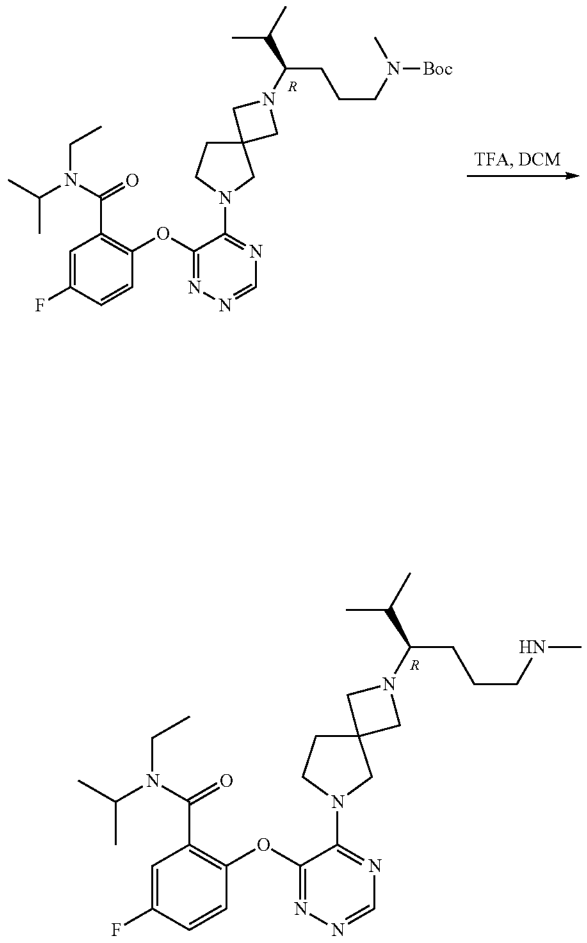

At 5° C., TFA (0.51 mL, 6.7 mmol) was added dropwise to a solution of tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate (Compound 56) (287 mg, 0.45 mmol) in DCM (7.5 mL) and the reaction mixture was stirred overnight. The reaction mixture was evaporated to dryness to give a crude mixture (540 mg) which was purified by silica gel chromatography (Stationary phase: irregular bare silica 12 g, Mobile phase: Gradient from 95% DCM, 5% MeOH (+10% $NH_4OH$) to 90% DCM, 10% MeOH (+10% $NH_4OH$)). The pure fractions were mixed and concentrated to afford 173 mg of an intermediate fractions which was freeze-dried with ACN/$H_2O$ (20/80, v/v) to afford of the title compound (170 mg, 70% yield).

LC-MS (ESI) (Method 4): $R_t$=2.08 min, m/z found 542.6 $[M+H]^+$.

Compound 51 tert-butyl (3-(6-(6-(2-(ethyl(isopropyl)carbamoyl)-4-fluorophenoxy)-1,2,4-triazin-5-yl)-2,6-diazaspiro[3.4]octan-2-yl)-4-methylpentyl)carbamate

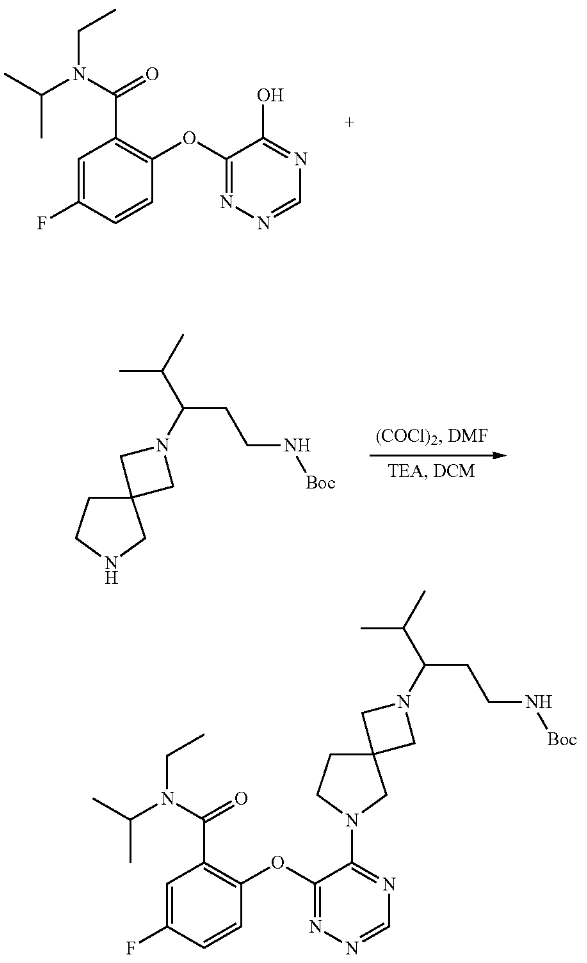

To a solution of N-ethyl-5-fluoro-2-((5-hydroxy-1,2,4-triazin-6-yl)oxy)-N-isopropylbenzamide (intermediate 25) (0.100 g, 0.312 mmol) in DCM (12 mL) was added oxalyl chloride (0.079 g, 0.624 mmol), followed by DMF (0.046 g, 0.624 mmol) at RT. The mixture was stirred at this temperature for 1 h. Then the mixture was added to a solution of tert-butyl (4-methyl-3-(2,6-diazaspiro[3.4]octan-2-yl)pentyl)carbamate hydrochloride (intermediate 22) (0.272 g, crude) and TEA (0.158 g, 1.56 mmol) in DCM (3 mL). The resulting mixture was stirred at 25° C. for 0.5 h. The reaction mixture was concentrated under reduced pressure and the residue was partitioned between DCM (35 mL) and $H_2O$ (35 mL), extracted with DCM (35 mL×3). The combined organic layers were dried over $Na_2SO_4$, filtered and concentrated. The residue was purified by FCC (PE/EtOAc (0.5% ammonia)=1/1) to afford the title compound (100 mg, 89% purity, 46% yield) as colorless oil.

Compound 52 and 53 tert-butyl (*R)-(5-(6-(6-(2-(4-cyclopropylpyrimidin-5-yl)-4-fluorophenoxy)-1,2,4-triazin-5-yl)-2,6-diazaspiro[3.4]octan-2-yl)-2,6-dimethylheptan-2-yl)carbamate tert-butyl (*S)-(5-(6-(6-(2-(4-cyclopropylpyrimidin-5-yl)-4-fluorophenoxy)-1,2,4-triazin-5-yl)-2,6-diazaspiro[3.4]octan-2-yl)-2,6-dimethylheptan-2-yl)carbamate

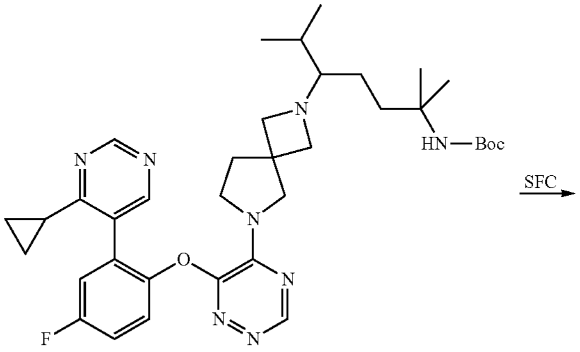

Compound 58

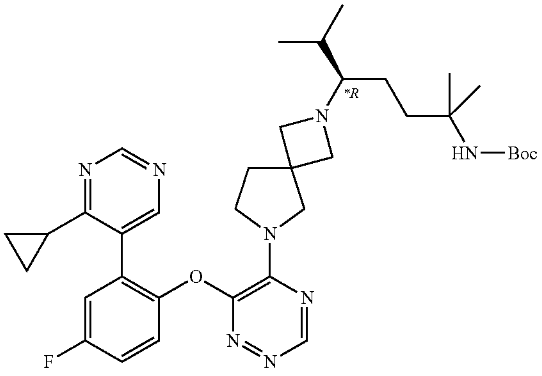

Compound 52

+

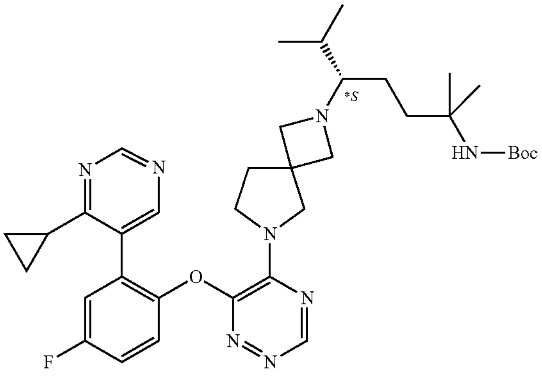

Compound 53 tert-butyl (5-(6-(6-(2-(4-cyclopropylpyrimidin-5-yl)-4-fluorophenoxy)-1,2,4-triazin-5-yl)-2,6-diazaspiro[3.4]octan-2-yl)-2,6-dimethylheptan-2-yl)carbamate (Compound 58) (150 mg, 0.227 mmol) was purified by SFC over DAICEL CHIRALPAK AD-H (column: 250×30 mm 5 μm; Mobile phase: A: Supercritical $CO_2$, B: IPA (0.1% ammonia), A:B=4:1 at 60 mL/min) to afford the title compounds Compound 52 (47 mg, 96.3% purity, 30.2% yield) and Compound 53 (56 mg, 97.7% purity, 36.5% yield) both as white solids.

Compound 54 and 55 tert-butyl (*R)-(5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)carbamate tert-butyl (*S)-(5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)carbamate

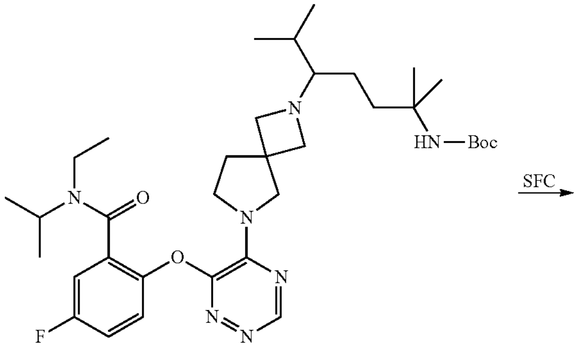

Compound 59

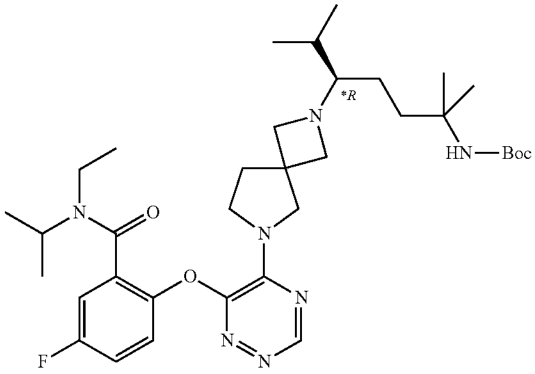

Compound 54

+

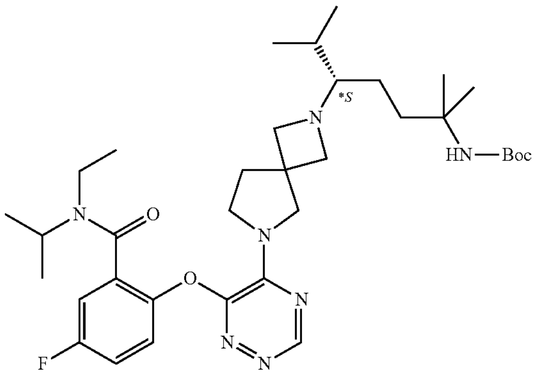

Compound 55 tert-butyl (5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)carbamate (Compound 59) (1.70 g, 2.59 mmol) was separated by SFC over DAICEL CHIRALPAK IG (column: 250×50 mm 10 μm)); Mobile phase: A: Supercritical $CO_2$, B: EtOH (0.1% ammonia), A:B=3:2 at 150 mL/min) to afford the title compounds Compound 54 (700 mg, 90% purity, 37% yield) and Compound 55 (700 mg, purity: 96% purity, 40% yield) both as a white solid.

Compound 408 tert-butyl (R)-(4-(6-(6-(2-(ethyl(isopropyl)carbamoyl)-4-fluorophenoxy)-3-(methylamino)-1,2,4-triazin-5-yl)-2,6-diazaspiro[3.4]octan-2-yl)-5-methylhexyl)carbamate The following compounds was synthesized by an analogous method as described above for Compound 395

| Co. No. | Structure | Starting Material | Conditions |
|---|---|---|---|
| 408 | 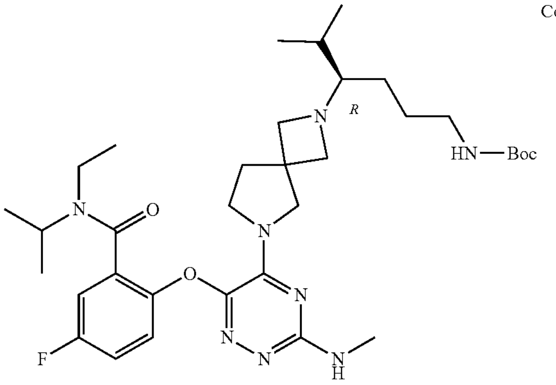 | Compound 404 | methanamine in EtOH (33%), 90° C., 1 h |

Compound 412 tert-butyl (R)-(4-(6-(6-(2-(ethyl(isopropyl)carbamoyl)-4-fluorophenoxy)-3-methyl-1,2,4-triazin-5-yl)-2,6-diazaspiro[3.4]octan-2-yl)-5-methylhexyl)carbamate

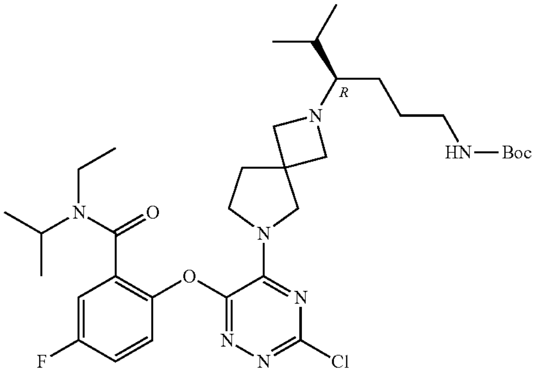

+

-continued

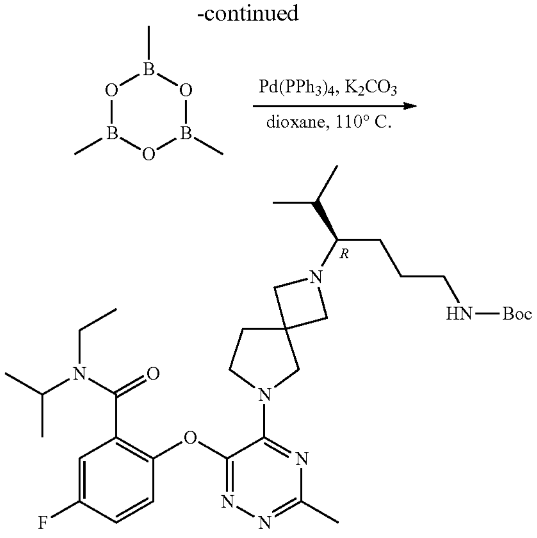

To the mixture of tert-butyl (R)-(4-(6-(3-chloro-6-(2-(ethyl(isopropyl)carbamoyl)-4-fluorophenoxy)-1,2,4-triazin-5-yl)-2,6-diazaspiro[3.4]octan-2-yl)-5-methylhexyl) carbamate (Compound 404) (50.0 mg, 0.076 mmol), 2,4,6-trimethyl-1,3,5,2,4,6-trioxatriborinane (76.0 mg, 0.303 mmol, 50% in THF) and $K_2CO_3$ (21.0 mg, 0.152 mmol) in anhydrous dioxane (1 mL) was added $Pd(PPh_3)_4$ (8.7 mg, 0.008 mmol) and the resulting mixture was stirred at 110° C. for 8 h under $N_2$ atmosphere. After cooled to RT, the mixture was diluted with $H_2O$ (40 mL) and extracted with EtOAc (20 mL×3). The combined organic layers were dried over anhydrous $Na_2SO_4$ and filtered. The filtrate was concentrated under reduced pressure to give the crude product which was purified by preparative TLC (DCM/MeOH=10/1) to afford the title compound (30.0 mg, 59.7% yield) as yellow solid.

Compounds 2, 3, 20, 30, 31, 37, 38, 26, 80, 209, 210, 218, 220, 221, 308, 309, 317, 328, 359, 373, 374, 409, 413

(S)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide formate 2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide formate (S)—N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide hydrochloride (*R)-2-((5-(2-(6-amino-2,6-dimethylheptan-3-yl)-2,6-diazaspiro[3.4]octan-6-yl)-1,2,4-triazin-6-yl)oxy)-N-ethyl-5-fluoro-N-isopropylbenzamide (*S)-2-((5-(2-(6-amino-2,6-dimethylheptan-3-yl)-2,6-diazaspiro[3.4]octan-6-yl)-1,2,4-triazin-6-yl)oxy)-N-ethyl-5-fluoro-N-isopropylbenzamide (*R)-5-(6-(6-(2-(4-cyclopropylpyrimidin-5-yl)-4-fluorophenoxy)-1,2,4-triazin-5-yl)-2,6-diazaspiro[3.4]octan-2-yl)-2,6-dimethylheptan-2-amine (*S)-5-(6-(6-(2-(4-cyclopropylpyrimidin-5-yl)-4-fluorophenoxy)-1,2,4-triazin-5-yl)-2,6-diazaspiro[3.4]octan-2-yl)-2,6-dimethylheptan-2-amine 2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((4-(2-(2-methyl-6-(methylamino)hexan-3-yl)-2,6-diazaspiro[3.4]octan-6-yl)pyridazin-3-yl)oxy)benzamide (*R)-2-((5-(2-(7-amino-2-methylheptan-3-yl)-2,6-diazaspiro[3.4]octan-6-yl)-1,2,4-triazin-6-yl)oxy)-N-ethyl-5-fluoro-N-isopropylbenzamide formate (*S)-2-((5-(2-(7-amino-2-methylheptan-3-yl)-2,6-diazaspiro[3.4]octan-6-yl)-1,2,4-triazin-6-yl)oxy)-N-ethyl-5-fluoro-N-isopropylbenzamide (*R)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide (*R)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide hydrochloride (*S)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide hydrochloride N-ethyl-5-fluoro-N-isopropyl-2-((5-(2-((3*R,5*R)-5-methoxy-2-methyl-6-(methylamino)hexan-3-yl)-2,6-diazaspiro[3.4]octan-6-yl)-1,2,4-triazin-6-yl)oxy)benzamide hydrochloride N-ethyl-5-fluoro-N-isopropyl-2-((5-(2-((3*R,5*S)-5-methoxy-2-methyl-6-(methylamino)hexan-3-yl)-2,6-diazaspiro[3.4]octan-6-yl)-1,2,4-triazin-6-yl)oxy)benzamide hydrochloride N-ethyl-5-fluoro-2-((5-(2-(5-hydroxy-2-methyl-6-(methylamino)hexan-3-yl)-2,6-diazaspiro[3.4]octan-6-yl)-1,2,4-triazin-6-yl)oxy)-N-isopropylbenzamide hydrochloride N-ethyl-2-((5-(2-(6-(ethylamino)-5-hydroxy-2-methylhexan-3-yl)-2,6-diazaspiro[3.4]octan-6-yl)-1,2,4-triazin-6-yl)oxy)-5-fluoro-N-isopropylbenzamide hydrochloride 5-fluoro-2-((5-(2-(5-hydroxy-2-methyl-6-(methylamino)hexan-3-yl)-2,6-diazaspiro[3.4]octan-6-yl)-1,2,4-triazin-6-yl)oxy)-N,N-diisopropylbenzamide hydrochloride N-ethyl-5-fluoro-N-isopropyl-2-((5-(2-((3*S,5*S)-5-methoxy-2-methyl-6-(methylamino)hexan-3-yl)-2,6-diazaspiro[3.4]octan-6-yl)-1,2,4-triazin-6-yl)oxy)benzamide hydrochloride N-ethyl-5-fluoro-N-isopropyl-2-((5-(2-((3*S,5*R)-5-methoxy-2-methyl-6-(methylamino)hexan-3-yl)-2,6-diazaspiro[3.4]octan-6-yl)-1,2,4-triazin-6-yl)oxy)benzamide hydrochloride (R)-2-((5-(2-(6-amino-2-methylhexan-3-yl)-2,6-diazaspiro[3.4]octan-6-yl)-3-(methylamino)-1,2,4-triazin-6-yl)oxy)-N-ethyl-5-fluoro-N-isopropylbenzamide hydrochloride (R)-2-((5-(2-(6-amino-2-methylhexan-3-yl)-2,6-diazaspiro[3.4]octan-6-yl)-3-methyl-1,2,4-triazin-6-yl)oxy)-N-ethyl-5-fluoro-N-isopropylbenzamide formate The following Compounds were synthesized by an analogous method described above for Compound 1 and 19

| Co. No. | Structure | Starting Material | Conditions | Spectra Details |
|---|---|---|---|---|
| 2 | 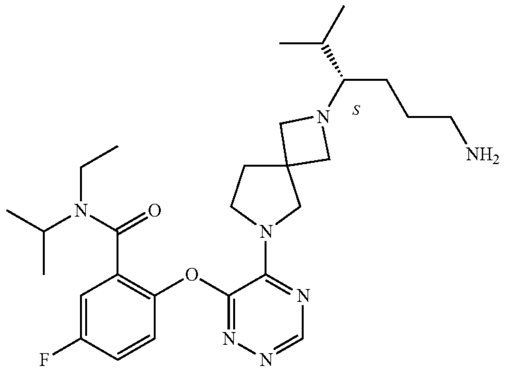 formate salt | Compound 63 | HCl 1,4-dioxane | LC-MS (ESI) (Method 1): $R_t$ = 3.028 min, m/z found 528.3 $[M + H]^+$. SFC (Method 12): $R_t$ = 1.502 min. |
| 3 | 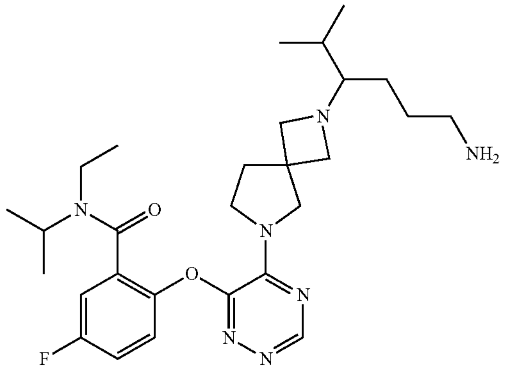 formate salt | Compound 61 | HCl 1,4-dioxane | LC-MS (ESI) (Method 1): $R_t$ = 2.977 min, m/z found 528.4 $[M + H]^+$. |
| 20 | 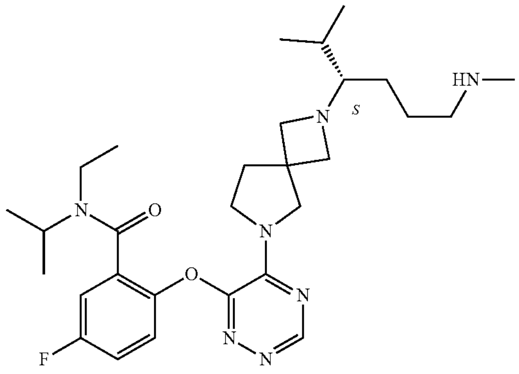 HCl salt | Compound 57 | HCl 1,4-dioxane | LC-MS (ESI) (Method 1): $R_t$ = 2.890 min, m/z found 542.3 $[M + H]^+$. SFC (Method 1): $R_t$ = 1.697 min. |
| 30 | 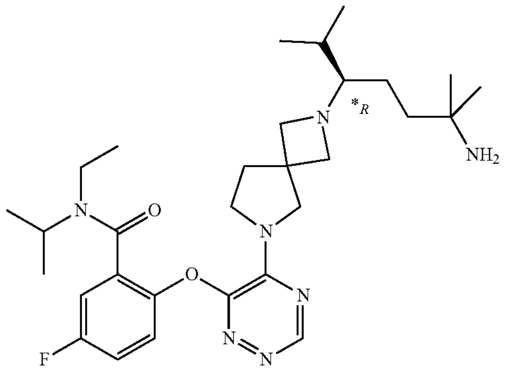 | Compound 54 | TFA DCM | LC-MS (ESI) (Method 1): $R_t$ = 2.931 min, m/z found 556.3 $[M + H]^+$. SFC (Method 2): $R_t$ = 4.431 min. |

-continued

| Co. No. | Structure | Starting Material | Conditions | Spectra Details |
|---|---|---|---|---|
| 31 | 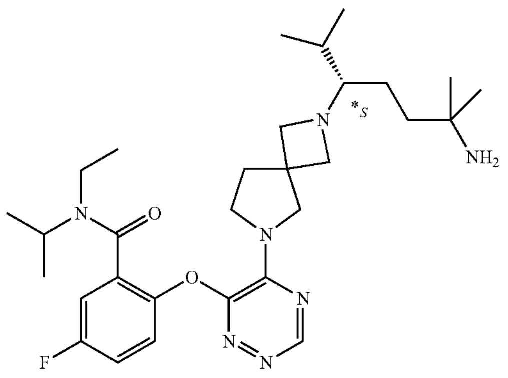 | Compound 55 | TFA DCM | LC-MS (ESI) (Method 1): $R_t$ = 2.897 min, m/z found 556.3 $[M + H]^+$. SFC (Method 2): $R_t$ = 4.997 min. |
| 37 | 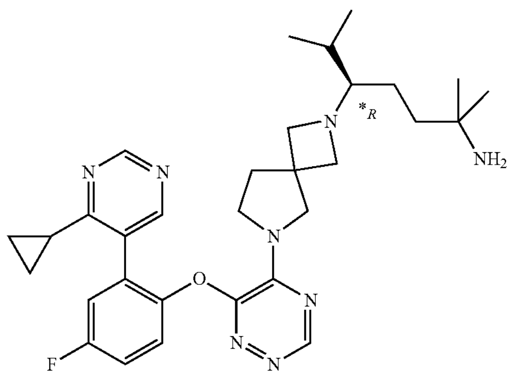 | Compound 52 | TFA DCM | $^1$H NMR (400 MHz, Methanol-$d_4$): δ 8.88 (brs, 1H), 8.46-8.36 (m, 2H), 7.58-7.45 (m, 1H), 7.44-7.26 (m, 2H), 4.07-3.52 (m, 4H), 3.31-3.11 (m, 4H), 2.24-2.02 (m, 3H), 1.99-1.78 (m, 2H), 1.55-1.38 (m, 3H), 1.37-1.20 (m, 2H), 1.14-1.06 (m, 8H), 0.99-0.83 (m, 7H). LC-MS (ESI) (Method 1): Rt = 3.21 min, m/z found 561.3 $[M + H]^+$. SFC (Method 3): $R_t$ = 5.566 min. |
| 38 | 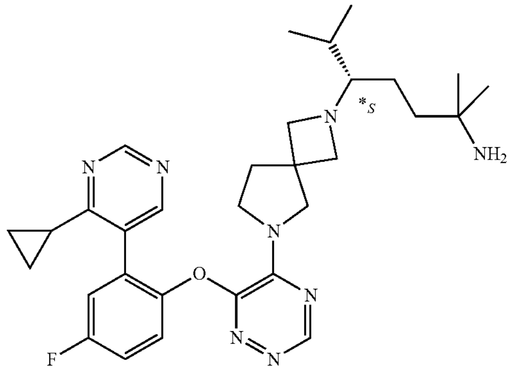 | Compound 53 | TFA DCM | LC-MS (ESI) (Method 1): $R_t$ = 3.26 min, m/z found 561.3 $[M + H]^+$. SFC (Method 3): $R_t$ = 5.929 min. |

-continued
| Co. No. | Structure | Starting Material | Conditions | Spectra Details |
|---|---|---|---|---|
| 26 | 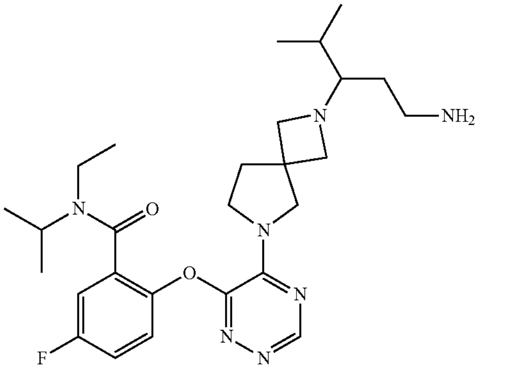 [SMILES: CCN(C(=O)c1cc(F)ccc1Oc1nncnc1N1CCC2(C1)CN(C(CCN)C(C)C)C2)C(C)C] | Compound 51 | TFA DCM | LC-MS (ESI) (Method 1): $R_t$ = 2.98 min, m/z found 514.4 M + H]$^+$. |
| 80 | 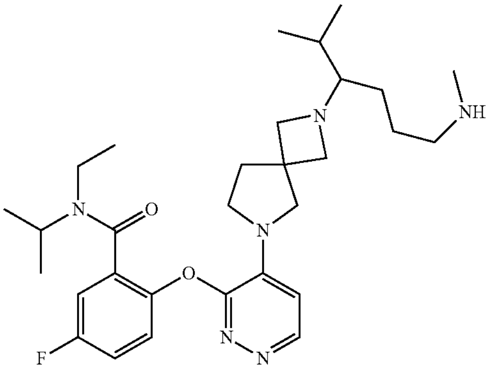 [SMILES: CCN(C(=O)c1cc(F)ccc1Oc1nnccc1N1CCC2(C1)CN(C(CCCNC)C(C)C)C2)C(C)C] | Compound 79 | TFA DCM | |
| 209 | 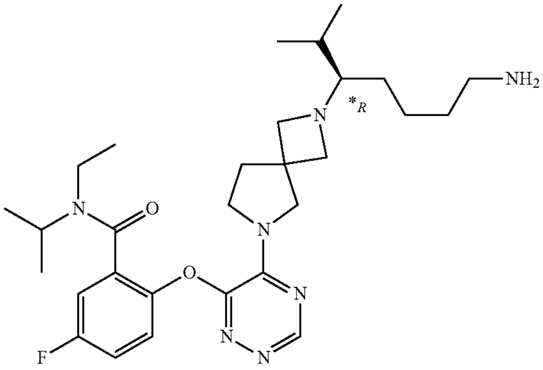 formate salt | Compound 207 | HCl 1,4-dioxane | LC-MS (ESI) (Method 1): $R_t$ = 2.950 min, m/z found 542.3 [M + H]$^+$. SFC (Method 18): $R_t$ = 2.021 min. |
| 210 | 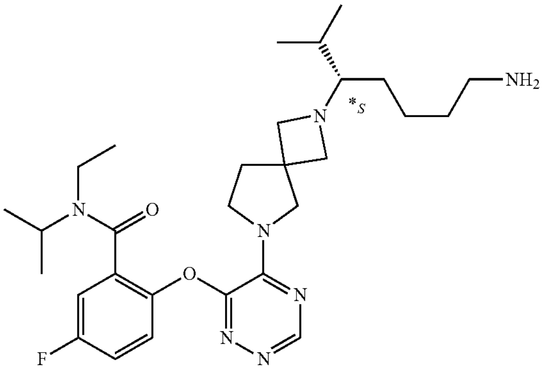 | Compound 208 | HCl 1,4-dioxane | LC-MS (ESI) (Method 1): $R_t$ = 2.919 min, m/z found 542.3 [M + H]$^+$. SFC (Method 18): $R_t$ = 2.201 min. |

-continued
| Co. No. | Structure | Starting Material | Conditions | Spectra Details |
| --- | --- | --- | --- | --- |
| 218 | 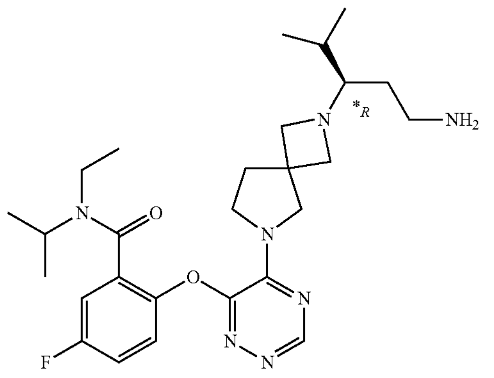 | Compound 216 | TFA DCM | |
| 220 | 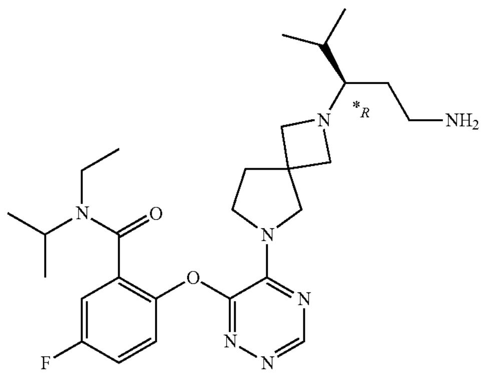 HCl salt | Compound 216 | HCl 1,4-dioxane | |
| 221 | 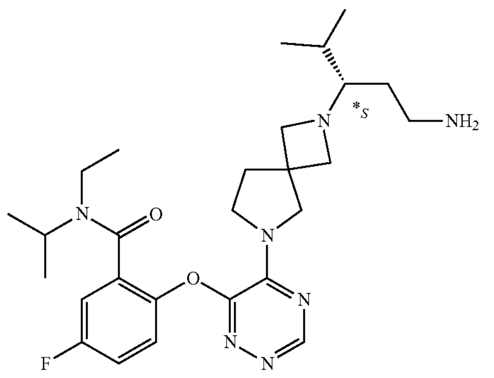 HCl salt | Compound 217 | HCl 1,4-dioxane | |

-continued
| Co. No. | Structure | Starting Material | Conditions | Spectra Details |
|---|---|---|---|---|
| 308 | 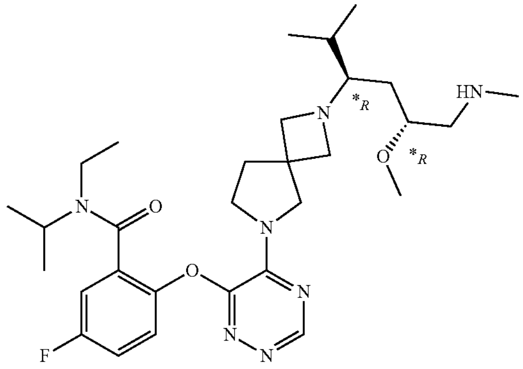<br>HCl salt | Compound 306 | HCl/1,4-dioxane, MeOH | |
| 309 | 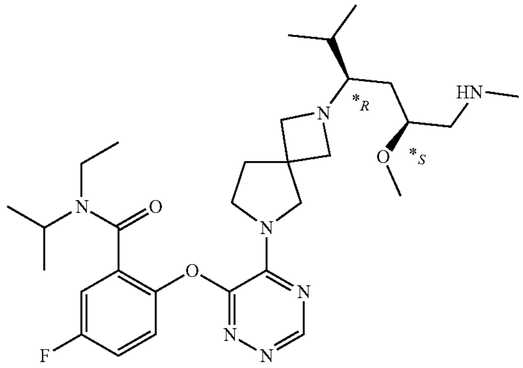<br>HCl salt | Compound 307 | HCl/1,4-dioxane, MeOH | |
| 317 | 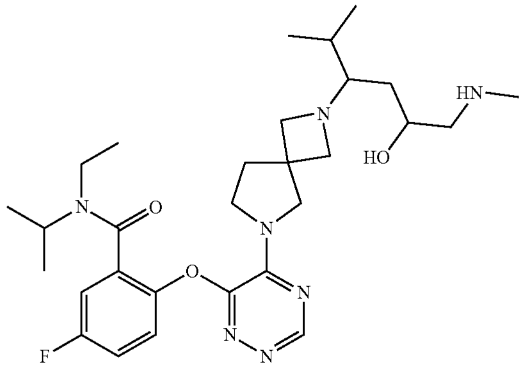<br>HCl salt | Compound 316 | HCl/1,4-dioxane, MeOH | |

-continued
| Co. No. | Structure | Starting Material | Conditions | Spectra Details |
|---|---|---|---|---|
| 328 | 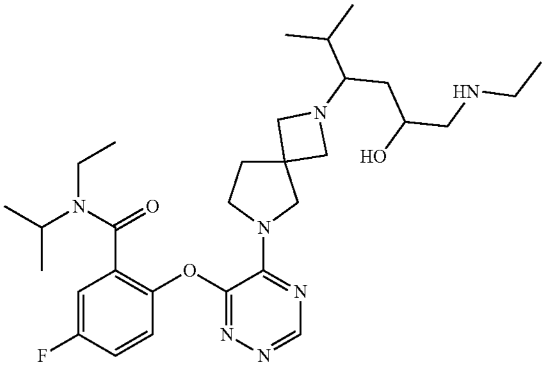 HCl salt | Compound 327 | HCl/1,4-dioxane, MeOH | |
| 359 | 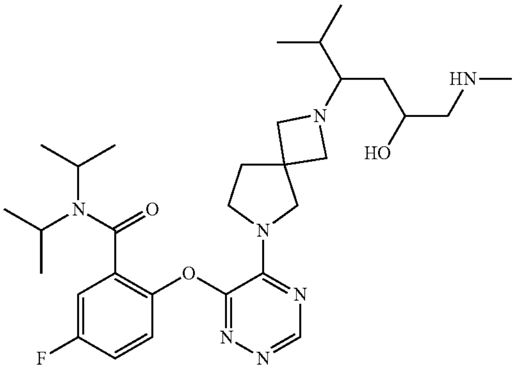 HCl salt | Compound 358 | HCl/1,4-dioxane, MeOH | |
| 373 | 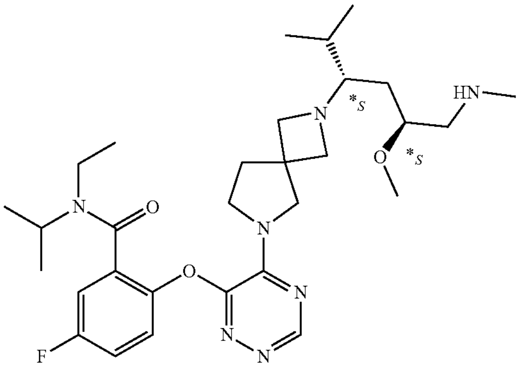 HCl salt | Compound 371 | HCl/1,4-dioxane, MeOH | |

-continued
| Co. No. | Structure | Starting Material | Conditions | Spectra Details |
|---|---|---|---|---|
| 374 | 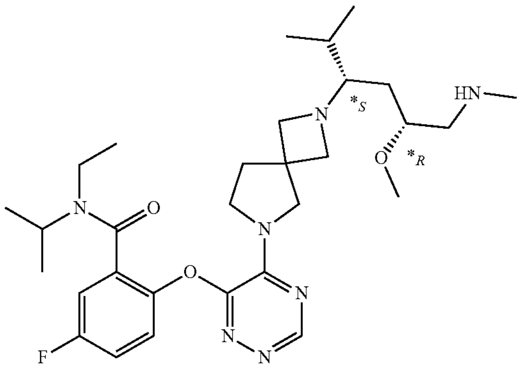 HCl salt | Compound 372 | HCl/1,4-dioxane, MeOH | |
| 409 | 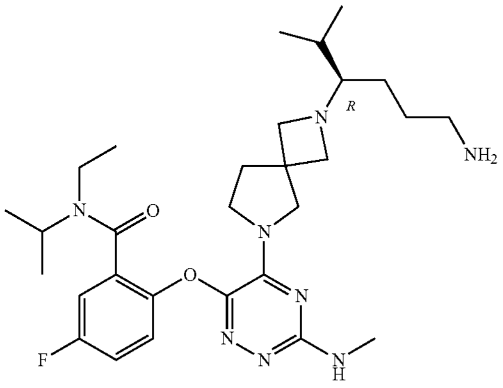 HCl salt | Compound 408 | HCl/1,4-dioxane, ACN | LC-MS (ESI) (Method 2): $R_t$ = 1.94 min, m/z found 557.3 $[M + H]^+$. SFC (Method 13): $R_t$ = 2.75 min. |
| 413 | 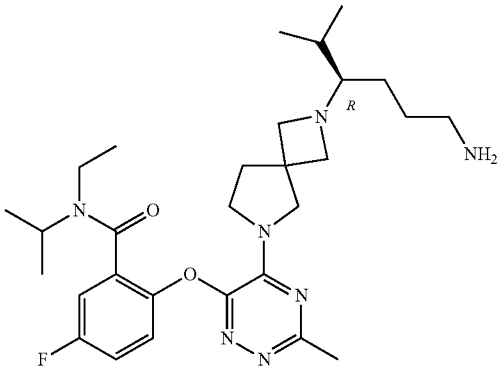 formate salt | Compound 412 | HCl/1,4-dioxane, MeOH | LC-MS (ESI) (Method 1): $R_t$ = 2.885 min, m/z found 542.3 $[M + H]^+$. SFC (Method 13): $R_t$ = 2.347 min. |

Compound 4

(R)-2-((5-(2-(6-(dimethylamino)-2-methylhexan-3-yl)-2,6-diazaspiro[3.4]octan-6-yl)-1,2,4-triazin-6-yl)oxy)-N-ethyl-5-fluoro-N-isopropylbenzamide

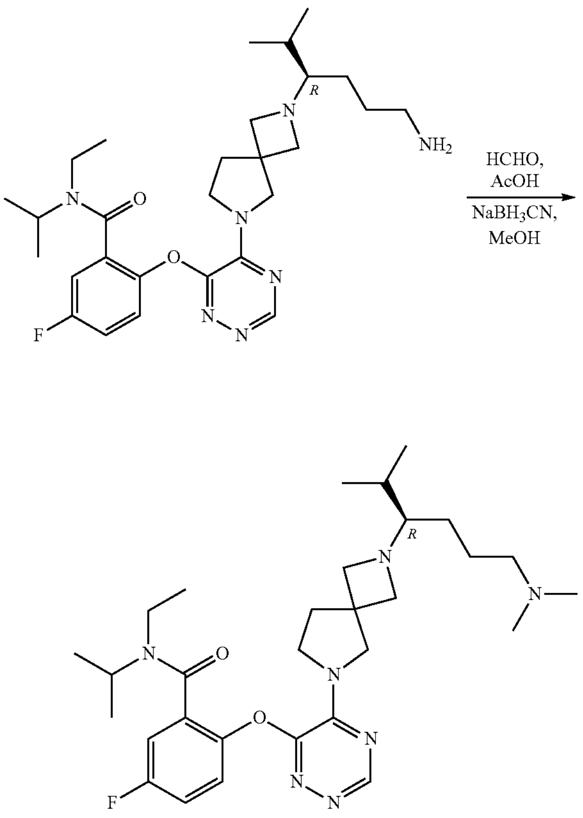

To the mixture of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide hydrochloride (Compound 65) (180 mg, crude), formaldehyde (0.085 mL, 1.1 mmol) and AcOH (0.043 mL, 0.76 mmol) in MeOH (10 mL) was added $NaBH_3CN$ (72.0 mg, 1.14 mmol), the resulting mixture was stirred at RT for 2 h. The mixture was filtered and the filtrate was purified by preparative HPLC over Welch Xtimate (column: C18 150×30 mm 5 um; eluent: ACN/$H_2O$ (0.225% FA) from 5% to 25%, v/v) and the desired fractions were collected and freeze dried. The resulting solid was further neutralized by 25% ammonia (15 mL) and extracted with DCM (20 mL×2). The combined organic layers were dried over anhydrous $Na_2SO_4$, filtered, and concentrated under reduced pressure to give a residue, which was further dissolved in ACN/water and freeze dried to afford the title compound (37.65 mg) as yellow solid.

LC-MS (ESI) (Method 1): $R_t$=2.95 min, m/z found 556.3 $[M+H]^+$.

SFC (Method 4): $R_t$=1.772 min.

Compound 5, 32, 33, 74, 81, 101, 211, 212, 222, 224, 231, 410

(S)-2-((5-(2-(6-(dimethylamino)-2-methylhexan-3-yl)-2,6-diazaspiro[3.4]octan-6-yl)-1,2,4-triazin-6-yl)oxy)-N-ethyl-5-fluoro-N-isopropylbenzamide formate (*R)-2-((5(2-(6-(dimethylamino)-2,6-dimethylheptan-3-yl)-2,6-diazaspiro[3.4]octan-6-yl)-1,2,4-triazin-6-yl)oxy)-N-ethyl-5-fluoro-N-isopropylbenzamide (*S)-2-((5-(2-(6-(dimethylamino)-2,6-dimethylheptan-3-yl)-2,6-diazaspiro[3.4]octan-6-yl)-1,2,4-triazin-6-yl)oxy)-N-ethyl-5-fluoro-N-isopropylbenzamide 2-((4-(2-(6-(dimethylamino)-2-methylhexan-3-yl)-2,6-diazaspiro[3.4]octan-6-yl)pyridazin-3-yl)oxy)-5-fluoro-N,N-diisopropylbenzamide 2-((4-(2-(6-(dimethylamino)-2-methylhexan-3-yl)-2,6-diazaspiro[3.4]octan-6-yl)pyridazin-3-yl)oxy)-N-ethyl-5-fluoro-N-isopropylbenzamide 2-((5-(2-(6-(dimethylamino)-2-methylhexan-3-yl)-2,6-diazaspiro[3.4]octan-6-yl)-1,2,4-triazin-6-yl)oxy)-5-fluoro-N,N-diisopropylbenzamide (*R)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide (*S)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide (*R)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide (*S)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide (*R)-2-((5-(2-(1-amino-2-oxoethyl)(methyl)amino)-4-methylpentan-3-yl)-2,6-diazaspiro[3.4]octan-6-yl)-1,2,4-triazin-6-yl)oxy)-N-ethyl-5-fluoro-N-isopropylbenzamide (R)-2-((5-(2-(6-(dimethylamino)-2-methylhexan-3-yl)-2,6-diazaspiro[3.4]octan-6-yl)-3-methoxy-1,2,4-triazin-6-yl)oxy)-N-ethyl-5-fluoro-N-isopropylbenzamide formate The following Compounds were synthesized by an analogous method described above for Compound 4

| Co. No. | Structure | Starting Materials | Spectra Details |
|---|---|---|---|
| 5 | 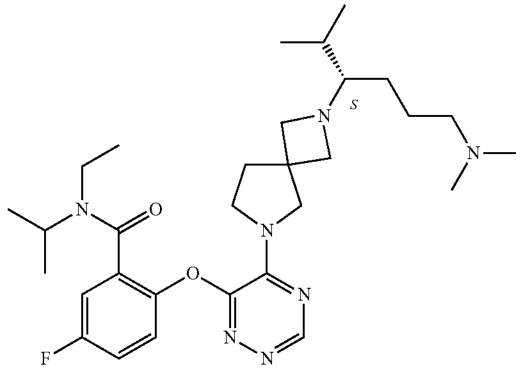 formate salt | Compound 66 | LC-MS (Method 1): $R_t$ = 2.977 min, m/z found 556.4 $[M + H]^+$. SFC (Method 4): $R_t$ = 1.402 min. |
| 32 | 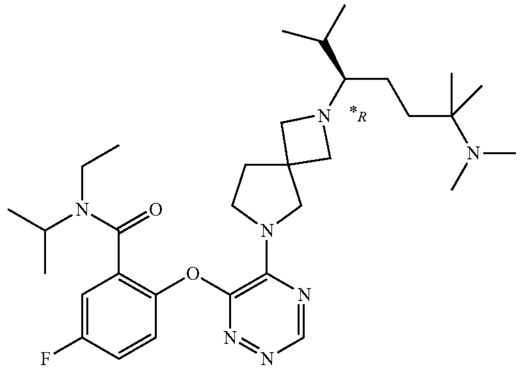 [SMILES: CCN(C(=O)c1cc(F)ccc1Oc1nncnc1N1CCC2(C1)CN([C@H](CCC(C)(C)N(C)C)C(C)C)C2)C(C)C] | Compound 30 | LC-MS (ESI) (Method 2): $R_t$ = 2.043 min, m/z found 584.3 $[M + H]^+$. SFC (Method 2): $R_t$ = 4.431 min. |
| 33 | 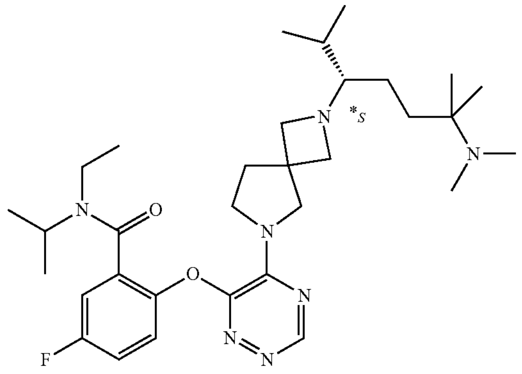 [SMILES: CCN(C(=O)c1cc(F)ccc1Oc1nncnc1N1CCC2(C1)CN([C@@H](CCC(C)(C)N(C)C)C(C)C)C2)C(C)C] | Compound 31 | LC-MS (ESI) (Method 2): $R_t$ = 2.008 min, m/z found 584.3 $[M + H]^+$. SFC (Method 2): $R_t$ = 4.997 min. |
| 74 | 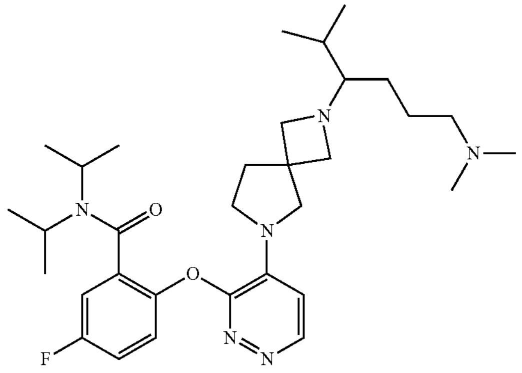 [SMILES: CC(C)C(CCCN(C)C)N1CC2(CCN(c3ccnnc3Oc3ccc(F)cc3C(=O)N(C(C)C)C(C)C)C2)C1] | Compound 73 | LC-MS (ESI) (Method 2): $R_t$ = 1.933 min, m/z found 569.4 $[M + H]^+$. |

-continued
| Co. No. | Structure | Starting Materials | Spectra Details |
|---|---|---|---|
| 81 | 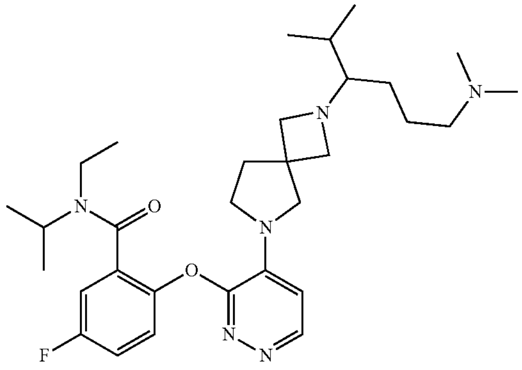 [SMILES: CCN(C(=O)c1cc(F)ccc1Oc1nnccc1N1CCC2(C1)CN(C(CCCN(C)C)C(C)C)C2)C(C)C] | Compound 80 | |
| 101 | 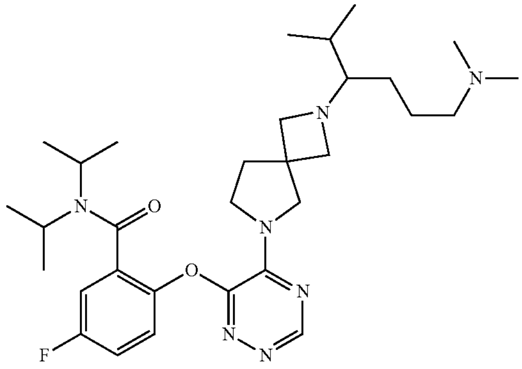 [SMILES: CC(C)C(CCCN(C)C)N1CC2(CCN(c3ncnnc3Oc3ccc(F)cc3C(=O)N(C(C)C)C(C)C)C2)C1] | Compound 97 | |
| 211 | 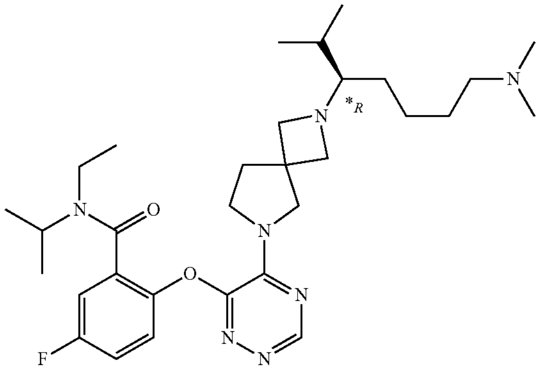 [SMILES: CCN(C(=O)c1cc(F)ccc1Oc1nncnc1N1CCC2(C1)CN([C@H](CCCCN(C)C)C(C)C)C2)C(C)C] | Compound 209 | LC-MS (ESI) (Method 2): $R_t$ = 1.946 min, m/z found 570.3 $[M + H]^+$. SFC (Method 8): $R_t$ = 2.243 min. |
| 212 | 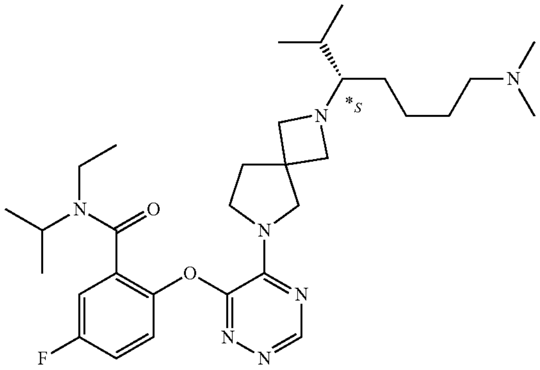 [SMILES: CCN(C(=O)c1cc(F)ccc1Oc1nncnc1N1CCC2(C1)CN([C@@H](CCCCN(C)C)C(C)C)C2)C(C)C] | Compound 210 | LC-MS (ESI) (Method 1): $R_t$ = 3.021 min, m/z found 570.3 $[M + H]^+$. SFC (Method 8): $R_t$ = 2.431 min. |

-continued
| Co. No. | Structure | Starting Materials | Spectra Details |
|---|---|---|---|
| 222 | 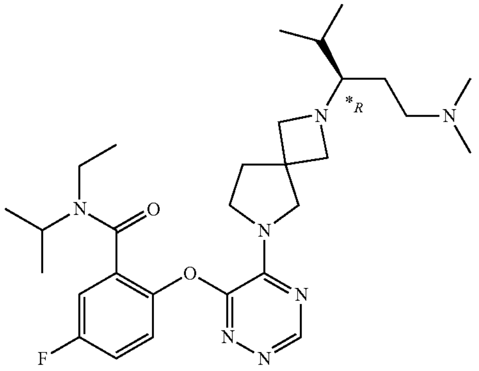 [SMILES: CCN(C(=O)c1cc(F)ccc1Oc1nncnc1N1CCC2(C1)CN([C@H](CCN(C)C)C(C)C)C2)C(C)C] | Compound 220 | |
| 224 | 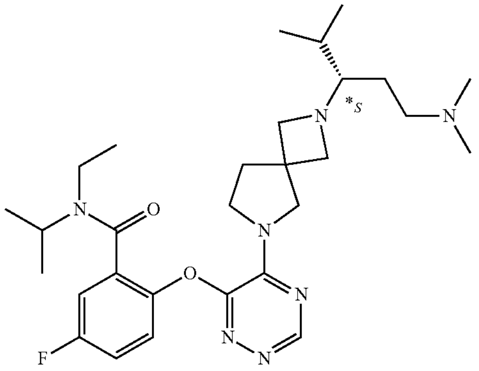 [SMILES: CCN(C(=O)c1cc(F)ccc1Oc1nncnc1N1CCC2(C1)CN([C@@H](CCN(C)C)C(C)C)C2)C(C)C] | Compound 221 | |
| 231 | 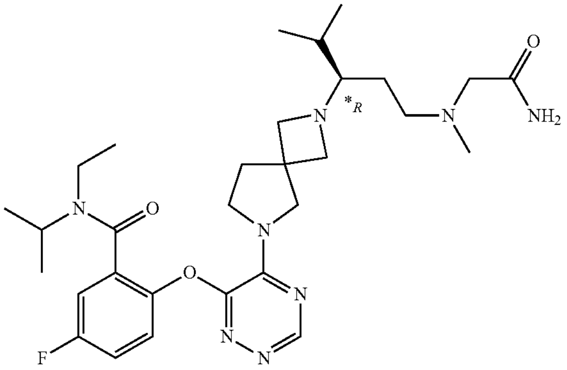 [SMILES: CCN(C(=O)c1cc(F)ccc1Oc1nncnc1N1CCC2(C1)CN([C@H](CCN(C)CC(N)=O)C(C)C)C2)C(C)C] | Compound 230 | LC-MS (ESI) (Method 1): $R_t$ = 2.858 min, m/z found 585.3 $[M + H]^+$. SFC (Method 6): $R_t$ = 1.454 min. |
| 410 | 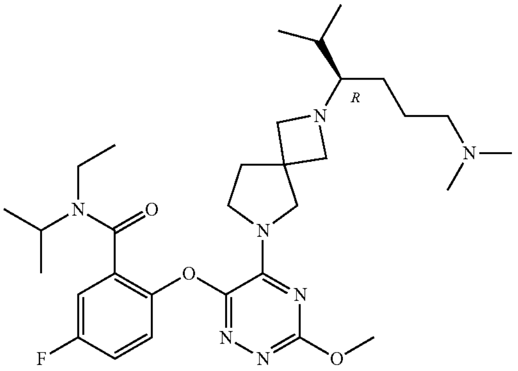 formate salt | Compound 407 | LC-MS (ESI) (Method 2): $R_t$ = 2.066 min, m/z found 586.3 $[M + H]^+$. SFC (Method 14): $R_t$ = 2.582 min. |

Compound 75, 76

(*R)-2-((4-(2-(6-(dimethylamino)-2-methylhexan-3-yl)-2,6-diazaspiro[3.4]octan-6-yl)pyridazin-3-yl)oxy)-5-fluoro-N,N-diisopropylbenzamide (*S)-2-((4-(2-(6-(dimethylamino)-2-methylhexan-3-yl)-2,6-diazaspiro[3.4]octan-6-yl)pyridazin-3-yl)oxy)-5-fluoro-N,N-diisopropylbenzamide

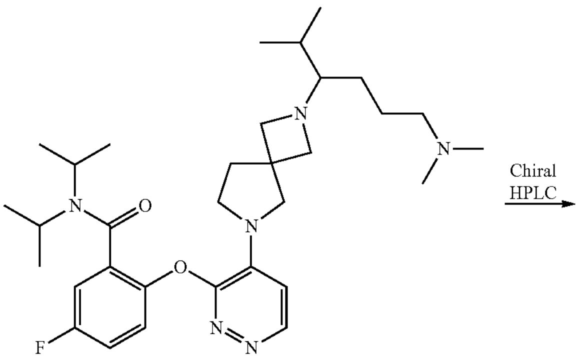

Compound 74

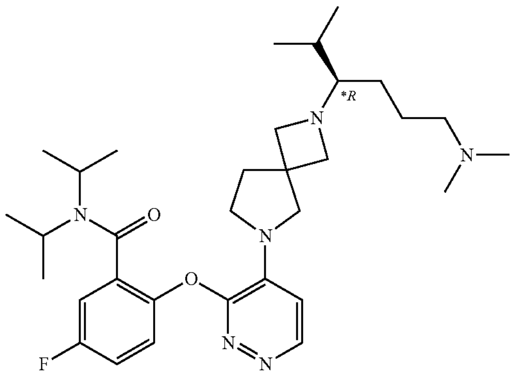

Compound 75

+

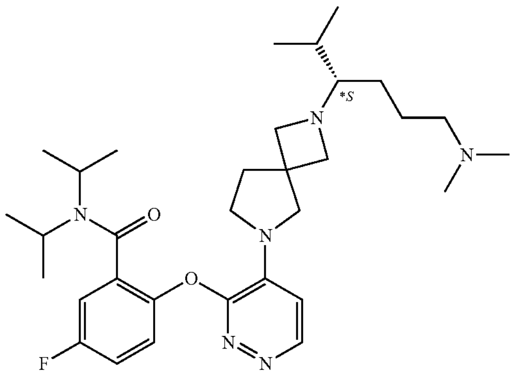

Compound 76

2-((4-(2-(6-(dimethylamino)-2-methylhexan-3-yl)-2,6-diazaspiro[3.4]octan-6-yl)pyridazin-3-yl)oxy)-5-fluoro-N,N-diisopropylbenzamide (Compound 74) (600 mg) was separated by chiral HPLC over DAICEL CHIRALPAK IG (column: 250×30 mm 10 um; Mobile phase: A: Heptane, B: EtOH, A:B from 20% to 70% (v/v); flowrate: 25 mL/min) to afford the title compounds Compound 75 (92 mg, 15%) and Compound 76 (84 mg) as white solid.

Compound 75

LC-MS (ESI) (Method 2): $R_t$=1.915 min, m/z found 569.3 $[M+H]^+$.

Chiral HPLC (Method 4): $R_t$=4.842 min.

Compound 76

LC-MS (ESI) (Method 2): $R_t$=1.924 min, m/z found 569.3 $[M+H]^+$.

Chiral HPLC (Method 4): $R_t$=6.200 min.

Compound 77, 78

(*R)-2-((4-(2-(6-(dimethylamino)-2-methylhexan-3-yl)-2,6-diazaspiro[3.4]octan-6-yl)pyridazin-3-yl)oxy)-N-ethyl-5-fluoro-N-isopropylbenzamide (*S)-2-((4-(2-(6-(dimethylamino)-2-methylhexan-3-yl)-2,6-diazaspiro[3.4]octan-6-yl)pyridazin-3-yl)oxy)-N-ethyl-5-fluoro-N-isopropylbenzamide

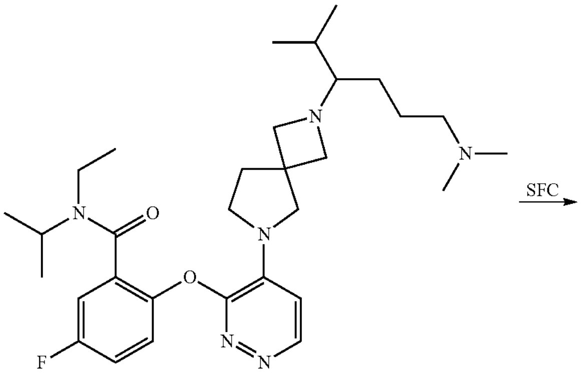

Compound 81

-continued

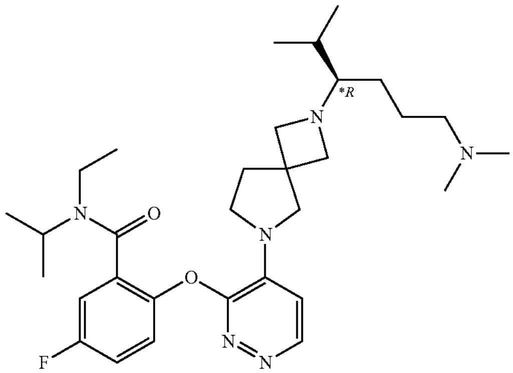

Compound 77

+

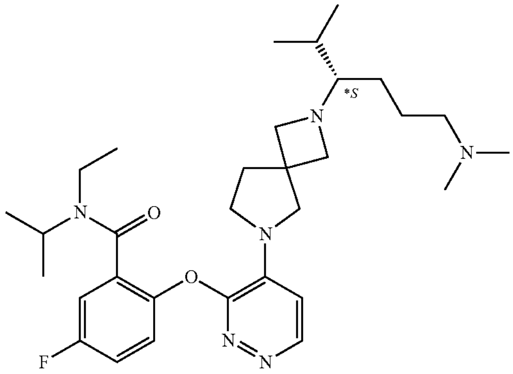

Compound 78

2-((4-(2-(6-(dimethylamino)-2-methylhexan-3-yl)-2,6-diazaspiro[3.4]octan-6-yl)pyridazin-3-yl)oxy)-N-ethyl-5-fluoro-N-isopropylbenzamide (Compound 81) (31.0 mg) was separated by SFC over DAICEL CHIRALPAK IE (column: 250×30 mm 10 um; eluent: 100% MeOH (0.1% ammonia); flowrate: 25 mL/min) to afford the title compounds Compound 77 (4.2 mg) and Compound 78 (1.3 mg) as white solid.

Compound 77

LC-MS (ESI) (Method 3): $R_t$=5.039 min, m/z found 555.3 $[M+H]^+$.

Chiral HPLC (Method 2): $R_t$=7.719 min.

Compound 78

LC-MS (ESI) (Method 3): $R_t$=4.870 min, m/z found 555.3 $[M+H]^+$.

Chiral HPLC (Method 2): $R_t$=8.754 min.

Compound 105, 106

(*R)-2-((5(2-(6-(dimethylamino)-2-methylhexan-3-yl)-2,6-diazaspiro[3.4]octan-6-yl)-1,2,4-triazin-6-yl)oxy)-5-fluoro-N,N-diisopropylbenzamide (*S)-2-((5-(2-(6-(dimethylamino)-2-methylhexan-3-yl)-2,6-diazaspiro[3.4]octan-6-yl)-1,2,4-triazin-6-yl)oxy)-5-fluoro-N,N-diisopropylbenzamide

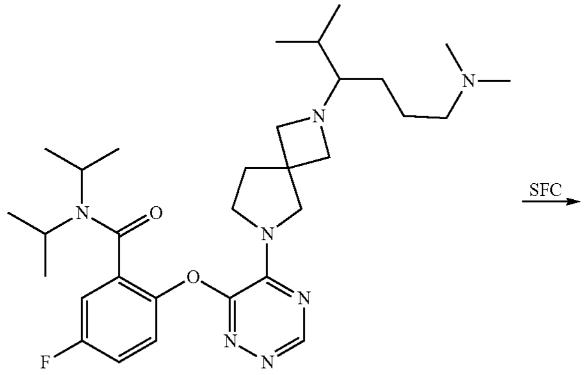

Compound 101

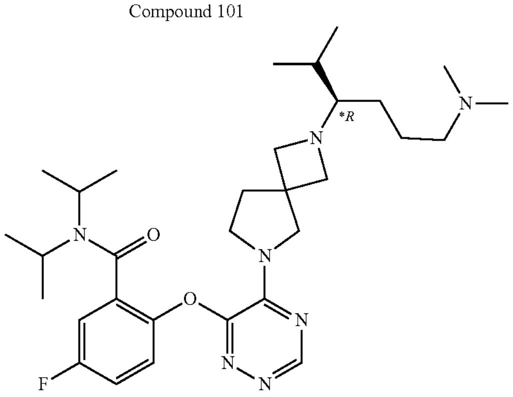

Compound 105

+

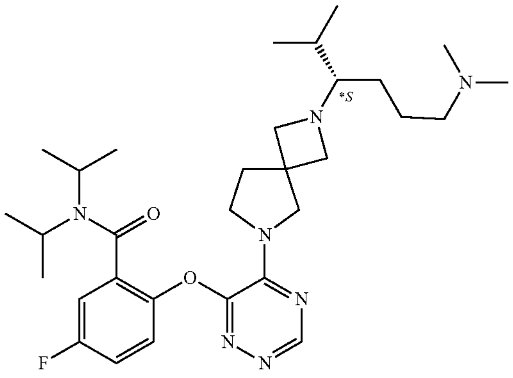

Compound 106

2-((5-(2-(6-(dimethylamino)-2-methylhexan-3-yl)-2,6-diazaspiro[3.4]octan-6-yl)-1,2,4-triazin-6-yl)oxy)-5-fluoro-N,N-diisopropylbenzamide (Compound 101) (1.5 g) was obtained by SFC over DAICEL CHIRALPAK IG (column: 250×50 mm 10 um; Mobile phase: A: Supercritical $CO_2$, B: MeOH (0.1% ammonia), A:B=55:45 at 200 mL/min; Column Temp: 38; Nozzle Pressure: 100 Bar; Nozzle Temp: 60; Evaporator Temp: 20; Trimmer Temp: 25; Wavelength: 220 nm) to afford the title compounds Compound 105 (600 mg, 40.0% yield) and Compound 106 (600 mg, 40.0% yield) as white solid.

Compound 102

(*R)-2-((5(2-(6-(dimethylamino)-2-methylhexan-3-yl)-2,6-diazaspiro[3.4]octan-6-yl)-1,2,4-triazin-6-yl) oxy)-5-fluoro-N,N-diisopropylbenzamide fumarate

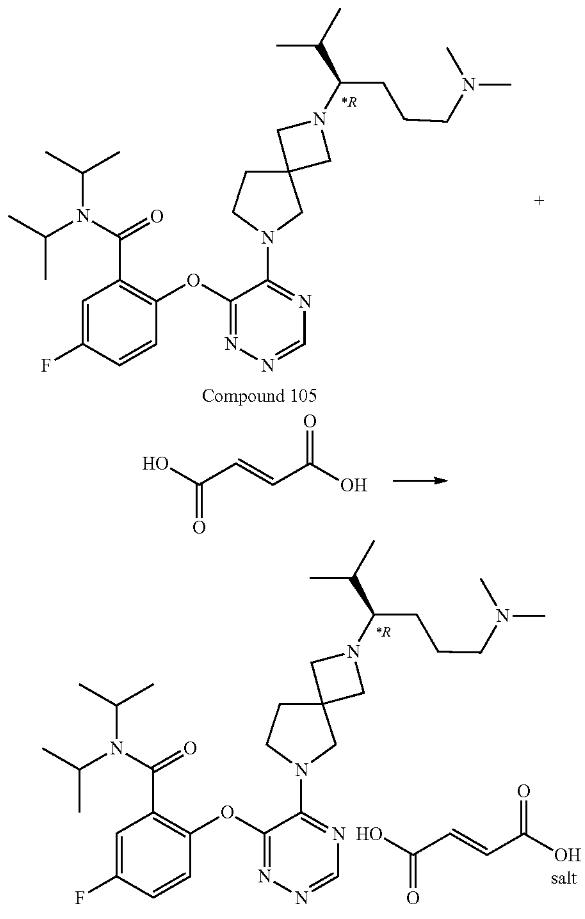

To a solution of (*R)-2-((5-(2-(6-(dimethylamino)-2-methylhexan-3-yl)-2,6-diazaspiro[3.4]octan-6-yl)-1,2,4-triazin-6-yl)oxy)-5-fluoro-N,N-diisopropylbenzamide (Compound 105) (300 mg, 0.527 mmol) in ACN (12 mL) and water (4 mL) was added fumaric acid (123 mg, 1.06 mmol). After a clear solution was formed, the mixture was concentrated under reduced pressure, the resulting residue was added to a mixture of ACN (3 mL) and water (10 mL). The mixture was lyophilized to dryness to afford the title compound (422 mg) as a white solid.

$^1$H NMR (400 MHz, Methanol-$d_4$): δ=8.50 (s, 1H), 7.50-7.15 (m, 3H), 6.72 (s, 4H), 4.51-3.89 (m, 7H), 3.86-3.69 (m, 2H), 3.61-3.49 (m, 1H), 3.25-3.07 (m, 3H), 2.88 (s, 6H), 2.50-2.20 (m, 2H), 2.19-2.06 (m, 1H), 1.97-1.77 (m, 2H), 1.75-1.57 (m, 2H), 1.51 (d, J=6.8 Hz, 3H), 1.37-1.14 (m, 6H), 1.11-0.97 (m, 6H), 0.78 (d, J=6.0 Hz, 3H).

LC-MS (ESI) (Method 2): $R_t$=2.08 min, m/z found 570.3 $[M+H]^+$.

SFC (Method 4): $R_t$=1.284 min.

Compound 103, 112, 114, 122, 123, 127, 128, 132, 133, 135, 137, 140, 142, 145, 146, 148, 150, 152, 154, 157, 159, 161, 165, 167, 170, 172, 176, 177, 179, 181, 184, 185, 188, 189, 191, 193, 195, 197, 199, 201, 203, 205, 219, 223, 225, 227, 233, 240, 241, 242, 243, 245, 256, 265, 266, 268, 270, 278, 280, 283, 259, 104, 229, 300, 302, 314, 315, 323, 324, 325, 326, 334, 335, 336, 337, 342, 343, 346, 352, 353, 356, 357, 365, 366, 369, 370, 377, 378, 382, 386, 387, 391, 392, 394, 397

(*S)-2-((5-(2-(6-(dimethylamino)-2-methylhexan-3-yl)-2,6-diazaspiro[3.4]octan-6-yl)-1,2,4-triazin-6-yl) oxy)-5-fluoro-N,N-diisopropylbenzamide fumarate N-ethyl-5-fluoro-N-isopropyl-2-(5(2-((R)-6-(((R)-1-methoxypropan-2-yl)amino)-2-methylhexan-3-yl)-2,6-diazaspiro[3.4]octan-6-yl)-1,2,4-triazin-6-yl)oxy) benzamide fumarate (R)-2-(5-(2-(6-((3,3-difluoropropyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (*R)—N-ethyl-5-fluoro-N-isopropyl-2-((5-(2-(6-(isopropyl(methyl)amino)-2-methylhexan-3-yl)-2,6-diazaspiro[3.4]octan-6-yl)-1,2,4-triazin-6-yl)oxy) benzamide fumarate (*S)—N-ethyl-5-fluoro-N-isopropyl-2-((5-(2-(6-(isopropyl(methyl)amino)-2-methylhexan-3-yl)-2,6-diazaspiro[3.4]octan-6-yl)-1,2,4-triazin-6-yl)oxy) benzamide fumarate (*R)—N-ethyl-5-fluoro-N-isopropyl-2-((2-methyl-6-(methyl(propyl)amino)hexan-3-yl)-2,6-diazaspiro [3.4]octan-6-yl)-1,2,4-triazin-6-yl)oxy)benzamide fumarate (*S)—N-ethyl-5-fluoro-N-isopropyl-2-((5-(2-(2-methyl-6-(methyl(propyl)amino)hexan-3-yl)-2,6-diazaspiro[3.4]octan-6-yl)-1,2,4-triazin-6-yl)oxy) benzamide fumarate (*R)—N-ethyl-2-((5-(2-(6-(ethyl(methyl)amino)-2-methylhexan-3-yl)-2,6-diazaspiro[3.4]octan-6-yl)-1,2,4-triazin-6-yl)oxy)-5-fluoro-N-isopropylbenzamide fumarate (*S)—N-ethyl-2-((5-(2-(6-(ethyl(methyl)amino)-2-methylhexan-3-yl)-2,6-diazaspiro[3.4]octan-6-yl)-1,2,4-triazin-6-yl)oxy)-5-fluoro-N-isopropylbenzamide fumarate (R)-N-ethyl-5-fluoro-N-isopropyl-2-((5-(2-(6-((2-methoxy-2-methylpropyl)amino)-2-methylhexan-3-yl)-2,6-diazaspiro[3.4]octan-6-yl)-1,2,4-triazin-6-yl) oxy)benzamide fumarate (R)-N-ethyl-5-fluoro-N-isopropyl-2-((5-(2-(6-((2-methoxy-2-methylpropyl)(methyl)amino)-2-methylhexan-3-yl)-2,6-diazaspiro[3.4]octan-6-yl)-1,2,4-triazin-6-yl)oxy)benzamide fumarate (R)-N-ethyl-5-fluoro-2-((5-(2-(6-((2-hydroxy-2-methylpropyl)(methyl)amino)-2-methylhexan-3-yl)-2,6-diazaspiro[3.4]octan-6-yl)-1,2,4-triazin-6-yl)oxy)-N-isopropylbenzamide fumarate (R)-N-ethyl-5-fluoro-N-isopropyl-2-((5-(2-(6-((3-methoxypropyl)(methyl)amino)-2-methylhexan-3-yl)-2,6-diazaspiro[3.4]octan-6-yl)-1,2,4-triazin-6-yl)oxy)benzamide fumarate (*R)-2-((5-(2-(6-((3-(dimethylamino)-3-oxopropyl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide fumarate (*S)-2-((5-(2-(6-((3-(dimethylamino)-3-oxopropyl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide fumarate (R)-N-ethyl-5-fluoro-N-isopropyl-2-((5-(2-(2-methyl-6-(methyl(2-(N-methylacetamido)ethyl)amino)hexan-3-yl)-2,6-diazaspiro[3.4]octan-6-yl)-1,2,4-triazin-6-yl)oxy)benzamide fumarate (R)-2-((5-(2-(6-((2,2-dimethoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (R)-2-((5-(2-(6-((4-(dimethylamino)-4-oxobutyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-N-isopropyl-2-((5-(2-((R)-6-(((R)-1-methoxypropan-2-yl)(methyl)amino)-2-methylhexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((R)-6-((S)-1-methoxypropan-2-yl)(methyl)amino)-2-methylhexan-3-yl)-2,6-diazaspiro[3.4]octan-6-yl)-1,2,4-triazin-6-yl)oxy)benzamide fumarate (R)-2-((5-(2-(6-((1,3-dimethoxypropan-2-yl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (R)-2-((5-(2-(6-((1,3-dimethoxypropan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-2-(5-(2-((R)-6-((R)-1-hydroxy-3-methoxypropan-2-yl)(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((R)-6-(((S)-1-hydroxy-3-methoxypropan-2-yl)(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3R)-6-((3-hydroxy-2-methoxypropyl)(methyl)amino)-2-methylhexan-3-yl)-2,6-diazaspiro[3.4]octan-6-yl)-1,2,4-triazin-6-yl)oxy)-N-isopropylbenzamide fumarate 2-((5-(2-((3R)-6-((2,3-dimethoxypropyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((R)-6-(((*R)-2,3-dimethoxypropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((R)-6-(((*S)-2,3-dimethoxypropyl)(methyl)amino)-2-methylhexan-3-yl-2,6-diazaspiro[3.4]octan-6-yl)-1,2,4-triazin-6-yl)oxy)-N-ethyl-5-fluoro-N-isopropylbenzamide fumarate 2-((5-(2-((3R)-6-((4-(dimethylamino)-4-oxobutan-2-yl)(methyl)amino)-2-methylhexan-3-yl)-2,6-diazaspiro[3.4]octan-6-yl)-1,2,4-triazin-1-yl)oxy)-N-ethyl-5-fluoro-N-isopropylbenzamide fumarate 2-((5-(2-((3R)-6-((3-(dimethylamino)-2-methyl-3-oxopropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((R)-6-(((*R)-4-(dimethylamino)-4-oxobutan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((R)-6-(((*S)-4-(dimethylamino)-4-oxobutan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((R)-6-(((*R)-3-(dimethylamino)-2-methyl-3-oxopropyl)(methyl)amino)-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((R)-6-(((*S)-3-(dimethylamino)-2-methyl-3-oxopropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-N-isopropyl-2-((5-(2-((R)-2-methyl-6-(methyl((R)-4-(methylamino)-4-oxobutan-2-yl)amino)hexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((R)-2-methyl-6-(methyl((S)-4-(methylamino)-4-oxobutan-2-yl)amino)hexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((R)-2-methyl-6-(methyl((R)-2-methyl-3-(methylamino)-3-oxopropyl)amino)hexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((R)-2-methyl-6-(methyl((S)-2-methyl-3-(methylamino)-3-oxopropyl)amino)hexan-3-yl)-2,6-diazaspiro[3.4]

octan-6-yl)-1,2,4-triazin-6-yl)oxy)benzamide fumarate 2-((5-(2-((*R)-6-(((R)-4-amino-4-oxobutan-2-yl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((*R)-6-(((S)-4-amino-4-oxobutan-2-yl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((*R)-6-(((S)-3-amino-2-methyl-3-oxopropyl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((*R)-6-(((S)-3-amino-2-methyl-3-oxopropyl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide fumarate (*R)-2-((5-(2-(1-amino-4-methylpentan-3-yl)-2,6-diazaspiro[3.4]octan-6-yl)-1,2,4-triazin-6-yl)oxy)-N-ethyl-5-fluoro-N-isopropylbenzamide fumarate (*R)-2-((5-(2-(1-(dimethylamino)-4-methylpentan-3-yl)-2,6-diazaspiro[3.4]octan-6-yl)-1,2,4-triazin-6-yl)oxy)-N-ethyl-5-fluoro-N-isopropylbenzamide fumarate (*S)-2-((5-(2-(1-(dimethylamino)-4-methylpentan-3-yl)-2,6-diazaspiro[3.4]octan-6-yl)-1,2,4-triazin-6-yl)oxy)-N-ethyl-5-fluoro-N-isopropylbenzamide fumarate (*R)—N-ethyl-5-fluoro-N-isopropyl-2-((5(2-(1-((2-methoxyethyl)amino)-4-methylpentan-3-yl)-2,6-diazaspiro[3.4]octan-6-yl)-1,2,4-triazin-6-yl)oxy)benzamide fumarate (R)-N-ethyl-5-fluoro-N-isopropyl-2-((5-(2-(6-((2-methoxyethyl-1,1-$d_2$)(methyl)amino)-2-methylhexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((3*R,5*R)-6-((2-methoxyethyl)(methyl)amino)-2,5-dimethylhexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((3*S,5*R)-6-((2-methoxyethyl)(methyl)amino)-2,5-dimethylhexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((3*R,5*S)-((2-methoxyethyl)(methyl)amino)-2,5-dimethylhexan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((3*S,5*S)-6-((2-methoxyethyl)(methyl)amino)-2,5-dimethylhexan-3-yl)-2,6-diazaspiro[3.4]octan-6-yl)-1,2,4-triazin-6-yl)oxy)benzamide fumarate (R)-2-((5-(2-(6-((2-acetamidoethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (R)-2-((5(2-(6-((1,3-dihydroxypropan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-N-isopropyl-2-((5-(2-(6-((2-methoxyethyl)(methyl)amino)-2,4-dimethylhexan-3-yl)-2,6-diazaspiro[3.4]octan-6-yl)-1,2,4-triazin-6-yl)oxy)benzamide (mixture of R,S and S,R; or mixture of RR and S,S) fumarate N-ethyl-5-fluoro-N-isopropyl-2-((5-(2-(6-((2-methoxyethyl)(methyl)amino)-2,4-dimethylhexan-3-yl)-2,6-diazaspiro[3.4]octan-6-yl)-1,2,4-triazin-6-yl)oxy)benzamide (mixture of R,R and S,S; or mixture of R,S and S,R) fumarate (*R)—N-ethyl-5-fluoro-2-((5-(2-(1-((2-hydroxyethyl)amino)-4-methylpentan-3-yl)-2,6-diazaspiro[3.4]octan-6-yl)-1,2,4-triazin-6-yl)oxy)-N-isopropylbenzamide fumarate (*R)—N-ethyl-5-fluoro-2-((5-(2-(1-((2-hydroxyethyl)(methyl)amino)-4-methylpentan-3-yl)-2,6-diazaspiro[3.4]octan-6-yl)-1,2,4-triazin-6-yl)oxy)-N-isopropylbenzamide fumarate (*R)-2-((5-(2-(1-((3-amino-3-oxopropyl)amino)-4-methylpentan-3-yl)-2,6-diazaspiro[3.4]octan-6-yl)-1,2,4-triazin-6-yl)oxy)-N-ethyl-5-fluoro-N-isopropylbenzamide fumarate (*R)-2-((5-(2-(1-((3-amino-3-oxopropyl)(methyl)amino)-4-methylpentan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-2-((5-(2-((R)-6-(((R)-2-hydroxy-3-methoxypropyl)(methyl)amino)-2-methylhexan-3-yl)-2,6-diazaspiro[3.4]octan-6-yl)-1,2,4-triazin-6-yl)oxy)-N-isopropylbenzamide fumarate (R)-N-ethyl-5-fluoro-2-((5-(2-(6-((2-hydroxyethyl)(methyl)amino)-2-methylhexan-3-yl)-2,6-diazaspiro[3.4]octan-6-yl)-1,2,4-triazin-6-yl)oxy)-N-isopropylbenzamide fumarate (R)-2-((5-(2-(6-((2,2-dimethoxyethyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (*R)—N-ethyl-5-fluoro-N-isopropyl-2-((5-(2-(1-(isopropylamino)-4-methylpentan-3-yl)-2,6-diazaspiro[3.4]octan-6-yl)-1,2,4-triazin-6-yl)oxy)benzamide fumarate N-ethyl-5-fluoro-N-isopropyl-2-((5-(2-((3R)-6-((2-methoxyethyl)(methyl)amino)-2-methylheptan-3-yl)-2,6-diazaspiro[3.4]octan-6-yl)-1,2,4-triazin-6-yl)oxy)benzamide fumarate N-ethyl-5-fluoro-N-isopropyl-2-((5-(6-(6-((2-methoxyethyl)(methyl)amino)-2-methylhexan-3-yl)-2,6-diazaspiro[3.4]octan-2-yl)-1,2,4-triazin-6-yl)oxy)benzamide fumarate 2-((5-(2-((3*R,5*R)-6-(dimethylamino)-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((3*R,5*S)-6-(dimethylamino)-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-2-((5-(2-((3*R,5*R)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*S,5*S)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*R,5*S)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*S,5*R)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide fumarate 2-((5-(2-((3*R,5*R)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((3*S,5*S)-6-diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((3*S,5*R)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-(5-(2-((3*R,5*S)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-2-((5-(2-((3*S,5S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide fumarate N-ethyl-2-((5-(2-((3*S,5S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide fumarate N-ethyl-2-((5-(2-((3*R,5R)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide fumarate N-ethyl-5-fluoro-2-((5-(2-((3*R,5S)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*S,5S)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*R,5R)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*S,5R)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide fumarate 2-((5-(2-((3*R,5*R)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((3*R,5*S)-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((3*S,5*S)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((3*S,5*R)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((3*S,5*R)-6-(dimethylamino)-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate 2-((5-(2-((3*S,5*R)-6-(dimethylamino)-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide fumarate N-ethyl-5-fluoro-2-((5-(2-(5-hydroxy-6-((2-methoxyethyl)(methyl)amino)-2,5-dimethylhexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*R,5*R)-5-hydroxy-2-methyl-6-(methyl(propyl)amino)hexan-3-yl)-2,6-diazaspiro[3.4]octan-6-yl)-1,2,4-triazin-6-yl)oxy)-N-isopropylbenzamide fumarate N-ethyl-5-fluoro-2-((5-(2-((3*S,5*S)-5-hydroxy-2-methyl-6-(methyl(propyl)amino)hexan-3-yl)-2,6-diazaspiro[3.4]octan-6-yl)-1,2,4-triazin-6-yl)oxy)-N-isopropylbenzamide fumarate 2-((5-(2-((3*R,5*S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide fumarate 2-((5-(2-((3*S,5*S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide fumarate (R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (R)-N-ethyl-5-fluoro-N-isopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide fumarate The following Compounds were synthesized by an analogous method described above for Compound 102

| Co. No. | Structure | Starting Materials | Spectra Details |
|---|---|---|---|
| 103 | 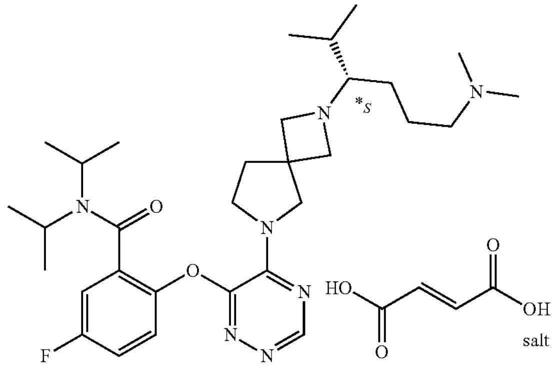 | Compound 106, fumaric acid | LC-MS (ESI) (Method 2): $R_t$ = 2.041 min, m/z found 570.3 $[M + H]^+$. SFC (Method 13): $R_t$ = 1.722 min. |
| 112 | 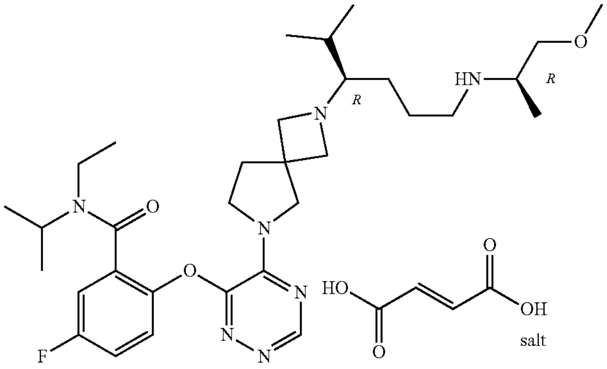 | Compound 111, fumaric acid | $^1H$ NMR (400 MHz, Methanol-$d_4$): δ = 8.49 (s, 1H), 7.45-7.22 (m, 3H), 6.71 (s, 4H), 4.20-3.63 (m, 9H), 3.51-3.40 (m, 6H), 3.31-2.95 (m, 5H), 2.47-2.23 (m, 2H), 2.19-1.98 (m, 1H), 1.94-1.54 (m, 4H), 1.35 (d, J = 5.6 Hz, 3H), 1.19-0.98 (m, 13H), 0.89-0.73 (m, 2H). LC-MS (ESI) (Method 1): $R_t$ = 3.063 min, m/z found 600.5 $[M + H]^+$. SFC (Method 6): $R_t$ = 1.214 min. |

-continued

| Co. No. | Structure | Starting Materials | Spectra Details |
|---|---|---|---|
| 114 | 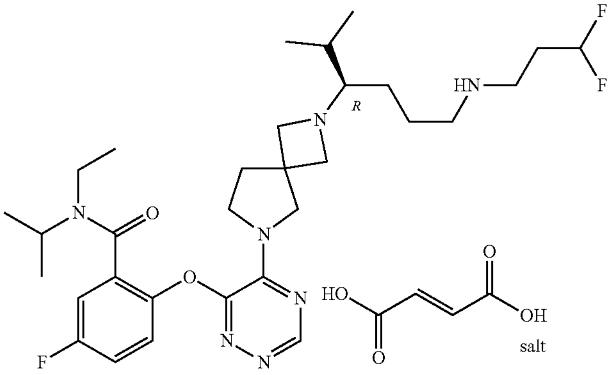 | Compound 113, fumaric acid | $^1$H NMR (400 MHz, Methanol-$d_4$): δ = 8.47 (s, 1H), 7.52-7.07 (m, 3H), 6.69 (s, 4H), 6.30-5.90 (m, 1H), 4.50-3.39 (m, 10H), 3.25-2.83 (m, 6H), 2.43-1.99 (m, 5H), 1.90-1.49 (m, 4H), 1.23-0.71 (m, 15H). LC-MS (ESI) (Method 1): $R_t$ = 3.056 min, m/z found 606.3 $[M + H]^+$. SFC (Method 13): $R_t$ = 1.944 min. |
| 122 | 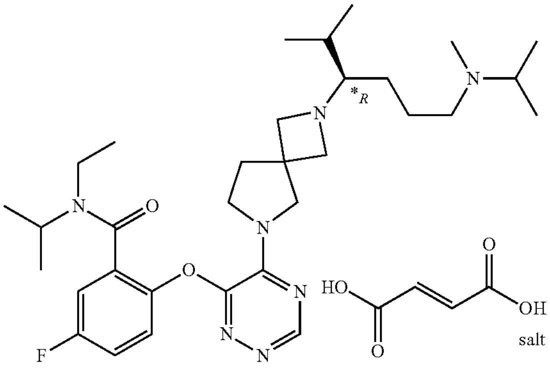 | Compound 120, fumaric acid | LC-MS (ESI) (Method 2): $R_t$ = 2.030 min, m/z found 584.3 $[M + H]^+$. SFC (Method 18): $R_t$ = 2.312 min. |
| 123 | 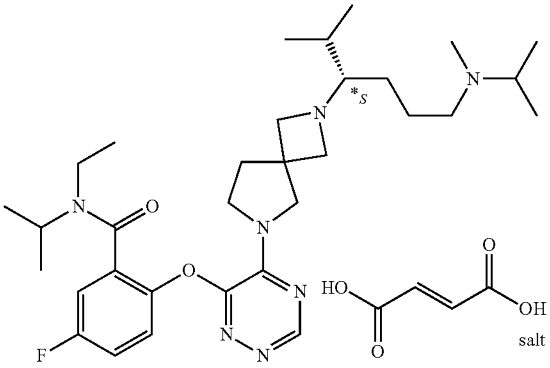 | Compound 121, fumaric acid | LC-MS (ESI) (Method 2): $R_t$ = 2.020 min, m/z found 584.3 $[M + H]^+$. SFC (Method 18): $R_t$ = 2.557 min. |
| 127 | 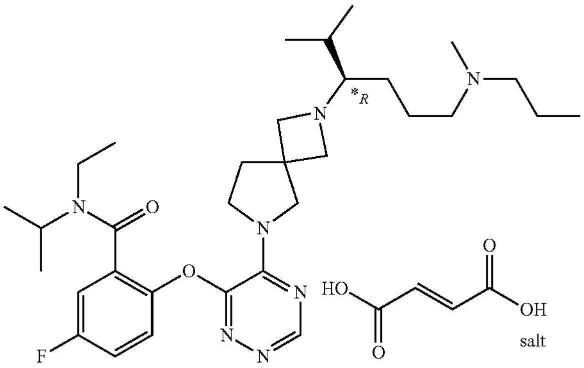 | Compound 125, fumaric acid | LC-MS (ESI) (Method 2): $R_t$ = 2.065 min, m/z found 584.3 $[M + H]^+$. Chiral HPLC (Method 7): $R_t$ = 3.197 min. |

-continued

| Co. No. | Structure | Starting Materials | Spectra Details |
|---|---|---|---|
| 128 | 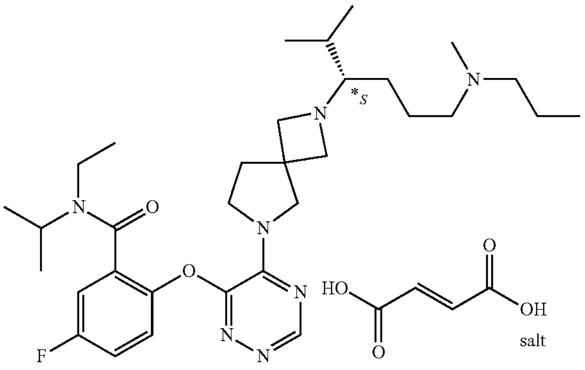 | Compound 126, fumaric acid | LC-MS (ESI) (Method 2): $R_t$ = 2.074 min, m/z found 584.3 $[M + H]^+$. Chiral HPLC (Method 7): $R_t$ = 3.805 min. |
| 132 | 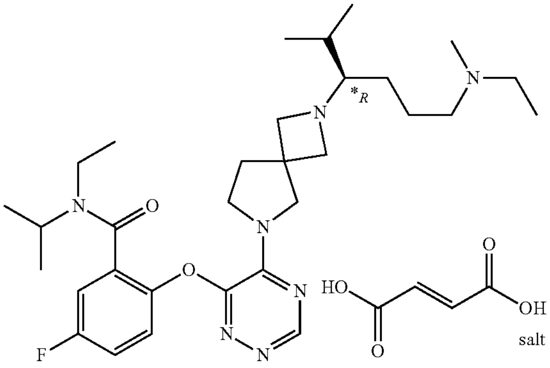 | Compound 130, fumaric acid | LC-MS (ESI) (Method 2): $R_t$ = 1.954 min, m/z found 570.3 $[M + H]^+$. Chiral HPLC (Method 7): $R_t$ = 3.702 min. |
| 133 | 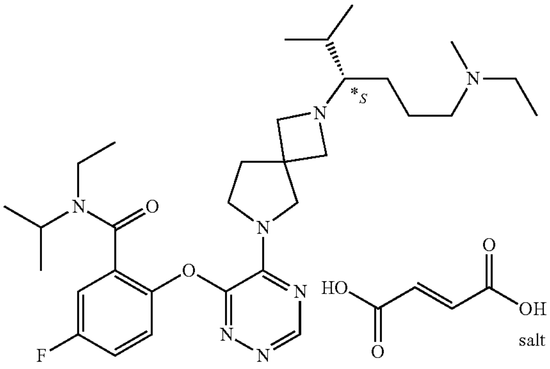 | Compound 131, fumaric acid | LC-MS (ESI) (Method 2): $R_t$ = 1.955 min, m/z found 570.3 $[M + H]^+$. Chiral HPLC (Method 7): $R_t$ = 4.808 min. |
| 135 | 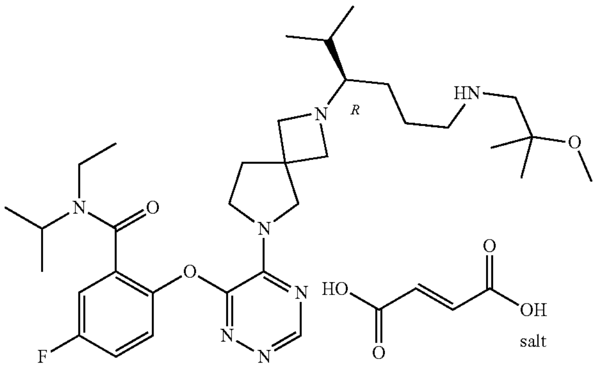 | Compound 134, fumaric acid | LC-MS (ESI) (Method 2): $R_t$ = 2.083 min, m/z found 614.4 $[M + H]^+$. SFC (Method 6): $R_t$ = 1.346 min. |

-continued

| Co. No. | Structure | Starting Materials | Spectra Details |
|---|---|---|---|
| 137 | 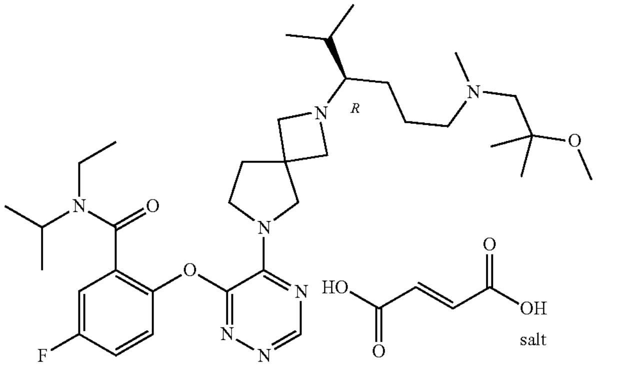 | Compound 136, fumaric acid | LC-MS (ESI) (Method 2): $R_t$ = 2.115 min, m/z found 628.4 $[M + H]^+$. SFC (Method 6): $R_t$ = 0.938 min. |
| 140 | 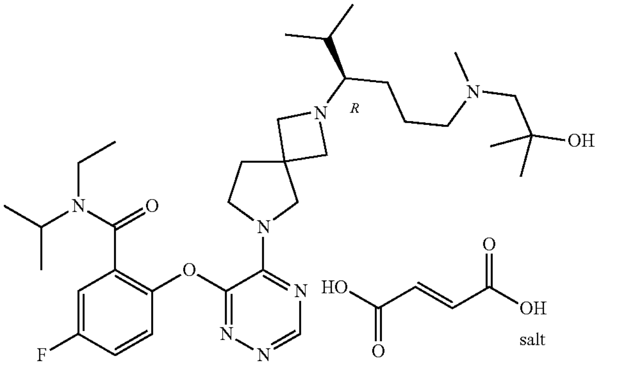 | Compound 139, fumaric acid | LC-MS (ESI) (Method 2): $R_t$ = 1.986 min, m/z found 614.4 $[M + H]^+$. SFC (Method 13): $R_t$ = 1.749 min. |
| 142 | 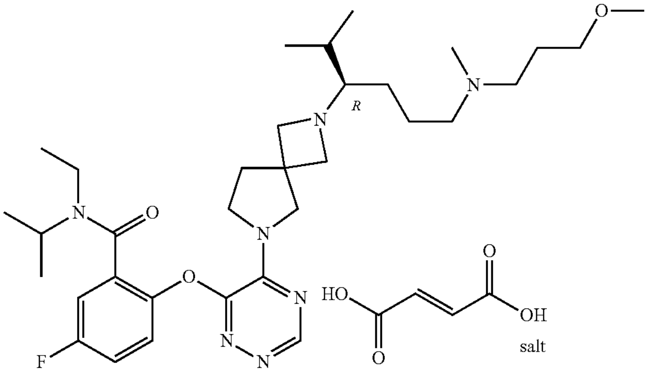 | Compound 141, fumaric acid | LC-MS (ESI) (Method 2): $R_t$ = 2.039 min, m/z found 614.4 $[M + H]^+$. SFC (Method 6): $R_t$ = 1.171 min. |
| 145 | 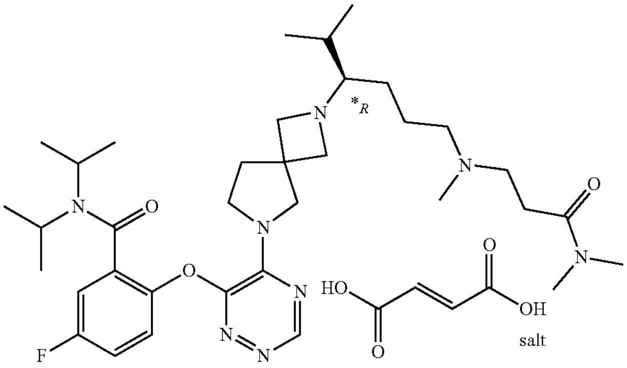 | Compound 143, fumaric acid | LC-MS (ESI) (Method 2): $R_t$ = 2.096 min, m/z found 655.6 $[M + H]^+$. SFC (Method 19): $R_t$ = 3.861 min. |

-continued

| Co. No. | Structure | Starting Materials | Spectra Details |
|---|---|---|---|
| 146 | 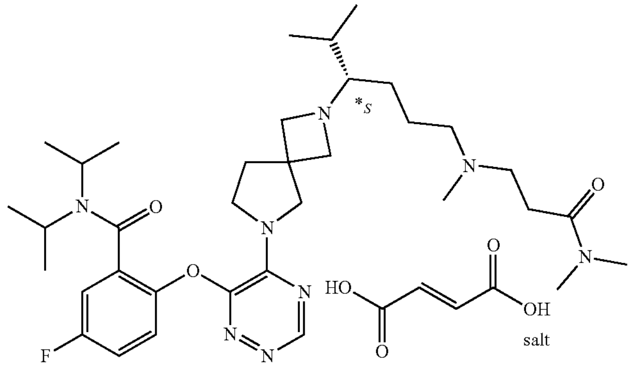 | Compound 144, fumaric acid | LC-MS (ESI) (Method 2): $R_t$ = 2.096 min, m/z found 655.6 $[M + H]^+$. SFC (Method 19): $R_t$ = 4.578 min. |
| 148 | 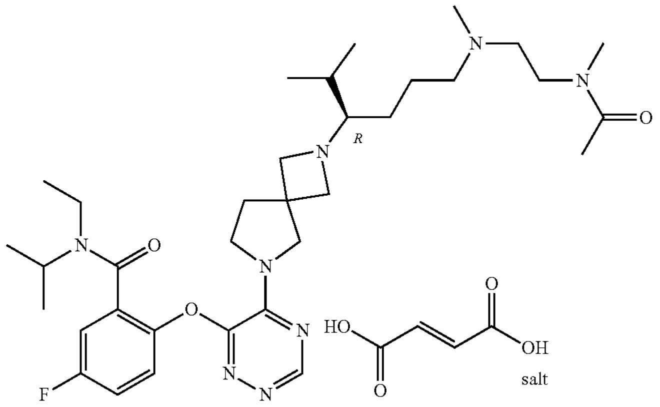 | Compound 147, fumaric acid | LC-MS (ESI) (Method 3): $R_t$ = 4.480 min, m/z found 641.6 $[M + H]^+$. SFC (Method 6): $R_t$ = 1.356 min. |
| 150 | 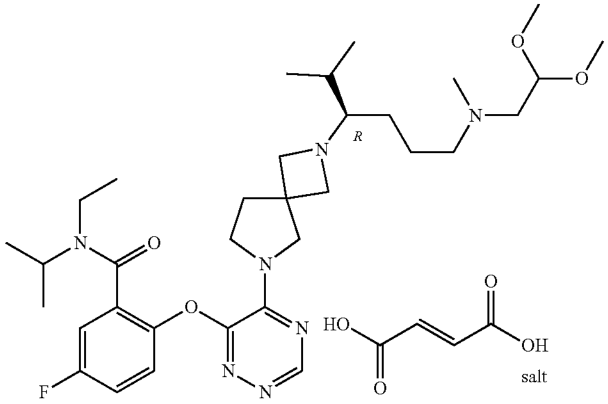 | Compound 149, fumaric acid | LC-MS (ESI) (Method 3): $R_t$ = 4.836 min, m/z found 630.4 $[M + H]^+$. SFC (Method 6): $R_t$ = 1.067 min. |
| 152 | 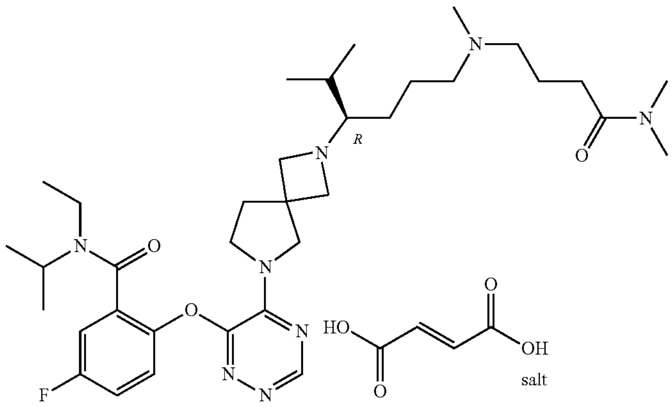 | Compound 151, fumaric acid | LC-MS (ESI) (Method 2): $R_t$ = 2.332 min, m/z found 655.5 $[M + H]^+$. SFC (Method 6): $R_t$ = 1.449 min. |

-continued

| Co. No. | Structure | Starting Materials | Spectra Details |
|---|---|---|---|
| 154 | 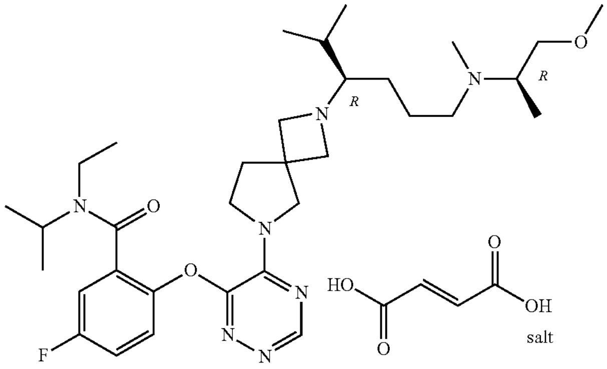 | Compound 153, fumaric acid | LC-MS (ESI) (Method 2): $R_t$ = 2.022 min, m/z found 614.4 $[M + H]^+$. SFC (Method 6): $R_t$ = 1.137 min. |
| 157 | 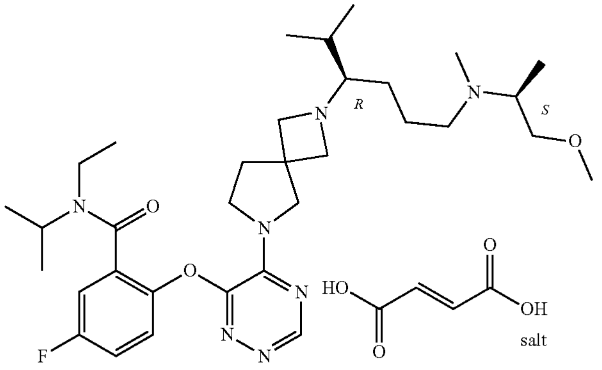 | Compound 156, fumaric acid | LC-MS (ESI) (Method 2): $R_t$ = 2.049 min, m/z found 614.4 $[M + H]^+$. SFC (Method 20): $R_t$ = 1.001 min. |
| 159 | 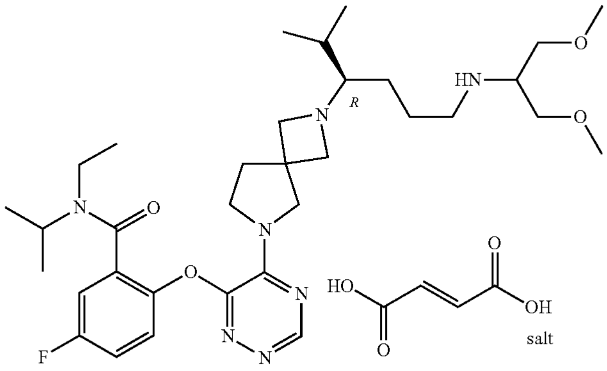 | Compound 158, fumaric acid | LC-MS (ESI) (Method 1): $R_t$ = 3.102 min, m/z found 630.4 $[M + H]^+$. SFC (Method 6): $R_t$ = 1.194 min. |
| 161 | 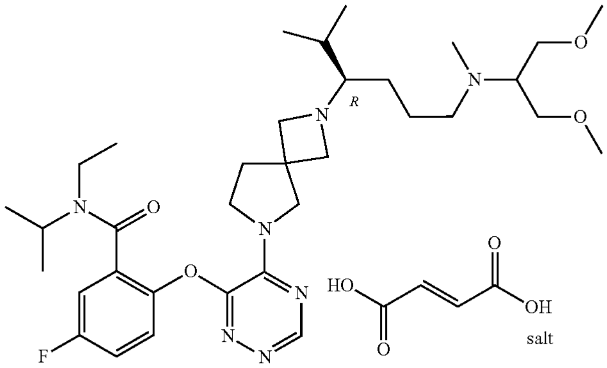 | Compound 160, fumaric acid | LC-MS (ESI) (Method 2): $R_t$ = 2.112 min, m/z found 644.3 $[M + H]^+$. SFC (Method 6): $R_t$ = 1.073 min. |

-continued

| Co. No. | Structure | Starting Materials | Spectra Details |
|---|---|---|---|
| 165 | 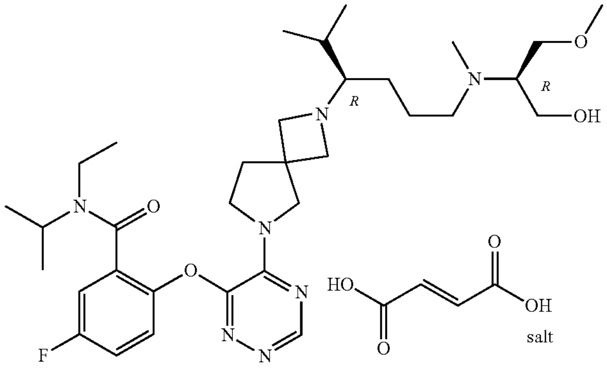 | Compound 164, fumaric acid | LC-MS (ESI) (Method 3): $R_t$ = 4.766 min, m/z found 630.3 $[M + H]^+$. SFC (Method 6): $R_t$ = 1.271 min. |
| 167 | 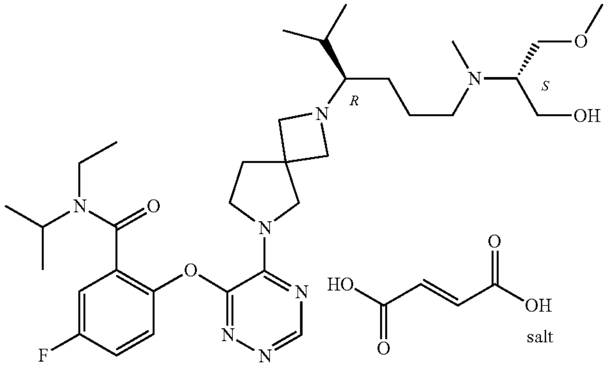 | Compound 166, fumaric acid | LC-MS (ESI) (Method 3): $R_t$ = 4.730 min, m/z found 630.3 $[M + H]^+$. SFC (Method 6): $R_t$ = 1.373 min. |
| 170 | 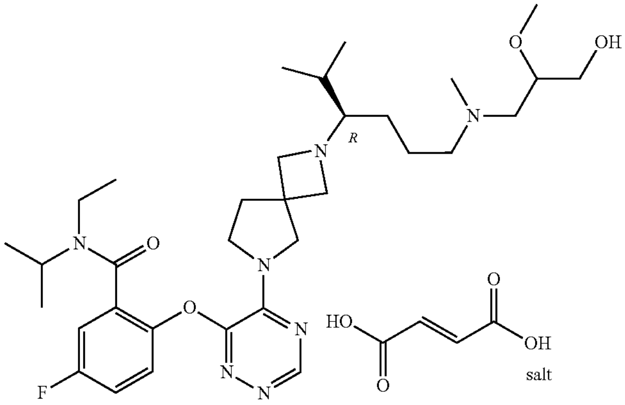 | Compound 169, fumaric acid | LC-MS (ESI) (Method 3): $R_t$ = 4.652 min, m/z found 630.4 $[M + H]^+$. |
| 172 | 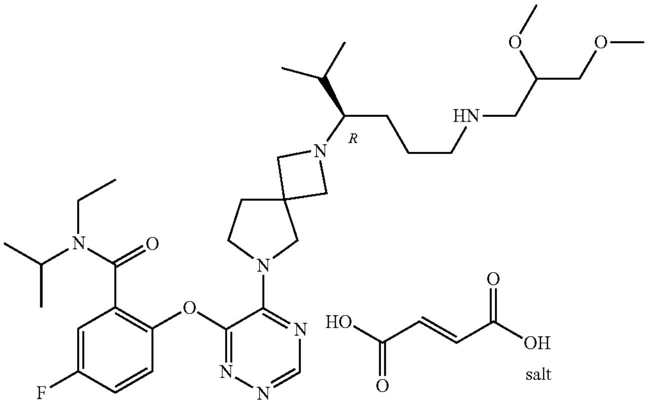 | Compound 171, fumaric acid | LC-MS (ESI) (Method 3): $R_t$ = 5.073 min, m/z found 630.4 $[M + H]^+$. |

-continued

| Co. No. | Structure | Starting Materials | Spectra Details |
|---|---|---|---|
| 176 | 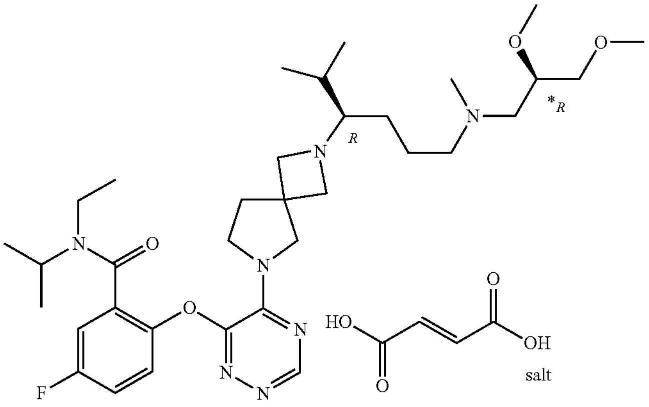 | Compound 174, fumaric acid | LC-MS (ESI) (Method 3): $R_t$ = 5.035 min, m/z found 644.5 $[M + H]^+$. SFC (Method 23): $R_t$ = 4.662 min. |
| 177 | 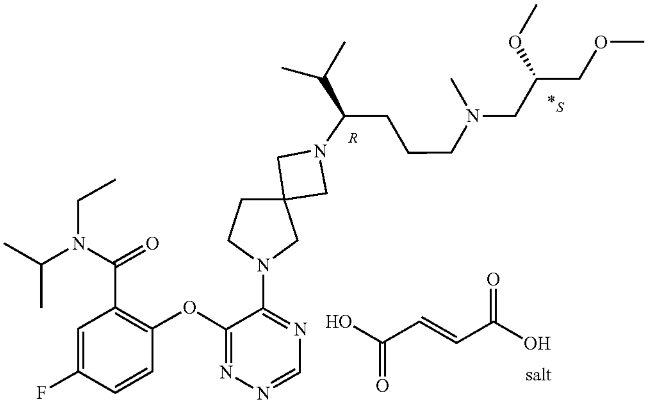 | Compound 175, fumaric acid | LC-MS (ESI) (Method 3): $R_t$ = 5.031 min, m/z found 644.5 $[M + H]^+$. SFC (Method 23): $R_t$ = 4.977 min. |
| 179 | 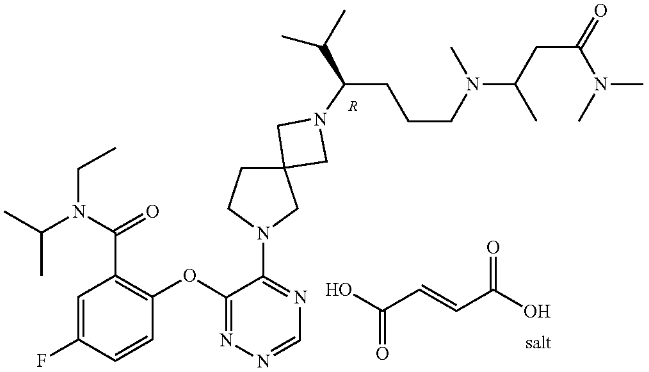 | Compound 178, fumaric acid | LC-MS (ESI) (Method 5): $R_t$ = 1.72 min, m/z found 655.5 $[M + H]^+$. |
| 181 | 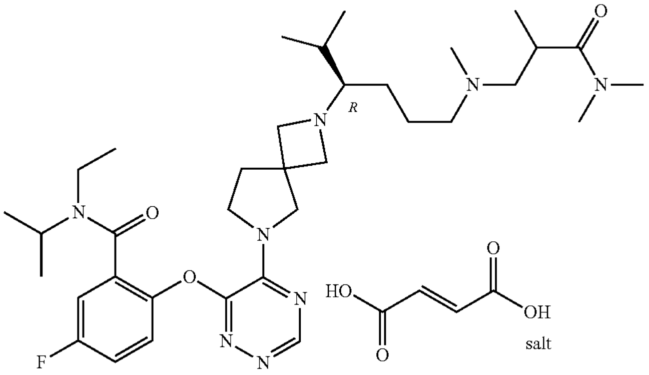 | Compound 180, fumaric acid | LC-MS (ESI) (Method 5): $R_t$ = 1.61 min, m/z found 655.5 $[M + H]^+$. |

-continued

| Co. No. | Structure | Starting Materials | Spectra Details |
|---|---|---|---|
| 184 | 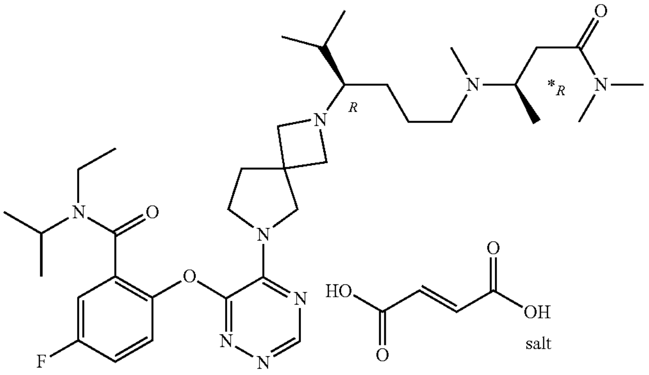 | Compound 182, fumaric acid | LC-MS (ESI) (Method 2): $R_t$ = 2.041 min, m/z found 655.4 $[M + H]^+$. SFC (Method 8): $R_t$ = 2.752 min. |
| 185 | 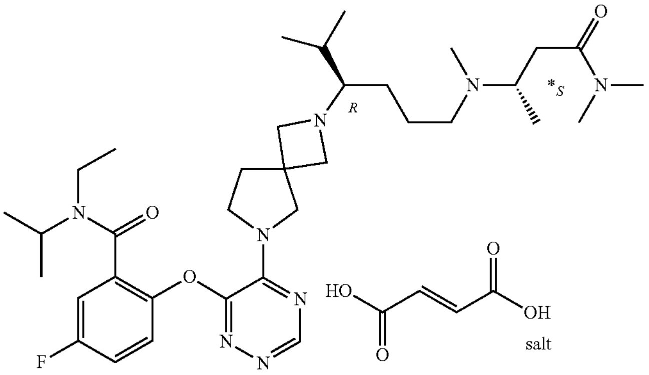 | Compound 183, fumaric acid | LC-MS (ESI) (Method 2): $R_t$ = 2.058 min, m/z found 655.4 $[M + H]^+$. SFC (Method 8): $R_t$ = 3.09 min. |
| 188 | 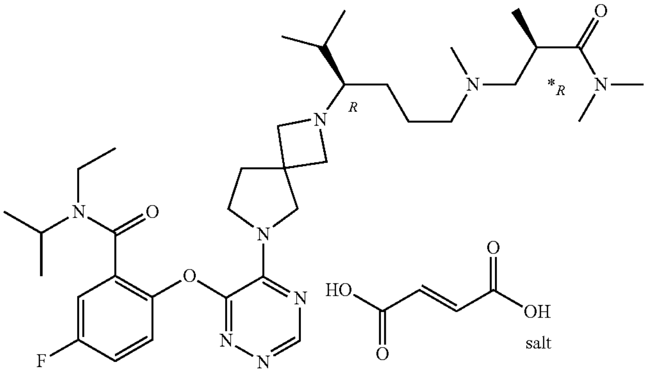 | Compound 186, fumaric acid | LC-MS (ESI) (Method 3): $R_t$ = 4.940 min, m/z found 655.4 $[M + H]^+$. SFC (Method 23): $R_t$ = 5.055 min. |
| 189 | 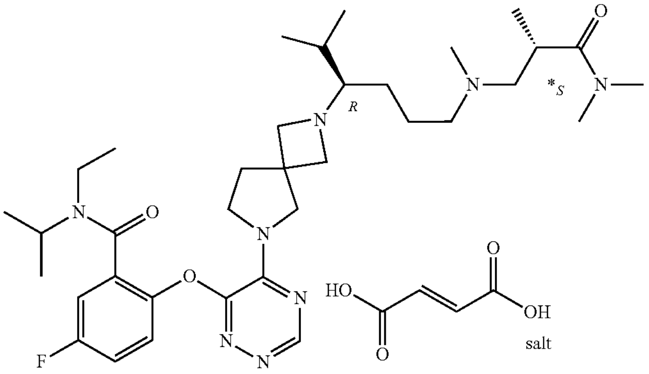 | Compound 187, fumaric acid | LC-MS (ESI) (Method 3): $R_t$ = 4.907 min, m/z found 655.4 $[M + H]^+$. SFC (Method 23): $R_t$ = 5.287 min. |

-continued
| Co. No. | Structure | Starting Materials | Spectra Details |
|---|---|---|---|
| 191 | 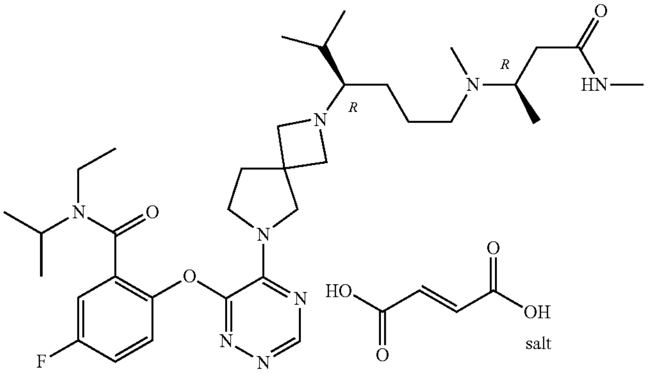 | Compound 190, fumaric acid | LC-MS (ESI) (Method 5): $R_t$ = 1.66 min, m/z found 641.3 $[M + H]^+$. |
| 193 | 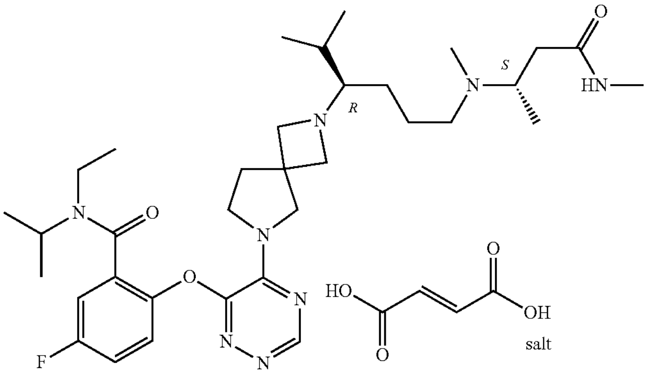 | Compound 192, fumaric acid | LC-MS (ESI) (Method 5): $R_t$ = 1.70 min, m/z found 641.3 $[M + H]^+$. |
| 195 | 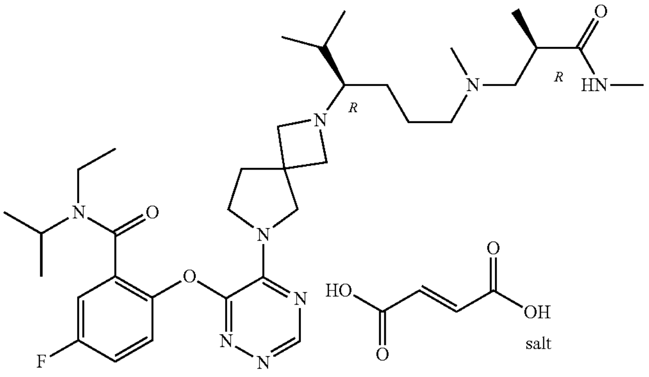 | Compound 194, fumaric acid | LC-MS (ESI) (Method 5): $R_t$ = 1.67 min, m/z found 641.3 $[M + H]^+$. |
| 197 | 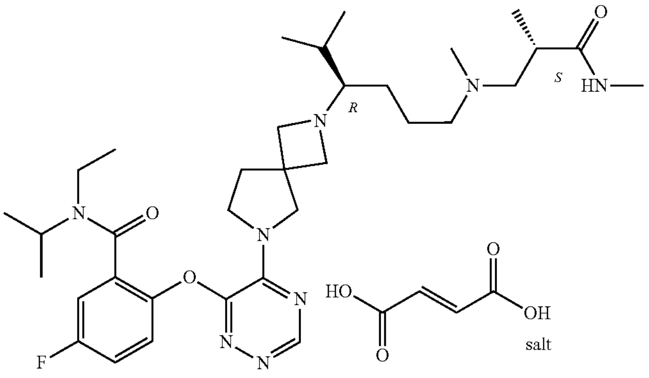 | Compound 196, fumaric acid | LC-MS (ESI) (Method 5): $R_t$ = 1.85 min, m/z found 641.3 $[M + H]^+$. |

-continued
| Co. No. | Structure | Starting Materials | Spectra Details |
|---|---|---|---|
| 199 | 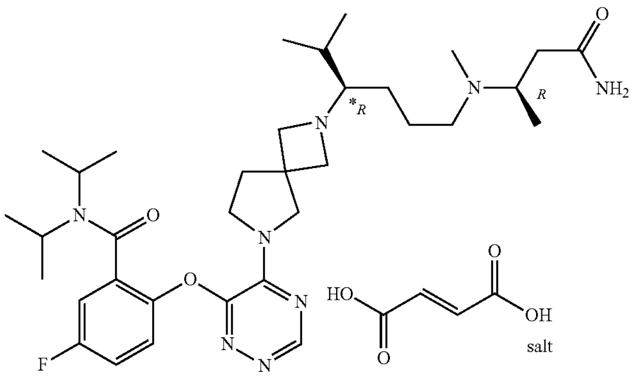 | Compound 198, fumaric acid | LC-MS (ESI) (Method 5): $R_t$ = 1.62 min, m/z found 641.3 $[M + H]^+$. |
| 201 | 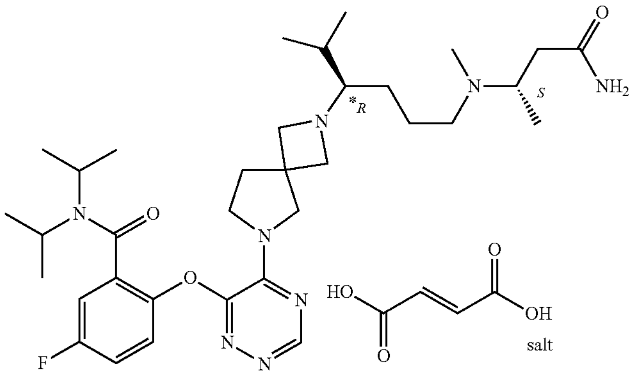 | Compound 200, fumaric acid | LC-MS (ESI) (Method 5): $R_t$ = 1.63 min, m/z found 641.3 $[M + H]^+$. |
| 203 | 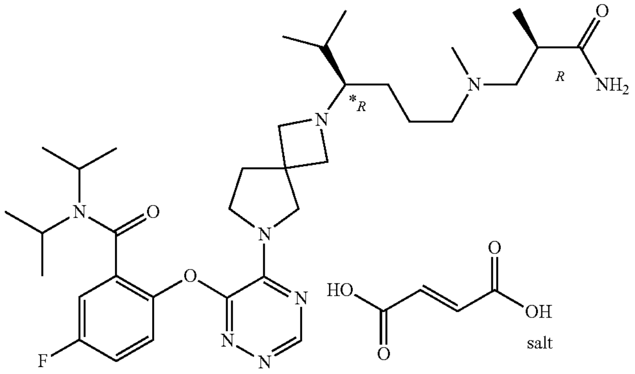 | Compound 202, fumaric acid | LC-MS (ESI) (Method 5): $R_t$ = 1.72 min, m/z found 641.3 $[M + H]^+$. |
| 205 | 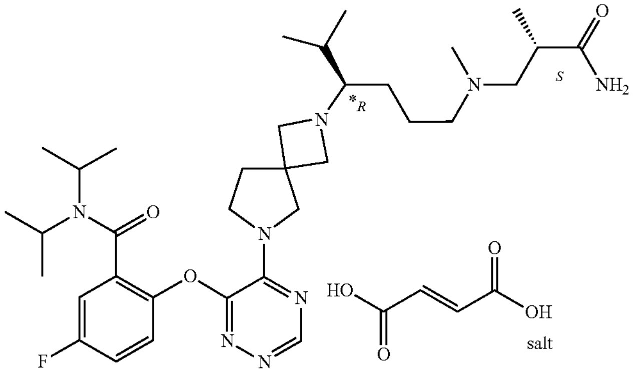 | Compound 204, fumaric acid | LC-MS (ESI) (Method 5): $R_t$ = 1.66 min, m/z found 641.2 $[M + H]^+$. |

-continued

| Co. No. | Structure | Starting Materials | Spectra Details |
|---|---|---|---|
| 219 | 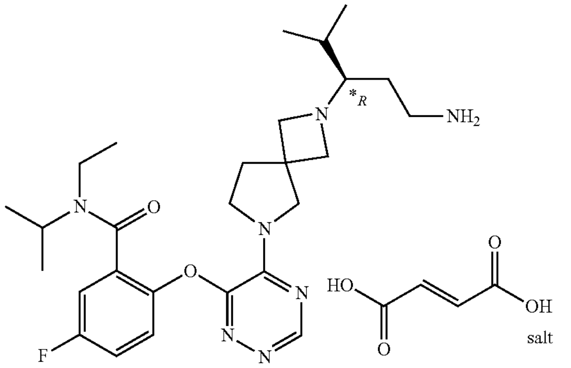 salt | Compound 218, fumaric acid | LC-MS (ESI) (Method 6): $R_t$ = 2.67 min, m/z found 514.2 $[M + H]^+$. |
| 223 | 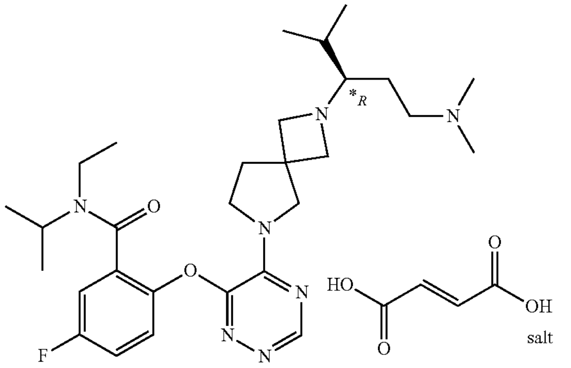 salt | Compound 222, fumaric acid | LC-MS (ESI) (Method 3): $R_t$ = 5.047 min, m/z found 542.3 $[M + H]^+$. SFC (Method 18): $R_t$ = 1.991 min. |
| 225 | 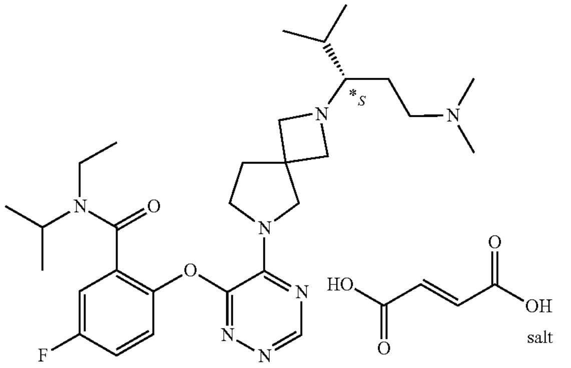 salt | Compound 224, fumaric acid | LC-MS (ESI) (Method 3): $R_t$ = 4.890 min, m/z found 542.3 $[M + H]^+$. SFC (Method 18): $R_t$ = 2.189 min. |
| 227 | 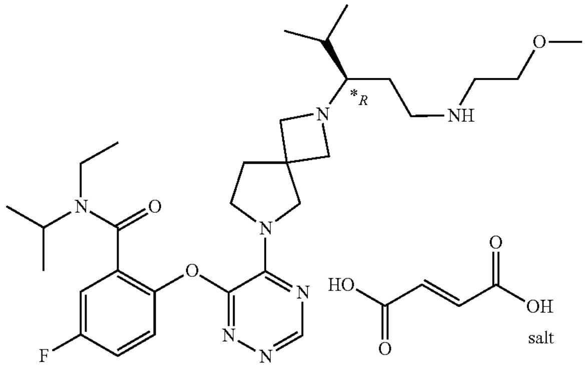 salt | Compound 226, fumaric acid | LC-MS (ESI) (Method 6): $R_t$ = 3.00 min, m/z found 572.3 $[M + H]^+$. |

-continued

| Co. No. | Structure | Starting Materials | Spectra Details |
|---|---|---|---|
| 233 | 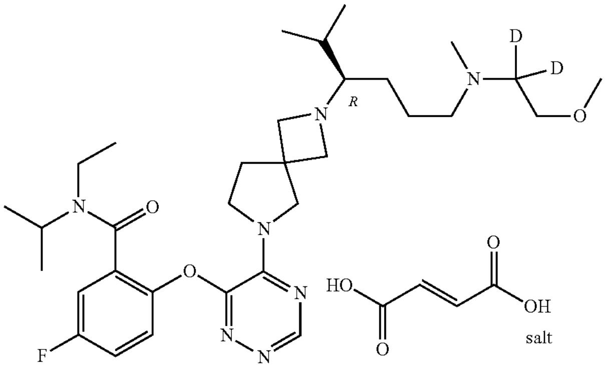 salt | Compound 232, fumaric acid | LC-MS (ESI) (Method 1): $R_t$ = 3.031 min, m/z found 602.3 $[M + H]^+$. SFC (Method 6): $R_t$ = 1.134 min. |
| 240 | 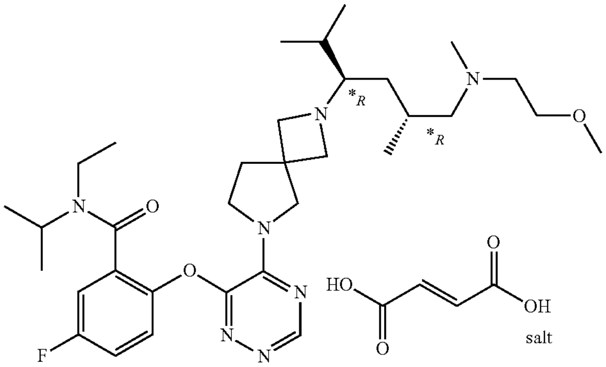 salt | Compound 236, fumaric acid | LC-MS (ESI) (Method 3): $R_t$ = 5.301 min, m/z found 614.4 $[M + H]^+$. SFC (Method 4): $R_t$ = 1.241 min. |
| 241 | 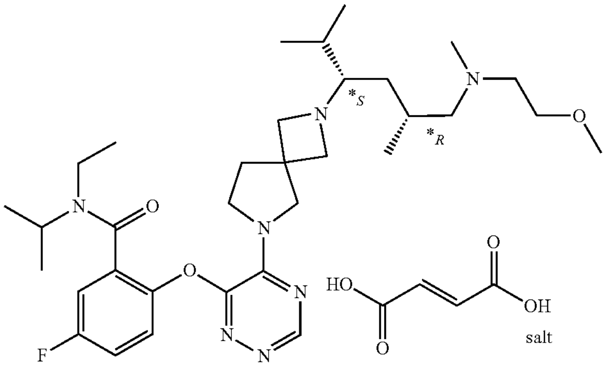 salt | Compound 237, fumaric acid | LC-MS (ESI) (Method 3): $R_t$ = 5.194 min, m/z found 614.4 $[M + H]^+$. SFC (Method 4): $R_t$ = 1.347 min. |
| 242 | 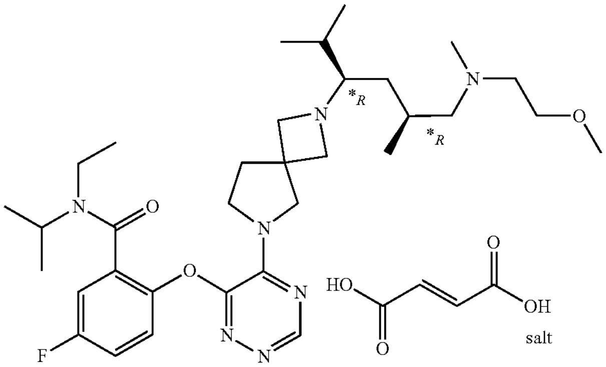 salt | Compound 238, fumaric acid | LC-MS (ESI) (Method 3): $R_t$ = 5.284 min, m/z found 614.4 $[M + H]^+$. SFC (Method 14): $R_t$ = 2.358 min. |

-continued

| Co. No. | Structure | Starting Materials | Spectra Details |
|---|---|---|---|
| 243 | 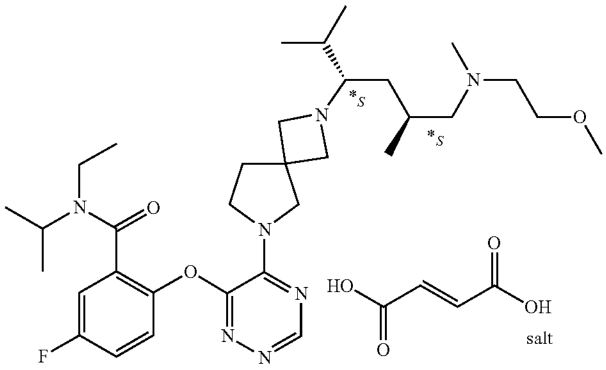 | Compound 239, fumaric acid | LC-MS (ESI) (Method 3): $R_t$ = 5.244 min, m/z found 614.4 $[M + H]^+$. SFC (Method 14): $R_t$ = 2.450 min. |
| 245 | 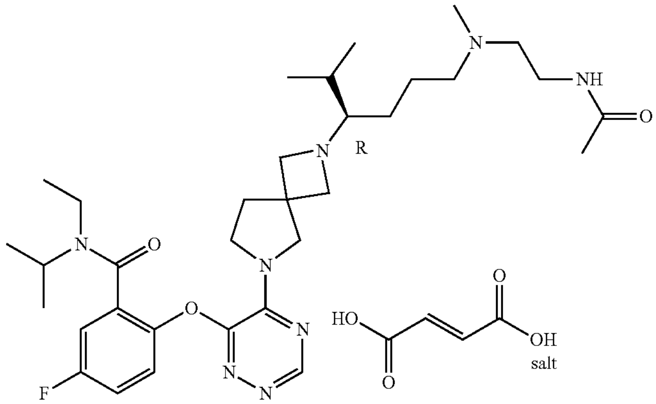 | Compound 244, fumaric acid | $^1H$ NMR (400 MHz, Methanol-$d_4$): δ = 8.51 (brs, 1H), 7.56-7.16 (m, 3H), 6.74 (s, 4H), 4.57-3.67 (m, 9H), 3.63-3.40 (m, 3H), 3.30-3.08 (m, 6H), 2.87 (s, 3H), 2.48-2.28 (m, 2H), 2.20-2.07 (m, 1H), 1.98 (s, 3H), 1.92-1.79 (m, 2H), 1.76-1.52 (m, 2H), 1.26-0.94 (m, 13H), 0.89-0.74 (m, 2H). LC-MS (ESI) (Method 1): $R_t$ = 2.916 min, m/z found 627.4 $[M + H]^+$. SFC (Method 25): $R_t$ = 1.707 min. |
| 256 | 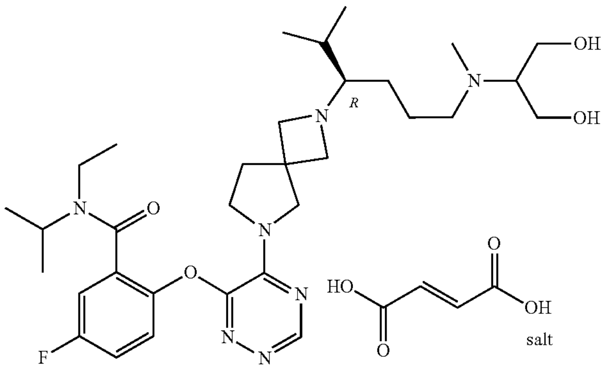 | Compound 255, fumaric acid | LC-MS (ESI) (Method 1): $R_t$ = 2.932 min, m/z found 616.3 $[M + H]^+$. SFC (Method 6): $R_t$ = 1.383 min. |

-continued
| Co. No. | Structure | Starting Materials | Spectra Details |
|---|---|---|---|
| 265 | 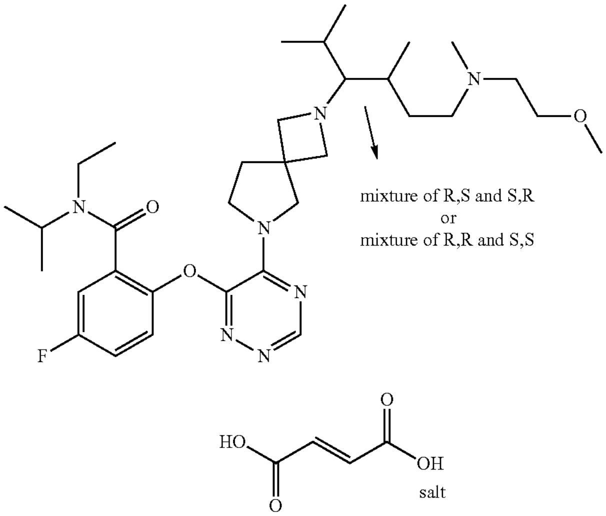 [SMILES: CCN(C(=O)c1cc(F)ccc1Oc1nncnc1N1CCC2(C1)CN(C(C(C)C)C(C)CCN(C)CCOC)C2)C(C)C ; O=C(O)/C=C/C(=O)O] mixture of R,S and S,R or mixture of R,R and S,S salt | Compound 263, fumaric acid | LC-MS (ESI) (Method 2): $R_t$ = 2.043 min, m/z found 614.3 $[M + H]^+$. |
| 266 | 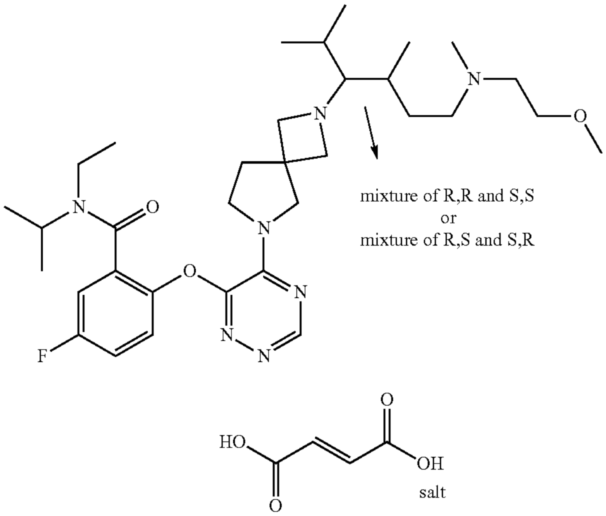 [SMILES: CCN(C(=O)c1cc(F)ccc1Oc1nncnc1N1CCC2(C1)CN(C(C(C)C)C(C)CCN(C)CCOC)C2)C(C)C ; O=C(O)/C=C/C(=O)O] mixture of R,R and S,S or mixture of R,S and S,R salt | Compound 264, fumaric acid | LC-MS (ESI) (Method 2): $R_t$ = 1.988 min, m/z found 614.5 $[M + H]^+$. |
| 268 | 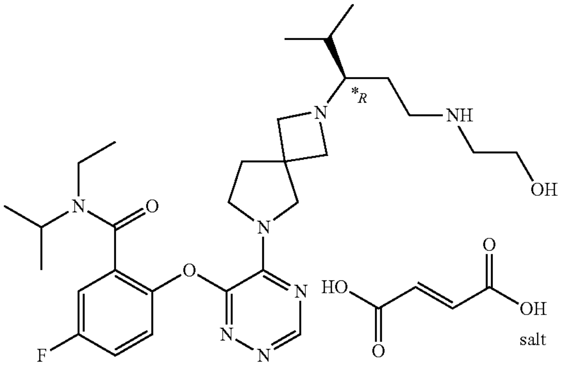 salt | Compound 267, fumaric acid | LC-MS (ESI) (Method 5): $R_t$ = 1.45 min, m/z found 558.2 $[M + H]^+$. |

-continued
| Co. No. | Structure | Starting Materials | Spectra Details |
|---|---|---|---|
| 270 | 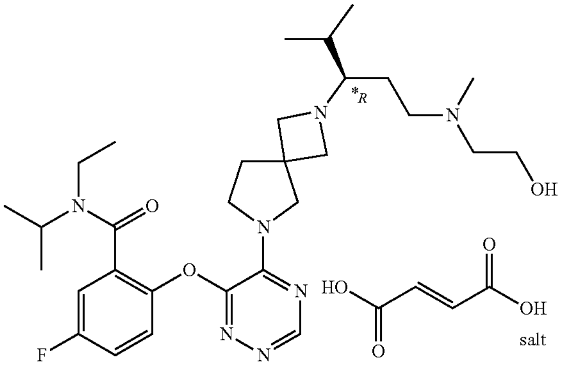 | Compound 269, fumaric acid | LC-MS (ESI) (Method 5): $R_t$ = 1.49 min, m/z found 572.3 $[M + H]^+$. |
| 278 | 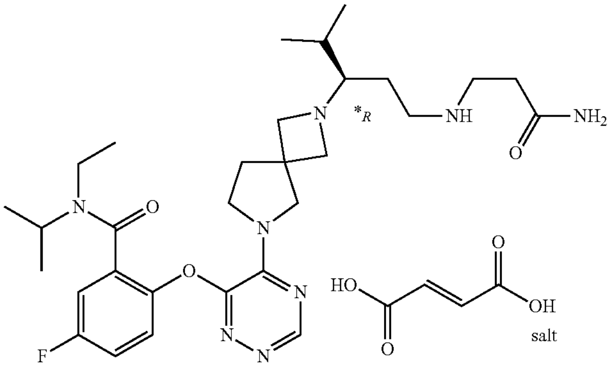 | Compound 277, fumaric acid | LC-MS (ESI) (Method 5): $R_t$ = 1.54 min, m/z found 585.2 $[M + H]^+$. |
| 280 | 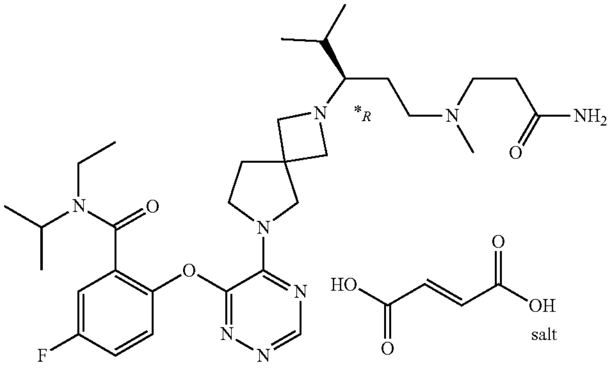 | Compound 279, fumaric acid | LC-MS (ESI) (Method 5): $R_t$ = 1.54 min, m/z found 599.3 $[M + H]^+$. |
| 283 | 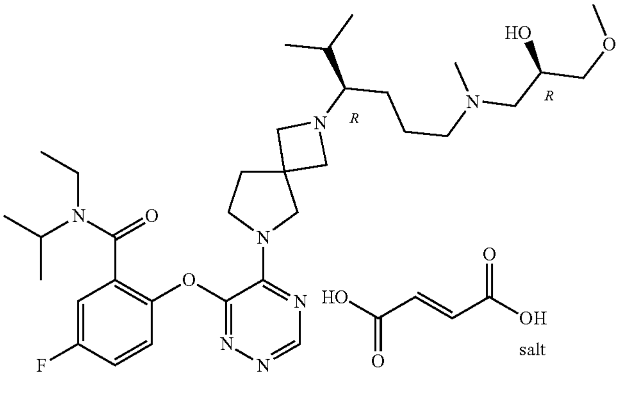 | Compound 282, fumaric acid | LC-MS (ESI) (Method 1): $R_t$ = 2.605 min, m/z found 630.3 $[M + H]^+$. SFC (Method 6): $R_t$ = 1.303 min. |

-continued

| Co. No. | Structure | Starting Materials | Spectra Details |
|---|---|---|---|
| 259 | 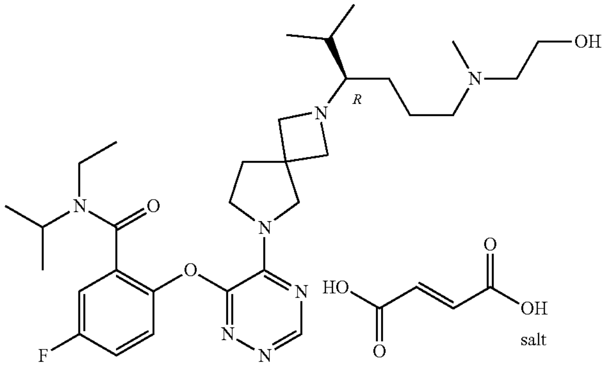 | Compound 286, fumaric acid | LC-MS (ESI) (Method 1): $R_t$ = 2.900 min, m/z found 586.6 $[M + H]^+$. SFC (Method 6): $R_t$ = 1.301 min. |
| 104 | 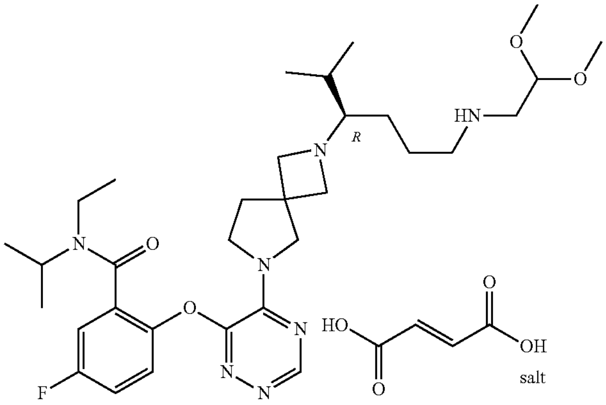 | Compound 287, fumaric acid | $^1H$ NMR (400 MHz, Methanol-$d_4$): δ = 8.45 (s, 1H), 7.50-7.09 (m, 3H), 6.67 (s, 4H), 4.48-3.60 (m, 10H), 3.45 (s, 6H), 3.23-2.87 (m, 6H), 2.44-2.18 (m, 2H), 2.16-1.96 (m, 1H), 1.89-1.50 (m, 4H), 1.29-0.91 (m, 14H), 0.87-0.70 (m, 2H). LC-MS (ESI) (Method 1): $R_t$ = 3.025 min, m/z found 616.3 $[M + H]^+$. SFC (Method 6): $R_t$ = 1.305 min. |
| 229 | 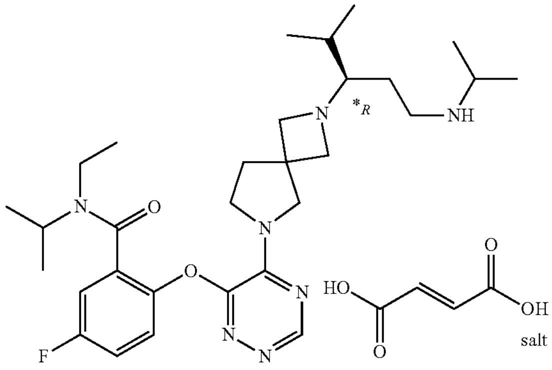 | Compound 228, fumaric acid | LC-MS (ESI) (Method 6): $R_t$ = 2.95 min, m/z found 556.3 $[M + H]^+$. |
| 300 | 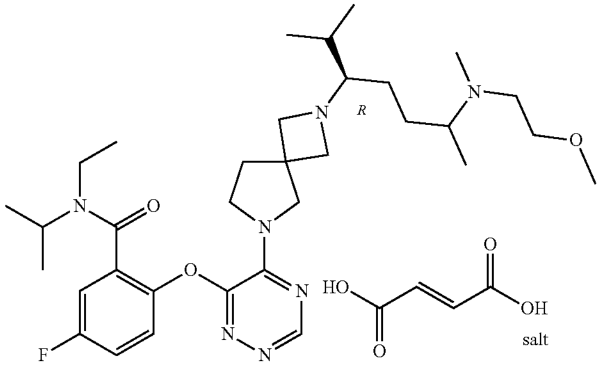 | Compound 299, fumaric acid | LC-MS (ESI) (Method 2): $R_t$ = 2.017 min, m/z found 614.4 $[M + H]^+$. Chiral HPLC (Method 8): $R_t$ = 5.212 min. |

-continued

| Co. No. | Structure | Starting Materials | Spectra Details |
|---|---|---|---|
| 302 | 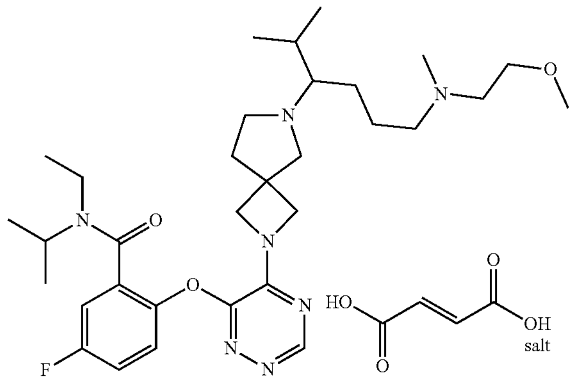 | Compound 301, fumaric acid | LC-MS (ESI) (Method 2): $R_t$ = 2.021 min, m/z found 600.7 $[M + H]^+$. |
| 314 | 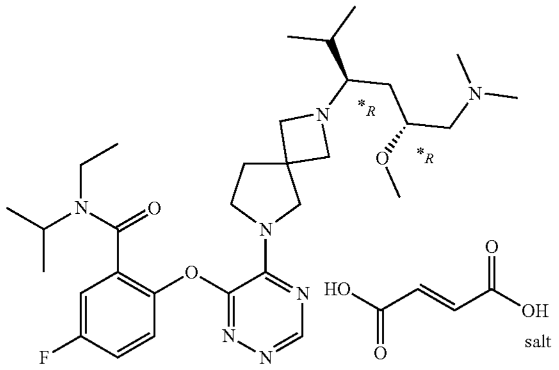 | Compound 310, fumaric acid | LC-MS (ESI) (Method 3): $R_t$ = 4.900 min, m/z found 586.3 $[M + H]^+$. SFC (Method 11): $R_t$ = 4.457 min. |
| 315 | 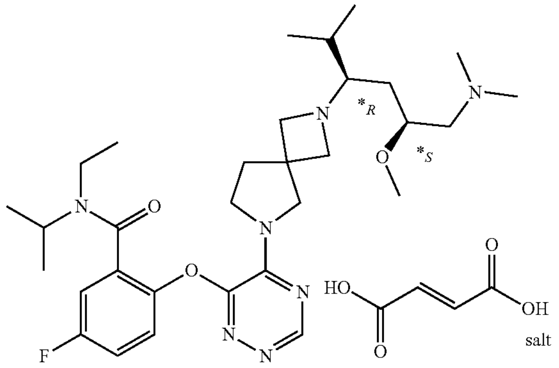 | Compound 312, fumaric acid | LC-MS (ESI) (Method 3): $R_t$ = 4.966 min, m/z found 586.3 $[M + H]^+$. SFC (Method 11): $R_t$ = 4.273 min. |
| 323 | 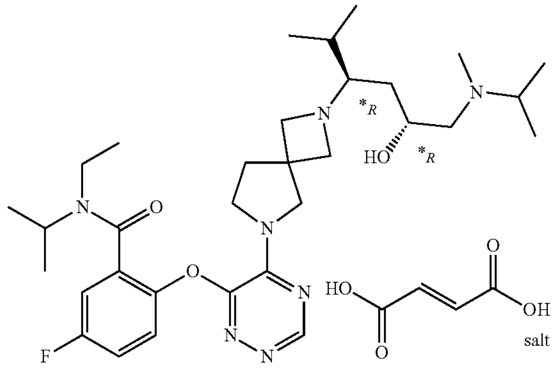 | Compound 319, fumaric acid | LC-MS (ESI) (Method 2): $R_t$ = 2.006 min, m/z found 600.3 $[M + H]^+$. SFC (Method 27): $R_t$ = 2.598 min. |

-continued

| Co. No. | Structure | Starting Materials | Spectra Details |
| --- | --- | --- | --- |
| 324 | 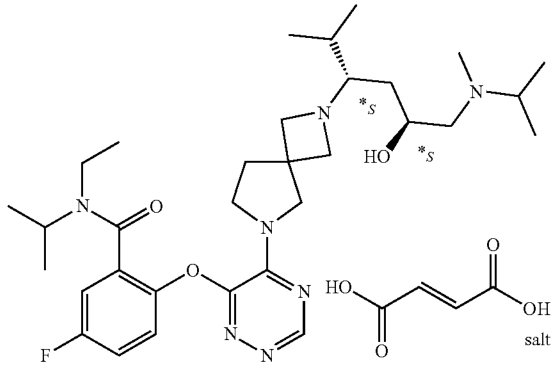 | Compound 320, fumaric acid | LC-MS (ESI) (Method 2): $R_t$ = 2.012 min, mz found 600.4 $[M + H]^+$. SFC (Method 27): $R_t$ = 4.487 min. |
| 325 | 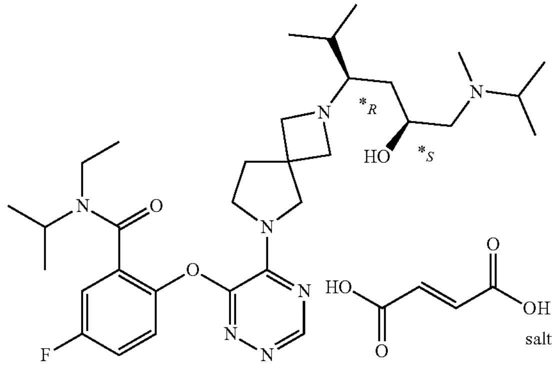 | Compound 321, fumaric acid | LC-MS (ESI) (Method 2): $R_t$ = 2.012 min, m/z found 600.3 $[M + H]^+$. SFC (Method 28): $R_t$ = 2.196 min. |
| 326 | 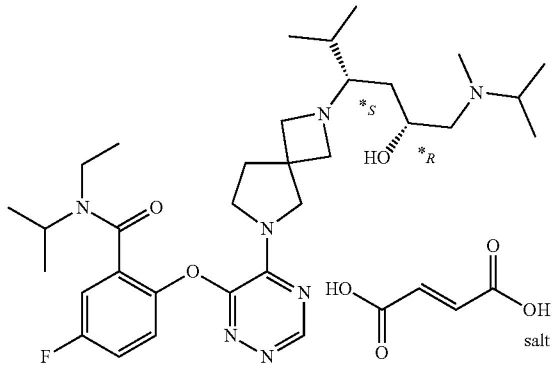 | Compound 322, fumaric acid | LC-MS (ESI) (Method 1): $R_t$ = 3.045 min, m/z found 600.3 $[M + H]^+$. SFC (Method 28): $R_t$ = 2.677 min. |
| 334 | 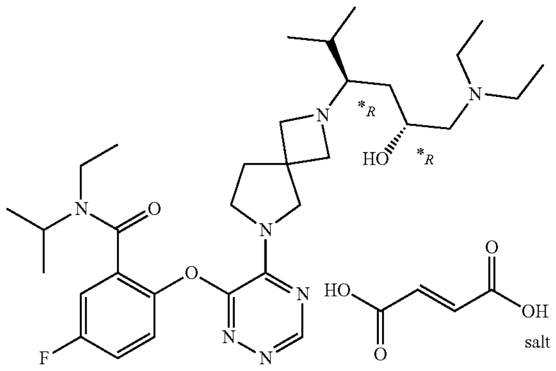 | Compound 330, fumaric acid | LC-MS (ESI) (Method 2): $R_t$ = 2.023 min, m/z found 600.3 $[M + H]^+$. Chiral HPLC (Method 9): $R_t$ = 4.014 min. |

-continued

| Co. No. | Structure | Starting Materials | Spectra Details |
|---|---|---|---|
| 335 | 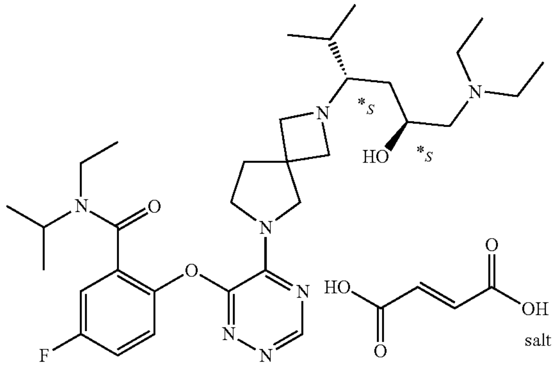 | Compound 331, fumaric acid | LC-MS (ESI) (Method 2): $R_t$ = 2.028 min, m/z found 600.3 [M + H]$^+$. Chiral HPLC (Method 9): $R_t$ = 4.265 min. |
| 336 | 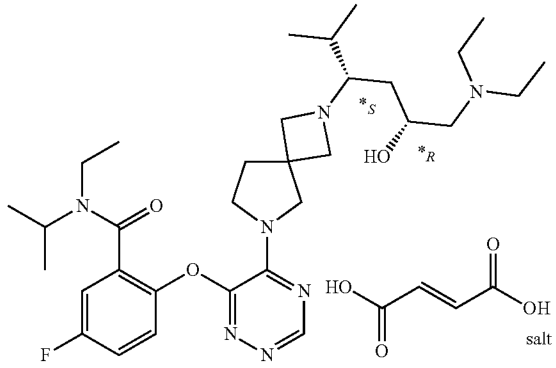 | Compound 332, fumaric acid | LC-MS (ESI) (Method 2): $R_t$ = 1.967 min, m/z found 600.3 [M + H]$^+$. SFC (Method 29): $R_t$ = 4.190 min. |
| 337 | 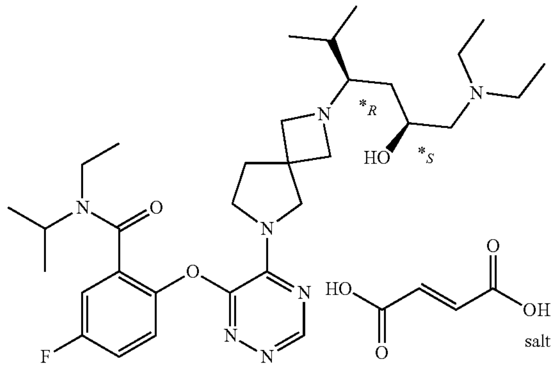 | Compound 333, fumaric acid | LC-MS (ESI) (Method 2): $R_t$ = 1.973 min, m/z found 600.3 [M + H]$^+$. SFC (Method 29): $R_t$ = 4.444 min. |
| 342 | 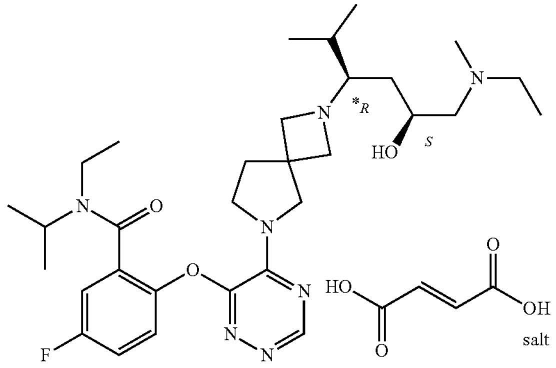 | Compound 340, fumaric acid | LC-MS (ESI) (Method 1): $R_t$ = 2.934 min, m/z found 586.5 [M + H]$^+$. SFC (Method 6): $R_t$ = 1.326 min. |

-continued

| Co. No. | Structure | Starting Materials | Spectra Details |
|---|---|---|---|
| 343 | 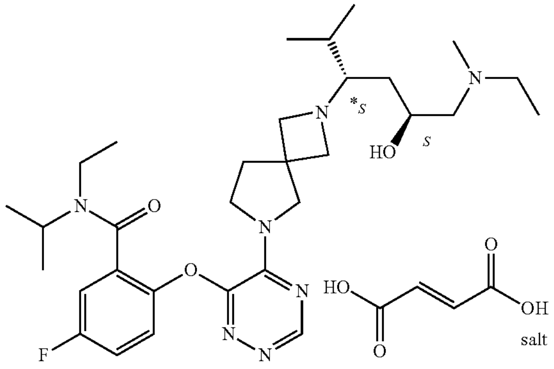 | Compound 341, fumaric acid | LC-MS (ESI) (Method 1): $R_t$ = 2.976 min, m/z found 586.5 $[M + H]^+$. SFC (Method 6): $R_t$ = 1.285 min. |
| 346 | 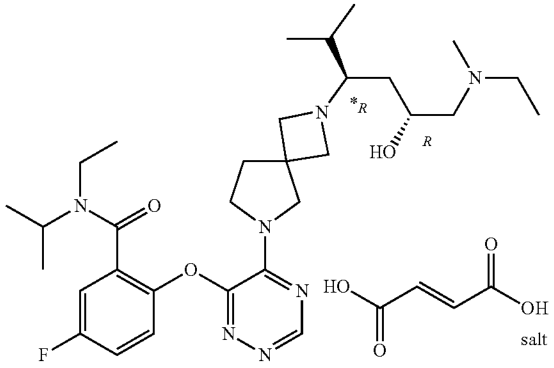 | Compound 344, fumaric acid | $^1H$ NMR (400 MHz, Methanol-$d_4$): δ = 8.47 (s, 1H), 7.53-7.16 (m, 3H), 6.68 (s, 4H), 4.49-3.65 (m, 10H), 3.42 (brs, 2H), 3.28-2.99 (m, 5H), 2.88 (s, 3H), 2.34 (brs, 2H), 2.23-2.11 (m, 1H), 1.85-1.63 (m, 2H), 1.40-0.74 (m, 18H). LC-MS (ESI) (Method 1): $R_t$ = 2.968 min, m/z found 586.3 $[M + H]^+$. SFC (Method 8): $R_t$ = 2.265 min. |
| 352 | 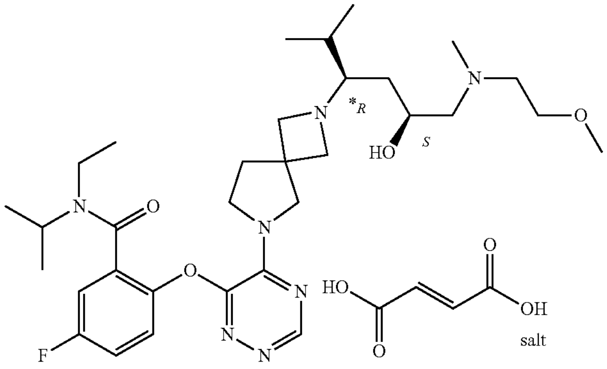 | Compound 350, fumaric acid | LC-MS (ESI) (Method 1): $R_t$ = 3.010 min, m/z found 616.3 $[M + H]^+$. SFC (Method 6): $R_t$ = 1.235 min. |
| 353 | 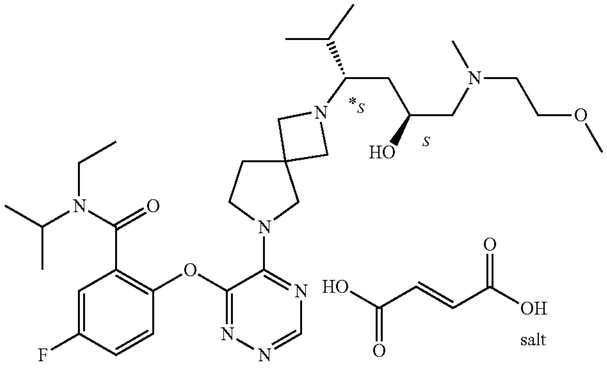 | Compound 351, fumaric acid | LC-MS (ESI) (Method 1): $R_t$ = 2.967 min, m/z found 616.3 $[M + H]^+$. SFC (Method 6): $R_t$ = 1.261 min. |

-continued

| Co. No. | Structure | Starting Materials | Spectra Details |
|---|---|---|---|
| 356 | 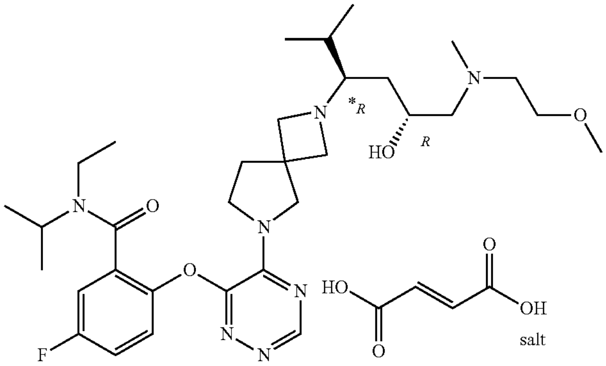 | Compound 354, fumaric acid | LC-MS (ESI) (Method 1): $R_t$ = 2.959 min, m/z found 616.4 $[M + H]^+$. SFC (Method 28): $R_t$ = 2.014 min. |
| 357 | 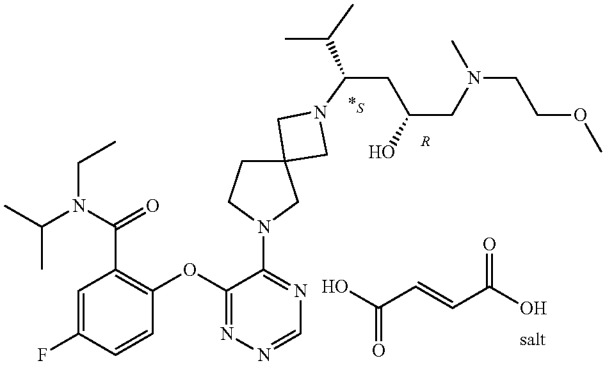 | Compound 355, fumaric acid | LC-MS (ESI) (Method 1): $R_t$ = 2.906 min, m/z found 616.3 $[M + H]^+$. SFC (Method 28): $R_t$ = 2.973 min. |
| 365 | 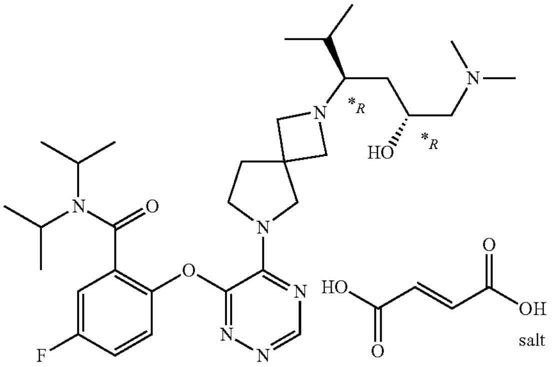 | Compound 363, fumaric acid | LC-MS (ESI) (Method 1): $R_t$ = 3.150 min, m/z found 586.3 $[M + H]^+$. SFC (Method 30): $R_t$ = 2.491 min. |
| 366 | 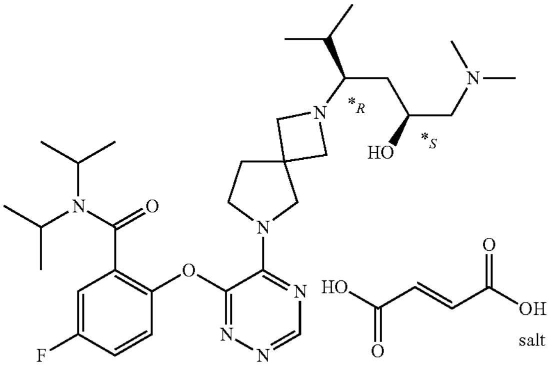 | Compound 364, fumaric acid | LC-MS (ESI) (Method 1): $R_t$ = 3.093 min, m/z found 586.3 $[M + H]^+$. SFC (Method 30): $R_t$ = 3.517 min. |

-continued

| Co. No. | Structure | Starting Materials | Spectra Details |
|---|---|---|---|
| 369 | 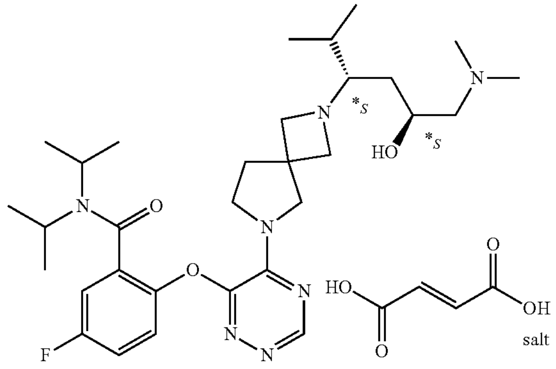 | Compound 367, fumaric acid | LC-MS (ESI) (Method 1): $R_t$ = 3.170 min, m/z found 586.3 $[M + H]^+$. SFC (Method 31): $R_t$ = 1.863 min. |
| 370 | 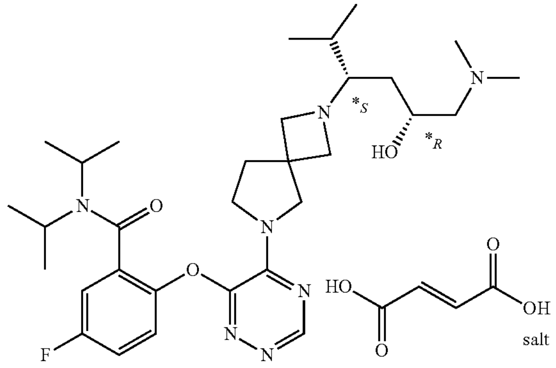 | Compound 368, fumaric acid | LC-MS (ESI) (Method 1): $R_t$ = 3.137 min, m/z found 586.3 $[M + H]^+$. SFC (Method 31): $R_t$ = 2.165 min. |
| 377 | 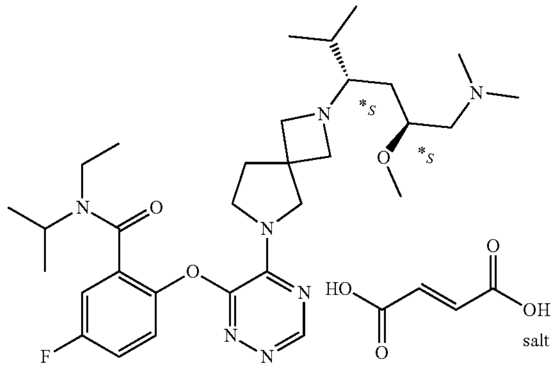 | Compound 375, fumaric acid | LC-MS (ESI) (Method 2): $R_t$ = 1.997 min, m/z found 586.3 $[M + H]^+$. SFC (Method 11): $R_t$ = 4.749 min. |
| 378 | 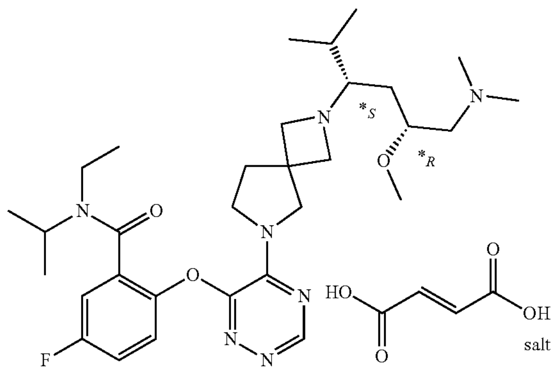 | Compound 376, fumaric acid | LC-MS (ESI) (Method 3): $R_t$ = 4.923 min, m/z found 586.3 $[M + H]^+$. SFC (Method 11): $R_t$ = 4.663 min. |

-continued

| Co. No. | Structure | Starting Materials | Spectra Details |
|---|---|---|---|
| 382 | 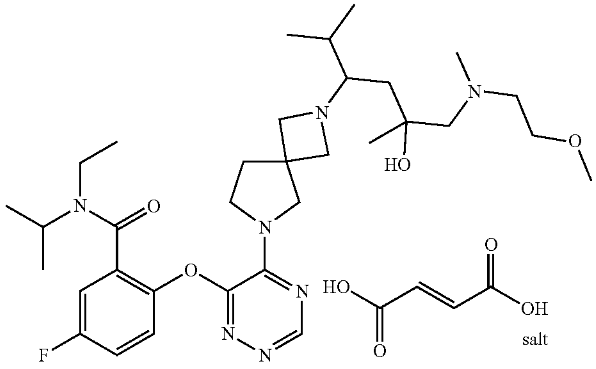 | Compound 381, fumaric acid | LC-MS (ESI) (Method 2): $R_t$ = 2.019/2.055 min, m/z found 630.5 $[M + H]^+$. |
| 386 | 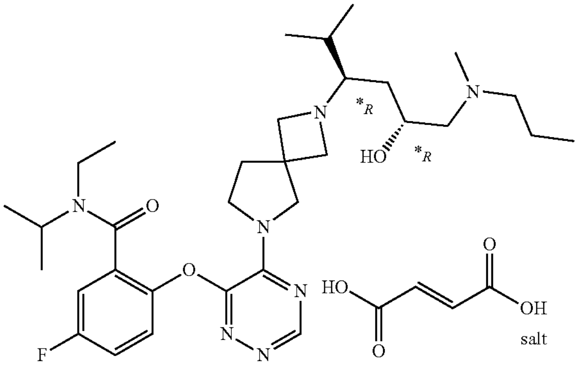 | Compound 384, fumaric acid | LC-MS (ESI) (Method 2): $R_t$ = 2.062 min, m/z found 600.3 $[M + H]^+$. SFC (Method 27): $R_t$ = 2.111 min. |
| 387 | 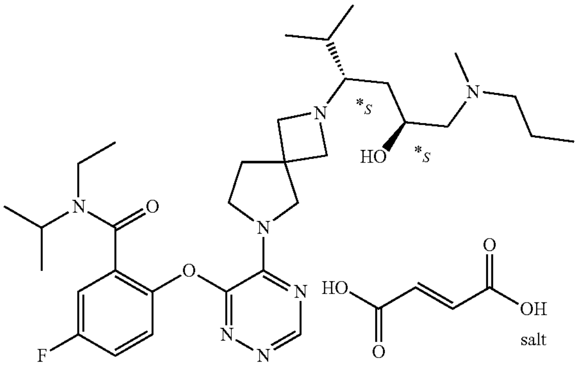 | Compound 385, fumaric acid | LC-MS (ESI) (Method 2): $R_t$ = 2.059 min, m/z found 600.3 $[M + H]^+$. SFC (Method 27): $R_t$ = 3.466 min. |
| 391 | 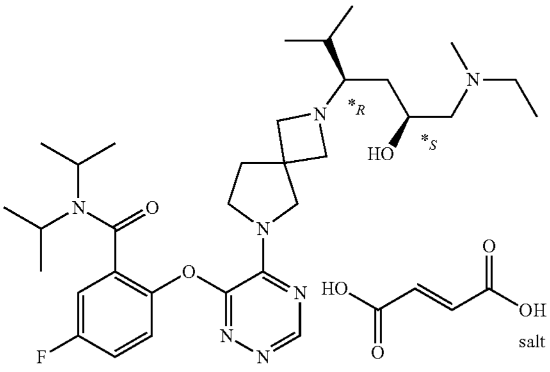 | Compound 389, fumaric acid | LC-MS (ESI) (Method 2): $R_t$ = 2.159 min, m/z found 600.3 $[M + H]^+$. Chiral HPLC (Method 9): $R_t$ = 3.862 min. |

-continued
| Co. No. | Structure | Starting Materials | Spectra Details |
|---|---|---|---|
| 392 | 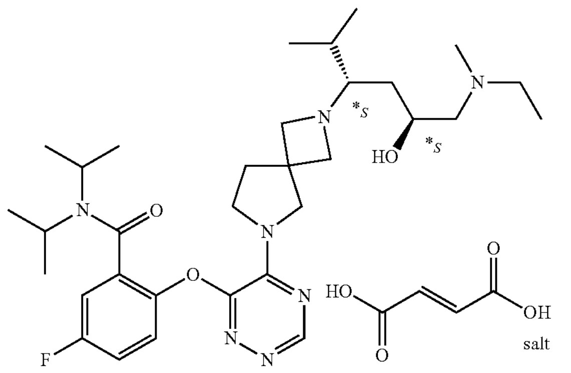 | Compound 390, fumaric acid | LC-MS (ESI) (Method 2): $R_t$ = 2.119 min, m/z found 600.3 $[M + H]^+$. SFC (Method 27): $R_t$ = 2.386 min. |
| 394 | 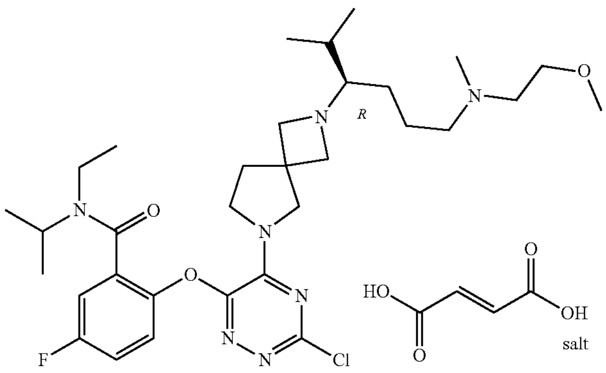 | Compound 393, fumaric acid | LC-MS (ESI) (Method 2): $R_t$ = 2.442 min, m/z found 634.3 $[M + H]^+$. SFC (Method 6): $R_t$ = 1.232 min. |
| 397 | 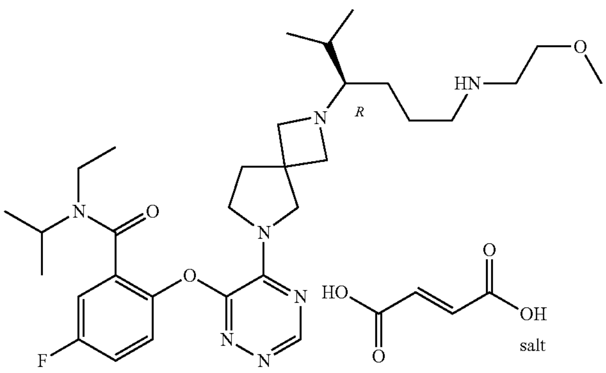 | Compound 11, fumaric acid | LC-MS (ESI) (Method 5): $R_t$ = 1.661 min, m/z found 586.2 $[M + H]^+$. |

Compound 6

(R)-2-((5(2-(6-acetamido-2-methylhexan-3-yl)-2,6-diazaspiro[3.4]octan-6-yl)-1,2,4-triazin-6-yl)oxy)-N-ethyl-5-fluoro-N-isopropylbenzamide formate

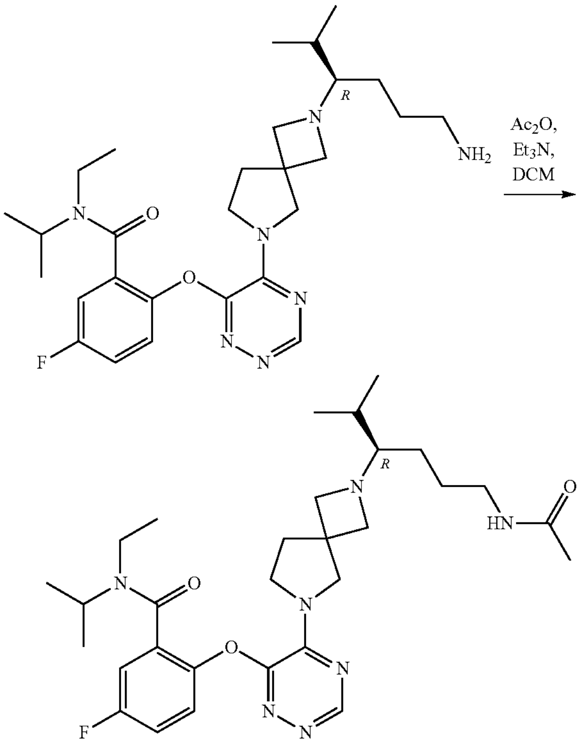

formate salt

To the solution of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide formate (Compound 1) (30 mg, 0.057 mmol) and TEA (60 uL, 0.43 mmol) in DCM (1 mL) cooled at 0° C. was added $Ac_2O$ (20 uL, 0.21 mmol), the resulting mixture was stirred at RT under $N_2$ atmosphere for 0.5 h. The reaction mixture was concentrated under reduced pressure and the residue was purified by preparative HPLC using a Welch Xtimate (column: C18 150×25 mm Sum; eluent: ACN/$H_2O$ (0.225% FA) from 30% to 50% (v/v)) to afford the title compound (3.31 mg, 9% yield) as a white solid.

LC-MS (ESI) (Method 5): $R_t$=0.633 min, m/z found 570.4 $[M+H]^+$.

SFC (Method 5): $R_t$=1.191 min.

Compound 7, 29, 34

(S)-2-((5-(2-(6-acetamido-2-methylhexan-3-yl)-2,6-diazaspiro[3.4]octan-6-yl)-1,2,4-triazin-6-yl)oxy)-N-ethyl-5-fluoro-N-isopropylbenzamide 2-((5(2-(1-acetamido-4-methylpentan-3-yl)-2,6-diazaspiro[3.4]octan-yl)-1,2,4-triazin-6-yl)oxy)-N-ethyl-5-fluoro-N-isopropylbenzamide (S)-2-((5-(2-(6-acetamido-2-methylhexan-3-yl)-2,6-diazaspiro[3.4]octan-6-yl)-1,2,4-triazin-6-yl)oxy)-N-ethyl-5-fluoro-N-isopropylbenzamide The following Compounds were synthesized by an analogous method described above for Compound 6

| Co. No. | Structure | Starting Materials | Conditions | Spectra Details |
|---|---|---|---|---|
| 7 | 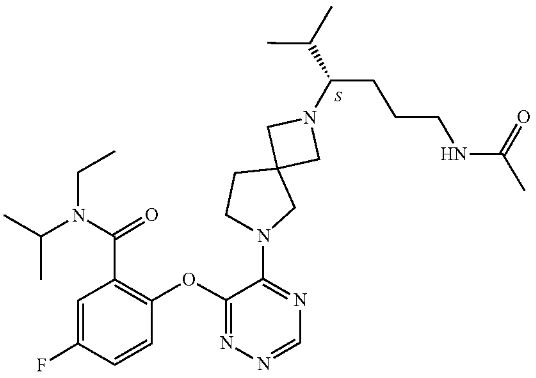 | Compound 2 | $AC_2O$, TEA, DCM | LC-MS (ESI) (Method 5): $R_t$ = 0.646 min, m/z found 570.3 $[M + H]^+$. SFC (Method 5): $R_t$ = 1.657 min. |

-continued

| Co. No. | Structure | Starting Materials | Conditions | Spectra Details |
|---|---|---|---|---|
| 29 | 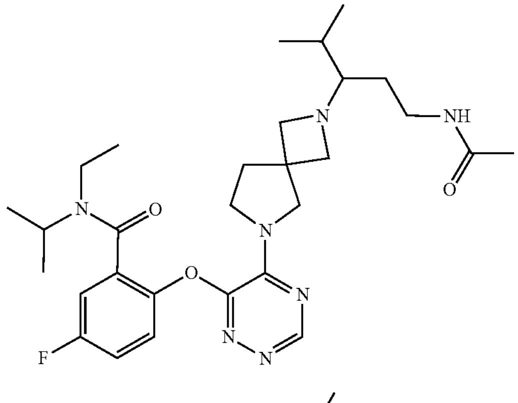 | Compound 26 | $Ac_2O$, TEA, DCM | LC-MS (ESI) (Method 1): $R_t$ = 3.250 min, m/z found 556.4 $[M + H]^+$. |
| 34 | 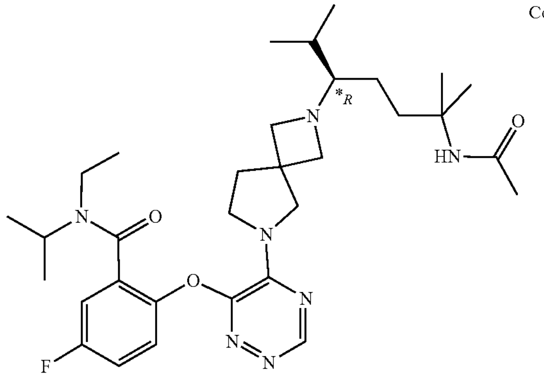 | Compound 30 | AcCl, TEA, DCM | LC-MS (ESI) (Method 3): $R_t$ = 4.573 min, m/z found 598.3 $[M + H]^+$. |

Compound 8

(R)-N-ethyl-5-fluoro-N-isopropyl-2-((5-(2-(2-methyl-6-(3-methylureido)hexan-3-yl)-2,6-diazaspiro[3.4]octan-6-yl)-1,2,4-triazin-6-yl)oxy)benzamide

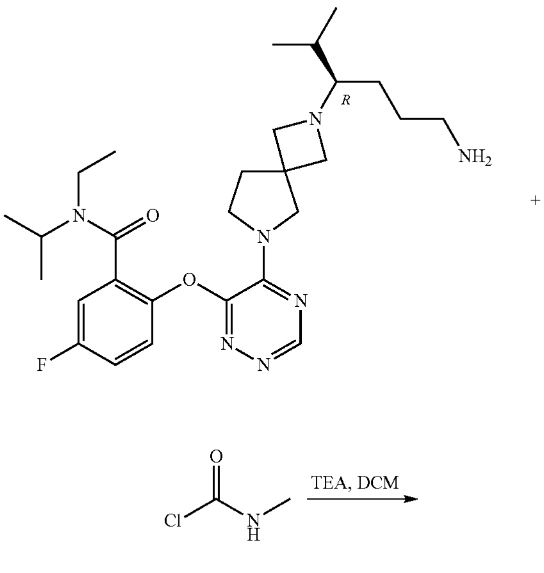

-continued

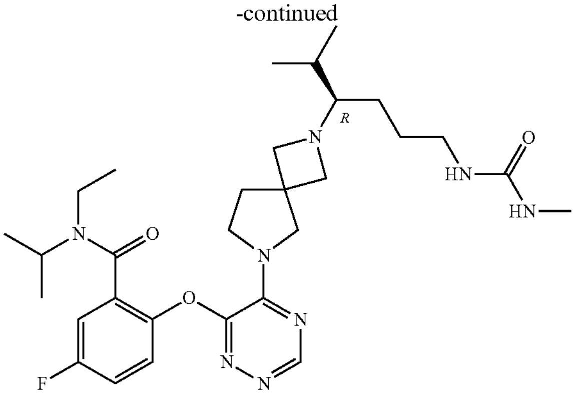

To the solution of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide formate (Compound 1) (70 mg, 0.12 mmol) and TEA (0.35 mL, 2.5 mmol) in DCM (10 mL) cooled at 0° C. was added methylcarbamic chloride (18 mg, 0.19 mmol) and the resulting mixture was stirred for 2 h at 0° C. The reaction mixture was concentrated under reduced pressure and the residue was purified by preparative HPLC over Phenomenex Gemini-NX (column: 150×30 mm 5 um; eluent: $ACN/H_2O$ (0.04% ammonia+10 mM $NH_4HCO_3$) from 35% to 65%, v/v) to afford the title compound (50 mg, 70% yield) as a white solid.

LC-MS (ESI) (method 1): $R_t$=3.34 min, m/z found 585.3 $[M+H]^+$.

SFC (Method 6): $R_t$=2.222 min.

Compound 9

(S)—N-ethyl-5-fluoro-N-isopropyl-2-((5-(2-(2-methyl-6-(3-methylureido)hexan-3-yl)-2,6-diazaspiro[3.4]octan-6-yl)-1,2,4-triazin-6-yl)oxy)benzamide The following Compound was synthesized by an analogous method described above for Compound 8

| Co. No. | Structure | Starting Materials | Spectra Details |
|---|---|---|---|
| 9 | 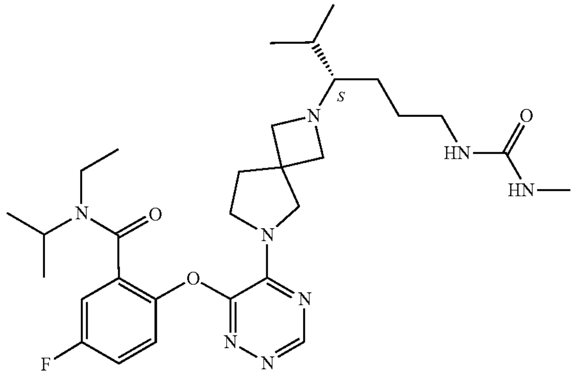 | Compound 2 | LC-MS (ESI) (method 1): Rt = 3.38 min, m/z found 585.3 $[M + H]^+$. SFC (Method 6): Rt = 2.418 min. |

Compound 10 methyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate

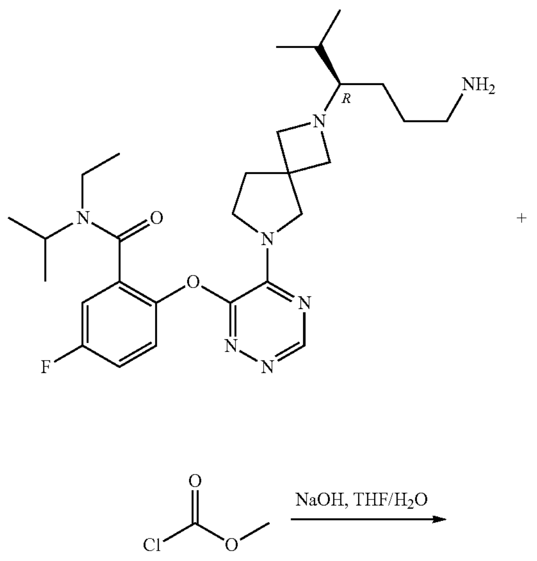

-continued

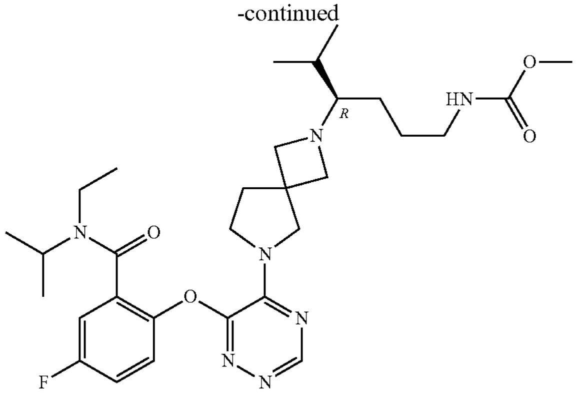

To the mixture of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide hydrochloride (Compound 65) (0.100 g, crude) in $THF/H_2O$ (2 mL/2 mL) cooled at 0° C. were added 2 M NaOH (0.15 mL, 0.30 mmol) and methyl carbonochloridate (0.030 g, 0.317 mmol, in 0.1 mL DCM). The resulting mixture was stirred at 0° C. for 0.5 h. The mixture was diluted with water (10 mL) and sat. aq. $NaHCO_3$ (15 mL), further extracted with EtOAc (15 mL×3). The combined organic layers were dried over ($Na_2SO_4$), filtered and evaporated in vacuo to give the crude product, which was further purified by preparative HPLC using Phenomenex Gemini NX (column: C18 75×30 mm 3 um; eluent: $ACN/H_2O$ (0.05% ammonia+10 mM $NH_4HCO_3$) 35% to 65% (v/v)) to afford the title compound (11.53 mg) as sticky oil.

LC-MS (ESI) (Method 1): $R_t$=3.283 min, m/z found 586.3 $[M+H]^+$.

Compound 22 methyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate The following Compound was synthesized by an analogous method described above for Compound 10

| Co. No. | Structure | Starting Materials | Spectra Details |
|---|---|---|---|
| 22 | 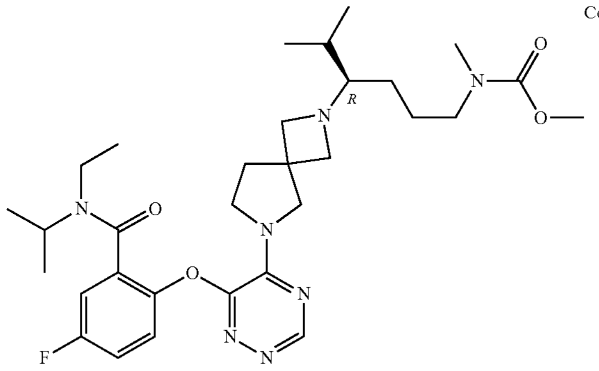 | Compound 19 | LC-MS (ESI) (Method 2): Rt = 2.472 min, m/z found 600.3 $[M + H]^+$. |

Compound 11

(R)-N-ethyl-5-fluoro-N-isopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide

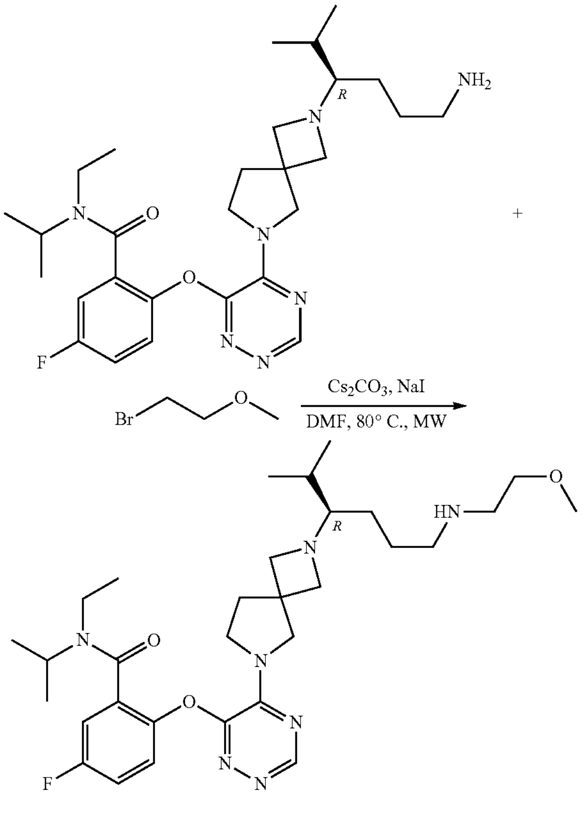

The mixture of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide (Compound 64) (120 mg, crude), 1-bromo-2-methoxyethane (32 mg, 0.23 mmol), $Cs_2CO_3$ (222 mg, 0.681 mmol), NaI (102 mg, 0.680 mmol) in DMF (1 mL) was stirred at 80° C. via microwave irradiation for 1 h. After cooling to RT, the mixture was diluted with $H_2O$ (10 mL) and extracted with EtOAc (3×10 mL). The combined organic layers were washed with $H_2O$ (10 mL), dried over $Na_2SO_4$, filtered and concentrated under reduced pressure to afford the crude product which was further purified by HPLC over a Phenomenex Gemini-NX (column: 150×30 mm 5 μm; eluent: ACN/$H_2O$ (10 mM $NH_4HCO_3$) from 51% to 71% (v/v)) and further purified by SFC over DAICEL CHIRALCEL OD-H (column: 250×30 mm 5 um; eluent: supercritical $CO_2$ in EtOH (0.1% v/v ammonia) 25/25, v/v) to afford the title compound (5.13 mg, 96% purity) as yellow solid.

LC-MS (ESI) (Method 1): $R_t$=2.997 min, m/z found 586.3 $[M+H]^+$.

Compound 28, 90, 93, 287, 149, 226, 257, 228

(S)—N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)benzamide (R)-2-((5-(2-(6-(bis(2-methoxyethyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide formate 5-fluoro-N,N-diisopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)benzamide formate (R)-2-((5-(2-(6-((2,2-dimethoxyethyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (R)-2-((5-(2-(6-((2,2-dimethoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (*R)—N-ethyl-5-fluoro-N-isopropyl-2-((5-(2-(1-((2-methoxyethyl)amino)-4-methylpentan-3-yl)-2,6-diazaspiro[3.4]octan-6-yl)-1,2,4-triazin-6-yl)oxy)benzamide (R)-2-((5-(2-(6-((2-ethoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropyl-benzamide (*R)—N-ethyl-5-fluoro-N-isopropyl-2-((5-(2-(1-(isopropylamino)-4-methylpentan-3-yl)-2,6-diazaspiro[3.4]octan-6-yl)-1,2,4-triazin-6-yl)oxy)benzamide The following Compounds were synthesized by an analogous method described above for Compound 11

| Co. No. | Structure | Starting Materials | Conditions | Spectra Details |
|---|---|---|---|---|
| 28 | 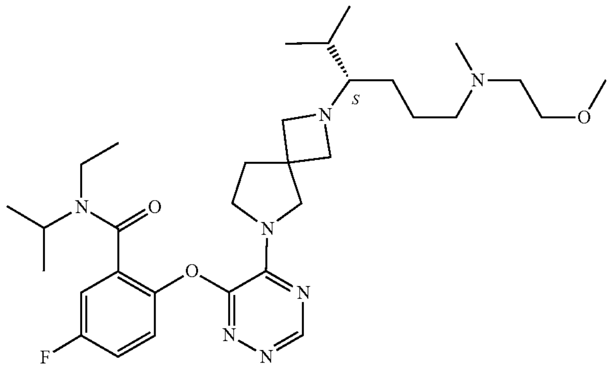 | Compound 20, 1-bromo-2-methoxyethane | $K_2CO_3$, NaI, DMF, 50° C. | LC-MS (ESI) (Method 2): $R_t$ = 2.047 min, m/z found 600.3 $[M + H]^+$. SFC (Method 11): $R_t$ = 5.404 min |
| 90 | 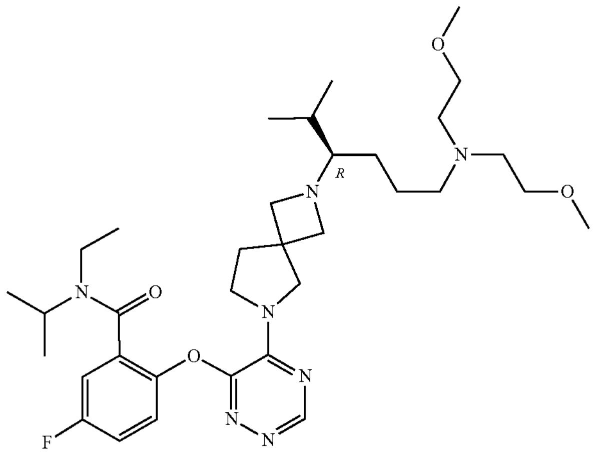 formate salt | Compound 1, 1-bromo-2-methoxyethane | $Cs_2CO_3$, DMF, 80° C., microwave | LC-MS (ESI) (Method 2): $R_t$ = 2.105 min, m/z found 644.4 $[M + H]^+$. SFC (Method 15): $R_t$ = 1.105 min. |

-continued
| Co. No. | Structure | Starting Materials | Conditions | Spectra Details |
|---|---|---|---|---|
| 93 | 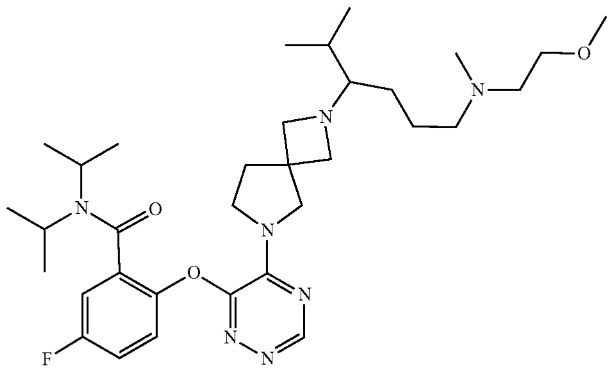 formate salt | Compound 92, 1-bromo-2-methoxyethane | $K_2CO_3$, NaI, DMF, 50° C. | |
| 287 | 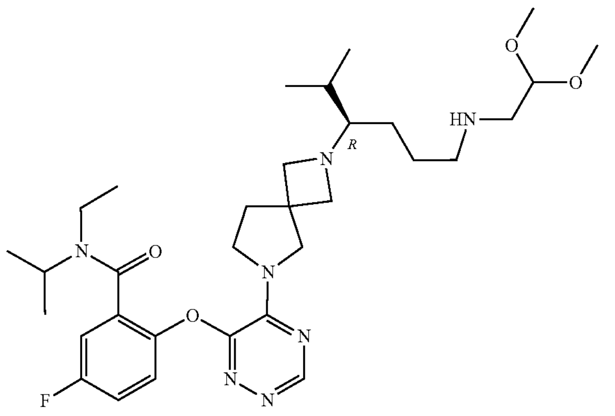 | Compound 1, 2-bromo-l,1-dimethoxy-ethane | $K_2CO_3$, NaI, DMF, 70° C. | |
| 149 | 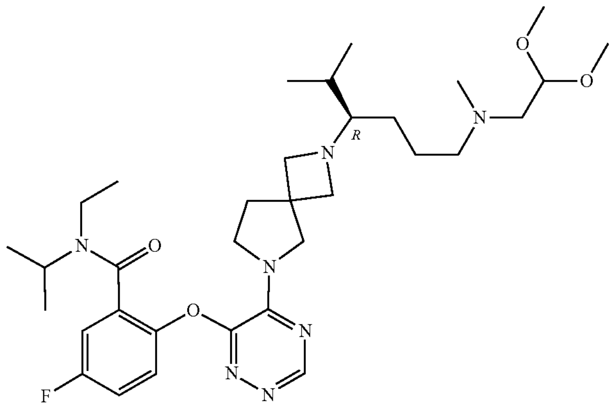 | Compound 19, 2-bromo-l,1-dimethoxy-ethane | $K_2CO_3$, KI, DMF, 80° C. | |
| 226 | 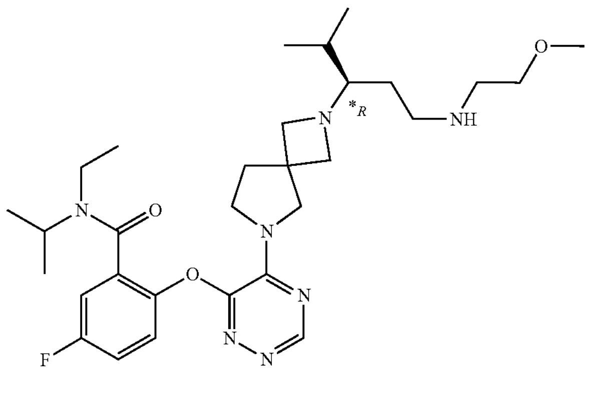 [SMILES: CCN(C(=O)c1cc(F)ccc1Oc1nncnc1N1CCC2(C1)CN([C@H](CCNCCOC)C(C)C)C2)C(C)C] | Compound 218, 1-bromo-2-methoxyethane | DIEA, ACN, 50° C. | |

-continued

| Co. No. | Structure | Starting Materials | Conditions | Spectra Details |
|---|---|---|---|---|
| 257 | 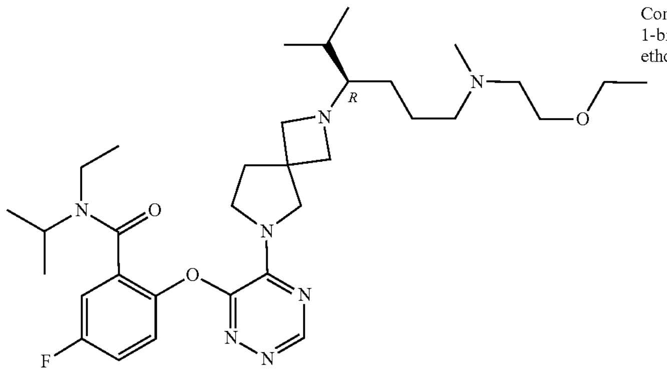 | Compound 19, 1-bromo-2-ethoxyethane | $K_2CO_3$, NaI, DMF, 50° C. | |
| 228 | 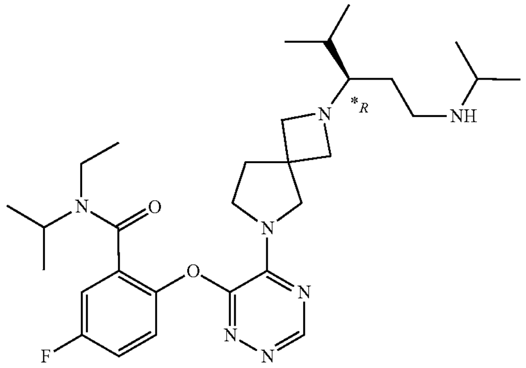 [SMILES: CCN(C(=O)c1cc(F)ccc1Oc1nncnc1N1CCC2(C1)CN([C@H](CCNC(C)C)C(C)C)C2)C(C)C] | Compound 218, 2-iodopropane | DIEA, ACN, RT | |

Compound 12

(R)-2-((5(2-(6-((2-cyanoethyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

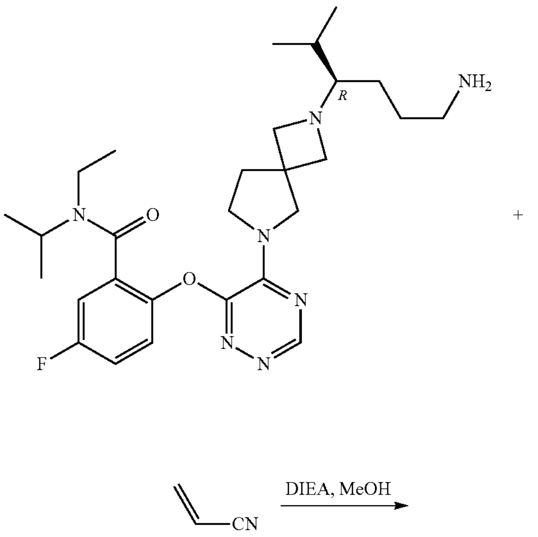

-continued

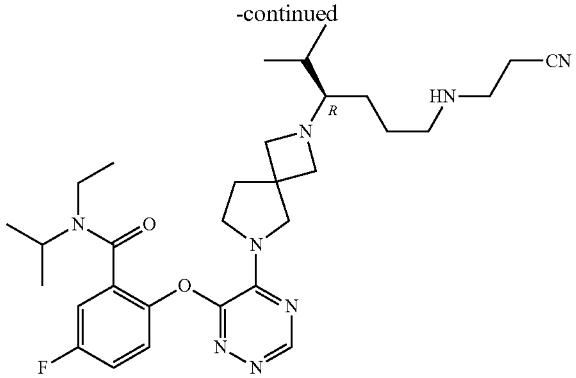

To a solution of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide hydrochloride (Compound 65) (260 mg, crude) and DIEA (200 mg, 1.98 mmol) in MeOH (15 mL) was added acrylonitrile (580 mg, 10.9 mmol) at 0° C. After addition, the reaction mixture was stirred at RT for 18 h. The reaction mixture was concentrated in vacuo and the residue was purified by preparative HPLC over Boston Prime (column: C18 150×30 mm 5 um, Mobile Phase A: water (0.04% ammonia+10 mM $NH_4HCO_3$), Mobile Phase B: ACN, Flow rate: 25 mL/min, gradient condition B/A from 40% to 70%) to afford the title compound (120 mg) as colorless oil.

LC-MS (ESI) (Method 1): $R_t$=2.938 min, m/z found 581.3 $[M+H]^+$.

Compound 18, 246

N-ethyl-5-fluoro-N-isopropyl-2-((5-(2-(2-methyl-6-((2-(methylsulfonyl)ethyl)amino)hexan-3-yl)-2,6-diazaspiro[3.4]octan-6-yl)-1,2,4-triazin-6-yl)oxy) benzamide (R)-2-((5-(2-(6-((3-(dimethylamino)-3-oxopropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide formate The following Compounds were synthesized by an analogous method described above for Compound 12

| Co. No. | Structure | Starting Materials | Conditions | Spectra Details |
|---|---|---|---|---|
| 18 | 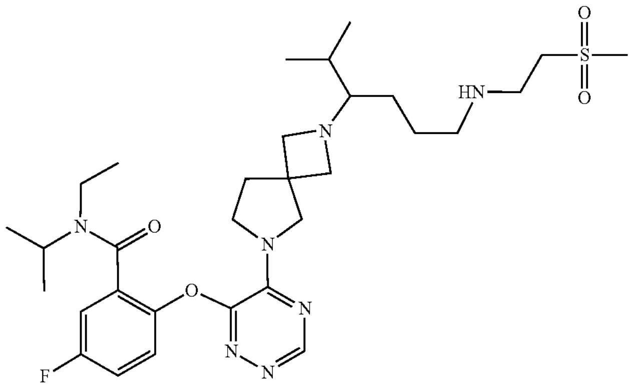 [SMILES: CCN(C(=O)c1cc(F)ccc1Oc1nncnc1N1CCC2(C1)CN(C(CCCNCCS(C)(=O)=O)C(C)C)C2)C(C)C] | Compound 3, (methylsulfonyl)-ethene | TEA, MeOH, RT | LC-MS (ESI) (Method 4): $R_t$ = 2.24 min, m/z found 634.7 $[M + H]^+$ |
| 246 | 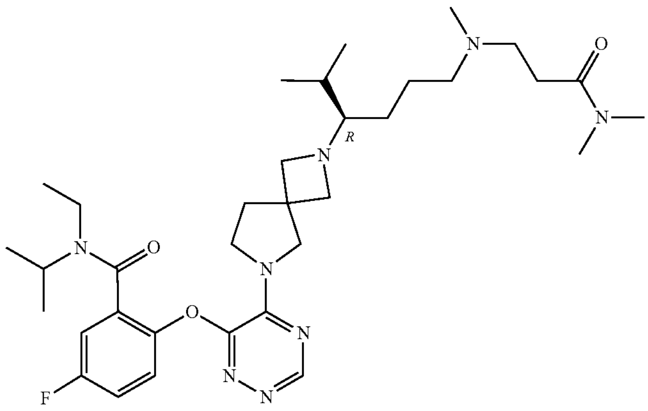 formate salt | Compound 19, N,N-dimethylacrylamide | TEA, MeOH, reflux | LC-MS (ESI) (Method 5): $R_t$ = 1.53 min, m/z found 641.5 $[M + H]^+$. |

Compound 27

(R)-N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)benzamide Preparation Method A

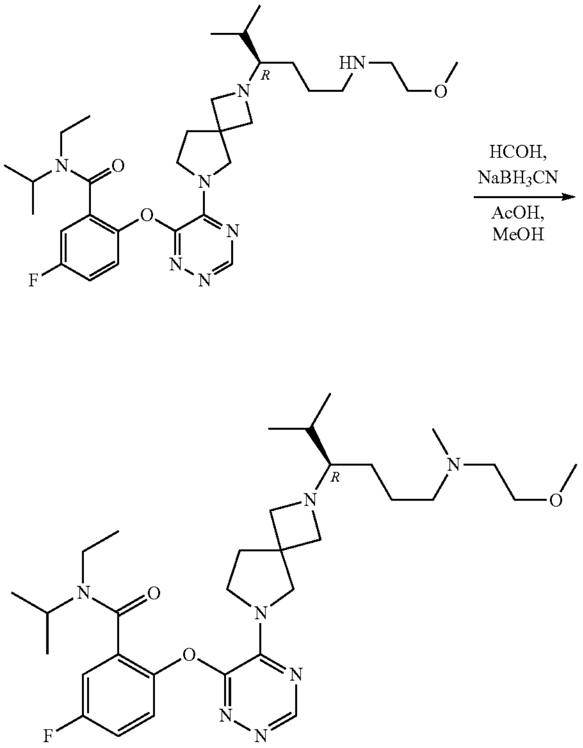

The mixture of (R)-N-ethyl-5-fluoro-N-isopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide (Compound 11) (40.0 mg, 0.068 mmol), formaldehyde (55.4 mg, 0.683 mol, 37% in water) and AcOH (8.2 mg, 0.137 mmol) in anhydrous MeOH (2 mL) was stirred at 45° C. for 1 h. Then, $NaBH_3CN$ (8.6 mg, 0.137 mmol) was added to the mixture and the resulting mixture was stirred at 45° C. for another 1 h. After cooling to RT, the reaction mixture was treated with sat. aq. $NaHCO_3$ (40 mL) to adjust the pH value to about 8 and further extracted with DCM (20 mL×3). The combined organic layers were dried over anhydrous $Na_2SO_4$, filtered and concentrated under reduced pressure to give the crude which was purified by preparative HPLC over Boston Prime (column: C18 150×30 mm 5um, Mobile Phase A: $H_2O$ (0.04% ammonia+10 mM $NH_4HCO_3$), Mobile Phase B: ACN, Flow rate: 25 mL/min, gradient condition B/A from 50% to 80% (50% B to 80% B)) to afford the title compound (9.62 mg, 99.10% purity, 23.3% yield) as yellow oil.

Preparation Method B

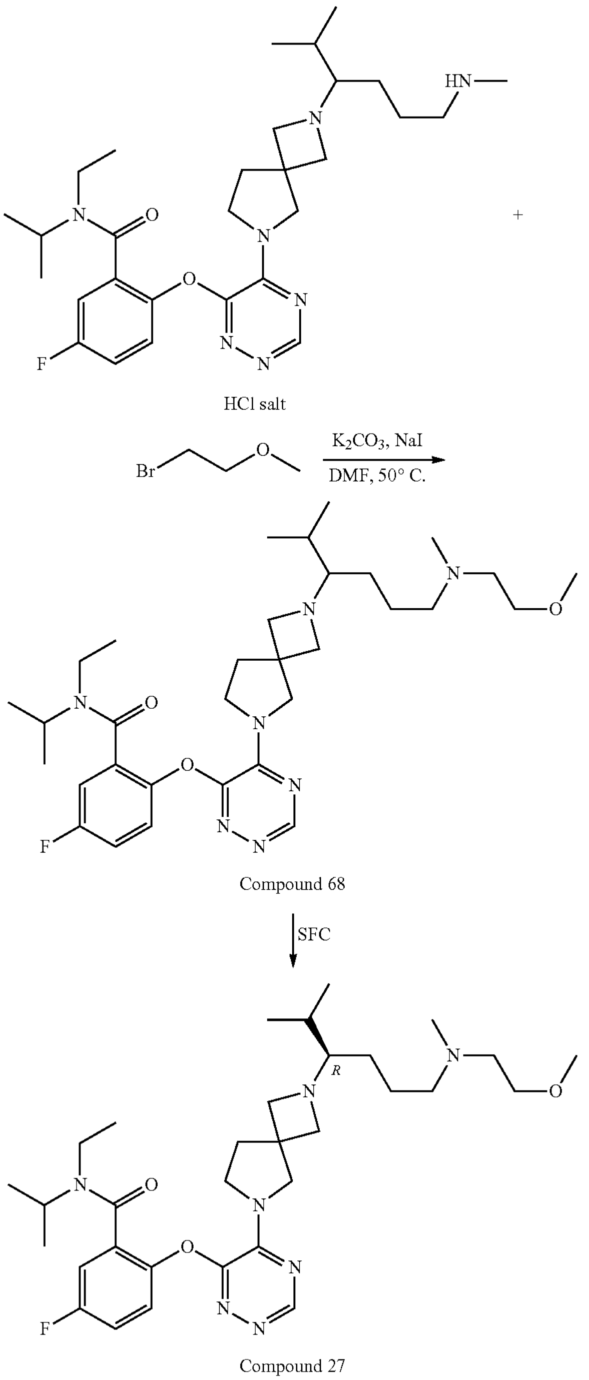

To the mixture of N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide hydrochloride (Compound 67) (480 mg, crude), $K_2CO_3$ (700 mg, 5.07 mmol) and NaI (400 mg, 2.67 mmol) in DMF (5 mL) was added 1-bromo-2-methoxyethane (230 mg, 1.65 mmol). The resulting mixture was stirred at 50° C. overnight. After cooled to RT, the reaction mixture was quenched with $H_2O$ (30 mL) and extracted with DCM (30 mL×3). The combined organic layers were washed with brine (30 mL×3), dried over $Na_2SO_4$, filtered and concentrated to give a crude residue. The residue was purified by FCC (DCM/MeOH=10:1) to afford N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy) benzamide (Compound 68) (250 mg, 48% yield) as yellow oil.

The N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)benzamide (Compound 68) (960 mg, combined from several batches obtained by Method B) was first separated by SFC using DAICEL CHIRALPAK IG (column: 250×30 mm 10 um; Mobile phase: A: Supercritical $CO_2$, B: EtOH (0.1% ammonia), A:B=40:60 at 60 mL/min) and further purified by preparative HPLC using Boston Prime (column: 150×30 mm 5um, Mobile Phase A: $H_2O$ (10 mM $NH_4HCO_3$), Mobile Phase B: ACN, Flow rate: 25 mL/min, gradient condition B/A from 55% to 85%) to afford the title compound (270 mg) as colorless oil.

$^1H$ NMR (400 MHz, Methanol-$d_4$): δ=8.40 (s, 1H), 7.47-7.32 (m, 1H), 7.30-7.10 (m, 2H), 4.24-4.01 (m, 2H), 3.89-3.60 (m, 3H), 3.48 (br s, 3H), 2.63-2.51 (m, 2H), 2.43-2.32 (m, 2H), 2.29-2.07 (m, 6H), 1.86-1.72 (m, 1H), 1.62-1.44 (m, 2H), 1.39-1.02 (m, 10H), 0.99-0.66 (m, 9H). Some protons were hidden by the solvent peak and are not reported.

LCMS (ESI) (Method 2): $R_t$=1.965 min, m/z found 600.3 $[M+H]^+$.

SFC (Method 11): $R_t$=4.904 min.

Preparation Method C

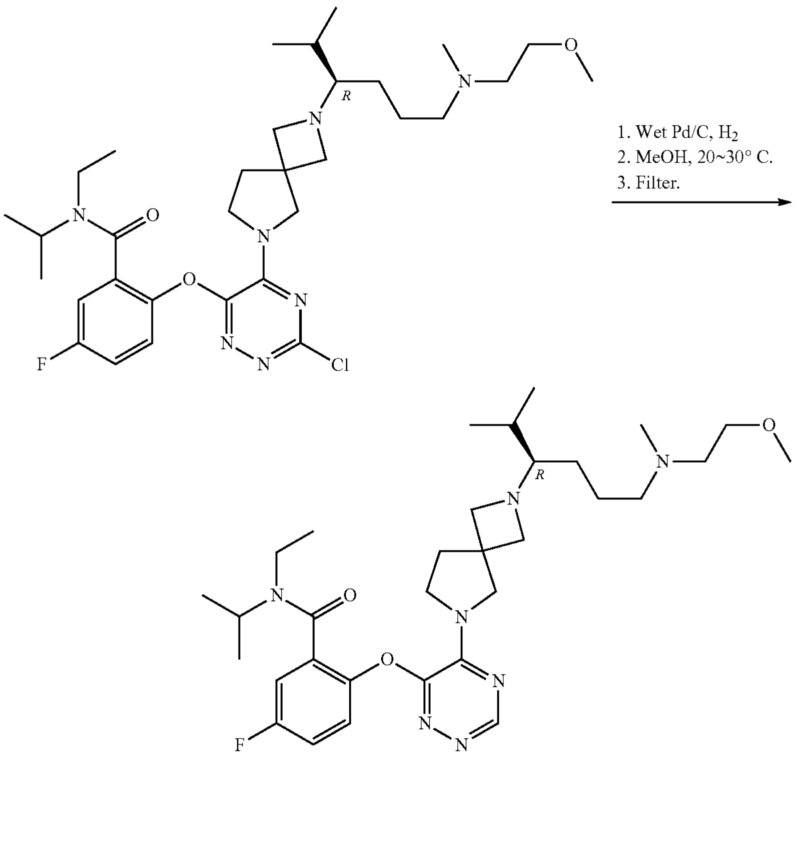

A methanol solution of (R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy-N-ethyl-5-fluoro-N-isopropylbenzamide (Compound 393) (163.93 g of a 60.1 wt % solution in MeOH, 100 g corrected of Compound 393), palladium on carbon (10 g) and MeOH (316 g) was stirred at 20 to 30° C. under a hydrogen atmosphere (0.20 to 0.30 Mpa) for 18 h. The mixture was filtered over diatomite (75 g) and the cake was washed with MeOH (158 g). The filtrate was concentrated under reduced pressure (≤40° C.) to ~3 vol., then flushed with isopropyl acetate (IPAc, 870 g) concentrating to ~3 vol. The mixture was then diluted with IPAc (696 g) and a 20% $Na_2CO_3$ aqueous solution was added (500 g). The mixture was stirred for 30 to 60 min. The aqueous layer was removed. The organic layer was washed with water (500 g) then concentrated under reduced pressure <45° C. to ~3 vol. The title intermediate was afforded in approximately 90% assay yield as a 48.1 wt % solution in IPAc.

Compound 70

(R)-N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)benzamide oxalate

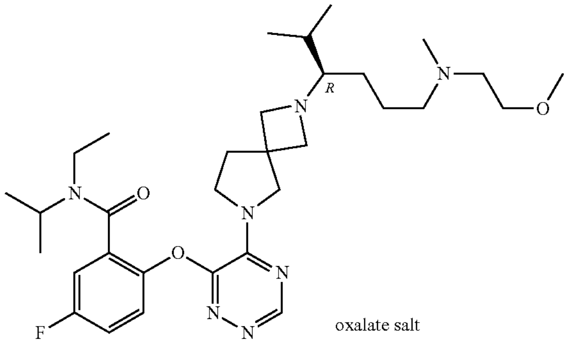

oxalate salt

To a solution of (R)-N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy) benzamide (Compound 27) (270 mg, 0.450 mmol) in 20 mL of ACN (20 mL) was added oxalic acid (81.0 mg, 0.900 mmol). After addition, the reaction mixture was stirred at RT for 1 h. Then the reaction mixture was concentrated, the residue was re-dissolved in ACN and deionized water, and lyophilized to afford the title compound (350 mg) as white solid.

$^1$H NMR (400 MHz, Methanol-$d_4$): δ=8.48 (s, 1H), 7.52-7.11 (m, 3H), 4.54-3.64 (m, 12H), 3.40-3.34 (m, 5H), 3.23-3.13 (m, 2H), 2.90 (s, 3H), 2.54-2.27 (m, 2H), 2.19-2.03 (m, 1H), 1.97-1.77 (m, 2H), 1.75-1.50 (m, 2H), 1.35-0.65 (m, 17H).

$^1$H NMR (400 MHz, DMSO-$d_6$): δ=8.51 (s, 1H), 7.51-7.29 (m, 3H), 4.29-3.34 (m, 12H), 3.23-2.84 (m, 7H), 2.70 (s, 3H), 2.35-2.09 (m, 2H), 2.05-1.85 (m, 1H), 1.81-1.58 (m, 2H), 1.56-1.33 (m, 2H), 1.18-0.60 (m, 17H).

LCMS (ESI) (Method 2): $R_t$=1.969 min, m/z found 600.4 $[M+H]^+$.

Preparation of Compound 70a

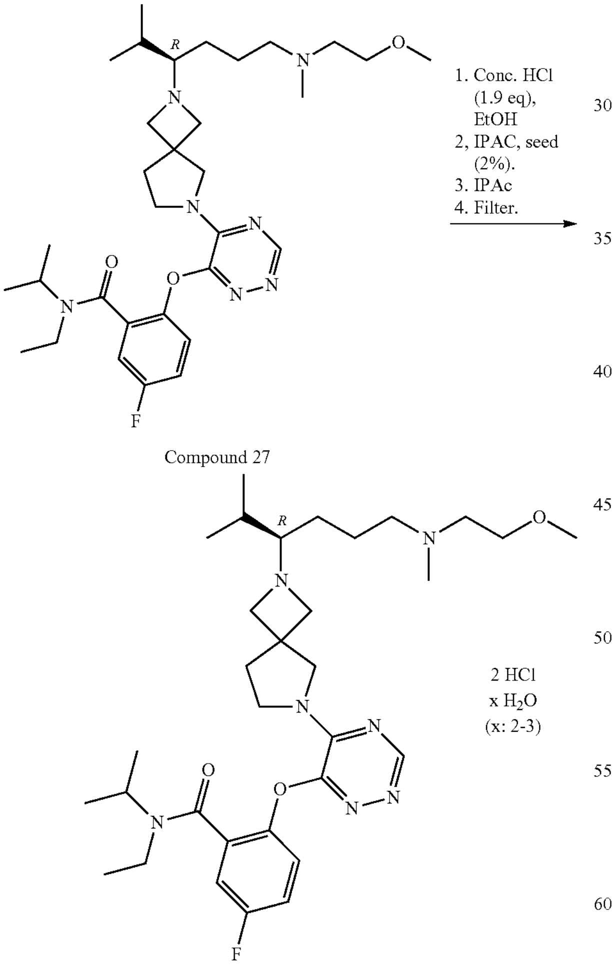

Compound 27

Compound 70a

To a solution of Compound 27 (207.90 g of a 48 wt % solution in IPAc, 100 g of active compound 27) in IPAc (360 g) was added EtOH (63 g) at 20 to 25° C. The solution was then treated with conc. HCl (32.9 g) in EtOH (49.5 g) over −15 min. The mixture was seeded with crystalline Compound 70a seed (2 g, 2% seed load) then aged for 18 h. IPAc (870 g) was added slowly over 4 h at between 20 to 25° C. and the slurry was stirred for an additional 18 h. After cooling to −5° C., the product was filtered, washed with IPAc (522 g) and dried under vac at 20-30° C. to afford the weakly crystalline Compound 70a as a white solid (91.0% yield, 115.4 g). (Note: A small amount of seed material used in the reaction was obtained via an analogous reaction protocol on small-scale.)

Recrystallisation: A solution of weakly crystalline Compound 70a (100 g), EtOH (166 g), purified water (21.5 g) and IPAc (178 g) was stirred at 20 to 30° C. for 0.5-2 h to get a clear solution. Extra IPAc (522 g) was added dropwise over 1-2 h, and then the mixture was seeded with crystalline Compound 70a seed (2 g, 2% seed load). Then the mixture was aged for 18-20 h, IPAc (348 g) was added slowly over 12 h at between 20 to 30° C., and the slurry was stirred for an additional 55-60 h. The product was filtered, washed with IPAc (158 g) and dried in vacuo at 20-30° C. to afford Compound 70a as a white solid (85% yield, 85.0 g, net).

$^1$H NMR (DMSO-$d_6$, 400 MHz): δ=11.60 (OH, brs), 10.8 (1H, brs), 8.52 (1H, s), 7.36 (3H, m), 3.97-4.20 (7H, m), 3.64-3.71 (4H, m), 3.47 (7H, m), 3.25 (2H, m), 3.05 (3H, m), 2.73 (3H, s), 2.10-2.45 (1H, m), 1.99 (1H, m), 1.78 (2H, m), 1.55 (2H, m), 0.83-1.12 (12H, m), 0.70 (2H, m).

LCMS (Method 7): $R_t$=0.669 min, m/z found 600.5 $[M+H]^+$.

Compound 83, 84, 94, 95, 88, 89, 99, 100, 250, 251, 252, 254, 258, 396, 402

(*R)—N-ethyl-5-fluoro-N-isopropyl-2-((4-(2-(6-((2-methoxyethyl)(methyl)amino)-methylhexan-3-yl)-2,6-diazaspiro[3.4]octan-6-yl)pyridazin-3-yl)oxy)benzamide oxalate (*S)—N-ethyl-5-fluoro-N-isopropyl-2-((4-(2-(6-((2-methoxyethyl)(methyl)amino)-2-methylhexan-3-yl)-2,6-diazaspiro[3.4]octan-6-yl)pyridazin-3-yl)oxy) benzamide oxalate (*R)-5-fluoro-N,N-isopropyl-2-((5-(2-(6-((2-methoxyethyl)(methyl)amino)-methylhexan-3-yl)-2,6-diazaspiro[3.4]octan-6-yl)-1,2,4-triazin-6-yl)oxy) benzamide oxalate (*S)-5-fluoro-N,N-isopropyl-2-((5-(2-(6-((2-methoxyethyl)(methyl)amino)-methylhexan-3-yl)-2,6-diazaspiro[3.4]octan-6-yl)-1,2,4-triazin-6-yl)oxy) benzamide oxalate (*R)-5-fluoro-N,N-isopropyl-2-((4-(2-(6-((2-methoxyethyl)(methyl)amino)-methylhexan-3-yl)-2,6-diazaspiro[3.4]octan-6-yl)pyridazin-3-yl)oxy)benzamide oxalate (*S)-5-fluoro-N,N-isopropyl-2-((4-(2-(6-((2-methoxyethyl)(methyl)amino)-methylhexan-3-yl)-2,6-diazaspiro[3.4]octan-6-yl)pyridazin-3-yl)oxy)benzamide oxalate (*R)-5-fluoro-N,N-isopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide oxalate (*S)-5-fluoro-N,N-isopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide oxalate N-ethyl-5-fluoro-N-isopropyl-2-((5-(2-((R)-6-(((*R)-2-methoxypropyl)(methyl)amino)-2-methylhexan-3-yl)-2,6-diazaspiro[3.4]octan-6-yl)-1,2,4-triazin-6-yl)oxy)benzamide oxalate N-ethyl-5-fluoro-N-isopropyl-2-((5-(2-((R)-6-(((*S)-2-methoxypropyl)(methyl)amino)-2-methylhexan-3-yl)-2,6-diazaspiro[3.4]octan-6-yl)-1,2,4-triazin-6-yl)oxy)benzamide oxalate N-ethyl-5-fluoro-N-isopropyl-2-((5-(2-((3R)-6-((2-methoxypropyl)(methyl)amino)-2-methylhexan-3-yl)-2,6-diazaspiro[3.4]octan-6-yl)-1,2,4-triazin-6-yl)oxy)benzamide oxalate N-ethyl-5-fluoro-N-isopropyl-2-((5-(2-((3S)-6-((2-methoxypropyl)(methyl)amino)-2-methylhexan-3-yl)-2,6-diazaspiro[3.4]octan-6-yl)-1,2,4-triazin-6-yl)oxy)benzamide oxalate (R)-2-((5-(2-(6-((2-ethoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide oxalate (*R)-2-((5-(2-(6-(dimethylamino)-2-methylhexan-3-yl)-2,6-diazaspiro[3.4]octan-6-yl)-1,2,4-triazin-6-yl)oxy)-5-fluoro-N,N-diisopropylbenzamide oxalate (R)-N-(ethyl-$^{13}C_2$)-5-fluoro-2-((5-(2-(6-((2-methoxyethyl)methyl)amino)-2-methylhexan-3-yl)-2,6-diazaspiro[3.4]octan-6-yl)-1,2,4-triazin-1-yl)oxy)-N-(propan-2-yl-$^{13}C_3$)benzamide oxalate The following Compounds were synthesized by an analogous method described above for Compound 70

| Co. No. | Structure | Starting Materials | Spectra Details |
|---|---|---|---|
| 83 | 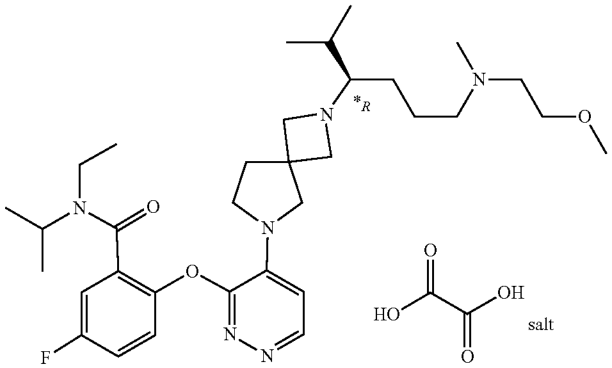 [SMILES: CCN(C(=O)c1cc(F)ccc1Oc1nnccc1N1CCC2(C1)CN([C@H](CCCN(C)CCOC)C(C)C)C2)C(C)C ; O=C(O)C(=O)O] | Compound 107, oxalic acid | LC-MS (ESI) (Method 3): $R_t$ = 5.034 min, m/z found 599.3 [M + H]$^+$. Chiral HPLC (Method 2): $R_t$ = 8.596 min. |
| 84 | 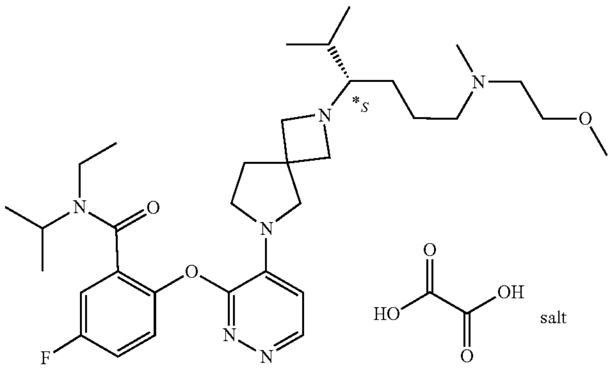 [SMILES: CCN(C(=O)c1cc(F)ccc1Oc1nnccc1N1CCC2(C1)CN([C@@H](CCCN(C)CCOC)C(C)C)C2)C(C)C ; O=C(O)C(=O)O] | Compound 108, oxalic acid | LC-MS (ESI) (Method 3): $R_t$ = 4.957 min, m/z found 599.3 [M + H]$^+$. Chiral HPLC (Method 2): $R_t$ = 9.726 min. |

-continued

| Co. No. | Structure | Starting Materials | Spectra Details |
|---|---|---|---|
| 94 | 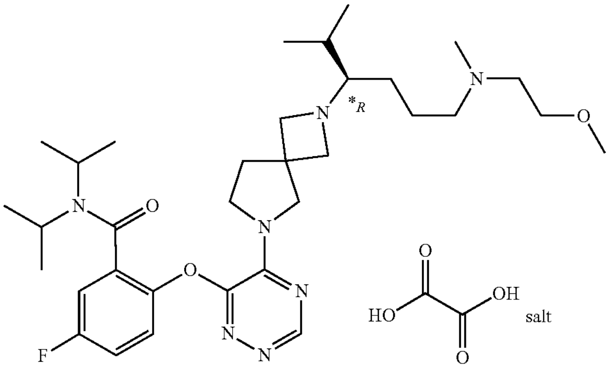 [SMILES: COCCN(C)CCC[C@H](C(C)C)N1CC2(CCN(c3ncnnc3Oc3ccc(F)cc3C(=O)N(C(C)C)C(C)C)C2)C1 ; O=C(O)C(=O)O] salt | Compound 109, oxalic acid | LC-MS (ESI) (Method 2): $R_t$ = 2.431 min, m/z found 614.5 $[M + H]^+$. Chiral HPLC (Method 3): $R_t$ = 4.967 min. |
| 95 | 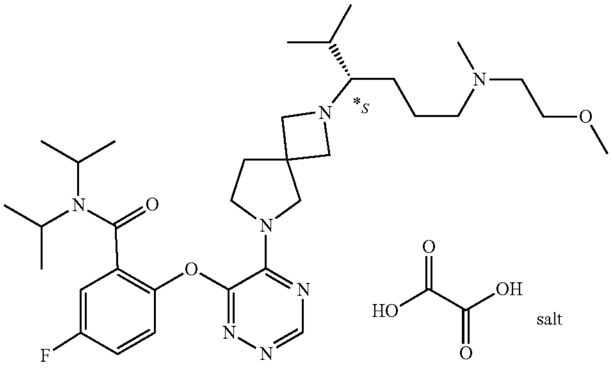 [SMILES: COCCN(C)CCC[C@@H](C(C)C)N1CC2(CCN(c3ncnnc3Oc3ccc(F)cc3C(=O)N(C(C)C)C(C)C)C2)C1 ; O=C(O)C(=O)O] salt | Compound 110, oxalic acid | LC-MS (ESI) (Method 2): $R_t$ = 2.471 min, m/z found 614.5 $[M + H]^+$. Chiral HPLC (Method 3): $R_t$ = 5.947 min. |
| 88 | 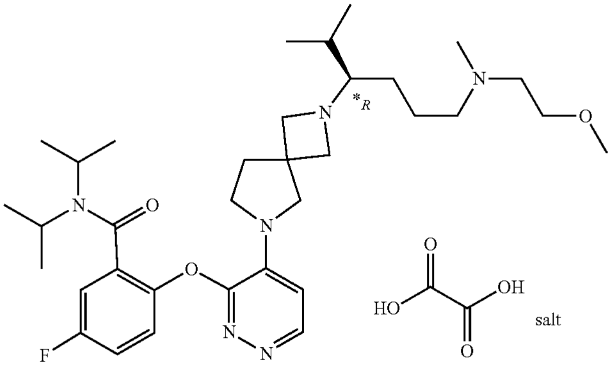 [SMILES: COCCN(C)CCC[C@H](C(C)C)N1CC2(CCN(c3ccnnc3Oc3ccc(F)cc3C(=O)N(C(C)C)C(C)C)C2)C1 ; O=C(O)C(=O)O] salt | Compound 117, oxalic acid | LC-MS (ESI) (Method 1): $R_t$ = 2.243 min, m/z found 613.4 $[M + H]^+$. Chiral HPLC (Method 5): $R_t$ = 4.873 min. |
| 89 | 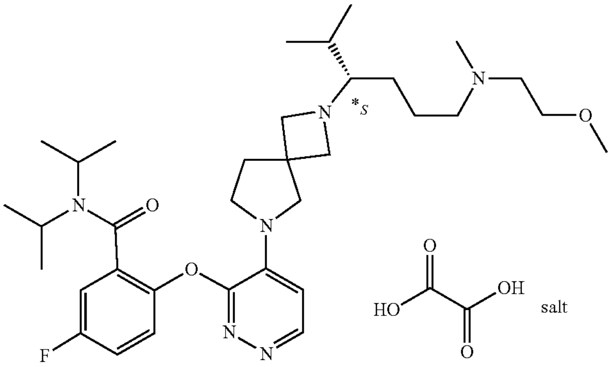 [SMILES: COCCN(C)CCC[C@@H](C(C)C)N1CC2(CCN(c3ccnnc3Oc3ccc(F)cc3C(=O)N(C(C)C)C(C)C)C2)C1 ; O=C(O)C(=O)O] salt | Compound 118, oxalic acid | LC-MS (ESI) (Method 1): $R_t$ = 2.271 min, m/z found 613.3 $[M + H]^+$. Chiral HPLC (Method 5): $R_t$ = 5.947 min. |

-continued

| Co. No. | Structure | Starting Materials | Spectra Details |
|---|---|---|---|
| 99 | 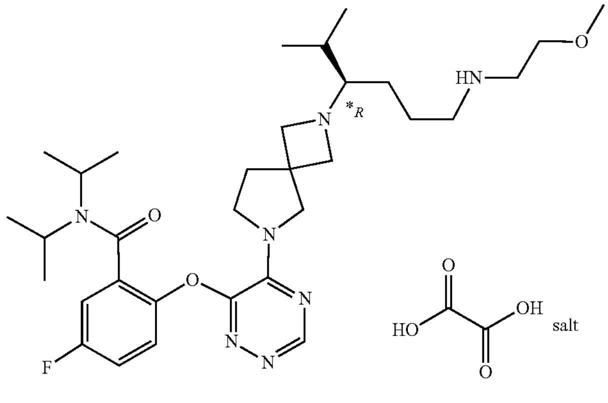 [SMILES: COCCNCCC[C@H](C(C)C)N1CC2(CCN(c3ncnnc3Oc3ccc(F)cc3C(=O)N(C(C)C)C(C)C)C2)C1 ; O=C(O)C(=O)O] | Compound 115, oxalic acid | LC-MS (ESI) (Method 2): $R_t$ = 2.224 min, m/z found 600.3 $[M + H]^+$. Chiral HPLC (Method 6): $R_t$ = 3.810 min. |
| 100 | 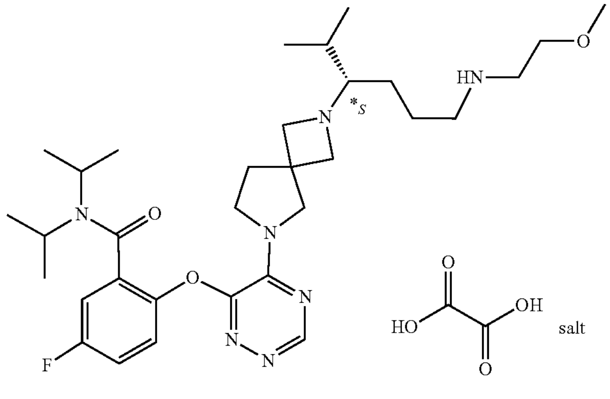 [SMILES: COCCNCCC[C@@H](C(C)C)N1CC2(CCN(c3ncnnc3Oc3ccc(F)cc3C(=O)N(C(C)C)C(C)C)C2)C1 ; O=C(O)C(=O)O] | Compound 116, oxalic acid | LC-MS (ESI) (Method 2): $R_t$ = 2.21 min, m/z found 600.4 $[M + H]^+$. Chiral HPLC (Method 6): $R_t$ = 5.322 min. |
| 250 | 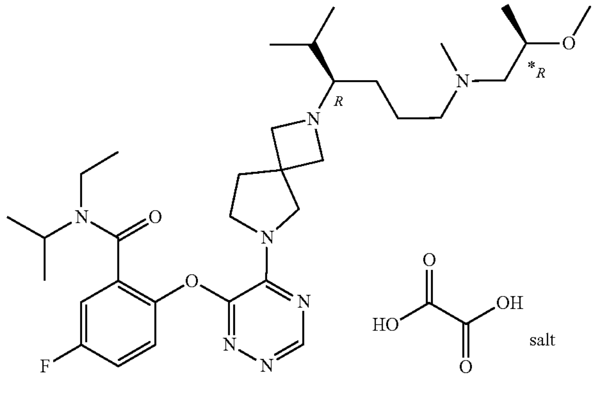 | Compound 248, oxalic acid | LC-MS (ESI) (Method 1): $R_t$ = 3.107 min, m/z found 614.4 $[M + H]^+$. SFC (Method 16): $R_t$ = 4.082 min. |
| 251 | 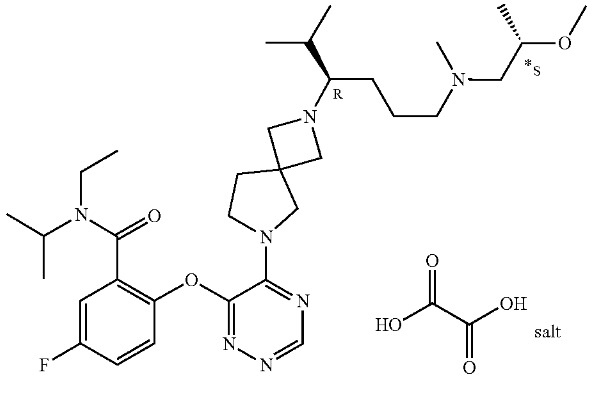 | Compound 249, oxalic acid | LC-MS (ESI) (Method 1): $R_t$ = 3.141 min, m/z found 614.4 $[M + H]^+$. SFC (Method 16): $R_t$ = 4.287 min. |

-continued

| Co. No. | Structure | Starting Materials | Spectra Details |
|---|---|---|---|
| 252 | 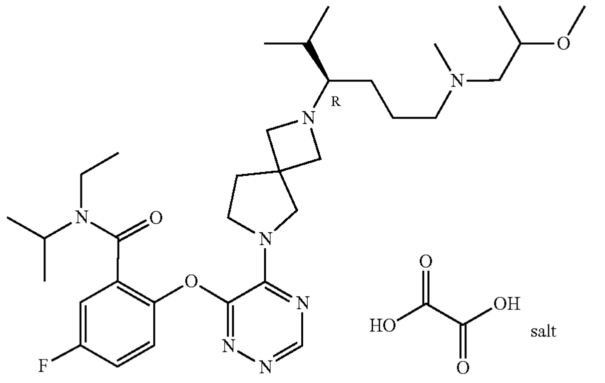 | Compound 247, oxalic acid | LC-MS (ESI) (Method 1): $R_t$ = 3.011 min, m/z found 614.4 $[M + H]^+$. |
| 254 | 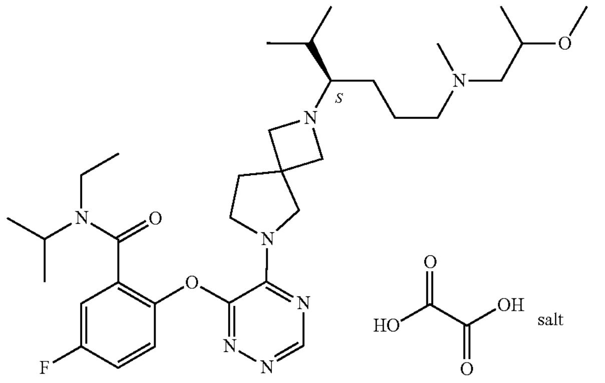 | Compound 253, oxalic acid | LC-MS (ESI) (Method 1): $R_t$ = 3.054 min, m/z found 614.4 $[M + H]^+$. |
| 258 | 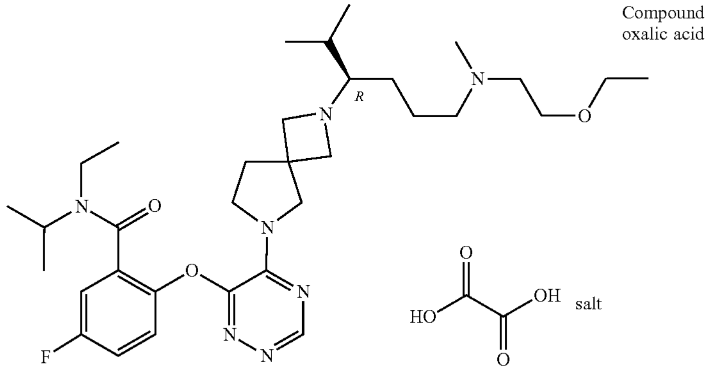 | Compound 257, oxalic acid | LC-MS (ESI) (Method 2): $R_t$ = 2.047 min, m/z found 614.4 $[M + H]^+$. SFC (Method 16): $R_t$ = 4.345 min. |
| 396 | 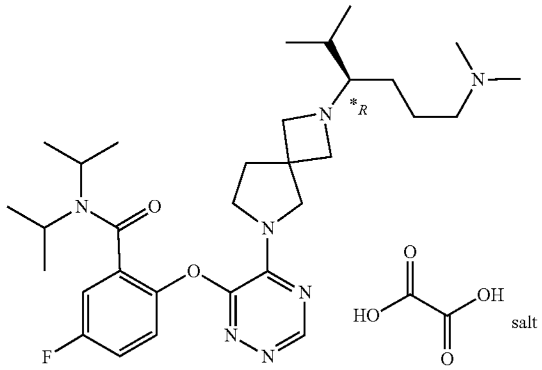 [SMILES: CC(C)[C@@H](CCCN(C)C)N1CC2(CCN(c3ncnnc3Oc3ccc(F)cc3C(=O)N(C(C)C)C(C)C)C2)C1 ; O=C(O)C(=O)O] | Compound 105, oxalic acid | LC-MS (ESI) (Method 2): $R_t$ = 2.071 min, m/z found 570.3 $[M + H]^+$. SFC (Method 4): $R_t$ = 1.364 min. |

-continued

| Co. No. | Structure | Starting Materials | Spectra Details |
|---|---|---|---|
| 402 | 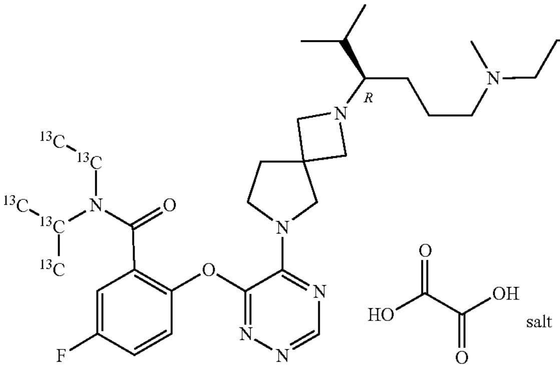 | Compound 401, oxalic acid | LC-MS (ESI) (Method 5): $R_t$ = 1.500 min, m/z found 605.3 [M + H]+. |

Compound 13, 16, 71, 136, 139, 153, 156, 160, 164, 166, 169, 173, 274, 275, 276, 279, 282, 285, 178, 180, 190, 192, 194, 196, 198, 200, 202, 204, 310, 311, 312, 313, 318, 329, 360, 375, 376, 379, 380, 383,388, 411

(R)-2-((5-((2-cyanoethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (R)-2-((5-(2-(6-((2,2-difluoroethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (R)-N-ethyl-2-((5-(2-(6-(ethyl(2-methoxyethyl)amino)-2-methylhexan-3-yl)-2,6-diazaspiro[3.4]octan-6-yl)-1,2,4-triazin-6-yl)oxy)-5-fluoro-N-isopropylbenzamide (R)-N-ethyl-5-fluoro-N-isopropyl-2-((5-(2-(6-((2-methoxy-2-methylpropyl)(methyl)amino)-2-methylhexan-3-yl)-2,6-diazaspiro[3.4]octan-6-yl)-1,2,4-triazin-6-yl)oxy)benzamide (R)-N-ethyl-5-fluoro-2-((5-(2-(6-((2-hydroxy-2-methylpropyl)(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-N-isopropyl-2-((5-(2-((R)-6-(((R)-1-methoxypropan-2-yl)(methyl)amino)-2-methylhexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-6-(((S)-1-methoxypropan-2-yl)(methyl)amino)-2-methylhexan-3-yl)-2,6-diazaspiro[3.4]octan-6-yl)-1,2,4-triazin-6-yl)oxy)benzamide (R)-2-((5-(2-(6-((1,3-dimethoxypropan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-2-((5-(2-((R)-6-(((R)-1-hydroxy-3-methoxypropan-2-yl)(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((R)-6-(((S)-1-hydroxy-3-methoxypropan-2-yl)(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((3R)-6-((3-hydroxy-2-methoxypropyl)(methyl)amino)-2-methylhexan-3-yl)-2,6-diazaspiro[3.4]octan-6-yl)-1,2,4-triazin-6-yl)oxy)-N-isopropylbenzamide 2-((5-(2-((3R)-6-((2,3-dimethoxypropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (*R)—N-ethyl-5-fluoro-2-((5-(2-(1-((3-hydroxypropyl)(methyl)amino)-4-methylpentan-3-yl)-2,6-diazaspiro[3.4]octan-6-yl)-1,2,4-triazin-6-yl)oxy)-N-isopropylbenzamide (*R)—N-ethyl-5-fluoro-N-isopropyl-2-((5-(2-(1-((3-methoxypropyl)(methyl)amino)-4-methylpentan-3-yl)-2,6-diazaspiro[3.4]octan-6-yl)-1,2,4-triazin-6-yl)oxy)benzamide (*R)—N-ethyl-5-fluoro-N-isopropyl-2-((5-(2-(1-((2-methoxyethyl)(methyl)amino)-4-methylpentan-3-yl)-2,6-diazaspiro[3.4]octan-6-yl)-1,2,4-triazin-6-yl)oxy)benzamide (*R)-2-((5-(2-(1-((3-amino-3-oxopropyl)(methyl)amino)-4-methylpentan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-2-((5-(2-((R)-6-(((R)-2-hydroxy-3-methoxypropyl)(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((R)-6-(((S)-2-hydroxy-3-methoxypropyl)(methyl)amino)-2-methylhexan-3-yl)-2,6-diazaspiro[3.4]octan-6-yl)-1,2,4-triazin-6-yl)oxy)-N-isopropylbenzamide formate 2-((5-(2-((3R)-6-((4-(dimethylamino)-4-oxobutan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((3R)-6-((3-(dimethylamino)-2-methyl-3-oxopropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((5-(2-((R)-2-methyl-6-(methyl((R)-4-(methylamino)-4-oxobutan-2-yl)amino)hexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-2-methyl-6-(methyl((S)-4-(methylamino)-4-oxobutan-2-yl)amino)hexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-2-methyl-6-(methyl((R)-2-methyl-3-(methylamino)-3-oxopropyl)amino)hexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-2-methyl-6-(methyl((S)-2-methyl-3-(methylamino)-3-oxopropyl)amino)hexan-3-yl)-2,6-diazaspiro[3.4]octan-6-yl)-1,2,4-triazin-6-yl)oxy)benzamide 2-((5-(2-((*R)-6-(((R)-4-amino-4-oxobutan-2-yl)(methyl)amino)-2-methylhexan-3-yl-2, diazaspiro[3.4]octan-6-yl)-1,2,4-triazin-6-yl)oxy)-5-fluoro-N,N-diisopropylbenzamide 2-((5-(2-((*R)-6-(((S)-4-amino-4-oxobutan-2-yl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((*R)-6-(((R)-3-amino-2-methyl-3-oxopropyl)(methyl)amino-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((*R)-6-(((S)-3-amino-2-methyl-3-oxopropyl)(methyl)amino)-2-methylhexan-3-yl)-2,6-diazaspiro[3.4]octan-6-yl)-1,2,4-triazin-6-yin-yl)oxy)-5-fluoro-N,N-diisopropylbenzamide 2-((5-(2-((3*R,5*R)-6-(dimethylamino-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-2-((5-(2-((3*R,5*R)-6-(ethyl(methyl)amino)-5-methoxy-2-methylhexan-3-yl)-2, diazaspiro[3.4]octan-6-yl)-1,2,4-triazin-6-yl)oxy)-5-fluoro-N-isopropylbenzamide 2-((5-(2-((3*R,5*S)-6-(dimethylamino)-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-(2-(((3-(2-(5 ethyl(methyl)amino)-5-methoxy-2-methylhexan-3-yl-2,&6-diazaspiro[3.4]octan-6-yl)-1,2,4-triazin-6-yl)oxy)-5-fluoro-N-isopropylbenzamide N-ethyl-5-fluoro-2-((5-(2-(5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide 2-((5-(2-(6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-(6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((3*S,5*S)-4-(dimethylamino)-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide (2(5-(2(3*S,5*R)-6-(dimethylamino-5-methoxy-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-2-((5-(2-((3*S,5*S)-6-(ethyl(methyl)amino)-5-methoxy-2-methylhexan-3-yl)-2,6-diazaspiro[3.4]octan-6-yl)-1,2,4-triazin-6-yl)oxy)-5-fluoro-N-isopropylbenzamide N-ethyl-2-((5-(2-((3*S,5*R)-6-(ethyl(methyl)amino)-5-methoxy-2-methylhexan-3-yl)-2,6-diazaspiro[3.4]octan-6-yl)-1,2,4-triazin-6-yl)oxy)-5-fluoro-N-isopropylbenzamide N-ethyl-5-fluoro-2-((5-(2-(5-hydroxy-2-methyl-6-(methyl(propyl)amino)hexan-3-yl)-2,6-diazaspiro[3.4]octan-6-yl)-1,2,4-triazin-6-yl)oxy)-N-isopropylbenzamide 2-((5-(2-(6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide (R)-2-((3-chloro-5-(2-(6-(dimethylamino)-2-methylhexan-3-yl)-2,6-diazaspiro[3.4]octan-6-yl)-1,2,4-triazin-6-yl)oxy)-N-ethyl-5-fluoro-N-isopropylbenzamide formate The following Compounds were synthesized by an analogous method described above for Compound 27 by method A

| Co. No. | Structure | Starting Material | Spectra Details |
|---|---|---|---|
| 13 | 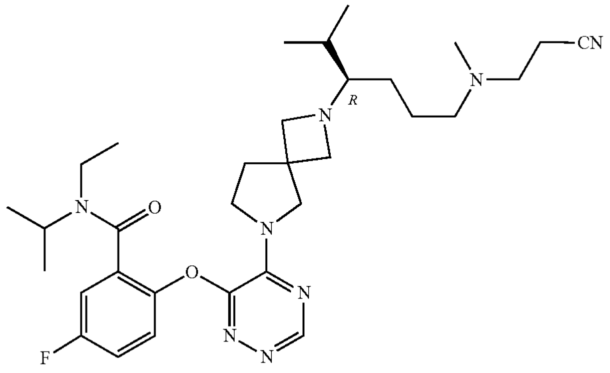 | Compound 12 | LC-MS (ESI) (Method 1): $R_t$ = 2.897 min, m/z found 595.3 $[M + H]^+$. |
| 16 | 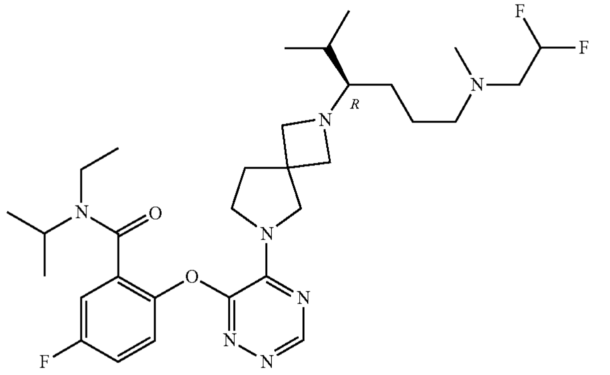 | Compound 15 | LC-MS (ESI) (Method 2): $R_t$ = 1.893 min, m/z found 606.3 $[M + H]^+$. |
| 71 | 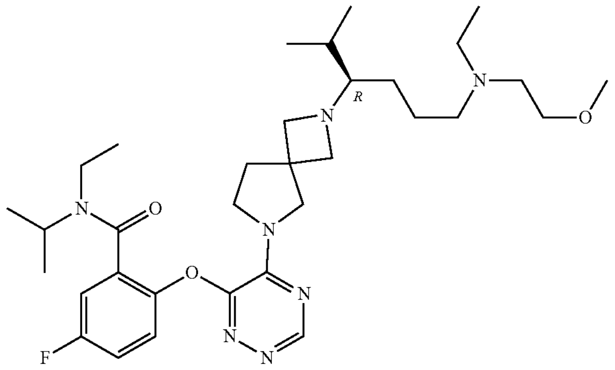 | Compound 11 | LC-MS (ESI) (Method 2): $R_t$ = 2.002 min, m/z found 614.4 $[M + H]^+$. SFC (Method 6): $R_t$ = 1.382 min. |
| 136 | 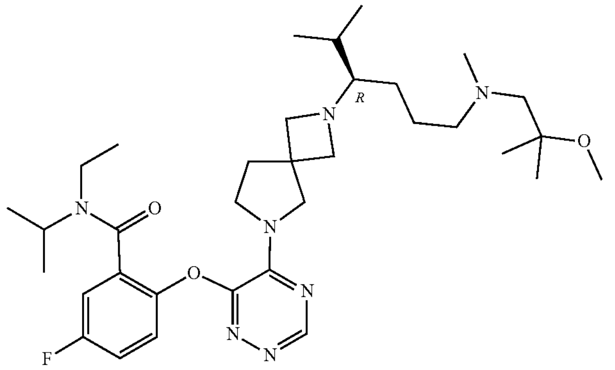 | Compound 134 | |

-continued
| Co. No. | Structure | Starting Material | Spectra Details |
|---|---|---|---|
| 139 | 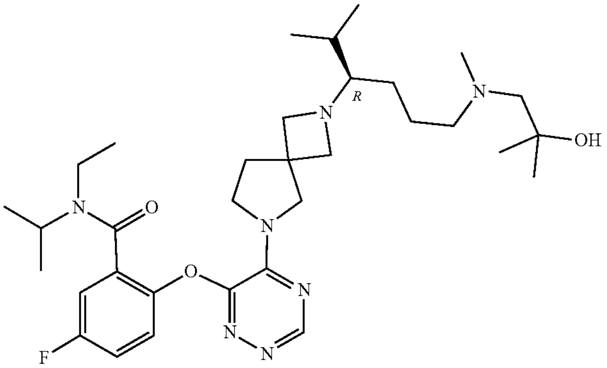 | Compound 138 | |
| 153 | 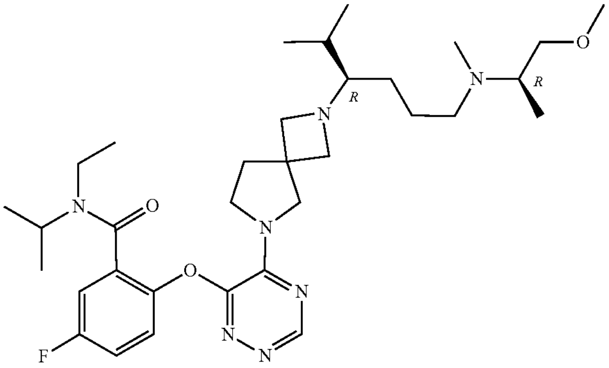 | Compound 111 | |
| 156 | 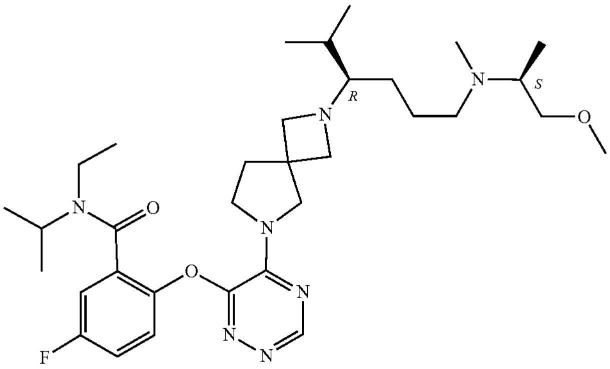 | Compoun 155 | |
| 160 | 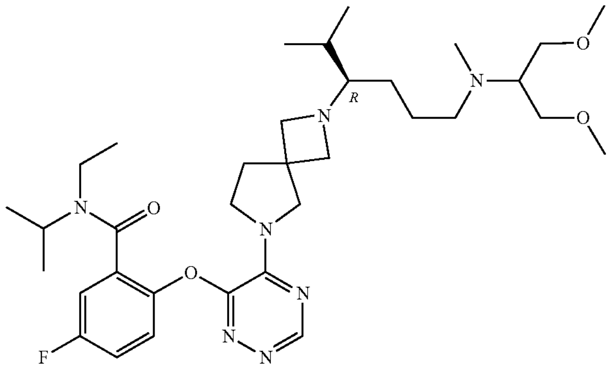 | Compound 158 | |

-continued
| Co. No. | Structure | Starting Material | Spectra Details |
|---|---|---|---|
| 164 | 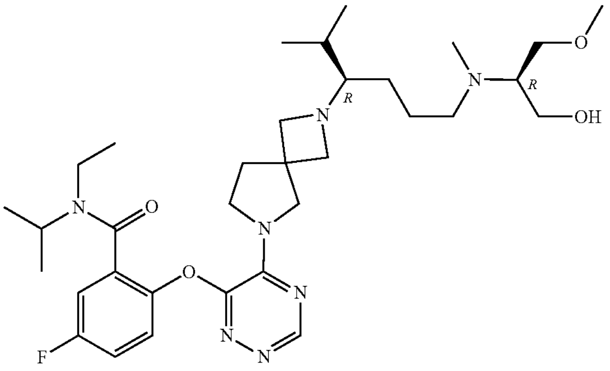 | Compound 162 | |
| 166 | 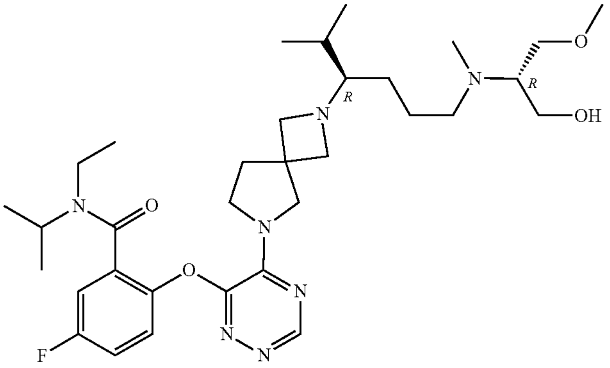 | Compound 163 | |
| 169 | 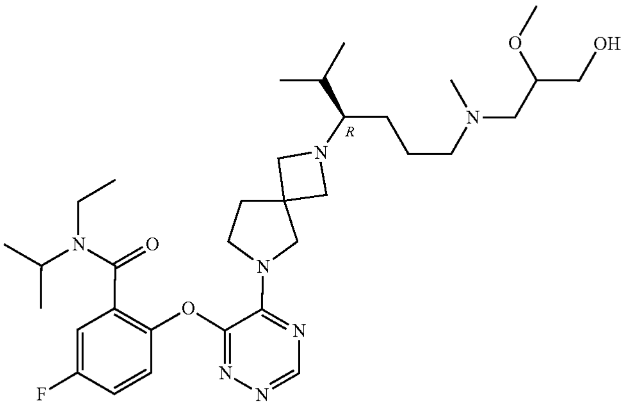 | Compound 168 | |
| 173 | 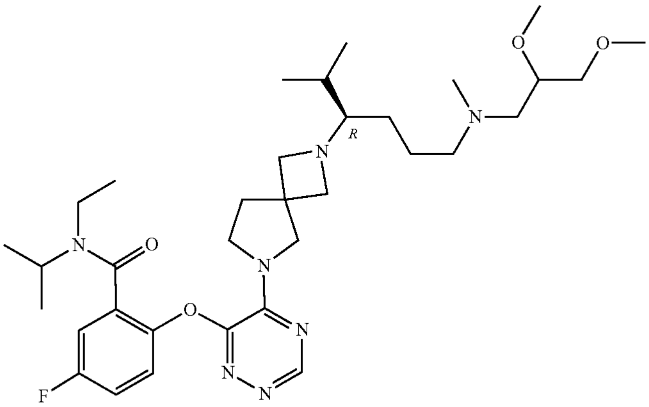 | Compound 171 | |

-continued
| Co. No. | Structure | Starting Material | Spectra Details |
|---|---|---|---|
| 274 | 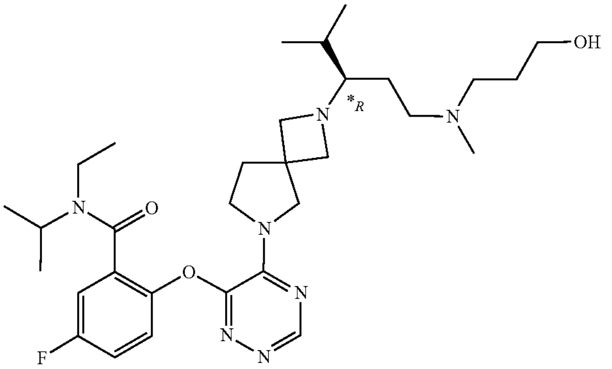 [SMILES: CCN(C(=O)c1cc(F)ccc1Oc1nncnc1N1CCC2(C1)CN([C@H](CCN(C)CCCO)C(C)C)C2)C(C)C] | Compound 273 | LC-MS (ESI) (Method 1): $R_t$ = 2.969 min, m/z found 586.3 $[M + H]^+$. SFC (Method 13): $R_t$ = 2.031 min. |
| 275 | 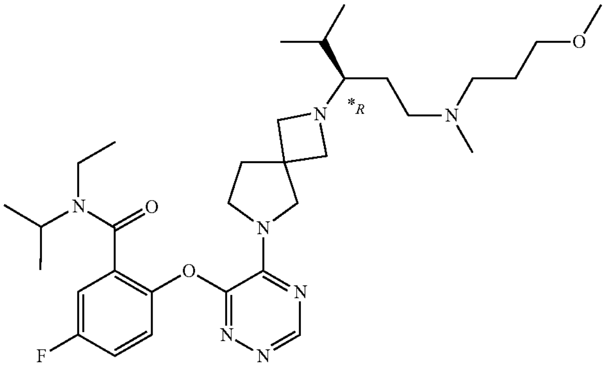 [SMILES: CCN(C(=O)c1cc(F)ccc1Oc1nncnc1N1CCC2(C1)CN([C@H](CCN(C)CCCOC)C(C)C)C2)C(C)C] | Compound 271 | LC-MS (ESI) (Method 2): $R_t$ = 2.031 min, m/z found 600.3 $[M + H]^+$. SFC (Method 3): $R_t$ = 3.479 min. |
| 276 | 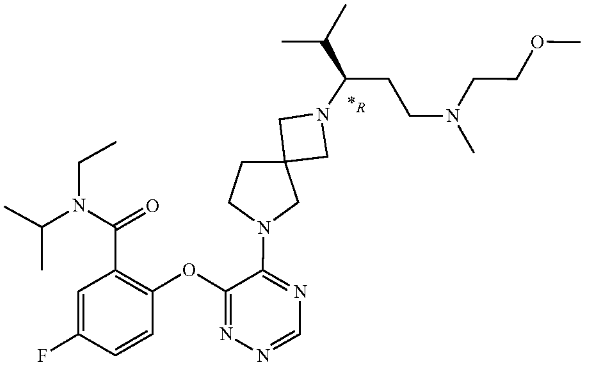 [SMILES: CCN(C(=O)c1cc(F)ccc1Oc1nncnc1N1CCC2(C1)CN([C@H](CCN(C)CCOC)C(C)C)C2)C(C)C] | Compound 227 | LC-MS (ESI) (Method 6): $R_t$ = 2.98 min, m/z found 586.2 $[M + H]^+$. |
| 279 | 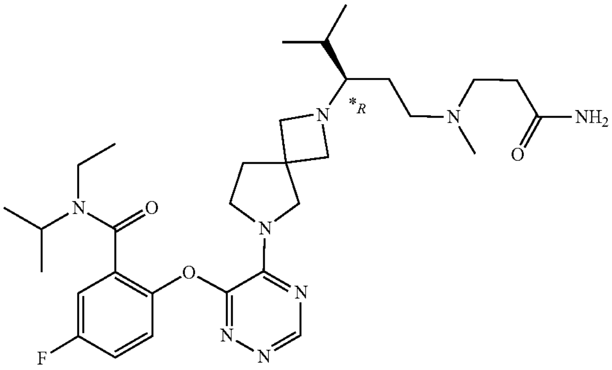 [SMILES: CCN(C(=O)c1cc(F)ccc1Oc1nncnc1N1CCC2(C1)CN([C@H](CCN(C)CCC(N)=O)C(C)C)C2)C(C)C] | Compound 277 | |

-continued
| Co. No. | Structure | Starting Material | Spectra Details |
| --- | --- | --- | --- |
| 282 | 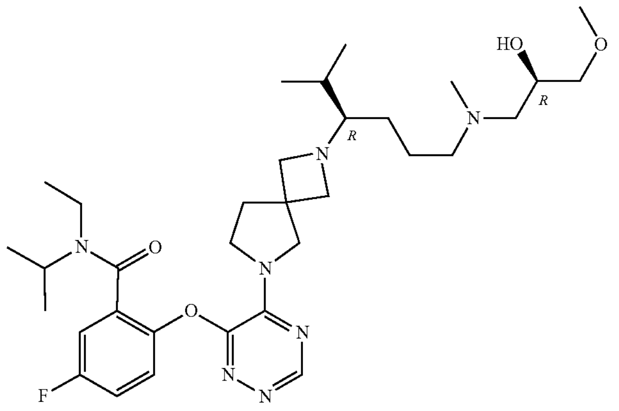 | Compound 281 | |
| 285 | 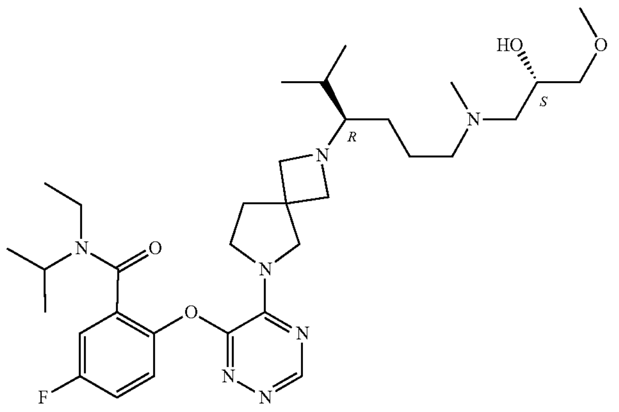 formate salt | Compound 284 | LC-MS (ESI) (Method 3): $R_t$ = 4.980 min, m/z found 630.3 $[M + H]^+$. SFC (Method 13): $R_t$ = 1.993 min. |
| 178 | 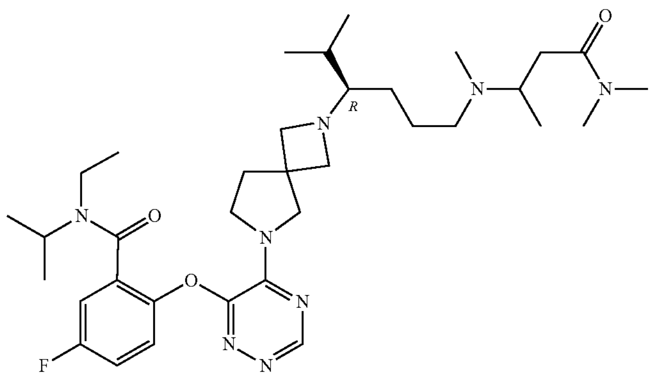 | Compound 288 | |

-continued
| Co. No. | Structure | Starting Material | Spectra Details |
|---|---|---|---|
| 180 | 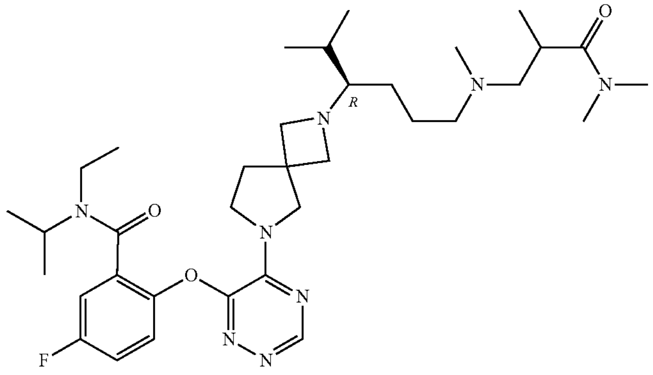 | Compound 289 | |
| 190 | 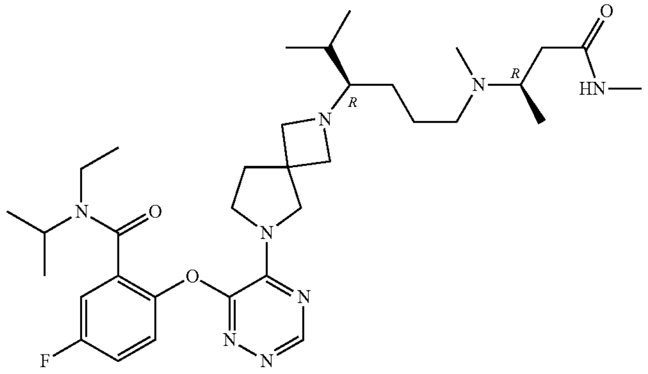 | Compound 290 | |
| 192 | 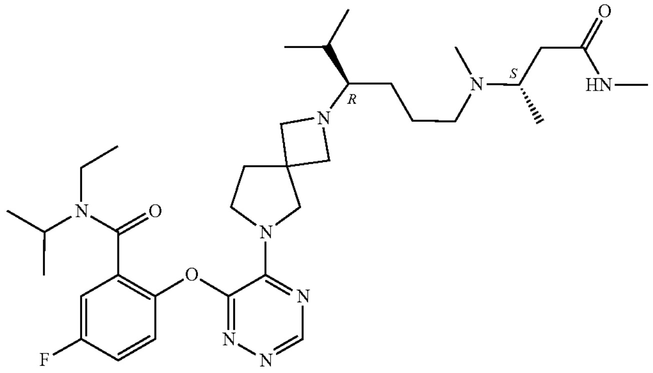 | Compound 291 | |
| 194 | 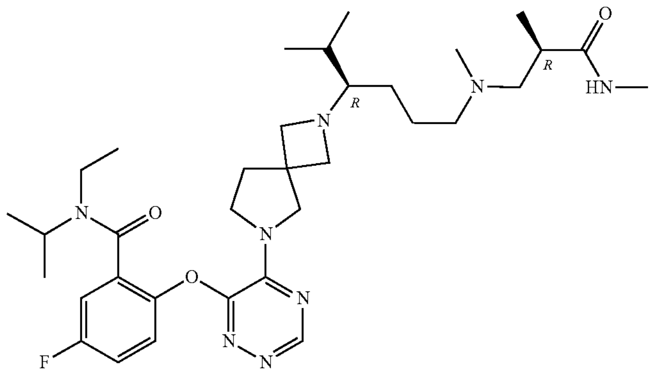 | Compound 292 | |

-continued
| Co. No. | Structure | Starting Material | Spectra Details |
|---|---|---|---|
| 196 | 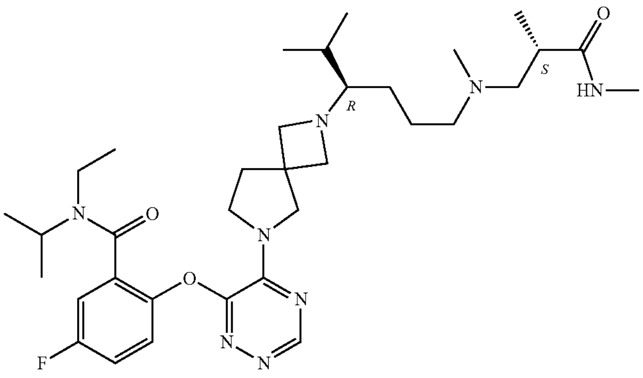 | Compound 293 | |
| 198 | 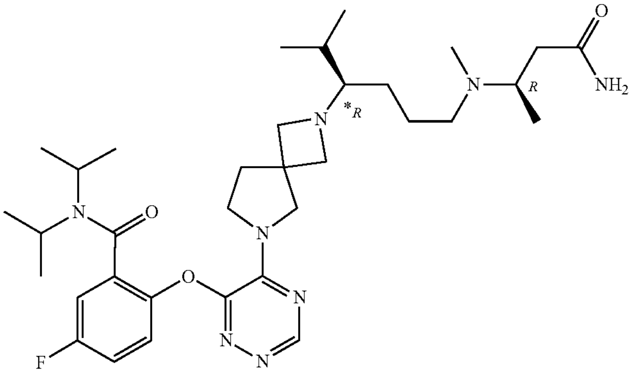 | Compound 294 | |
| 200 | 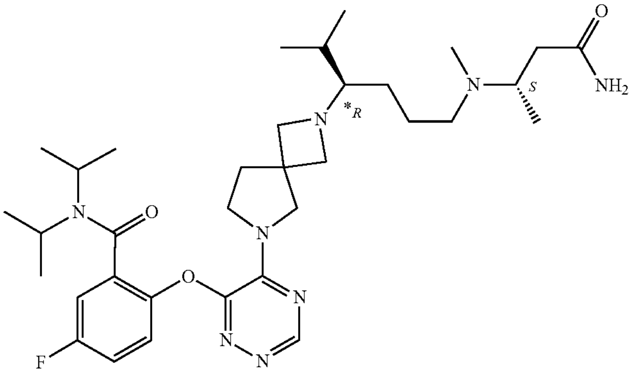 | Compound 295 | |
| 202 | 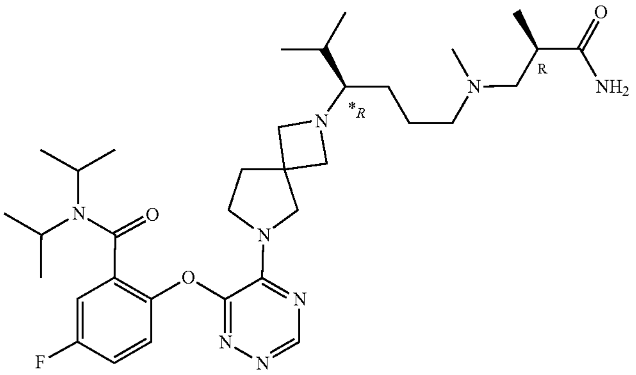 | Compound 296 | |

-continued
| Co. No. | Structure | Starting Material | Spectra Details |
|---|---|---|---|
| 204 | 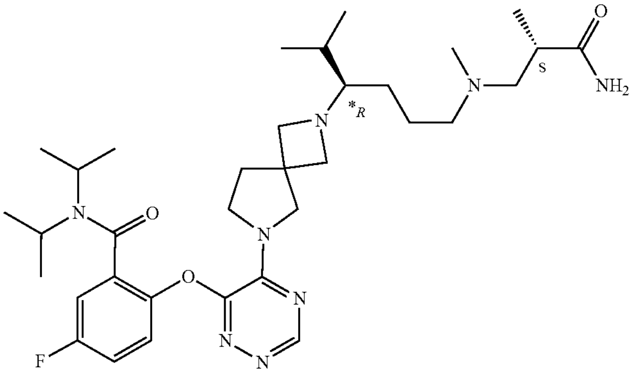 | Compound 297 | |
| 310 | 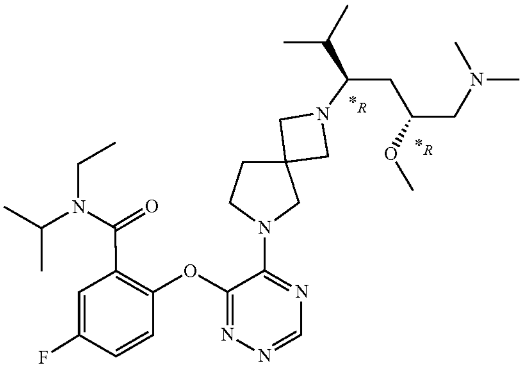 [SMILES: CCN(C(=O)c1cc(F)ccc1Oc1nncnc1N1CCC2(C1)CN([C@H](C[C@H](CN(C)C)OC)C(C)C)C2)C(C)C] | Compound 308 | |
| 311 | 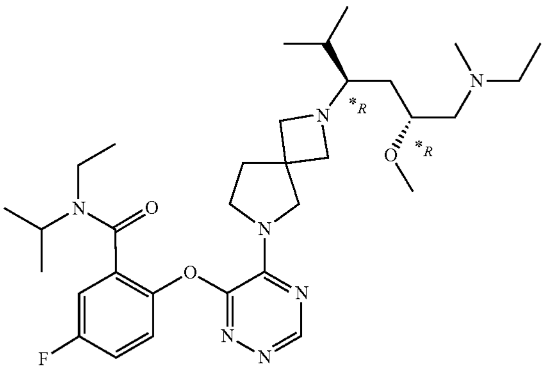 | Compound 308 | LC-MS (ESI) (Method 2): $R_t$ = 2.032 min, m/z found 630.3 $[M + H]^+$. SFC (Method 24): $R_t$ = 1.955 min. |
| 312 | 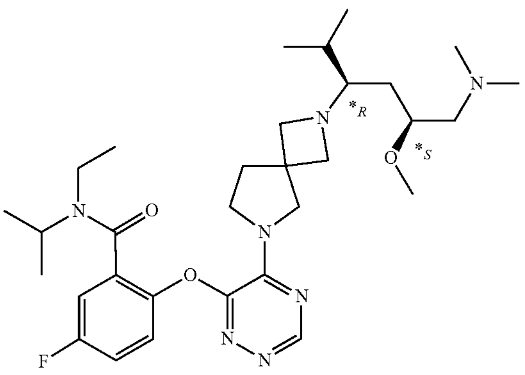 [SMILES: CCN(C(=O)c1cc(F)ccc1Oc1nncnc1N1CCC2(C1)CN([C@H](C[C@@H](CN(C)C)OC)C(C)C)C2)C(C)C] | Compound 309 | |

-continued
| Co. No. | Structure | Starting Material | Spectra Details |
|---|---|---|---|
| 313 | 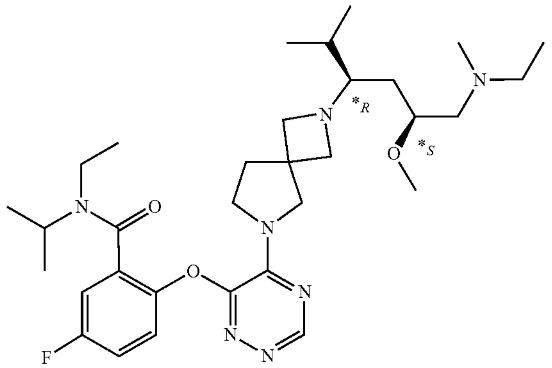 | Compound 309 | LC-MS (ESI) (Method 2): $R_t$ = 2.048 min, m/z found 630.3 $[M + H]^+$. SFC (Method 24): $R_t$ = 1.937 min. |
| 318 | 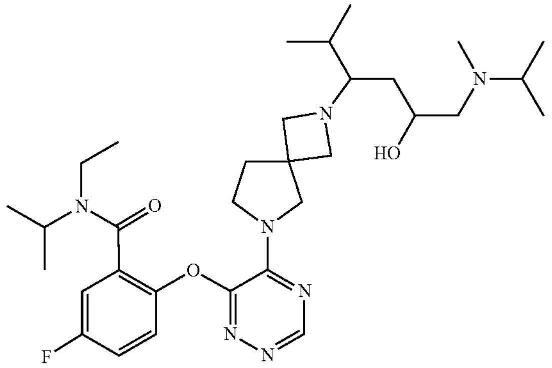 [SMILES: CCN(C(=O)c1cc(F)ccc1Oc1nncnc1N1CCC2(C1)CN(C(CC(O)CN(C)C(C)C)C(C)C)C2)C(C)C] | Compound 317 | |
| 329 | 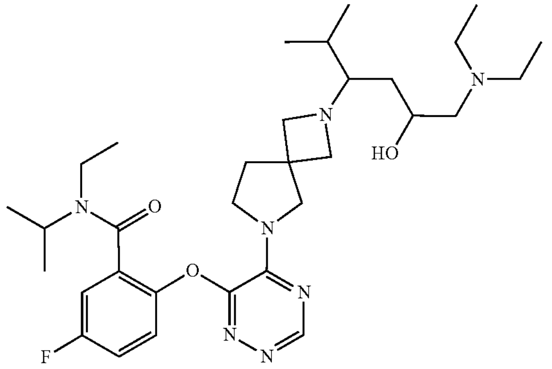 [SMILES: CCN(CC)CC(O)CC(C(C)C)N1CC2(CCN(c3ncnnc3Oc3ccc(F)cc3C(=O)N(CC)C(C)C)C2)C1] | Compound 328 | |
| 360 | 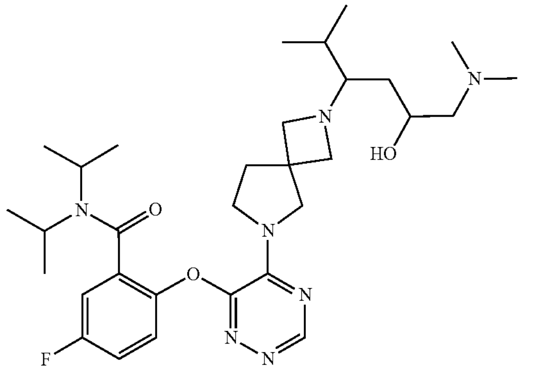 [SMILES: CC(C)C(CC(O)CN(C)C)N1CC2(CCN(c3ncnnc3Oc3ccc(F)cc3C(=O)N(C(C)C)C(C)C)C2)C1] | Compound 359 | |

-continued
| Co. No. | Structure | Starting Material | Spectra Details |
|---|---|---|---|
| 375 | 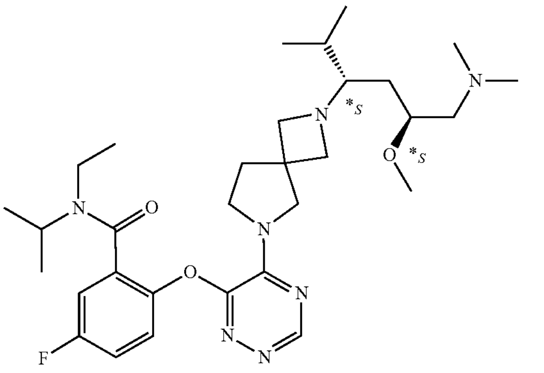 [SMILES: CCN(C(=O)c1cc(F)ccc1Oc1nncnc1N1CCC2(C1)CN([C@@H](C[C@@H](CN(C)C)OC)C(C)C)C2)C(C)C] | Compound 373 | |
| 376 | 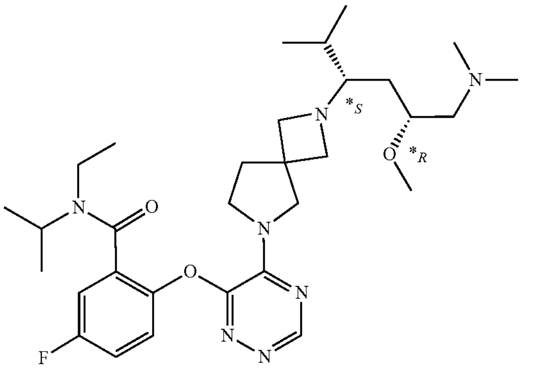 [SMILES: CCN(C(=O)c1cc(F)ccc1Oc1nncnc1N1CCC2(C1)CN([C@@H](C[C@H](CN(C)C)OC)C(C)C)C2)C(C)C] | Compound 374 | |
| 379 | 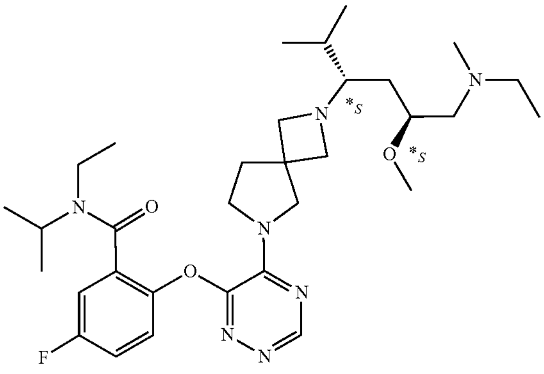 [SMILES: CCN(C)C[C@H](C[C@@H](C(C)C)N1CC2(CCN(c3ncnnc3Oc3ccc(F)cc3C(=O)N(CC)C(C)C)C2)C1)OC] | Compound 373 | LC-MS (ESI) (Method 2): $R_t$ = 2.039 min, m/z found 600.3 $[M + H]^+$. SFC (Method 24): $R_t$ = 1.907 min. |
| 380 | 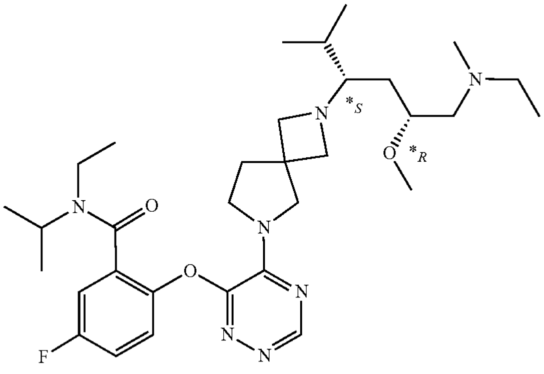 [SMILES: CCN(C)C[C@@H](C[C@@H](C(C)C)N1CC2(CCN(c3ncnnc3Oc3ccc(F)cc3C(=O)N(CC)C(C)C)C2)C1)OC] | Compound 374 | LC-MS (ESI) (Method 2): $R_t$ = 2.047 min, m/z found 600.3 $[M + H]^+$. SFC (Method 24): $R_t$ = 1.922 min. |

-continued
| Co. No. | Structure | Starting Material | Spectra Details |
|---|---|---|---|
| 383 | 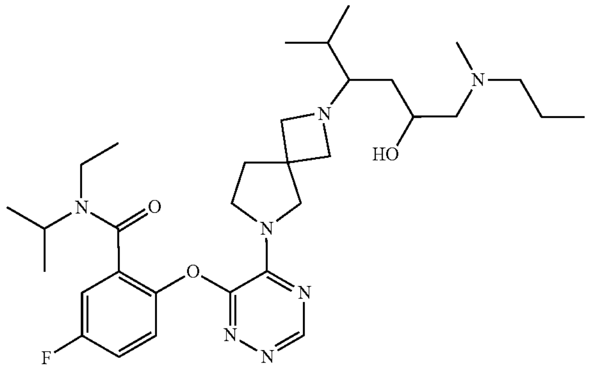 [SMILES: CCCN(C)CC(O)CC(C(C)C)N1CC2(CCN(c3ncnnc3Oc3ccc(F)cc3C(=O)N(CC)C(C)C)C2)C1] | Compound 317 | |
| 388 | 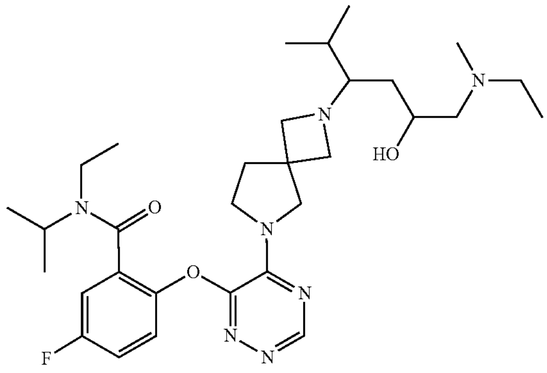 [SMILES: CCN(C)CC(O)CC(C(C)C)N1CC2(CCN(c3ncnnc3Oc3ccc(F)cc3C(=O)N(CC)C(C)C)C2)C1] | Compound 359 | |
| 411 | 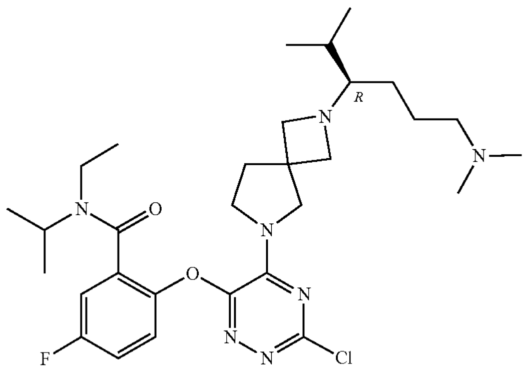 formate salt | Compound 406 | LC-MS (ESI) (Method 2): $R_t$ = 2.376 min, m/z found 590.3 $[M + H]^+$. SFC (Method 13): $R_t$ = 1.823 min. |

Compound 401, 415

(R)-N-(ethyl-$^{13}C_2$)-5-fluoro-2-((5-(2-(6-((2-methoxyethyl)(methyl)amino)-2-methylhexan-3-yl)-2,6-diazaspiro[3.4]octan-6-yl)-1,2,4-triazin-6-yl)oxy)-N-(propan-2-yl-$^{13}C_3$)benzamide (R)-5-fluoro-N-isopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)-N-methylbenzamide The following compounds were synthesized by an analogous method described above for Compound 27 by method C

| Co. No. | Structure | Starting Material | Spectra Details |
|---|---|---|---|
| 401 | 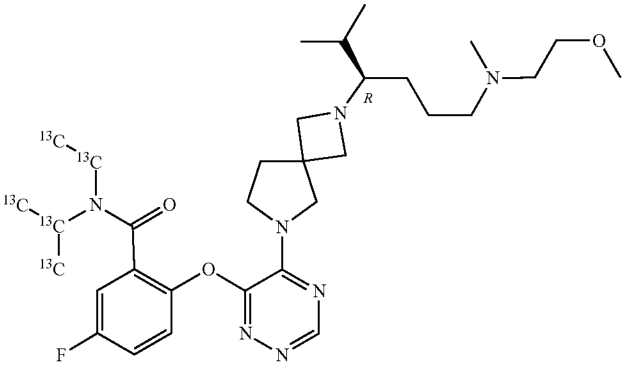 | Compound 400 | |
| 415 | 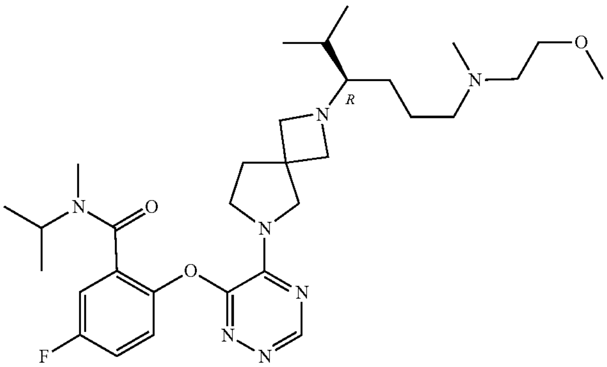 | Compound 414 | LC-MS (ESI) (Method 1): $R_t$ = 2.851 min, m/z found 586.5 $[M+H]^+$. SFC (Method 13): $R_t$ = 1.772 min. |

Compound 107, 108

(*R)—N-ethyl-S-fluoro-N-isopropyl-2-((4-(2-(6-((2-methoxyethyl)(methyl)amino)-methylhexan-3-yl)-2,6-diazaspiro[3.4]octan-6-yl)pyridazin-3-yl)oxy)benzamide (*S)—N-ethyl-fluoro-N-isopropyl-2-((4-(2-(6-((2-methoxyethyl)(methyl)amino)-2-methylhexan-3-yl)-2,6-diazaspiro[3.4]octan-6-yl)pyridazin-3-yl)oxy)benzamide

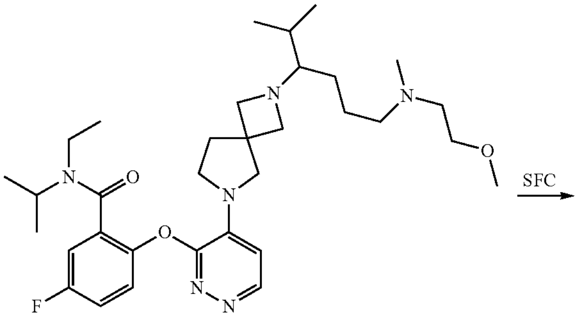

Compound 82

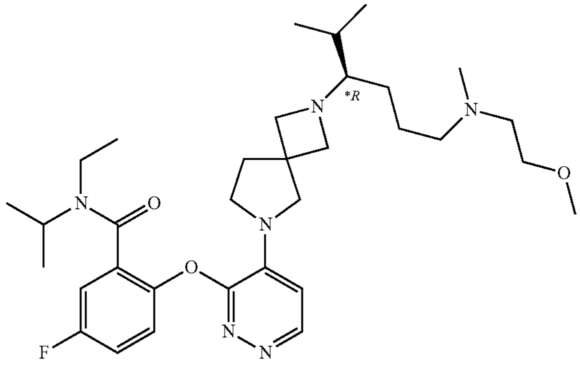

Compound 107

+

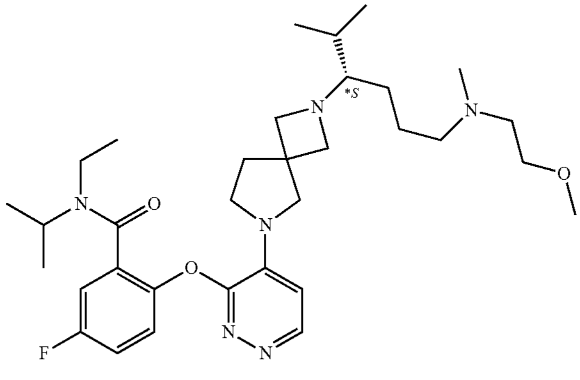

Compound 108

N-ethyl-5-fluoro-N-isopropyl-2-((4-(2-(6-((2-methoxyethyl)(methyl)amino)-2-methylhexan-3-yl)-2,6-diazaspiro[3.4]octan-6-yl)pyridazin-3-yl)oxy)benzamide (Compound 82) (47.0 mg) was purified by SFC over DAICEL CHIRALPAK IE (column: 250×30 mm 10 um; eluent: 100% MeOH (0.1% ammonia); flowrate: 25 ml/min) to afford the title compounds Compound 107 (19.0 mg, 40%) and Compound 108 (21.2 mg, 45%) as white solid.

Compound 117, 118

(*R)-5-fluoro-N,N-diisopropyl-2-((4-(2-(6-((2-methoxyethyl)(methyl)amino)-methylhexan-3-yl)-2,6-diazaspiro[3.4]octan-6-yl)pyridazin-3-yl)oxy)benzamide (*S)-5-fluoro-N,N-diisopropyl-2-((4-(2-(6-((2-methoxyethyl)(methyl)amino)-methylhexan-3-yl)-2,6-diazaspiro[3.4]octan-6-yl)pyridazin-3-yl)oxy)benzamide

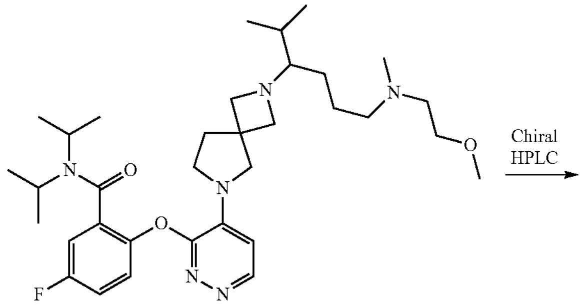

Compound 87

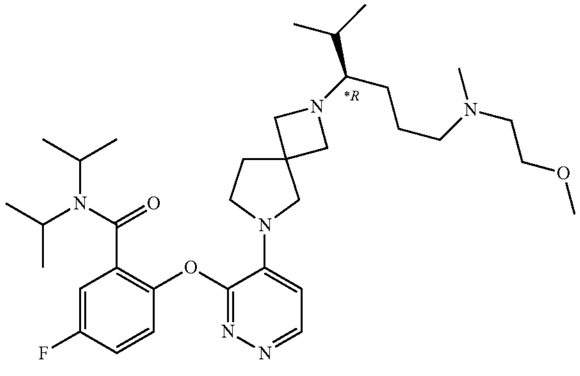

Compound 117

+

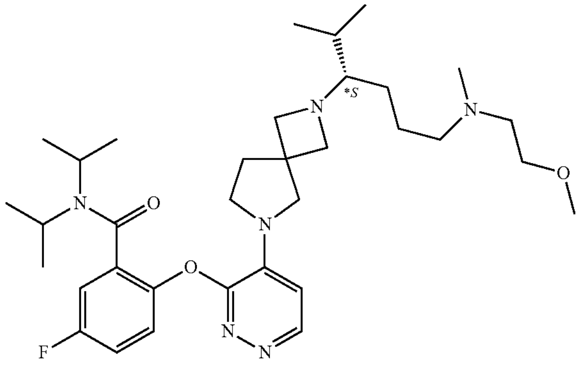

Compound 118

5-fluoro-N,N-diisopropyl-2-((4-(2-(6-((2-methoxyethyl)(methyl)amino)-2-methylhexan-3-yl)-2,6-diazaspiro[3.4]octan-6-yl)pyridazin-3-yl)oxy)benzamide (Compound 87) (300 mg) was purified by chiral HPLC over CHIRALPAK AD-H (column: 5×25 cm, 10 um; Isocratic elution: n-Hexane/EtOH/DEA=90/10/0.1 (v/v/v); Flow rate: 60 mL/min, Temperature: 35° C.) to afford the title compounds Compound 117 (122.8 mg) and Compound 118 (137.0 mg) both as white solid.

Compound 109, 110

(*R)-5-fluoro-N,N-diisopropyl-2-((5-(2-(6-((2-methoxyethyl)(methyl)amino)-methylhexan-3-yl)-2,6-diazaspiro[3.4]octan-6-yl)-1,2,4-triazin-6-yl)oxy)benzamide (*S)-5-fluoro-N,N-diisopropyl-2-((5-(2-(6-((2-methoxyethyl)(methyl)amino)-methylhexan-3-yl)-2,6-diazaspiro[3.4]octan-6-yl)-1,2,4-triazin-6-yl)oxy)benzamide

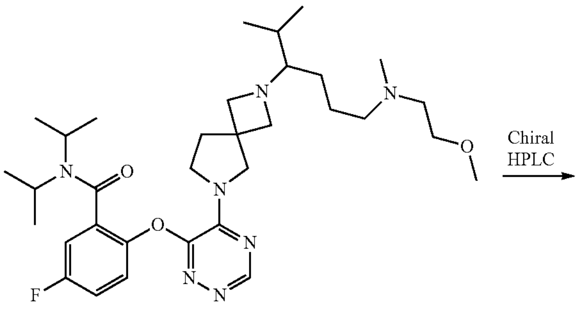

Compound 93

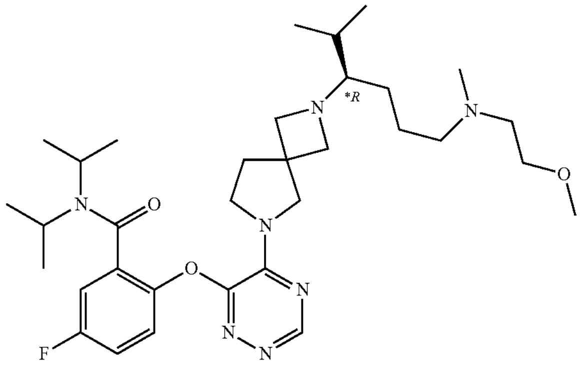

Compound 109

+

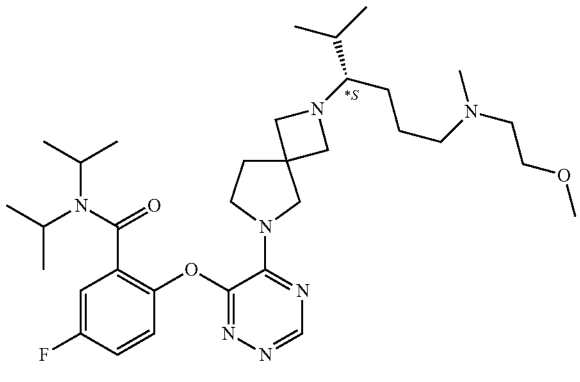

Compound 110

5-fluoro-N,N-diisopropyl-2-((5-(2-(6-((2-methoxyethyl)(methyl)amino)-2-methylhexan-3-yl)-2,6-diazaspiro[3.4]octan-6-yl)-1,2,4-triazin-6-yl)oxy)benzamide (Compound 93) (110 mg) was first separated by preparative chiral HPLC over DAICEL CHIRALPAK AD (column: 5×25 cm 10 um; Mobile phase: A: n-Hexane, B: Ethanol/DEA=10/0.1 (v/v), A:B=90:10 at 60 mL/min; Column Temp: 38° C.) and further purified by preparative HPLC using Phenomenex Gemini NX (column: 75×30 mm 3 um; Mobile Phase A: water (0.05% $NH_3H_2O$+10 mM $NH_4HCO_3$), B: ACN, gradient from 50% B to 80% B; Flow rate: 25 mL/min) to afford the title compounds Compound 109 (27 mg) and Compound 110 (27 mg).

Compound 69

N-ethyl-5-fluoro-N-isopropyl-2-((5-(2-(6-((2-methoxy-2-methylpropyl)amino)-2-methylhexan-3-yl)-2,6-diazaspiro[3.4]octan-6-yl)-1,2,4-triazin-6-yl)oxy)benzamide

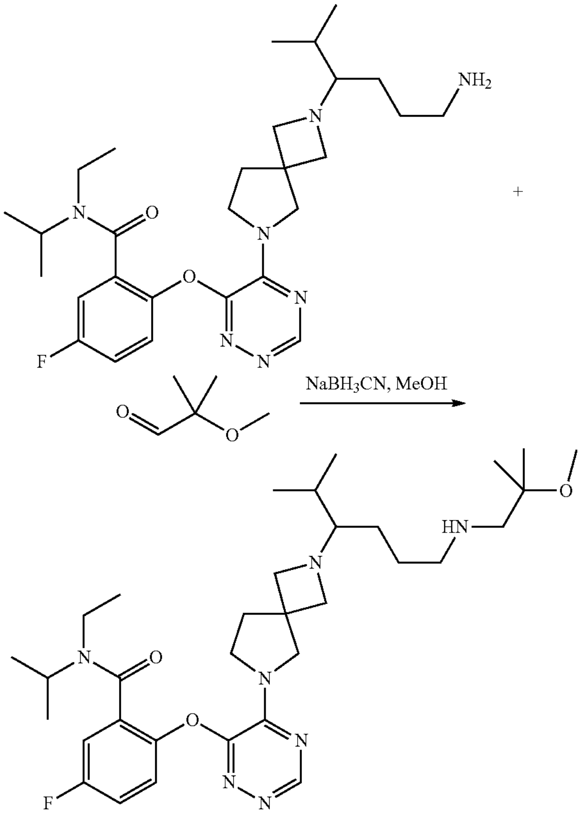

$NaBH_3CN$ (42 mg, 0.666 mmol) was added to a mixture of 2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide (Compound 3) (200 mg, 0.333 mmol) and 2-methoxy-2-methylpropanal (72 mg, 0.333 mmol) in MeOH (5 mL) and the reaction mixture was stirred at RT overnight. The reaction mixture was diluted with DCM and basified with 10% aq. $K_2CO_3$ solution. The organic layer was decanted, filtered through Chromabond® and evaporated to dryness. The residue was purified twice by chromatography over silica gel (irregular SiOH, 24 g; mobile phase: gradient from 0.3% $NH_4OH$, 3% MeOH, 97%

DCM to 1% $NH_4OH$, 10% MeOH, 90% DCM). The pure fractions were collected and evaporated to dryness to afford the title compound (68 mg, 33% yield).

LC-MS (ESI) (Method 4): $R_t$=2.39 min, m/z found 614.8 $[M+H]^+$.

Compound 14, 17, 255, 82, 87

(R)-N-ethyl-5-fluoro-N-isopropyl-2-((5-(2-(2-methyl-6-((3,3,3-trifluoropropyl)amino)hexan-3-yl)-2,6-diazaspiro[3.4]octan-6-yl)-1,2,4-triazin-6-yl)oxy)benzamide (R)-N-ethyl-5-fluoro-N-isopropyl-2-((5-(2-(2-methyl-6-((2,2,2-trifluoroethyl)amino)hexan-3-yl)-2,6-diazaspiro[3.4]octan-6-yl)-1,2,4-triazin-6-yl)oxy)benzamide (R)-2-((5(2-(6-((1,3-dihydroxypropan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((4-(2-(6-((2-methoxyethyl)(methyl)amino)-2-methylhexan-3-yl)-2,6-diazaspiro[3.4]octan-6-yl)pyridazin-3-yl)oxy)benzamide 5-fluoro-N,N-diisopropyl-2-((4-(2-(6-((2-methoxyethyl)(methyl)amino)-2-methylhexan-3-yl)-2,6-diazaspiro[3.4]octan-6-yl)pyridazin-3-yl)oxy)benzamide The following Compounds were synthesized by an analogous method described above for Compound 69

| Ex. No. | Structure | Starting Materials | Conditions | Spectra Details |
|---|---|---|---|---|
| 14 | 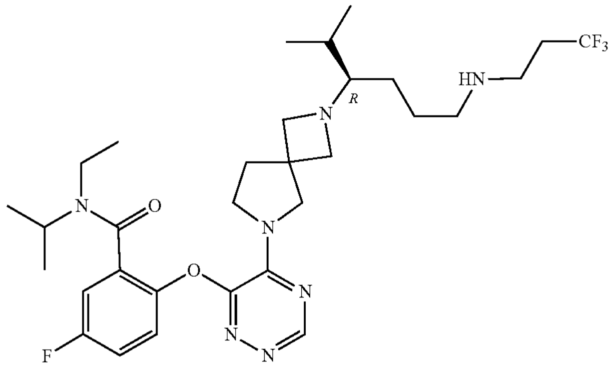 | Compound 64, 3,3,3-trifluoro-propanal | $ZnCl_2$, $NaBH_3CN$, MeOH, RT | LC-MS (ESI) (Method 2): $R_t$ = 2.145 min, m/z found 624.3 $[M + H]^+$. |
| 17 | 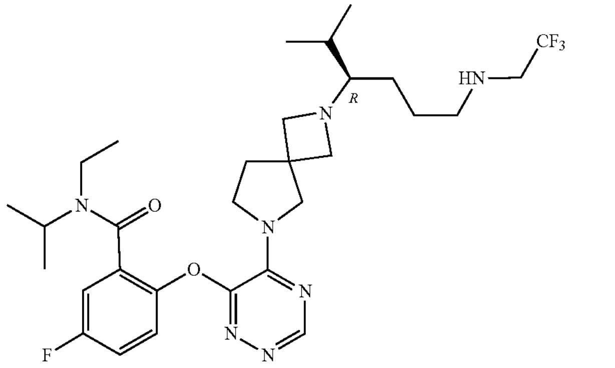 | Compound 64, 2,2,2-trifluoro-acetal-dehyde | $ZnCl_2$, $NaBH_3CN$, MeOH, 80° C. | LC-MS (ESI) (Method 2): $R_t$ = 2.085 min, m/z found 610.3 $[M + H]^+$. |

-continued
| Ex. No. | Structure | Starting Materials | Conditions | Spectra Details |
| --- | --- | --- | --- | --- |
| 255 | 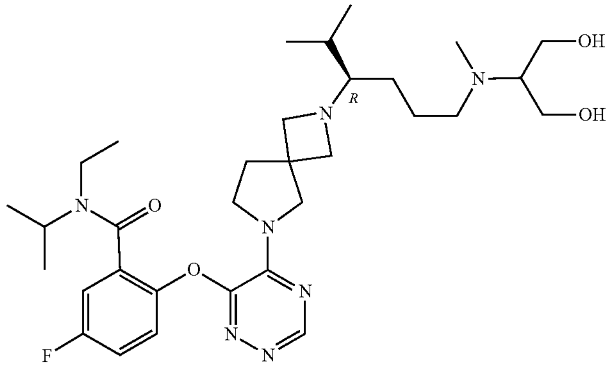 | Compound 19, 1,3-dihydroxy-propan-2-one | $ZnCl_2$, $NaBH_3CN$, MeOH, 45° C. | |
| 82 | 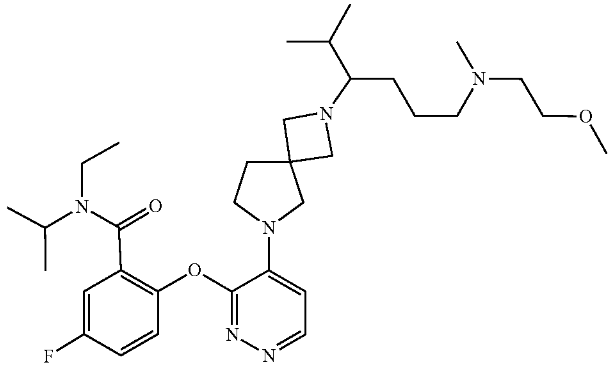 [SMILES: CCN(C(=O)c1cc(F)ccc1Oc1nnccc1N1CCC2(C1)CN(C(CCCN(C)CCOC)C(C)C)C2)C(C)C] | Compound 80, 1,1,2-trimethoxy-ethane, HCl | $NaBH_3CN$, AcOH, EtOH | |
| 87 | 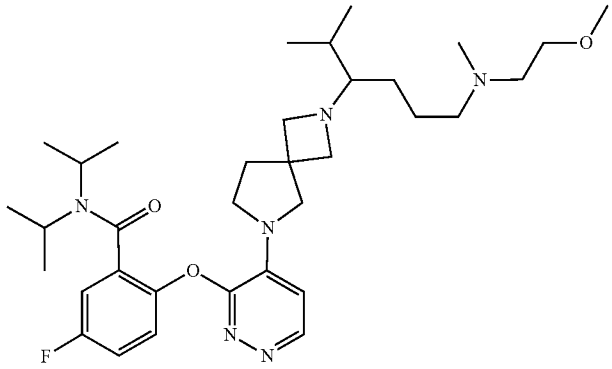 [SMILES: COCCN(C)CCCC(C(C)C)N1CC2(CCN(c3ccnnc3Oc3ccc(F)cc3C(=O)N(C(C)C)C(C)C)C2)C1] | Compound 86, 1,1,2-trimethoxy-ethane, HCl | $NaBH_3CN$, AcOH, EtOH | |

Compound 21

(R)-N-ethyl-5-fluoro-N-isopropyl-2-((5-(2-(2-methyl-6-(methyl(2,2,2-trifluormethyl)amino)hexan-3-yl)-2,6-diazaspiro[3.4]octan-6-yl)-1,2,4-triazin-6-yl)oxy)benzamide

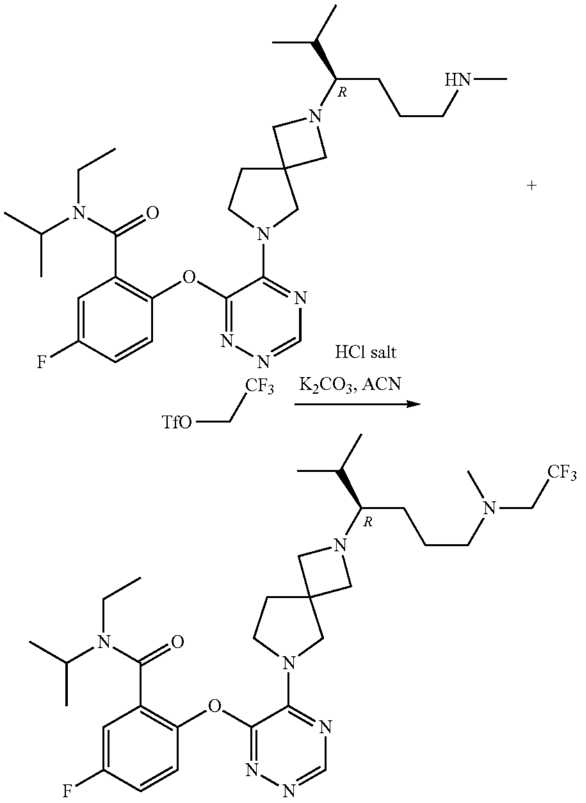

The mixture of (R)-N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide hydrochloride (Compound 19) (50 mg, 0.086 mmol), 2,2,2-trifluoroethyl trifluoromethanesulfonate (60.2 mg, 0.259 mmol) and $K_2CO_3$ (112 mg, 0.865 mmol) in ACN (1 mL) was stirred at RT for 16 h. The reaction mixture was filtered and the filtrate was purified by preparative HPLC over Phenomenex Gemini-NX (column: 80×40 mm 3 um, Mobile Phase A: water (0.05% ammonia+10 mM $NH_4HCO_3$), Mobile Phase B: ACN, Flow rate: 25 mL/min, gradient condition B/A from 52% B to 82%) to afford the title compound (12.06 mg, 97% purity, 22% yield) as brown oil.

LC-MS (ESI) (Method 2): $R_t$=2.345 min, m/z found 624.3 $[M+H]^+$.

Compound 15, 23, 247, 253

(R)-2-((5-(2-(6-((2,2-difluoroethyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (R)-2-((5-(2-(6-((2-(dimethylamino)-2-oxoethyl)(methyl)amino-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((5-(2-((3R)-6-((2-methoxypropyl)(methyl)amino)-2-methylhexan-3-yl)-2,6-diazaspiro[3.4]octan-6-yl)-1,2,4-triazin-6-yl)oxy)benzamide N-ethyl-5-fluoro-N-isopropyl-2-((5-(2-((3S)-6-((2-methoxypropyl)(methyl)amino)-2-methylhexan-3-yl)-2,6-diazaspiro[3.4]octan-6-yl)-1,2,4-triazin-6-yl)oxy)benzamide The following Compounds were synthesized by an analogous method described above for Compound 21

| Co. No. | Structure | Starting Materials | Conditions | Spectra Details |
|---|---|---|---|---|
| 15 | 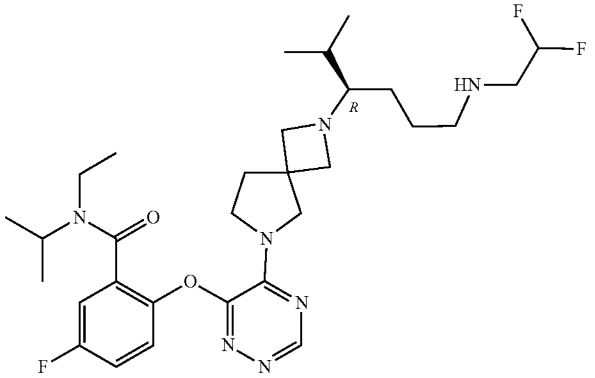 | Compound 65, 2,2-difluoroethyl trifluoro-methane-sulfonate | DIEA, DMF, 40° C. | LC-MS (ESI) (Method 2): $R_t$ = 3.025 min, m/z found 592.3 $[M + H]^+$. |

-continued
| Co. No. | Structure | Starting Materials | Conditions | Spectra Details |
|---|---|---|---|---|
| 23 | 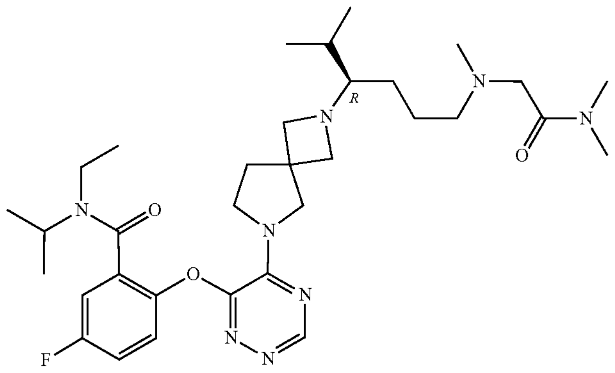 | Compound 19, 2-chloro-N,N-dimethyl-acetamide | $K_2CO_3$, MeOH | LC-MS (ESI) (Method 1): $R_t$ = 2.875 min, m/z found 627.3 $[M + H]^+$. |
| 247 | 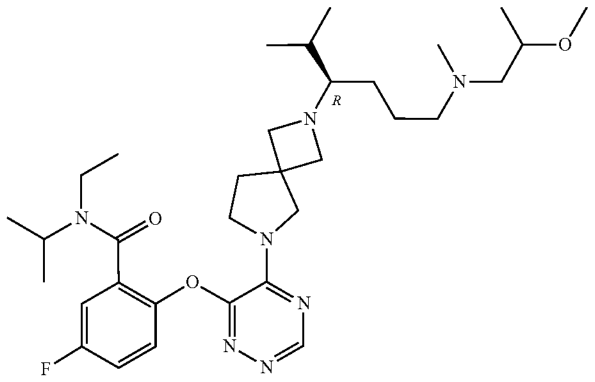 | Compound 19, intermediate 139 | $Cs_2CO_3$, NaI, DMF | |
| 253 | 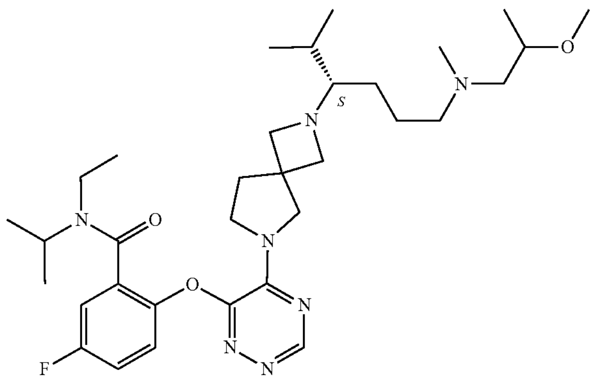 | Compound 20, intermediate 139 | $Cs_2CO_3$, NaI, DMF | |

Compound 24

(*S)-2-((5-(2-(1-amino-3-methylbutan-2-yl)-2,6-diazaspiro[3.4]octan-6-yl)-1,2,4-triazin-6-yl)oxy)-N-ethyl-5-fluoro-N-isopropylbenzamide

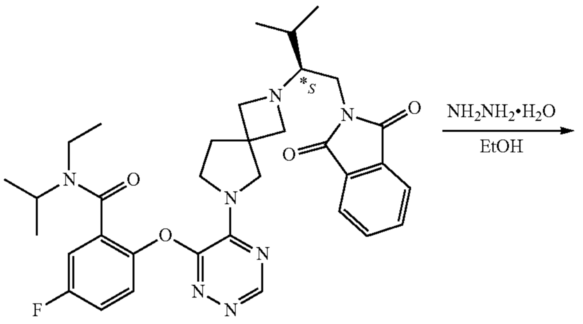

-continued

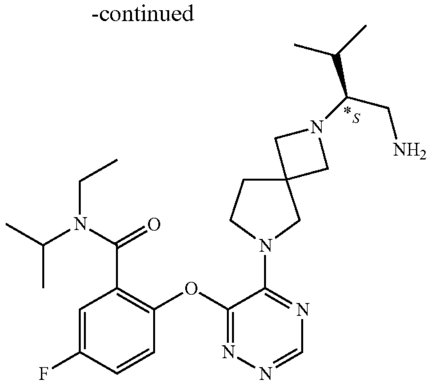

To a solution of (*S)-2-((5-(2-(1-(1,3-dioxoisoindolin-2-yl)-3-methylbutan-2-yl)-2,6-diazaspiro[3.4]octan-6-yl)-1,2,4-triazin-6-yl)oxy)-N-ethyl-5-fluoro-N-isopropylbenzamide (intermediate 18) (0.05 g, 0.079 mmol) in EtOH (2 ML) was added hydrazinium hydroxide (0.127 g, 3.97 mmol). The resulting mixture was stirred at 25° C. for 8 h. The reaction was concentrated under reduced pressure and the residue was purified by preparative HPLC over Boston Prime (column: C18 150×30 mm Sum, Mobile Phase A: water (0.04% ammonia+10 mM $NH_4HCO_3$), Mobile Phase B: ACN, Flow rate: 30 mL/min, gradient condition B/A from 25% to 55%) to afford the title compound (5.74 mg, 99.5% purity, 14.4% yield) as a white solid.

LC-MS (ESI) (Method 1): $R_t$=2.94 min, m/z found 500.4 $[M+H]^+$.

SFC (Method 7): $R_t$=5.183 min.

Compound 25

(*R)-2-((5-(2-(1-amino-3-methylbutan-2-yl)-2,6-diazaspiro[3.4]octan-6-yl)-1,2,4-triazin-6-yl)oxy)-N-ethyl-5-fluoro-N-isopropylbenzamide The following Compound was synthesized by an analogous method described above for Compound 24

| Co. No. | Structure | Starting Materials | Spectra Details |
|---|---|---|---|
| 25 | 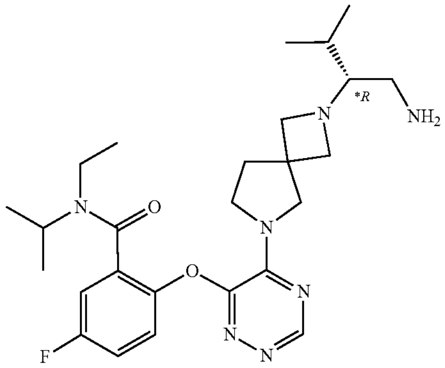 [SMILES: CCN(C(=O)c1cc(F)ccc1Oc1nncnc1N1CCC2(C1)CN([C@@H](CN)C(C)C)C2)C(C)C] | intermediate 17 | LC-MS (ESI) (Method 1): $R_t$ = 2.91 min, m/z found 500.4 $[M + H]^+$. SFC (Method 7): $R_t$ = 3.879 min. |

Compound 35

(*R)-2-((5-(2-(2,6-dimethyl-6-(methylamino)heptan-3-yl)-2,6-diazaspiro[3.4]octan-6-yl)-1,2,4-triazin-6-yl)oxy)-N-ethyl-5-fluoro-N-isopropylbenzamide hydrochloride

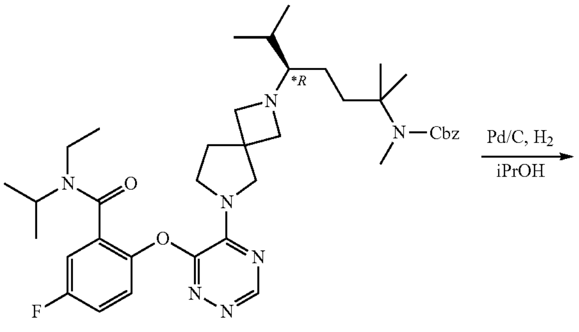

-continued

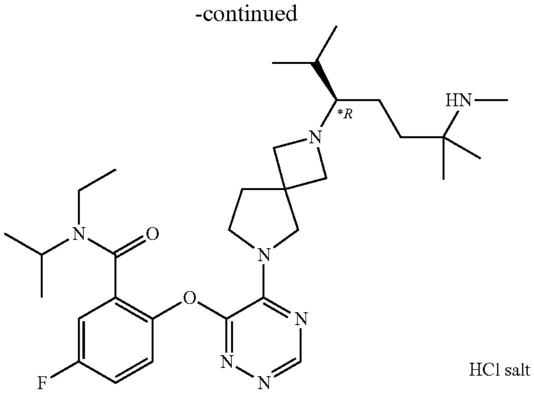

HCl salt

To the mixture of benzyl (*R)-(5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)(methyl)carbamate (intermediate 40) (210 mg, 0.298 mmol) and HCl (18 μL, 0.22 mmol) in i-PrOH (5 mL) was added Pd/C (20 mg, 10%) under Ar. The resulting mixture was stirred at 25° C. for 12 h under $H_2$ (15 PSI) atmosphere. The mixture was filtered and the filtrate was concentrated under reduced pressure to give a crude product, which was further purified by preparative HPLC over Phenomenex Gemini-NX (column: 150×30 mm Sum, Mobile Phase A: $H_2O$ (0.05% HCl), Mobile Phase B: ACN, Flow rate: 35 mL/min, gradient condition B/A from 3% to 29%) to afford the title compound (170 mg, 98% purity, 92% yield) as a white solid.

LC-MS (ESI) (Method 2): $R_t$=2.040 min, m/z found 570.3 $[M+H]^+$.

SFC (Method 8): $R_t$=2.145 min.

Compound 36

(*S)-2-((5-(2-(2,6-dimethyl-6-(methylamino)heptan-3-yl)-2,6-diazaspiro[3.4]octan-6-yl)-1,2,4-triazin-6-yl)oxy)-N-ethyl-5-fluoro-N-isopropylbenzamide hydrochloride The following Compound was synthesized by an analogous method described above for Compound 35

| Co. No. | Structure | Starting Materials | Spectra Details |
| --- | --- | --- | --- |
| 36 | 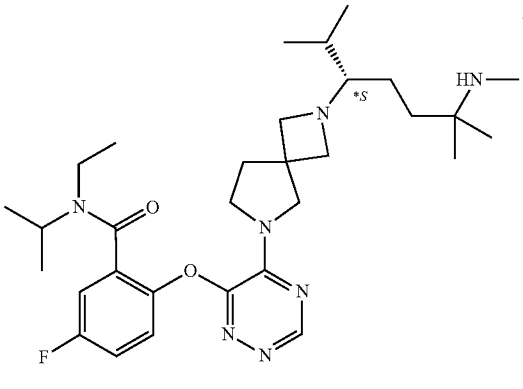 [SMILES: CCN(C(=O)c1cc(F)ccc1Oc1nncnc1N1CCC2(C1)CN([C@@H](CCC(C)(C)NC)C(C)C)C2)C(C)C] HCl salt | intermediate 41 | LC-MS (ESI) (Method 2): $R_t$ = 1.970 min, m/z found 570.3 $[M + H]^+$. SFC (Method 8): $R_t$ = 2.347 min. |

Compound 39

1-((((R)-4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamoyl)oxy)ethyl isobutyrate

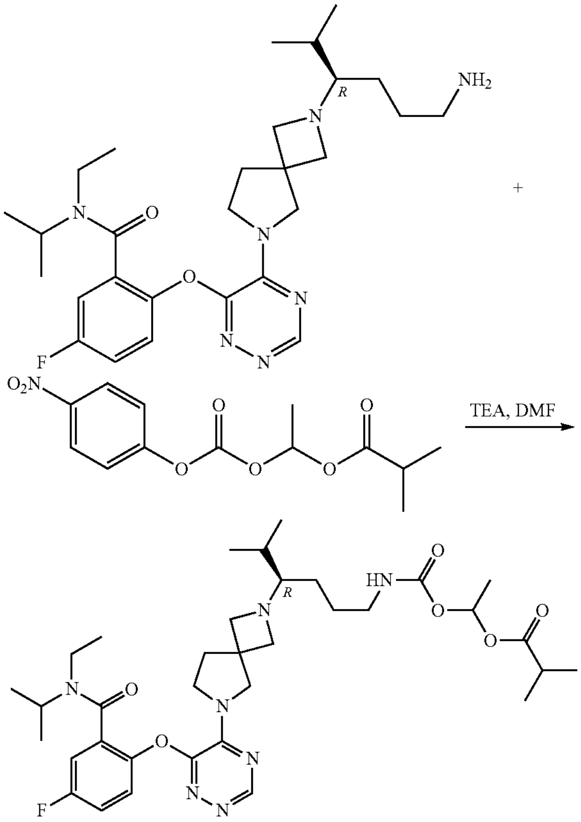

The mixture of (R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide (Compound 64) (150 mg, crude), 1-(((4-nitrophenoxy)carbonyl)oxy)ethyl isobutyrate (102 mg, 0.343 mmol) and TEA (144 mg, 1.42 mmol) in anhydrous DMF (5 mL) was stirred at 25° C. for 2 h. The mixture was concentrated under reduced pressure to give the crude product which was further purified by preparative HPLC over Boston Prime (column: C18 150×30 mm Sum, Mobile Phase A: $H_2O$ (0.04% ammonia+10 mM $NH_4HCO_3$), Mobile Phase B: ACN, Flow rate: 25 mL/min, gradient condition B/A from 55% to 85%) to afford the title compound (82.20 mg) as a yellow solid.

LC-MS (ESI) (Method 1): $R_t$=3.901 min, m/z found 686.3 $[M+H]^+$.

Compound 40, 41, 42

1-((((R)-4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamoyl)oxy)ethyl isobutyrate 1-((((R)-4-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)carbamoyl)oxy)ethyl isobutyrate formate 1-((((R)-4-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)carbamoyl)oxy)ethyl isobutyrate The following Compounds were synthesized by an analogous method described above for Compound 39

| Co. No. | Structure | Starting Materials | Spectra Details |
|---|---|---|---|
| 40 | 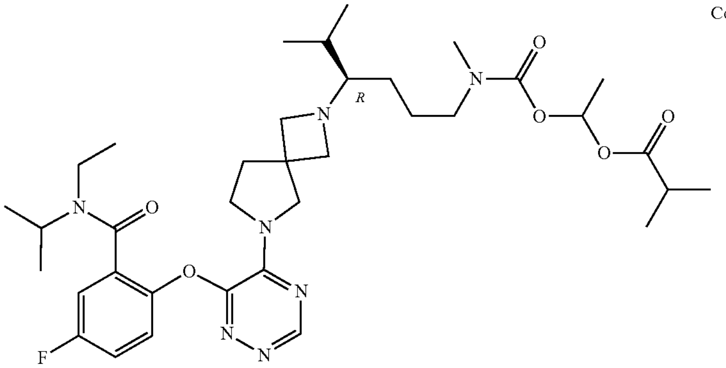 | Compound 19 | LC-MS (ESI) (method 2): $R_t$ = 2.990 min, m/z found 700.3 $[M + H]^+$. |
| 41 | 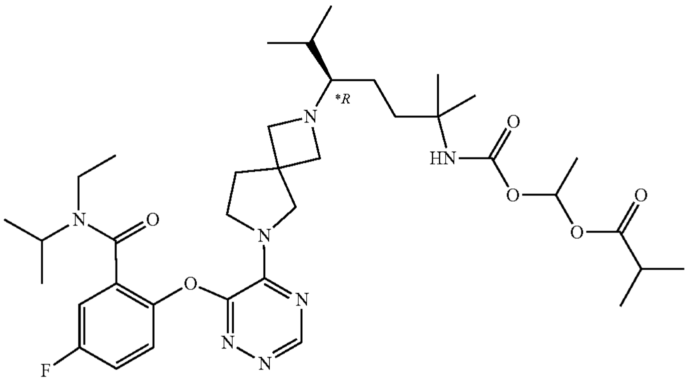 [SMILES: CCN(C(=O)c1cc(F)ccc1Oc1nncnc1N1CCC2(C1)CN([C@H](CCC(C)(C)NC(=O)OC(C)OC(=O)C(C)C)C(C)C)C2)C(C)C] formate salt | Compound 30 | LC-MS (ESI) (method 3) $R_t$ = 5.523 min, m/z found 714.3 $[M + H]^+$. |
| 42 | 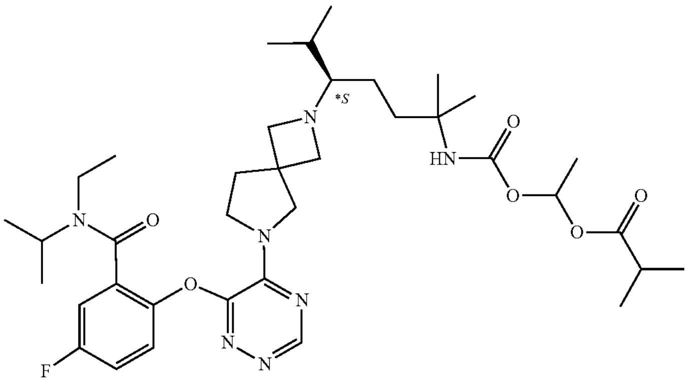 [SMILES: CCN(C(=O)c1cc(F)ccc1Oc1nncnc1N1CCC2(C1)CN([C@H](CCC(C)(C)NC(=O)OC(C)OC(=O)C(C)C)C(C)C)C2)C(C)C] | Compound 31 | LC-MS (ESI) (Method 3): $R_t$ = 5.516 min, m/z found 714.4 $[M + H]^+$. |

Compound 43

(*R)-4-(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanamido

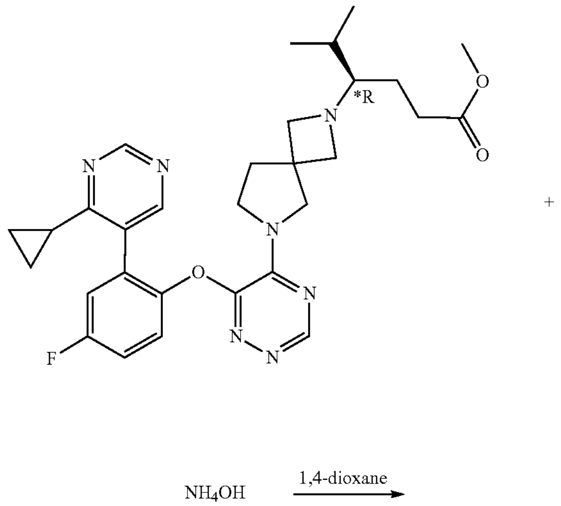

-continued

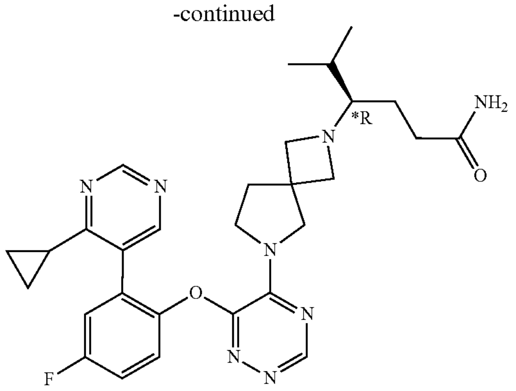

To the mixture of methyl (*R)-4-(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanoate (intermediate 48) (110 mg, 0.178 mmol) in $NH_4OH$ (10 mL) and 1,4-dioxane (5 mL) was added $NH_4Cl$ (95 mg, 1.78 mmol). The resulting mixture was stirred at 40° C. for 16 h. After cooling to RT, the reaction mixture was concentrated in vacuo and the residue was purified by preparative HPLC using a Boston Prime (column: C18 150×30 mm 5 um; eluent: $ACN/H_2O$ (0.04% ammonia+10 mM $NH_4HCO_3$) from 30% to 60% (v/v)) to afford the title compound (34 mg, 34%) as a white solid.

LC-MS (ESI) (Method 1): $R_t$=3.287 min, m/z found 547.2 $[M+H]^+$.

SFC (Method 9): $R_t$=6.275 min.

Compound 44

The following Compound was synthesized by an analogous method described above for Compound 43

| Co. No. | Structure | Starting Materials | Spectra Details |
|---|---|---|---|
| 44 | 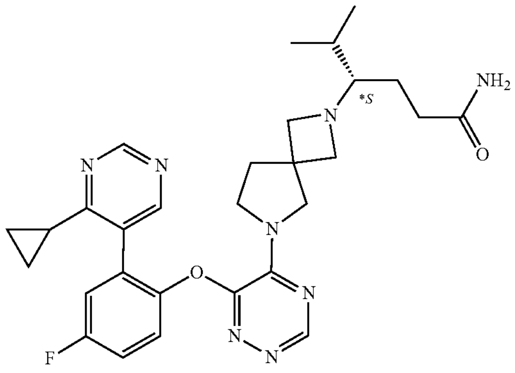 [SMILES: CC(C)[C@H](CCC(N)=O)N1CC2(CCN(c3ncnnc3Oc3ccc(F)cc3-c3cncnc3C3CC3)C2)C1] | intermediate 49 | LC-MS (ESI) (Method 1): $R_t$ = 3.292 min, m/z found 547.2 $[M + H]^+$. SFC (Method 9): $R_t$ = 7.506 min. |

Compound 50

4-(6-(6-(2-(4-cyclopropylpyrimidin-5-yl)-4-fluorophenoxy)-1,2,4-triazin-5-yl)-2,6-diazaspiro[3.4]octan-2-yl)-N,5-dimethylhexanamide

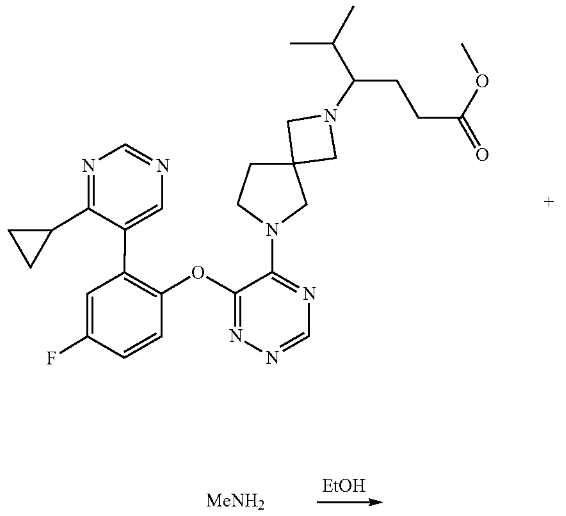

-continued

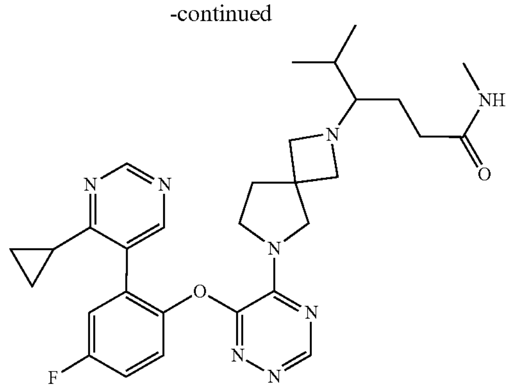

Methanamine hydrochloride (600 mg, 8.89 mmol) was added to a solution consisting of methyl 4-(6-(6-(2-(4-cyclopropylpyrimidin-5-yl)-4-fluorophenoxy)-1,2,4-triazin-5-yl)-2,6-diazaspiro[3.4]octan-2-yl)-5-methylhexanoate (intermediate 47) (500 mg, 0.890 mmol) in $MeNH_2$/EtOH (33%, 20 mL). The reaction mixture was stirred at 80° C. for 5 h. After cooling to RT, the reaction mixture was concentrated under reduced pressure to afford the crude product which was further purified by FCC (DCM/MeOH=10:1) to afford the title compound (100 mg, 18% yield) as a yellow solid.

Compound 45 and 46

(*S)-4-(6-(6-(2-(4-cyclopropylpyrimidin-5-yl)-4-fluorophenoxy)-1,2,4-triazin-5-yl)-2,6-diazaspiro[3.4]octan-2-yl)-N,5-dimethylhexanamide (*R)-4-(6-(6-(2-(4-cyclopropylpyrimidin-5-yl)-4-fluorophenoxy)-1,2,4-triazin-5-yl)-2,6-diazaspiro[3.4]octan-2-yl)-N,5-dimethylhexanamide

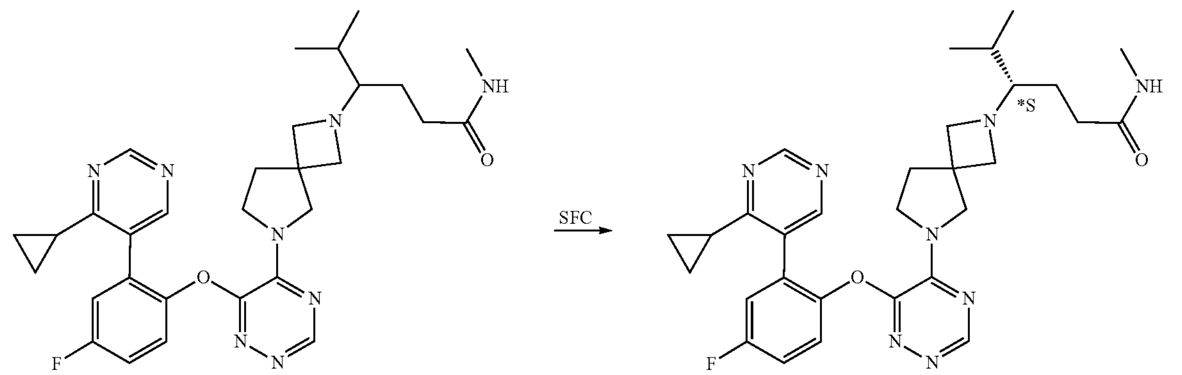

Compound 45

+

-continued

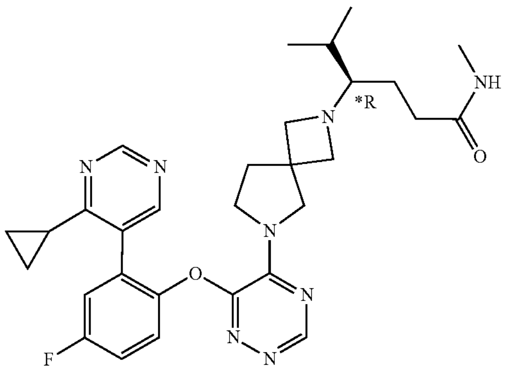

Compound 46

4-(6-(6-(2-(4-cyclopropylpyrimidin-5-yl)-4-fluorophenoxy)-1,2,4-triazin-5-yl)-2,6-diazaspiro[3.4]octan-2-yl)-N,5-dimethylhexanamide (Compound 50) (250 mg, 0.446 mmol) was purified by SFC over DAICEL CHIRALPAK AS (250x30 mm 10 um) (eluent: supercritical $CO_2$ in EtOH (0.1% v/v ammonia) 20/20, v/v) to afford the title compounds Compound 45 (81.10 mg, 98% purity, 32% yield) and Compound 46 (72.53 mg, 98% purity, 28% yield) both as white solid.

Compound 45

LC-MS (ESI) (Method 1): $R_t$=3.323 min, m/z found 561.2 $[M+H]^+$.

SFC (Method 10): $R_t$=3.880 min.

Compound 46

LC-MS (ESI) (Method 1): $R_t$=3.353 min, m/z found 561.2 $[M+H]^+$.

SFC (Method 10): $R_t$=3.707 min.

Compound 49

N-ethyl-5-fluoro-2-((5-(2-(6-hydroxy-2-methylhexan-3-yl)-2,6-diazaspiro[3.4]octan-6-yl)-1,2,4-triazin-6-yl)oxy)-N-isopropylbenzamide

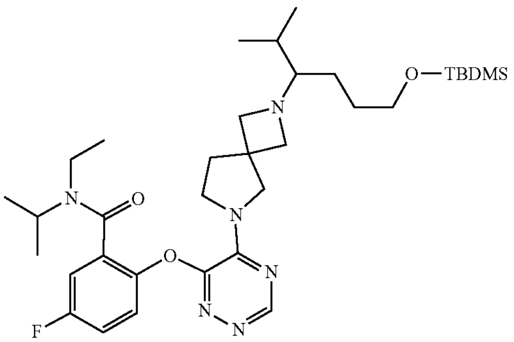

+

-continued

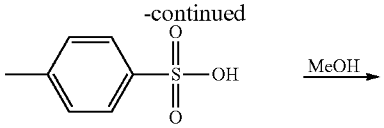

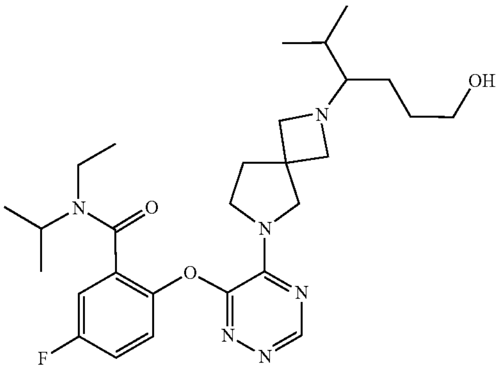

To the solution of 2-((5-(2-(6-((tert-butyldimethylsilyl)oxy)-2-methylhexan-3-yl)-2,6-diazaspiro[3.4]octan-6-yl)-1,2,4-triazin-6-yl)oxy)-N-ethyl-5-fluoro-N-isopropylbenzamide (intermediate 55) (217 mg, 0.338 mmol) in MeOH (2 mL) was added 4-methylbenzenesulfonic acid (203 mg, 1.18 mmol). The reaction mixture was stirred at RT overnight. The mixture was concentrated under reduced pressure to give the crude product which was further purified by preparative HPLC using a Phenomenex Gemini NX-C18 (column: 75x30 mm 3 μm; eluent: $ACN/H_2O$ (0.04% amimonia+10 mM $NH_4HCO_3$) from 35% to 60% (v/v)) to afford the title compound (45 mg, 25% yield) as a white solid.

Compound 47 and 48

(*R)—N-ethyl-5-fluoro-2-((5-(2-(6-hydroxy-2-methylhexan-3-yl)-2,6-diazaspiro[3.4]octan-6-yl)-1,2,4-triazin-6-yl)oxy)-N-isopropylbenzamide (*S)—N-ethyl-5-fluoro-2-((5-(2-(6-hydroxy-2-methylhexan-3-yl)-2,6-diazaspiro[3.4]octan-6-yl)-1,2,4-triazin-6-yl)oxy)-N-isopropylbenzamide

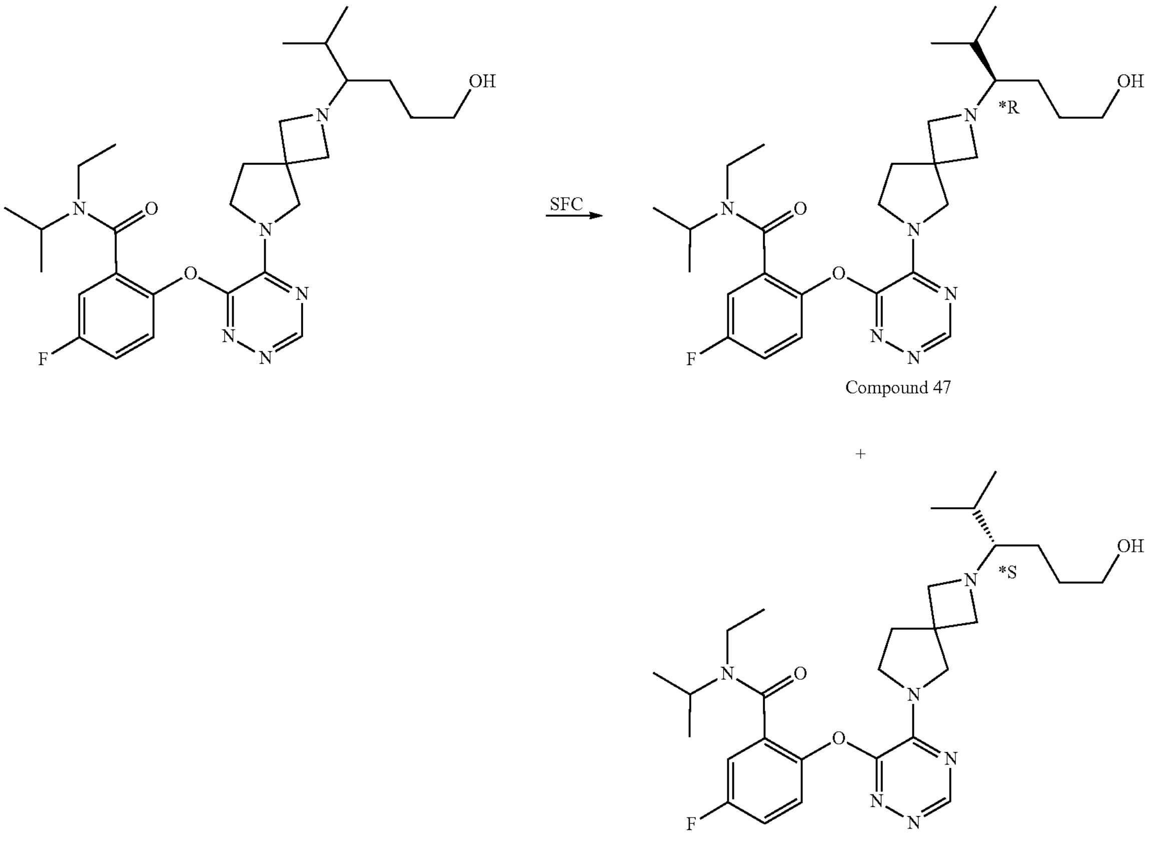

Compound 47

+

Compound 48

N-ethyl-5-fluoro-2-((5-(2-(6-hydroxy-2-methylhexan-3-yl)-2,6-diazaspiro[3.4]octan-6-yl)-1,2,4-triazin-6-yl)oxy)-N-isopropylbenzamide (Compound 49) (45.0 mg, 0.0850 mmol) was further purified by SFC over DAICEL CHIRALPAK IG (250×30 mm 10 um) (eluent: 40% to 40% (v/v) supercritical $CO_2$ in EtOH with 0.1% ammonia) to afford the title compounds Compound 47 (17.38 mg, 39% yield) and Compound 48 (15.79 mg, 35% yield) both as a white solid.

Compound 47

LCMS (ESI) (Method 1): $R_t$=3.240 min, m/z found 529.2 $[M+H]^+$.

SFC (Method 11): $R_t$=4.778 min

Compound 48

LCMS (ESI) (Method 1): $R_t$=3.212 min, m/z found 529.3 $[M+H]^+$.

SFC (Method 11): $R_t$=5.161 min.

Compound 64

(R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide

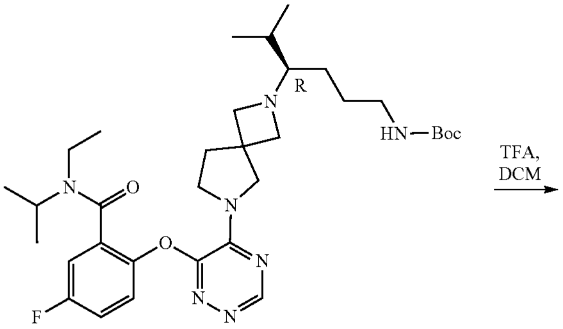

-continued

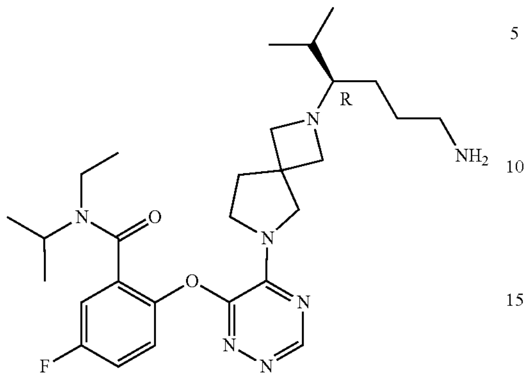

To the solution of tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate (Compound 62) (550 mg, 0.876 mmol) in DCM (4 mL) was slowly added TFA (4 mL), and the resulting mixture was stirred at 25° C. for 1 h. The reaction mixture was concentrated under reduced pressure to give a residue. The residue was diluted in DCM (40 mL) and the pH value was adjusted to around 12 by aq. NaOH (2 M, 16 mL) solution. The aqueous layer was extracted with DCM (10 mL×2). The combined organic layers were dried over anhydrous $Na_2SO_4$, filtered and concentrated in vacuo to afford the title compound (460 mg, crude) as yellow solid, which was used directly in next step without further purification.

Compound 97

2-((5-(2-(6-amino-2-methylhexan-3-yl)-2,6-diazaspiro[3.4]octan-6-yl)-1,2,4-triazin-6-yl)oxy)-5-fluoro-N,N-diisopropylbenzamide The following compound was synthesized by an analogous method as described above for Compound 64

| Co. No. | Structure | Starting Material |
|---|---|---|
| 97 | 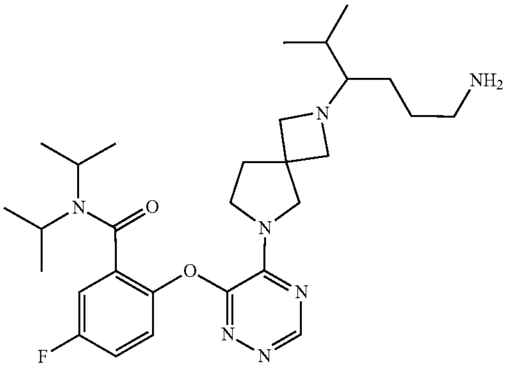 [SMILES: CC(C)C(CCCN)N1CC2(CCN(c3ncnnc3Oc3ccc(F)cc3C(=O)N(C(C)C)C(C)C)C2)C1] | Compound 96 |

Compound 65

(R)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide hydrochloride

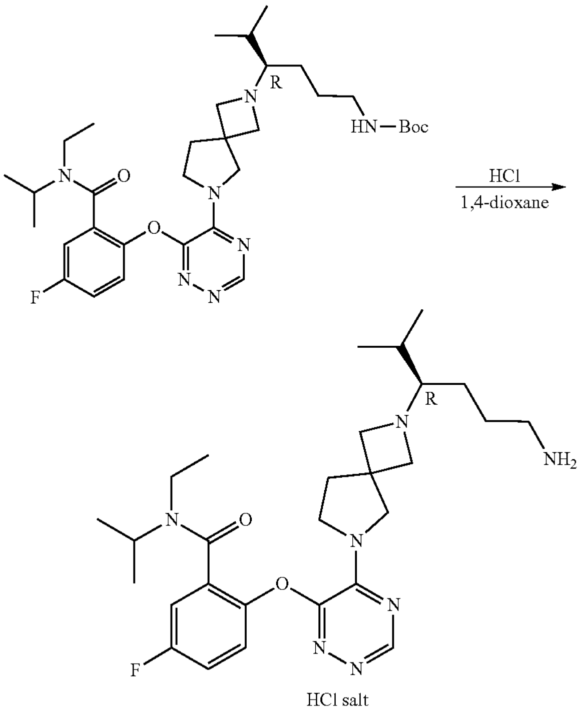

To the solution of tert-butyl (R)-(4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate (Compound 62) (250 mg, 0.398 mmol) in 1,4-dioxane (5 mL) was added a solution of 4M HCl in dioxane (10 mL, 40 mmol), the resulting mixture was stirred at RT for 16 h. The reaction mixture was concentrated in vacuo to afford the title compound (220 mg. crude. HCl salt) as yellow oil, which was used directly in next step without further purification.

Compound 67

N-ethyl-5-fluoro-N-isopropyl-2-((5-(2-(2-methyl-6-(methylamino)hexan-3-yl)-2,6-diazaspiro[3.4]octan-6-yl)-1,2,4-triazin-6-yl)oxy)benzamide hydrochlroide

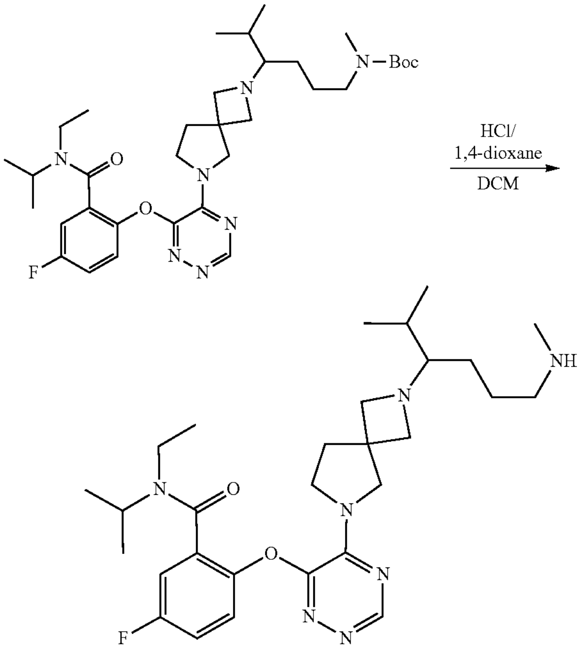

HCl salt

To a solution of tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-5-methylhexyl)(methyl)carbamate (Compound 60) (1 g, 1.56 mmol) in DCM (10 mL) was added 4M HCl in dioxane (5 mL, 20 mmol), the resulting mixture was stirred at RT for 1 h. The reaction mixture was concentrated in vacuo to afford the title compound (960 mg, crude, HCl salt) which was used directly in next step without further purification.

Compound 66, 73, 92

(S)-2-((5-(2-(6-amino-2-methylhexan-3-yl)-2,6-diazaspiro[3.4]octan-6-yl)-1,2,4-triazin-6-yl)oxy)-N-ethyl-5-fluoro-N-isopropylbenzamide hydrochloride 2-((4-(2,6-amino-2-methylhexan-3-yl)-2,6-diazaspiro[3.4]octan-6-yl)pyridazin-3-yl)oxy)-5-fluoro-N,N-diisopropylbenzamide hydrochloride 5-fluoro-N,N-diisopropyl-2-((5-(2-(2-methyl-6-(methylamino)hexan-3-yl)-2,6-diazaspiro[3.4]octan-6-yl)-1,2,4-triazin-6-yl)oxy)benzamide hydrochloride The following compounds were synthesized by an analogous method as described above for Compound 65 and Compound 67

| Co. No. | Structure | Starting Material |
| --- | --- | --- |
| 66 | 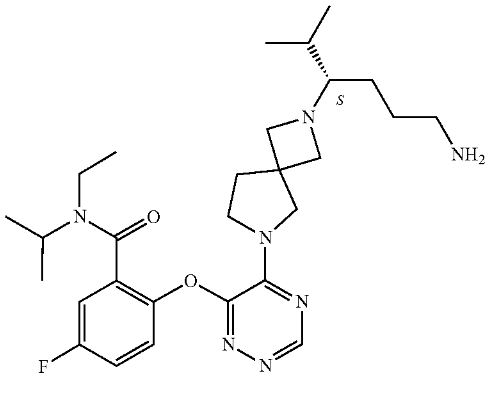 HCl salt | Compound 63 |

-continued

| Co. No. | Structure | Starting Material |
|---|---|---|
| 73 | 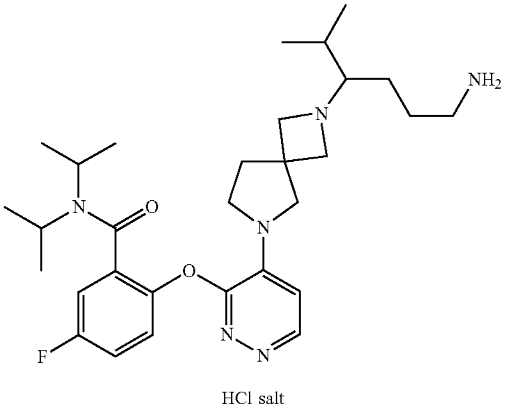 HCl salt | Compound 72 |
| 92 | 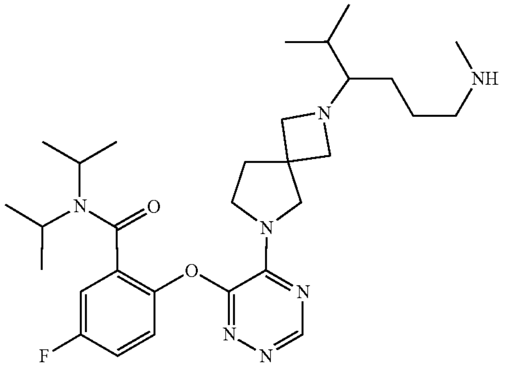 [SMILES: CNCCCC(C(C)C)N1CC2(CCN(c3ncnnc3Oc3ccc(F)cc3C(=O)N(C(C)C)C(C)C)C2)C1] HCl salt | Compound 91 |

Compound 86

5-fluoro-N,N-diisopropyl-2-((4-(2-(2-methyl-6-(methylamino)hexan-3-yl)-2,6-diazaspiro[3.4]octan-6-yl)pyridazin-3-yl)oxy)benzamide

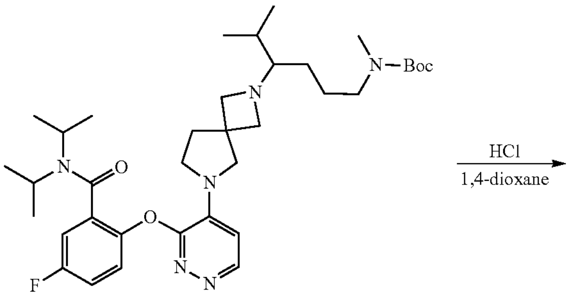

-continued

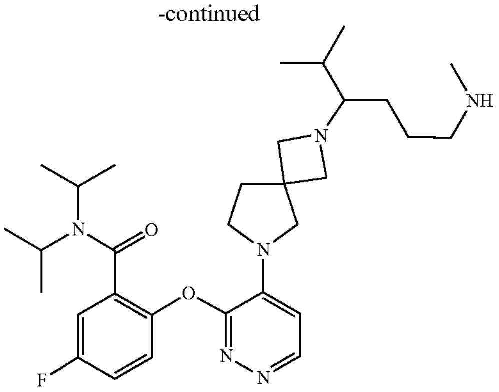

To the solution of tert-butyl (4-(6-(3-(2-(diisopropylcarbamoyl)-4-fluorophenoxy)pyridazin-4-yl)-2,6-diazaspiro[3.4]octan-2-yl)-5-methylhexyl)(methyl)carbamate (Compound 85) (1.0 g, 1.5 mmol) in 1,4-dioxane (10 mL) cooled at 0° C. was added a solution of 4M HCl in 1,4-dioxane (5 mL, 20 mmol) in portions. The resulting mixture was slowly warmed to 25° C. and stirred for 2 h. The reaction mixture was concentrated under reduced pressure to give a residue, which was re-dissolved in DCM (30 mL). Then, 1 M NaOH (20 mL) was added to adjust the pH value to about 12. The resulting mixture was further extracted with DCM (30 mL×3). The combined organic layers were dried over anhydrous $Na_2SO_4$, filtered, and concentrated in vacuo to afford the title compound (1.26 g, crude) as a yellow solid, which was used directly in next step without further purification.

Compound 58, 59, 213, 234, 235, 260, 303, 79, 85, 91, 72, 96, 206, 316, 327, 338, 339, 348, 349, 358, 381, 399, 403 tert-butyl (5-(6-(6-(2-(4-cyclopropylpyrimidin-5-yl)-4-fluorophenoxy)-1,2,4-triazin-5-yl)-2,6-diazaspiro[3.4]octan-2-yl)-2,6-dimethylheptan-2-yl)carbamate tert-butyl (5-(6-(6-(2-(ethyl(isopropyl)carbamoyl)-4-fluorophenoxy)-1,2,4-triazin-5-yl)-2,6-diazaspiro[3.4]octan-2-yl)-2,6-dimethylheptan-2-yl)carbamate N-ethyl-5-fluoro-2-((5-(2-(1-hydroxy-4-methylpentan-3-yl)-2,6-diazaspiro[3.4]octan-6-yl)-1,2,4-triazin-6-yl)oxy)-N-isopropylbenzamide N-ethyl-5-fluoro-N-isopropyl-2-((5-(2-((5*R)-6-((2-methoxyethyl)(methyl)amino)-2,5-dimethylhexan-3-yl)-2,6-diazaspiro[3.4]octan-6-yl)-1,2,4-triazin-6-yl)oxy)benzamide N-ethyl-5-fluoro-N-isopropyl-2-((5-(2-((5*S)-6-((2-methoxyethyl)(methyl)amino)-2,5-dimethylhexan-3-yl)-2,6-diazaspiro[3.4]octan-6-yl)-1,2,4-triazin-6-yl)oxy)benzamide N-ethyl-5-fluoro-2-((5-(2-(6-hydroxy-2,4-dimethylhexan-3-yl)-2,6-diazaspiro[3.4]octan-6-yl)-1,2,4-triazin-6-yl)oxy)-N-isopropylbenzamide tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-2-methoxy-5-methylhexyl)(methyl)carbamate tert-butyl (4-(6-(3-(2-(ethyl(isopropyl)carbamoyl)-4-fluorophenoxy)pyridazin-4-yl)-2,6-diazaspiro[3.4]octan-2-yl)-5-methylhexyl)(methyl)carbamate tert-butyl (4-(6-(3-(2-(diisopropylcarbamoyl)-4-fluorophenoxy)pyridazin-4-yl)-2,6-diazaspiro[3.4]octan-2-yl)-5-methylhexyl)(methyl)carbamate tert-butyl (4-(6-(6-(2-(diisopropylcarbamoyl)-4-fluorophenoxy)-1,2,4-triazin-5-yl)-2,6-diazaspiro[3.4]octan-2-yl)-5-methylhexyl)(methyl)carbamate tert-butyl (4-(6-(3-(2-(diisopropylcarbamoyl)-4-fluorophenoxy)pyridazin-4-yl)-2,6-diazaspiro[3.4]octan-2-yl)-5-methylhexyl)carbamate tert-butyl (4-(6-(6-(2-(diisopropylcarbamoyl)-4-fluorophenoxy)-1,2,4-triazin-5-yl)-2,6-diazaspiro[3.4]octan-2-yl)-5-methylhexyl)carbamate tert-butyl (5-(6-(6-(2-(ethyl(isopropyl)carbamoyl)-4-fluorophenoxy)-1,2,4-triazin-5-yl)-2,6-diazaspiro[3.4]octan-2-yl)-6-methylheptyl)carbamate tert-butyl (4-(6-(6-(2-(ethyl(isopropyl)carbamoyl)-4-fluorophenoxy)-1,2,4-triazin-5-yl)-2,6-diazaspiro[3.4]octan-2-yl)-2-hydroxy-5-methylhexyl)(methyl)carbamate tert-butyl ethyl(4-(6-(6-(2-(ethyl(isopropyl)carbamoyl)-4-fluorophenoxy)-1,2,4-triazin-5-yl)-2,6-diazaspiro[3.4]octan-2-yl)-2-hydroxy-5-methylhexyl)carbamate N-ethyl-2-((5-(2-((5S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide N-ethyl-2-((5-(2-((5R)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide N-ethyl-5-fluoro-2-((5-(2-((5S)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((5R)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide tert-butyl (4-(6-(6-(2-(diisopropylcarbamoyl)-4-fluorophenoxy)-1,2,4-triazin-5-yl)-2,6-diazaspiro[3.4]octan-2-yl)-2-hydroxy-5-methylhexyl)(methyl)carbamate N-ethyl-5-fluoro-2-((5-(2-(5-hydroxy-6-((2-methoxyethyl)(methyl)amino)-2,5-dimethylhexan-3-yl)-2,6-diazaspiro[3.4]octan-6-yl)-1,2,4-triazin-6-yl)oxy)-N-isopropylbenzamide N-ethyl-5-fluoro-N-isopropyl-2-((5-(2-(6-((2-methoxyethyl)(methyl)amino)-methylhexan-3-yl-3-d)-2,6-diazaspiro[3.4]octan-6-yl)-1,2,4-triazin-6-yl)oxy)benzamide tert-butyl (4-(6-(3-chloro-6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate The following compounds were synthesized by an analogous method as described for Compound 60 and Compound 61

| Co. No. | Structure | Starting Material | Conditions |
| --- | --- | --- | --- |
| 58 | 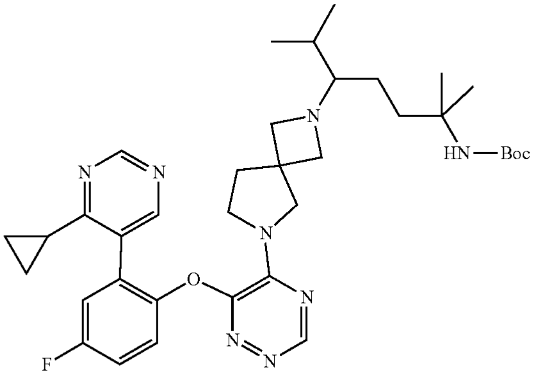 [SMILES: CC(C)C(CCC(C)(C)NC(=O)OC(C)(C)C)N1CC2(CCN(c3ncnnc3Oc3ccc(F)cc3-c3cncnc3C3CC3)C2)C1] | intermediate 59, intermediate 30 | $ZnCl_2$, $NaBH_3CN$, MeOH, 65° C. |
| 59 | 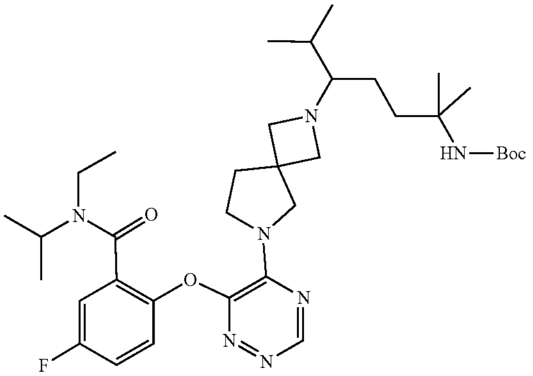 [SMILES: CCN(C(=O)c1cc(F)ccc1Oc1nncnc1N1CCC2(C1)CN(C(CCC(C)(C)NC(=O)OC(C)(C)C)C(C)C)C2)C(C)C] | intermediate 3, intermediate 30 | $ZnCl_2$, $NaBH_3CN$, MeOH, 65° C. |
| 213 | 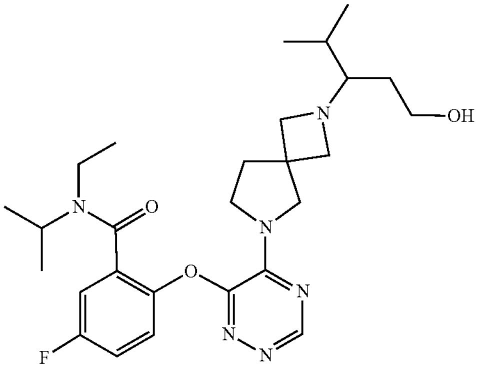 [SMILES: CCN(C(=O)c1cc(F)ccc1Oc1nncnc1N1CCC2(C1)CN(C(CCO)C(C)C)C2)C(C)C] | intermediate 3, intermediate 116 | AcOH, $NaBH_3CN$, MeOH, RT |
| 234 | 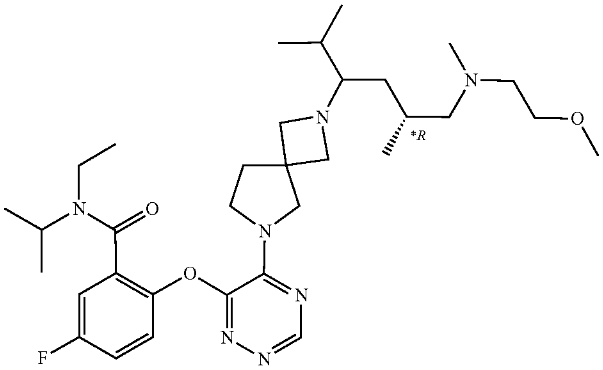 [SMILES: CCN(C(=O)c1cc(F)ccc1Oc1nncnc1N1CCC2(C1)CN(C(C[C@@H](C)CN(C)CCOC)C(C)C)C2)C(C)C] | intermediate 3, intermediate 135 | $ZnCl_2$, $NaBH_3CN$, MeOH, 60° C. |

-continued
| Co. No. | Structure | Starting Material | Conditions |
|---|---|---|---|
| 235 | 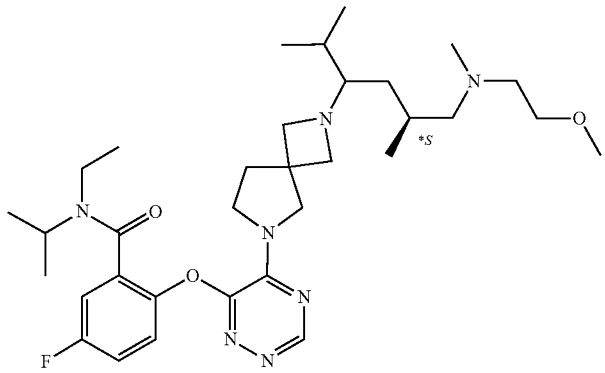 [SMILES: CCN(C(=O)c1cc(F)ccc1Oc1nncnc1N1CCC2(C1)CN(C(C[C@H](C)CN(C)CCOC)C(C)C)C2)C(C)C] | intermediate 3, intermediate 136 | $ZnCl_2$, $NaBH_3CN$, MeOH, 60° C. |
| 260 | 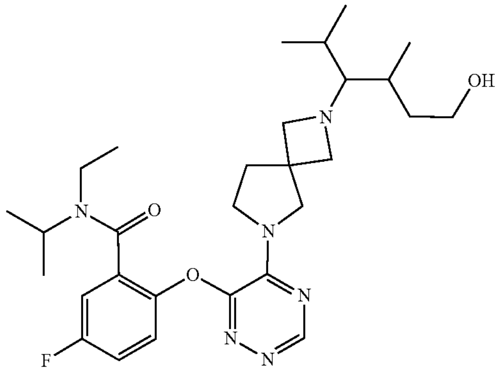 [SMILES: CCN(C(=O)c1cc(F)ccc1Oc1nncnc1N1CCC2(C1)CN(C(C(C)C)C(C)CCO)C2)C(C)C] | intermediate 3, intermediate 141 | $Ti(OiPr)_4$, $NaBH_3CN$, MeOH, 80° C. |
| 303 | 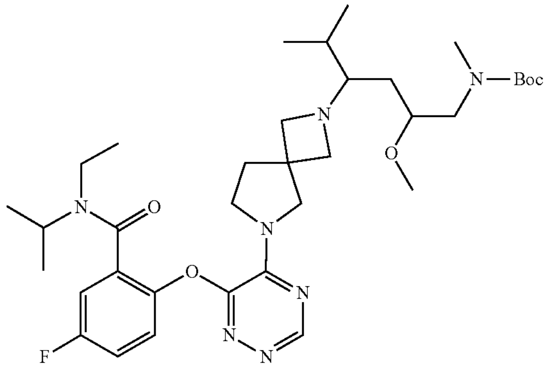 [SMILES: CCN(C(=O)c1cc(F)ccc1Oc1nncnc1N1CCC2(C1)CN(C(CC(CN(C)C(=O)OC(C)(C)C)OC)C(C)C)C2)C(C)C] | intermediate 244, intermediate 166 | NaOAc, $NaBH_3CN$, MeOH, RT |
| 79 | 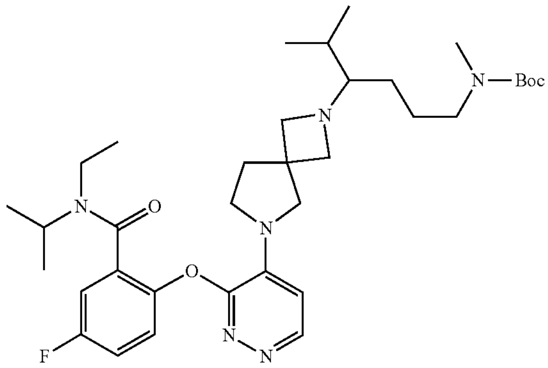 [SMILES: CCN(C(=O)c1cc(F)ccc1Oc1nnccc1N1CCC2(C1)CN(C(CCCN(C)C(=O)OC(C)(C)C)C(C)C)C2)C(C)C] | intermediate 9, intermediate 75 | $ZnCl_2$, $NaBH_3CN$, MeOH, 80° C. |

-continued
| Co. No. | Structure | Starting Material | Conditions |
|---|---|---|---|
| 85 | 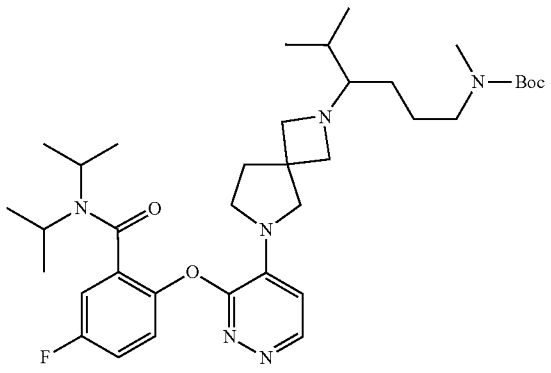 [SMILES: CC(C)C(CCCN(C)C(=O)OC(C)(C)C)N1CC2(CCN(c3ccnnc3Oc3ccc(F)cc3C(=O)N(C(C)C)C(C)C)C2)C1] | intermediate 9, intermediate 71 | AcOH, $NaBH_3CN$, MeOH, 70° C. |
| 91 | 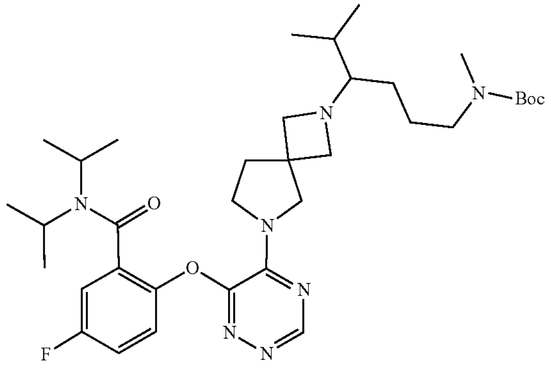 [SMILES: CC(C)C(CCCN(C)C(=O)OC(C)(C)C)N1CC2(CCN(c3ncnnc3Oc3ccc(F)cc3C(=O)N(C(C)C)C(C)C)C2)C1] | intermediate 9, intermediate 85 | $ZnCl_2$, $NaBH_3CN$, MeOH, 80° C. |
| 72 | 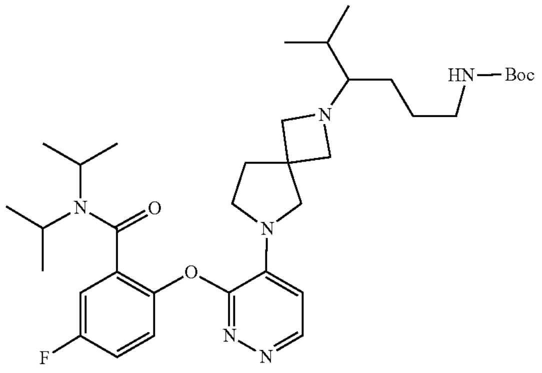 [SMILES: CC(C)C(CCCNC(=O)OC(C)(C)C)N1CC2(CCN(c3ccnnc3Oc3ccc(F)cc3C(=O)N(C(C)C)C(C)C)C2)C1] | intermediate 1, intermediate 71 | AcOH, $NaBH_3CN$, MeOH, 80° C. |
| 96 | 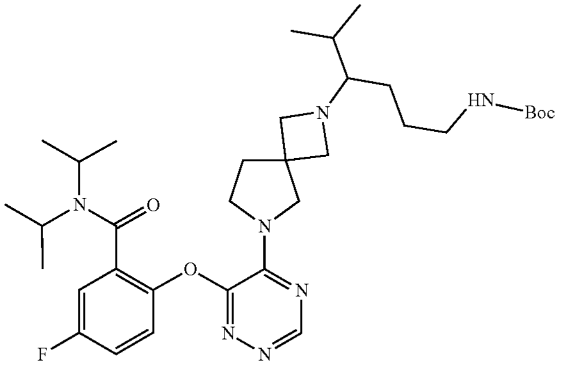 [SMILES: CC(C)C(CCCNC(=O)OC(C)(C)C)N1CC2(CCN(c3ncnnc3Oc3ccc(F)cc3C(=O)N(C(C)C)C(C)C)C2)C1] | intermediate 1, intermediate 85 | $ZnCl_2$, $NaBH_3CN$, MeOH, 80° C. |

-continued
| Co. No. | Structure | Starting Material | Conditions |
|---|---|---|---|
| 206 | 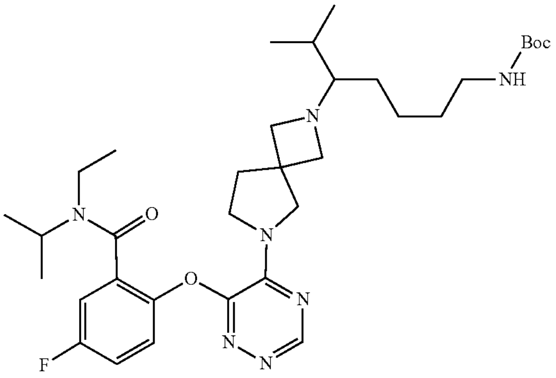 [SMILES: CCN(C(=O)c1cc(F)ccc1Oc1nncnc1N1CCC2(C1)CN(C(CCCCNC(=O)OC(C)(C)C)C(C)C)C2)C(C)C] | intermediate 110, intermediate 3 | $ZnCl_2$, $NaBH_3CN$, MeOH, 65° C. |
| 316 | 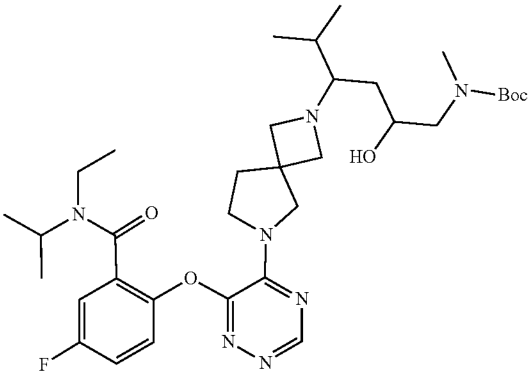 [SMILES: CCN(C(=O)c1cc(F)ccc1Oc1nncnc1N1CCC2(C1)CN(C(CC(O)CN(C)C(=O)OC(C)(C)C)C(C)C)C2)C(C)C] | intermediate 165, intermediate 244 | NaOAc, $NaBH_3CN$, MeOH, 26° C. |
| 327 | 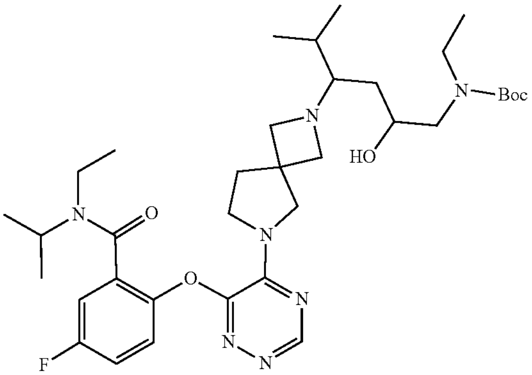 [SMILES: CCN(CC(O)CC(C(C)C)N1CC2(CCN(c3ncnnc3Oc3ccc(F)cc3C(=O)N(CC)C(C)C)C2)C1)C(=O)OC(C)(C)C] | intermediate 174, intermediate 244 | NaOAc, $NaBH_3CN$, MeOH, RT |
| 338 | 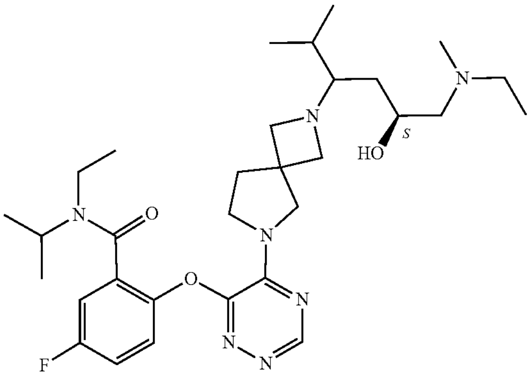 | intermediate 195, intermediate 244 | NaOAc, $NaBH_3CN$, MeOH, RT |

-continued
| Co. No. | Structure | Starting Material | Conditions |
|---|---|---|---|
| 339 | 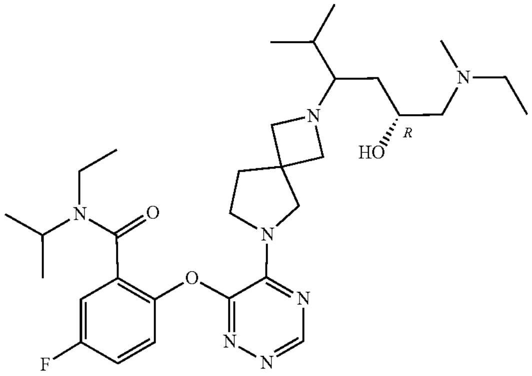 | intermediate 196, intermediate 244 | NaOAc, $NaBH_3CN$, MeOH, RT |
| 348 | 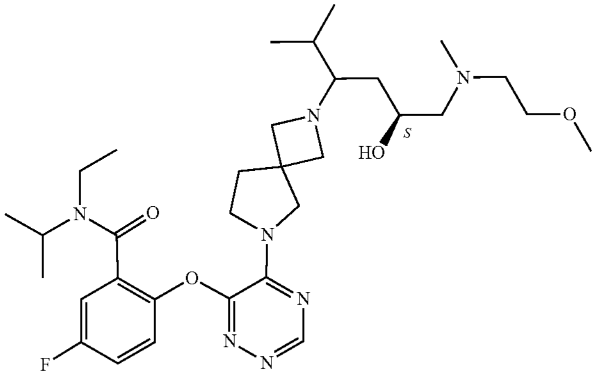 | intermediate 209, intermediate 244 | TEA, $NaBH_3CN$, DCM, 30° C. |
| 349 | 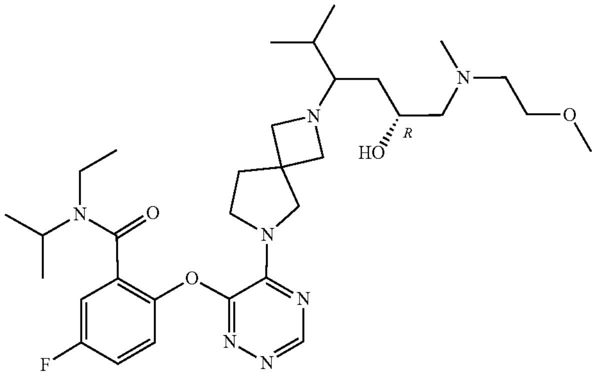 | intermediate 210, intermediate 244 | TEA, $NaBH(OAc)_3$, DCM, 35° C. |
| 358 | 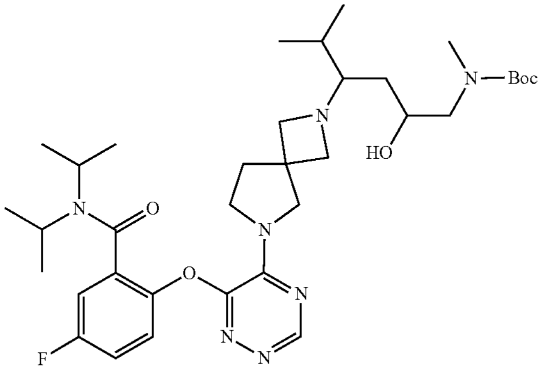 [SMILES: CC(C)C(CC(O)CN(C)C(=O)OC(C)(C)C)N1CC2(CCN(c3ncnnc3Oc3ccc(F)cc3C(=O)N(C(C)C)C(C)C)C2)C1] | intermediate 165, intermediate 243 | NaOAc, $NaBH_3CN$, MeOH, RT |

-continued
| Co. No. | Structure | Starting Material | Conditions |
|---|---|---|---|
| 381 | 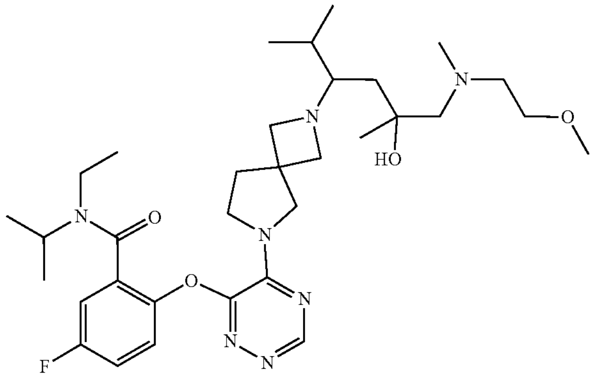 [SMILES: CCN(C(=O)c1cc(F)ccc1Oc1nncnc1N1CCC2(C1)CN(C(CC(C)(O)CN(C)CCOC)C(C)C)C2)C(C)C] | intermediate 221, intermediate 244 | NaOAc, $NaBH_3CN$, MeOH, 60° C. |
| 399 | 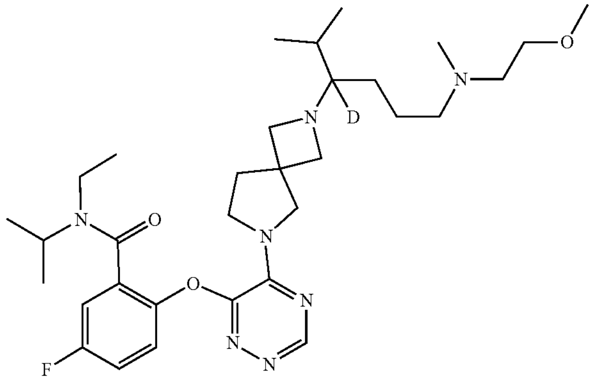 [SMILES: [2H]C(CCCN(C)CCOC)(C(C)C)N1CC2(CCN(c3ncnnc3Oc3ccc(F)cc3C(=O)N(CC)C(C)C)C2)C1] | intermediate 162, intermediate 3 | $NaBD_3CN$, $CD_3OD$, RT |
| 403 | 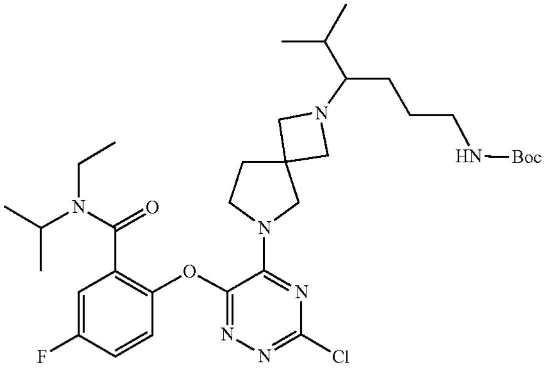 [SMILES: CCN(C(=O)c1cc(F)ccc1Oc1nnc(Cl)nc1N1CCC2(C1)CN(C(CCCNC(=O)OC(C)(C)C)C(C)C)C2)C(C)C] | intermediate 1, intermediate 238 | NaOAc, $NaBH_3CN$, MeOH, 45° C. |
For Co. No. 399: LC-MS (ESI) (Method 8): Rt=1.21 min, m/z found 601.6 $[M+H]^+$ Compound 111

N-ethyl-5-fluoro-N-isopropyl-2-((5-(2-((R)-6-(((R)-1-methoxypropan-2-yl)amino)-2-methylhexan-3-yl)-2,6-diazaspiro[3.4]octan-6-yl)-1,2,4-triazin-6-yl)oxy)benzamide

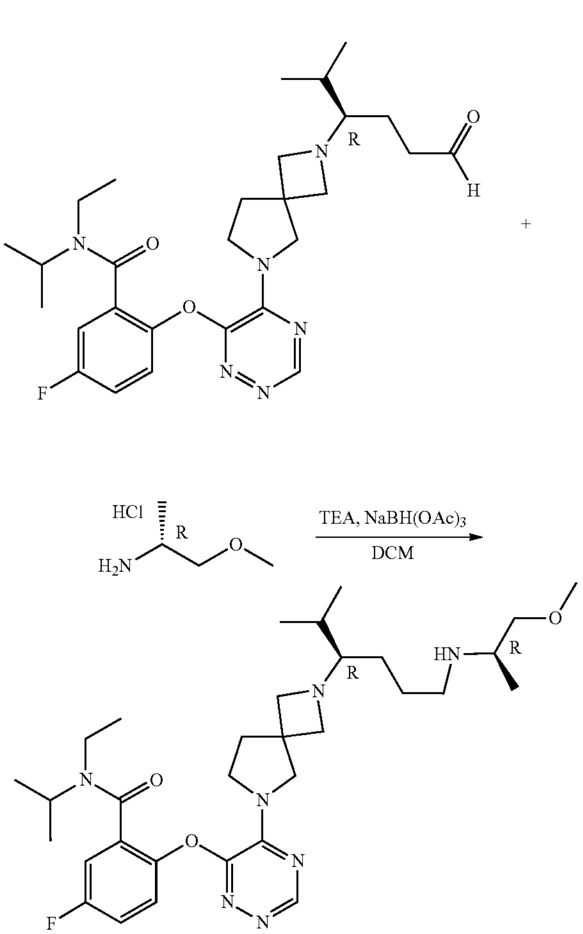

The mixture of (R)-N-ethyl-5-fluoro-N-isopropyl-2-((5-(2-(2-methyl-6-oxohexan-3-yl)-2,6-diazaspiro[3.4]octan-6-yl)-1,2,4-triazin-6-yl)oxy)benzamide (intermediate 97) (150 mg, 0.285 mmol) and (R)-1-methoxypropan-2-amine hydrochloride (71.5 mg, 0.569 mmol) and TEA (288 mg, 2.85 mmol) in DCM (2 mL) was stirred at 25° C. for 2 h. Then $NaBH(OAc)_3$ (181 mg, 0.854 mmol) was added to above mixture and the reaction was further stirred at 25° C. for additional 8 h. The mixture was quenched with $H_2O$ (20 mL) and extracted with DCM (30 mL*3). The combined organic layers were dried over anhydrous $Na_2SO_4$, filtered and concentrated under reduced pressure to afford a crude product, which was purified by preparative HPLC (column: Boston Green ODS 150×30 mm Sum; Mobile Phase: A: $H_2O$ (0.05% ammonia)), B: ACN, flow rate: 30 mL/min, gradient condition: from 45% B to 85% B) to afford the title compound Compound 111 (63 mg, 98.5% purity, 36.3% yield) as a colorless sticky oil.

Compound 113

(R)-2-(5-(2-(6-((3,3-difluoropropyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

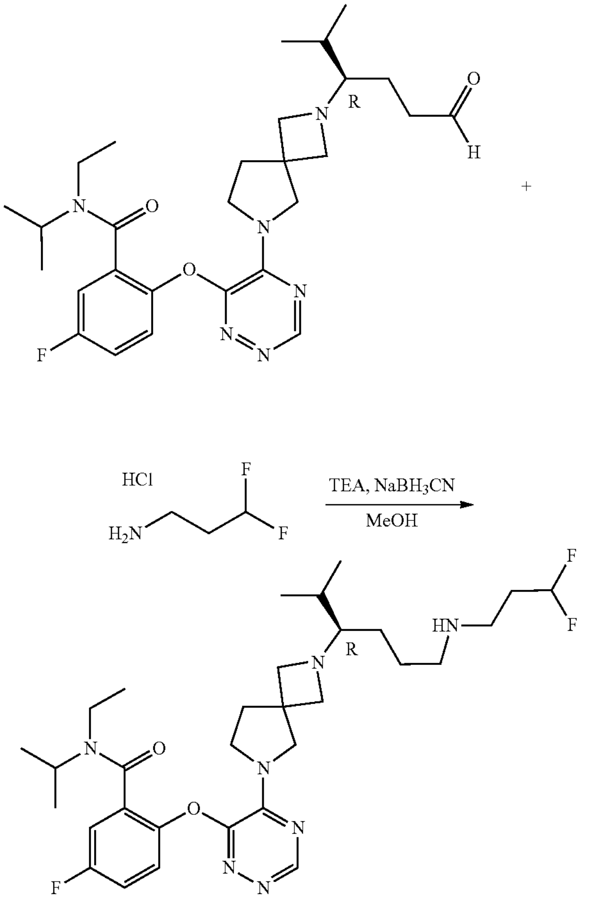

The mixture of (R)-N-ethyl-5-fluoro-N-isopropyl-2-((5-(2-(2-methyl-6-oxohexan-3-yl)-2,6-diazaspiro[3.4]octan-6-yl)-1,2,4-triazin-6-yl)oxy)benzamide (intermediate 97) (160 mg, 0.304 mmol), 3,3-difluoropropan-1-amine hydrochloride (160 mg, 1.22 mmol) and TEA (128 mg, 1.27 mmol) in MeOH (5 ml) was first stirred at RT for 10 min. Then AcOH (39 mg, 0.649 mmol) and $NaBH_3CN$ (77 mg, 1.26 mmol) were added and the resulting mixture was stirred at RT for additional 16 h. The mixture was concentrated under reduced pressure to remove MeOH. The resulting residue was diluted with $H_2O$ (30 mL) and extracted with DCM (20 mL×3). The combined organic layers were washed with brine (10 mL×2), dried over $Na_2SO_4$, filtered and concentrated to afford a crude product, which was purified by preparative HPLC (column: Boston Prime C18 150×30 mm 5 μm; Mobile phase: A: water (0.05% ammonia), B: ACN; gradient condition: 46% B to 76% B (v/v)) to afford the title compound Compound 113 (32 mg, 17% yield) as a white solid.

Compound 115, 116, 119, 124, 129, 134, 138, 141, 143, 144, 147, 151, 155, 158, 162, 163, 168, 171, 288, 289, 290, 291, 292, 293, 294, 295, 296, 297, 232, 244, 263, 264, 281, 284, 299

(*R)-5-fluoro-N,N-diisopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide (*S)-5-fluoro-N,N-diisopropyl-2-((5-(2-(6-((2-methoxyethyl)amino)-2-methylhexan-3-yl)-2,6-diazaspiro[3.4]octan-6-yl)-1,2,4-triazin-6-yl)oxy)benzamide N-ethyl-5-fluoro-N-isopropyl-2-((5-(2-(6-(isopropyl(methyl)amino)-2-methylhexan-3-yl)-2,6-diazaspiro[3.4]octan-6-yl)-1,2,4-triazin-6-yl)oxy)benzamide N-ethyl-5-fluoro-N-isopropyl-2-((5-(2-(2-methyl-6-(methyl(propyl)amino)hexan-3-yl)-2,6-diazaspiro[3.4]octan-6-yl)-1,2,4-triazin-6-yl)oxy)benzamide N-ethyl-2-((5-(2-(6-(ethyl(methyl)amino)-2-methylhexan-3-yl)-2,6-diazaspiro[3.4]octan-6-yl)-1,2,4-triazin-6-yl)oxy)-5-fluoro-N-isopropylbenzamide (R)-N-ethyl-5-fluoro-N-isopropyl-2-((5-(2-(6-((2-methoxy-2-methylpropyl)amino)-2-methylhexan-3-yl)-2,6-diazaspiro[3.4]octan-6-yl)-1,2,4-triazin-6-yl)oxy)benzamide (R)-N-ethyl-5-fluoro-2-((5-(2-(6-((2-hydroxy-2-methylpropyl)amino)-2-methylhexan-3-yl)-2,6-diazaspiro[3.4]octan-6-yl)-1,2,4-triazin-6-yl)oxy)-N-isopropylbenzamide (R)-N-ethyl-5-fluoro-N-isopropyl-2-((5-(2-(6-((3-methoxypropyl)(methyl)amino)-2-methylhexan-3-yl)-2,6-diazaspiro[3.4]octan-6-yl)-1,2,4-triazin-6-yl)oxy)benzamide (*R)-2-((5-(2-(6-((3-(dimethylamino)-3-oxopropyl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide (*S)-2-((5-(2-(6-((3-(dimethylamino)-3-oxopropyl)(methyl)amino)-2-methylhexan-3-yl)-2,6-diazaspiro[3.4]octan-6-yl)-1,2,4-triazin-6-yl)oxy)-5-fluoro-N,N-diisopropylbenzamide (R)-N-ethyl-5-fluoro-N-isopropyl-2-((5-(2-(2-methyl-6-(methyl(2-(N-methylacetamido)ethyl)amino)hexan-3-yl)-2,6-diazaspiro[3.4]octan-6-yl)-1,2,4-triazin-6-yl)oxy)benzamide (R)-2-((5-(2-(6-((4-(dimethylamino)-4-oxobutyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((5-(2-((R)-6-(((S)-1-methoxypropan-2-yl)amino)-2-methylhexan-3-yl)-2,6-diazaspiro[3.4]octan-6-yl)-1,2,4-triazin-6-yl)oxy)benzamide (R)-2-((5(2-(6-((1,3-dimethoxypropan-2-yl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-2-((5-(2-((R)-6-(((R)-1-hydroxy-3-methoxypropan-2-yl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((R)-6-(((S)-1-hydroxy-3-methoxypropan-2-yl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((3R)-6-((3-hydroxy-2-methoxypropyl)amino)-2-methylhexan-3-yl)-2,6-diazaspiro[3.4]octan-6-yl)-1,2,4-triazin-6-yl)oxy)-N-isopropylbenzamide 2-((5-(2-((3R)-6-((2,3-dimethoxypropyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((3R)-6-((4-(dimethylamino)-4-oxobutan-2-yl)amino)-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((3R)-6-((3-(dimethylamino)-2-methyl-3-oxopropyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((5-(2-((R)-2-methyl-6-(((R)-4-(methylamino)-4-oxobutan-2-yl)amino)hexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-2-methyl-6-(((S)-4-(methylamino)-4-oxobutan-2-yl)amino)hexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-2-methyl-6-(((R)-2-methyl-3-(methylamino)-3-oxopropyl)amino)hexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-2-methyl-6-(((S)-2-methyl-3-(methylamino)-3-oxopropyl)amino)hexan-3-yl)-2,6-diazaspiro[3.4]octan-6-yl)-1,2,4-triazin-6-yl)oxy)benzamide 2-((5-(2-((*R)-6-(((R)-4-amino-4-oxobutan-2-yl)amino)-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((*R)-6-(((S)-4-amino-4-oxobutan-2-yl)amino)-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((*R)-6-(((R)-3-amino-2-methyl-3-oxopropyl)amino)-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((*R)-6-(((S)-3-amino-2-methyl-3-oxopropyl)amino)-2-methylhexan-3-yl)-2,6-diazaspiro[3.4]octan-6-yl)-1,2,4-triazin-6-yl)oxy)-5-fluoro-N,N-diisopropylbenzamide (R)-N-ethyl-5-fluoro-N-isopropyl-2-((5-(2-(6-((2-methoxyethyl-1,1-$d_2$)(methyl)amino)-2-methylhexan-3-yl)-2,6-diazaspiro[3.4]octan-6-yl)-1,2,4-triazin-6-yl)oxy)benzamide (R)-2-((5-(2-(6-((2-acetamidoethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide N-ethyl-5-fluoro-N-isopropyl-2-((5-(2-(6-((2-methoxyethyl)(methyl)amino)-2,4-dimethylhexan-3-yl)-2,6-diazaspiro[3.4]octan-6-yl)-1,2,4-triazin-6-yl)oxy)benzamide (mixture of R,S and S,R; or mixture of R,R and S,S)

N-ethyl-5-fluoro-N-isopropyl-2-((5-(2-(6-((2-methoxyethyl)(methyl)amino)-2,4-dimethylhexan-3-yl)-2,6-diazaspiro[3.4]octan-6-yl)-1,2,4-triazin-6-yl)oxy)benzamide (mixture of R,R and S,S; or mixture of R,S and S,R)

N-ethyl-5-fluoro-2-((5-(2-((R)-6-(((R)-2-hydroxy-3-methoxypropyl)amino)-2-methylhexan-3-yl)-2,6-diazaspiro[3.4]octan-6-yl)-1,2,4-triazin-6-yl)oxy)-N-isopropylbenzamide formate N-ethyl-5-fluoro-2-((5-(2-((R)-6-(((S)-2-hydroxy-3-methoxypropyl)amino)-2-methylhexan-3-yl)-2,6-diazaspiro[3.4]octan-6-yl)-1,2,4-triazin-6-yl)oxy)-N-isopropylbenzamide formate N-ethyl-5-fluoro-N-isopropyl-2-((5-(2-((3R)-6-((2-methoxyethyl)(methyl)amino)-methylheptan-3-yl)-2,6-diazaspiro[3.4]octan-6-yl)-1,2,4-triazin-6-yl)oxy)benzamide The following compounds were synthesized by an analogous method as described above for Compound 111 and 113

| Co. No. | Structure | Starting Material | Conditions | Spectra Details |
|---|---|---|---|---|
| 115 | 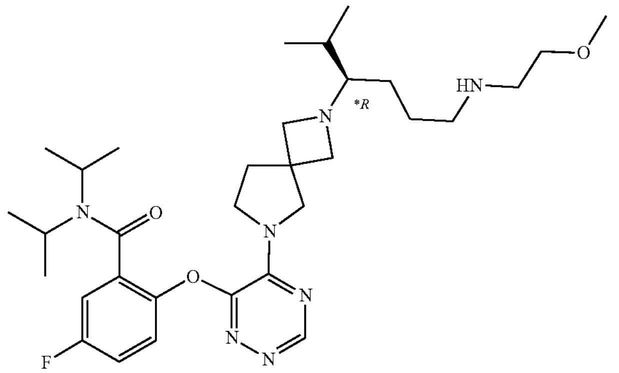 [SMILES: COCCNCCC[C@H](C(C)C)N1CC2(CCN(c3ncnnc3Oc3ccc(F)cc3C(=O)N(C(C)C)C(C)C)C2)C1] | intermediate 101, 2-methoxy ethan-1-amine | NaOAc, $NaBH_3CN$, MeOH, 60° C. | |
| 116 | 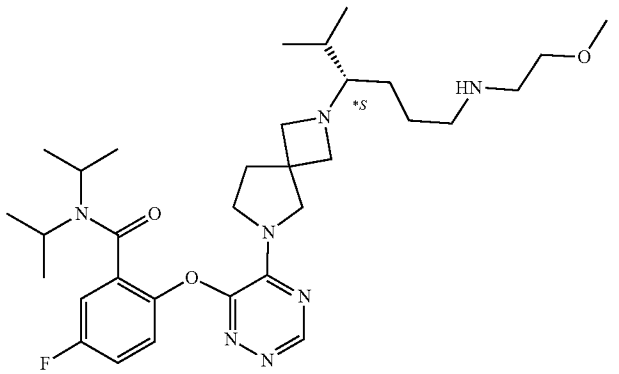 [SMILES: COCCNCCC[C@@H](C(C)C)N1CC2(CCN(c3ncnnc3Oc3ccc(F)cc3C(=O)N(C(C)C)C(C)C)C2)C1] | intermediate 102, 2-methoxy ethan-1-amine | NaOAc, $NaBH_3CN$, MeOH, 60° C. | |

-continued
| Co. No. | Structure | Starting Material | Conditions | Spectra Details |
| --- | --- | --- | --- | --- |
| 119 | 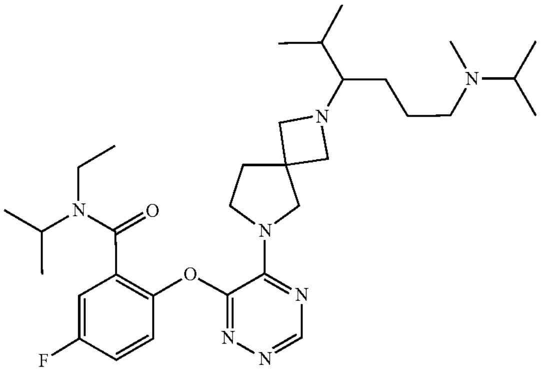 [SMILES: CCN(C(=O)c1cc(F)ccc1Oc1nncnc1N1CCC2(C1)CN(C(CCCN(C)C(C)C)C(C)C)C2)C(C)C] | intermediate 103, N-methylpropan-2-amine | $NaBH(OAc)_3$, TEA, DCM, 25° C. | |
| 124 | 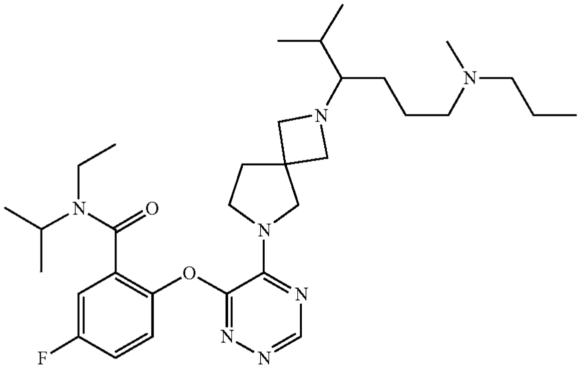 [SMILES: CCCN(C)CCCC(C(C)C)N1CC2(CCN(c3ncnnc3Oc3ccc(F)cc3C(=O)N(CC)C(C)C)C2)C1] | intermediate 103, N-methylpropan-1-amine | $NaBH(OAc)_3$, DCM, 25° C. | |
| 129 | 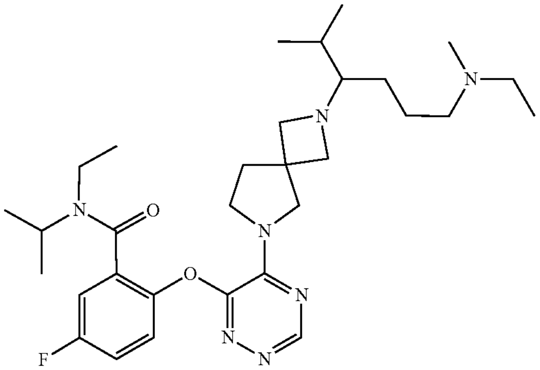 [SMILES: CCN(C)CCCC(C(C)C)N1CC2(CCN(c3ncnnc3Oc3ccc(F)cc3C(=O)N(CC)C(C)C)C2)C1] | intermediate 103, N-methylethanamine | $NaBH(OAc)_3$, DCM, 25° C. | |
| 134 | 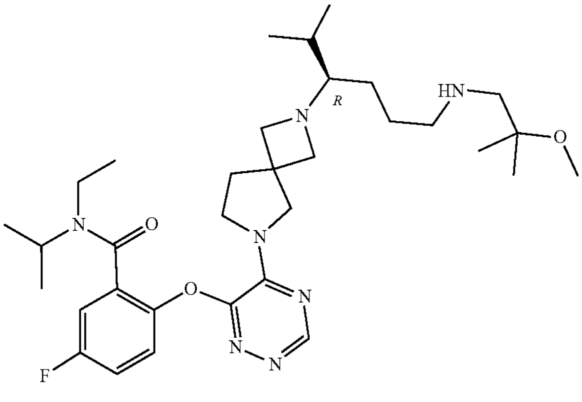 | intermediate 97, 2-methoxy-2-methylpropan-1-amine | NaOAc, $NaBH_3CN$, MeOH, 45° C. | |

-continued
| Co. No. | Structure | Starting Material | Conditions | Spectra Details |
|---|---|---|---|---|
| 138 | 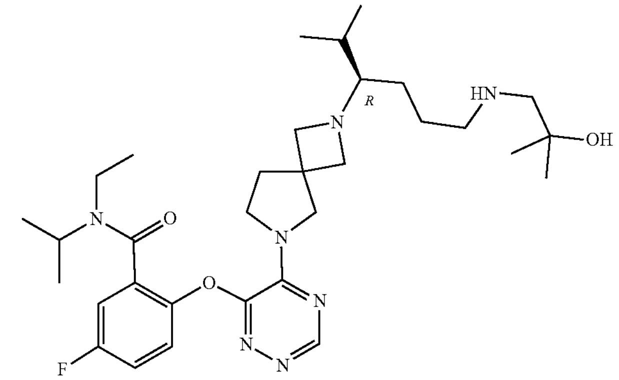 | intermediate 97, l-amino-2-methylpropan-2-ol | $NaBH_3CN$, AcOH, MeOH, 45° C. | |
| 141 | 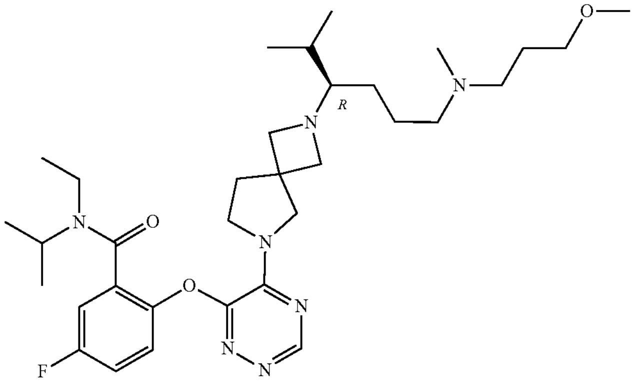 | intermediate 97, 3-methoxy-N-methylpropan-1-amine | NaOAc, $NaBH_3CN$, MeOH, RT | |
| 143 | 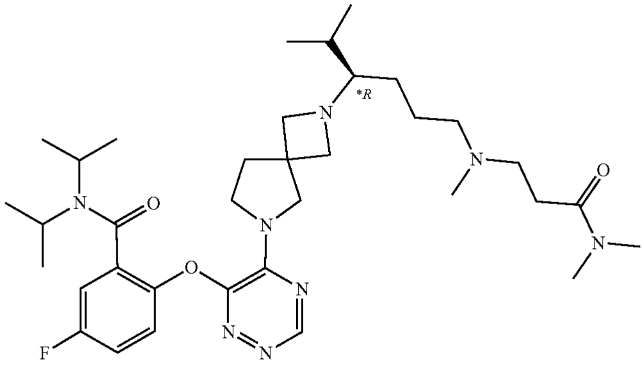 [SMILES: CC(C)[C@@H](CCCN(C)CCC(=O)N(C)C)N1CC2(CCN(c3ncnnc3Oc3ccc(F)cc3C(=O)N(C(C)C)C(C)C)C2)C1] | intermediate 101, N,N-dimethy 1-3-(methylamino) propanamide | $NaBH(OAc)_3$, TEA, DCM, 25° C. | |
| 144 | 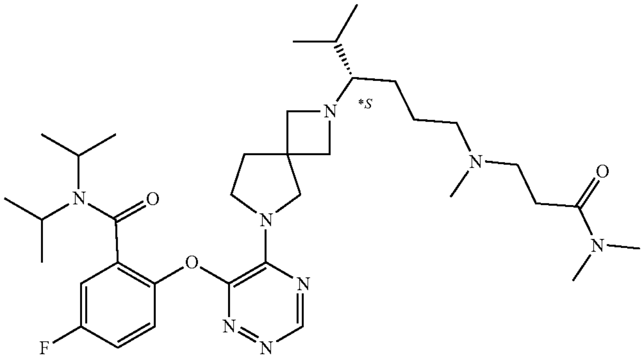 [SMILES: CC(C)[C@H](CCCN(C)CCC(=O)N(C)C)N1CC2(CCN(c3ncnnc3Oc3ccc(F)cc3C(=O)N(C(C)C)C(C)C)C2)C1] | intermediate 102, N,N-dimethy 1-3-(methylamino) propanamide | $NaBH(OAc)_3$, TEA, DCM, 25° C. | |

-continued
| Co. No. | Structure | Starting Material | Conditions | Spectra Details |
| --- | --- | --- | --- | --- |
| 147 | 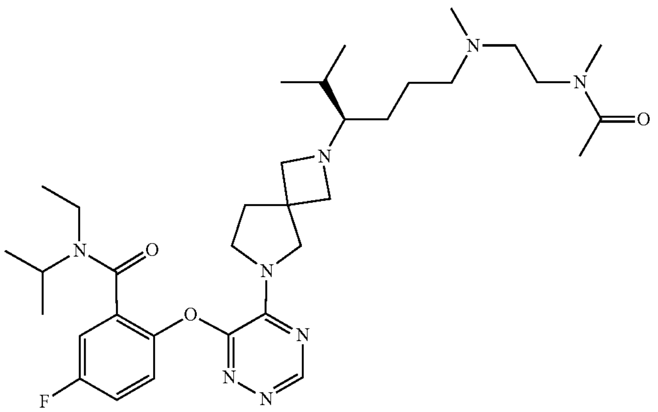 [SMILES: CCN(C(=O)c1cc(F)ccc1Oc1nncnc1N1CCC2(C1)CN([C@H](CCCN(C)CCN(C)C(C)=O)C(C)C)C2)C(C)C] | intermediate 97, N-methyl-N-(2-(methylamino) ethyl)acetamide | TEA, DCM, 45° C. | |
| 151 | 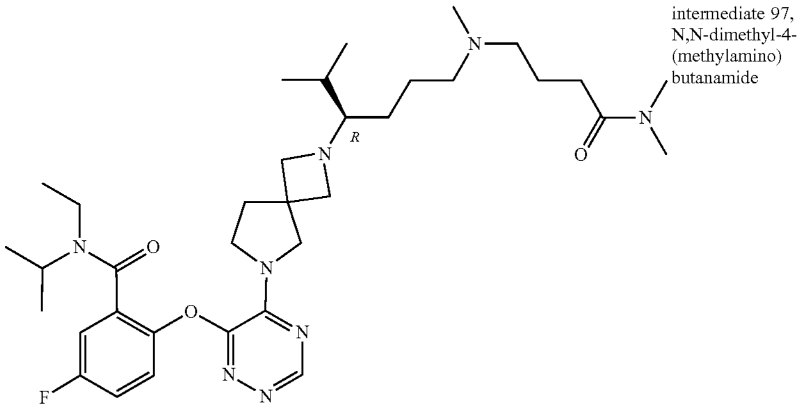 | intermediate 97, N,N-dimethyl-4-(methylamino) butanamide | NaOAc, $NaBH_3CN$, MeOH, RT | |
| 155 | 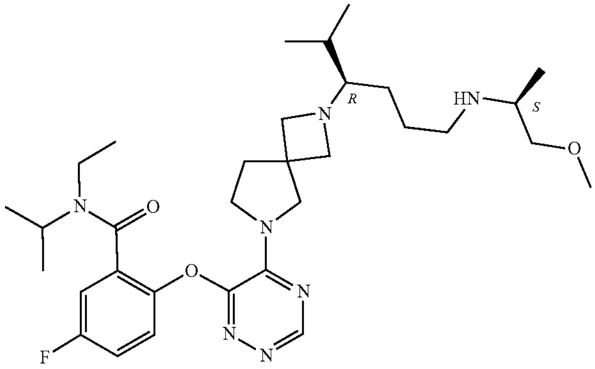 | intermediate 97, (S)-1-methoxypropan-2-amine | $NaBH(OAc)_3$, DCM, 25° C. | |
| 158 | 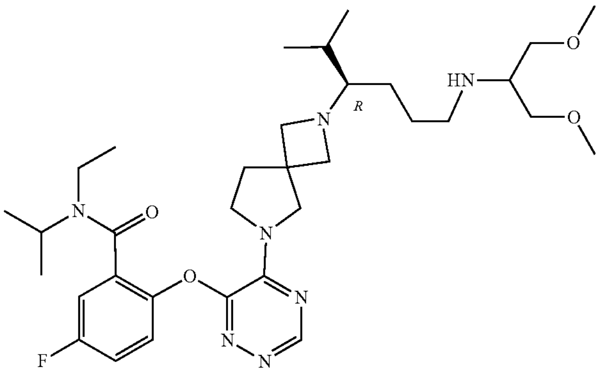 | intermediate 97, 1,3-dimethoxypropan-2-amine | $NaBH_3CN$, TEA, DCM, RT | |

-continued

| Co. No. | Structure | Starting Material | Conditions | Spectra Details |
|---|---|---|---|---|
| 162 | 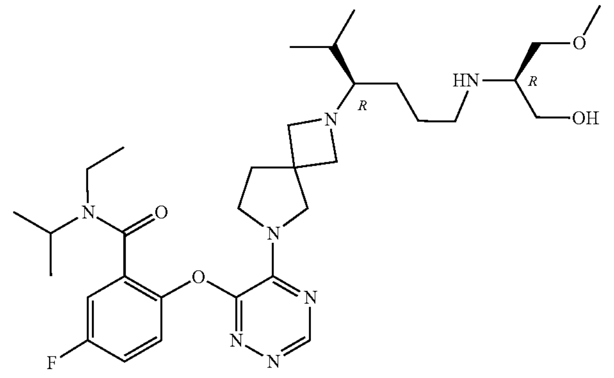 | intermediate 97, (R)-2-amino-3-methoxypropan-1-ol | $NaBH_3CN$, AcOH, MeOH, 50° C. | LC-MS (ESI) (Method 1): $R_t$ = 2.912 min, m/z found 616.3 $[M + H]^+$. SFC (Method 3): $R_t$ = 4.465 min. |
| 163 | 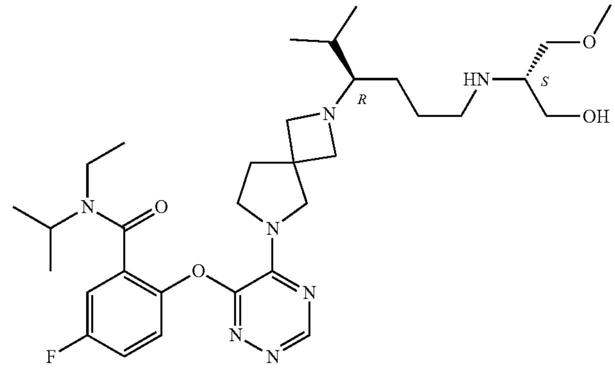 | intermediate 97, (S)-2-amino-3-methoxypropan-1-ol | $NaBH_3CN$, AcOH, MeOH, 40° C. | LC-MS (ESI) (Method 3): $R_t$ = 4.462 min, m/z found 616.4 $[M + H]^+$. SFC (Method 3): $R_t$ = 4.812 min. |
| 168 | 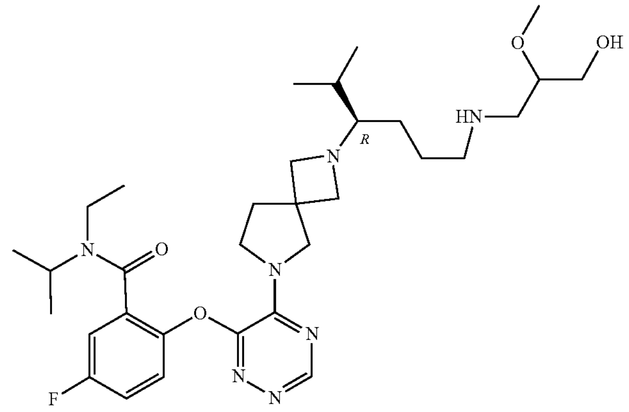 | intermediate 97, 3-amino-2-methoxypropan-1-ol | $NaBH_3CN$, AcOH, MeOH, 60° C. | LC-MS (ESI) (Method 3): $R_t$ = 4.791 min, m/z found 616.5 $[M + H]^+$. |
| 171 | 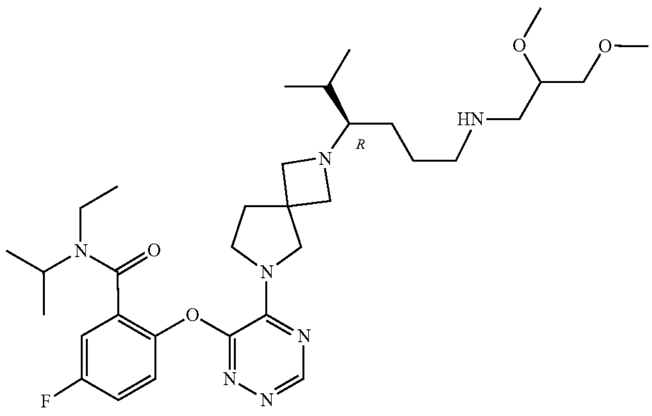 | intermediate 97, 2,3-dimethoxypropan-1-amine | $NaBH_3CN$, AcOH, MeOH, 25° C. | |

-continued
| Co. No. | Structure | Starting Material | Conditions | Spectra Details |
|---|---|---|---|---|
| 288 | 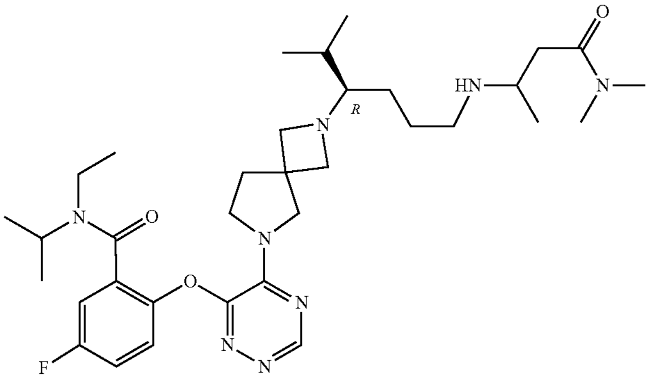 | intermediate 97, 3-amino-N,N-dimethylbutanamide | NaOAc, $NaBH_3CN$, MeOH, 20° C. | |
| 289 | 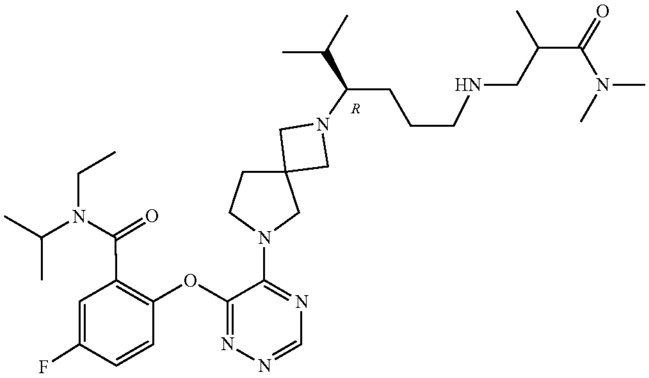 | intermediate 97, 3-amino-N,N,2-trimethylpropanamide | NaOAc, $NaBH_3CN$, MeOH, 20° C. | |
| 290 | 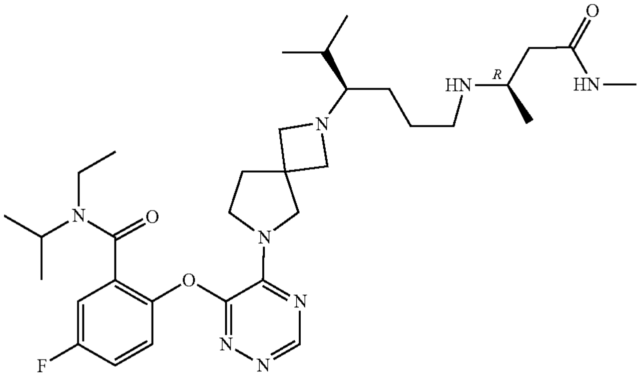 | intermediate 97, (R)-3-amino-N-methylbutanamide | NaOAc, $NaBH_3CN$, MeOH, 20° C. | |
| 291 | 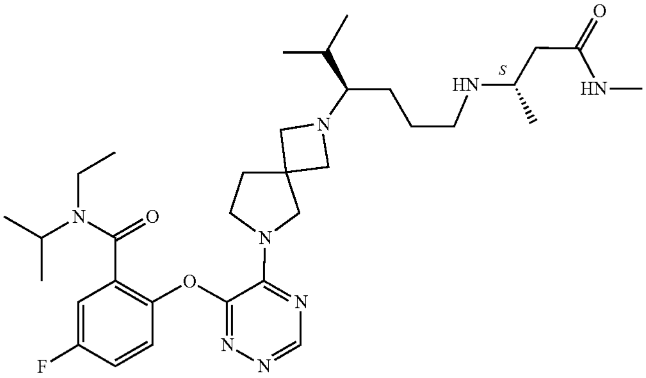 | intermediate 97, (S)-3-amino-N-methylbutanamide | NaOAc, $NaBH_3CN$, MeOH, 20° C. | |

-continued
| Co. No. | Structure | Starting Material | Conditions | Spectra Details |
|---|---|---|---|---|
| 292 | 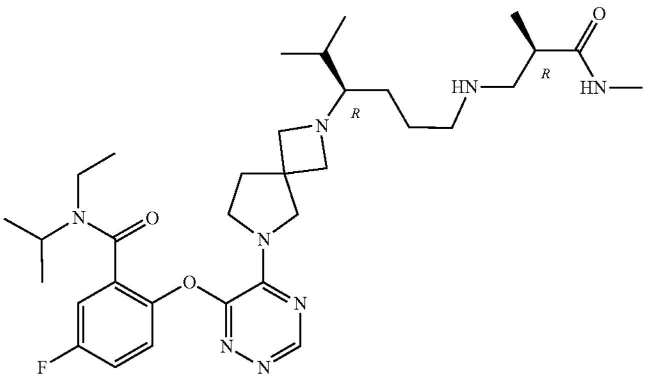 | intermediate 97, (R)-3-amino-N,2-dimethylpropanamide | NaOAc, $NaBH_3CN$, MeOH, 20° C. | |
| 293 | 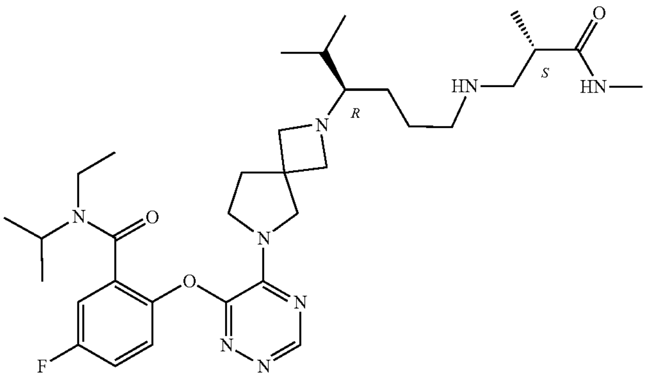 | intermediate 97, (S)-3-amino-N,2-dimethylpropanamide | NaOAc, $NaBH_3CN$, MeOH, 20° C. | |
| 294 | 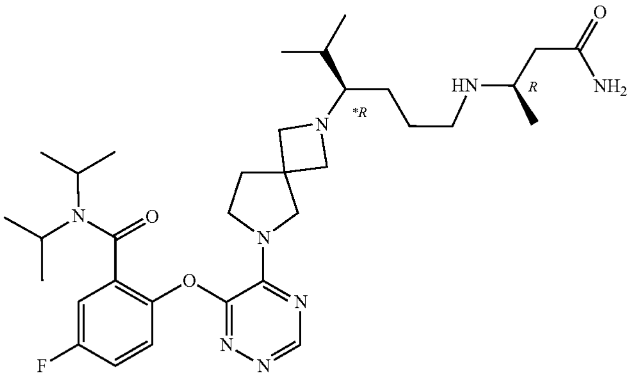 | intermediate 101, (R)-3-aminobutanamide | NaOAc, $NaBH_3CN$, MeOH, 20° C. | |
| 295 | 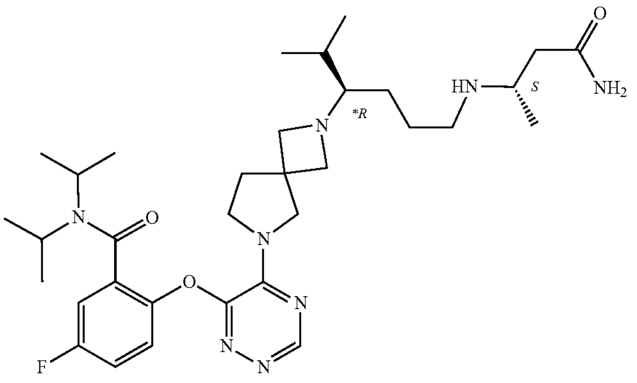 | intermediate 101, (S)-3-aminobutanamide | NaOAc, $NaBH_3CN$, MeOH, 20° C. | |

-continued
| Co. No. | Structure | Starting Material | Conditions | Spectra Details |
|---|---|---|---|---|
| 296 | 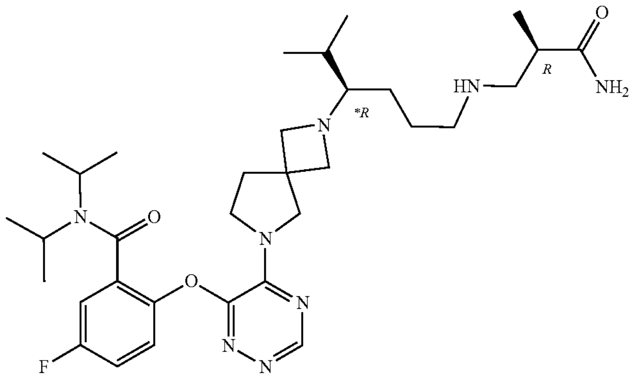 | intermediate 101, (R)-3-amino-2-methylpropanamide | NaOAc, $NaBH_3CN$, MeOH, 20° C. | |
| 297 | 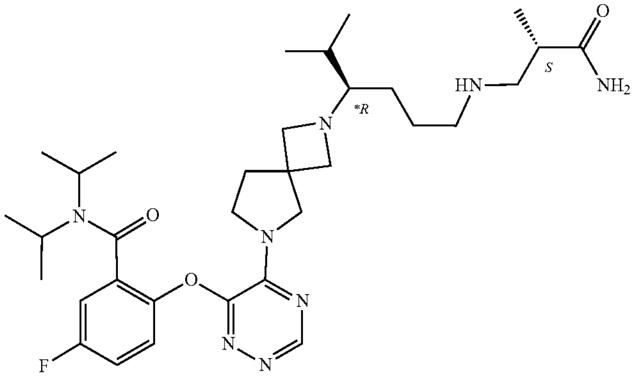 | intermediate 101, (S)-3-amino-2-methylpropanamide | NaOAc, $NaBH_3CN$, MeOH, 20° C. | |
| 232 | 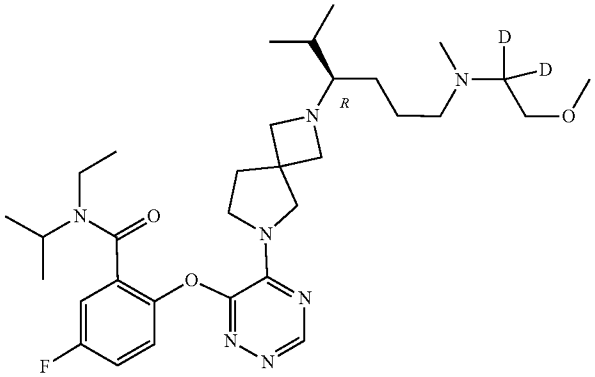 | intermediate 97, intermediate 127 | $NaBH_3CN$, MeOH, 25° C. | |
| 244 | 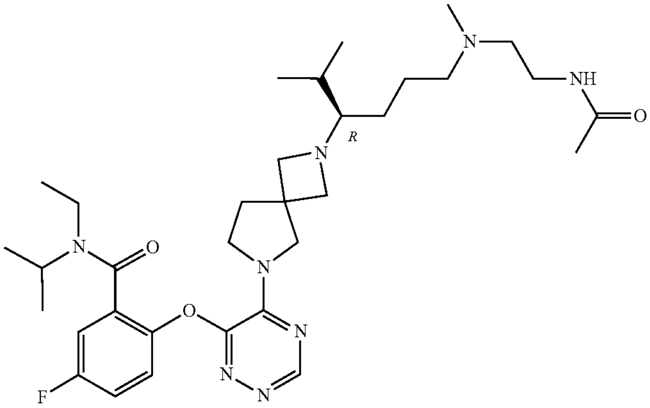 | intermediate 97, N-(2-(methylamino) ethyl)acetamide | $NaBH_3CN$, TEA, MeOH, RT | |

-continued

| Co. No. | Structure | Starting Material | Conditions | Spectra Details |
|---|---|---|---|---|
| 263 | 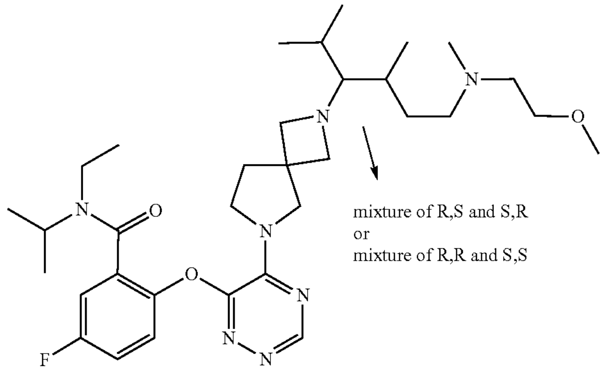 [SMILES: CCN(C(=O)c1cc(F)ccc1Oc1nncnc1N1CCC2(C1)CN(C(C(C)C)C(C)CCN(C)CCOC)C2)C(C)C] mixture of R,S and S,R or mixture of R,R and S,S | intermediate 145, 2-methoxy-N-methylethan-1-amine | $NaBH_3CN$, MeOH, 40° C. | |
| 264 | 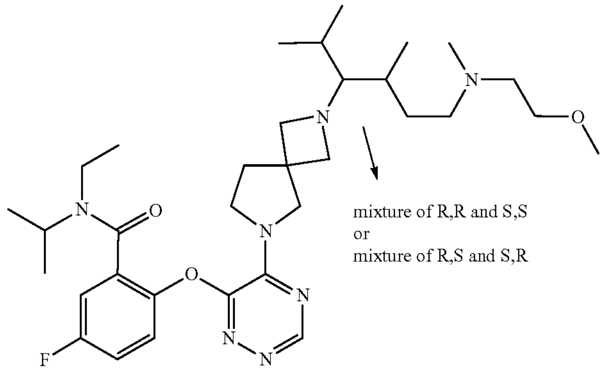 [SMILES: CCN(C(=O)c1cc(F)ccc1Oc1nncnc1N1CCC2(C1)CN(C(C(C)C)C(C)CCN(C)CCOC)C2)C(C)C] mixture of R,R and S,S or mixture of R,S and S,R | intermediate 146, 2-methoxy-N-methylethan-1-amine | $NaBH_3CN$, MeOH, 40° C. | |
| 281 | 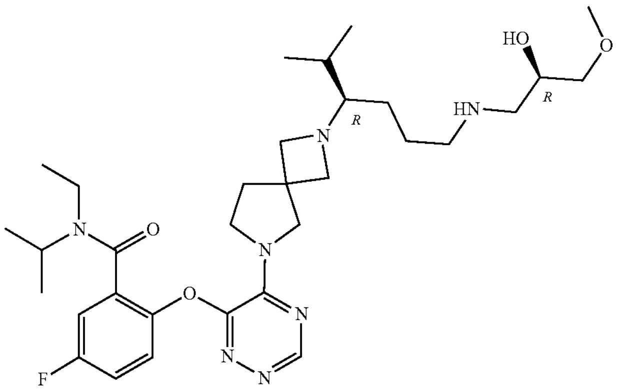 formate salt | intermediate 97, (R)-1-amino-3-methoxypropan-2-ol | $NaBH_3CN$, MeOH, 25° C. | LC-MS (ESI) (Method 1): $R_t$ = 3.016 min, m/z found 616.3 $[M + H]^+$. SFC (Method 13): $R_t$ = 2.306 min. |
| 284 | 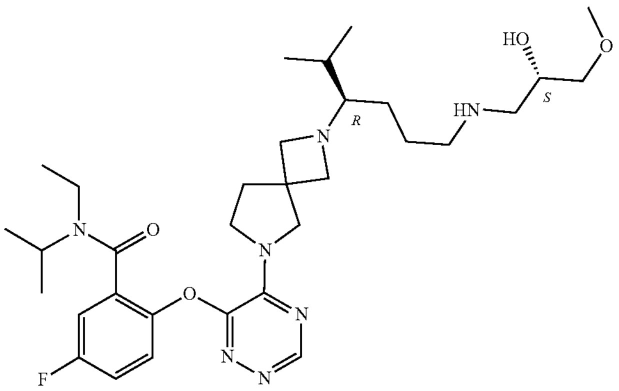 | intermediate 97, (S)-1-amino-3-methoxypropan-2-ol | $NaBH_3CN$, $ZnCl_2$, MeOH, 25° C. | LC-MS (ESI) (Method 1): $R_t$ = 3.048 min, m/z found 616.3 $[M + H]^+$. SFC (Method 13): $R_t$ = 2.333 min. |

-continued

| Co. No. | Structure | Starting Material | Conditions | Spectra Details |
|---|---|---|---|---|
| | formate salt | | | |
| 299 | 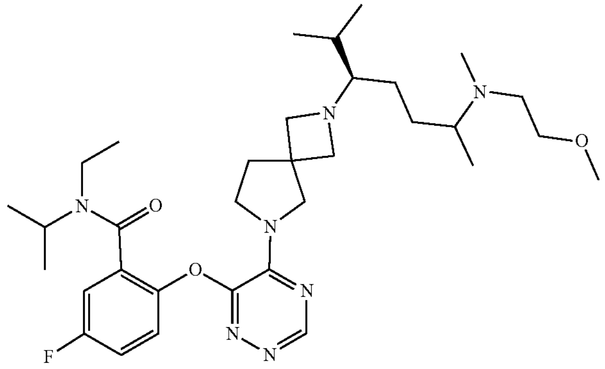 [SMILES: CCN(C(=O)c1cc(F)ccc1Oc1nncnc1N1CCC2(C1)CN([C@H](CCC(C)N(C)CCOC)C(C)C)C2)C(C)C] | intermediate 158, 2-methoxy-N-methylethan-1-amine | NaOAc, $NaBH_3CN$, MeOH, RT | |

Compound 120 and 121

(*R)—N-ethyl-5-fluoro-N-isopropyl-2-((5-(2-(6-(isopropyl(methyl)amino)-2-methylhexan-3-yl)-2,6-diazaspiro[3.4]octan-6-yl)-1,2,4-triazin-6-yl)oxy) benzamide (*S)—N-ethyl-5-fluoro-N-isopropyl-2-((5-(2-(6-(isopropyl(methyl)amino)-2-methylhexan-3-yl)-2,6-diazaspiro[3.4]octan-6-yl)-1,2,4-triazin-6-yl)oxy) benzamide

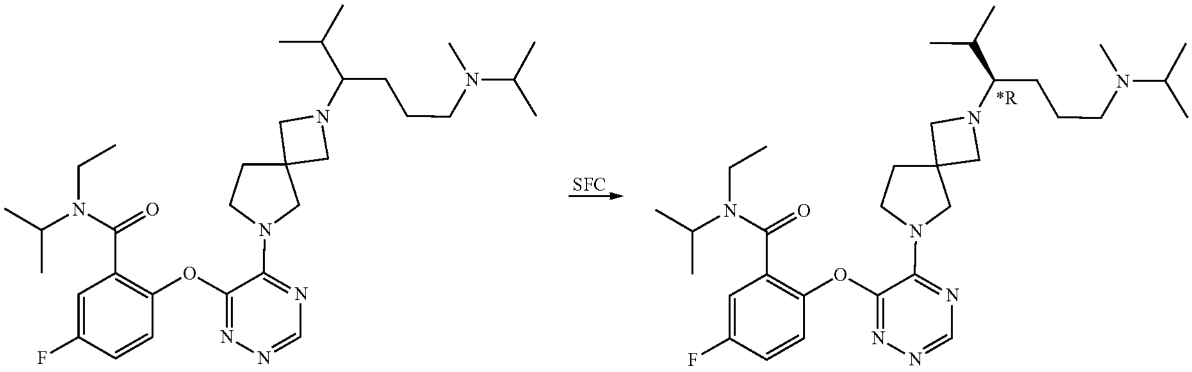

Compound 119

Compound 120

+

-continued

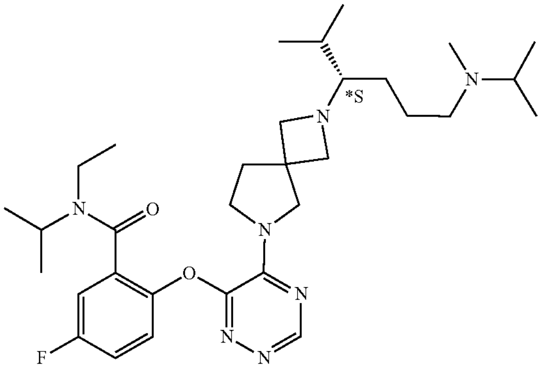

Compound 121

N-ethyl-5-fluoro-N-isopropyl-2-((5-(2-(6-(isopropyl (methyl)amino)-2-methylhexan-3-yl)-2,6-diazaspiro[3.4] octan-6-yl)-1,2,4-triazin-6-yl)oxy)benzamide (Compound 119) (100 mg) was separated by SFC over DAICEL CHIRALPAK IG (column: 250×30 mm 10 um; Mobile phase: A: Supercritical $CO_2$, B: MeOH (0.1% ammonia), A:B=55:45 at 70 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compounds (Compound 120) (22.1 mg) and (Compound 121) (32.5 mg) both as light yellow solid.

Compound 125 and 126

(*R)—N-ethyl-5-fluoro-N-isopropyl-2-((5-(2-(2-methyl-6-(methyl(propyl)amino)hexan-3-yl)-2,6-diazaspiro[3.4]octan-6-yl)-1,2,4-triazin-6-yl)oxy) benzamide (*S)—N-ethyl-5-fluoro-N-isopropyl-2-((5-(2-(2-methyl-6-(methyl(propyl)amino)hexan-3-yl)-2,6-diazaspiro[3.4]octan-6-yl)-1,2,4-triazin-6-yl)oxy) benzamide

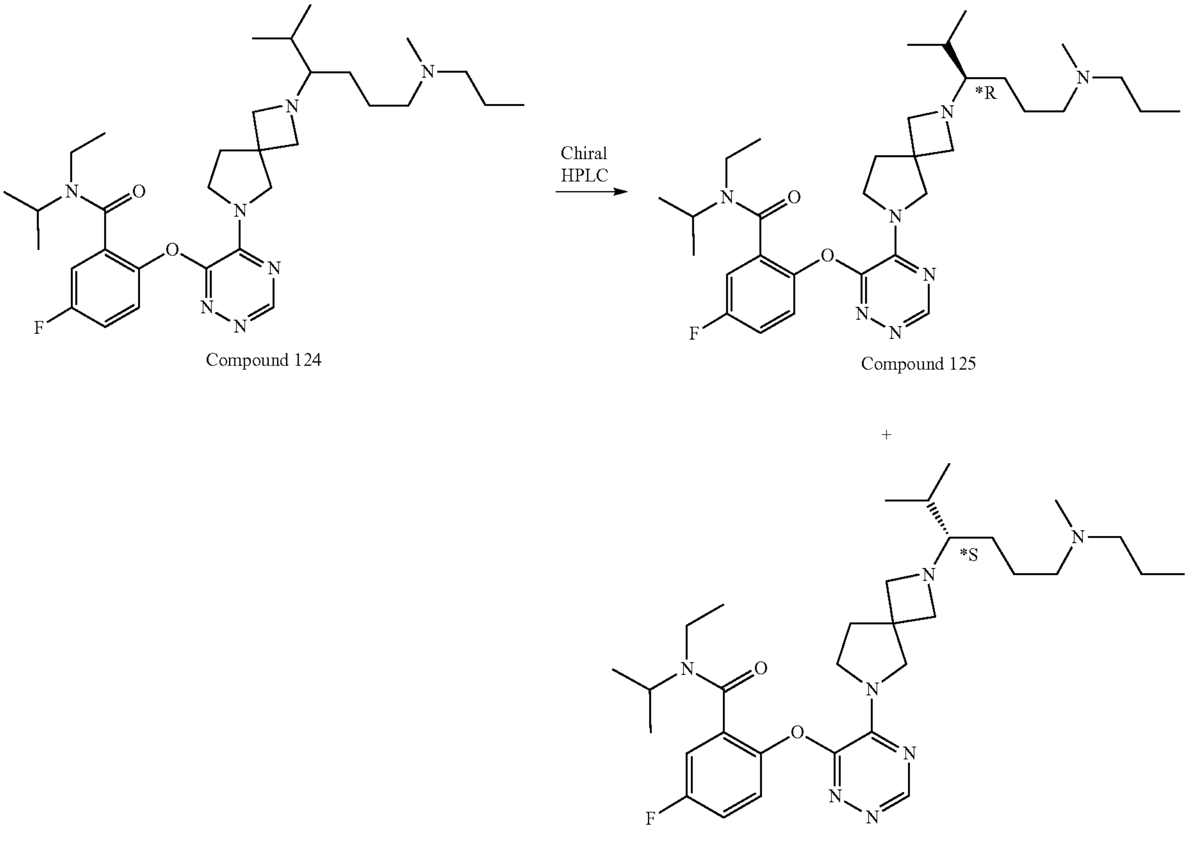

Compound 126

N-ethyl-5-fluoro-N-isopropyl-2-((5-(2-(2-methyl-6-(methyl(propyl)amino)hexan-3-yl)-2,6-diazaspiro[3.4]octan-6-yl)-1,2,4-triazin-6-yl)oxy)benzamide (Compound 124) (150 mg) was separated by chiral HPLC over Daicel Chiralpak IG (column: 250×30 mm 10 um; Mobile Phase A: Hexane; Mobile Phase B: EtOH; Flow rate: 20 mL/min; gradient condition from 20% B to 100% B) to afford the title compounds (Compound 125) (38.0 mg) and (Compound 126) (27.2 mg) both as light yellow solid.

Compound 130 and 131

(*R)—N-ethyl-2-((5-(2-(6-(ethyl(methyl)amino)-2-methylhexan-3-yl)-2,6-diazaspiro[3.4]octan-6-yl)-1,2,4-triazin-6-yl)oxy)-5-fluoro-N-isopropylbenzamide (*S)—N-ethyl-2-((5-(2-(6-(ethyl(methyl)amino)-2-methylhexan-3-yl)-2,6-diazaspiro[3.4]octan-6-yl)-1,2,4-triazin-6-yl)oxy)-5-fluoro-N-isopropylbenzamide

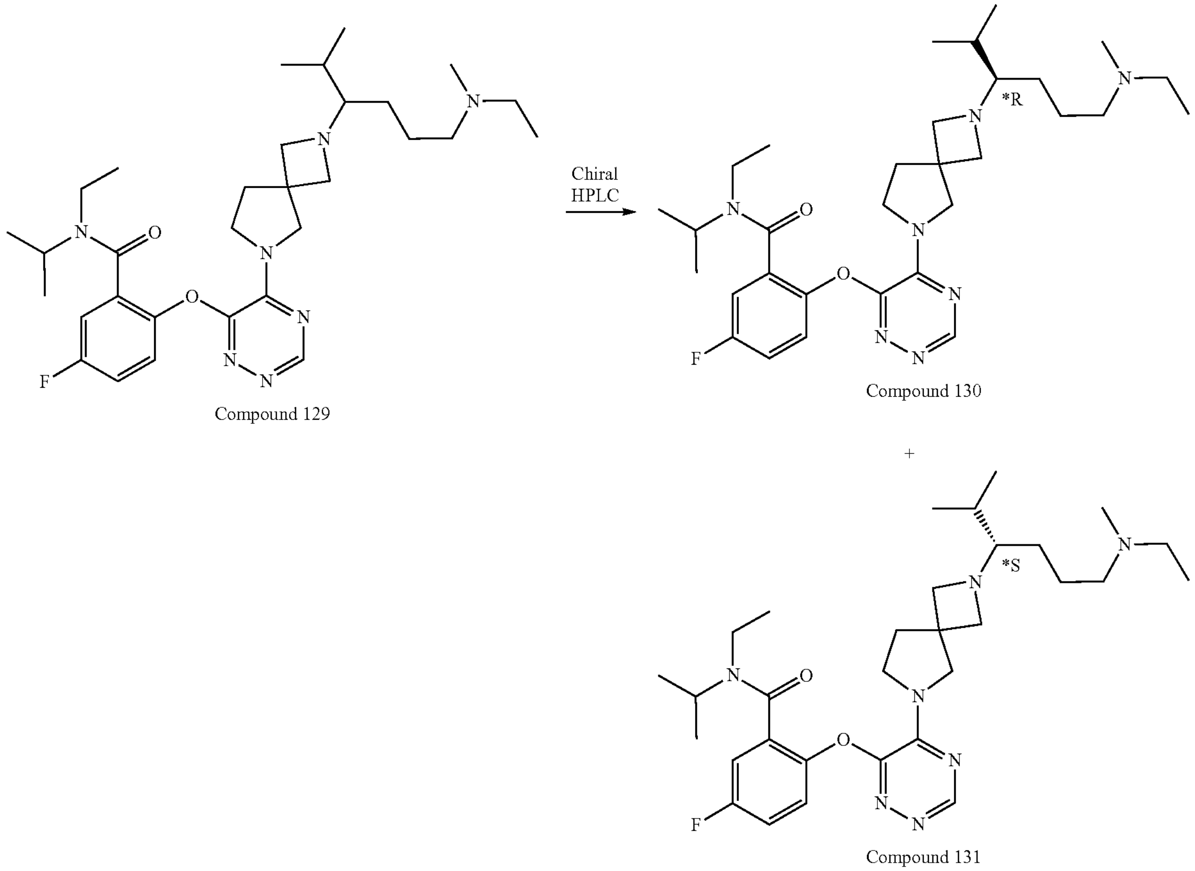

Compound 129

Compound 130

+

Compound 131

N-ethyl-2-((5-(2-(6-(ethyl(methyl)amino)-2-methylhexan-3-yl)-2,6-diazaspiro[3.4]octan-6-yl)-1,2,4-triazin-6-yl)oxy)-5-fluoro-N-isopropylbenzamide (Compound 129) (300 mg) was separated by chiral HPLC over Daicel ChiralPak IG (column: 250×30 mm 10 um; Mobile Phase A: Hexane; Mobile Phase B: EtOH; Flow rate: 20 mL/min; gradient condition from 20% B to 100% B) to afford the title compounds (Compound 130) (68.4 mg) and (Compound 131) (54.8 mg) both as light yellow solid.

Compound 174 and 175

2-((5-(2-((R)-6-(((*R)-2,3-dimethoxypropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((R)-6-(((*S)-2,3-dimethoxypropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

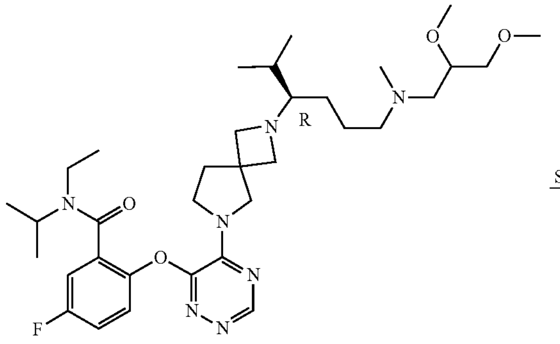

Compound 173

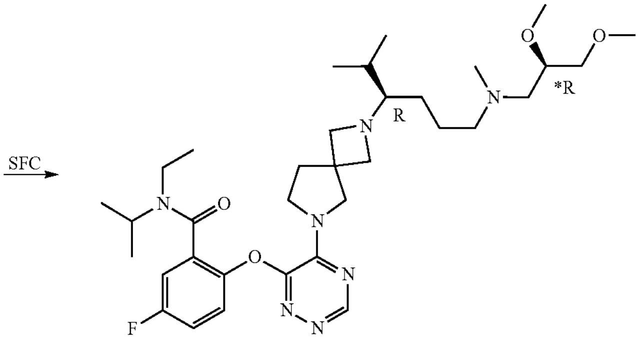

Compound 174

+

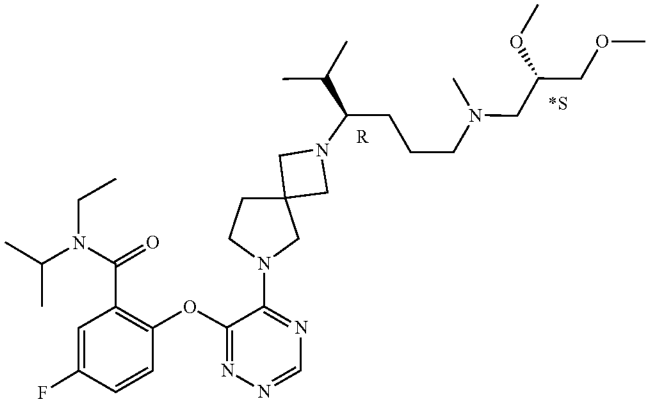

Compound 175

2-((5-(2-((3R)-6-((2,3-dimethoxypropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (Compound 173) (60 mg) was purified by SFC over DAICEL CHIRALPAK AD (column: 250×30 mm 10 um; Mobile phase: A: Supercritical $CO_2$, B: IPA (0.1% ammonia), A:B=70%:30% isocratic (v/v) at 70 mL/min) to afford the title compounds (Compound 174) (10 mg) and (Compound 175) (10 mg) both as colorless sticky oil.

Compound 182 and 183

2-((5-(2-((R)-6-(((*R)-4-(dimethylamino)-4-oxobutan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((R)-6-(((*S)-4-(dimethylamino)-4-oxobutan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

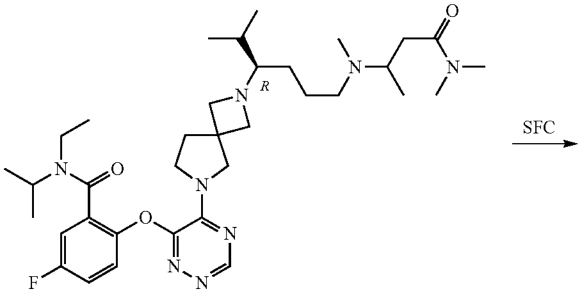

Compound 179

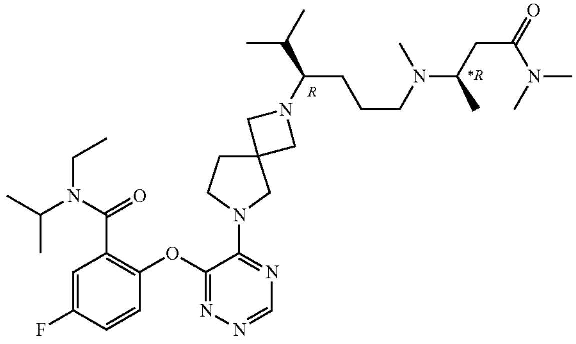

Compound 182

+

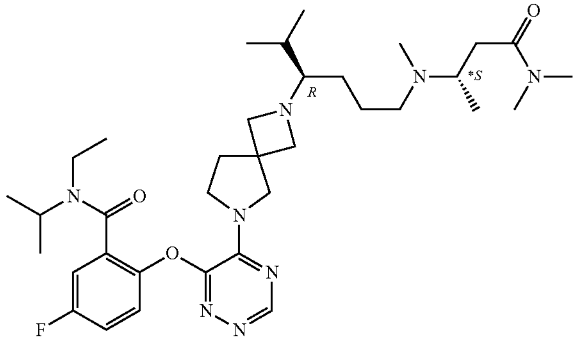

Compound 183

2-((5-(2-((3R)-6-((4-(dimethylamino)-4-oxobutan-2-yl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide fumarate (Compound 179) (58.0 mg) was separated by SFC over DAICEL CHIRALPAK IG (column: 250×30 mm 10 um; Mobile phase: A: Supercritical $CO_2$, B: EtOH (0.1% ammonia), A:B=45:55 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compounds (Compound 182) (12.0 mg) and (Compound 183) (16.0 mg) both as colorless sticky oil.

Compound 186 and 187

2-((5-(2-((R)-6-(((*R)-3-(dimethylamino)-2-methyl-3-oxopropyl)(methyl)amino)-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((R)-6-(((*S)-3-(dimethylamino)-2-methyl-3-oxopropyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

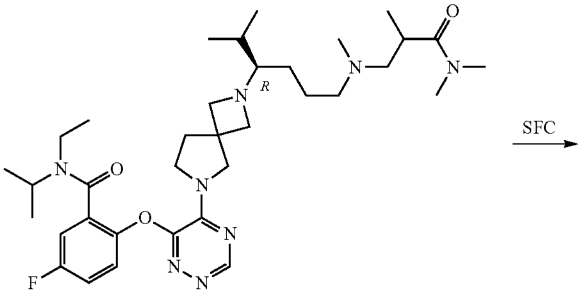

Compound 180

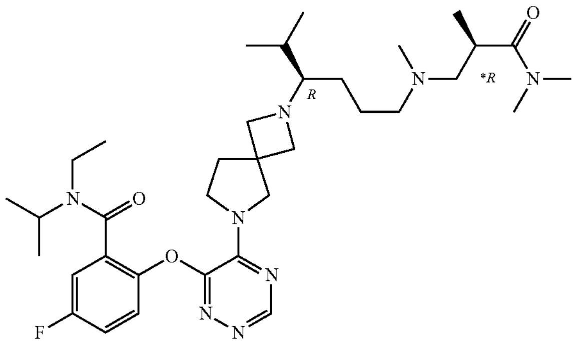

Compound 186

+

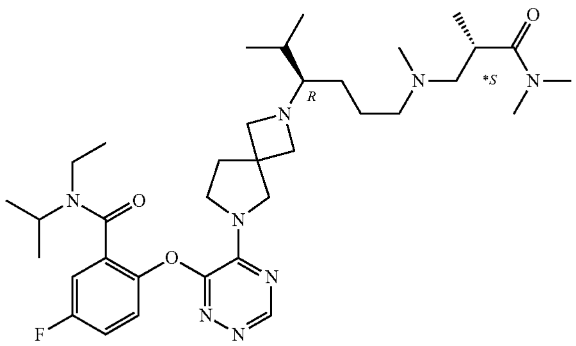

Compound 187

2-((5-(2-((3R)-6-((3-(dimethylamino)-2-methyl-3-oxopropyl)(methyl)amino)-2-methylhexan-3-yl)-2,6-diazaspiro[3.4]octan-6-yl)-1,2,4-triazin-6-yl)oxy)-N-ethyl-5-fluoro- N-isopropylbenzamide (Compound 180) (42.0 mg) was separated by SFC over DAICEL CHIRALPAK AD-H (column: 250×30 mm 5 um; Mobile phase: A: Supercritical $CO_2$, B: IPA (0.1% ammonia), A:B=70:30 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compounds (Compound 186) (20.0 mg) and (Compound 187) (20.0 mg) both as light yellow sticky oil.

Compound 214 and 215

(*R)—N-ethyl-5-fluoro-2-((5-(2-(1-hydroxy-4-methylpentan-3-yl)-2,6-diazaspiro[3.4]octan-6-yl)-1,2,4-triazin-6-yl)oxy)-N-isopropylbenzamide (*S)—N-ethyl-5-fluoro-2-((5-(2-(1-hydroxy-4-methylpentan-3-yl)-2,6-diazaspiro[3.4]octan-6-yl)-1,2,4-triazin-6-yl)oxy)-N-isopropylbenzamide

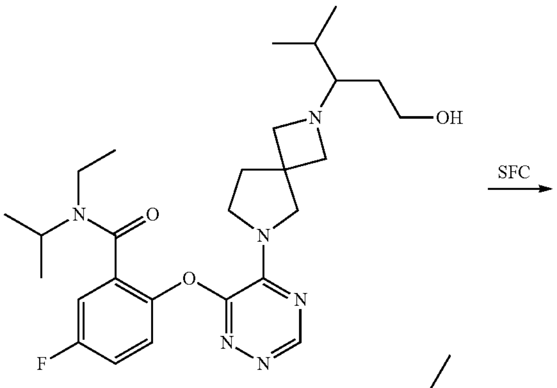

Compound 213

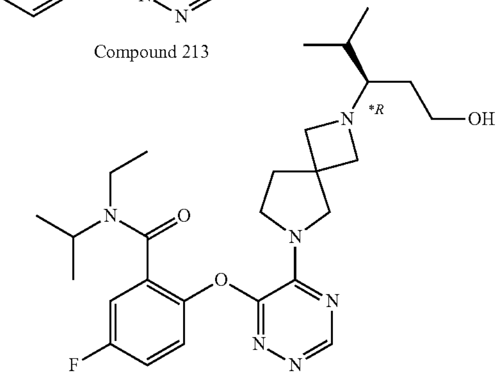

Compound 214

+

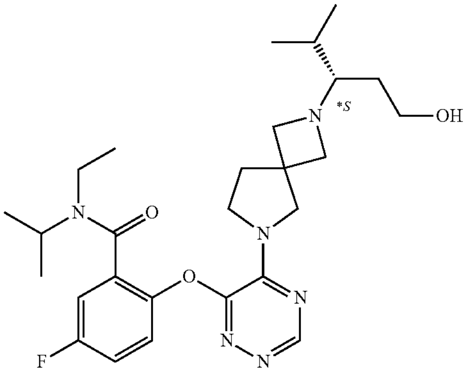

Compound 215

N-ethyl-5-fluoro-2-((5-(2-(1-hydroxy-4-methylpentan-3-yl)-2,6-diazaspiro[3.4]octan-6-yl)-1,2,4-triazin-6-yl)oxy)-N-isopropylbenzamide (Compound 213) (300 mg, crude) was first purified by preparative HPLC over Phenomenex Gemini-NX (column: C18 75×30 mm 3 um; eluent: ACN/$H_2O$ (0.05% ammonia+10 mM $NH_4HCO_3$) from 30% to 60%, v/v) to afford a pure product (100 mg). This pure product was further purified by SFC over DAICEL CHIRALPAK IG (column: 250×30 mm 10 μm; Mobile phase: A: supercritical $CO_2$, B: MeOH (containing 0.1% ammonia), A:B=45%:55% isocratic elution) to afford the title compounds (Compound 214) (38.8 mg) and (Compound 215) (40.7 mg) both as white solid.

Compound 214

LC-MS (ESI) (Method 1): $R_t$=3.000 min, m/z found 515.2 $[M+H]^+$.

SFC (Method 22): $R_t$=4.406 min.

Compound 215

LC-MS (ESI) (Method 1): $R_t$=3.145 min, m/z found 515.2 $[M+H]^+$.

SFC (Method 22): $R_t$=4.925 min.

Compound 216 and 217 tert-butyl (*R)-(3-(6-(6-(2-(ethyl(isopropyl)carbamoyl)-4-fluorophenoxy)-1,2,4-triazin-5-yl)-2,6-diazaspiro[3.4]octan-2-yl)-4-methylpentyl)carbamate tert-butyl (*S)-(3-(6-(6-(2-(ethyl(isopropyl)carbamoyl)-4-fluorophenoxy)-1,2,4-triazin-5-yl)-2,6-diazaspiro[3.4]octan-2-yl)-4-methylpentyl)carbamate

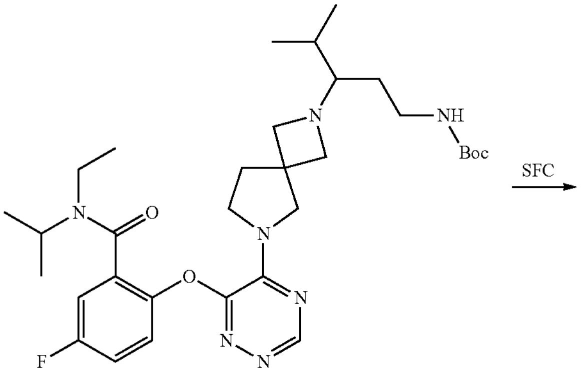

Compound 51

-continued

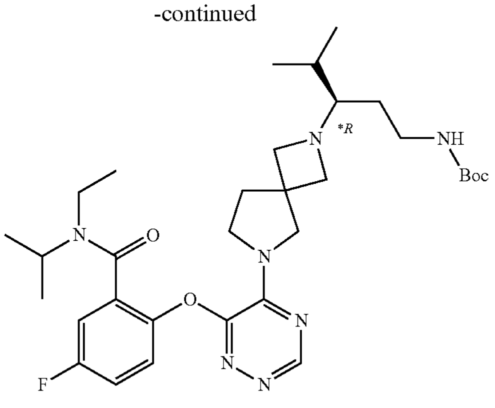

Compound 216

+

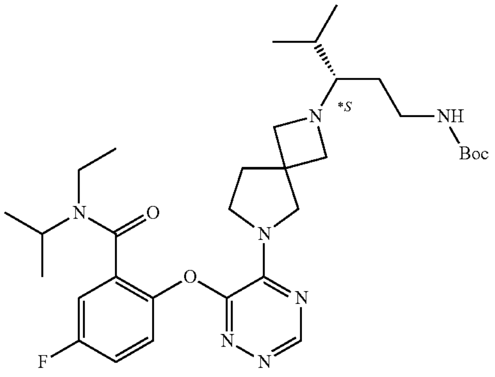

Compound 217

Tert-butyl (3-(6-(6-(2-(ethyl(isopropyl)carbamoyl)-4-fluorophenoxy)-1,2,4-triazin-5-yl)-2,6-diazaspiro[3.4]octan-2-yl)-4-methylpentyl)carbamate (Compound 51) (1.00 g) was purified by SFC over DAICEL CHIRALPAK IG (column: 250×30 mm 10 um; Mobile phase: A: Supercritical $CO_2$, B: MeOH (0.1% ammonia), A:B=60:40 (v/v)) to afford the title compounds (Compound 216) (400 mg) and (Compound 217) (450 mg) both as white solid.

Compound 230

(*R)-2-((5-(2-(1-((2-amino-2-oxoethyl)amino)-4-methylpentan-3-yl)-2,6-diazaspiro[3.4]octan-6-yl)-1,2,4-triazin-6-yl)oxy)-N-ethyl-5-fluoro-N-isopropylbenzamide

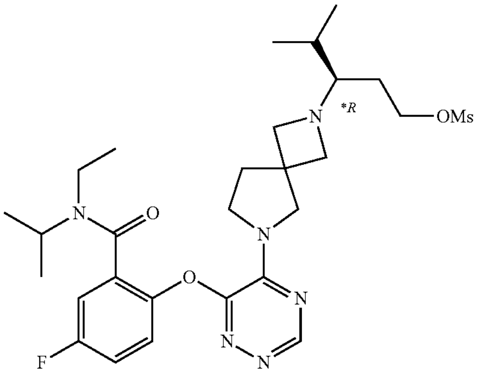

+

-continued

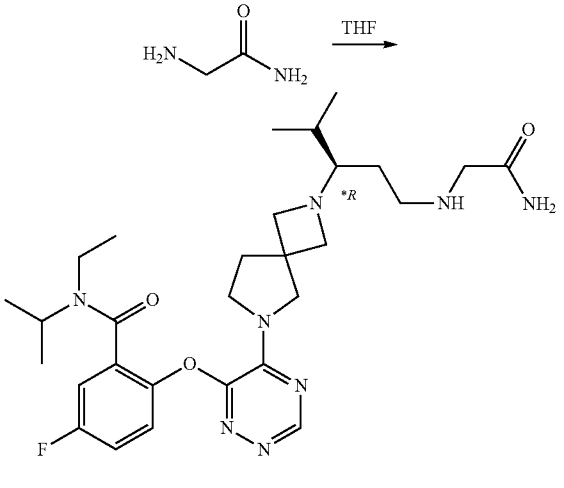

The solution of (*R)-3-(6-(6-(2-(ethyl(isopropyl)carbamoyl)-4-fluorophenoxy)-1,2,4-triazin-5-yl)-2,6-diazaspiro[3.4]octan-2-yl)-4-methylpentyl methanesulfonate (intermediate 124) (160 mg, crude) in THF (2 mL) was added to a solution 2-aminoacetamide (150 mg, 2.03 mmol) in THF (5 mL). The resulting mixture was stirred at RT for 2 h. The reaction mixture was filtered and washed with THF (20 mL). The filtrate was concentrated in vacuo to afford the crude product, which was purified by preparative HPLC over a Xtimate (column: C18 150×40 mm 5 um; eluent: ACN/$H_2O$ (0.05% ammonia) from 25% to 55%, v/v) to afford the title compound (22.1 mg) as a white solid.

LC-MS (ESI) (Method 1): $R_t$=2.849 min, m/z found 571.2 $[M+H]^+$.

SFC (Method 6): $R_t$=1.598 min.

Compound 267, 269, 271, 272, 273, 277

(*R)—N-ethyl-5-fluoro-2-((5-(2-(1-((2-hydroxyethyl)amino)-4-methylpentan-3-yl)-2,6-diazaspiro[3.4]octan-6-yl)-1,2,4-triazin-6-yl)oxy)-N-isopropylbenzamide (*R)—N-ethyl-5-fluoro-2-((5-(2-(1-((2-hydroxyethyl)(methyl)amino)-4-methylpentan-3-yl)-2,6-diazaspiro[3.4]octan-6-yl)oxy)-N-isopropylbenzamide (*R)—N-ethyl-5-fluoro-N-isopropyl-2-((5-(2-(1-((3-methoxypropyl)amino)-4-methylpentan-3-yl)-2,6-diazaspiro[3.4]octan-6-)-1,2,4-triazin-6-yl)oxy)benzamide (*R)—N-ethyl-2-((5-(2-(1-(ethylamino)-4-methylpentan-3-yl)-2,6-diazaspiro[3.4]octan-6-yl)-1,2,4-triazin-6-yl)oxy)-5-fluoro-N-isopropylbenzamide formate (*R)—N-ethyl-5-fluoro-2-((5-(2-(1-((3-hydroxypropyl)amino)-4-methylpentan-3-yl)-2,6-diazaspiro[3.4]octan-6-yl)-1,2,4-triazin-6-yl)oxy)-N-isopropylbenzamide (*R)-2-((5-(2-(1-((3-amino-3-oxopropyl)amino)-4-methylpentan-3-yl)-2,6-diazaspiro[3.4]octan-6-yl)-1,2,4-triazin-6-yl)oxy)-N-ethyl-5-fluoro-N-isopropylbenzamide The following compounds were synthesized by an analogous method as described above for Compound 230

| Co. No. | Structure | Starting Material | Conditions | Spectra Details |
|---|---|---|---|---|
| 267 | 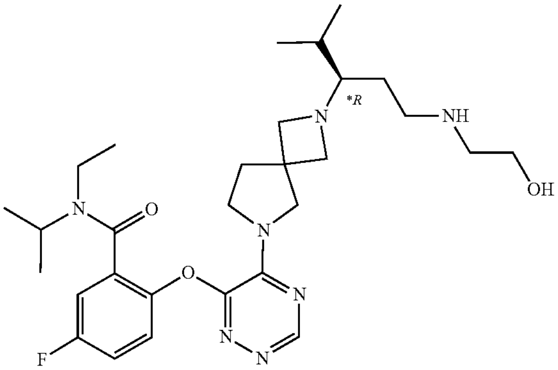 [SMILES: CCN(C(=O)c1cc(F)ccc1Oc1nncnc1N1CCC2(C1)CN([C@H](CCNCCO)C(C)C)C2)C(C)C] | intermediate 124, 2-aminoethan-1-ol | ACN, 60° C. | |
| 269 | 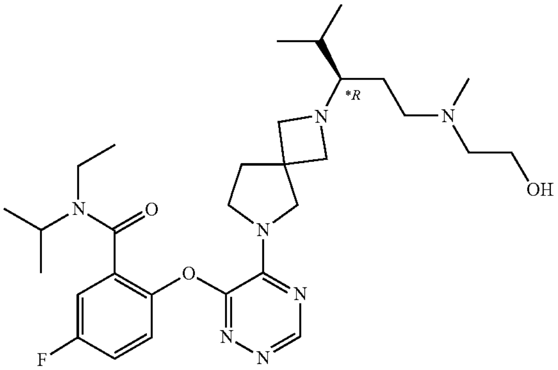 [SMILES: CCN(C(=O)c1cc(F)ccc1Oc1nncnc1N1CCC2(C1)CN([C@H](CCN(C)CCO)C(C)C)C2)C(C)C] | intermediate 124, 2-(methyl-amino)ethan-1-ol | ACN, 60° C. | |
| 271 | 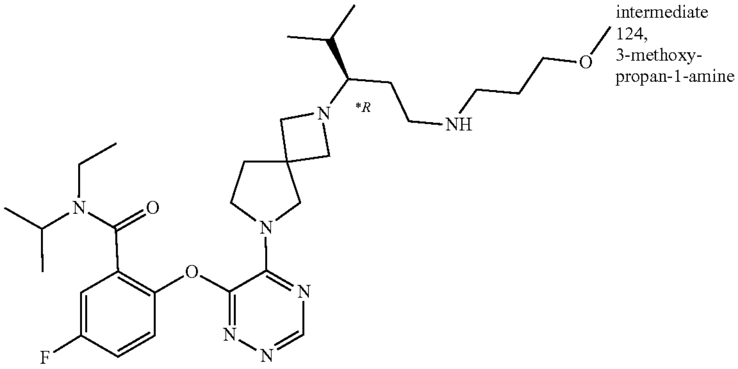 | intermediate 124, 3-methoxy-propan-1-amine | THF, RT | LC-MS (ESI) (Method 2): $R_t$ = 1.995 min, m/z found 586.3 $[M + H]^+$. SFC (Method 13): $R_t$ = 2.152 min. |
| 272 | 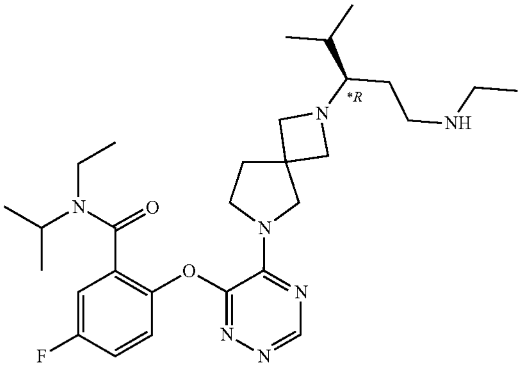 [SMILES: CCNCC[C@H](C(C)C)N1CC2(CCN(c3ncnnc3Oc3ccc(F)cc3C(=O)N(CC)C(C)C)C2)C1] formate salt | intermediate 124, ethanamine | THF, RT | LC-MS (ESI) (Method 2): $R_t$ = 1.892 min, m/z found 542.3 $[M + H]^+$. SFC (Method 14): $R_t$ = 2.753 min. |

-continued

| Co. No. | Structure | Starting Material | Conditions | Spectra Details |
|---|---|---|---|---|
| 273 | 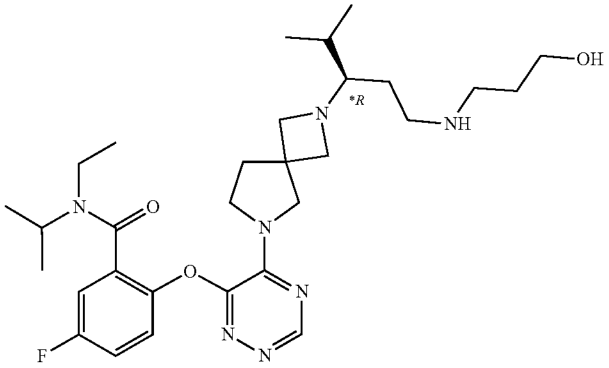 [SMILES: CCN(C(=O)c1cc(F)ccc1Oc1nncnc1N1CCC2(C1)CN([C@H](CCNCCCO)C(C)C)C2)C(C)C] | intermediate 124, 3-aminopropan-1-ol | THF, RT | LC-MS (ESI) (Method 1): $R_t$ = 2.894 min, m/z found 572.4 $[M + H]^+$. SFC (Method 6): $R_t$ = 1.421 min. |
| 277 | 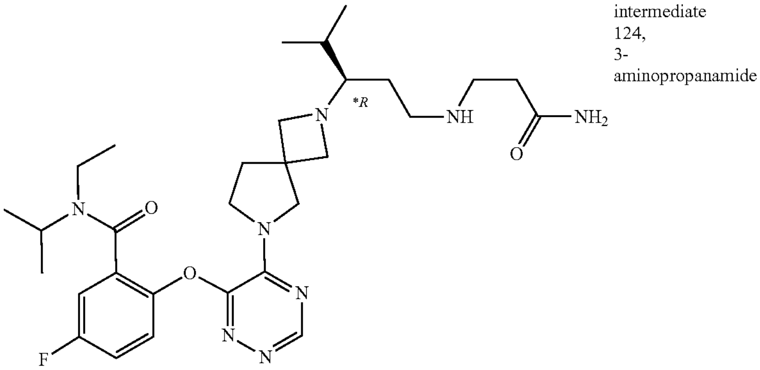 | intermediate 124, 3-aminopropanamide | THF, 60° C. | |

Compound 236 and 237

N-ethyl-5-fluoro-N-isopropyl-2-((5-(2-((3*R,5*R)-6-((2-methoxyethyl)(methyl)amino)-2,5-dimethylhexan-3-yl)-2,6-diazaspiro[3.4]octan-6-yl)-1,2,4-triazin-6-yl)oxy)benzamide N-ethyl-5-fluoro-N-isopropyl-2-((5-(2-((3*S,5*R)-6-((2-methoxyethyl)(methyl)amino)-2,5-dimethylhexan-3-yl)-2,6-diazaspiro[3.4]octan-6-yl)-1,2,4-triazin-6-yl)oxy)benzamide

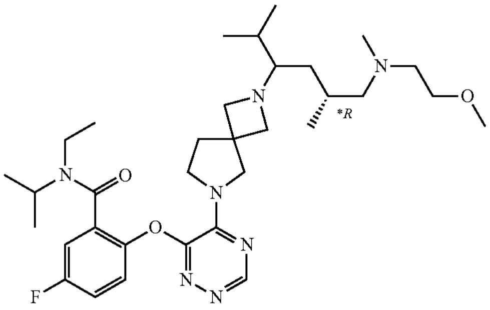

Compound 234

-continued

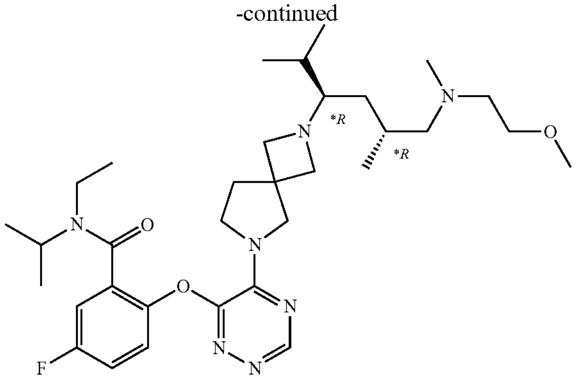

Compound 236

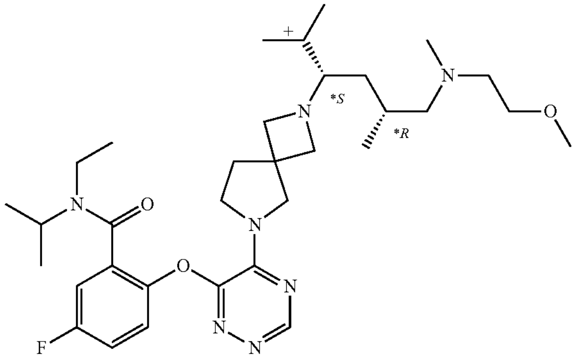

Compound 237

N-ethyl-5-fluoro-N-isopropyl-2-((5-(2-((5*R)-6-((2-methoxyethyl)methyl)amino)-2,5-dimethylhexan-3-yl)-2,6-diazaspiro[3.4]octan-6-yl)-1,2,4-triazin-6-yl)oxy)benzamide (Compound 234) (89.0 mg) was purified by SFC over DAICEL CHIRALPAK AD (column: 250×30 mm 10 um; Mobile phase: A: Supercritical $CO_2$, B: IPA (0.1% ammonia), A:B=80:20 at 60 mL/min) to afford the title compounds (Compound 236) (31.0 mg, 34% yield) and (Compound 237) (24.7 mg, 27% yield) both as yellow sticky solid.

Compound 238 and 239

N-ethyl-5-fluoro-N-isopropyl-2-((5-(2-((3*R,5*S)-6-((2-methoxyethyl)(methyl)amino)-2,5-dimethylhexan-3-yl)-2,6-diazaspiro[3.4]octan-6-yl)-1,2,4-triazin-6-yl)oxy)benzamide N-ethyl-5-fluoro-N-isopropyl-2-((5-(2-((3*S,5*S)-6-((2-methoxyethyl)(methyl)amino)-2,5-dimethylhexan-3-yl)-2,6-diazaspiro[3.4]octan-6-yl)-1,2,4-triazin-6-yl)oxy)benzamide

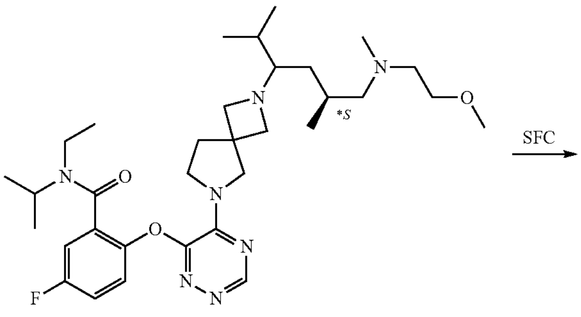

Compound 235

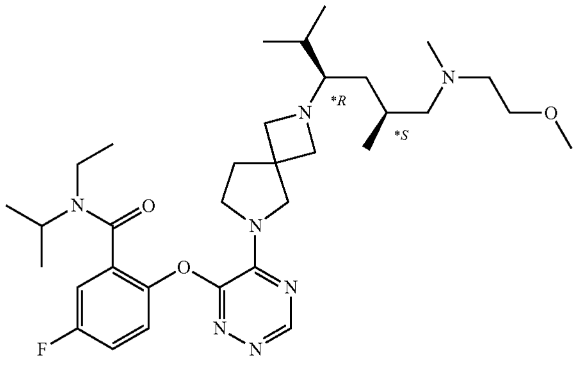

Compound 238

+

-continued

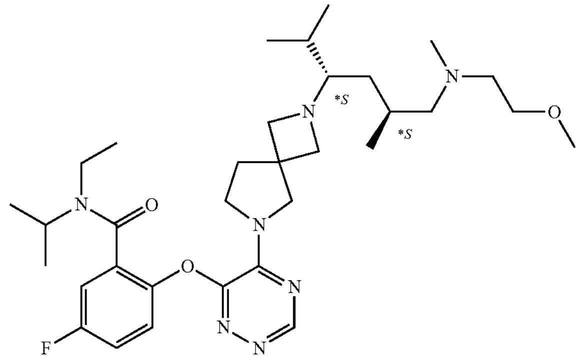

Compound 239

N-ethyl-5-fluoro-N-isopropyl-2-((5-(2-((5*S)-6-((2-methoxyethyl)methyl)amino)-2,5-dimethylhexan-3-yl)-2,6-diazaspiro[3.4]octan-6-yl)-1,2,4-triazin-6-yl)oxy)benzamide (Compound 235) (51 mg) was purified by SFC over DAICEL CHIRALCEL OD-H (column: 250×30 mm Sum; Mobile phase: A: Supercritical $CO_2$, B: EtOH (0.1% ammonia), A:B=85:15 at 60 mL/min) to afford the title compounds (Compound 238) (17.9 mg, 35%) and (Compound 239) (14.3 mg, 28%) both as white solid.

Compound 248 and 249

N-ethyl-5-fluoro-N-isopropyl-2-((5-(2-((R)-6-(((*R)-2-methoxypropyl)(methyl)amino)-2-methylhexan-3-yl)-2,6-diazaspiro[3.4]octan-6-yl)-1,2,4-triazin-6-yl)oxy)benzamide N-ethyl-5-fluoro-N-isopropyl-2-((5-(2-((R)-6-(((*S)-2-methoxypropyl)(methyl)amino)-2-methylhexan-3-yl)-2,6-diazaspiro[3.4]octan-6-yl)-1,2,4-triazin-6-yl)oxy)benzamide

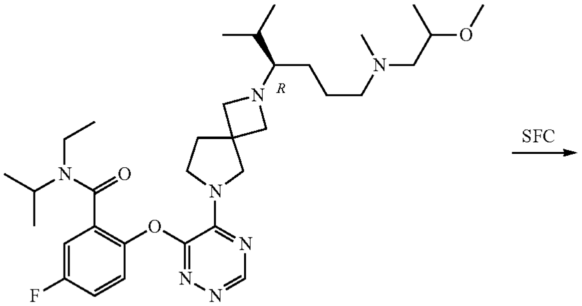

Compound 247

-continued

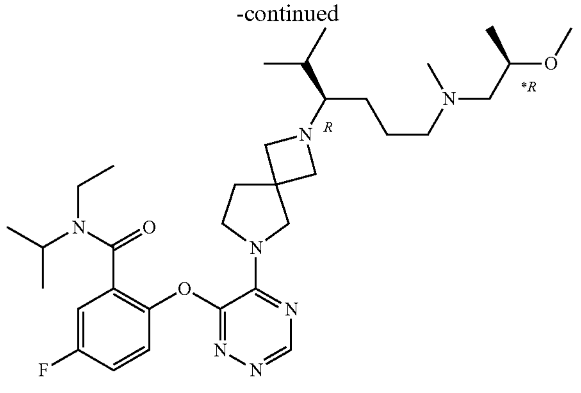

Compound 248

+

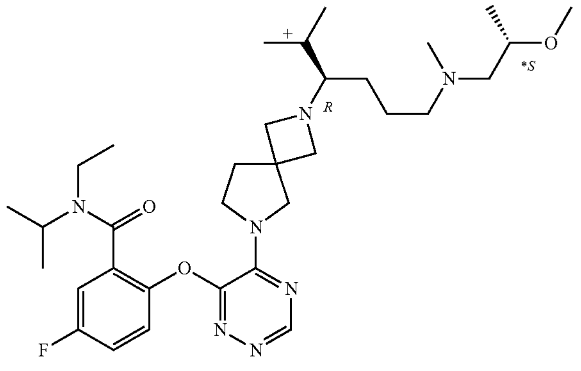

Compound 249

N-ethyl-5-fluoro-N-isopropyl-2-((5-(2-((3R)-6-((2-methoxypropyl)(methyl)amino)-2-methylhexan-3-yl)-2,6-diazaspiro[3.4]octan-6-yl)-1,2,4-triazin-6-yl)oxy)benzamide (Compound 247) (70 mg) was purified by SFC over DAICEL CHIRALPAK AD-H (column: 250×30 mm 5 μm; Mobile phase: A: supercritical $CO_2$, B: IPA (0.1% ammonia), A:B=75%:25% at 60 mL/min) to afford the title compounds (Compound 248) (10 mg) and (Compound 249) (30 mg) both as light yellow sticky oil.

Compound 261 and 262

N-ethyl-5-fluoro-2-((5-(2-(6-hydroxy-2,4-dimethylhexan-3-yl)-2,6-diazaspiro[3.4]octan-6-yl)-1,2,4-triazin-6-yl)oxy)-N-isopropylbenzamide (mixture of R,S and S,R; or mixture of R,R and S,S)

N-ethyl-5-fluoro-2-((5-(2-(6-hydroxy-2,4-dimethylhexan-3-yl)-2,6-diazaspiro[3.4]octan-6-yl)-1,2,4-triazin-6-yl)oxy)-N-isopropylbenzamide (mixture of R,R and S,S; or mixture of R,S and S,R)

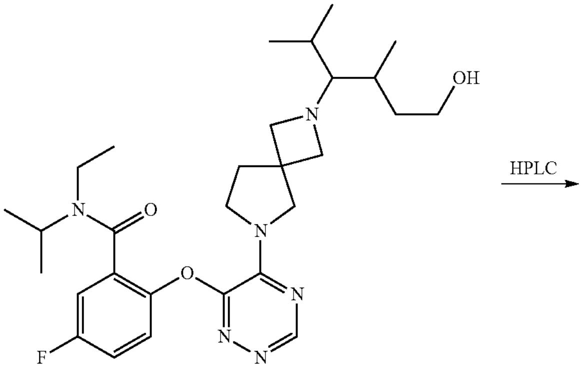

Compound 260

-continued

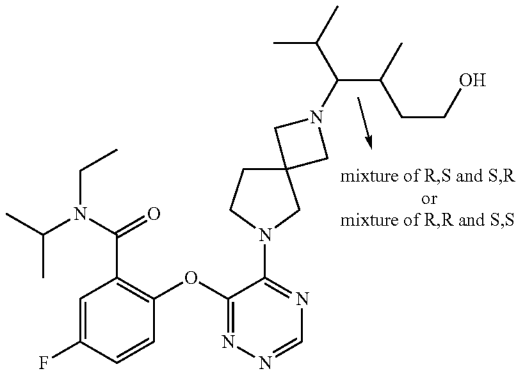

Compound 261

+

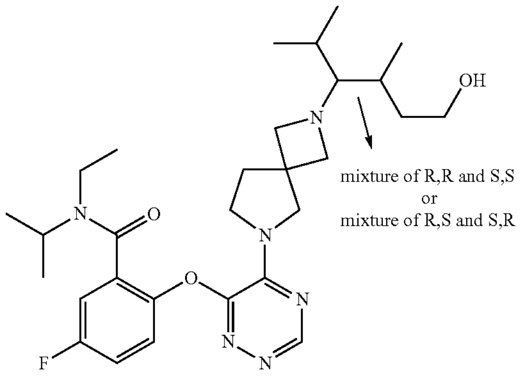

Compound 262

N-ethyl-5-fluoro-2-((5-(2-(6-hydroxy-2,4-dimethylhexan-3-yl)-2,6-diazaspiro[3.4]octan-6-yl)-1,2,4-triazin-6-yl)oxy)-N-isopropylbenzamide (Compound 260) (5.0 g, crude) was purified by HPLC (column: Xtimate C18 150×40 mm 5 μm; Mobile Phase: A: $H_2O$ (0.05% ammonia), B: ACN, Flow rate: 60 mL/min, gradient: from 40% B to 60% B) to afford the title compounds (Compound 261) (220 mg) and (Compound 262) (300 mg) both as white solid.

Compound 298

N-ethyl-5-fluoro-2-((5-(2-((3R)-6-hydroxy-2-methylheptan-3-yl)-2,6-diazaspiro[3.4]octan-6-yl)-1,2,4-triazin-6-yl)oxy)-N-isopropylbenzamide The following compound was synthesized by an analogous method described above for intermediate 53

| Co. No. | Structure | Starting Materials |
|---|---|---|
| 298 | 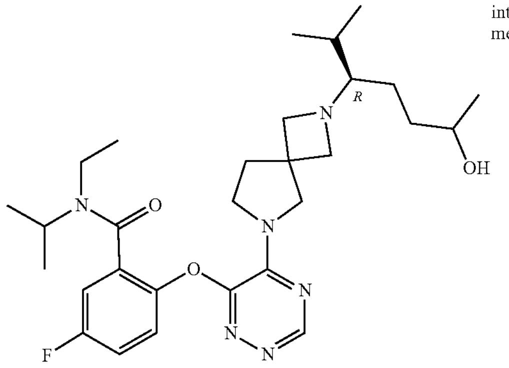 | intermediate 97, methylmagnesium bromide |

Compound 301

N-ethyl-5-fluoro-N-isopropyl-2-((5-(6-(6-((2-methoxyethyl)(methyl)amino)-2-methylhexan-3-yl)-2,6-diazaspiro[3.4]octan-2-yl)-1,2,4-triazin-6-yl)oxy)benzamide

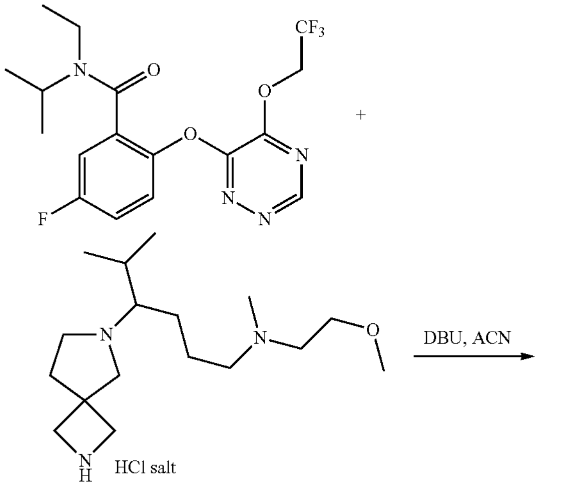

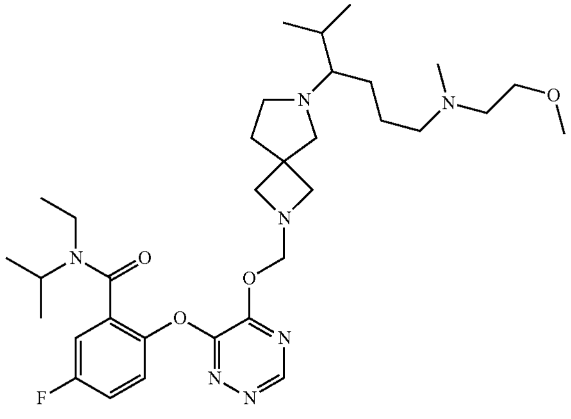

To a solution of N-(2-methoxyethyl)-N,5-dimethyl-4-(2,6-diazaspiro[3.4]octan-6-yl)hexan-1-amine hydrochloride (intermediate 164) (2.10 g, crude) and DBU (1.80 g, 11.8 mmol) in ACN (40 mL) was added N-ethyl-5-fluoro-N-isopropyl-2-((5-(2,2,2-trifluoroethoxy)-1,2,4-triazin-6-yl)oxy)benzamide (intermediate 159) (600 mg, 88% purity, 1.31 mmol) under $N_2$ atmosphere. The resulting mixture was stirred at 26° C. for 16 h. The reaction mixture was concentrated under reduced pressure and the residue was purified by preparative HPLC over Phenomenex Gemini-NX (column: 80×40 mm 3 μm, Mobile Phase: A: $H_2O$ (0.05% ammonia), B: ACN, Flow rate: 30 mL/min, gradient condition: from 29% B to 99% B) to afford the title compound (130 mg) as colorless oil.

Compound 319, 320, 321 and 322

N-ethyl-5-fluoro-2-((5-(2-((3*R,5*R)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((3*S,5*S)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((3*R,5*S)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((3*S,5*R)-5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide

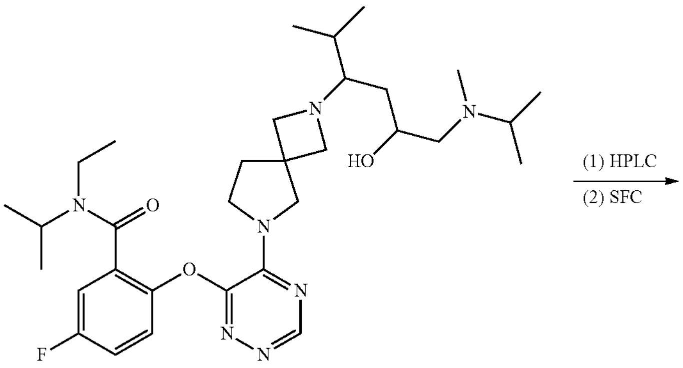

Compound 318

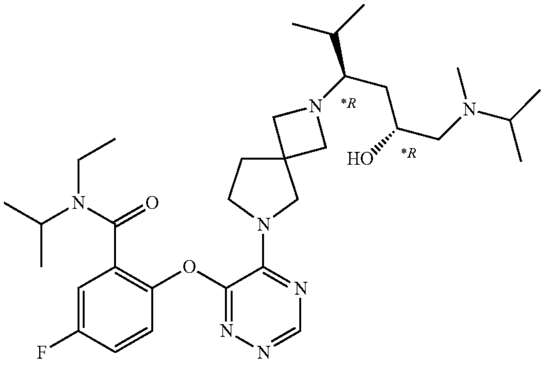

Compound 319

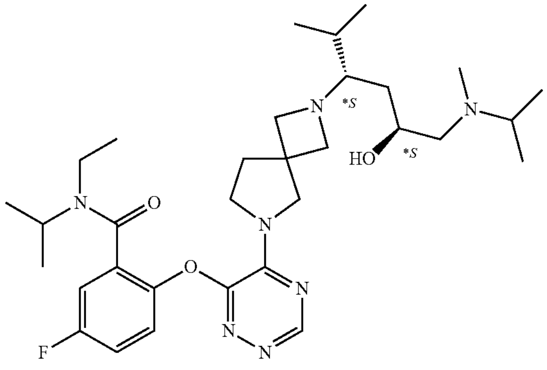

Compound 320

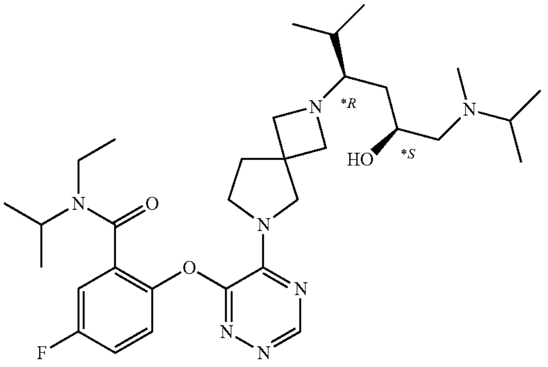

Compound 321

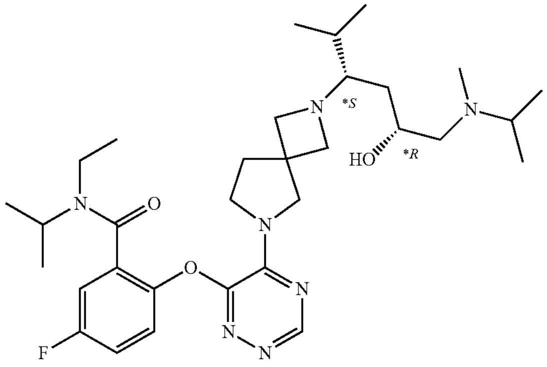

Compound 322

N-ethyl-5-fluoro-2-((5-(2-(5-hydroxy-6-(isopropyl(methyl)amino)-2-methylhexan-3-yl)-2,6-diazaspiro[3.4]octan-6-yl)-1,2,4-triazin-6-yl)oxy)-N-isopropylbenzamide (Compound 318) (235 mg, 91.5% purity) was first separated by preparative HPLC over Welch Xtimate (column: 150×25 mm 5 μm, Mobile Phase A: $H_2O$ (0.2% FA), Mobile Phase B: ACN, Flow rate: 25 mL/min, gradient condition: from 2% B to 32%) to afford a mixture of (Compound 319 and Compound 320) (95 mg, 88% purity by LCMS) and a mixture of (Compound 321 and Compound 322) (97 mg, 81% purity by LCMS).

The mixture of (Compound 319 and Compound 320) (95 mg, 88% purity by LCMS) and the mixture of (Compound 321 and Compound 322) (97 mg, 81% purity by LCMS) were further separately purified by preparative HPLC over Welch Xtimate (column: C18 100×40 mm 3 μm, Mobile Phase A: $H_2O$ (0.075% TFA), Mobile Phase B: ACN, Flow rate: 30 mL/min, gradient condition: from 10% B to 40% B) to afford a mixture of (Compound 319 and Compound 320) (73 mg, 98.9% purity by LCMS) and a mixture of (Compound 321 and Compound 322) (70 mg, 100% purity by LCMS) both as TFA salts.

The mixture of (Compound 319 and Compound 320) (70 mg, 98.9% purity by LCMS, as TFA salt) was further separated by SFC over DAICEL CHIRALPAK IG (column: 250×30 mm, 10 um); Mobile phase: A: Supercritical $CO_2$, B: MeOH (0.1% ammonia), A:B=40:60 at 80 mL/min) to afford Compound 319 (15.5 mg) and Compound 320 (16.2 mg) both as colorless sticky oil.

The mixture of (Compound 321 and Compound 322) (65 mg, 100% purity by LCMS, as TFA salt) was further separated by SFC over DAICEL CHIRALPAK IG (column: 250×30 mm, 10 um; Mobile phase: A: Supercritical $CO_2$, B: MeOH (0.1% ammonia), A:B=65:35 at 80 mL/min) to afford Compound 322 (24 mg) and another fraction (22 mg) which was further separated by SFC over DAICEL CHIRALPAK AD (column: 250×30 mm, 10 um; Mobile phase: A: Supercritical $CO_2$, B: EtOH (0.1% ammonia), A:B=75:25 at 60 mL/min) to afford Compound 321 (16 mg).

Compound 330, 331, 332, 333

2-((5-(2-((3*R,5*R)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((3*S,5*S)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((3*S,5*R)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide 2-((5-(2-((3*R,5*S)-6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide

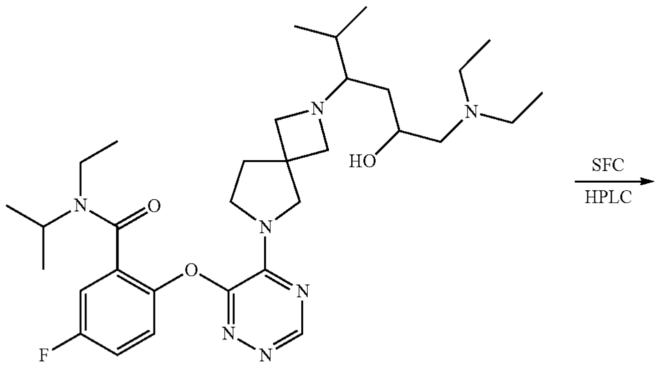

Compound 329

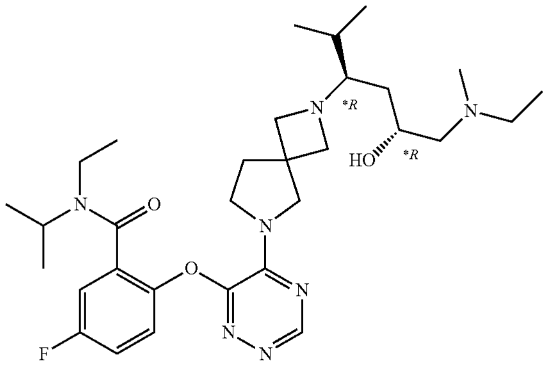

Compound 330

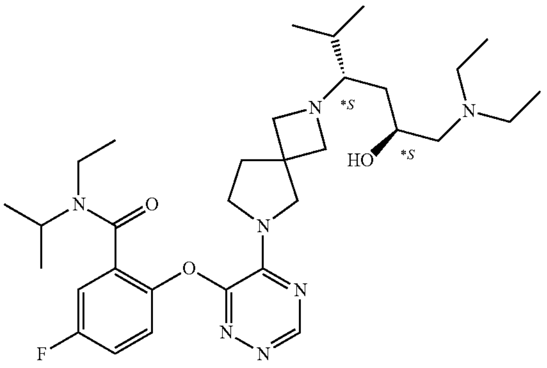

Compound 331

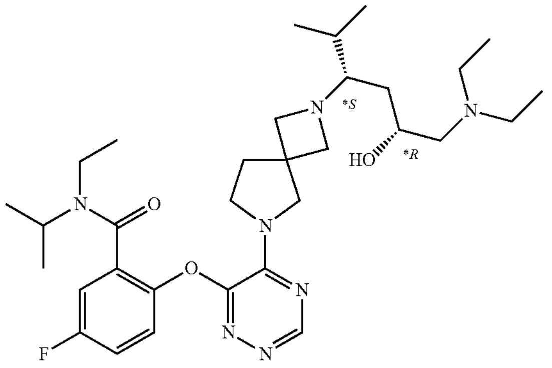

Compound 332

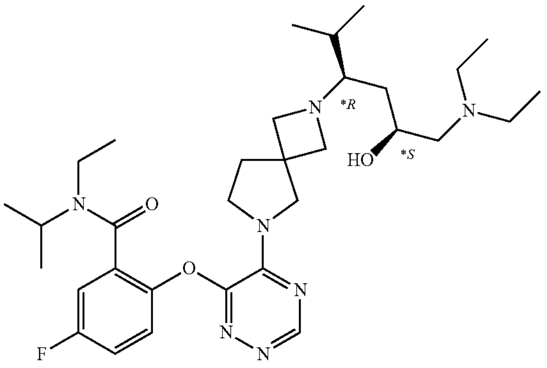

Compound 333

2-((5-(2-(6-(diethylamino)-5-hydroxy-2-methylhexan-3-yl)-2,6-diazaspiro[3.4]octan-6-yl)-1,2,4-triazin-6-yl)oxy)-N-ethyl-5-fluoro-N-isopropylbenzamide (Compound 329) (450 mg) was first separated by SFC over Daicel Chiralpak AD (column: 250×30 mm, 10 μm, Mobile phase: A: Supercritical $CO_2$, B: EtOH (0.1% ammonia), A:B=80:20 at 60 mL/min) to afford a mixture of (Compound 330 and Compound 331) (200 mg), Compound 332 (70 mg, 100% purity by LCMS) and Compound 333 (170 mg, 88.9% purity by LCMS).

The Compound 333 (170 mg, 88.9% purity by LCMS) was further purified by preparative HPLC over Phenomenex Gemini-NX (column: 75×30 mm, 3 um, Mobile phase: A: $H_2O$ (0.05% ammonia+10 mM $NH_4HCO_3$), B: ACN, gradient condition: from 33% B to 63%, Flow rate: 25 mL/min) to afford Compound 333 (69 mg, 97.5% purity by LCMS).

The mixture of (Compound 330 and Compound 331) (200 mg) was further separated by chiral HPLC over DAICEL CHIRALPAK IG (column: 250×30 mm, 10 μm, Mobile phase: A: Heptane, B: EtOH (0.1% ammonia), gradient from 30% B to 50%, Flow rate: 25 mL/min) to afford Compound 330 (60 mg, 75% purity by LCMS) and Compound 331 (60 mg, 92% purity by LCMS).

The Compound 330 (60 mg, 75% purity by LCMS) and Compound 331 (60 mg, 92% purity by LCMS) were further separately purified by preparative HPLC over Welch Xtimate (column: 150×25 mm, 5 μm; Mobile phase: A: $H_2O$ (0.2% FA), B: ACN, Flow rate: 25 mL/min, gradient condition: from 2% B to 32% B) and basified with ammonia to afford Compound 330 (29 mg, 100% purity by LCMS) and Compound 331 (23 mg, 100% purity by LCMS).

Compound 340 and 341

N-ethyl-2-((5-(2-((3*R,5S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide N-ethyl-2-((5-(2-((3*S,5S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide

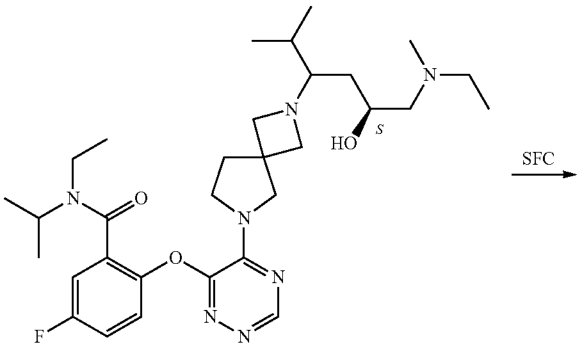

Compound 338

-continued

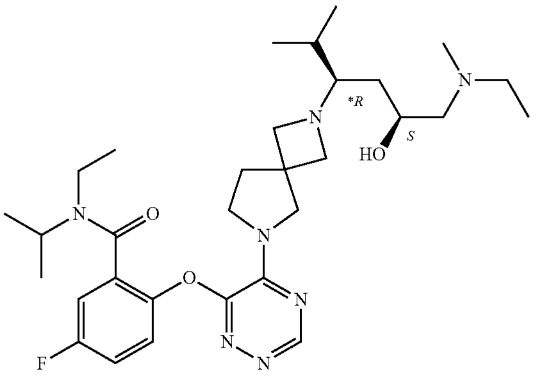

Compound 340

+

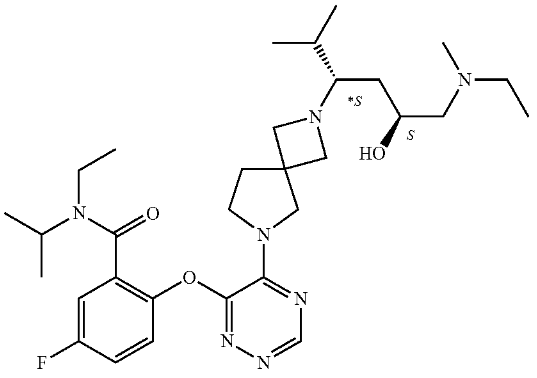

Compound 341

N-ethyl-2-((5-(2-((5S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide (Compound 338) (160 mg) was separated by SFC over DAICEL CHIRALPAK IG (column: 250×30 mm, 10 μm; Mobile phase: A: Supercritical $CO_2$, B: IPA (0.1% ammonia), A:B=55:45 at 80 mL/min) to afford the title compounds (Compound 340) (30 mg) and (Compound 341) (66 mg) both as colorless oil.

Compound 344 and 345

N-ethyl-2-((5-(2-((5)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide N-ethyl-2-((5-(2-((3*S,5R)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide

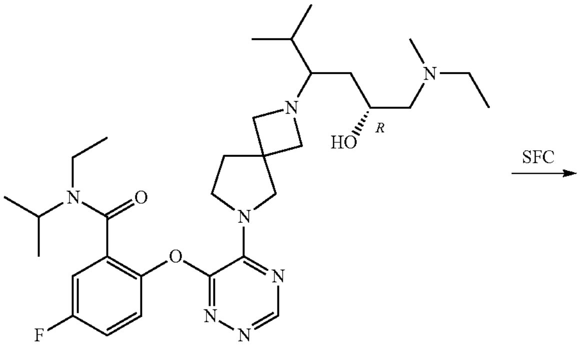

Compound 339

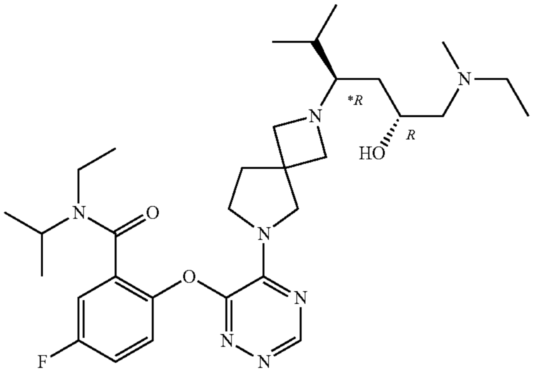

Compound 344

+

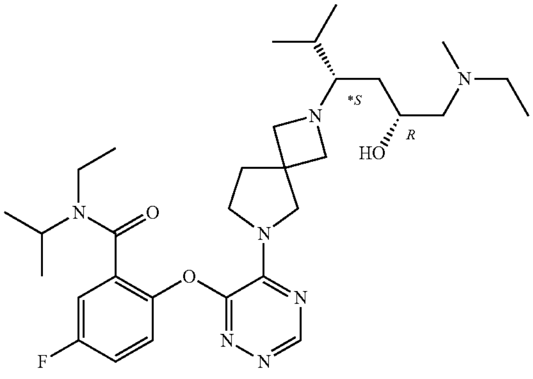

Compound 345

N-ethyl-2-((5-(2-((5R)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide (Compound 339) (200 mg) was separated by SFC over DAICEL CHIRALPAK IG (column: 250×30 mm, 10 μm; Mobile phase: A: Supercritical $CO_2$, B: EtOH (0.1% ammonia), A:B=45:55 at 80 mL/min) to afford Compound 344 (100 mg, 98.4% purity by LCMS) and Compound 345 (70 mg, 76% purity by LCMS) both as colorless sticky solid.

Compound 347

N-ethyl-2-((5-(2-((3*S,5R)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide formate

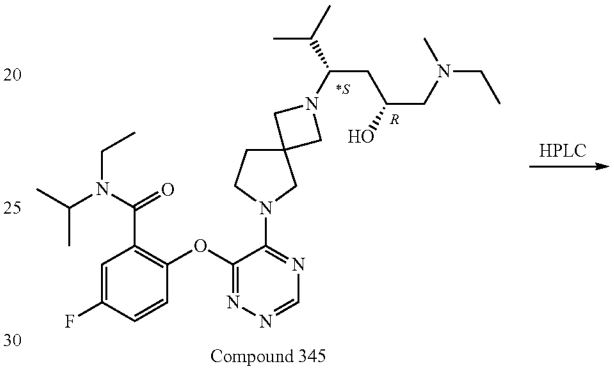

Compound 345

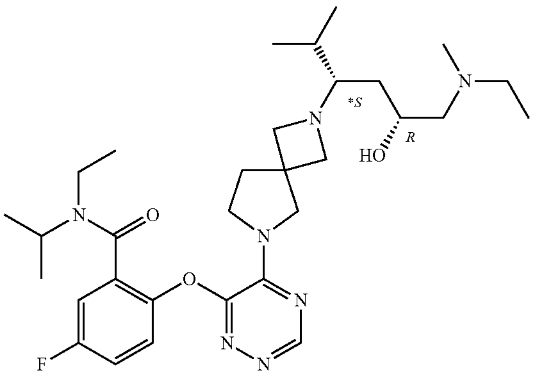

formate salt

Compound 347

N-ethyl-2-((5-(2-((3*S,5R)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N-isopropylbenzamide (Compound 345) (70 mg, 76% purity by LCMS) was further purified by preparative HPLC over Phenomenex Gemini-NX (column: 150×30 mm, 5 um; Mobile Phase A: $H_2O$ (0.225% FA), Mobile Phase B: ACN, Flow rate: 35 mL/min, gradient condition: from 15% B to 45% B) to afford the title compound (40.0 mg, 99.6% purity by LCMS) as a white solid.

LC-MS (ESI) (Method 1): $R_t$=2.891 min, m/z found 586.4 $[M+H]^+$.

SFC (Method 8): $R_t$=2.652 min.

Compound 350 and 351

N-ethyl-5-fluoro-2-((5-(2-((3*R,5S)-5-hydroxy-6-((2-methoxyethyl)(methyl)amino)-4-methylhexan-3-yl)-2,6-diazaspiro[3.4]octan-6-yl)-1,2,4-triazin-6-yl)oxy)-N-isopropylbenzamide N-ethyl-5-fluoro-2-((5-(2-((3*S,5S)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide

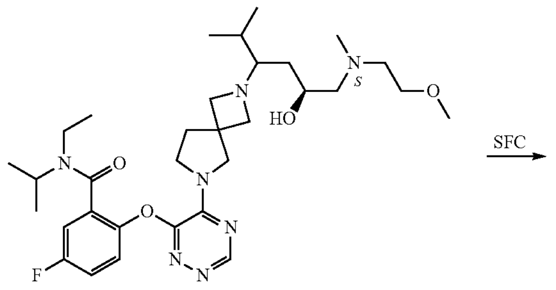

Compound 348

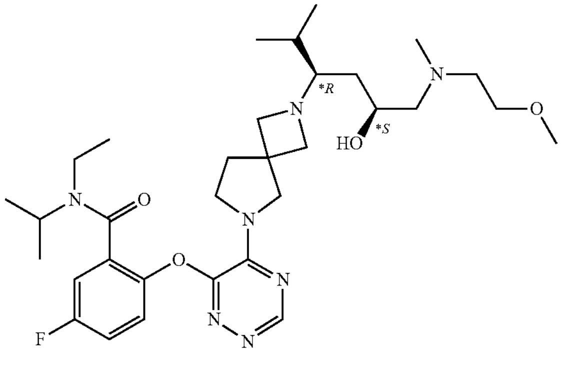

Compound 350

+

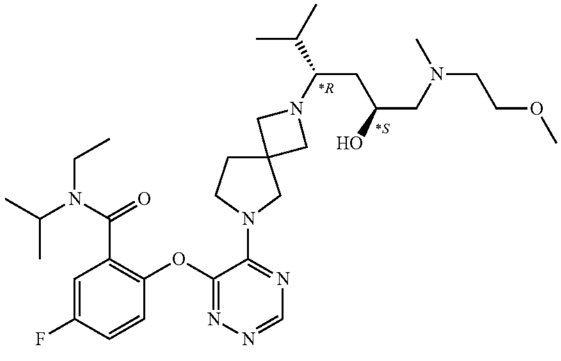

Compound 351

N-ethyl-5-fluoro-2-((5-(2-((5S)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide (Compound 348) (60 mg) was separated by SFC over DAICEL CHIRALPAK IG (column: 250×30 mm, 10 um; Mobile phase: A: Supercritical $CO_2$, B: EtOH (0.1% ammonia), A:B=55:45 at 80 mL/min) to afford the title compounds (Compound 350) (22 mg) and (Compound 351) (27.7 mg).

Compound 354 and 355

N-ethyl-5-fluoro-2-((5-(2-((3*R,5R)-5-hydroxy-6-((2-methoxyethyl)(methyl)amino)-4-methylhexan-3-yl)-2,6-diazaspiro[3.4]octan-6-yl)-1,2,4-triazin-6-yl)oxy)-N-isopropylbenzamide N-ethyl-5-fluor-2-((5-(2-((3*S,5R)-5-hydroxy-6-((2-methoxyethyl)(methyl)amino)-methylhexan-3-yl)-2,6-diazaspiro[3.4]octan-6-yl)-1,2,4-triazin-6-yl)oxy)-N-isopropylbenzamide

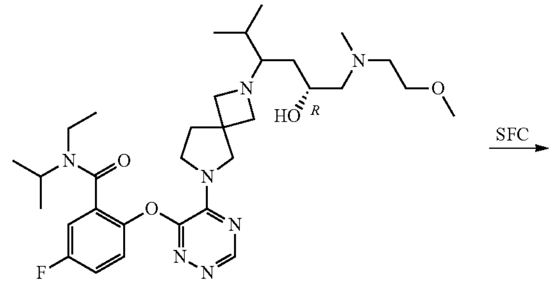

Compound 349

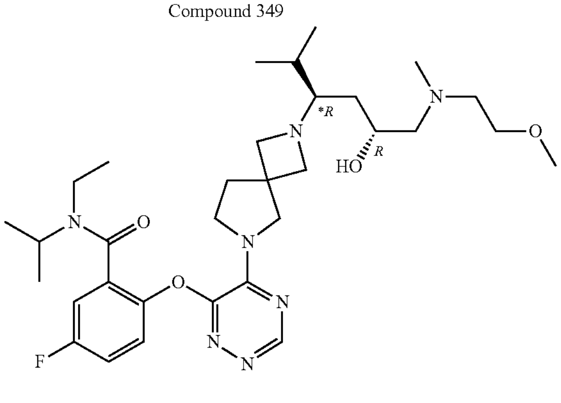

Compound 354

+

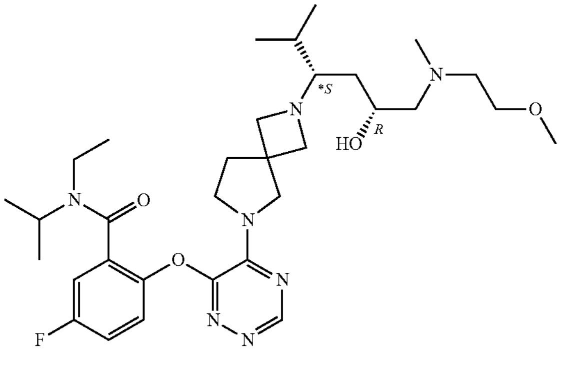

Compound 355

N-ethyl-5-fluoro-2-((5-(2-((5R)-5-hydroxy-6-((2-methoxyethyl)(methyl)amino)-2-methylhexan-3-yl)-2,6-diazaspiro[3.4]octan-6-yl)-1,2,4-triazin-6-yl)oxy)-N-isopropylbenzamide (Compound 349) (200 mg) was separated by SFC over DAICEL CHIRALPAK IG (column: 250×30 mm, 10 um; Mobile phase: A: Supercritical $CO_2$, B: EtOH (0.1% ammonia), A:B=50:50 at 80 mL/min) to afford the title compounds (Compound 354) (100 mg) and (Compound 355) (70 mg) both as colorless sticky solid.

Compound 361 and 362

2-((5-(2-((3*R)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((3*S)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide

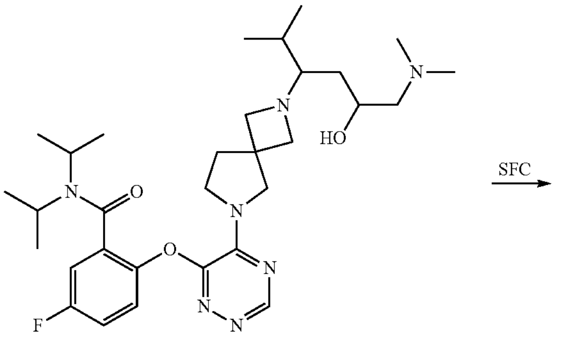

Compound 360

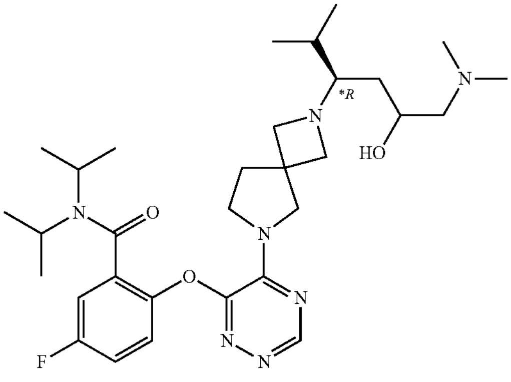

Compound 361

+

-continued

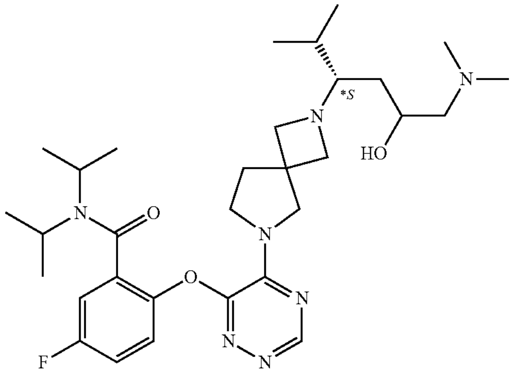

Compound 362

2-((5-(2-(6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide (Compound 360) (250 mg) was separated by SFC over DAICEL CHIRALPAK IG (column: 250×30 mm, 10 um; Mobile phase: A: Supercritical $CO_2$, B: IPA (0.1% ammonia), A:B=40:40 at 80 mL/min) to afford the title compounds (Compound 361) (105 mg) and (Compound 362) (120 mg) both as white solid.

Compound 363 and 364

2-((5-(2-((3*R,5*R)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((3*R,5*S)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide

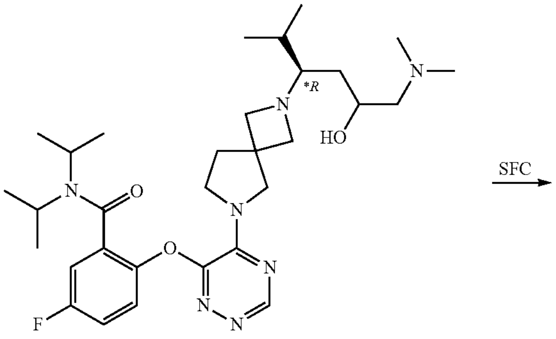

Compound 361

-continued

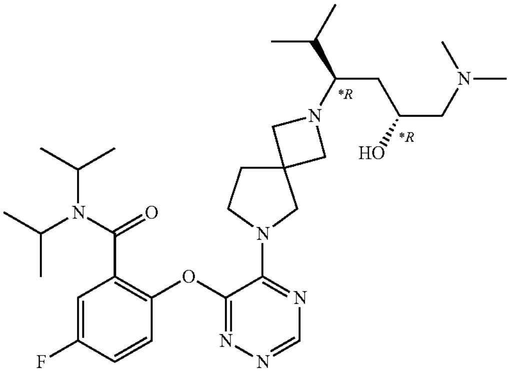

Compound 363

+

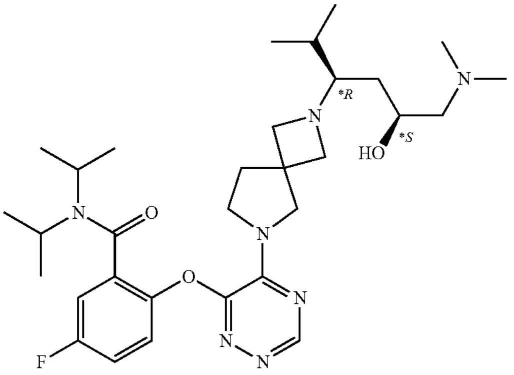

Compound 364

2-((5-(2-((3*R)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide (Compound 361) (105 mg) was separated by SFC over Phenomenex-Cellulose-2 (column: 250×30 mm, 10 um; Mobile phase: A: Supercritical $CO_2$, B: 0.1% $NH_3H_2O$ EtOH (0.1% ammonia), A:B=65:35 at 80 mL/min) to afford the title compounds (Compound 363) (45 mg) and (Compound 364) (35 mg) both as colorless sticky solid.

Compound 367 and 368

2-((5-(2-((3*S,5*S)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((3*S,5*R)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide

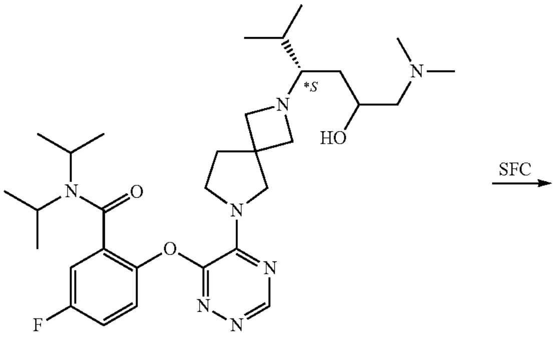

Compound 362

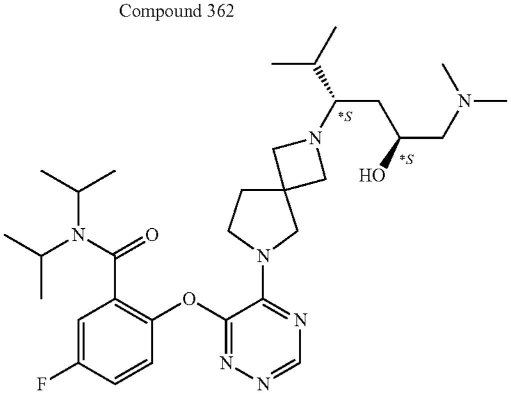

Compound 367

+

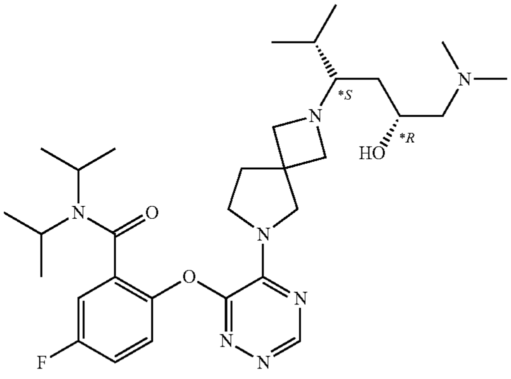

Compound 368

2-((5-(2-((3*S)-6-(dimethylamino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide (Compound 362) (120 mg) was separated by SFC over DAICEL CHIRALPAK AS (column: 250×30 mm, 10 um; Mobile phase:

A: Supercritical $CO_2$, B: EtOH (0.1% ammonia), A:B=75:25 at 60 mL/min) to afford the title compounds (Compound 367) (48 mg) and (Compound 368) (34 mg) both as colorless oil.

Compound 384 and 385

N-ethyl-5-fluoro-2-((5-(2-((3*R,5*R)-5-hydroxy-2-methyl-6-(methyl(propyl)amino)hexan-3-yl)-2,6-diazaspiro[3.4]octan-6-yl)-1,2,4-triazin-6-yl)oxy)-N-isopropylbenzamide N-ethyl-5-fluoro-2-((5-(2-((3*S,5*S)-5-hydroxy-2-methyl-6-(methyl(propyl)amino)hexan-3-yl)-2,6-diazaspiro[3.4]octan-6-yl)-1,2,4-triazin-6-yl)oxy)-N-isopropylbenzamide

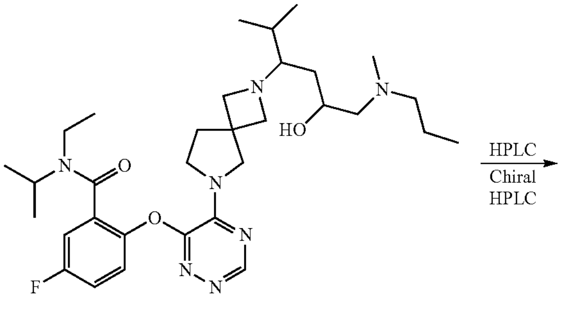

Compound 383

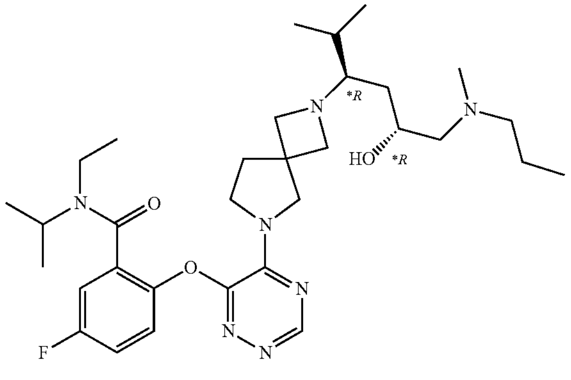

Compound 384

+

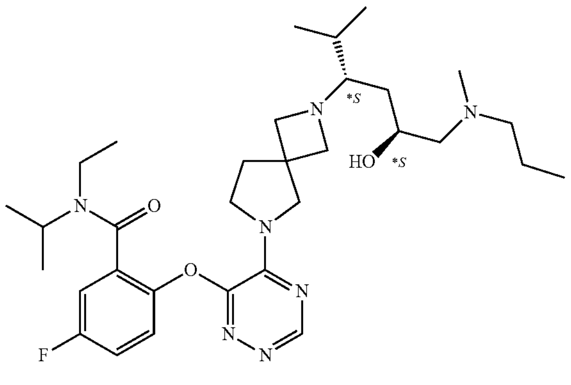

Compound 385

N-ethyl-5-fluoro-2-((5-(2-(5-hydroxy-2-methyl-6-(methyl(propyl)amino)hexan-3-yl)-2,6-diazaspiro[3.4]octan-6-yl)-1,2,4-triazin-6-yl)oxy)-N-isopropylbenzamide (Compound 383) (432 mg) was purified by preparative HPLC over Welch Xtimate (column: C18 100×40 mm 3 µm, Mobile Phase A: $H_2O$ (0.075% TFA), Mobile Phase B: ACN, Flow rate: 30 mL/min, gradient condition: from 10% B to 40% B) to afford a mixture of Compound 384 and Compound 385 (166 mg, as TFA salt).

The mixture of Compound 384 and Compound 385 (166 mg, TFA salt) was further separated by chiral HPLC over Daicel ChiralPak IG (column: 250×30 mm, 10 µm; Mobile phase: A: Heptane, B: EtOH (0.1% ammonia), Flow rate: 25 mL/min, gradient condition: from 20% B to 50% B) to afford the title compounds (Compound 384) (30.7 mg) and (Compound 385) (14.4 mg) both as colorless sticky oil.

Compound 389 and 390

2-((5-(2-((3*R,5*S)-6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide 2-((5-(2-((3*S,5*S)-6-ethyl(methyl)amino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide

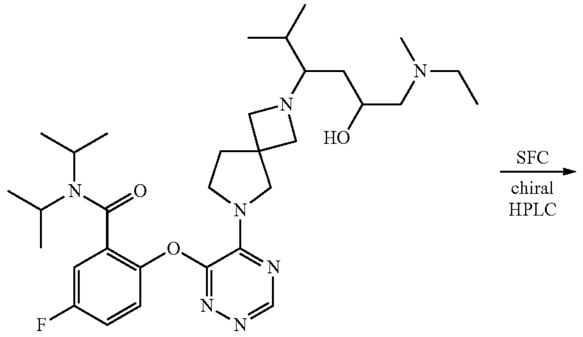

Compound 388

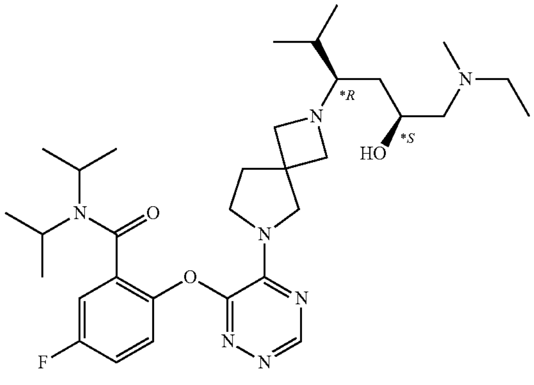

Compound 389

+

-continued

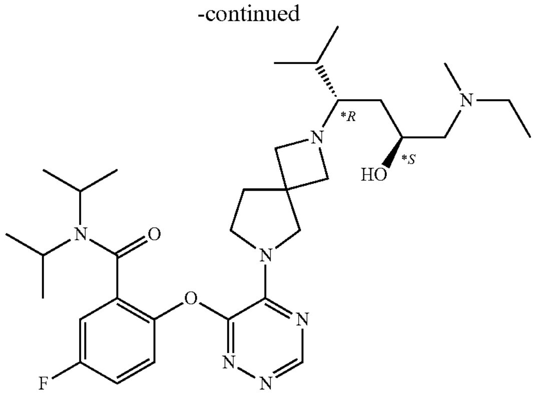

Compound 390

2-((5-(2-(6-(ethyl(methyl)amino)-5-hydroxy-2-methylhexan-3-yl)-2,6-diazaspiro[3.4]octan-6-yl)-1,2,4-triazin-6-yl)oxy)-5-fluoro-N,N-diisopropylbenzamide (Compound 388) (190 mg) was first separated by SFC over Daicel Chiralpak IG (column: 250×30 mm, 10 μm; Mobile phase: A: Supercritical $CO_2$, B: EtOH (0.1% ammonia), A:B=60:40; Flow rate: 80 mL/min) to afford Compound 390 (45 mg) and a mixture of 3 diastereoisomers. (120 mg).

The mixture of 3 diastereoisomers (120 mg) was further separated by chiral HPLC over Daicel Daicel chiralpak IG (column: 250×30 mm, 10 μm), Mobile phase: A: Heptane, B: EtOH (0.1% ammonia), A:B=from 70:30 to 50:50, Flow rate: 25 mL/min) to afford Compound 389 (22.0 mg, 86.6% purity by LCMS).

The Compound 389 (22.0 mg, 86.6% purity by LCMS) was further purified by preparative HPLC over Welch Xtimate (column: C18 150×25 mm 5 μm, Mobile phase: A: $H_2O$ (0.2% FA), B: ACN, gradient condition: from 2% B to 32%, Flow rate: 25 mL/min) and basified with ammonia to afford Compound 389 (15.0 mg, 100% purity by LCMS).

Compound 393

(R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide

Preparation Method A

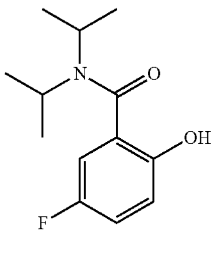

+

-continued

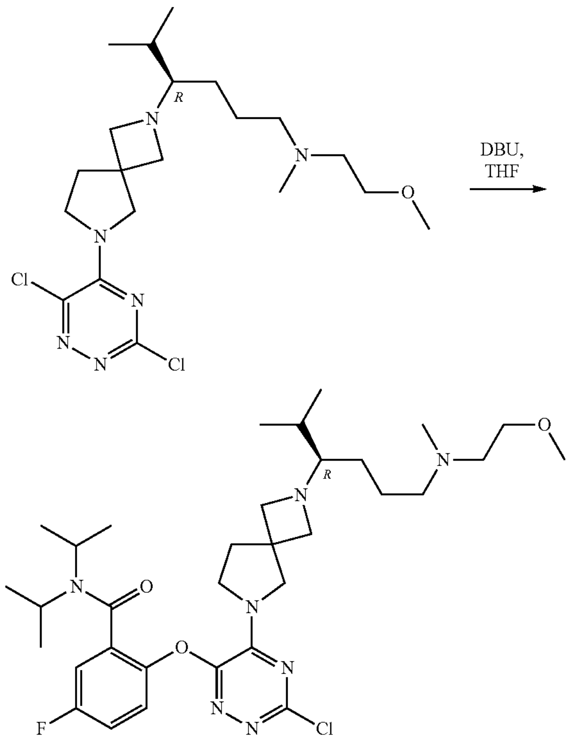

The mixture of N-ethyl-5-fluoro-2-hydroxy-N-isopropylbenzamide (intermediate 28) (1.10 g, 4.88 mmol), (R)-4-(6-(3,6-dichloro-1,2,4-triazin-5-yl)-2,6-diazaspiro[3.4]octan-2-yl)-N-(2-methoxyethyl)-N,5-dimethylhexan-1-amine (intermediate 225) (1.70 g, 3.82 mmol) and DBU (750 mg, 4.93 mmol) in anhydrous THF (15 mL) was stirred at 40° C. for 8 h. After cooled to RT, the mixture was concentrated under reduced pressure, the resulting residue was diluted with DCM (60 mL) and washed with $H_2O$ (20 mL×3). The organic layer was dried over anhydrous $Na_2SO_4$, filtered and concentrated under reduced pressure to give the crude product which was purified FCC (MeOH/DCM=0% to 10%) to afford a yellow oil (1.40 g), which was further separated by SFC over DAICEL CHIRALPAK AD (column: 250×50 mm, 10 um; Mobile phase: A: Supercritical $CO_2$, B: EtOH (0.1% ammonia), A:B=50:50 at 70 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compound (1.0 g).

Preparation Method B

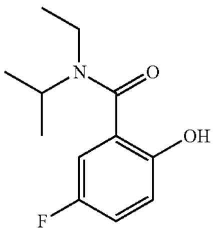

+

-continued

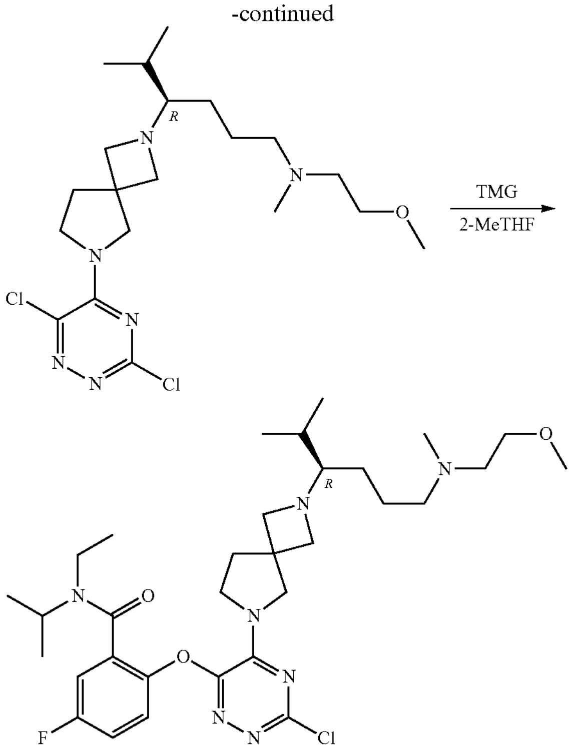

To a 2-MeTHF solution of (R)-4-(6-(3,6-dichloro-1,2,4-triazin-5-yl)-2,6-diazaspiro[3.4]octan-2-yl)-N-(2-methoxyethyl)-N,5-dimethylhexan-1-amine (intermediate 225) (676 g of a 14.8 wt/o solution in 2-MeTHF, 100 g corrected of intermediate 225) and N-ethyl-5-fluoro-2-hydroxy-N-isopropylbenzamide (intermediate 28) (50.6 g) in 2-MeTHF (40 g) at 20 to 30° C. was added tetramethylguanidine (31 g) and the mixture was stirred for 40 to 48 h. A 7% $NaHCO_3$ aqueous solution (500 g) was added and the mixture was stirred for 30 to 60 min. The aqueous layer was removed and the organic layer was washed with twice with 4% NaOH aqueous solution (2×500 g) and once with 10% $Na_2SO_4$ aqueous solution (500 g). The organic layer was concentrated under reduced pressure (<40° C.) to 2.2-3.0 vol. and flushed three times with MeOH (1×790 g and 2×395 g) until both 2-MeTHF and water content were both ≤1.0% to afford the desired compound in 86% assay yield as a 60.1 wt % solution in methanol.

Compound 400, 414

(R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy)-N-(ethyl-$^{13}C_2$)-5-fluoro-N-(propan-2-yl-$^{13}C_3$)benzamide (R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy)-5-fluoro-N-isopropyl-N-methylbenzamide The following compounds were synthesized by an analogous method described above for compound 393 by method A

| Co. No. | Structure | Starting Materials |
|---|---|---|
| 400 | 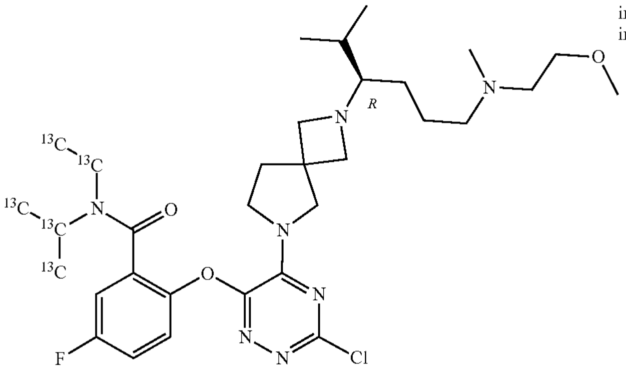 | intermediate 237, intermediate 225 |
| 414 | 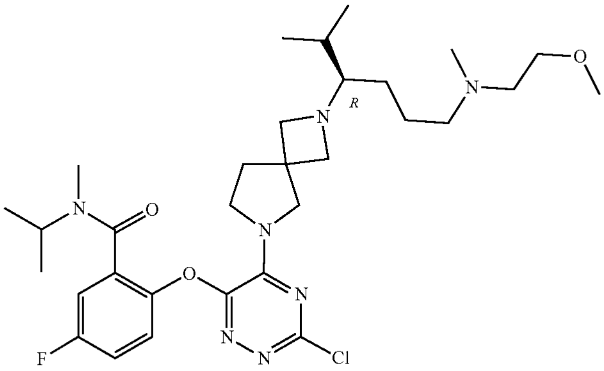 | intermediate 247, intermediate 225 |

Compound 395

(R)-N-ethyl-5-fluoro-N-isopropyl-2-((5-(2-(6-((2-methoxyethyl)(methyl)amino)-2-methylhexan-3-yl)-2,6-diazaspiro[3.4]octan-6-yl)-3-(methylamino)-1,2,4-triazin-6-yl)oxy)benzamide formate

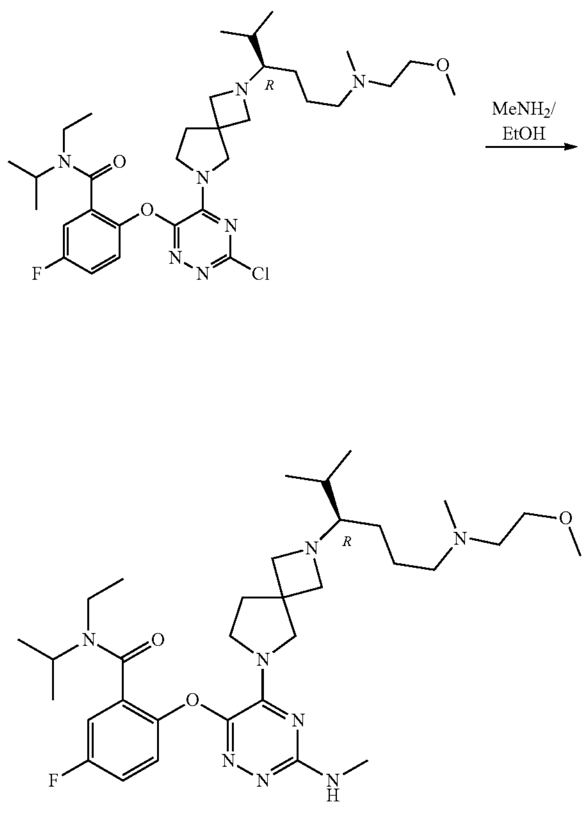

formate salt

The mixture of (R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (Compound 393) (100 mg, 0.158 mmol) and methanamine (1 mL, 33% in EtOH) was stirred at 90° C. for 1 h. After cooled to RT, the mixture was concentrated under reduced pressure to give the crude product which was purified by preparative HPLC (Column: Welch Xtimate C18 150×25 mm 5 um, Mobile Phase A: $H_2O$ (0.2% FA), Mobile Phase B: ACN, Flow rate: 25 mL/min, gradient condition: from 5% B to 35%) to afford the title compound (49.8 mg, 43.6% yield) as sticky solid.

LC-MS (ESI) (Method 2): $R_t$=1.997 min, m/z found 629.4 $[M+H]^+$.

SFC (Method 6): $R_t$=1.228 min.

Compound 406 and 407

(R)-2-((5-(2-(6-amino-2-methylhexan-3-yl)-2,6-diazaspiro[3.4]octan-6-yl)-3-chloro-1,2,4-triazin-6-yl)oxy)-N-ethyl-5-fluoro-N-isopropylbenzamide formate (R)-2-((5-(2-(6-amino-2-methylhexan-3-yl)-2,6-diazaspiro[3.4]octan-6-yl)-3-methoxy-1,2,4-triazin-6-yl)oxy)-N-ethyl-5-fluoro-N-isopropylbenzamide formate

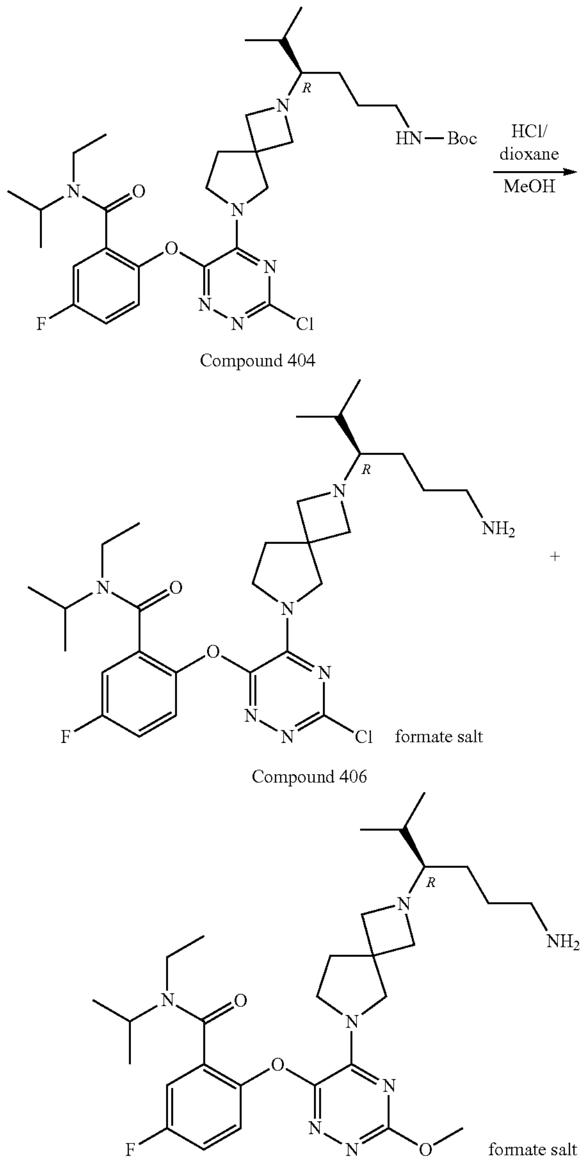

Compound 404

Compound 406

Compound 407

To a solution of tert-butyl (R)-(4-(6-(3-chloro-6-(2-(ethyl(isopropyl)carbamoyl)-4-fluorophenoxy)-1,2,4-triazin-5-yl)-2,6-diazaspiro[3.4]octan-2-yl)-5-methylhexyl)carbamate (Compound 404) (1.10 g, 1.66 mmol) in MeOH (15.0 mL) was added HCl/dioxane (15.0 mL, 60.0 mmol, 4M) and the resulting mixture was stirred at 20° C. for 12 h. The reaction mixture was concentrated under reduced pressure to give a residue which was purified by preparative HPLC over Welch Xtimate (column: C18 150×25 mm, 5 um, Mobile Phase A: $H_2O$ (0.2% FA), Mobile Phase B: ACN, Flow rate: 25 mL/min, gradient condition from 3% B to 33% B) to afford the title compounds (Compound 406) (360 mg) and (Compound 407) (160 mg) both as sticky oil.

(Compound 406) (60 mg) was further purified by preparative HPLC over Boston Green ODS (column: 150×30 mm, 5 um; Mobile Phase A: $H_2O$ (0.225% FA), Mobile Phase B: ACN, Flow rate: 35 mL/min, gradient condition from 5% B to 35% B) to afford the title compound (Compound 406) (40 mg).

Compound 406

LC-MS (ESI) (Method 1): $R_t$=3.400 min, m/z found 562.3 $[M+H]^+$.

SFC (Method 32): $R_t$=2.093 min.

Compound 407

LC-MS (ESI) (Method 1): $R_t$=2.028 min, m/z found 558.3 $[M+H]^+$.

SFC (Method 6): $R_t$=1.42 min.

Compound 416

(R)-N-ethyl-5-fluoro-N-isopropyl-2-((3-methoxy-5-(2-(6-((2-methoxyethyl)(methyl)amino)-2-methylhexan-3-yl)-2,6-diazaspiro[3.4]octan-6-yl)-1,2,4-triazin-6-yl)oxy)benzamide formate

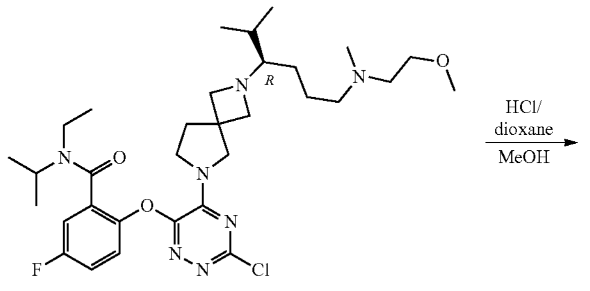

Compound 393

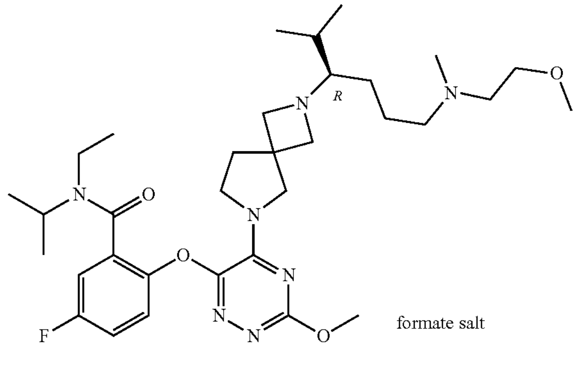

Compound 416

To the solution of (R)-2-((3-chloro-5-(2-(6-((2-methoxyethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (Compound 393) (100 mg, 0.158 mmol) in anhydrous MeOH (2 mL) was added HCl (1.6 mL, 6.40 mmol, 4 M in dioxane). The resulting mixture was stirred at 25° C. for 60 h. The mixture was concentrated under reduced pressure to give the crude product which was purified by preparative HPLC (Column: Boston Green ODS 150×30 mm 5 um, Mobile Phase A: $H_2O$ (0.225% FA), Mobile Phase B: ACN, Flow rate: 35 mL/min, gradient condition from 12% B to 42% B) to afford the title compound (70.6 mg, 65.2% yield) as yellow sticky solid.

LC-MS (ESI) (Method 2): $R_t$=2.096 min, m/z found 630.4 $[M+H]^+$.

SFC (Method 33): $R_t$=2.587 min.

Compound 286

(R)-N-ethyl-5-fluoro-2-((5-(2-(6-((2-hydroxyethyl)(methyl)amino)-2-methylhexan-3-yl)-2,6-diazaspiro[3.4]octan-6-yl)-1,2,4-triazin-6-yl)oxy)-N-isopropylbenzamide

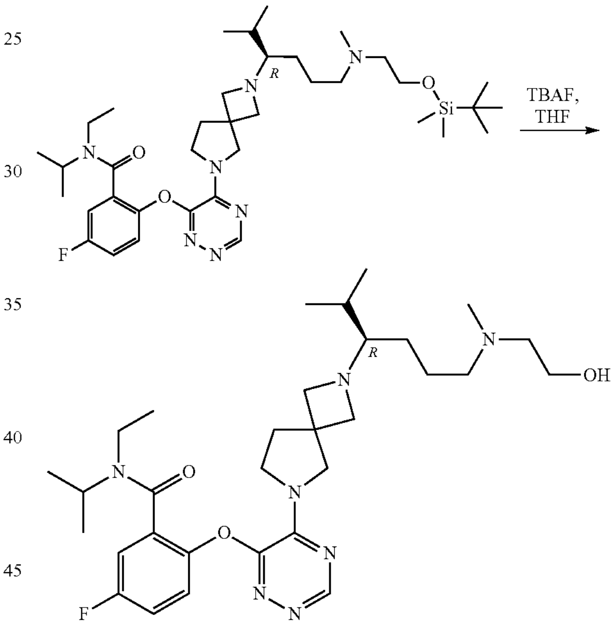

TBAF (79 μL; 0.079 mmol) was added dropwise to a solution of (R)-2-((5-(2-(6-((2-((tert-butyldimethylsilyl)oxy)ethyl)(methyl)amino)-2-methylhexan-3-yl)-2,6-diazaspiro[3.4]octan-6-yl)-1,2,4-triazin-6-yl)oxy)-N-ethyl-5-fluoro-N-isopropylbenzamide (intermediate 245) (46 mg, 0.066 mmol) in THF (2 mL) at RT. The reaction mixture was stirred at RT for 20 h, then poured out into ice water and EtOAc was added. The mixture was basified with a 10% aqueous solution of $K_2CO_3$ and the organic layer was separated, washed with brine, dried over $MgSO_4$ and filtered. The solvent was evaporated to dryness to give a crude (45 mg) which was purified by silica gel chromatography (Stationary phase: irregular bare silica 4 g, Mobile phase: 0.7% $NH_4OH$, 93% DCM, 7% MeOH). The fractions containing the product were mixed and concentrated. The resulting product was freeze-dried with ACN/$H_2O$ 20/80 to give the title compound (30 mg, 78% yield).

LC-MS (ESI) (Method 4): $R_t$=3.048 min, m/z found 586.6 $[M+H]^+$; 644.6 $[M+CH_3COO]^-$ Analytical Methods The analytical information in the Compounds above or in the Tables below, was generated by using the analytical methods described below.

NMR-Methods

Some NMR experiments were carried out using a Bruker Avance III 400 spectrometer at ambient temperature (298.6 K), using internal deuterium lock and equipped with BBO 400 MHz S1 5 mm probe head with z gradients and operating at 400 MHz for the proton and 100 MHz for carbon. Chemical shifts (S) are reported in parts per million (ppm). J values are expressed in Hz.

Some NMR experiments were carried out using a Varian 400-MR spectrometer at ambient temperature (298.6 K), using internal deuterium lock and equipped with Varian 400 4NUC PFG probe head with z gradients and operating at 400 MHz for the proton and 100 MHz for carbon. Chemical shifts (S) are reported in parts per million (ppm). J values are expressed in Hz.

Some NMR experiments were carried out using a Varian 400-VNMRS spectrometer at ambient temperature (298.6 K), using internal deuterium lock and equipped with Varian 400 ASW PFG probe head with z gradients and operating at 400 MHz for the proton and 100 MHz for carbon. Chemical shifts (S) are reported in parts per million (ppm). J values are expressed in Hz.

Some NMR experiments were carried out using a Bruker AVANCE III HD 300 spectrometer at ambient temperature (298.6 K), using internal deuterium lock and equipped with PA BBO 300S1 BBF-H-D-05 Z 5 mm probe head with z gradients and operating at 300 MHz for the proton and 75 MHz for carbon. Chemical shifts (d) are reported in parts per million (ppm). J values are expressed in Hz.

LCMS (Liquid Chromatography/Mass Spectrometry)

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 1a

LCMS Method Codes (Flow expressed in mL/min; column temperature (T) in ° C.; Run time in minutes).

| Method code | Instrument | Column | Mobile phase | Gradient | Flow / Column T | Run time |
|---|---|---|---|---|---|---|
| 1 | Agilent | Waters XBridge C18 (2.0 × 50 mm, 5 uM) | mobile phase A: $H_2O$ with 0.04% TFA; mobile phase B: ACN with 0.02% TFA | A gradient from 100% A to 100% A was held for 1 min, 40% A is applied in 4 min, and 40% A down to 15% A in 2.5 min. And then return to 100% A in 2 min and held for 0.5 min. The post time is 0.5 min. | 0.8 / 50 | 10 |
| 2 | Agilent | Waters XBridge C18 (2.0 × 50 mm, 5 um) | mobile phase A: $H_2O$ with 0.04% TFA; mobile phase B: ACN with 0.02% TFA | First, 90% A was held for 0.8 min. Then a gradient was applied to 20% A and 80% B in 3.7 min and held for 3 min. min. And then return to 90% A in 2 min and held for 0.5 min. The post time is 0.5 min. | 0.8 / 50 | 10 |
| 3 | Agilent | Waters XBridge Shield RP18 (2.1 × 50 mm, 5 um) | mobile phase A: $H_2O$ with 0.05% ammonia; mobile phase B: ACN | First, 100% A was held for 1 min. Then a gradient was applied to 40% A and 60% B in 4 min and then to 5% A and 95% B in 2.5 min. Finally return to 100% A in 2 min and held for 0.5 min. Post Time is 0.5 min. | 0.8 / 40 | 10 |
| 4 | Waters: Acquity UPLC ® - DAD and Quattro Micro ™ | Waters BEH C18 (2.1 × 100 mm, 1.7 uM) | mobile phase A: 95% $CH_3COONH_4$ 7 mM/5% ACN mobile phase B: ACN | 84.2% A for 0.49 min, to 10.5% A in 2.18 min, held for 1.94 min, back to 84.2% A in 0.73 min, held for 0.73 min. | 0.343 / 40 | 6.2 |

TABLE 1a-continued

LCMS Method Codes (Flow expressed in mL/min; column temperature (T) in ° C.; Run time in minutes).

| Method code | Instrument | Column | Mobile phase | Gradient | Flow / Column T | Run time |
|---|---|---|---|---|---|---|
| 5 | Agilent 1260/6120 | Waters Sunfire C18 (2.0 × 30 mm, 2.5 uM) | mobile phase A: $H_2O$ with 0.1% FA; mobile phase B: ACN | gradient from 5% B to 95% B is applied in 2.5 min, and held for 1.0 min. The post time is 0.8 min. | 1 / 40 | 3.5 |
| 6 | Agilent 1260/6120 | Waters Sunfire C18 (2.0 × 30 mm, 2.5 uM) | mobile phase A: $H_2O$ with 0.1% FA; mobile phase B: ACN | 5% B was held for 1 min, gradient from 5% B to 30% B is applied in 2 min, and 30% B to 95% B in 0.5 min, and held for 1.0 min. The post time is 0.8 min. | 1 / 40 | 4.5 |
| 7 | Agilent LC 1260 with MS6120 | XBridge C18, 4.6 × 150 mm, 3.5 um | Mobile phase A 0.05% TFA in $H_2O$ Mobile phase B 0.05% TFA in ACN | Time (min) / A% / B%: Initial 95 5; 11.0 65 35; 13.0 5 95; 15.0 5 95; 16.0 95 5; 20.0 95 5 | 1.5 / 45 | 20 |
| 8 | Waters: Acquity ® H-Class - DAD and SQD2 ™ | C18 (1.7 um, Waters BEH® 2.1 × 50 mm) | A: $CH_3COONH_4$ 7mM 95%/ $CH_3CN$ 5%, B: $CH_3CN$ | From 95% A/5% B to 5% A in 1 min, held for 1.6 min, back to 95% A/5% B in 0.2 min, held for 0.5 min. | 0.5 / 40 | 3.5 |

Analytical SFC

General Procedure for SFC Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE 2a

Analytical SFC Methods (Flow expressed in mL/min; column temperature (T) in ° C.; Run time in minutes, Backpressure (BPR) in bars or pound-force per square inch (psi). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 1 | Waters UPCC with PDA (Chiralpak IG-3 100 × 4.6 mm I.D., 3 um) | A: Super-critical $CO_2$ B: MeOH (0.05% DEA) | 40% of MeOH (0.05% DEA) in $CO_2$ | 3.2 35 | 10 1500 psi |
| 2 | Waters UPCC with PDA (Chiralpak IG-3 100 × 4.6 mm I.D., 3 um) | A: Super-critical $CO_2$ B: IPA (0.05% DEA) | from 5% to 40% of B in 4 min and hold 40% for 2.5 min, then 5% of B for 1.5 min | 2.8 35 | 8 1500 psi |

TABLE 2a-continued

Analytical SFC Methods (Flow expressed in mL/min; column temperature (T) in ° C.; Run time in minutes, Backpressure (BPR) in bars or pound-force per square inch (psi). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 3 | Agilent 1260 with DAD (ChiralPak AD-3 150 × 4.6 mm I.D., 3 um) | A: Super-critical $CO_2$ B: EtOH (0.05% DEA) | from 5% to 40% of B in 5.5 min and hold 40% for 3 min, then 5% of B for 1.5 min | 2.5 40 | 10 100 bar |
| 4 | Waters UPCC with PDA (Chiralpak AD-3 50 × 4.6 mm I.D., 3 um) | A: Super-critical $CO_2$ B: IPA (0.05% DEA) | from 5% to 40% of B in 2 min and hold 40% for 1.2 min, then 5% of B for 0.8 min | 4 35 | 4 1500 psi |
| 5 | Waters UPCC with PDA IG-3 (Chiralpak 100 × 4.6 mm I.D., 3 um) | A: Supe critical $CO_2$ B: MeOH (0.05% DEA) | 40% of MeOH (0.05% DEA) in $CO_2$ | 3.2 35 | 3 1500 psi |
| 6 | Waters UPCC with PDA (Chiralpak AD-3 50 × 4.6 mm I.D., 3 um) | A: Super-critical $CO_2$ B: EtOH (0.05% DEA) | from 5% to 40% of B in 2 min and hold 40% for 1.2 min, then 5% of B for 0.8 min | 4 35 | 4 1500 psi |
| 7 | Waters UPCC with PDA (Chiralpak IG-3 100 × 4.6 mm I.D., 3 um) | A: Super-critical $CO_2$ B: MeOH (0.05% DEA) | 25% of MeOH (0.05% DEA) in $CO_2$ | 3.5 35 | 9 1500 psi |

TABLE 2a-continued

Analytical SFC Methods (Flow expressed in mL/min; column temperature (T) in ° C.; Run time in minutes, Backpressure (BPR) in bars or pound-force per square inch (psi). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 8 | Waters UPCC with PDA (Chiralpak IG-3 50 × 4.6 mm I.D., 3 um) | A: Super-critical $CO_2$ B: EtOH (0.05% DEA) | from 5% to 40% of B in 2 min and hold 40% for 1.2 min, then 5% of B for 0.8 min | 4 35 | 4 1500 psi |
| 9 | Waters UPCC with PDA (Cellulose 2 150 × 4.6 mm I.D., 5 um) | A: Super-critical $CO_2$ B: EtOH (0.05% DEA) | 50% B hold for 10 min | 2.5 35 | 11 1500 psi |
| 10 | Agilent 1260 with DAD (ChiralPak AS-3 150 × 4.6 mm I.D., 3 um) | A: Super-critical $CO_2$ B: EtOH (0.05% DEA) | from 5% to 40% of B in 5.5min, then 5% of B for 1.5 min | 2.5 40 | 7 100 bar |
| 11 | Waters UPCC with PDA (Chiralpak IG-3 100 × 4.6 mm I.D., 3 um) | A: Super-critical $CO_2$ B: EtOH (0.05% DEA) | from 5% to 40% of B in 4 min and hold 40% for 2.5 min, then 5% of B for 1.5 min | 2.8 35 | 8 1500 psi. |
| 12 | Agilent 1260 with DAD (ChiralPak IG-3 100 × 4.6 mm I.D., 3 um) | A: Super-critical $CO_2$ B: MeOH (0.1% Ethanol-amine) | Isocratic: 40% B | 3 40 | 3 100 bar |
| 13 | Waters UPCC with PDA (Chiralpak AS-3 100 × 4.6 mm I.D., 3 um) | A: Super-critical $CO_2$ B: EtOH (0.05% DEA) | from 5% to 40% of B in 4 min and hold 40% for 2.5 min, then 5% of B for 1.5 min | 2.8 35 | 8 1500 psi |
| 14 | Waters UPCC with PDA (Chiralcel OD-3 100 × 4.6 mm I.D., 3 um) | A: Super-critical $CO_2$ B: EtOH (0.05% DEA) | from 5% to 40% of B in 4 min and hold 40% for 2.5 min, then 5% of B for 1.5 min | 2.8 35 | 8 1500 psi |
| 15 | Waters UPCC with PDA (Chiralcel OD-3 50 × 4.6 mm I.D., 3 um) | A: Super-critical $CO_2$ B: EtOH (0.05% DEA) | from 5% to 40% of B in 2 min and hold 40% for 1.2 min, then 5% of B for 0.8 min | 4 35 | 4 1500 psi |
| 16 | Waters UPCC with PDA (Chiralpak AD-3 150 × 4.6 mm I.D., 3 um) | A: Super-critical $CO_2$ B: IPA (0.05% DEA) | from 5% to 40% of B in 5 min and from 40% to 5% of B in 0.5 min, hold 5% of B for 1.5 min | 2.5 35 | 7 1500 psi |
| 17 | Waters UPCC with PDA (Cellulose-4 100 × 4.6 mm I.D., 3 um) | A: Super-critical $CO_2$ B: EtOH (0.05% DEA) | Isocratic: 40% B | 28 35 | 6 1500 psi |
| 18 | Waters UPCC with PDA (Chiralpak IG-3 50 × 4.6 mm I.D., 3 um) | A: Super-critical $CO_2$ B: MeOH (0.05% DEA) | from 5% to 40% of B in 2 min and hold 40% for 1.2 min, then 5% of B for 0.8 min | 1 35 | 10 1500 psi |
| 19 | Agilent 1260 with DAD (ChiralPak IG-3 100 × 4.6 mm I.D., 3 um) | A: Super-critical $CO_2$ B: IPA (0.05% DEA) | Isocratic: 40% B | 2.5 40 | 7 1500 psi |
| 20 | Agilent 1260 with DAD (ChiralPak AD-3 150 × 4.6 mm I.D., 3 um) | A: Super critical-$CO_2$ B: EtOH (0.05% DEA) | Isocratic: 40% B | 2.5 40 | 5 1500 psi |
| 21 | Waters UPCC with PDA (Chiralpak AD-3 150 × 4.6 mm I.D., 3 um) | A: Super-critical $CO_2$ B: IPA (0.05% DEA) | from 5% to 40% of B in 5 min and hold 40% for 2.5 min, then 5% of B for 2.5 min | 2.5 35 | 10 1500 psi |
| 22 | Waters UPCC with PDA (Chiralpak IG-3 100 × 4.6 mm I.D., 3 um) | A: Super-critical $CO_2$ B: MeOH (0.05% DEA) | from 5% to 40% of B in 4 min and hold 40% for 2.5 min, then hold 5% of B for 1.5 min | 2.8 35 | 8 1500 psi |
| 23 | Agilent 1260 with DAD (ChiralPak AD-3 150 × 4.6 mm I.D., 3 um) | A: Super-critical $CO_2$ B: IPA (0.05% DEA) | from 5% to 40% of B in 5.5 min and hold 40% for 3 min, then 5% of B for 1.5 min | 2.5 40 | 10 100 bar |
| 24 | Waters UPCC with PDA Chiralcel (OJ-3 150 × 4.6 mm I.D., 3 um) | A: Super-critical $CO_2$ B: EtOH (0.05% DEA) | from 5% to 40% of B in 0.5 min, from 40% to 5% hold 5% of B for 1.5 min of B in 5min and | 2.5 35 | 7 1500 psi |
| 25 | Waters UPCC with PDA (Chiralpak AS-3 100 × 4.6 mm I.D., 3 um) | A: Super-critical $CO_2$ B: EtOH (0.05% DEA) | from 5% to 40% of B in 2 min and hold 40% for 2.5 min, then 5% of B for 1.5 min | 2.8 35 | 6 1500 psi |
| 26 | Waters UPCC with PDA (Chiralpak AD-3 150 × 4.6 mm I.D., 3 um) | A: Super-critical $CO_2$ B: EtOH (0.05% DEA) | from 5% to 40% of B in 5 min and hold 40% for 2.5 min, then 5% of B for 2.5 min | 2.5 35 | 10 1500 psi |
| 27 | Waters UPCC with PDA (Chiralpak IG-3 100 × 4.6 mm I.D., 3 um) | A: Super-critical $CO_2$ B: EtOH (0.05% DEA) | Isocratic: 40% B | 3.2 35 | 9 1500 psi |
| 28 | Agilent 1260 with DAD (ChiralPak IG-3 100 × 4.6 mm I.D., 3 um) | A: Super-critical $CO_2$ B:MeOH (0.05% DEA) | Isocratic: 40% B | 2.5 40 | 6 100 bar |
| 29 | Waters UPCC with PDA (Chiralpak AD-3 150 × 4.6 mm I.D., 3 um) | A: Super-critical $CO_2$ B: EtOH (0.05% DEA) | from 5% to 40% of B in 5 min from 40% to 5% of B in 0.5 min, hold 5% of B for 1.5 min | 2.5 35 | 7 1500 psi |

TABLE 2a-continued

Analytical SFC Methods (Flow expressed in mL/min; column temperature (T) in ° C.; Run time in minutes, Backpressure (BPR) in bars or pound-force per square inch (psi). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 30 | Waters UPCC with PDA (Cellulose-2 100 × 4.6 mm I.D., 3 um) | A: Super-critical $CO_2$ B: EtOH (0.05% DEA) | Isocratic: 40% B | 2.8 35 | 5 1500 psi |
| 31 | Agilent 1260 with DAD (ChiralPak IG-3 100 × 4.6 mm I.D., 3 um) | A: Super-critical $CO_2$ B: EtOH (0.05% DEA) | Isocratic: 40% B | 2.5 40 | 6 100 bar |
| 32 | Waters UPCC with PDA Chiralcel OJ-3 100 × 4.6 mm I.D., 3 um | A: Super-critical $CO_2$ B: EtOH (0.05% DEA) | from 5% to 40% of B in 4 min and hold 40% for 2.5 min, then 5% of B for 1.5 min | 2.8 35 | 8 1500 psi |
| 33 | Waters UPCC with PDA Chiralcel OD-3 100 × 4.6 mm I.D., 3 um | A: Super-critical $CO_2$ B: EtOH (0.05% DEA) | from 5% to 40% of B in 4 min and hold 40% for 0.5 min, then 5% of B for 1.5 min | 2.8 35 | 6 1500 psi |

Analytical Chiral HPLC

General Method

The Chiral HPLC measurement was performed using a Chiral High Performance Liquid Chromatography (Chiral HPLC) system composed by a LC pump, a diode-array (DAD) or a UV detector and a chiral column as specified in the respective methods. Data acquisition was performed with appropriate software.

TABLE 2b

Analytical chiral HPLC Methods (Flow expressed in mL/min; column temperature (T) in ° C.; Run time in minutes, Backpressure (BPR) in bars or pound-force per square inch (psi). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 1 | Shimadzu LC-20AB with PDA (Lux Cellulose 2 150 × 4.6 mm I.D., 3 um) | A: Hexane (0.1% DEA) B: EtOH (0.1% DEA) | Isocratic: A:B = 70:30 | 1 35 | 15 1500 psi |
| 2 | Agilent 1260 with DAD (IE-3 150 × 4.6 mm I.D., 3 um) | MeOH (0.05% DEA) | hold 100% of MeOH (0.05% DEA) for 20 min | 1 25 | 20 100 bar |
| 3 | Shimadzu LC-20AT (CHIRALPAK AD-3 150 × 4.6 mm I.D., 5 um) | A: Hexane B: EtOH | Isocratic: A:B = 90:10 | 1 35 | 11 1500 psi |

TABLE 2b-continued

Analytical chiral HPLC Methods (Flow expressed in mL/min; column temperature (T) in ° C.; Run time in minutes, Backpressure (BPR) in bars or pound-force per square inch (psi). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 4 | Shimadzu LC-20AB with PDA (Chiralpak IG-3 50 × 4.6 mm I.D., 3 um) | A: Hexane (0.1% DEA) B: IPA | Isocratic: A:B = 80:20 | 1 35 | 15 1500 psi |
| 5 | Shimadzu LC-20 AT CP-HPLC-09 (CHIRALPAK AD-H 150 × 4.6 mm I.D., 5 um) | A: Hexane (0.1% DEA) B: EtOH (0.1% DEA) | Isocratic: A:B = 90:10 | 1 35 | 15 1500 psi |
| 6 | Shimadzu LC-20AB with PDA (Chiralpak IG-3 50 × 4.6 mm I.D., 3 um) | A: Hexane (0.1% DEA) B: EtOH (0.1% DEA) | Isocratic: A:B = 70:30 | 1 35 | 10 1500 psi |
| 7 | Shimadzu LC-20AB with PDA (Chiralpak IG-3 50 × 4.6 mm I.D., 3 um) | A: Hexane (0.1% DEA) B: EtOH (0.1% DEA) | Isocratic: A:B = 80:20 | 1 35 | 10 1500 psi |
| 8 | Shimadzu LC-20AD with PDA (Chirapak IE 100 × 4.6 mm I.D., 3 um) | A: Hexane (0.1% DEA) B: EtOH (0.1% DEA) | Isocratic: A:B = 40:60 | 1 35 | 15 1500 psi |
| 9 | Shimadzu LC-20AD with PDA (Chirapak ID 100 × 4.6 mm I.D., 3 um) | A: Hexane (0.1% DEA) B: EtOH (0.1% DEA) | Isocratic: A:B = 60:40 | 1 35 | 10 1500 psi |

Pharmacological Part

1) Menin/MLL Homogenous Time-Resolved Fluorescence (HTRF) Assay

To an untreated, white 384-well microtiter plate was added 40 nL 200× test compound in DMSO and 4 µL 2× terbium chelate-labeled menin (vide infra for preparation) in assay buffer (40 mM Tris.HCl, pH 7.5, 50 mM NaCl, 1 mM DTT (dithiothreitol) and 0.05% Pluronic F-127). After incubation of test compound and terbium chelate-labeled menin for 30 min at ambient temperature, 4 µL 2×FITC-MBM1 peptide (FITC-β-alanine-SARWRFPARPGT-$NH_2$ (SEQ ID NO: 2)) ("FITC" means fluorescein isothiocyanate) in assay buffer was added, the microtiter plate centrifuged at 1000 rpm for 1 min and the assay mixtures incubated for 15 min at ambient temperature. The relative amount of menin.FITC-MBM1 complex present in an assay mixture is determined by measuring the homogenous time-resolved fluorescence (HTRF) of the terbium/FITC donor/acceptor fluorphore pair using an EnVision microplate reader (ex. 337 nm/terbium em. 490 nm/FITC em. 520 nm) at ambient temperature. The degree of fluorescence resonance energy transfer (the HTRF value) is expressed as the ratio of the fluorescence emission intensities of the FITC and terbium fluorophores ($F^{em}$ 520 nm/$F^{em}$ 490 nm). The final concentrations of reagents in the binding assay are 200 pM terbium chelate-labeled menin, 75 nM FITC-MBM1 peptide and 0.5% DMSO in assay buffer. Dose-response titrations of test compounds are conducted using an 11 point, four-fold serial dilution scheme, starting typically at 10 µM.

Compound potencies were determined by first calculating % inhibition at each compound concentration according to equation 1:

$$\% \text{ inhibition}=((HC-LC)-(HTRF^{compound}-LC))/(HC-LC))*100 \quad \text{(Eqn 1)}$$

Where LC and HC are the HTRF values of the assay in the presence or absence of a saturating concentration of a compound that competes with FITC-MBM1 for binding to menin, and $HTRF^{compound}$ is the measured HTRF value in the presence of the test compound. HC and LC HTRF values represent an average of at least 10 replicates per plate. For each test compound, % inhibition values were plotted vs. the logarithm of the test compound concentration, and the $IC_{50}$ value derived from fitting these data to equation 2:

$$\% \text{ inhibition}=\text{Bottom}+(\text{Top}-\text{Bottom})/(1+10\hat{}((\log IC_{50}-\log[\text{cmpd}])*h)) \quad \text{(Eqn 2)}$$

Where Bottom and Top are the lower and upper asymptotes of the dose-response curve, respectively, $IC_{50}$ is the concentration of compound that yields 50% inhibition of signal and h is the Hill coefficient.

Preparation of Terbium cryptate labeling of Menin: Menin (a.a 1-610-6×his tag, 2.3 mg/mL in 20 mM Hepes (2-[4-(2-Hydroxyethyl)-1-piperazinyl]ethane sulfonic acid), 80 mM NaCl, 5 mM DTT (Dithiothreitol), pH 7.5) was labeled with terbium cryptate as follows. 200 μg of Menin was buffer exchanged into 1× Hepes buffer. 6.67 μM Menin was incubated with 8-fold molar excess NHS (N-hydroxysuccinimide)-terbium cryptate for 40 minutes at room temperature. Half of the labeled protein was purified away from free label by running the reaction over a NAP5 column with elution buffer (0.1M Hepes, pH 7+0.1% BSA (bovine serum albumin)). The other half was eluted with 0.1M phosphate buffered saline (PBS), pH7. 400 μl of eluent was collected for each, aliquoted and frozen at −80° C. The final concentration of terbium-labeled Menin protein was 115 μg/mL in Hepes buffer and 85 μg/mL in PBS buffer, respectively.

```
MENIN Protein Sequence (SEQ ID NO: 1):
MGLKAAQKTLFPLRSIDDVVRLFAAELGREEPDLVLLSLVLGFVEHFLAV

NRVIPTNVPELTFQPSPAPDPPGGLTYFPVADLSIIAALYARFTAQIRGA

VDLSLYPREGGVSSRELVKKVSDVIWNSLSRSYFKDRAHIQSLFSFITGT

KLDSSGVAFAVVGACQALGLRDVHLALSEDHAWVVFGPNGEQTAEVTWHG

KGNEDRRGQTVNAGVAERSWLYLKGSYMRCDRKMEVAFMVCAINPSIDLH

TDSLELLQLQQKLLWLLYDLGHLERYPMALGNLADLEELEPTPGRPDPLT

LYHKGIASAKTYYRDEHIYPYMYLAGYHCRNRNVREALQAWADTATVIQD

YNYCREDEEIYKEFFEVANDVIPNLLKEAASLLEAGEERPGEQSQGTQSQ

GSALQDPECFAHLLRFYDGICKWEEGSPTPVLHVGWATFLVQSLGRFEGQ

VRQKVRIVSREAEAAEAEEPWGEEAREGRRRGPRRESKPEEPPPPKKPAL

DKGLGTGQGAVSGPPRKPPGTVAGTARGPEGGSTAQVPAPAASPPPEGPV

LTFQSEKMKGMKELLVATKINSSAIKLQLTAQSQVQMKKQKVSTPSDYTL

SFLKRQRKGLHHHHHH
```

2a) Proliferation Assay

The anti-proliferative effect of menin/MLL protein/protein interaction inhibitor test compounds was assessed in human leukemia cell lines. The cell line MOLM14 harbors a MLL translocation and expresses the MLL fusion protein MLL-AF9, respectively, as well as the wildtype protein from the second allele. OCI-AML3 cells that carry the NPM1c gene mutation were also tested. MLL rearranged cell lines (e.g. MOLM14) and NPM1c mutated cell lines exhibit stem cell-like HOXA/MEIS1 gene expression signatures. KO-52 was used as a control cell line containing two MLL (KMT2A) wildtype alleles in order to exclude compounds that display general cytotoxic effects.

MOLM14 cells were cultured in RPMI-1640 (Sigma Aldrich) supplemented with 10% heat-inactivated fetal bovine serum (HyClone), 2 mM L-glutamine (Sigma Aldrich) and 50 μg/ml gentamycin (Gibco). KO-52 and OCI-AML3 cell lines were propagated in alpha-MEM (Sigma Aldrich) supplemented with 20% heat-inactivated fetal bovine serum (HyClone), 2 mM L-glutamine (Sigma Aldrich) and 50 μg/ml gentamycin (Gibco). Cells were kept at 0.3-2.5 million cells per ml during culturing and passage numbers did not exceed 20.

In order to assess the anti-proliferative effects, 200 MOLM14 cells, 200 OCI-AML3 cells or 300 KO-52 cells were seeded in 200 μl media per well in %-well round bottom, ultra-low attachment plates (Costar, catalogue number 7007). Cell seeding numbers were chosen based on growth curves to ensure linear growth throughout the experiment. Test compounds were added at different concentrations and the DMSO content was normalized to 0.3%. Cells were incubated for 8 days at 37° C. and 5% $CO_2$. Spheroid like growth was measured in real-time by live-cell imaging (IncuCyteZOOM, Essenbio, 4× objective) acquiring images at day 8. Confluence (%) as a measure of spheroid size was determined using an integrated analysis tool.

In order to determine the effect of the test compounds over time, the confluence in each well as a measure of spheroid size, was calculated. Confluence of the highest dose of a reference compound was used as baseline for the LC (Low control) and the confluence of DMSO treated cells was used as 0% cytotoxicity (High Control, HC).

Absolute $IC_{50}$ values were calculated as percent change in confluence as follows:

LC=Low Control: cells treated with e.g. 1 μM of the cytotoxic agent staurosporin, or e.g. cells treated with a high concentration of an alternative reference compound HC=High Control: Mean confluence (%) (DMSO treated cells)

$$\% \text{ Effect}=100-(100*(\text{Sample}-LC)/(HC-LC))$$

GraphPad Prism(version 7.00) was used to calculate the $IC_{50}$. Dose-response equation was used for the plot of % Effect vs Log 10 compound concentration with a variable slope and fixing the maximum to 100% and the minimum to 0%.

2b) MEIS1 mRNA Expression Assay

MEIS1 mRNA expression upon treatment of compound was examined by Quantigene Singleplex assay (Thermo Fisher Scientific). This technology allows for direct quantification of mRNA targets using probes hybridizing to defined target sequences of interest and the signal is detected using a Multimode plate reader Envision (PerkinElmer). The MOLM14 cell line was used for this experiment. Cells were plated in 96-well plates at 3,750 cells/well in the presence of increasing concentrations of compounds. After incubation of 48 hours with compounds, cells were lysed in lysis buffer and incubated for 45 minutes at 55° C. Cell lysates were mixed with human MEIS1 specific capture probe or human RPL28 (Ribosomal Protein L28) specific probe as a normalization control, as well as blocking probes. Cell lysates were then transferred to the custom assay hybridization plate (Thermo Fisher Scientific) and incubated for 18 to 22 hours at 55° C. Subsequently, plates were washed to remove unbound materials followed by sequential addition of pre-amplifiers, amplifiers, and label probe. Signals (=gene counts) were measured with a Multimode plate reader Envision. $IC_{50}$s were calculated by dose-response modelling using appropriate software. For all non-housekeeper genes response equal counts corrected for background and relative expression. For each sample, each test gene signal (background subtracted) was divided by the normalization gene signal (RPL28: background subtracted). Fold changes were calculated by dividing the normalized values for the treated samples by the normalized values for the DMSO treated sample. Fold changes of each target gene were used for the calculation of $IC_{50}$s.

TABLE 3

Biological data—HTRF assay, proliferation assay, and MEIS1 mRNA expression assay

| Compound Number | HTRF-30 min incubation $IC_{50}$ (nM) | MEIS1 $IC_{50}$ (μM) | spheroid assay_ OneTime MOLM14 $IC_{50}$ (μM) | OCI-AML3 $IC_{50}$ (μM) | spheroid assay_ OneTime KO-52 $IC_{50}$ (μM) |
|---|---|---|---|---|---|
| 1 | 0.13 | 0.075 | 0.23 | 0.17 | >15 |
| 2 | 3.31 | >2.5 | 2.22 | | >15 |
| 3 | 0.10 | 0.095 | 0.042 | 0.31 | >15 |
| 4 | 0.095 | 0.02 | 0.03 | 0.39 | >15 |
| 5 | 2.26 | ~0.99 | 0.84 | | >15 |
| 6 | 0.61 | 0.36 | 0.48 | 1.86 | >15 |
| 7 | 86.20 | >2.5 | >3.75 | | >15 |
| 8 | 0.43 | ~0.65 | 1.02 | 2.15 | >15 |
| 9 | 44.66 | | >3.75 | | >15 |
| 10 | 0.18 | 0.41 | 0.34 | 1.68 | >15 |
| 11 | 0.11 | 0.018 | 0.021 | 0.21 | 8.38 |
| 12 | 0.12 | 0.039 | 0.036 | 0.63 | 8.24 |
| 13 | 0.40 | 0.077 | 0.061 | 0.21 | >15 |
| 14 | 0.05 | 0.0085 | 0.01 | 0.069 | 3.10 |
| 15 | 0.25 | 0.071 | 0.10 | 0.46 | 3.70 |
| 16 | 1.85 | ~0.67 | 0.37 | | 10.51 |
| 17 | 0.61 | 0.24 | 0.30 | 1.44 | 6.79 |
| 18 | 0.30 | 0.15 | 0.12 | 0.66 | >15 |
| 19 | 0.11 | 0.033 | 0.058 | 0.16 | >15 |
| 20 | 4.19 | >1 | >0.94 | | >15 |
| 21 | 10.41 | >1 | >0.94 | | >15 |
| 22 | 1.79 | ~0.76 | 0.36 | | 12.82 |
| 23 | 0.22 | 0.15 | 0.17 | 0.81 | 13.82 |
| 24 | 0.97 | ~0.84 | 0.69 | 2.68 | >15 |
| 25 | 10.52 | ~1.2 | >3.75 | | >15 |
| 26 | 0.28 | 0.49 | 0.27 | 1.34 | >15 |
| 27 | 0.09 | 0.02 | 0.021 | 0.091 | 6.85 |
| 28 | 2.75 | >1 | 0.60 | 1.36 | >15 |
| 29 | 2.42 | ~2.25 | 0.97 | | >15 |
| 30 | 0.067 | 0.099 | 0.13 | 0.47 | >15 |
| 31 | 2.28 | >1 | >0.94 | | >15 |
| 32 | 0.10 | 0.088 | 0.058 | 0.28 | 12.9 |
| 33 | 2.84 | >1 | >0.94 | | >15 |
| 34 | 0.87 | >1 | 3.84 | 3.44 | >15 |
| 35 | 0.15 | 0.12 | 0.20 | 0.49 | >15 |
| 36 | 2.60 | >1 | >0.94 | | >15 |
| 37 | 0.12 | 0.039 | 0.04 | 0.43 | >15 |
| 38 | 1.16 | ~1.1 | 0.52 | | >15 |
| 39 | 0.26 | 0.044 | 0.027 | 0.14 | >15 |
| 40 | 0.40 | 0.019 | 0.019 | 0.074 | 9.54 |
| 41 | 0.36 | 0.024 | 0.011 | 0.17 | >15 |
| 42 | 15.00 | | | | |
| 43 | 0.55 | ~0.24 | 0.29 | 1.20 | >15 |
| 44 | 46.62 | >2.5 | >3.75 | | >15 |
| 45 | 0.37 | 0.21 | 0.22 | 1.25 | >15 |
| 46 | 59.70 | >2.5 | >3.75 | | >15 |
| 47 | 0.31 | 0.14 | 0.22 | 0.6 | 10.84 |
| 48 | 70.39 | >1 | >0.94 | | >15 |
| 69 | 0.099 | 0.016 | 0.02 | 0.087 | 7.18 |
| 70 | 0.098 | 0.017 | 0.017 | 0.12 | 7.75 |
| 70a | 0.18 | 0.017 | 0.011 | 0.08 | |
| 71 | | 0.38 | 0.56 | 1.47 | 12.81 |
| 74 | 0.51 | 0.26 | 0.14 | 1.29 | 10.57 |
| 75 | 0.21 | 0.14 | 0.053 | 0.41 | >15 |
| 76 | 2.56 | | 0.34 | 2.39 | |
| 77 | 0.51 | 0.12 | 0.10 | 1.32 | 13.66 |
| 78 | 3.69 | >1 | >0.94 | 12.18 | >15 |
| 83 | 0.14 | 0.092 | 0.17 | 0.42 | 6.24 |
| 84 | 5.90 | >1 | >0.94 | 7.17 | >15 |
| 88 | 0.083 | 0.13 | 0.12 | 0.81 | 14 |
| 89 | 3.79 | | | | |
| 90 | 0.16 | | 0.04 | 0.19 | 1 |
| 94 | 0.12 | 0.0082 | 0.01 | 0.096 | 4.75 |
| 95 | 4.98 | ~0.62 | 0.39 | 1.62 | >15 |
| 99 | 0.20 | 0.026 | 0.0085 | 0.082 | 11.5 |
| 100 | 2.05 | | | | |
| 102 | 0.11 | 0.033 | 0.016 | 0.11 | >15 |
| 103 | 2.43 | 0.42 | 0.29 | 1.36 | >15 |
| 104 | 0.074 | 0.015 | 0.0067 | 0.15 | 10.74 |
| 112 | 0.049 | 0.009 | 0.0098 | 0.081 | >15 |
| 114 | 0.05 | 0.022 | 0.014 | 0.042 | 1.69 |
| 122 | 0.065 | 0.034 | 0.021 | 0.15 | >15 |
| 123 | 3.98 | >1 | >0.94 | 3.55 | >15 |
| 127 | 0.089 | 0.044 | 0.026 | 0.14 | 11.27 |
| 128 | 1.64 | ~0.68 | 0.63 | 1.99 | 11.39 |
| 132 | 0.11 | 0.015 | 0.033 | 0.19 | 10.41 |
| 133 | 2.13 | >1 | >0.94 | 3.50 | >15 |
| 135 | 0.057 | 0.016 | 0.013 | 0.23 | 9.69 |
| 137 | 0.18 | 0.025 | 0.045 | 0.16 | 7.29 |
| 140 | 0.093 | 0.028 | 0.11 | 0.33 | 5.75 |
| 142 | 0.071 | 0.051 | 0.012 | 0.22 | >15 |
| 145 | 0.07 | 0.021 | 0.014 | 0.11 | >15 |
| 146 | 0.081 | 0.44 | 0.32 | 1.79 | >15 |
| 148 | 0.35 | 0.06 | 0.041 | 0.34 | >15 |
| 150 | 0.26 | 0.013 | 0.014 | 0.16 | 8.70 |
| 152 | 0.19 | 0.087 | 0.037 | 0.35 | >15 |
| 154 | 0.051 | 0.027 | 0.022 | 0.067 | >15 |
| 157 | 0.12 | 0.022 | 0.021 | 0.083 | 13.80 |
| 159 | 0.10 | ~0.017 | 0.01 | 0.012 | 6.30 |
| 161 | 0.23 | 0.041 | 0.016 | 0.055 | >15 |
| 162 | 0.096 | ~0.019 | 0.013 | 0.026 | >15 |
| 163 | 0.089 | 0.02 | 0.018 | 0.12 | >15 |
| 165 | 0.06 | 0.023 | 0.03 | 0.099 | >15 |
| 167 | 0.16 | 0.018 | 0.017 | 0.065 | >15 |
| 168 | 0.10 | 0.074 | 0.049 | 0.37 | >15 |
| 170 | 0.10 | 0.037 | 0.025 | 0.041 | >15 |
| 172 | 0.13 | 0.013 | 0.023 | 0.038 | 13.4 |
| 176 | 0.13 | 0.017 | 0.038 | 0.12 | >15 |
| 177 | 0.062 | 0.0073 | 0.024 | 0.064 | >15 |
| 179 | 0.13 | 0.027 | 0.033 | 0.059 | >15 |
| 181 | 0.079 | 0.017 | 0.023 | 0.044 | 14.02 |
| 184 | ~0.36 | 0.11 | 0.23 | 0.19 | 3.00 |
| 185 | 0.20 | 0.044 | 0.079 | 0.061 | 1.7 |
| 188 | 0.43 | 0.034 | 0.055 | 0.34 | >15 |
| 189 | 0.22 | 0.019 | 0.03 | 0.19 | >15 |
| 191 | 0.28 | 0.22 | 0.28 | 0.56 | >15 |
| 193 | ~0.26 | 0.12 | 0.17 | 0.29 | >15 |
| 195 | ~0.4 | 0.056 | 0.07 | 0.058 | >15 |
| 197 | 0.30 | 0.036 | 0.045 | 0.036 | >15 |
| 199 | 0.13 | ~0.26 | 0.46 | 1.91 | >15 |
| 201 | 0.13 | 0.052 | 0.04 | 0.065 | >15 |
| 203 | 0.30 | 0.042 | 0.038 | 0.075 | >15 |
| 205 | 0.21 | 0.035 | 0.029 | 0.043 | >15 |
| 209 | 0.27 | 0.13 | 0.27 | 0.24 | >15 |
| 210 | 5.57 | >1 | >0.94 | 4.63 | |
| 211 | 0.35 | 0.11 | 0.15 | 0.097 | >15 |
| 212 | 9.45 | | | | |
| 214 | 0.49 | 0.14 | 0.12 | 0.38 | >15 |
| 215 | 88.84 | >1 | 1.49 | 9.24 | |
| 219 | 0.27 | ~0.23 | 0.13 | 0.43 | >15 |

TABLE 3-continued

Biological data—HTRF assay, proliferation assay, and MEIS1 mRNA expression assay

| Compound Number | HTRF-30 min incubation $IC_{50}$ (nM) | MEIS1 $IC_{50}$ (μM) | spheroid assay_ OneTime MOLM14 $IC_{50}$ (μM) | OCI-AML3 $IC_{50}$ (μM) | spheroid assay_ OneTime KO-52 $IC_{50}$ (μM) |
|---|---|---|---|---|---|
| 223 | 0.40 | 0.20 | 0.18 | 0.99 | >15 |
| 225 | 8.31 | >1 | >0.94 | 7.09 | |
| 227 | 0.15 | 0.076 | 0.046 | 0.13 | >15 |
| 229 | 0.37 | 0.36 | 0.32 | 0.87 | >15 |
| 230 | ~0.88 | ~0.94 | >0.94 | 1.16 | >15 |
| 231 | 1.77 | ~0.56 | 0.79 | 1.80 | |
| 233 | 0.058 | 0.019 | 0.026 | 0.15 | 5.03 |
| 240 | 12.31 | | | | |
| 241 | 1.36 | 0.28 | 0.18 | 1.12 | |
| 242 | 0.26 | 0.23 | 0.17 | 1.07 | >15 |
| 243 | 7.39 | | | | |
| 245 | 0.26 | 0.14 | 0.073 | 0.43 | >15 |
| 246 | 0.063 | 0.18 | 0.06 | 0.38 | >15 |
| 250 | 0.18 | 0.091 | 0.22 | 0.41 | 7.05 |
| 251 | 0.18 | 0.019 | 0.052 | 0.13 | 3.90 |
| 252 | 0.065 | 0.053 | 0.032 | 0.64 | 7.26 |
| 254 | 4.16 | | 0.59 | 4.69 | >15 |
| 256 | 0.15 | 0.13 | 0.084 | 0.36 | >15 |
| 258 | 0.33 | 0.026 | 0.027 | 0.74 | 5.44 |
| 259 | 0.16 | 0.065 | 0.046 | 0.25 | >15 |
| 265 | 0.29 | | 0.028 | 0.061 | |
| 266 | 0.92 | 0.039 | 0.029 | 0.049 | >15 |
| 268 | 0.29 | 0.34 | 0.20 | 0.53 | >15 |
| 270 | 0.54 | 0.22 | 0.14 | 0.48 | >15 |
| 271 | 0.27 | 0.1 | 0.065 | 0.16 | >15 |
| 272 | 0.58 | 0.17 | 0.13 | 0.44 | >15 |
| 273 | 0.21 | ~0.39 | 0.39 | 0.83 | >15 |
| 274 | 0.38 | 0.23 | 0.20 | 0.64 | >15 |
| 275 | 0.66 | 0.1 | 0.078 | 0.33 | >15 |
| 276 | 0.50 | 0.39 | 0.24 | 1.61 | >15 |
| 278 | 0.068 | >1 | >0.94 | 3.21 | >15 |
| 280 | 0.20 | 1.07 | 0.69 | 0.92 | >15 |
| 281 | 0.24 | 0.038 | 0.048 | 0.09 | >15 |
| 283 | 0.054 | 0.01 | 0.014 | 0.046 | >15 |
| 284 | ~0.36 | 0.05 | 0.023 | 0.073 | >15 |
| 285 | 1.02 | 0.27 | 0.16 | 0.13 | >15 |
| 286 | | 0.096 | 0.076 | 0.29 | 22.94 |
| 300 | 0.066 | 0.029 | 0.036 | 0.071 | >15 |
| 302 | 0.26 | 0.16 | 0.097 | 0.77 | |
| 311 | 1.01 | ~0.63 | 0.51 | 2.88 | >15 |
| 313 | 1.99 | ~0.26 | | | |
| 314 | 1.53 | 0.16 | 0.30 | | |
| 315 | 0.51 | ~0.33 | 0.29 | 1.09 | >15 |
| 323 | 0.49 | 0.062 | 0.11 | 0.17 | 13.39 |
| 324 | 18.4 | | | | |
| 325 | ~0.16 | 0.015 | 0.016 | 0.19 | >15 |
| 326 | 18.51 | | | | |
| 334 | 0.079 | 0.011 | 0.012 | 0.13 | >15 |
| 335 | 5.49 | | | | |
| 336 | 0.21 | 0.061 | 0.07 | 0.87 | >15 |
| 337 | 4.57 | >1 | | | |
| 342 | 0.17 | 0.078 | 0.01 | 0.025 | 0.023 |
| 343 | ~3.93 | 0.53 | | | |
| 346 | 0.058 | 0.033 | 0.036 | 0.13 | >15 |
| 347 | 12.02 | >1 | >0.94 | 4.98 | |
| 352 | 0.077 | 0.13 | 0.018 | 0.15 | >15 |
| 353 | 4.19 | | | | |
| 356 | 0.053 | ~0.0082 | 0.007 | 0.046 | >15 |
| 357 | 7.77 | | | | |
| 365 | 0.097 | 0.01 | 0.011 | 0.037 | >15 |
| 366 | 0.088 | 0.02 | 0.017 | 0.076 | >15 |
| 369 | 1.82 | ~0.36 | 0.42 | | |
| 370 | 5.42 | | | | |
| 377 | 15.41 | | | | |
| 378 | 27.28 | | | | |
| 379 | 14.21 | | | | |
| 380 | 40.55 | | | | |
| 382 | 0.41 | 0.15 | 0.14 | 0.40 | 11.82 |
| 386 | ~0.59 | 0.061 | 0.16 | 0.81 | 9.6 |
| 387 | 9.52 | | | | |
| 391 | 0.90 | 0.16 | 0.49 | 2.10 | >15 |
| 392 | 10.34 | | | | |
| 394 | 0.23 | 0.049 | 0.11 | 0.33 | >15 |
| 395 | 0.20 | 0.14 | 0.056 | 0.28 | |
| 396 | 0.08 | 0.017 | 0.023 | 0.14 | 8.51 |
| 397 | 0.08 | 0.018 | 0.015 | 0.027 | >15 |
| 398 | 0.24 | 0.043 | 0.064 | 0.22 | >15 |
| 402 | 0.067 | 0.018 | 0.007 | 0.04 | |
| 406 | 0.033 | 0.13 | 0.22 | 0.49 | |
| 407 | 0.086 | 0.38 | | | |
| 409 | 0.12 | ~0.44 | 0.64 | 1.85 | |
| 410 | 0.12 | 0.12 | 0.16 | 0.38 | |
| 411 | 0.33 | 0.11 | 0.21 | 0.68 | |
| 413 | 0.051 | ~0.59 | 0.72 | 1.49 | |
| 415 | 0.084 | | | | |
| 416 | ~0.035 | 0.049 | | | |

3) Mouse PK (In Vivo T1/2 and Oral Bioavailability)

In vivo pharmacokinetics (PK) were assessed in fasted male CD-1 mice (age 6-8 weeks) following a single intravenous (IV, 0.5 or 1.0 mg/kg administered at 2.5 ml/kg) or oral (PO, 5 mg/kg administered at 10 ml solution/kg) dose of test article formulated in a 20% (w:vol) HP-β-CD solution or in Pyrogen free water.

Plasma and/or whole blood samples were collected from the dorsal metatarsal vein at desired timepoints via serial capillary microsampling (approx. 0.03 mL) using EDTA as an anticoagulant. Concentrations of compound in the plasma and blood samples were analyzed using a qualified LC-MS/MS method. In silico analysis of main pharmacokinetic parameters was performed using WinNonlin (Phoenix™, version 6.1) or similar software. (Results see Table 4)

4) Metabolic Stability in Human/Mouse Liver Microsomes

Experimental Procedure

The objective of this study is to measure in vitro metabolic stability of test compound(s) in human and mouse liver microsomes and provide quantitative information on the rate of metabolic turnover (i.e. determination of the apparent intrinsic clearance of test).

Test items were prepared at a stock concentration of 10 mM in DMSO. For determination of metabolic turnover, a final working solution was prepared by adding 2 μL of 10 mM DMSO stock solution for test compound or positive control compounds to 198 μL of acetonitrile (100 μM final concentration).

Incubations were performed as follows: First, liver microsomes were thawed on ice and a master solution containing liver microsomes in 100 mM PBS (phosphate-buffered saline) at pH 7.4 is prepared. Next, the liver microsomes solution was added to the incubation plates and 10 mM NADPH (Nicotinamide-adenine dinucleotide phosphate) was added (MW: 833.4 g/mol; Roche Diagnostics GmbH, Germany. Dissolved in phosphate buffer (100 mmol/L, pH 7.4)). The mixture was mixed for 10 seconds and pre-warmed in the incubation plate at 37° C. for 10 minutes. The metabolic reaction was initiated with the addition of 5 μL of the 100 μM working solution for test compound or positive control compounds to incubation plate (final test item concentration=1 μM). The reaction final mixture should contain 1 mM NADPH, 0.5 mg/mL microsomes protein and 1 μM test compound or positive control compound in 100 mM PBS at pH 7.4. The percentage of organic solvent in incubation mixture is 1% with DMSO ≤0.02%.

The reaction was quenched by transferring 50 μL of the incubated mixture at selected time points into the quenching plate containing 200 μL of cold methanol. After sampling of all the timepoints the quenching plate was centrifuged at 4000 rpm for 40 minutes to precipitate protein. A total of 90 μL of the supernatant was transferred to an analysis plate and ultra-pure $H_2O$ water is added into each well for LC/MS/MS analysis. All incubations and analysis were performed in duplicate.

Data Analysis

All calculations were carried out using Microsoft Excel. The slope value, k, was determined by linear regression of the natural logarithm of the remaining percentage of the parent drug vs. incubation time curve.

The in vitro half-life (in vitro tin) was determined from the slope value:

$$\text{in vitro } t_{1/2} = -(0.693/k)$$

Conversion of the in vitro tin (in min) into the in vitro intrinsic clearance (in vitro $CL_{int}$, in μL/min/mg proteins) was done using the following equation:

$$\text{in vitro } Cl_{int} = \left(\frac{0.693}{t_{\frac{1}{2}}}\right) * \left(\frac{\text{volume of incubation } (\mu L)}{\text{amount of proteins (mg)}}\right)$$

Results see Table 4

TABLE 4

Mouse PK and metabolic stability

| Example number | Formulating agent | In vivo T1/2 (IV) (h) | Bioavailability (PO) (%) | Human LM Clint (μl/min/mg) | Mouse LM Clint (μl/min/mg) |
|---|---|---|---|---|---|
| 27 | HP-β-CD | 6.7 | 17 | 19 | <7.5 |
| 70 | Pyrogen free water | 9.0 | 34 | 19 | <7.5 |
| 346 | HP-β-CD | 5.2 | 5.1 | 11 | <7.5 |
| 102 | HP-β-CD | 11 | 9.7 | NA | NA |
| 396 | | NA | NA | 22 | <7.5 |
| 104 | HP-β-CD | 8.7 | 6.1 | 19 | <7.5 |
| 114 | HP-β-CD | 9.5 | 8.7 | 26 | 15 |
| 1 | HP-β-CD | 15 | <1 | <7.5 | 21 |
| 112 | HP-β-CD | 6.2 | 4.0 | 17 | <7.5 |
| 245 | HP-β-CD | 7.0 | <1 | 18 | <7.5 |
| 37 | HP-β-CD | >12 | <1 | <7.5 | <7.5 |
| 6 | HP-β-CD | NA | NA | 35 | 28 |
| 45 | HP-β-CD | NA | NA | 43 | 110 |
| 13 | HP-β-CD | NA | NA | 75 | 44 |
| 47 | HP-β-CD | NA | NA | 38 | 47 |
| 83 | HP-β-CD | NA | NA | 539 | >1000 |
| 161 | HP-β-CD | NA | NA | 70 | 55 |
| 214 | HP-β-CD | NA | NA | 44 | 80 |
| 99 | HP-β-CD | NA | NA | 27 | 13 |
| 397 | HP-β-CD | NA | NA | 14 | <7.5 |
| 11 | HP-β-CD | NA | NA | 14 | <7.5 |

"NA" means not analyzed

5) Protocol for Pharmacodynamics (PD) Activity in Subcutaneous (Sc or SC) Xenografts of MOLM-14 or OCI-AML3 Cells Test Agents and Controls Compound 70 was formulated in 20% hydroxypropyl-beta-cyclodextrin (HP-β-CD) and prepared to reach a total volume of 0.2 mL (10 mL/kg) per dose for a 20 g animal. Doses were adjusted by individual body weight each day. Working stocks of Compound 70 were prepared once per week for each study and stored at room temperature. Compound 70 was administered orally (PO), daily.

Assay

The in vivo pharmacodynamics (PD) activity of compounds was evaluated in subcutaneous (SC) xenografts of MOLM14 cells or OCI-AML3. Nude NMRI mice (Crl: NMRI-Foxn1nu/−) harboring MOLM14 or OCI-AML3 tumors were treated with 3 daily doses of vehicle or compounds. Plasma samples were collected at 23 hours after day 2 dose, 0.5 hours post final dose, and 16 hours post final dose and tumor samples were collected 16 hours post final dose. To examine the effects of compounds on the expression of multiple Menin-MLL target genes (e.g. MEIS1, MEF2C, FLT3) QuantiGene Plex technology (Thermo Fisher Scientific) was used. Frozen tumors were homogenized and transferred to individual lysing matrix tubes in lysis buffer and incubated for 30 minutes at 55° C. Cell lysates were mixed with target-specific capture probes, Luminex beads, and blocking probes, transferred to the custom assay hybridization plate (Thermo Fisher Scientific) and incubated for 18 to 22 hours at 54° C. Subsequently, plates were transferred to a magnetic separation plate and washed to remove unbound materials from beads followed by sequential hybridization of preamplifiers, amplifiers, and label probe and subsequent streptavidin phycoerythrin binding. Signals from the beads were measured with a Luminex FlexMap three-dimensional instrument. For all non-housekeeper genes response equal counts corrected for background and relative expression. For each sample, each test gene signal (background subtracted) was divided by the normalization gene signal (RPL19, RPL28, ATP6V1A: background subtracted). Fold changes were calculated by dividing the normalized values for the treated samples by the normalized values for the DMSO treated sample.

TABLE 5

Expression level (% relative to vehicle) of selected genes from MOLM14 SC model (mean values and standard deviations).

| Compound 70 (mg/kg) | MEIS1 | FLT3 | MEF2C |
|---|---|---|---|
| 0 | 101.30 ± 15.06 | 104.80 ± 10.07 | 103.50 ± 11.02 |
| 3 | 83.49 ± 25.48 | 78.67 ± 20.74 | 85.50 ± 22.77 |
| 10 | 62.84 ± 4.06 | 74.91 ± 8.97 | 68.04 ± 14.43 |
| 30 | 23.16 ± 2.75 | 52.61 ± 4.51 | 27.83 ± 2.17 |
| 50 | 14.40 ± 3.39 | 36.14 ± 3.50 | 18.75 ± 2.38 |
| 100 | 10.97 ± 3.21 | 35.82 ± 1.10 | 14.18 ± 1.56 |

TABLE 6

Expression level (% relative to vehicle) of selected genes from OCI-AML3 SC model (mean values and standard deviations).

| Compound 70 (mg/kg) | MEIS1 |
|---|---|
| 0 | 100.30 ± 8.53 |
| 3 | 87.90 ± 39.75 |
| 10 | 48.81 ± 15.30 |
| 30 | 32.66 ± 3.71 |
| 50 | 23.83 ± 1.34 |
| 100 | 16.76 ± 1.92 |

6) Efficacy Study in MOLM-14 Subcutaneous Model

Test Agents and Controls

Compound 70 was formulated in 20% hydroxypropyl-beta-cyclodextrin (HP-β-CD) and prepared to reach a total volume of 0.2 mL (10 mL/kg) per dose for a 20 g animal. Doses were adjusted by individual body weight each day. Working stocks of Compound 70 were prepared once per week for each study and stored at 25° C.

Animals

Female NMRI Nude mice (MOLM-14 SC) were used when they were approximately 6 to 8 weeks of age and weighed approximately 25 g. All animals could acclimate and recover from any shipping-related stress for a minimum of 7 days prior to experimental use. Autoclaved water and irradiated food were provided ad libitum, and the animals were maintained on a 12 hour light and dark cycle. Cages, bedding, and water bottles were autoclaved before use and changed weekly.

| Tissue Culture and Cell Injection Reagents |
| --- |
| DPBS (Dulbecco's phosphate-buffered saline) |
| Heat-inactivated fetal bovine serum |
| RPMI 1640 medium |
| L-glutamine |
| Gentamycin |
| T175 Culture Flask |
| Roller Bottle |

Tumor Model and Cell Culture Method

Human AML cells MOLM-14 were cultured at 37° C., 5% $CO_2$ in the indicated complete culture media (RPMI 1640+10% HI-FBS+2 mM L-glutamine+50 ug/ml Gentamycin). Cells were harvested while in logarithmic growth and resuspended in cold (4° C.) Roswell Park Memorial Institute (RPMI) 1640 in serum-free medium.

Each mouse received $5\times10^6$ MOLM-14 cells in 50% Matrigel in the right flank, in a total volume of 0.2 mL using a 1 cc syringe and a 27-gauge needle.

Study Designs

Compound 70 was administered orally (PO), daily.

Day 0 is the day of tumor cell implantation and study initiation Mice bearing SC MOLM-14 tumors were randomized on Day 16 post-tumor implantation and assigned to treatment groups according to tumor volume (mean of ~130 $mm^3$; n=10/group). Treatment with vehicle or Compound 70 (at 30 and 100 mg/kg) was initiated on the same day, with daily oral dosing for 21 days. Plasma was collected at 1, 2, 4, 8, and 23 hours after the last dose (n=4-5/group/time point) for PK (pharmacokinetics) analysis.

Animal Monitoring

SC tumor volume were measured for each animal 2 to 3 times per week or more throughout the study.

Calculations

Tumor volume was calculated using the formula:

Tumor volume ($mm^3$)=($D\times d^2/2$); where 'D' represents the larger diameter and 'd' the smaller diameter of the tumor as determined by caliper measurements. Tumor volume data was graphed as the mean tumor volume SEM.

The % ΔTGI was defined as the difference between mean tumor burden of the treatment and control groups, calculated as % $\Delta TGI=([(TV_cTV_{c0})(TV_tTV_{t0})]/(TV_cTV_{c0}))\times100$ where '$TV_c$' is the mean tumor burden of a given control group, '$TV_{c0}$' is the mean initial tumor burden of a given control group, '$TV_t$' is the mean tumor burden of the treatment group, and '$TV_{t0}$' is the mean initial tumor burden of the treatment group. % TGI was defined as the difference between Mean tumor volumes of the treated and control groups, calculated as:

% $TGI=((TV_cTV_t)/TV_c)\times100$ where '$TV_c$' is the mean tumor volume of the control group and '$TV_t$' is the mean tumor volume of the treatment group. As defined by National Cancer Institute criteria, ≥60% TGI is considered biologically significant.

The % Tumor Regression (TR), quantified to reflect the treatment-related reduction of tumor volume as compared to baseline independent of the control group, was calculated as % $TR=(1-\text{mean }(TV_ti/TV_{t0}i))\times100$ where '$TV_ti$' is the tumor burden of individual animals in a treatment group, and '$TV_{t0}i$' is the initial tumor burden of the animal.

Data Analysis

Tumor volume were graphed using Prism software (GraphPad version 7 or 8). Statistical significance for most studies was evaluated for Compound 70-treated groups compared with HPβCD vehicle-treated controls on the last day of the study when ⅔ or more mice remained in each group. Differences between groups were considered significant when $p\leq0.05$.

Statistical significance for animal tumor volume was calculated using the linear mixed-effects (LME) analysis in R software version 3.4.2 (using Janssen's internally developed Shiny application version 4.0), with treatment and time as fixed effects and animal as random effect. Logaritmic transformation was performed if individual longitudinal response trajectories were not linear.

The information derived from this model was used to make pairwise treatment comparisons of tumor volumes to that of the control group or between all the treatment groups. Results in FIG. 1.

7) Cardio-Electrophysiological Effects of the Testing Compounds in Synchronously Beating Human Pluripotent Stem Cell-Derived Cardiomyocytes (hSC-CMs) Using a $Ca^{2+}$-Fluorescence Assay (CTCM Human)

Protocol

Compounds were tested in the 96-well plates

Compounds were tested at 0.1 μM, 0.2 μM, 0.5 μM, 1 μM, 2.5 μM and 5 μM (n=4 per dose) on Cor.4U 9-Cardiomyocytes or on iCell® Cardiomyocytes2

Alternatively, compounds were tested at 0.1 μM, 0.3 μM; 1 μM, 3 μM, 10 μM and 30 μM (n=4 per dose) mostly on iCell® Cardiomyocytes2

| Positive and Negative controls | |
| --- | --- |
| Dofetilide | at 3 nM |
| Isoproterenol | at 100 nM |
| Nimodipine | at 100-300 nM |
| Cetirizine | at 3 μM |

Vehicle Control:

Dimethylsulfoxide (DMSO). The solutions of the compound in DMSO or its solvent (final concentration of 0.1% DMSO; n=8)

Preparation of Test Article and Controls

Tested compounds were dissolved in DMSO at 1000-fold the intended concentrations. A compound "mother-plate" was made, containing the test compounds and positive and negative controls at 1000-fold the final concentrations. At the experiment day, these stock solutions were diluted with Tyrode (Sigma), supplemented with 10 mM HEPES (Gibco), to 2-fold the intended concentration (in round bottom compound plates). Final DMSO concentration in test solutions and vehicle control was 0.1%.

Cells hSC-CMs (Cor.4U® Cardiomyocytes) were obtained from CDI (Ncardia, Germany). Cells are pre-plated and seeded in fibronectin-coated 96-well plates at a density suited to form a monolayer and maintained in culture in a stage incubator (37° C., 5% $CO_2$), according to the instructions of the cell provider.

Second line hSC derived cardiomyocyte called iCell®, Cardiomyocytes2 were purchased from FUJIFILM Cellular Dynamics (USA). The experiments with test drugs are carried out 5 to 7 days after plating the cells onto the plate to have a living, beating monolayer of hiPSC-derived cardiomyocytes. The beating monolayer in 96-well-plates are normally taken from 2 Vials of frozen iCell) Cardiomyocytes2 (≈5 million cells/vial), which will be plated onto three 96-well plates (≈50K/well).

Before Start of Experiment

At least one hour before the start of the experiments the normal cell medium was replaced with Tyrode solution with Calcium dye (see below).

Cal 520 dye (AAT Bioquest) was dissolved in 11 ml of Tyrode supplemented with 10 mM HEPES and warmed up to 37° C. before adding to the cells.

35 μl cell culture medium was removed from each well and replaced with 35 μl of pre-warmed Cal 520 dye solution and cell plate was incubated for 45 min at 37° C./5% $CO_2$. Cells were incubated for 5 min at 37° C.

Experiment

Spontaneous electrical activity is recorded, using Cal520™ (AAT Bioquest) calcium fluorescence-dye signaling. This dye integrates the total intracellular calcium activity over the whole well. A bottle of Cal520 dye (50 μg, MW: 1103/mol) is dissolved with 50 μl DMSO as a stock solution of 0.9 mM. 50 μL of the stock solution of the dye was added to 10 ml Tryodes solution to have dye concentration of 4.5 μM. Subsequently, 35 μl of this dye solution was added into each well, to have a final dye concentration of 1.58 μM. The current dye protocol on this CTCM human assay was established recently (Ivan Kopljar et al, Journal of Pharmacological and toxicological methods 2018. 91: 80-86; Lu et al., Tox Sci 2019. 170 (2): 345-356).

Fluorescent signals ($Ca^{2+}$ transient morphology) were measured using the Functional Drug Screen System (FDSS/μCell; Hamamatsu, Japan) and the recordings were subsequently analyzed off-line, using appropriate software e.g. Notocord.

The cell plate was loaded into the FDSS/μCell for a test run: $Ca^{2+}$ transients were measured for 4 minutes to check for synchronous beating of the cardiomyocytes in each well. All 96 wells were measured simultaneously (sampling interval: 0.06 s, short exposure time: 10 ms; excitation wavelength 480 nm; emission wavelength 540 nm; FDSS/μCell warmed to 37° C.). When all showed synchronous beating, the 96-well plate was measured repeatedly for 3 times (to verify synchronous beating in all 96-well at baseline, wells that did not meet the preset criteria were excluded from the study and not treated with compound):

T=0: control period (−5 to −1 min)+compound addition, followed for 3 min.

T=30: measured from 29 to 34 min after compound addition

During the compound addition step, 100 μl of the respective double-concentrated test solutions was pipetted into each well simultaneously.

Data were analyzed off-line using appropriate software e.g. Notocord-Hem (version 4.3).

The following parameters of the $Ca^{2\prime}$ transient morphology were measured:

beat rate (BR)

amplitude of the $Ca^{2+}$ transient (Amp), $CTD_{90}$: $Ca^{2+}$ transient duration at 90% (time to 90% of the initial base value).

The presence of various 'arrhythmia-like' activities were also noted during the experimental periods. These included:

'early afterdepolarization-like' (EAD-like) events (defined as "an extra small peak of the transient waveform following the initial peak of the transient"), 'ventricular tachycardia-like' (VT-like) events (defined as a very fast beating rate) or 'ventricular fibrillation-like' (VF-like) events (defined as "small amplitude, fast-rate $Ca^{2+}$ waveforms with irregularities and non-measurable transient potentials)

'cessation of beating' of the cells (no $Ca^{2+}$ transients observed).

If compound-induced changes on the calcium transient signal could not be analyzed by the software, then these signals were identified as BQL (below quality analyses level).

Data Analysis

Data, measured from the FDSS-μCell, were copied for off-line analysis and were analyzed and uploaded in SPEC-II (our operational management system) for further analysis. The values of the variables before and after administration of the compound were collected and transferred into an Excel workbook.

All values (actual units and percentage changes from the baseline values) are expressed as median (minimum and maximum). Changes versus the corresponding baseline values (in actual units) observed in the compound group were compared with those in the solvent control group using the Wilcoxon-Mann-Whitney Test. Two-tailed tests with Bonferroni correction for multiplicity adjustment were conducted. Since there are 10 treatment groups each compared to the solvent group, alpha level of 0.05/10 (0.005) was considered to reflect a statistically significant difference from the solvent group. All statistical analysis was performed using appropriate software e.g. R software version 3.5.2.

Quality Control of the hiPSC-CMs in the plate:

Plates were rejected if they did not meet following criteria:

Stable regular beating

Amplitude ≥500 relative units

Beat rate between 25 and 80 beats per minute $CTD_{90}$ between 300 and 800 ms

In the present study, the hiPSC-CMs in the plates met the above criteria.

These parameters combined with incidence of arrhythmia or cessation of beating were used to calculate the potential hazard level using a weighted scoring method (based on Kopljar et al., Stem Cell Reports 2018. 11, 1365-1377). This hazard score is calculated per concentration by adding weighted points based on the Tolerance Intervals (TI) on the changes of $CTD_{90}$, the beat rate and amplitude (AA %) and incidence of beating stop and early afterdepolarization (EAD). Consequently, for each concentration one of four different hazard levels will be generated. This will be done after 30-min of incubated with compound. The hazard levels are:

No hazard: within the vehicle effect levels or small non-relevant changes.

Low hazard: relevant effect but potentially low risk for cardiac liabilities.

High hazard: relative high risk for cardiac liabilities.

Very high hazard: very high risk due to arrhythmic like events (EAD's).

The 'Hazard Score' results provide an identification for potential acute cardiac drug-induced effects at free drug equivalent (as no plasma proteins are added to the wells). Evaluation of hazard identification is conducted using a 'scoring reference book' called CTCM_Scoring_version 1 (Kopljar et al., Stem Cell Reports 2018. 11: 1365-1377), and levels are indicated according to the following color scheme:

| Color | Hazard identification legend |
|---|---|
| Green | No concern |
| Yellow | Low concern |
| Red | High concern |
| Black | Very high concern due to arrhythmic events |

Ranking of a testing compound according to hazard score severity on the $Ca^{2+}$ transient assay measured in HiPSc-CMs as listed above in different colors and in the associated table.

Results

Using iCell® Cardiomyocytes2 as Cell Line

Positive and Negative Controls:

The positive and negative controls all had expected pharmacological effects in this assay

| Compounds: | | | | | | |
|---|---|---|---|---|---|---|
| Compound | Color @ 0.1 μM | Color @ 0.2 μM | Color @ 0.5 μM | Color @ 1 μM | Color @ 2.5 μM | Color @ 5 μM |
| 70 | Green | Green | Green | Green | Green | Green |
| 246 | Green | Green | Green | Green | Green | Green |

| Compound | Color @ 0.1 μM | Color @ 0.3 μM | Color @ 1 μM | Color @ 3 μM | Color @ 10 μM | Color @ 30 μM |
|---|---|---|---|---|---|---|
| 70a | Green | Green | Green | Green | Green | yellow |
| 398 | Green | Green | Green | Green | Green | Green |
| 11 | Green | Green | Green | Green | Green | Green |
| 286 | Green | Green | Green | Green | Green | Green |

For compound 70a: with an efficacious dose in mouse xenograft models of 30 mpk (mg/kg), CTCM human concentration vs free Cmax would be estimated as followed
Margin CTCM human 10 μM vs free Cmax > 16 (mouse, human)
Margin CTCM human 30 μM vs free Cmax > 45 (mouse, human)

| Using Cor.4U ®-Cardiomyocytes as cell line | | | | | | |
|---|---|---|---|---|---|---|
| Compounds | Color @ 0.1 μM | Color @ 0.2 μM | Color @ 0.5 μM | Color @ 1 μM | Color @ 2.5 μM | Color @ 5 μM |
| 37 | Green | Green | Green | Green | Green | Green |
| 19 | Green | Green | Green | Green | Green | Green |

8) Effect on the Membrane Potassium Current $I_{Kr}$ in hERG Transfected Cell Lines Protocol 1:

LIST OF ABBREVIATIONS

Abbreviations

CHO Chinese hamster ovary cell line
DMSO Dimethylsulfoxide
hERG human ether-á-go-go-related gene
$I_{Kr}$ rapidly activating delayed-rectifier $K^+$ current Methods Experiments were performed using CHO cells stably expressing the hERG potassium channel. Cells were grown at 37° C. and 5% $CO_2$ in culture flasks in Ham's F12 Medium supplemented with 10% heat-inactivated fetal calf serum, hygromycin B (100 μg/ml) and geneticin (100 μg/ml). For use in the automated patch-clamp system QPatch (Sophion) cells were harvested to obtain cell suspension of single cells.

Solutions: The bath solution contained (in mM) 145 NaCl, 4 KCl, 10 glucose, 10 HEPES ((4-(2-hydroxyethyl)-1-piperazineethanesulfonic acid), 2 $CaCl_2$ and 1 $MgCl_2$ (pH 7.4 with NaOH). The pipette solution contained (in mM) 120 KCl, 10 EGTA (Ethylene glycol-bis(2-aminoethylether)-N,N,N',N'-tetraacetic acid), 10 HEPES, 5.374 $CaCl_2$ and 1.75 $MgCl_2$ (pH 7.2 with KOH).

Patch-clamp experiments were performed in the voltage-clamp mode and whole-cell currents were recorded with an automated patch-clamp assay utilizing the QPatch system (Sophion). Current signals were amplified and digitized, stored and analyzed by using the QPatch assay software.

The holding potential was −80 mV. The hERG current ($K^+$-selective outward current) was determined as the maximal tail current at −40 mV after a 2 second depolarization to +60 mV. Pulse cycling rate was 15 s. A short pulse (90 ms) to −40 mV served as a baseline step to calculate the tail current amplitude. After establishing whole-cell configuration and a stability period, the solvent control (0.3% DMSO) was applied for 5 minutes followed by the test substance by four increasing concentrations of $3\times10^{-7}$ M, $3\times10^{-6}$ M, $10^{-5}$ M and $3\times10^{-5}$ M. Each concentration of the test substance was applied twice. The effect of each concentration was determined after 5 min as an average current of 3 sequential voltage pulses. To determine the extent of block the residual current was compared with vehicle pre-treatment.

Concentration/response relations were calculated by non-linear least-squares fits to the individual data points. The half-maximal inhibiting concentration (IC50) was calculated by the fitting routine.

Protocol 2:

Cells

The compound, vehicle control and positive control were tested on hERG-transfected HEK293 cells. A human embryonic kidney cell line (HEK293) with a stable transfection of hERG (Zhou Z et al. Biophysical Journal 1998. 74, 230-241; McDonald T. V. et al, Nature 1997. 388, 289-292) was used (University of Wisconsin, Madison, USA). The cells were kept in culture in MEM (Minimum Essential Medium, Gibco) which was supplemented with (amounts indicated added to 500 ml MEM): 5 ml L-Glutamine-Penicillin-Streptomycin (Sigma), 50 ml Fetal Bovine serum (Bio-Whittaker), 5 ml Non-essential Amino Acids 100× (Gibco), 5 ml sodium pyruvate 100 mM (Gibco) and 4 ml geneticin 50 mg/ml (Gibco) using T175 flasks. The cells were incubated at 37° C. in 5% $CO_2$ atmosphere (in air).

Cell Harvesting for Assay

Cells were harvested as described below using Accumax™ (Sigma) as the dissociating reagent. Cells were then resuspended in a mixture of 33% DMEM/F12 (Dulbecco's Modified Eagle Medium/Nutrient Mixture F-12—Sigma) media/67% extracellular physiological solution.

The flasks were washed twice carefully with ~5-10 ml phosphate buffered saline (PBS) (Gibco™) containing 2 mM EDTA (Ethylenediaminetetraacetic acid) (Sigma). The cells were dissociated using ~3 ml of Accumax™ (cell detachment solution) and incubated for ~5 to 10 min. at 37° C. Cold external physiological solution (2-5 ml) was added and the flasks are incubated at ~4° C. for 5-10 min. Then, the cell suspension in each flask was gently dissociated with a 5 ml pipette. The cell suspension was transferred to a low binding petri-dish (~10 mm diameter). Each flask was washed with ~additional 5 ml cold external physiological solution and this solution was also added to the petri-dish. The petri-dish was then incubated for another 5 to 10 minutes at ~4° C. After another gentle dissociation of the cell suspension in the petri dish, the cells were transferred to a reservoir kept on an orbital shaker at 200 rpm at 16° C. Before experiments were performed, the cells recovered for ~20 min.

Compounds

A 10 mM solution of the compound was used and plated in a 384 well plate. Aliquots of the stock solutions are diluted with the recording solution (see section 3) using automated liquid handling (Biomek FXP; final DMSO concentration: 0.03 to 0.3%). A standard range of screening concentrations was used ranging from 1 μM to 30 μM.

A positive control (E-4031) was included within each run to evaluate the sensitivity of the assay.

External and Intracellular Solutions Used in the Experiments

In the table below the composition of the intracellular and external buffer solutions is shown in [mM] ("NMDG" means N-methyl-D-glucamine)

| Intracellular Solution | | Extracellular Physiological Solution/Chip Fill Solution | | Seal Enhancer Solution | | Recording Solution | |
|---|---|---|---|---|---|---|---|
| KCl | 10 | NaCl | 140 | NMDG | 60 | NMDG | 60 |
| KF | 110 | KCl | 4 | NaCl | 80 | NaCl | 80 |
| NaCl | 10 | Glucose | 5 | KCl | 4 | KCl | 4 |
| HEPES | 10 | HEPES | 10 | $CaCl_2$ | 10 | $CaCl_2$ | 2 |
| EGTA | 10 | $CaCl_2$ | 2 | $MgCl_2$ | 1 | $MgCl_2$ | 1 |
| pH 7.2 (KOH) | | $MgCl_2$ | 1 | Glucose | 5 | Glucose | 5 |
| | | pH 7.4 (NaOH) | | HEPES | 10 | HEPES | 10 |
| | | | | pH 7.4 (HCL) | | pH 7.4 (HCL) | |

Study Design

The whole cell patch clamp technique on transfected cells allows the study of ion-channels with no—or limited interference from other ion-channels. The effects of the compounds on the hERG current were studied with an automated planar patch clamp system, SyncroPatch 384PE (Obergrussberger et al, Journal of Laboratory Automation 2016. 21 (6). 779-793). All cells were recorded in the whole cell mode of the patch clamp technique. The module is incorporated in a liquid handling pipetting robot system, Biomek FXP, for application of cells and compounds, vehicle control and positive control.

The different concentrations of the compounds were applied in two cumulatively increasing concentrations for the compounds (1 μM and 10 μM, and 3 μM and 30 μM, respectively). The hERG current was determined as the maximal tail current at −30 mV and percent inhibition upon compound or vehicle and positive control addition was reported.

After cells are caught onto the individual holes of the recording chips using the chip fill solution, the seal is increased with the seal enhancer solution (increased [$Ca^{2+}$]; then the cells were washed twice with recording solution before using a pressure protocol to go into the whole cell mode.

After the whole cell mode was achieved, test pulses were given for ~10 minutes to quantify the hERG current in control conditions. During this control period vehicle control solution (recording solution containing 0.03% DMSO) was added three times into the individual wells. While continuing the pulse protocol, cumulatively increasing concentrations of the vehicle control, compound or positive control was added. The effect of the vehicle, compound and positive control was measured after 5 minutes of drug application. Two concentrations of the compound were tested per cell.

The use of the internal and recording solutions will result in ~10 mV liquid junction potential and the command voltage step will take this into account.

Electrophysiological measurements: The membrane current of the cells was measured at distinct membrane potentials with the patch clamp technique by means of an automated patch clamp system. The holding potential is −70 mV. The hERG current ($K^+$-selective outward current) was determined as the maximal tail current at −30 mV after a 2 second depolarization to +70 mV (refs. 1, 4). Pulse cycling rate was 15 s.

Data Analysis

The leak corrected hERG current ($K^+$-selective outward current) was determined as the maximal tail current at −30 mV after a 2-second of depolarization to +70 mV measured between 2336.3 ms and 3083.6 ms. The median of three current amplitudes was taken at the end of the control period and at the end of each addition of compound, vehicle and positive control to calculate the percent inhibition.

QC parameters were set in the SyncroPatch 384PE PatchControl384 software to automatically exclude wells from the analysis if values fall outside the range. The QC criteria are dependent on the type of recording plate (chip). Typically, a 4×Chip (medium size hole) was used to record from hERG-transfected HEK293 cells. QC criteria 4-6 were set before the first addition of the compound; QC criteria 4 and 5 were also set at the end of each compound addition.

QC Criteria and Acceptable Ranges:

1. Board Check: −500 pA-500 pA
2. Contact seal resistance: −100 kOhm-10 MOhm
3. Junction potential offset: 0-100 mV
4. Rseal≥100 MOhm
5. Rseries: between 1-25 MOhm
6. hERG tail current ≥0.2 nA before compound addition Each compound was replicated on the same plate in at least 5 wells. Percent inhibition of at least 2-3 replicates per concentration will be reported as median.

Results:

| Protocol 1 | |
|---|---|
| Compound Number | hERG-$IC_{50}$ (μM) |
| 17 | 4.1 |
| 40 | 5.0 |

-continued

| Protocol 1 | |
|---|---|
| Compound Number | hERG-$IC_{50}$ (μM) |
| 83 | 6.0 |
| 41 | 6.3 |
| 39 | 7.6 |
| 45 | 12.6 |
| 14 | 20.0 |
| 22 | 20.9 |
| 13 | 25.7 |
| 94 | 30.9 |
| 1 | >30.2 |
| 4 | >30.2 |
| 37 | >30.2 |
| 30 | >30.2 |
| 19 | >30.2 |
| 12 | >30.2 |
| 18 | >30.2 |
| 11 | >30.2 |
| 34 | >30.2 |
| 49 | >30.2 |
| 47 | >30.2 |
| 35 | >30.2 |
| 27 | >30.2 |
| 32 | >30.2 |
| 23 | >30.2 |
| 10 | >30.2 |
| 71 | >30.2 |
| 258 | >30.2 |
| 75 | >30.2 |
| 252 | >30.2 |
| 396 | >30.2 |

| Protocol 2: | |
|---|---|
| Example Number | hERG-$IC_{50}$ (μM) |
| 148 | 12.3 |
| 11 | >30.2 |
| 246 | >30.2 |
| 99 | >30.2 |
| 132 | >30.2 |
| 233 | >30.2 |
| 104 | >30.2 |
| 242 | >30.2 |
| 146 | >30.2 |
| 112 | >30.2 |
| 114 | >30.2 |
| 245 | >30.2 |
| 223 | >30.2 |
| 227 | >30.2 |

9) Efficacy Study in Disseminated OCI-AML3 Model

Test Agents and Controls

Compound 70 was formulated in 20% hydroxypropyl-beta-cyclodextrin (HP-β-CD) and prepared to reach a total volume of 0.2 mL (10 mL/kg) per dose for a 20 g animal. Doses were adjusted by individual body weight each day. Working stocks of Compound 70 were prepared once per week for each study and stored at 25° C.

Animals

Female SCID beige mice (CB17.Cg-PrkdcscidLystbg-J/Crl/−) were used when they were approximately 6 to 8 weeks of age and weighed approximately 25 g. All animals could acclimate and recover from any shipping-related stress for a minimum of 7 days prior to experimental use. Autoclaved water and irradiated food were provided ad libitum, and the animals were maintained on a 12 hour light and dark cycle. Cages, bedding, and water bottles were autoclaved before use and changed weekly.

| Tissue Culture and Cell Injection Reagents |
|---|
| DPBS (Dulbecco's phosphate-buffered saline) |
| Heat-inactivated fetal bovine serum |
| MEM Alpha medium |
| L-glutamine |
| Gentamycin |
| T175 Culture Flask |
| Roller Bottle |

Tumor Model and Cell Culture Method

Human AML cell line OCI-AML3 was cultured at 37° C., 5% $CO_2$ in the indicated complete culture media (MEM Alpha+20% HI-FBS (Heat-Inactivated Fetal Bovine Serum)+2 mM L-glutamine+50 ug/ml Gentamycin). Cells were harvested while in logarithmic growth and resuspended in cold (4° C.) MEM ((Minimum Essential Medium) Alpha in serum-free medium. For the disseminated OCI-AML3 model, each mouse received $5\times10^5$ cells via IV injection in a total volume of 0.2 mL using a 26-gauge needle.

Study Designs

Compound 70 was administered orally (PO), daily.

Day 0 is the day of tumor cell implantation and study initiation

In the efficacy study, mice bearing IV OCI-AML3 xenograft tumors were randomly assigned to treatment groups 3 days post-tumor cell engraftment. Treatment with vehicle or Compound 70 (at 30, 50,100 mg/kg) was initiated on the same day, with daily dosing for 28 days.

Animal Monitoring

Animals were monitored daily for clinical signs related to either compound toxicity or tumor burden (i.e., hind limb paralysis, lethargy, etc.).

Calculations

For survival assessment, results were plotted as the percentage survival against days post tumor implant. Negative clinical signs and/or ≥20% body weight loss was used as a surrogate endpoint for death. Median survival was determined utilizing Kaplan-Meier survival analysis. The percent increased life span (ILS) was calculated as: ((median survival day of treated group−median survival day of control group)/median survival day of control group)×100. Animals failing to reach the surrogate endpoint due to adverse clinical signs (such as ulcerated tumors, body weight loss, etc.) or death unrelated to treatment were censored for the survival assessment. As defined by NCI criteria, ≥25% ILS is considered biologically significant. (Johnson J I et al. Br J Cancer. 2001. 84(10), 1424-1431).

Data Analysis

Survival and body weight data were graphically represented utilizing Prism (Version 7). Statistical significance for body weights was evaluated as described above. Statistical significance was evaluated for Kaplan-Meier survival plots comparing therapeutic treatment group vs. appropriate vehicle-treated control using log-rank (Mantel-Cox) test in R software version 3.4.2. Differences between groups were considered significant when the p value was ≤0.05.

Survival

The Kaplan-Meier survival curve is shown in below figure. Mice bearing established OCI-AML3 tumors were orally dosed daily with Compound 70 at 30, 50, 100 mg/kg in 20% HP-β-CD formulation for a total of 28 days (n=9-10/group). For Compound 70 treated groups, the median days of survival were reached at the following days for 30 mg/kg at day 75.5, for 50 mg/kg at day 58.5 and for 100 mg/kg at day 75 this compared to a median survival of 38.5 days for the vehicle-treated control group. Compound 70 treatment resulted in statistically significant increased lifespan of OCI-AML3 tumor-bearing mice by 96.1%, 51.9% and 94.8% (at the 30, 50 and 100 mg/kg dose levels) as compared to that of control mice, ($p \leq 0.001$). This was a biologically significant ILS as per NCI criteria threshold of ≥25% ILS (Johnson J I et al. Br J Cancer. 2001. 84(10), 1424-1431).

Figure 2:
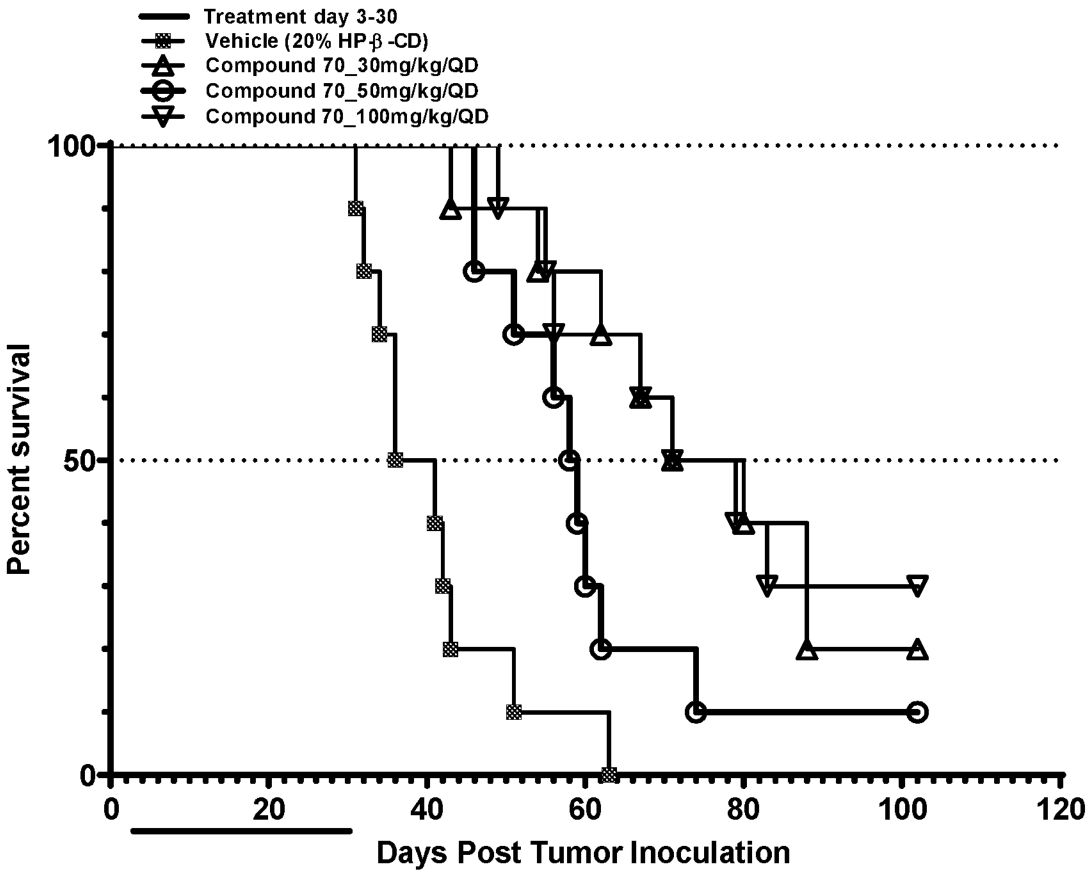
FIG. 2: Efficacy study in disseminated OCI-AML3 model.

Results in FIG. 2.

The invention claimed is:

1. A compound wherein the compound is

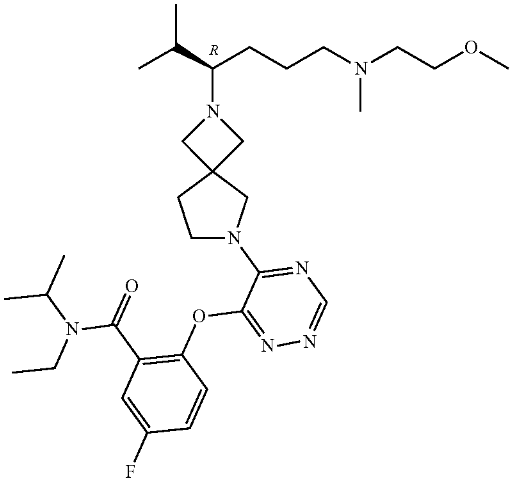

or a pharmaceutically acceptable salt or a solvate thereof.

2. The compound according to claim 1, wherein the compound is the pharmaceutically acceptable salt.

3. The compound according to claim 1, wherein the compound is the solvate.

4. The compound according to claim 1, wherein the compound is the solvate of the pharmaceutically acceptable salt.

5. The compound according to claim 1, wherein the compound is

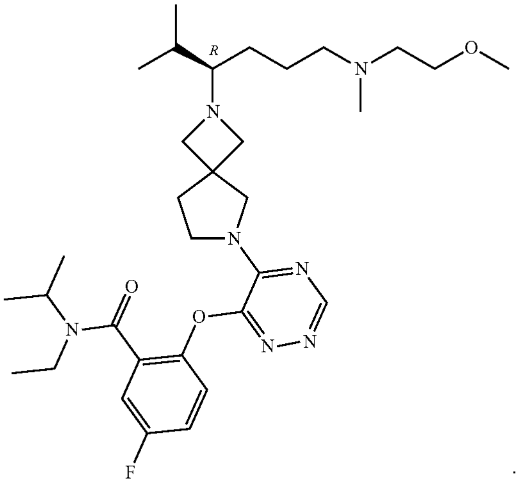

6. The compound according to claim 1, wherein the compound is

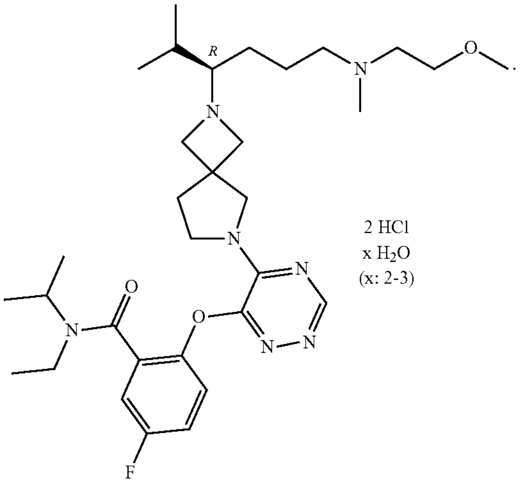

7. The compound according to claim 6, wherein the compound is

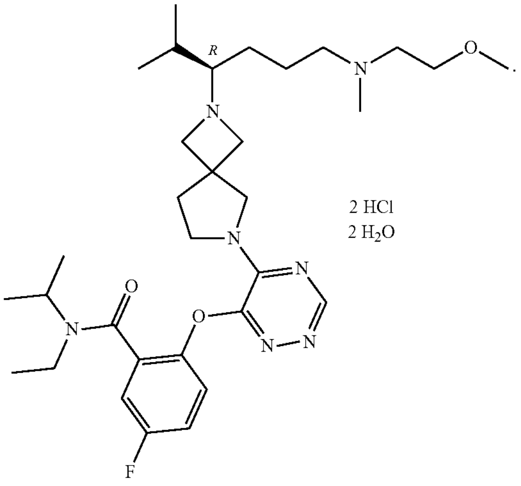

8. The compound according to claim 1, wherein the compound is

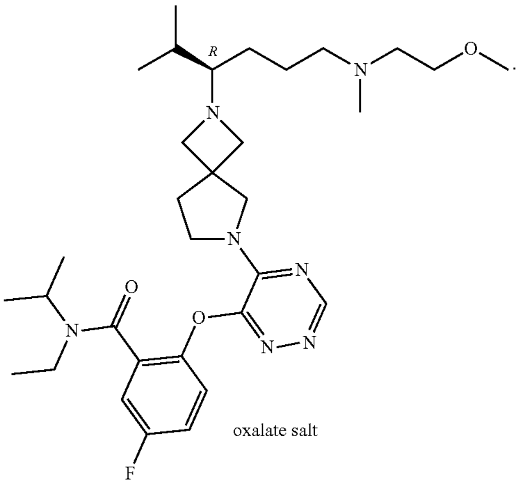

9. A pharmaceutical composition comprising a compound of claim 1 and a pharmaceutically acceptable carrier or diluent.

10. A process for preparing a pharmaceutical composition comprising mixing a pharmaceutically acceptable carrier with a therapeutically effective amount of a compound of claim 1.

11. A method of treating leukemia, myelodysplastic syndrome (MDS), or myeloproliferative neoplasms (MPN) in a subject in need thereof comprising administering a therapeutically effective amount of a compound of claim 1 or a pharmaceutical composition of claim 9.

12. The method of claim 11, wherein the method comprises treating leukemia, wherein the leukemia is (NPM1)-mutated leukemia.

13. The method of claim 11, wherein the method comprises treating leukemia, wherein the leukemia is selected from acute leukemias, chronic leukemias, myeloid leukemias, myelogeneous leukemias, lymphoblastic leukemias, and lymphocytic leukemias.

14. The method of claim 11, wherein the method comprises treating leukemia, wherein the leukemia is an acute leukemia.

15. The method of claim 14, wherein the acute leukemia is AML.

16. The method of claim 14, wherein the acute leukemia is ALL.

17. The method of claim 14, 15 or 16, wherein the acute leukemia has KMT2A gene alterations or NPM1 mutations.

18. The method of claim 14, 15 or 16, wherein the acute leukemia has KMT2A gene rearrangements.

19. The method of claim 14, 15 or 16, wherein the acute leukemia has NPM1 mutations.

20. The method of claim 11, wherein the method comprises treating leukemia, wherein the leukemia is selected from Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, and leukemias exhibiting HOX/MEIS1 gene expression signatures.

* * * * *